(12) United States Patent
Ewing et al.

(10) Patent No.: US 8,815,909 B2
(45) Date of Patent: Aug. 26, 2014

(54) DIAMINOCYCLOHEXANE COMPOUNDS AND USES THEREOF

(75) Inventors: William R. Ewing, Yardley, PA (US);
Yeheng Zhu, Stockton, NJ (US);
Chongqing Sun, East Windsor, NJ (US);
Yanting Huang, Pennington, NJ (US);
Maheswaran Sivasamban Karatholuvhu, Periyar Nagar (IN);
Scott A. Bolton, Newtown, PA (US);
Laxman Pasunoori, Warangal (IN);
Sunil Kumar Mandal, Bangalore (IN);
Philip M. Sher, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 13 days.

(21) Appl. No.: 13/549,767

(22) Filed: Jul. 16, 2012

(65) Prior Publication Data
US 2013/0184284 A1 Jul. 18, 2013

Related U.S. Application Data

(60) Provisional application No. 61/508,849, filed on Jul. 18, 2011.

(51) Int. Cl.
| | | |
|---|---|---|
| A01N 43/40 | (2006.01) | |
| A61K 31/445 | (2006.01) | |
| A01N 43/42 | (2006.01) | |
| A61K 31/44 | (2006.01) | |
| A01N 57/00 | (2006.01) | |
| A61K 31/43 | (2006.01) | |

(52) U.S. Cl.
USPC ........... 514/326; 514/299; 514/318; 514/321; 546/112; 546/118; 546/194; 546/198

(58) Field of Classification Search
None
See application file for complete search history.

(56) References Cited

FOREIGN PATENT DOCUMENTS

| | | |
|---|---|---|
| EP | 2 404 896 | 1/2012 |
| WO | WO 2008/052769 | 5/2008 |

OTHER PUBLICATIONS

International Search Report mailed Sep. 3, 2012.

*Primary Examiner* — James D Anderson
*Assistant Examiner* — William Lee
(74) *Attorney, Agent, or Firm* — Elliott Korsen

(57) ABSTRACT

The present invention provides compounds of Formula (I):

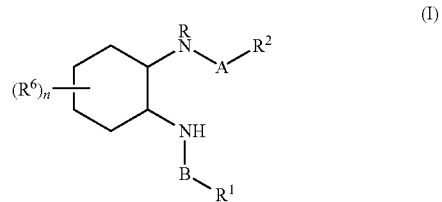

or a stereoisomer, or a pharmaceutically acceptable salt thereof, wherein all of the variables are as defined herein. These compounds are agonists, partial agonists and modulators of the NPY Y4 receptor and may be used for the treatment and prophylaxis of various diseases and conditions.

6 Claims, No Drawings

DIAMINOCYCLOHEXANE COMPOUNDS AND USES THEREOF

FIELD OF THE INVENTION

The present invention provides substituted diaminocyclohexanes, and analogues thereof, which are agonists, partial agonists or modulators of the NPY Y4 receptor, compositions containing the compounds, and methods of using them, for example, for the treatment or prophylaxis of obesity, to control appetite, feeding, food intake, energy expenditure, caloric intake, gastric motility, diabetes and other related conditions.

BACKGROUND OF THE INVENTION

Obesity and its associated disorders are common and very serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia.

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., Br. Med. J. 301:835-837 (1990)). Obesity is also a risk factor for the group of conditions called insulin resistance syndrome, or "Syndrome X" and metabolic syndrome. The worldwide medical cost of obesity and associated disorders is enormous.

Obesity remains a poorly treated, chronic, essentially intractable metabolic disorder. Accordingly, a need exists for new therapies useful in weight reduction and/or weight maintenance in a subject. Such therapies would lead to a profound beneficial effect on the subject's health.

The present invention provides methods and compositions useful in the control, treatment, and prevention of obesity and obesity-related conditions, disorders, and diseases, such as those referenced above.

Pancreatic polypeptide ((PP) is a member of the PP-fold family of peptides which also includes neuropeptide Y (NPY) and peptide YY (PYY). PP is an endogen-ously secreted 36 amino acid, C-terminally amidated peptides, which is characterized by a three-dimensional structure, the PP-fold, which is shared by NPY and PYY.

PP is released from endocrine cells in pancreatic islets, almost exclusively governed by vagal cholinergic stimuli elicited especially by food intake. PP has various effects on the gastrointestinal tract, but none of these are observed in isolated cells and organs, and all appear to be dependent on an intact vagal nerve supply. PP simulates Y4 receptors located in the periphery and in the brain. In the brain, there is a strong expression of Y4 receptors in the nucleus tractus solitarius (NTS), the activation of which results in the effects of PP as a satiety hormone. The effect of PP on food intake may be mediated through an action on neurons, especially the POMC/CVART neurons in the arcuate nucleus.

There are four well established types of NPY receptors in man; Y1, Y2, Y4 and Y5, which all recognize NPY1-36 and PYY1-36 with similar affinity. In contrast PP demonstrates selectivity among the NPY receptor subtypes having subnanomolar affinity for the Y4 receptor.

PP and related analogs have been suggested for use in the treatment of obesity and associated diseases, including for example, Prader Willi's syndrome, based on the demonstrated effects of certain of these peptides in animal models and in man. Additionally obese subjects have been shown to have low basal levels of PP and lower secreted levels in response to a meal. High PP levels are found in patients with anorexia nervosa.

Since the mid 1970's it has been shown that PP reduces food intake in rodents. Studies have demonstrated that after peripheral administration to animals, PP is a powerful and efficient anorexigenic agent. Later it was shown that PP has no effect on food intake and appetite in Y4 receptor knock-out mice, strongly suggesting that PP's actions on food intake are through it's interactions with the Y4 receptor. PP has also been shown to have an effect on food intake in diet induced obese animals.

PP has been found to reduce food intake in humans. In 1993, it was reported that infusion of PP in morbidly obese patients with Prader Willi's syndrome decreased food intake. In a subsequent study, infusion of PP in normal human subjects showed a long lasting suppression of appetite and reduced food intake over 24 hours.

PP has a short circulating half-life in humans limiting its use as a therapeutic agent. For the treatment of conditions responsive to Y4 receptor modulation, such as obesity, diabetes and intestinal hypersecretion, it would be desirable to have a more druggable molecule with better pharmacokinetics, selectivity and potential for oral delivery.

In particular, it would be highly desirable to use such agents which are selective for the Y4 receptor over the Y1 receptor. This is particularly important since activation of the Y1 receptor is expected to potentially cause unwanted cardiovascular and renal side effects such as vasoconstriction and natriuresis.

Thus, use of selective and efficacious Y4 receptor agonists over Y1 receptor agonists would be particularly useful in diseases and conditions susceptible to Y4 receptor activation.

The present invention relates to novel substituted diaminocyclohexane compounds which have the ability to activate, partially activate and/or modulate the NPY Y4 receptor. Such compounds are therefore potentially useful for the treatment or prophylaxis of obesity, to control appetite, feeding, food intake, energy expenditure, caloric intake, gastric motility, diabetes and other related conditions.

SUMMARY OF THE INVENTION

The present invention provides substituted diaminocyclohexane compounds, and analogues thereof, which are useful as NPY Y4 receptor agonists, partial agonists or modulators, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and one or more of the compounds of the present invention or stereoisomers, tautomers, pharmaceutically acceptable salts, or solvates thereof.

The compounds of the invention may be used in the treatment and/or prophylaxis of multiple diseases or disorders associated with the NPY Y4 receptor, such as obesity, appetite control, feeding behavior, food intake, energy expenditure, caloric intake, gastric motility, Metabolic Syndrome and its component conditions, disorders of glucose metabolism, diabetes and related conditions, microvascular complications associated with diabetes, the macrovascular complications associated with diabetes, cardiovascular diseases and other maladies.

The compounds of the invention may be used in therapy.

The compounds of the invention may be used for the manufacture of a medicament for the treatment and/or prophylaxis of multiple diseases or disorders associated with the NPY Y4 receptor.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, a compound of Formula (I):

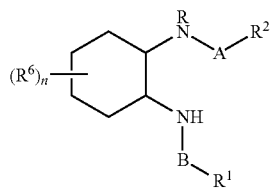

(I)

wherein:

A is a nitrogen containing 5- to 8-membered heterocyclyl or azabicycloalkyl ring, optionally substituted with $(C_1-C_6)$ alkyl, —OH or halogen;

B is a heterocyclyl or a heteroaryl ring, said heteroaryl ring containing 1-4 heteroatoms selected from N, O, and S, wherein the heterocyclyl and heteroaryl may be optionally substituted with one or more $R^1$;

R is hydrogen or $(C_1-C_6)$ alkyl;

$R^1$ is hydrogen, cyano, halogen, —$(C_1-C_6)$alkyl, —$(C_2-C_6)$alkenyl, —$(C_2-C_6)$alkynyl, —$CO(C_1-C_6)$alkyl, —$CO_2(C_1-C_6)$alkyl, —$CONR^9R^{10}$, $(C_6)$aryl, $(C_3-C_8)$cycloalkyl, heterocyclyl, bicyclic heterocycle or heteroaryl, said heteroaryl containing 1-4 heteroatoms selected from N, O, and S, wherein the alkyl, alkenyl, alkynyl, cycloalkyl, aryl, heterocyclyl, bicyclic heterocycle and heteroaryl may be optionally substituted with one or more $R^3$;

$R^2$ is $(C_6)$aryl or heteroaryl, said heteroaryl containing 1-4 heteroatoms selected from N, O, and S, wherein both the aryl and heteroaryl may be optionally substituted with one or more $R^4$; wherein $R^2$ is connected to ring A through the nitrogen atom of ring A;

$R^3$ is independently one or more halogen, —OH, —CN, —$NO_2$, —COOH, —$CO_2(C_1-C_6)$alkyl, —$CF_3$, —$OCHF_2$, —$OCF_3$, —$(C_1-C_6)$-alkyl, —$(C_2-C_6)$alkenyl, —$(C_2-C_6)$alkynyl, $(C_3-C_8)$cycloalkyl, —$(C_1-C_6)$-alkyloxy, —$CONR^9R^{10}$, —$O(C=O)NR^9R^{10}$, —$NR^9R^{10}$, —$NHCOO(C_1-C_6)$alkyl, —$(C_1-C_6)$-alkyl-COOH, —$(C_1-C_6)$-alkyl-$CO_2(C_1-C_6)$-alkyl, —$(C_1-C_6)$-alkyl-OH, —$(C_1-C_6)$-alkylCONR^9R^{10}$, —$SO_2(C_1-C_6)$-alkyl, —$SO_2(C_3-C_6)$-cycloalkyl, $SO_2NR^9R^{10}$, $(C_{6-10})$aryl, heteroaryl, which contains 1-4 heteroatoms selected from N, O, and S; and a 5- to 10-membered heterocyclyl, which contains 1-4 heteroatoms selected from N, O, and S, wherein —$SO_2(C_1-C_6)$-alkyl, —$SO_2(C_3-C_6)$-cycloalkyl, $SO_2NR^9R^{10}$ or any alkyl, alkenyl, alkynyl, aryl, heteroaryl, and heterocyclyl groups may be optionally substituted with one or more substituents selected from halogen, —OH, cyano, nitro, —$CF_3$, —$OCF_3$, —$OCF_2H$, $(C_1-C_6)$-alkyl, $(C_2-C_6)$-alkynyl, $(C_1-C_6)$-alkyloxy, —COOH, —$CO_2(C_1-C_6)$-alkyl, —$CONR^9R^{10}$, —$NR^9R^{10}$, —$O(C=O)$—$(C_1-C_6)$-alkyl, —$O(C=O)NR^9R^{10}$; —$(C_1-C_6)$-alkyl-COOH, —$(C_1-C_6)$-alkyl-OH, —$(C_1-C_6)$-alkylCONR^9R^{10}$, —$(C_1-C_6)$-alkyl-$CO_2(C_1-C_6)$-alkyl, $(C_{6-10})$aryl, a 5- to 8-membered heteroaryl, which contains 1-4 heteroatoms selected from N, O, and S, a 5- to 10-membered heterocyclyl, which contains 1-4 heteroatoms selected from N, O, and S; and when $R^3$ is or contains any alkyl, alkenyl, alkynyl, or heterocyclyl group, they may be optionally substituted with oxo; or when $R^1$ is —$(C_1-C_6)$alkyl, —$(C_3-C_6)$alkenyl, —$(C_3-C_6)$alkynyl, —$CO(C_1-C_6)$alkyl, —$CO_2(C_1-C_6)$alkyl, $(C_3-C_8)$cycloalkyl or heterocyclyl, $R^3$ may be oxo;

$R^4$ is halogen, —OH, $CF_3$, —$OCF_2H$, —$OCF_3$, —CN, —$NO_2$, —COOH, $(C_1-C_6)$-alkyl, —$(C_2-C_6)$alkenyl, —$(C_2-C_6)$alkynyl, $(C_1-C_6)$-alkyloxy, —$CO(C_1-C_6)$-alkyl, —$CO_2(C_1-C_6)$-alkyl, —$CONR^9R^{10}$, —$CN_2HR^9R^{10}$, —$NR^9R^{10}$, or a 5- to 10-membered heteroaryl containing 1-4 heteroatoms selected from N, O, and S, optionally substituted with one or more $R^5$;

$R^5$ is halogen, —OH, —$CF_3$, —$OCF_2H$, —$OCF_3$, —CN, —$NO_2$, —$(C_1-C_6)$alkyl, —$(C_3-C_8)$cycloalkyl, or $(C_1-C_6)$ alkyloxy;

$R^6$ is halogen, —OH, —$(C_1-C_6)$-alkyl or $(C_3-C_6)$-cycloalkyl wherein the $(C_1-C_6)$-alkyl is optionally substituted with $R^{11}$;

$R^9$ and $R^{10}$, at each occurrence, are independently hydrogen, —$(C_1-C_8)$-alkyl, —$(C_3-C_6)$alkenyl, —$(C_3-C_6)$alkynyl, —$(C_3-C_8)$-cycloalkyl, $(C_6)$aryl, 5- to 8-membered heteroaryl, —$CO(C_3-C_6)$-cycloalkyl, —$CO_2(C_3-C_6)$-cycloalkyl, —$CO(C_1-C_6)$-alkyl, —$CO_2(C_1-C_6)$-alkyl, —$CO(C_2-C_6)$-alkenyl, —$CO_2(C_3-C_6)$-alkenyl, —$CO(C_2-C_6)$-alkynyl, —$CO_2(C_3-C_6)$-alkynyl, —$CONR^9R^{10}$, —$SO_2(C_1-C_6)$-alkyl, —$SO_2(C_3-C_6)$-cycloalkyl, or $SO_2NR^9R^{10}$, all of which may be optionally substituted with one or more $R^{11}$; or $R^9$ and $R^{10}$ may be taken together with the nitrogen to which both are attached to form a 3-8 membered ring, which may optionally contain 1-4 heteroatoms selected from N, O, and S and be optionally substituted with one or more $R^{11}$;

$R^{11}$ is halo, —OH, cyano, —$(C_3-C_8)$-cycloalkyl, or —$(C_1-C_6)$-alkyl;

n is 1, 2 or 3;

or a stereoisomer, tautomer, or pharmaceutically acceptable salt thereof.

In a second aspect within the scope of the first aspect, the invention is directed to a compound of formula Ia

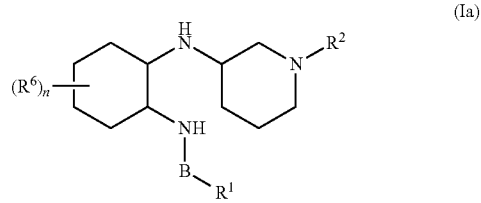

(Ia)

or a stereoisomer, tautomer, or pharmaceutically acceptable salt thereof.

In a third aspect within the scope of the first or second aspect, the invention is directed to a compound of formula Ia wherein:

B is selected from the group consisting of thiazole, oxazole, oxadiazole, isoxazole, pyridine and pyrimidine, all of which may be substituted with one or more $R^1$;

or a stereoisomer, tautomer, or pharmaceutically acceptable salt thereof.

In a fourth aspect within the scope of the first, second or third aspect, the invention is directed to a compound of formula Ia wherein:

$R^1$ is $(C_6)$aryl or 5- to 6-membered heteroaryl, said heteroaryl containing 1-4 heteroatoms selected from N, O, and S, wherein said aryl and heteroaryl may be optionally substituted with one or more $R^3$;

or a stereoisomer, tautomer, or pharmaceutically acceptable salt thereof.

In a fifth aspect, the invention is directed to a compound of formula Ia wherein:

$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, —$CF_3$, —$OCF_2H$, —$OCF_3$, —CN, —$NO_2$, or a 5- to 6-membered heteroaryl containing 1-4 heteroatoms selected from N, O, and S, optionally substituted with one or more $R^5$;

$R^5$ is halogen, —OH, —$CF_3$, —$OCF_2H$, —$OCF_3$, —CN, $(C_1-C_6)$alkyl, or $(C_1-C_6)$alkyloxy;

or a stereoisomer, tautomer, or pharmaceutically acceptable salt thereof.

In a sixth aspect, the invention is directed to a compound of formula Ia wherein:

$R^2$ is phenyl, pyridyl, pyrimidinyl, pyridazinyl, or pyrazinyl, substituted with one or more $R^4$; and $R^4$ is fluoro, chloro, $CF_3$, —$OCF_2H$, —$OCF_3$, —CN or —$NO_2$;

or a stereoisomer, tautomer, or pharmaceutically acceptable salt thereof.

In a seventh aspect, the invention is directed to a compound of formula Ia wherein:

$R^2$ is phenyl, pyridyl, pyrimidinyl, pyridazinyl, or pyrazinyl, substituted with one or more $R^4$;

$R^4$ is tetrazole, oxadiazole, oxazole, pyrazole or isoxazole, optionally substituted with one or more $R^5$; and $R^5$ is halogen, —OH, —$CF_3$, —$OCF_2H$, —$OCF_3$, —CN, methyl, ethyl, cyclopropyl, methoxy, ethoxy or cyclopropyloxy;

or a stereoisomer, tautomer, or pharmaceutically acceptable salt thereof.

In an eighth aspect, the invention is directed to a compound of formula Ia wherein B is oxazole.

In a ninth aspect, the invention is directed to a compound of formula Ia wherein B is pyridine.

In another aspect, the invention is directed to a compound of formula Ib

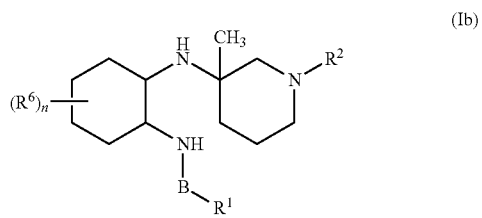

(Ib)

or a stereoisomer, tautomer, or pharmaceutically acceptable salt thereof.

In another aspect, the invention is directed to a compound of formula Ib wherein:

B is selected from the group consisting of thiazole, oxazole, oxadiazole, isoxazole, pyridine and pyrimidine, all of which may be substituted with one or more $R^1$;

or a stereoisomer, tautomer, or pharmaceutically acceptable salt thereof.

In another aspect, the invention is directed to a compound of formula Ib wherein:

$R^1$ is $(C_6)$aryl or 5- to 6-membered heteroaryl, said heteroaryl containing 1-4 heteroatoms selected from N, O, and S, wherein said aryl and heteroaryl may be optionally substituted with one or more $R^3$;

or a stereoisomer, tautomer, or pharmaceutically acceptable salt thereof.

In another aspect, the invention is directed to a compound of formula Ib wherein:

$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, $CF_3$, —$OCF_2H$, —$OCF_3$, —CN, —$NO_2$, or a 5- to 6-membered heteroaryl containing 1-4 heteroatoms selected from N, O, and S, optionally substituted with one or more $R^5$; and $R^5$ is halogen, —OH, —$CF_3$, —$OCF_2H$, —$OCF_3$, —CN, $(C_1-C_6)$alkyl, or $(C_1-C_6)$alkyloxy;

or a stereoisomer, tautomer, or pharmaceutically acceptable salt thereof.

In another aspect, the invention is directed to a compound of formula Ib wherein:

$R^2$ is phenyl, pyridyl, pyrimidinyl, pyridazinyl, or pyrazinyl, substituted with one or more $R^4$; and $R^4$ is fluoro, chloro, $CF_3$, —$OCF_2H$, —$OCF_3$, —CN or —$NO_2$;

or a stereoisomer, tautomer, or pharmaceutically acceptable salt thereof.

In another aspect, the invention is directed to a compound of formula Ib wherein:

$R^2$ is phenyl, pyridyl, pyrimidinyl, pyridazinyl, or pyrazinyl, substituted with one or more $R^4$;

$R^4$ is tetrazole, oxadiazole, oxazole, pyrazole or isoxazole, optionally substituted with one or more $R^5$; and $R^5$ is halogen, —OH, —$CF_3$, —$OCF_2H$, —$OCF_3$, —CN, methyl, ethyl, cyclopropyl, methoxy, ethoxy or cyclopropyloxy;

or a stereoisomer, tautomer, or pharmaceutically acceptable salt thereof.

In another aspect, the invention is directed to a compound of formula Ib wherein: B is oxazole.

In another aspect, the invention is directed to a compound of formula Ib wherein B is pyridine.

In another aspect, the invention is directed to a compound of formula Ic

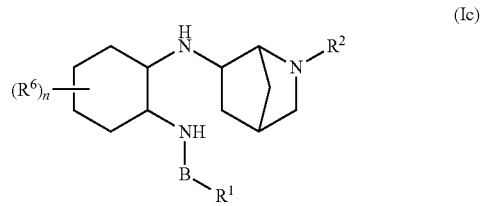

(Ic)

or a stereoisomer, tautomer, or pharmaceutically acceptable salt thereof.

In another aspect, the invention is directed to a compound of formula Ic wherein:

B is selected from the group consisting of thiazole, oxazole, oxadiazole, isoxazole, pyridine and pyrimidine, all of which may be substituted with one or more $R^1$;

or a stereoisomer, tautomer, or pharmaceutically acceptable salt thereof.

In another aspect, the invention is directed to a compound of formula Ic wherein:

$R^1$ is $(C_6)$aryl or 5- to 6-membered heteroaryl, said heteroaryl containing 1-4 heteroatoms selected from N, O, and S, wherein aryl and heteroaryl may be optionally substituted with one or more $R^3$;

or a stereoisomer, tautomer, or pharmaceutically acceptable salt thereof.

In another aspect, the invention is directed to a compound of formula Ic wherein:

$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, $CF_3$, —$OCF_2H$, —$OCF_3$, —CN, —$NO_2$, or a 5- to 6-membered heteroaryl containing 1-4 heteroatoms selected from N, O, and S, optionally substituted with one or more $R^5$; and $R^5$ is halogen, —OH, —$CF_3$, —$OCF_2H$, —$OCF_3$, —CN, $(C_1-C_6)$alkyl, or $(C_1-C_6)$alkyloxy;

or a stereoisomer, tautomer, or pharmaceutically acceptable salt thereof.

In another aspect, the invention is directed to a compound of formula Ic wherein:

$R^2$ is phenyl, pyridyl, pyrimidinyl, pyridazinyl, or pyrazinyl, substituted with one or more $R^4$;

$R^4$ is fluoro, chloro, $CF_3$, —$OCF_2H$, —$OCF_3$, —CN or —$NO_2$;

or a stereoisomer, tautomer, or pharmaceutically acceptable salt thereof.

In another aspect, the invention is directed to a compound of formula Ic wherein:

$R^2$ is phenyl, pyridyl, pyrimidinyl, pyridazinyl, or pyrazinyl, substituted with one or more $R^4$, $R^4$ is tetrazole, oxadiazole, oxazole, pyrazole or isoxazole optionally substituted with one or more $R^5$; and $R^5$ is halogen, —OH, —$CF_3$, —$OCF_2H$, —$OCF_3$, —CN, methyl, ethyl, cyclopropyl, methoxy, ethoxy or cyclopropyloxy;

or a stereoisomer, tautomer, or pharmaceutically acceptable salt thereof.

In another aspect, the invention is directed to a compound of formula Ic wherein: B is oxazole.

In another aspect, the invention is directed to a compound of formula Ic wherein B is pyridine.

In another aspect, the invention is directed to a compound of formula I wherein A is piperidinyl, $R^6$ is hydrogen or methyl, $R^2$ is phenyl, pyridyl or pyrimidinyl, $R^4$ is $CF_3$, B is oxazole, $R^1$ is phenyl and $R^3$ is $CONH_2$, CONH-cyclopropyl, $CONHCH_3$, $NHCOOCH_3$ or $NHCOOCH_2CH_3$.

In another aspect, the invention provides a compound selected from those exemplified or a stereoisomer, tautomer, or pharmaceutically acceptable salt thereof.

II. Other Embodiments of the Invention

In another embodiment, the present invention provides a composition comprising one or more of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and one or more of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of one or more of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention methods provides a pharmaceutical composition for treating diabetes, especially Type II diabetes, which includes the step of administering a therapeutically effective amount of at least one compound according to Formula I alone or in combination with one or more additional anti-diabetic agents to a patient in need of such treatment, wherein the anti-diabetic agent is described herein.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example, an agent selected from saxagliptin, sitagliptin, vildagliptin and alogliptin).

In another embodiment, the present invention provides a pharmaceutical composition further comprising additional therapeutic agent(s). In a preferred embodiment, the present invention provides pharmaceutical composition, wherein the additional therapeutic agent is, for example, a sodium glucose transport (SGLT) inhibitor (for example, dapagliflozin).

In another embodiment, the present invention provides a method for the treatment and/or prophylaxis of multiple diseases or disorders that have been associated to be treated through the modulation of the NPY Y4 receptor comprising administering to a patient in need of such treatment and/or prophylaxis a therapeutically effective amount of one or more of the compounds of the present invention, alone, or, optionally, in combination with another compound of the present invention and/or one or more other type of therapeutic agent.

Examples of diseases or disorders that have been associated to be treated through the modulation of the NPY Y4 receptor according to the present invention include, but are not limited to, gastric motility, obesity and being overweight and conditions in which obesity and being overweight are considered contributory factors. These include bulimia, bulimia nervosa, Syndrome X (Metabolic Syndrome), diabetes, type 2 diabetes mellitus or Non Insulin Dependent Diabetes Mellitus (NIDDM), hyperglycemia, impaired glucose tolerance, insulin resistance, cardiovascular disease, hypertension, atherosclerosis, coronary artery disease, myocardial infarction, peripheral vascular disease, stroke, thromboembolic diseases, hyperlipidemia, hypercholesterolemia, gall bladder disease, osteoarthritis, sleep apnea, reproductive disorders such as polycystic ovarian syndrome, or cancer of the breast, prostate or colon.

In another embodiment, the present invention provides a method for the treatment and/or prophylaxis of obesity, appetite control, food intake, energy expenditure, caloric intake, diabetes, hyperglycemia, gestational diabetes, dyslipidemia, hypertension and cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent. Preferably, the second therapeutic agent is an anti-obesity, or an anti-diabetic agent.

In another embodiment, the invention provides a method for decreasing motility of the upper GI tract, e.g., decreasing gastric emptying.

In another embodiment, the present invention provides a compound of the present invention for use in therapy.

In another embodiment, the present invention provides a compound of the present invention for use in therapy for the treatment and/or prophylaxis of multiple diseases or disorders that have been associated to be treated through the modulation of the NPY Y4 receptor.

In another embodiment, the present invention also provides the use of a compound of the present invention for the manufacture of a medicament for the treatment and/or prophylaxis of multiple diseases or disorders that have been associated to be treated through the modulation of the NPY Y4 receptor.

In another embodiment, the present invention provides a method for the treatment and/or prophylaxis of multiple diseases or disorders that have been associated to be treated through the modulation of the NPY Y4 receptor, comprising: administering to a patient in need thereof a therapeutically effective amount of a first and second therapeutic agent, wherein the first therapeutic agent is a compound of the present invention. Preferably, the second therapeutic agent is, for example, dipeptidyl peptidase-IV (DPP4) inhibitor (for example, an agent selected from saxagliptin, sitagliptin, vildagliptin and alogliptin).

In another embodiment, the present invention provides a method for the treatment and/or prophylaxis of multiple diseases or disorders that have been associated to be treated through the modulation of the NPY Y4 receptor, comprising: administering to a patient in need thereof a therapeutically effective amount of a first and second therapeutic agent, wherein the first therapeutic agent is a compound of the present invention. Preferably, the second therapeutic agent is, for example, a sodium glucose transport (SGLT) inhibitor (for example, dapagliflozin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders that have been associated to be treated through the modulation of the NPY Y4 receptor.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Definitions

The following are definitions of terms that may be used in the present specification. The initial definition provided for a group or term herein applies to that group or term throughout the present specification individually or as part of another group, unless otherwise indicated.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" refers to straight or branched chain unsubstituted hydrocarbon groups of 1 to 20 carbon atoms, preferably 1 to 6 carbon atoms. The expression "lower alkyl" refers to unsubstituted alkyl groups of 1 to 4 carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g., $SO_2NH_2$, substituted sulfonamido, nitro, cyano, carboxy, carbamyl, e.g., $CONH_2$, substituted carbamyl e.g., CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "halogen" or "halo" refers to fluorine, chlorine, bromine and iodine.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and terahydronaphthyl. The fused aryls may be connected to another group either at a suitable position on the cycloalkyl ring or the aromatic ring. For example:

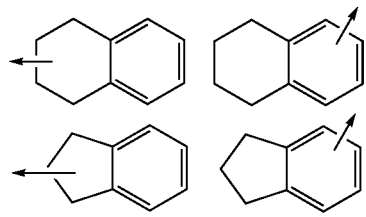

Arrowed lines drawn from the ring system indicate that the bond may be attached to any of the suitable ring atoms.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g., imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, bicycloheptane, bicyclooctane and adamantyl. Exemplary substituents include one or more alkyl groups as described above, or one or more groups described above as alkyl substituents.

The term "benzyl," as used herein, refers to a methyl group on which one of the hydrogen atoms is replaced by a phenyl group, wherein said phenyl group may optionally be substituted with 1 to 5 groups, preferably 1 to 3 groups, OH, OCH$_3$, Cl, F, Br, I, CN, NO$_2$, NH$_2$, N(CH$_3$)H, N(CH$_3$)$_2$, CF$_3$, OCF$_3$, C(=O)CH$_3$, SCH$_3$, S(=O)CH$_3$, S(=O)$_2$CH$_3$, CH$_3$, CH$_2$CH$_3$, CO$_2$H, and CO$_2$CH$_3$.

As used herein, the term "heterocyclo", "heterocyclyl" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl. Examples of heterocycles include, but are not limited to, azetidinyl, pyrrolinyl, piperidinyl, piperazinyl, tetrahydrofuranyl, morpholinyl, dihydropyrrazolyl, dihydro-isoxazolyl. Also included are fused ring and spiro compounds containing, for example, the above heterocycles.

As used herein, the term "heteroaryl", is intended to mean a stable, 5-, 6-, or 7-membered monocyclic or bicyclic or 7-, 8-, 9-, 10-, 11-, 12-, 13-, or 14-membered polycyclic heteroaryl ring that is fully unsaturated, and that contains carbon atoms and 1, 2, 3 or 4 heteroatoms independently selected from the group consisting of N, O and S; and including any polycyclic group in which any of the above-defined heteroaryl rings is fused to a benzene ring or a heterocyclyl ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heteroaryl ring may be attached to its pendant group at any heteroatom or carbon atom that results in a stable structure. The heteroaryl rings described herein may be substituted on carbon or on a nitrogen atom if the resulting compound is stable. A nitrogen in the heteroaryl may optionally be quaternized. Examples of heteroaryls include, but are not limited to, pyridinyl, pyrimidinyl, pyrazinyl, pyridazinyl, furanyl, thienyl, pyrrolyl, pyrazolyl, imidazolyl, indolyl, tetrazolyl, isoxazolyl, oxazolyl, oxadiazolyl, thiadiazolyl, thiazolyl, benzimidazolyl, 1H-indazolyl, benzofuranyl, benzothiofuranyl, benztetrazolyl, benzotriazolyl, benzisoxazolyl, benzoxazolyl, isoquinolinyl, isoxazolopyridinyl, quinazolinyl, quinolinyl, isothiazolopyridinyl, thiazolopyridinyl, oxazolopyridinyl, imidazopyridinyl, and pyrazolopyridinyl.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzene ring, each fused to a second ring. The second ring is a 5- or 6-membered monocyclic ring which is saturated, partially unsaturated, or unsaturated, and comprises a 5-membered heterocycle; a 6-membered heterocycle or a carbocycle (provided the first ring is not benzene when the second ring is a carbocycle). The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of bicyclic heterocyclic groups are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydroquinazolinyl.

As used herein, the term "azabicycloalkyl" is intended to mean a stable bicyclic hydrocarbon that includes one nitrogen and optionally another heteroatom chosen from the group of N, O, S. The two fused rings are connected at non adjacent atoms.

Examples of azabicycloalkyl groups are, but not limited to, 2-azabicyclo[2.2.1]heptane, 2-azabicyclo[2.2.2]octane, 2-azabicyclo[3.1.1]heptane, 6-azabicyclo[3.1.1]heptane, 8-azabicyclo[3.2.1]octane, 6-azabicyclo[3.2.1]octane, 1,4-diazabicyclo[3.2.1]octane, 6-azabicyclo[3.2.2]nonane.

The term "heteroatoms" shall include oxygen, sulfur and nitrogen.

The term "alkylsulfone" refers to —R$^k$S(=O)$_2$R$^k$, wherein R$^k$ is an alkyl or substituted alkyl.

The term "oxo" refers to the divalent radical =O.

The term "carbamate" refers to the group —OC(=O)NH$_2$.

The term "amide" refers to the group —C(=O)NH$_2$.

The term "sulfonamide" refers to the group —SO$_2$NH$_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —C(=O)NR$^m$R$^n$ wherein R$^m$ and R$^n$ are independently selected from H, alkyl, substituted alkyl, alkenyl, substituted alkenyl, cycloalkyl, and substituted cycloalkyl, provided at least one of R$^m$ or R$^n$ is a substituted moiety.

A substituted sulfonamide, for example, refers to the group —SO$_2$NR$^o$R$^p$ wherein R$^o$ and R$^p$ are independently selected from alkyl, substituted alkyl, alkenyl, substituted alkenyl, cycloalkyl, and substituted cycloalkyl, provided at least one of R$^o$ or R$^p$ is a substituted moiety.

A substituted carbamate, for example, refers to the group —OC(=O)NR$^q$R$^r$ wherein R$^q$ and R$^r$ are independently selected from alkyl, substituted alkyl, alkenyl, substituted alkenyl, cycloalkyl, and substituted cycloalkyl, provided at least one of R$^q$ or R$^r$ is a substituted moiety.

The term "ureido" refers to the group —NHC(=O)NH$_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —N(O)$_2$.

The term "thio" refers to the group —SH.

The term "alkylthio" refers to the group —SR$^s$ where R$^s$ is an alkyl, substituted alkyl, cycloalkyl, or substituted cycloalkyl.

The term "thioalkyl" refers to the group —R$^t$S where R$^t$ is an alkyl, substituted alkyl, cycloalkyl, or substituted cycloalkyl.

The term "alkylsulfonyl" refers to the group —S(=O)$_2$R$^u$ where R$^u$ is an alkyl, substituted alkyl, cycloalkyl, or substituted cycloalkyl.

The term "alkylsulfinyl" refers to the group —S(=O)R$^v$ where R$^v$ is an alkyl, substituted alkyl, cycloalkyl, or substituted cycloalkyl.

The term "carboxy" refers to the group —C(=O)OH.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —C(=O)OR$^w$ where R$^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —OC(=O)R$^x$, where R$^x$ is an alkyl or substituted alkyl, or an aryl or substituted aryl, respectively.

The term "carbamoyl" refers to the groups —OC(=O)NH$_2$, —OC(=O)NHR$^x$, and/or —OC(=O)NR$^y$R$^z$, wherein R$^y$ and R$^z$ are independently selected from alkyl and substituted alkyl.

The term "carbonyl" refers to a C(=O).

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group S(=O)$_2$.

The term "sulfinyl" refers to an S(=O).

The term "carboxyalkyl" refers to an alkyl or substituted alkyl bonded to a carboxy.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, Bundgaard, H., ed., Elsevier (1985), and *Methods in Enzymology,* 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

The present invention is intended to include all isotopes of atoms occurring in the present compounds. Isotopes include those atoms having the same atomic number but different mass numbers. By way of general example and without limitation, isotopes of hydrogen include deuterium and tritium.

Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that there presently recited compounds do not contain a N-halo, $S(O)_2H$, or $S(O)H$ group.

The term "modulator" refers to a compound that acts at the NPY Y4 receptor to alter its ability to regulate downstream signaling events. Examples of receptor modulators include agonists, antagonists, partial agonists, inverse agonists, allosteric antagonists and allosteric potentiators as defined in standard pharmacology textbooks (e.g., Ross, E. M. et al. in *Goodman and Gilman's The Pharmacological Basis of Therapeutics*, 10th Edition, Chapter 2, pp. 31-43, McGraw Hill (2001)).

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition, Mack Publishing Company, Easton, Pa. (1985), which is incorporated herein by reference in its entirety.

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, impaired glucose hemostasis, insulin resistance, hypercholesterolemia, hypertriglyceridemia, choletithiasis, dislipidemic conditions, bulimia nervosa and compulsive eating disorders); gastrointestinal disorders and inflammatory diseases such as inflammatory bowel disease, colitis and/or Crohn's disease.

Dosage Forms

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope pharmaceutical compositions comprising a therapeutically effective amount of at least one of the compounds of Formula I, together with a pharmaceutically acceptable carrier or diluent. Compounds of the present invention can be used alone or in pharmaceutical combinations comprising other suitable therapeutic agents useful in the treatment of the aforementioned disorders including anti-obesity agents, anti-diabetic agents, appetite suppressants, lipid-lowering agents, HDL-raising agents, cognition enhancing agents, agents used to treat neurodegeneration, agents used to treat bowel disorders, anti-inflammatory agents, anti-anxiety agents, and anti-depressants.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the NPY Y4 receptor agonist in accordance with the invention.

Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, DPP4 inhibitors, triple monoamine reuptake inhibitors, CCK agonists, GLP-1 agonists, and other Pre-proglucagon-derived peptides; NPY1 or NPY5 antagonist, NPY2 modulators, MCHR1 antagonists, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adiponectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

Examples of suitable anti-diabetic agents for use in combination with the compounds of the present invention include: oral antihyperglycemic agents, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glucokinase inhibitors, glycogen phosphorylase inhibitors, and/or meglitinides, as well as insulin, and/or glucagon-like peptide-1 (GLP-1), GLP-1 agonist, a PTP-1B inhibitor (protein tyrosine phosphatase-1B inhibitor), and/o a histone deacetylase modulator such as a SIRT1 activator.

The compounds of the present invention may be employed in combination with anti-hyperlipidemia agents, or agents used to treat arteriosclerosis. An example of an hypolipidemic agent would be a fibric acid derivatives, bile acid sequestrants, nicotinic acid, aspirin, poly(diallylmethylamine) derivatives, quaternary amine poly(diallyldimethylammonium chloride) and ionenes and other known serum cholesterol lowering agents. Hypolipidemic agents include ACAT inhibitors, an upregulator of LDL receptor activity, and cholesterol absorption inhibitors.

Lipid agent or lipid-modulating agents include cholesteryl transfer protein inhibitors (CETP) The hypolipidemic agent may be an ileal $Na^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compounds, a beta-lactam cholesterol absorption inhibitor, a PPAR α-agonist and/or an FXR agonist; an LDL catabolism promoter, a sodium-proton exchange inhibitor; an LDL-receptor inducer or a steroidal glycoside; an anti-oxidant, an antihomocysteine agent, a cholesterol absorption inhibitor, an HMG-CoA synthase inhibitor, or a lanosterol demethylase inhibitor, a sterol regulating element binding protein-I (SREBP-1).

Biological Data

NPY4 cAMP HTRF Agonist Assay

The functionality of the compound at Y4 receptor was analyzed using a inhibitory cAMP assay (CISBIO, HTRF cAMP kit #62AM4PEC) to measure the Gi activation by Y4 agonism.

The human Y4 stable CHO clonal cells were maintained in culture medium (F-12 containing 10% Fetal Bovine Serum, 50 mg/ml GENETICIN®, 100 mg/ml Zeocin). Before the experiment, 5 μL of 1 uM Forskolin (Sigma, # F6886) and 100 uM IBMX (Sigma, # I5879) in PBS buffer were added into 384-well plates (PE, Proxi-plate) that were pre-dotted with 100 nL compounds. The cells were removed from the flasks by Cellstripper, counted and adjusted to $1.0×10^6$ cells/mL in PBS buffer, and added 5 μL/well (5000 cells/well) into the above 384-well plates. The cells were then covered and incubated for 30 minutes at room temperature. After incubation, 5 μL/well of D2-conjugate in HTRF lysis buffer was first added, followed by adding 5 μL/well of anti-cAMP Cryptate in HTRF lysis buffer. The plates were incubated for another 1 hour at room temperature and read on the EnVision Multilabel Plate Reader.

Compounds described herein were tested in the above assay. The following results were obtained.

TABLE 1

| NPY4 cAMP HTRF Agonist Assay EC50 (nM) | |
|---|---|
| Example No. | EC50 (nM) |
| Example 1 | 6 |
| Example 2 | 3 |
| Example 3 | 69 |
| Example 4 | 236 |
| Example 5 | 9 |
| Example 6 | 6 |
| Example 7 | 185 |
| Example 8 | 16 |
| Example 9 | 4 |
| Example 10 | 26 |
| Example 11 | 49 |
| Example 12 | 1 |
| Example 13 | 3 |
| Example 14 | 920 |
| Example 15 | 8 |
| Example 16 | 6 |
| Example 17 | 911 |
| Example 18 | 7 |
| Example 19 | 23 |
| Example 20 | 10 |
| Example 21 | 11 |
| Example 22 | 43 |
| Example 23 | 71 |
| Example 24 | 69 |
| Example 25 | 14 |
| Example 26 | 8 |
| Example 27 | 60 |
| Example 28 | 217 |
| Example 29 | 389 |
| Example 30 | 203 |
| Example 31 | 241 |
| Example 32 | 60 |
| Example 33 | 322 |
| Example 34 | 150 |
| Example 35 | 42 |
| Example 36 | 262 |
| Example 37 | 82 |
| Example 38 | 8 |
| Example 39 | 35 |
| Example 40 | 29 |
| Example 41 | 2511 |
| Example 42 | 45 |
| Example 43 | 18 |
| Example 44 | 50 |
| Example 45 | 19 |
| Example 46 | 208 |
| Example 47 | 34 |
| Example 48 | 6 |
| Example 49 | 2 |
| Example 50 | 231 |
| Example 51 | 548 |
| Example 52 | 193 |
| Example 53 | 95 |
| Example 54 | 272 |
| Example 55 | 463 |
| Example 56 | 23 |
| Example 57 | 25 |
| Example 58 | 1169 |
| Example 59 | 297 |
| Example 60 | 500 |
| Example 61 | 861 |
| Example 62 | 61 |
| Example 63 | 174 |
| Example 64 | 89 |
| Example 65 | 62 |
| Example 66 | 1259 |
| Example 67 | 57 |
| Example 68 | 489 |
| Example 69 | 384 |
| Example 70 | 799 |
| Example 71 | 45 |
| Example 72 | 15 |
| Example 73 | 83 |
| Example 74 | 420 |
| Example 75 | 252 |
| Example 76 | 21 |

TABLE 1-continued

NPY4 cAMP HTRF Agonist Assay EC50 (nM)

| Example No. | EC50 (nM) |
| --- | --- |
| Example 77 | 34 |
| Example 78 | 75 |
| Example 79 | 83 |
| Example 80 | 242 |
| Example 81 | 41 |
| Example 82 | 107 |
| Example 83 | 9 |
| Example 84 | 9 |
| Example 85 | 145 |
| Example 86 | 91 |
| Example 87 | 185 |
| Example 88 | 704 |
| Example 89 | 58 |
| Example 90 | 132 |
| Example 91 | 288 |
| Example 92 | 469 |
| Example 93 | 33 |
| Example 94 | 210 |
| Example 95 | 10 |
| Example 96 | 1 |
| Example 97 | 6 |
| Example 98 | 0.7 |
| Example 99 | 0.8 |
| Example 100 | 3 |
| Example 101 | 2 |
| Example 102 | 0.4 |
| Example 103 | 3 |
| Example 104 | 0.2 |
| Example 105 | 0.2 |
| Example 106 | 0.3 |
| Example 107 | 4 |
| Example 108 | 21 |
| Example 109 | 119 |
| Example 110 | 515 |
| Example 111 | 562 |
| Example 112 | 590 |
| Example 113 | 91 |
| Example 114 | 70 |

III. Methods of Preparation

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "(β", "R", "S", "E", and "Z" are stereochemical designations familiar to one skilled in the art.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

SYNTHESIS

General Synthetic Schemes

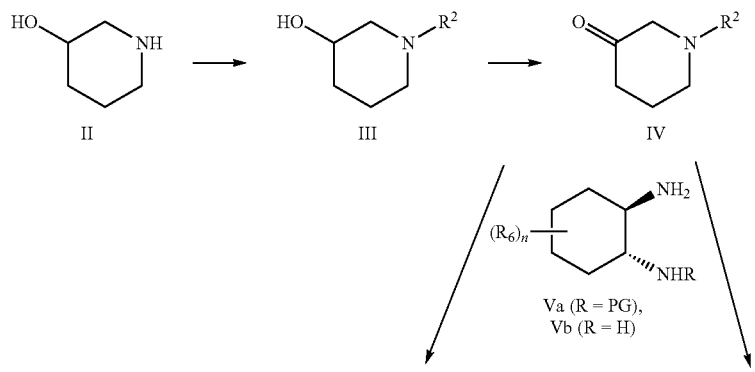

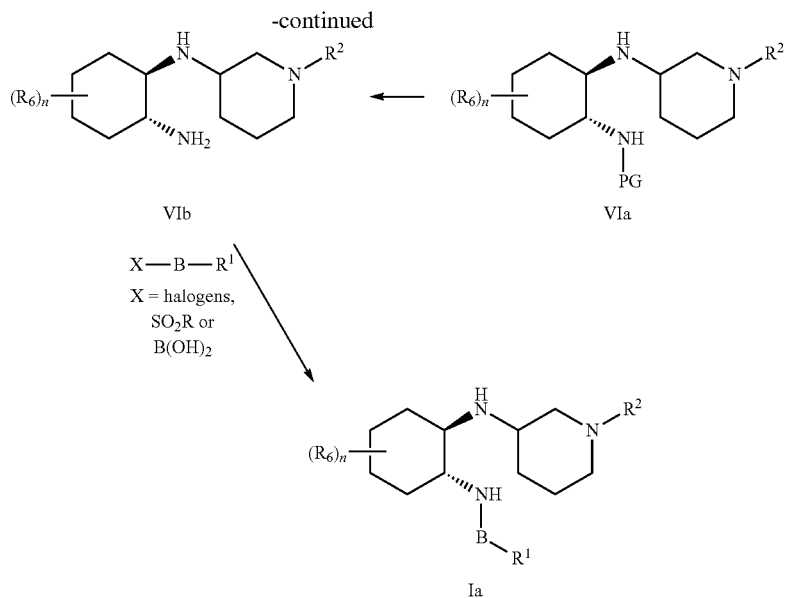

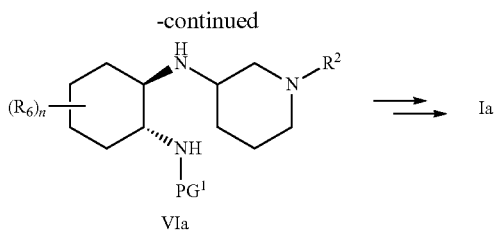

Compounds of formula Ia can be synthesized as outlined in Scheme 1. Intermediate III can be prepared by reaction of 3-hydroxypiperidine II with halides or boronic acids of aryl or heteroarl compounds by known methods in the literature. Oxidation of alcohol III, for example by Swern oxidation or sulfer trioxide pyridine complex in DMSO, generates ketone IV. Reaction of ketone IV with mono-protected diamine Va under reductive amination conditions affords VIa as a diastereomeric mixture. Removal of the protecting group of VIa gives amine VIb. Intermediate VIb can also be prepared by reductive amination of ketone IV directly with diamine Vb. Reaction of amine VIb with X—B—$R^1$ either by nucleophilic displacement (X=halogens or sulfones) or by Chan-Lam coupling (X=boronic acids) affords compounds of formula Ia. Single diastereomers can be obtained by chiral HPLC separation either at intermediate stage (VIa or VIb) or of final products Ia.

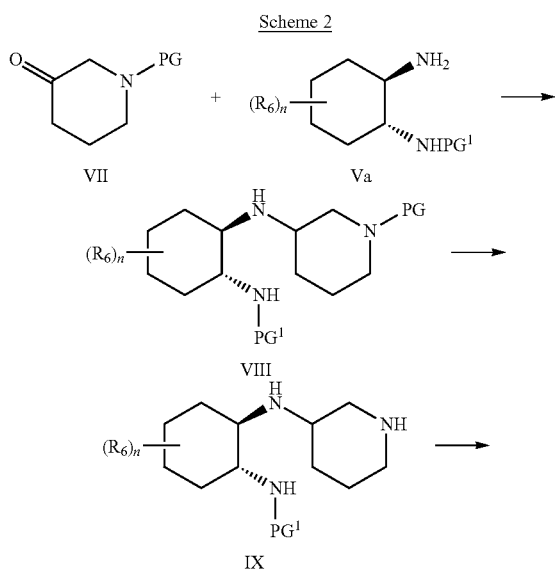

Alternatively, compounds of formula Ia can be prepared by a different sequence oulined in Scheme 2. Reaction of N-protected piperidin-3-one VII with mono-protected amine Va under reductive amination conditions affords intermadiate VIII as a diastereomeric mixture. Selective removal of the piperidine protecting group (i.e., PG=Cbz) of VIII by catalytic hydrogenolysis gives IX. Reaction of IX with halides or boronic acids of aryl or heteroarl compounds by known methods in the literature affords intermediate VIa, which can be used to synthesize compounds of formula Ia by following the reactions outlined in Scheme 1.

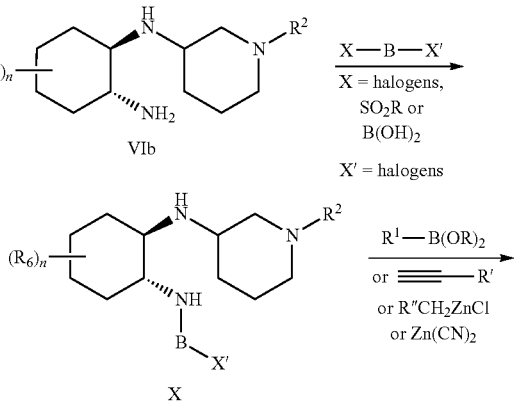

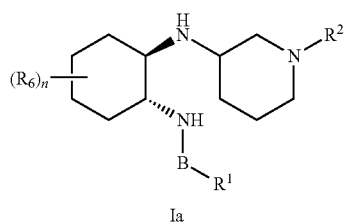

Ia

Compounds of formula Ia can also be synthesized from intermediate VIb as outlined in Scheme 3. Reaction of VIb with X—B—X' by either nucleophilic displacement (X=halogens or sulfones) or by Chan-Lam coupling (X=boronic acids) affords intermediate X. Compounds of formula Ia can be prepared by reaction of intermediate X with a boronic acid or a boronic ester ($R1B(OR)_2$) under palladium mediated cross coupling conditions, or with an alkyne under copper/palladium mediated coupling conditions, or with an organozinc reagent such as $R''CH_2ZnCl$ under Nigishi coupling conditions, or with $Zn(CN)_2$ under palladium catalyzed coupling conditions.

Scheme 4

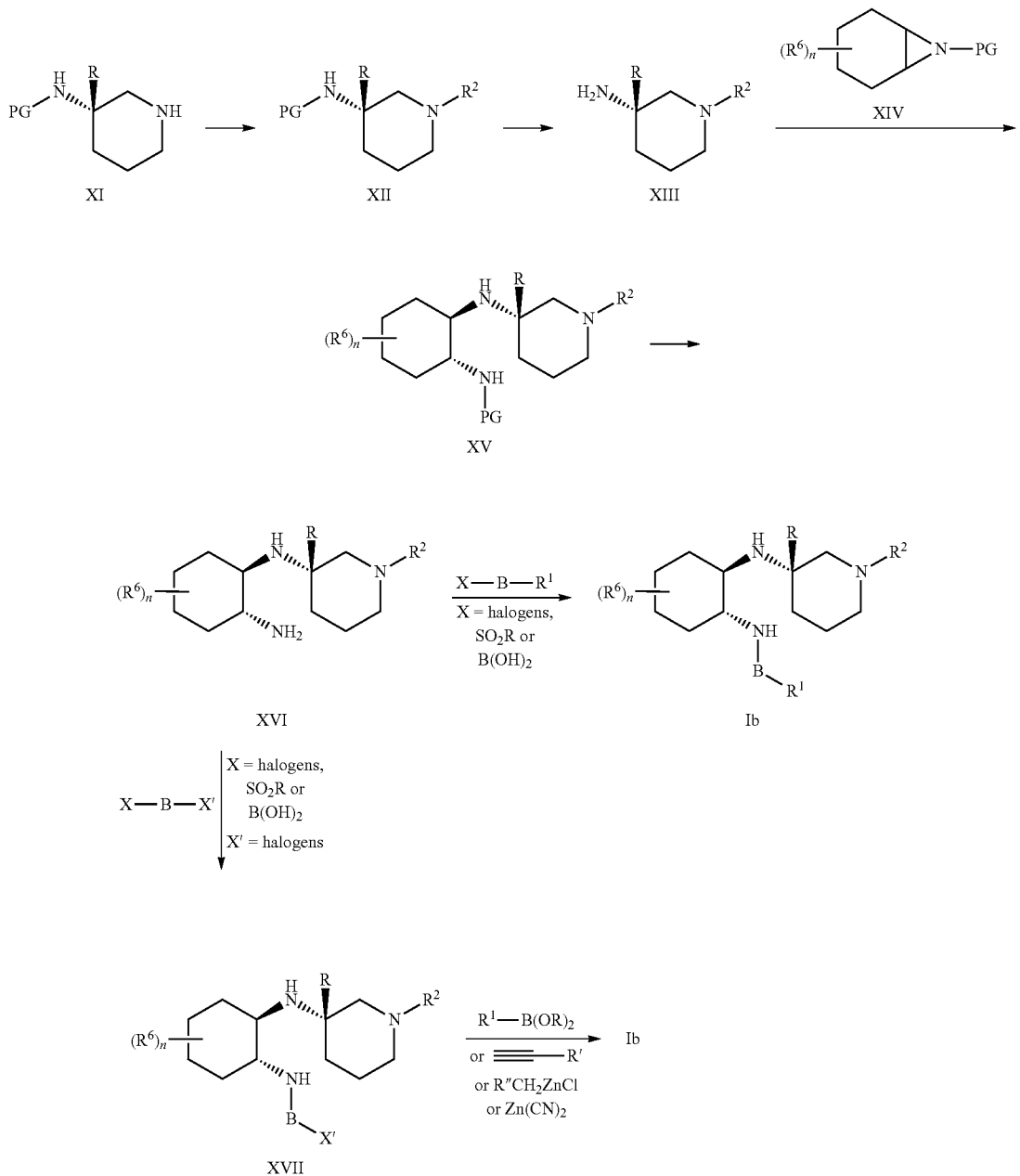

Compounds of formula Ib can be synthesized as outlined in Scheme 4. Intermediate XII can be prepared by reaction of XI with halides or boronic acids of aryl or heteroarl compounds by known methods in the literature. Removal of the protecting group of XII gives amine XIII, which can be reacted with aziridine derivatives XIV in a aprotic solvent, optionally in the presence of a catalytic amount of a lithium salt (such as $LiClO_4$ or N-lithiotrifluoromethanesulfonimide). The desired diastereoisomer XV can be separated by silica gel chromatography or chiral HPLC. Removal of the protecting group of XV gives amine XVI, which can be reacted with X—B—$R^1$ either by nucleophilic displacement (X=halogens or sulfones) or by Chan-Lam coupling (X=boronic acids) to afford compounds of formula Ib. Reaction of amine XVI with X—B—X' by either nucleophilic displacement (X=halogens or sulfones) or by Chan-Lam coupling (X=boronic acids) affords intermediate XVII. Compounds of formula Ib can be prepared by reaction of intermediate XVII with a boronic acid or a boronic ester ($R^1B(OR)_2$) under palladium mediated cross coupling conditions, or with an alkyne under copper/palladium mediated coupling conditions, or with an organozinc reagent such as R"$CH_2ZnCl$ under Nigishi coupling conditions, or with $Zn(CN)_2$ under palladium catalyzed coupling conditions.

Compounds of formula Ic can be synthesized as outlined in Scheme 5. Intermediate XIX can be prepared by reaction of XVIII with halides or boronic acids of aryl or heteroarl compounds by known methods in the literature. Oxidation of alcohol XIX, for example by Swern oxidation or sulfer trioxide pyridine complex in DMSO, generates ketone XX. Reaction of ketone XX with mono-protected diamine Va under reductive amination conditions affords XXIa. Removal of the protecting group of XXIa gives amine XXIb. Intermediate XXIb can also be obtained by reductive amination of ketone XX directly with diamine Vb. Reaction of amine XXIb with X—B—$R^1$ either by nucleophilic displacement (X=halogens or sulfones) or by Chan-Lam coupling (X=boronic acids) affords compounds of formula Ic. Reaction of amine XXIb with X—B—X' by either nucleophilic displacement (X=halogens or sulfones) or by Chan-Lam coupling (X=boronic acids) affords intermediate XXII. Compounds of formula Ic can be prepared by reaction of intermediate XXII with a boronic acid or a boronic ester ($R^1B(OR)_2$) under palladium mediated coupling conditions, or with an alkyne under copper/palladium mediated coupling conditions, or with an organozinc reagent such as R"$CH_2ZnCl$ under Nigishi coupling conditions, or with $Zn(CN)_2$ under palladium catalyzed coupling conditions.

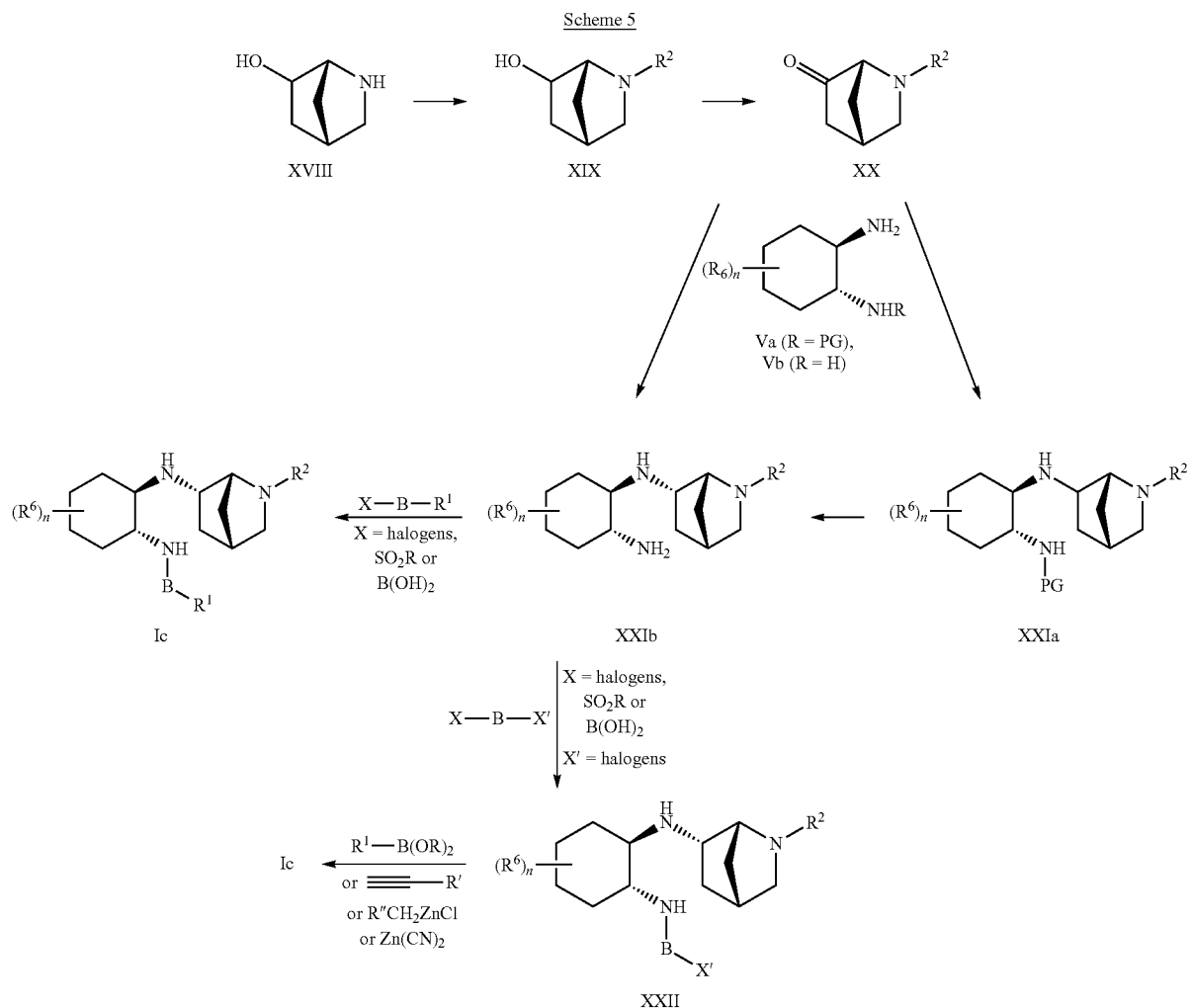

Scheme 5

Scheme 6

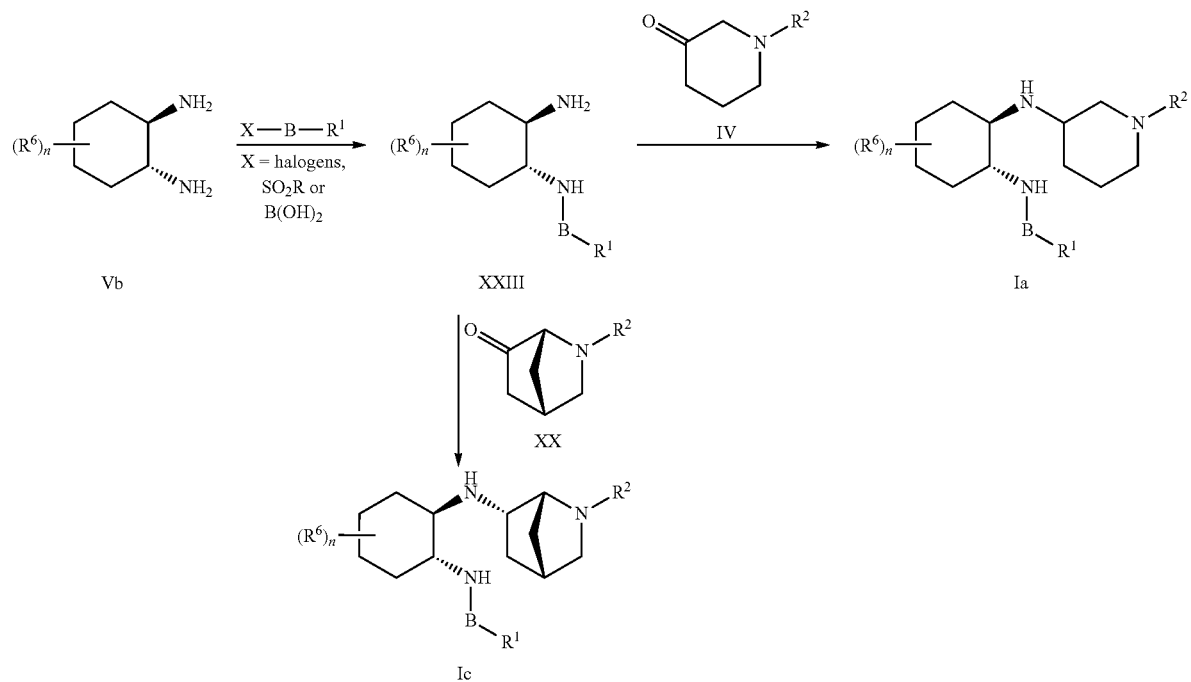

Alternatively, compounds of formula Ia and Ic can be prepared by a different sequence oulined in Scheme 6. Reaction of diamine Vb with X—B—R¹ either by nucleophilic displacement (X=halogens or sulfones) or by Chan-Lam coupling (X=boronic acids) affords intermediate XXIII. Compounds of formula Ia can be obtained by reductive amination of XXIII with ketone IV. In a similar fashion, Compounds of formula Ic can be obtained by reductive amination of XXIII with ketone XX. Single diastereomers can be obtained by chiral HPLC separation of final products (Ia or Ic).

Compounds of formula Ia² can be prepared as oulined in Scheme 7. Reaction of Ia¹ with a boronic acid or a boronic ester under palladium mediated cross coupling conditions affords compounds of formula Ia². Single diastereomers can be obtained by chiral HPLC separation of final products Ia².

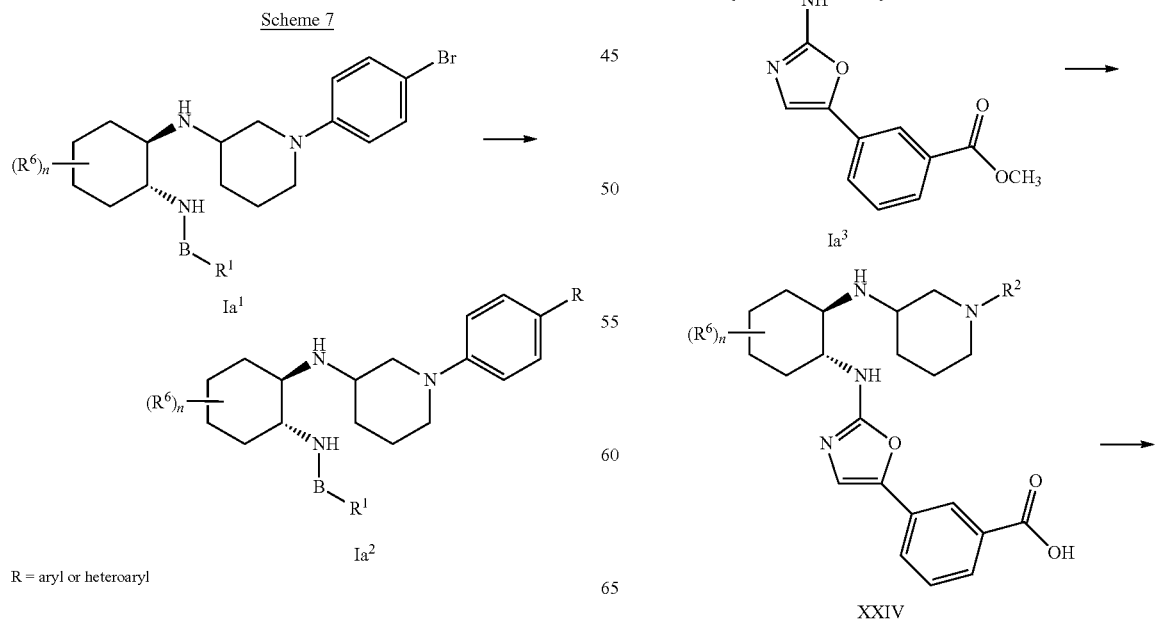

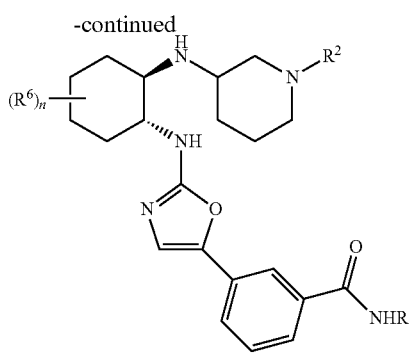

Ia⁴

R = H or alkyl

Compounds of formula Ia⁴ can be prepared as oulined in Scheme 8. Hydrolysis of ester Ia³ generates acid XXIV. Compounds of formula Ia⁴ can be synthesized by standard amide formation reactions of acid XXIV with ammonia or an amine Single diastereomers can be obtained by chiral HPLC separation of intermediate XXIV or final products Ia⁴.

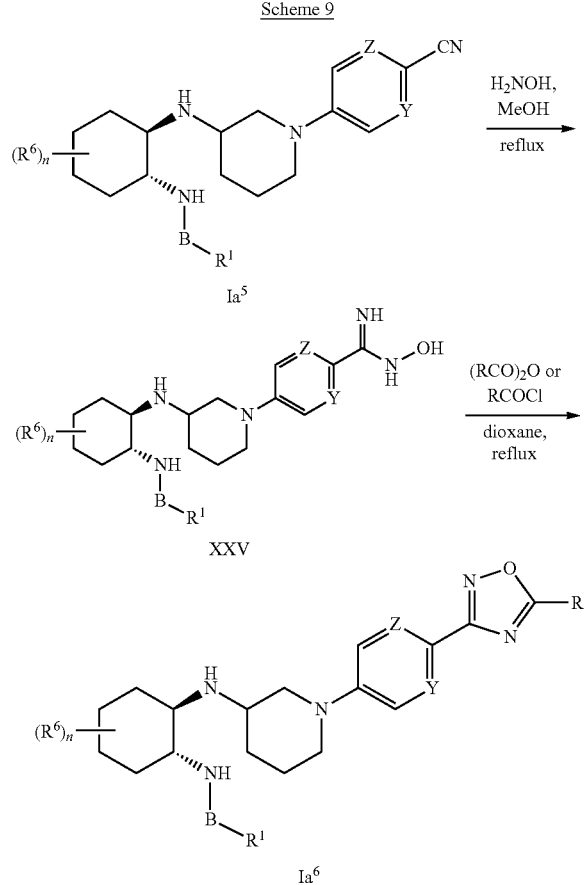

Y = Z = CH or
Y = Z = N or
Y = CH, Z = N

R = H or alkyl

Compounds of formula Ia⁶ can be prepared as oulined in Scheme 9. Reaction of Ia⁵ with hydroxyamine in a protic solvent such as methanol at elevated temperature affords intermediate XXV. Compounds of formula Ia⁶ can be obtained by reaction of XXV with an anhydride or an acylchloride at elevated temperature. Single diastereomers can be obtained by chiral HPLC separation of final products Ia⁶.

It is understood that during the course of manipulating any functional group within the various R groups of compounds of Formula I or at any stage of their synthesis, standard protecting groups, as described in Protective Groups in Organic Synthesis (4$^{th}$ Edition, P. G. M. Wuts and T. W. Greene, pub. Wiley, 2006), may be employed to avoid undesired reactions of any other functional group.

| | Abbreviations |
|---|---|
| $CH_2Cl_2$ | methylene chloride |
| DMF | dimethyl formamide |
| DMSO | dimethyl sulfoxide |
| EDC | 1-[3-(dimethylamino)propyl]-3-ethylcarbodiimide hydrochloride |
| eq | equivalent |
| $Et_3N$ | triethyl amine |
| EtOAc | ethyl acetate |
| HCl | hydrogen chloride |
| Hex | hexanes |
| HOAc | acetic acid |
| HOBT | 1-hydroxybenzotriazole hydrate |
| HPLC | high performance liquid chromatography |
| ISCO | automated chromatographic purification system |
| $K_2CO_3$ | potassium carbonate |
| MeOH | methanol |
| $MgSO_4$ | magnesium sulfate |
| mmol | millimole |
| min | minute |
| $Na_2SO_4$ | sodium sulfate |
| NaCl | sodium chloride |
| $NaHCO_3$ | sodium bicarbonate |
| $NH_3$ | ammonia |
| PG | Protecting group (*) |
| RP | reverse phase |
| rt | room temperature |
| TFA | trifluoroacetic acid |
| THF | tetrahydrofuran |

(*) - Any standard protecting group known to those skilled in the art - see Protective Groups in Organic Synthesis (4$^{th}$ Edition, P.G.M. Wuts and T.W. Greene, pub. Wiley, 2006)

Preparatory HPLC Method A was performed on a Shimadzu SCL-10A liquid chromatograph with a linear gradient of 20-100% Solvent B over 10 or 30 minutes, with either a 2 or 5 minutes (respectively) hold at 100% Solvent B;

UV visualization at 220 nm;

Column: Axia Luna 5u C18 30×100 mm;

Flow rate: 20 mL/min;

Solvent A: 10% MeOH, 90% Water, 0.1% Trifluoroacetic Acid; and

Solvent B: 90% MeOH, 10% Water, 0.1% Trifluoroacetic Acid.

Preparatory HPLC Method B was performed on a Shimadzu SCL-10A liquid chromatograph with a linear gradient of 10-100% Solvent B over 15 minutes, with a 5 minutes hold at 100% Solvent B;

UV visualization at 220 nm;

Column: Sunfire 5u C18 19×100 mm;

Flow rate: 14 mL/min;

Solvent A: 10% Acetonitrile, 90% Water, 0.1% Trifluoroacetic Acid; and

Solvent B: 90% Acetonitrile, 10% Water, 0.1% Trifluoroacetic Acid.

Preparatory HPLC Method C was performed on a Shimadzu SCL-10A liquid chromatograph with a linear gradient of 10-100% Solvent B over 14 minutes, with a 4 minutes hold at 100% Solvent B;

UV visualization at 220 nm;
Column: Symmetry Shield 7u C18 19×300 mm;
Flow rate: 15 mL/min;
Solvent A: 10% Acetonitrile, 90% Water, 0.1% Trifluoroacetic Acid; and
Solvent B: 90% Acetonitrile, 10% Water, 0.1% Trifluoroacetic Acid.

Preparatory HPLC Method D was performed on a Shimadzu SCL-10A liquid chromatograph with a linear gradient of 10-100% Solvent B over 22 minutes, with a 5 minutes hold at 100% Solvent B;
UV visualization at 220 nm;
Column: X-bridge Phenyl 5u C18 19×250 mm;
Flow rate: 15 mL/min;
Solvent A: 10% Acetonitrile, 90% Water, 20 nM Ammonium acetate in water; and
Solvent B: 90% Acetonitrile, 10% Water, 20 nM Ammonium acetate in water.

Chiral preparatory HPLC method A was performed on a Shimadzu liquid chromatograph:
Column: CHIRALPAK® OJ, 250×20 mm ID, 5 μm
Flow rate: 10 mL/min
Mobile Phase: 5% Ethanol/95% Hex with 0.1% DEA
Detector Wavelength: 254 nm Chiral preparatory HPLC method B was performed on a Berger MGII SFC liquid chromatograph:
Column: CHIRALCEL® OD-H 25×3 cm ID, 5 μm
Flow rate: 60.0 mL/min
Mobile Phase: 85/15 $CO_2$/MeOH-0.1 v/v % DEA
Detector Wavelength: 237 nm
Injection Volume: 200 μL Chiral preparatory HPLC method C was performed on a Berger MGII SFC liquid chromatograph:
Column: CHIRALPAK® AD, 250×30 mm ID, 5 μm
Flow rate: 115 mL/min, 100 Bar, 35 μC
Mobile Phase: 25% Methanol/75% $CO_2$
Detector Wavelength: 230 nm
Injection Volume: 1000 μL Analytical HPLC Method A was performed on a Shimadzu SCL-10A liquid chromatograph with a linear gradient of 0-100% Solvent B over 4 minutes, with a 1 minute hold at 100% Solvent B;
UV visualization at 220 nm;
Column: Phenomenex Luna 3u C18 2.0×50 mm;
Flow rate 0.08 mL/min;
Solvent A: 10% MeOH, 90% Water, 0.1% Trifluoroacetic Acid; and
Solvent B: 90% MeOH, 10% Water, 0.1% Trifluoroacetic Acid.

Analytical HPLC Method B was performed on a Shimadzu SCL-10A liquid chromatograph with a linear gradient of 0-100% Solvent B over 4 minutes, with either a 1 minute hold at 100% Solvent B;
UV visualization at 220 nm;
Column: Phenomenex Luna 3u C18 2.0×50 mm;
Flow rate 0.08 mL/min;
Solvent A: 10% MeOH, 90% Water, 0.2% Phosphoric Acid; and
Solvent B: 90% MeOH, 10% Water, 0.2% Phosphoric Acid.

Analytical HPLC Method C was performed on a Shimadzu SCL-10A liquid chromatograph with a linear gradient of 0-100% Solvent B over 3 minutes, with a 0.75 minute hold at 100% Solvent B;
UV visualization at 220 nm;
Column: Waters Acquity BEH C18 2.1×50 mm; 1.7 um;
Flow rate: 1.11 mL/min;
Solvent A: 10% $CH_3CN$, 90% Water, 0.05% Trifluoroacetic Acid; and
Solvent B: 90% $CH_3CN$, 10% Water, 0.05% Trifluoroacetic Acid.

Analytical HPLC Method D was performed on a Shimadzu SCL-10A liquid chromatograph with a linear gradient of 0-100% Solvent B over 3 minutes, with a 0.75 minute hold at 100% Solvent B;
UV visualization at 220 nm;
Column: Waters Acquity BEH C18 2.1×50 mm; 1.7 um;
Flow rate: 1.11 mL/min;
Solvent A: 10% CH3CN, 90% Water, 10 mM ammonium acetate; and
Solvent B: 90% CH3CN, 10% Water, 10 mM ammonium acetate.

Analytical HPLC Method E was performed on a Shimadzu SCL-10A liquid chromatograph with a linear gradient of 0-100% Solvent B over 12 minutes, with a 3 minute hold at 100% Solvent B;
UV visualization at 220 nm;
Column: Sunfire C18 3.5 um, 3.0×150 mm;
Flow rate: 1 mL/min;
Solvent A: 10% MeOH, 90% Water, 0.05% Trifluoroacetic Acid; and
Solvent B: 90% MeOH, 10% Water, 0.05% Trifluoroacetic Acid.

Analytical HPLC Method F was performed on a Shimadzu SCL-10A liquid chromatograph with a linear gradient of 0-100% Solvent B over 12 minutes, with a 3 minute hold at 100% Solvent B;
UV visualization at 220 nm;
Column: Xbridge Phenyl 3.5 um, 3.0×150 mm;
Flow rate: 1 mL/min;
Solvent A: 10% MeOH, 90% Water, 0.05% Trifluoroacetic Acid; and
Solvent B: 90% MeOH, 10% Water, 0.05% Trifluoroacetic Acid.

Analytical HPLC Method G was performed on a Shimadzu SCL-10A liquid chromatograph with a linear gradient of 0-100% Solvent B over 2 minutes, with a 1 minute hold at 100% Solvent B;
UV visualization at 220 nm;
Column: Phenomenex Luna 3u C18 2.0×50 mm; Flow rate 0.08 mL/min;
Solvent A: 10% MeOH, 90% Water, 0.1% Trifluoroacetic Acid; and
Solvent B: 90% MeOH, 10% Water, 0.1% Trifluoroacetic Acid.

Analytical HPLC Method H was performed on a Shimadzu SCL-10A liquid chromatograph with a linear gradient of 0-100% Solvent B over 8 minutes, with a 1 minute hold at 100% Solvent B;
UV visualization at 220 nm;
Column: Supelco Ascentis Express 2.7 um, 4.6×50 mm;
Flow rate: 2 mL/min;
Solvent A: 5% $CH_3CN$, 95% Water, 10 mM $NH_4OAc$; and
Solvent B: 95% $CH_3CN$, 5% Water, 10 mM $NH_4OAc$.

Analytical HPLC Method I was performed on a Shimadzu SCL-10A liquid chromatograph with a linear gradient of 0-100% Solvent B over 6 minutes, with a 2 minute hold at 100% Solvent B;
UV visualization at 220 nm;
Column: Waters Xbridge 3.5 um, 4.6×50 mm;
Flow rate: 1 mL/min;
Solvent A: Water, 0.1 TFA; and
Solvent B: $CH_3CN$, 5% Water, 0.1 TFA.

Analytical HPLC Method J was performed on a Agilent 1200 series liquid chromatograph with a linear gradient of 10-100% Solvent B over 12 minutes, with a 3 minute hold at 100% Solvent B;
  UV visualization at 220 nm;
  Column: Sunfire 3.5 um, 4.6×150 mm;
  Flow rate: 1 mL/min;
  Solvent A: 5% $CH_3CN$, 95% Water, 0.05% Trifluoroacetic Acid; and
  Solvent B: 95% $CH_3CN$, 5% Water, 0.05% Trifluoroacetic Acid.

Analytical HPLC Method K was performed on a Agilent 1200 series liquid chromatograph with a linear gradient of 0-100% Solvent B over 25 minutes, with a 5 minute hold at 100% Solvent B;
  UV visualization at 220 nm;
  Column: Sunfire 3.5 um, 4.6×150 mm, 4.6×150 mm;
  Flow rate: 1 mL/min;
  Solvent A: 5% $CH_3CN$, 95% Water, 0.05% Trifluoroacetic Acid; and
  Solvent B: 95% $CH_3CN$, 5% Water, 0.05% Trifluoroacetic Acid.

Analytical HPLC Method L was performed on a Shimadzu SCL-10A liquid chromatograph with a linear gradient of 0-100% Solvent B over 2 minutes, with a 1 minute hold at 100% Solvent B;
  UV visualization at 220 nm;
  Column: Phenomenex Luna 3u C18 2.0×30 mm;
  Flow rate: 1 mL/min;
  Solvent A: 10% MeOH, 90% Water, 0.1% Trifluoroacetic Acid; and
  Solvent B: 90% MeOH, 10% Water, 0.1% Trifluoroacetic Acid.

Analytical HPLC Method M was performed on a Agilent 1200 series liquid chromatograph with a linear gradient of 0-100% Solvent B over 12 minutes, with a 3 minute hold at 100% Solvent B;
  UV visualization at 220 nm;
  Column: Xbridge Phenyl 3.5 um, 4.6×150 mm;
  Flow rate: 1 mL/min;
  Solvent A: 5% $CH_3CN$, 95% Water, 0.05% Trifluoroacetic Acid; and
  Solvent B: 95% $CH_3CN$, 5% Water, 0.05% Trifluoroacetic Acid.

Chiral preparatory HPLC method D was performed on a Berger MGII SFC liquid chromatograph:
  Column: CHIRALPAK® IA, 250×30 mm ID, 5 um
  Flow rate: 95 mL/min
  Mobile Phase: 25% Methanol/75% CO2, 150 Bar, 40° C.
  Detector Wavelength: 275 nm
  Injection Volume: 1000 µL Chiral preparatory HPLC method E was performed on a Berger MGII SFC liquid chromatograph:
  Column: CHIRALPAK® IA, 250×30 mm ID, 5 µm
  Flow rate: 95 mL/min
  Mobile Phase: 17% Ethanol w/0.1% DEA/83% CO2, 150 Bar, 35° C.
  Detector Wavelength: 270 nm
  Injection Volume: 2000 µL Preparatory HPLC Method E was performed on a Shimadzu SCL-10A liquid chromatograph with a linear gradient of 0-75% Solvent B over 30 minutes, with a 5 min hold at 100% Solvent B;
  UV visualization at 220 nm;
  Column: Phenomenex 5u C18 30×250 mm;
  Flow rate: 30 mL/min;
  Solvent A: 10% MeOH, 90% Water, 0.1% Trifluoroacetic Acid; and
  Solvent B: 90% MeOH, 10% Water, 0.1% Trifluoroacetic Acid.

GENERAL PROCEDURES

General Procedure A

N-Arylation of Piperidinol Using an Aryl Fluoride

To a round bottom flask was added piperidin-3-ol (1 eq), aryl fluoride (1 eq), DMF and $K_2CO_3$ (1.2 eq). The reaction was stirred at 65° C. for 6 hrs. After this time, the reaction was diluted with EtOAc. The resulting solution was washed with water (4×) and saturated aqueous NaCl. The organic layer was separated, dried over $MgSO_4$, filtered and concentrated. The resulting residue was purified using silica gel chromatography (ISCO system) eluting with a gradient of 0-100% EtOAc/Hex to give product N-arylpiperidin-3-ol or N-heteroarylpiperidin-3-ol.

General Procedure B

N-Arylation of Piperidinol Using Cut

Piperidin-3-ol (1 eq), aryl-bromide, $K_2CO_3$ (2 eq), L-proline (0.2 eq), copper (I) iodide (0.1 eq) and DMSO were added to a glass pressure tube. After addition, the tube was sealed and placed in a heating bath at 65° C. The reaction was stirred at 65° C. for 48 hrs. After this time the reaction was cooled to rt. The reaction mixture was diluted with EtOAc. The resulting solution was washed with water (2×) and saturated aqueous NaCl. The organic layer was separated, dried over $MgSO_4$, filtered and concentrated. The resulting residue was purified using silica gel chromatography (ISCO system) eluting with a gradient of 0-100% EtOAc/Hex to give product N-arylpiperidin-3-ol.

General Procedure C

Oxidation of N-Aryl-Piperidinol Using Pyridine Sulfur Trioxide Complex

To a round bottom flask was added N-arylpiperidinol (1 eq), $Et_3N$ (5 eq) and $CH_2Cl_2$. The resulting solution was cooled to 0° C. In a separate vial, pyridine sulfur trioxide (5 eq) and DMSO (20 eq) were mixed until the solution turned clear. The resulting solution was then added to the reaction at 0° C. The reaction mixture was slowly warmed to rt and stirred for an additional 2 hrs. After this time, the solution was diluted with $CH_2Cl_2$. The resulting solution was wash with water (2×) and saturated aqueous NaCl. The organic layer was separated, dried over $MgSO_4$, filtered and concentrated. The resulting residue was purified using silica gel chromatography (ISCO system) eluting with a gradient of 0-100% EtOAc/Hex to give the product N-arylpiperidinone.

General Procedure D

Oxidation of N-Aryl-Piperidinol Using Swern Oxidation Conditions

To a round bottom flask was added $CH_2Cl_2$ and 2M oxalyl chloride (1.4 eq). The resulting solution was cooled to −78° C. DMSO (2.8 eq) was slowly added to the solution over 10 min.

The reaction was then stirred at −78° C. for 15 min. The N-aryl-piperidinol (1 eq) pre-dissolved in CH₂Cl₂ was added to the reaction mixture over 10 min. The resulting solution was stirred at −78° C. for 2 hrs. After this time, Et₃N (4.4 eq) was added to the reaction mixture and the resulting solution was slowly warmed to 0° C. over 20 min. The reaction mixture was then diluted with CH₂Cl₂. The reaction mixture was wash with saturated aqueous NaHCO₃, water and saturated aqueous NaCl. The organic layer was separated, dried over MgSO₄, filtered and concentrated to give crude product. The resulting residue was purified using silica gel chromatography (ISCO system) eluting with a gradient of 0-100% EtOAc/Hex to give the product N-arylpiperidinone.

General Procedure E

Reductive Amination Using Cyclohexane Diamine and an N-Arylpiperidinone

To a round bottom flask under argon was added the N-arylpiperidinone (1 eq), (1R,2R)-cyclohexane-1,2-diamine (1 eq), CH₂Cl₂, solid anhydrous Na₂SO₄ and HOAc (1 eq). Argon was bubbled through the reaction mixture for 1 min and then the reaction was stirred under argon at rt for 1 hr. After this time, sodium triacetoxy borohydride (3 eq) was added to the reaction which was then stirred at rt for additional 4 hrs. At this time, HPLC analysis showed the starting material was consumed. The reaction mixture was then diluted with CH₂Cl₂. The resulting solution was wash with water (2×) and saturated aqueous NaCl. The organic layer was separated, dried over MgSO₄, filtered and concentrated. The resulting residue was purified using RP prep-HPLC. The desired fractions containing the product were concentrated to give product amine.

General Procedure F

Reductive Amination Using tert-butyl (1R,2R)-2-aminocyclohexylcarbamate and an N-arylpiperidinone To a round bottom flask under argon was added the N-arylpiperidinone (1 eq), tert-butyl (1R,2R)-2-aminocyclohexylcarbamate (1 eq), CH₂Cl₂, solid anhydrous Na₂SO₄ and HOAc (1 eq). Argon was bubbled through the reaction mixture for 1 min and then the reaction was stirred under argon at rt for 1 hr. After this time, sodium triacetoxy borohydride (3 eq) was added to the reaction which was then stirred at rt or additional 4 hrs. After this time, HPLC analysis showed the starting material was consumed. The reaction mixture was then diluted with CH₂Cl₂. The resulting solution was wash with water (2×) and saturated aqueous NaCl. The organic layer was separated, dried over MgSO₄, filtered and concentrated. The resulting residue was purified using silica gel chromatography (ISCO system) eluting with a gradient of 0-100% EtOAc/Hex. The desired fractions containing the product were concentrated to give product.

General Procedure G

Removal of the Boc Group Using Trifluoroacetic Acid

To a round bottom flask was added the Boc protected compound, 1:1 mixture of CH₂Cl₂ and TFA. The reaction was stirred at rt for 1 hr. The solvent was removed to give product amine as a TFA salt.

General Procedure H

Coupling of Heteroaryl Halide with Cyclohexane Diamine Derivatives

To a round bottom flask was added the cyclohexane diamine derivative (1 eq), DMF, K₂CO₃ (4 eq) and a heteroaryl halide (1 eq). The reaction was stirred at 65° C. for 2-4 hrs. The reaction was diluted with EtOAc, washed with water (4×) and saturated aqueous NaCl. The organic layer was dried over MgSO₄, filtered and concentrated. The resulting residue was purified using RP prep-HPLC. The desired fractions containing product were concentrated to give the desired N-heteroaryl cyclohexane diamine derivative.

General Procedure I

Coupling of Substituted Phenyl Boronic Acid or Phenyl Boronic Acid Ester with an N-(halopyridin-2-ylamino)cyclohexylamino-piperidin-1-yl Derivative To a round bottom flask was added a N-(halopyridin-2-ylamino)cyclohexylamino-piperidin-1-yl derivative (1 eq), boronic acid or boronic ester (1 eq), potassium phosphate (2 eq) and tetrakis(triphenylphosphine)palladium (0) (0.035 eq). After purging the resulting heterogeneous solution with argon, DMA was then added. The reaction mixture was stirred at 110° C. for 3 hr. After cooling to rt, the reaction mixture was partitioned between EtOAc and water. The separated aqueous phase was extracted with EtOAc (2×). The combined EtOAc extracts were washed with water, saturated aqueous NaCl solution, dried over Na₂SO₄, filtered and concentrated. The resulting residue was purified using silica gel chromatography (ISCO system) eluting with a gradient of 0-100% EtOAc/Hex. The desired fractions containing the product were concentrated to give the product.

INTERMEDIATES

Intermediate 1

2-Chloro-5-phenyloxazole

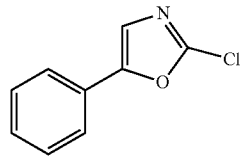 [SMILES: Clc1ncc(-c2ccccc2)o1]

To a round bottom flask was added 5-phenyloxazole (1.0 gm, 6.89 mmol) and THF (10 mL). The reaction was cooled to −78° C. Then 2.5 M nBuLi (3.03 mL, 7.58 mmol) was added to the reaction at −78° C. The reaction turned to deep red color. After 15 min, hexachloroethane (1.170 mL, 10.33 mmol) was added at −78° C. The reaction was slowly warmed to rt over 2 hrs and then was poured onto ice. The resulting solution was extracted with EtOAc (2×30 ml). The combined EtOAc layers were washed with saturated aqueous NaCl, dried over MgSO₄, filtered and concentrated. The resulting residue was purified using silica gel chromatography (ISCO system) eluting with a gradient of 0-100% EtOAc/Hex to give the product, 2-chloro-5-phenyloxazole, (600 mg, 3.34 mmol, 49% yield) as a light pale liquid. Anal. Calcd. for C₉H₆ClNO m/z 179.1, found: 180.1 (M+H)⁺; ¹H NMR (500 MHz, CDCl₃) δ ppm 7.60 (d, J=7.15 Hz, 2H), 7.43 (t, J=7.42 Hz, 2H), 7.38-7.33 (m, 1H), 7.29 (s, 1H); $^{13}$C NMR (126 MHz, CDCl₃) δ ppm 153.78, 146.16, 129.01, 126.93, 124.03, 123.31.

Intermediate 2

2-Chloro-5-(4-(trifluoromethoxy)phenyl)oxazole

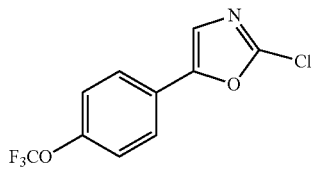 [SMILES: FC(F)(F)Oc1ccc(-c2cnc(Cl)o2)cc1]

A: 5-(4-(Trifluoromethoxy)phenyl)oxazole

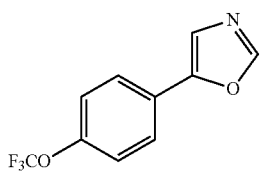

To a round bottom flask was added K₂CO₃ (5.09 g, 36.8 mmol), 1-(isocyanomethylsulfonyl)-4-methylbenzene (3.95 g, 20.25 mmol), MeOH (30 mL) and 4-(trifluoromethoxy)benzaldehyde (2.63 mL, 18.41 mmol). The reaction was refluxed for 2 hrs. After this time, the reaction mixture was concentrated under reduced pressure. The remaining residue was dissolved in water (50 ml). The aqueous solution was extract with EtOAc (50 ml). The EtOAc layer was washed with saturated aqueous NaCl (30 ml), dried over MgSO₄, filtered and concentrated. The resulting residue was purified using silica gel chromatography (ISCO system) eluting with a gradient of 0-100% EtOAc/Hex to give the product, 5-(4-(trifluoromethoxy)phenyl)oxazole, (3.5 g, 15.27 mmol, 83% yield) as an off white solid. Anal. Calcd. for C₁₀H₆F₃NO₂ m/z 229.1, found: 230.1 (M+H)⁺; $^1$H NMR (500 MHz, CDCl₃) δ ppm 7.94 (s, 1H), 7.70 (d, J=8.80 Hz, 2H), 7.37 (s, 1H), 7.29 (d, J=8.25 Hz, 2H).

B: 2-Chloro-5-(4-(trifluoromethoxy)phenyl)oxazole

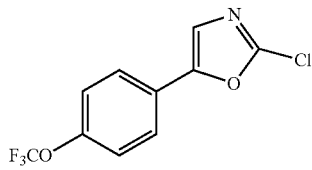

To a round bottom flask was added 5-(4-(trifluoromethoxy)phenyl)oxazole (3.49 g, 15.23 mmol) and THF (15 mL). The reaction was cooled to −78° C. Then 2.5 M nBuLi (6.70 mL, 16.75 mmol) was added to the reaction at −78° C. The reaction turned to deep red color. After 15 min, hexachloroethane (2.59 mL, 22.84 mmol) was added at −78° C. The reaction was slowly warmed to rt over 2 hrs. The reaction was then poured onto ice and extracted with EtOAc (2×30 ml). The combined EtOAc layers were washed with saturated aqueous NaCl, dried over MgSO₄, filtered and concentrated. The resulting residue was purified using silica gel chromatography (ISCO system) eluting with a gradient of 0-100% EtOAc/Hex to give the product, 2-chloro-5-(4-(trifluoromethoxy)phenyl)oxazole, (2 g, 7.59 mmol, 49.8% yield) as a light orange liquid. Anal. Calcd. for C₁₀H₅F₃NO₂ m/z 263.1, found: 264.1 (M+H)⁺; $^1$H NMR (500 MHz, CDCl₃) δ ppm 7.64 (s, 2 H), 7.30 (s, 4 H); $^{13}$C NMR (126 MHz, CDCl₃) δ ppm 152.51, 149.41, 146.62, 125.57, 123.83, 121.41, 119.36.

Intermediate 3

2-Chloro-5-(4-(trifluoromethyl)phenyl)oxazole

2-Chloro-5-(4-(trifluoromethyl)phenyl)oxazole (2.1 g, 8.64 mmol) was synthesized as described for the preparation of Intermediate 2 using 4-(trifluoromethyl)benzaldehyde in step A. Anal. Calcd. for C₁₀H₅ClF₃NO m/z 246.9, found: 247.9 (M+H)⁺.

Intermediate 4

2-Chloro-5-(3-fluoro-4-(trifluoromethoxy)phenyl)oxazole

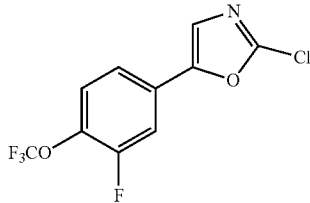 [SMILES: Fc1cc(-c2cnc(Cl)o2)ccc1OC(F)(F)F]

2-Chloro-5-(3-fluoro-4-(trifluoromethoxy)phenyl)oxazole (1.15 gm, 4.08 mmol) was synthesized as described for the preparation of Intermediate 2 using 3-fluoro-4-(trifluoromethoxy)benzaldehyde in step A. Anal. Calcd. for C₁₀H₄ClF₄NO₂ m/z 280.9, found: 281.8 (M+H)⁺.

Intermediate 5

5-(4-tert-Butoxyphenyl)-2-chlorooxazole

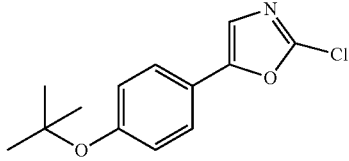 [SMILES: CC(C)(C)Oc1ccc(-c2cnc(Cl)o2)cc1]

5-(4-tert-Butoxyphenyl)-2-chlorooxazole (1.4 g, 5.56 mmol) was synthesized as described for the preparation of Intermediate 2 using 4-tert-butoxybenzaldehyde in step A. Anal. Calcd. for $C_{13}H_{14}ClNO_2$ m/z 250.9, found: 252.0 $(M+H)^+$.

Intermediate 6

2-Chloro-5-(2-fluorophenyl)oxazole

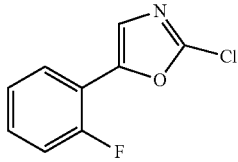 [SMILES: Fc1ccccc1-c1cnc(Cl)o1]

2-Chloro-5-(2-fluorophenyl)oxazole (2.4 g, 12.15 mmol) was synthesized as described for the preparation of Intermediate 2 using 2-fluorobenzaldehyde in step A. Anal. Calcd. for $C_9H_5ClNO$ m/z 196.9, found: 197.9 $(M+H)^+$.

Intermediate 7

2-Chloro-5-(3-fluorophenyl)oxazole

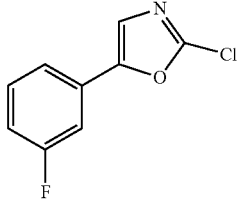 [SMILES: Fc1cccc(-c2cnc(Cl)o2)c1]

2-Chloro-5-(3-fluorophenyl)oxazole (1.8 g, 9.11 mmol) was synthesized as described for the preparation of Intermediate 2 using 3-fluorobenzaldehyde in step A. Anal. Calcd. for $C_9H_5ClNO$ m/z 196.9, found: 197.0 $(M+H)^+$; $^1H$ NMR (400 MHz, $CDCl_3$) δ ppm 7.39 (m, 2H), 7.31 (m, 2H), 7.20 (m, 1H), 7.05 (m, 1H).

Intermediate 8

2-Chloro-5-(4-fluorophenyl)oxazole

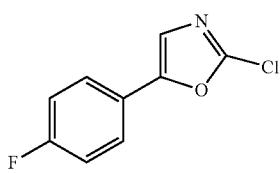 [SMILES: Fc1ccc(-c2cnc(Cl)o2)cc1]

2-Chloro-5-(4-fluorophenyl)oxazole (1.95 g, 9.87 mmol) was synthesized as described for the preparation of Intermediate 2 using 4-fluorobenzaldehyde in step A. Anal. Calcd. for $C_9H_5ClFNO$ m/z 196.9, found: 197.9 $(M+H)^+$.

Intermediate 9

2-Chloro-5-(3,4-difluorophenyl)oxazole

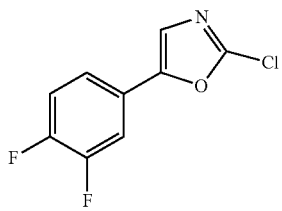 [SMILES: Fc1ccc(-c2cnc(Cl)o2)cc1F]

2-Chloro-5-(3,4-difluorophenyl)oxazole (1.94 g, 9.00 mmol) was synthesized as described for the preparation of Intermediate 2 using 3,4-difluorobenzaldehyde in step A. Anal. Calcd. for $C_9H_4ClF_2NO$ m/z 214.9, found: 215.9 $(M+H)^+$.

Intermediate 10

2-Chloro-5-(4-(difluoromethoxy)phenyl)oxazole

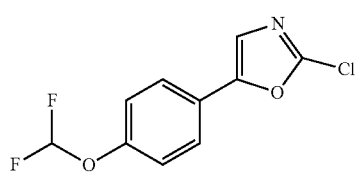 [SMILES: FC(F)Oc1ccc(-c2cnc(Cl)o2)cc1]

2-Chloro-5-(4-(difluoromethoxy)phenyl)oxazole (1.48 g, 6.03 mmol) was synthesized as described for the preparation of Intermediate 2 using 4-(difluoromethoxy)benzaldehyde in step A. Anal. Calcd. for $C_{10}H_6ClF_2NO_2$ m/z 244.9, found: 245.9 $(M+H)^+$.

Intermediate 11

2-Chloro-5-(2-methyl-4-(trifluoromethoxy)phenyl) oxazole

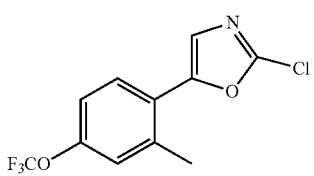

2-Chloro-5-(2-methyl-4-(trifluoromethoxy)phenyl)oxazole (400 mg, 1.441 mmol) was synthesized as described for the preparation of Intermediate 2 using 2-methyl-4-(trifluoromethoxy)benzaldehyde in step A. Anal. Calcd. for $C_{10}H_6ClF_2NO_2$ m/z 276.9, found: 277.9 (M+H)+.

Intermediate 12

2-Chloro-5-(2-fluoro-4-methoxyphenyl)oxazole

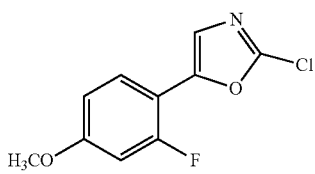 [SMILES: COc1ccc(-c2cnc(Cl)o2)c(F)c1]

2-Chloro-5-(2-fluoro-4-methoxyphenyl)oxazole (970 mg, 4.26 mmol) was synthesized as described for the preparation of Intermediate 2 using 2-fluoro-4-methoxybenzaldehyde in step A. Anal. Calcd. for $C_{10}H_7ClFNO_2$ m/z 226.9, found: 228.0 (M+H)+.

Intermediate 13

2-Chloro-5-(2,4-difluorophenyl)oxazole

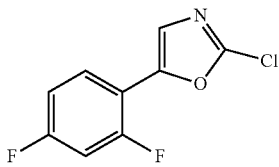

2-Chloro-5-(2,4-difluorophenyl)oxazole (810 mg, 3.76 mmol) was synthesized as described for the preparation of Intermediate 2 using 2,4-difluorobenzaldehyde in step A. Anal. Calcd. for $C_9H_4ClF_2NO$ m/z 214.9, found: 215.9 (M+H)+.

Intermediate 14

2-Chloro-5-(3-(trifluoromethoxy)phenyl)oxazole

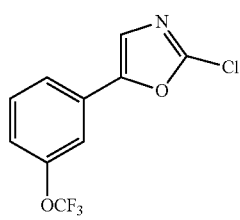 [SMILES: FC(F)(F)Oc1cccc(-c2cnc(Cl)o2)c1]

2-Chloro-5-(3-(trifluoromethoxy)phenyl)oxazole (2.5 g, 10.96 mmol) was synthesized as described for the preparation of Intermediate 2 using 3-(trifluoromethoxy)benzaldehyde in step A. Anal. Calcd. for $C_{10}H_5ClF_3NO_2$ m/z 263.0, found: 264.2 (M+H)+; $^1H$ NMR (400 MHz, CDCl$_3$) δ ppm 7.38 (m, 1H), 7.46 (m, 1H), 7.48 (m, 3H).

Intermediate 15

2-Chloro-4-(4-(trifluoromethoxy)phenyl)pyrimidine

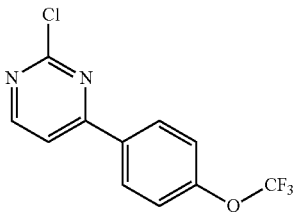 [SMILES: FC(F)(F)Oc1ccc(-c2ccnc(Cl)n2)cc1]

To a sealed tube was added 2,4-dichloropyrimidine (100 mg, 0.671 mmol), 4-(trifluoromethoxy)phenylboronic acid (138 mg, 0.671 mmol), tetrakis(triphenylphosphine)palladium0) (78 mg, 0.067 mmol), acetonitrile (2 mL) and 2M Na$_2$CO$_3$ in H$_2$O (1.007 mL, 2.014 mmol). Argon was bubbled through the reaction mixture for 1 min. The reaction mixture was then sealed and stirred at 90° C. for 16 hrs. The reaction was cooled to rt and diluted with EtOAc (30 ml). The resulting organic solution was washed with water (30 ml) and saturated aqueous NaCl (30 ml). The organic layer was dried over MgSO$_4$, filtered and concentrated. The resulting residue was purified using silica gel chromatography (ISCO system) eluting with a gradient of 0-40% EtOAc/Hex to give the product, 2-chloro-4-(4-(trifluoromethoxy)phenyl)pyrimidine, (62 mg, 0.226 mmol, 33.6% yield) as a white solid. Anal. Calcd. for $C_{11}H_6ClF_3N_2O$ m/z 273.9, found: 275.0 (M+H)+.

Intermediate 16

(1R,2R)—N1-((6S)-2-(4-Nitrophenyl)-2-azabicyclo [2.2.1]heptan-6-yl)cyclohexane-1,2-diamine

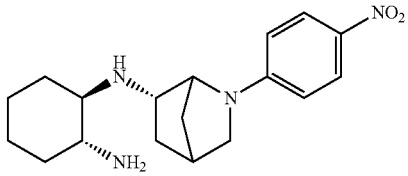 [SMILES: N[C@@H]1CCCC[C@H]1N[C@H]1CC2CC1N(c1ccc([N+](=O)[O-])cc1)C2]

A: 2-Benzyl-2-azabicyclo[2.2.1]heptan-6-ol

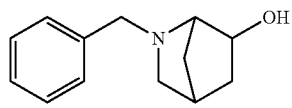 [SMILES: OC1CC2CC1N(Cc1ccccc1)C2]

To a round bottom flask was added 2-benzyl-2-azabicyclo [2.2.1]hept-5-ene (1 g, 5.40 mmol) and THF (7 mL). The reaction was cooled to 0° C. and 1N BH$_3$.THF (10.80 mL, 10.80 mmol) was slowly added to the reaction. The reaction was stirred at 0° C. for 1 hr and then water (0.5 ml) was added to the reaction dropwise to quench the excess BH$_3$. 1N NaOH (5.94 mL, 5.94 mmol) and 30% H$_2$O$_2$ (0.182 mL, 5.94 mmol) were added to the reaction and the reaction was stirred at 40° C. for 1 hr. The reaction was cooled to rt and K$_2$CO$_3$ (1 g) was added. The reaction was diluted with CH$_2$Cl$_2$ (50 ml) and washed with water (2×20 ml) and saturated aqueous NaCl (30 ml). The organic layer was dried over MgSO$_4$, filtered and concentrated. The residue was purified by RP prep-HPLC. The major peak was collected and fractions were concentrated to give 2-benzyl-2-azabicyclo[2.2.1]heptan-6-ol (850 mg, 4.18 mmol, 77% yield). Anal. Calcd. for C$_{13}$H$_{17}$NO m/z 203.3, found: 204.3 (M+H)$^+$; $^1$H NMR (500 MHz, CDCl$_3$) δ ppm 7.48-7.32 (m, 5 H), 4.47 (d, J=6.60 Hz, 1 H), 4.29 (br. s., 1 H), 4.23-4.05 (m, 2 H), 3.78 (s, 1 H), 3.29 (dd, J=11.00, 4.40 Hz, 1 H), 2.81-2.72 (m, 1 H), 2.68 (br. s., 1 H), 2.09 (d, J=11.55 Hz, 1 H), 2.04-1.95 (m, 1 H), 1.77 (d, J=12.10 Hz, 1 H), 1.60-1.50 (m, 1 H); $^{13}$C NMR (126 MHz, CDCl$_3$) δ ppm 130.61, 130.04, 129.42, 68.31, 67.72, 59.17, 58.03, 37.98, 35.49, 31.24.

B: 2-Azabicyclo[2.2.1]heptan-6-ol

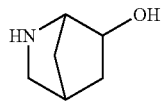

To a hydrogenation bottle was added 2-benzyl-2-azabicyclo[2.2.1]heptan-6-ol (400 mg, 1.968 mmol), MeOH (15 mL), Pd(OH)$_2$ (69.1 mg, 0.492 mmol) and 3 drops of conc. HCl. The reaction was stirred under an atmosphere of hydrogen at 35 psi for 24 hrs. The reaction mixture was filtered through CELITE® and the filtrate was concentrated to give the product, 2-azabicyclo[2.2.1]heptan-6-ol, (200 mg, 1.767 mmol, 90% yield) as a clear oil. The product was used in the next step without further purification. Anal. $^1$H NMR (500 MHz, CDCl$_3$) δ ppm 4.35 (br. s., 1 H), 3.95 (br. s., 1H), 3.10 (br. s., 1 H), 2.88 (br. s., 1 H), 2.68 (br. s., 1 H), 2.02 (d, J=9.90 Hz, 2 H), 1.74 (d, J=10.45 Hz, 1 H), 1.58 (d, J=11.55 Hz, 1 H).

C: 2-(4-Nitrophenyl)-2-azabicyclo[2.2.1]heptan-6-ol

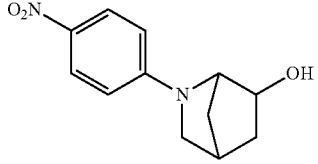 [SMILES: O=[N+]([O-])c1ccc(N2CC3CC(O)C2C3)cc1]

To a round bottom flask was added 2-azabicyclo[2.2.1]heptan-6-ol (150 mg, 1.326 mmol), 1-fluoro-4-nitrobenzene (187 mg, 1.326 mmol), K$_2$CO$_3$ (366 mg, 2.65 mmol) and DMF (5 mL). The reaction was stirred at 65° C. for 4 hrs. The reaction was then diluted with EtOAc (35 ml). The organic solution was washed with water (3×20 ml) and saturated aqueous NaCl (20 ml). The organic layer was dried over MgSO$_4$, filtered and concentrated. The resulting residue was purified using silica gel chromatography (ISCO system) eluting with a gradient of 0-100% EtOAc/Hex to give the product, 2-(4-nitrophenyl)-2-azabicyclo[2.2.1]heptan-6-ol (150 mg, 0.640 mmol, 49% yield), as a yellow solid. Anal. Calcd. for C$_{12}$H$_{14}$N$_2$O$_3$ m/z 234.2, found: 235.2 (M+H)$^+$; $^1$H NMR (500 MHz, CDCl$_3$) δ ppm 8.10 (d, J=9.90 Hz, 2 H), 6.49 (d, J=8.25 Hz, 2 H), 4.10 (s, 1 H), 3.99 (br. s., 1 H), 3.39 (dt, J=8.80, 2.75 Hz, 1 H), 2.78 (d, J=8.80 Hz, 1 H), 2.74 (br. s., 1 H), 1.97 (d, J=9.90 Hz, 1 H), 1.92 (ddd, J=13.61, 7.01, 2.47 Hz, 1 H), 1.78-1.71 (m, 2 H), 1.59-1.53 (m, 1 H); $^{13}$C NMR (126 MHz, CDCl$_3$) δ ppm 151.32, 136.88, 126.54, 110.27, 71.10, 61.88, 54.11, 40.73, 35.91, 34.23.

D: 2-(4-Nitrophenyl)-2-azabicyclo[2.2.1]heptan-6-one

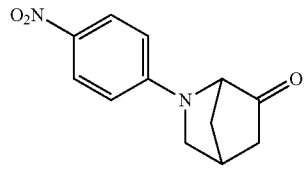 [SMILES: O=C1CC2CC1N(c1ccc([N+](=O)[O-])cc1)C2]

To a round bottom flask was added 2-(4-nitrophenyl)-2-azabicyclo[2.2.1]heptan-6-ol (150 mg, 0.640 mmol), Et$_3$N (0.446 mL, 3.20 mmol) and CH$_2$Cl$_2$ (3 mL). The reaction was cooled to 0° C. Pyridine sulfur trioxide (510 mg, 3.20 mmol) and DMSO (0.909 mL, 12.81 mmol) were mixed in a vial until the solution turned clear and then this clear solution was added to the reaction mixture at 0° C. The reaction was slowly warmed to rt and then was stirred at rt for 2 hrs. The reaction was diluted with CH$_2$Cl$_2$ (25 ml). The organic solution was washed with water (2×20 ml) and saturated aqueous NaCl (20 ml). The organic layer was dried over MgSO$_4$, filtered and concentrated. The resulting residue was purified using silica gel chromatography (ISCO system) eluting with a gradient of 0-100% EtOAc/Hex to give the product, 2-(4-nitrophenyl)-2-azabicyclo[2.2.1]heptan-6-one, (80 mg, 0.344 mmol, 54% yield) as a yellow solid. Anal. Calcd. for C$_{12}$H$_{12}$N$_2$O$_3$ m/z 232.2, found: 233.2 (M+H)$^+$.

E: (1R,2R)—N1-((6S)-2-(4-Nitrophenyl)-2-azabicyclo[2.2.1]heptan-6-yl)cyclohexane-1,2-diamine

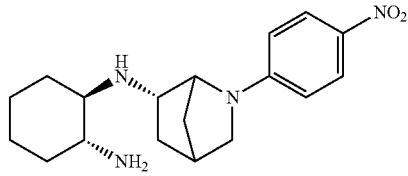 [SMILES: N[C@@H]1CCCC[C@H]1N[C@H]1CC2CC1N(c1ccc([N+](=O)[O-])cc1)C2]

To a round bottom flask was added 2-(4-nitrophenyl)-2-azabicyclo[2.2.1]heptan-6-one (120 mg, 0.517 mmol), CH$_2$Cl$_2$ (3 mL) and Na$_2$SO$_4$ (5 gms). The reaction was purged with argon. Then (1R,2R)-cyclohexane-1,2-diamine (118 mg, 1.033 mmol) and acetic acid (0.592 mL, 10.33 mmol) were added to the reaction. The reaction was stirred at rt for 1 hr. After this time, sodium triacetoxyborohydride (548 mg, 2.58 mmol) was added to the reaction and the reaction was stirred at rt overnight. The reaction was diluted with CH$_2$Cl$_2$ (50 ml) and filtered. The organic layer was washed with 0.5N NaOH (30 ml), water (30 ml) and saturated aqueous NaCl (30 ml). The organic layer was dried over MgSO$_4$, filtered and concentrated. The residue was purified by RP prep-HPLC. Two isomers were separated from RP prep-HPLC. The fractions with the desired product, which eluted later than the undesired isomer, were concentrated to give (1R,2R)—N1-

((6S)-2-(4-nitrophenyl)-2-azabicyclo[2.2.1]heptan-6-yl)cyclohexane-1,2-diamine (80 mg, 0.242 mmol, 46% yield) as a yellow solid. Anal. Calcd. for $C_{18}H_{26}N_4O_2$ m/z 330.4, found: 331.3 (M+H)$^+$.

Intermediate 17

(1R,2R)—N1-((S)-1-(4-Nitrophenyl)piperidin-3-yl)cyclohexane-1,2-diamine

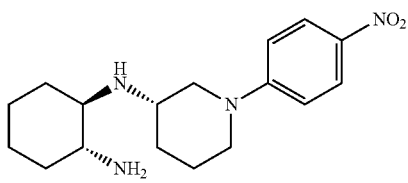 [SMILES: N[C@@H]1CCCC[C@H]1N[C@H]1CCCN(c2ccc([N+](=O)[O-])cc2)C1]

A: 1-(4-Nitrophenyl)piperidin-3-ol

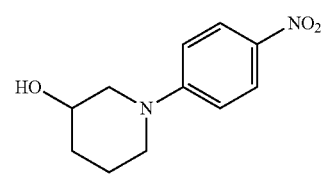 [SMILES: O=[N+]([O-])c1ccc(N2CCCC(O)C2)cc1]

1-(4-Nitrophenyl)piperidin-3-ol was synthesized as described in General Procedure A using 1-fluoro-4-nitrobenzene (4.41 g, 31.2 mmol) and piperidin-3-ol (4.3 g, 31.2 mmol) to give an orange solid (6.8 g, 30.6 mmol, 98% yield). Anal. Calcd. for $C_{11}H_{14}N_2O_3$ m/z 222.2, found: 223.3 (M+H)$^+$; $^1$H NMR (500 MHz, CDCl$_3$) δ ppm 8.14-7.98 (m, 2 H), 6.83 (d, J=9.35 Hz, 2 H), 3.89 (d, J=3.85 Hz, 1 H), 3.72 (dd, J=12.92, 3.57 Hz, 1 H), 3.53 (ddd, J=13.06, 5.91, 3.02 Hz, 1 H), 3.33-3.16 (m, 2 H), 2.10-1.97 (m, 2 H), 1.96-1.84 (m, 1 H), 1.75-1.50 (m, 2 H).

B: 1-(4-Nitrophenyl)piperidin-3-one

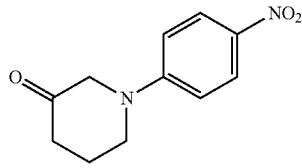 [SMILES: O=C1CCCN(c2ccc([N+](=O)[O-])cc2)C1]

1-(4-Nitrophenyl)piperidin-3-one was synthesized as described in General Procedure C using 1-(4-nitrophenyl)piperidin-3-ol (5.0 g, 22.50 mmol) to give an orange solid (4.2 g, 85% yield). Anal. Calcd. for $C_{11}H_{12}N_2O_3$ m/z 220.2, found: 221.2 (M+H)$^+$; $^1$H NMR (500 MHz, CDCl$_3$) δ ppm 8.16 (d, J=9.35 Hz, 2 H), 6.75 (d, J=9.35 Hz, 2 H), 4.04 (s, 2 H), 3.64 (t, J=6.05 Hz, 2 H), 2.60 (t, J=6.60 Hz, 2 H), 2.22 (t, J=6.05 Hz, 2 H); $^{13}$C NMR (126 MHz, CDCl$_3$) δ ppm 204.84, 153.09, 138.61, 126.04, 111.52, 56.05, 45.70, 37.99, 21.49.

C: (1R,2R)—N1-(1-(4-Nitrophenyl)piperidin-3-yl)cyclohexane-1,2-diamine

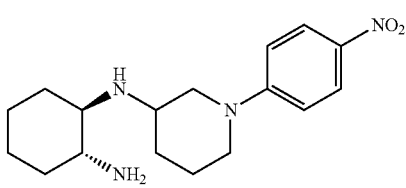

(1R,2R)—N1-(1-(4-Nitrophenyl)piperidin-3-yl)cyclohexane-1,2-diamine was synthesized as described in General Procedure E using 1-(4-nitrophenyl)piperidin-3-one (3.0 g, 13.62 mmol) to give a yellow solid (3.5 g, 81% yield). Anal. Calcd. for $C_{17}H_{26}N_4O_2$ m/z 318.4, found: 319.3 (M+H)$^+$.

D: (1R,2R)—N1-((S)-1-(4-Nitrophenyl)piperidin-3-yl)cyclohexane-1,2-diamine

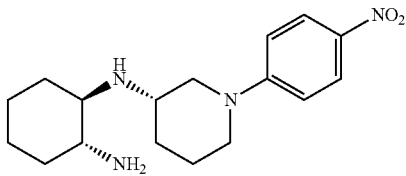 [SMILES: N[C@@H]1CCCC[C@H]1N[C@H]1CCCN(c2ccc([N+](=O)[O-])cc2)C1]

(1R,2R)—N1-((S)-1-(4-Nitrophenyl)piperidin-3-yl)cyclohexane-1,2-diamine was separated from its diastereomer using Chiral preparatory HPLC method A.

Intermediate 18

4-((S)-3-((1R,2R)-2-Aminocyclohexylamino)piperidin-1-yl)benzonitrile

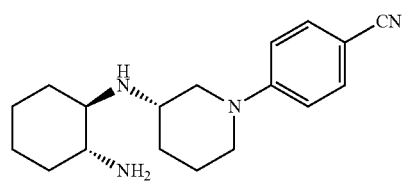

A: 4-(3-Hydroxypiperidin-1-yl)benzonitrile

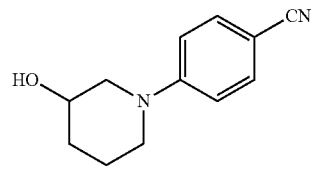 [SMILES: N#Cc1ccc(N2CCCC(O)C2)cc1]

4-(3-Hydroxypiperidin-1-yl)benzonitrile (7.27 gm, 35.9 mmol) was synthesized in 75% yield as described in General Procedure A using 4-fluorobenzonitrile (5.82 gm, 48.0 mmol). Anal. Calcd. for $C_{12}H_{14}N_2O$ m/z 202.2, found: 203.2 (M+H)$^+$; $^1$H NMR (500 MHz, CDCl$_3$) δ ppm 7.48 (d, J=9.35 Hz, 2 H), 6.88 (d, J=8.80 Hz, 2 H), 3.89 (br. s., 1 H), 3.60 (dd, J=12.65, 3.30 Hz, 1 H), 3.40 (ddd, J=12.78, 6.46, 3.30 Hz, 1 H), 3.24-3.02 (m, 2 H), 2.01-1.84 (m, 3 H), 1.73-1.56 (m, 2 H); $^{13}$C NMR (126 MHz, CDCl$_3$) δ ppm 153.68, 133.50, 120.01, 114.69, 100.03, 66.12, 54.84, 47.74, 32.51, 21.88.

B: 4-(3-Oxopiperidin-1-yl)benzonitrile

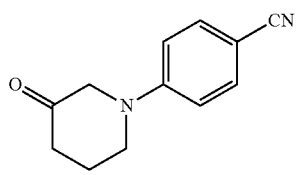 [SMILES: N#Cc1ccc(N2CCCC(=O)C2)cc1]

4-(3-Oxopiperidin-1-yl)benzonitrile (3.3 gm, 16.48 mmol) was synthesized in 95% yield as described in General Procedure D using 4-(3-hydroxypiperidin-1-yl)benzonitrile (3.5 g, 17.31 mmol). Anal. Calcd. for $C_{12}H_{12}N_2O$ m/z 200.2, found: 201.2 (M+H)$^+$; $^1$H NMR (500 MHz, CDCl$_3$) δ ppm 7.53 (d, J=8.80 Hz, 2 H), 6.79 (d, J=8.80 Hz, 2 H), 3.96 (s, 2 H), 3.58 (t, J=6.05 Hz, 2 H), 2.58 (t, J=6.87 Hz, 2 H), 2.18 (t, J=6.32 Hz, 2 H); $^{13}$C NMR (126 MHz, CDCl$_3$) δ ppm 205.32, 151.52, 133.66, 119.89, 112.91, 100.25, 56.25, 45.66, 38.13, 21.78.

C: 4-(3-((1R,2R)-2-Aminocyclohexylamino)piperidin-1-yl)benzonitrile

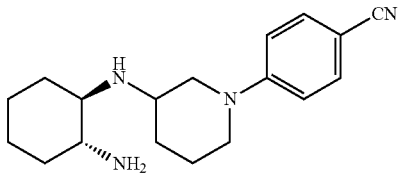

4-(3-((1R,2R)-2-Aminocyclohexylamino)piperidin-1-yl) benzonitrile (360 mg, 1.21 mmol) was synthesized in 38% yield as described in General Procedure E using 4-(3-oxopiperidin-1-yl)benzonitrile (640 mg, 3.20 mmol). Anal. Calcd. for $C_{18}H_{26}N_4$ m/z 298.4, found: 299.3 (M+H)$^+$; $^1$H NMR (500 MHz, MeOH-d$_3$) δ ppm 7.61-7.44 (m, 2 H), 7.03 (d, J=9.35 Hz, 2 H), 4.02-3.86 (m, 1 H), 3.85-3.74 (m, 1 H), 3.05-2.83 (m, 3 H), 2.82-2.62 (m, 1 H), 2.27 (d, J=14.30 Hz, 1 H), 2.13 (d, J=12.10 Hz, 1 H), 2.02 (s, 1 H), 1.92-1.78 (m, 3 H), 1.76-1.62 (m, 1 H), 1.34-1.56 (m, 4 H), 1.21-1.34 (m, 2 H).

D: 4-((S)-3-((1R,2R)-2-Aminocyclohexylamino) piperidin-1-yl)benzonitrile

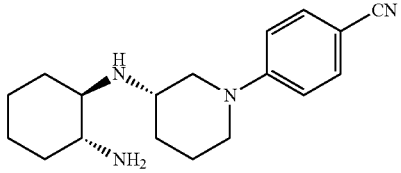

4-((S)-3-((1R,2R)-2-Aminocyclohexylamino)piperidin-1-yl)benzonitrile was separated from its diastereomer using Chiral preparatory HPLC method B.

Intermediate 19

(1R,2R)—N1-((S)-1-(4-(1H-Pyrazol-1-yl)phenyl) piperidin-3-yl)cyclohexane-1,2-diamine

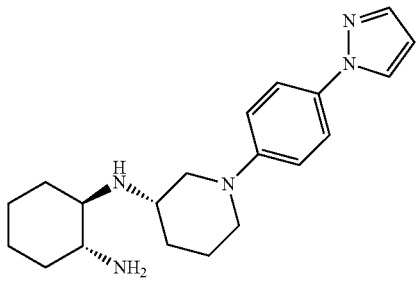 [SMILES: N[C@@H]1CCCC[C@H]1N[C@H]1CCCN(c2ccc(-n3cccn3)cc2)C1]

A: 1-(4-(1H-Pyrazol-1-yl)phenyl)piperidin-3-one

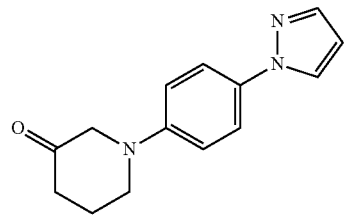 [SMILES: O=C1CCCN(c2ccc(-n3cccn3)cc2)C1]

1-(4-(1H-Pyrazol-1-yl)phenyl)piperidin-3-one (300 mg, 1.243 mmol) was synthesized as described in General Procedure B using 1-(4-bromophenyl)-1H-pyrazole. The resulting product 1-(4-(1H-pyrazol-1-yl)phenyl)piperidin-3-ol was oxidized using General Procedure D to give the title compound.

B: tert-Butyl (1R,2R)-2-((S)-1-(4-(1H-pyrazol-1-yl) phenyl)piperidin-3-ylamino)cyclohexylcarbamate

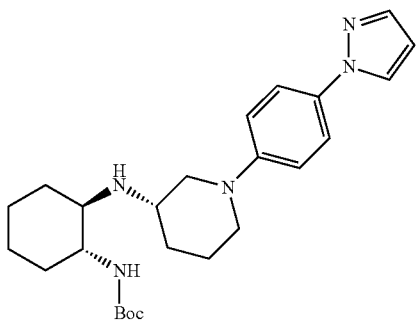 [SMILES: CC(C)(C)OC(=O)N[C@@H]1CCCC[C@H]1N[C@H]1CCCN(c2ccc(-n3cccn3)cc2)C1]

tert-Butyl (1R,2R)-2-((S)-1-(4-(1H-pyrazol-1-yl)phenyl) piperidin-3-ylamino)cyclohexylcarbamate (172 mg, 0.391 mmol) was synthesized as described in General Procedure F using 1-(4-(1H-pyrazol-1-yl)phenyl)piperidin-3-one. The crude product was purified using silica gel chromatography (ISCO system) which separated the two diastereomers. The desired product was collected to give the title compound.

C: (1R,2R)—N1-((S)-1-(4-(1H-Pyrazol-1-yl)phenyl) piperidin-3-yl)cyclohexane-1,2-diamine

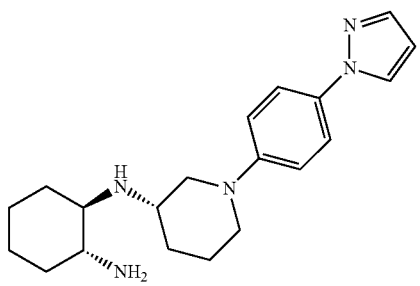 [SMILES: N[C@@H]1CCCC[C@H]1N[C@H]1CCCN(c2ccc(-n3cccn3)cc2)C1]

(1R,2R)—N1-((S)-1-(4-(1H-Pyrazol-1-yl)phenyl)piperidin-3-yl)cyclohexane-1,2-diamine bis-trifluoroacetate (220 mg, 0.388 mmol, 100% yield) was synthesized as described in General Procedure G using tert-butyl (1R,2R)-2-((S)-1-(4-(1H-pyrazol-1-yl)phenyl)piperidin-3-ylamino)cyclohexylcarbamate (170 mg, 0.388 mmol). Anal. Calcd. for $C_{20}H_{29}N_5$ m/z 339.4, found: 340.3 $(M+H)^+$.

Intermediate 20

(1R,2R)—N1-((S)-1-(4-(Trifluoromethyl)phenyl) piperidin-3-yl)cyclohexane-1,2-diamine bis-trifluoroacetate

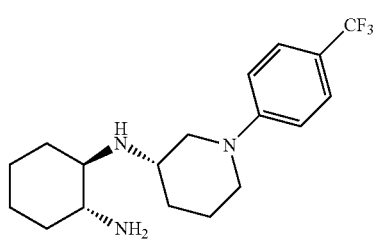 [SMILES: N[C@@H]1CCCC[C@H]1N[C@H]1CCCN(c2ccc(C(F)(F)F)cc2)C1]

A: 1-(4-(Trifluoromethyl)phenyl)piperidin-3-ol

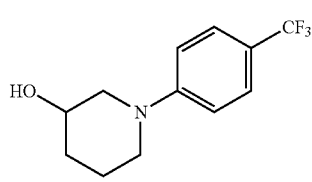 [SMILES: OC1CCCN(c2ccc(C(F)(F)F)cc2)C1]

1-(4-(Trifluoromethyl)phenyl)piperidin-3-ol (760 mg, 3.10 mmol) was synthesized in 70% yield as described in General Procedure B using 1-bromo-4-(trifluoromethyl)benzene (1 gm, 4.44 mmol).

B: 1-(4-(Trifluoromethyl)phenyl)piperidin-3-one

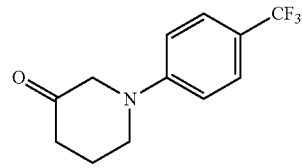 [SMILES: O=C1CCCN(c2ccc(C(F)(F)F)cc2)C1]

1-(4-(Trifluoromethyl)phenyl)piperidin-3-one (240 mg, 0.987 mmol) was synthesized in 60% yield as described in General Procedure D using 1-(4-(trifluoromethyl)phenyl)piperidin-3-ol. Anal. Calcd. for $C_{12}H_{12}F_3NO$ m/z 243.3, found: 244.1 $(M+H)^+$.

C: tert-Butyl (1R,2R)-2-((S)-1-(4-(trifluoromethyl) phenyl)piperidin-3-ylamino)cyclohexylcarbamate

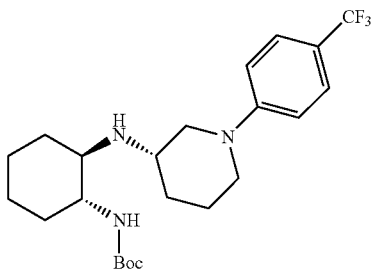 [SMILES: CC(C)(C)OC(=O)N[C@@H]1CCCC[C@H]1N[C@H]1CCCN(c2ccc(C(F)(F)F)cc2)C1]

tert-Butyl (1R,2R)-2-((S)-1-(4-(trifluoromethyl)phenyl) piperidin-3-ylamino)cyclohexylcarbamate (31 mg, 0.070 mmol, 17% yield) was synthesized as described in General Procedure F using 1-(4-(trifluoromethyl)phenyl)piperidin-3-one (100 mg, 0.441 mmol). During the ISCO purification, two diastereomers were separated and the desired product was collected. Anal. Calcd. For $C_{23}H_{34}F_3N_3O_2$ m/z 441.26, found: 442.4 $(M+H)^+$. $^1H$ NMR (400 MHz, $CDCl_3$) δ ppm 7.46 (d, J=8.8 Hz, 2H), 6.92 (d, J=8.7 Hz, 2H), 4.49 (s, 1H), 3.65 (d, J=11.4 Hz, 1H), 3.58-3.49 (m, 1H), 3.28-3.13 (m, 1H), 2.95-2.84 (m, 1H), 2.84-2.72 (m, 1H), 2.70-2.61 (m, 1H), 2.34 (td, J=10.1, 3.9 Hz, 1H), 2.14-1.97 (m, 2H), 1.96-1.87 (m, 1H), 1.86-1.75 (m, 1H), 1.75-1.62 (m, 3H), 1.61-1.50 (m, 1H), 1.42 (s, 9H), 1.36-1.10 (m, 4H).

D: (1R,2R)—N1-((S)-1-(4-(Trifluoromethyl)phenyl) piperidin-3-yl)cyclohexane-1,2-diamine bis-trifluoroacetate

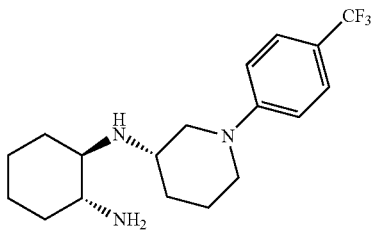 [SMILES: N[C@@H]1CCCC[C@H]1N[C@H]1CCCN(c2ccc(C(F)(F)F)cc2)C1]

(1R,2R)—N1-((S)-1-(4-(Trifluoromethyl)phenyl)piperidin-3-yl)cyclohexane-1,2-diamine bis-trifluoroacetate (39 mg, 0.068 mmol) was synthesized in 100% yield as described in General Procedure G using tert-butyl (1R,2R)-2-((S)-1-(4-

(trifluoromethyl)phenyl)piperidin-3-ylamino)cyclohexylcarbamate (30 mg, 0.068 mmol). Anal. Calcd. for C$_{18}$H$_{26}$F$_3$N3 m/z 341.41, found: 242.3 (M+H)$^+$.

Intermediate 21

(1R,2R)—N1-((S)-1-(5-Nitropyrimidin-2-yl)piperidin-3-yl)cyclohexane-1,2-diamine

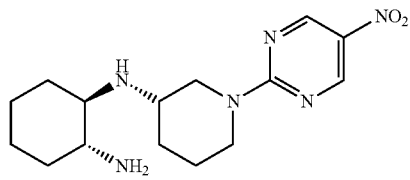

A: 1-(5-Nitropyrimidin-2-yl)piperidin-3-ol

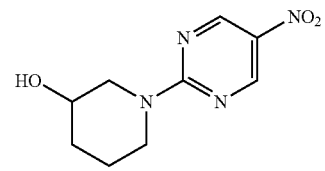 [SMILES: O=[N+]([O-])c1cnc(N2CCCC(O)C2)nc1]

To a stirring solution of piperidin-3-ol (0.333 g, 3.29 mmol) and 2-chloro-5-nitropyrimidine (0.500 g, 3.13 mmol) in DMF (8 mL) was added K$_2$CO$_3$ (1.04 g, 7.52 mmol). The resulting yellowish suspension was stirred at 70° C. for 1.5 h. After this time, the reaction was determined to be complete by LC/MS. The reaction mixture was cooled to rt, then partitioned between water and EtOAc. The separated aqueous phase was extracted with EtOAc (2×). The combined EtOAc extracts were washed with water (1×), saturated aqueous NaCl (2×), dried over Na$_2$SO$_4$, filtered and concentrated. The resulting residue was dried under vacuum for 30 min to afford the desired product 1-(5-nitropyrimidin-2-yl)piperidin-3-ol (536 mg, 2.391 mmol, 76% yield) as a yellow solid. Anal. Calcd. for C$_9$H$_{12}$N$_4$O$_3$ m/z 224.2, found: 225.1 (M+H)$^+$; $^1$H NMR (400 MHz, CDCl$_3$) δ ppm 9.17-8.91 (m, 2 H), 4.20 (dd, J=13.14, 3.03 Hz, 1 H), 4.03 (ddd, J=13.07, 7.14, 3.79 Hz, 1 H), 3.96-3.74 (m, 2 H), 2.95 (s, 1 H), 2.11-1.87 (m, 2 H), 1.81-1.50 (m, 3 H).

B: 1-(5-Nitropyrimidin-2-yl)piperidin-3-one

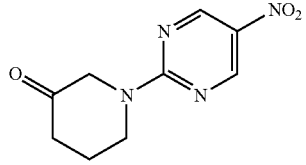 [SMILES: O=C1CCCN(c2ncc([N+](=O)[O-])cn2)C1]

1-(5-Nitropyrimidin-2-yl)piperidin-3-one (260 mg, 1.179 mmol, 50.5% yield) was synthesized as described in General Procedure D. Anal. Calcd. for C$_9$H$_{10}$N$_4$O$_3$ m/z 222.2, found: 223.0 (M+H)$^+$; $^1$H NMR (400 MHz, CDCl$_3$) δ ppm 9.11 (d, J=4.95 Hz, 2 H), 4.56 (s, 2 H), 4.17-4.02 (m, 2 H), 2.60 (t, J=6.60 Hz, 2 H), 2.26-2.06 (m, 2 H).

C: tert-Butyl (1R,2R)-2-((S)-1-(5-nitropyrimidin-2-yl)piperidin-3-ylamino)cyclohexylcarbamate

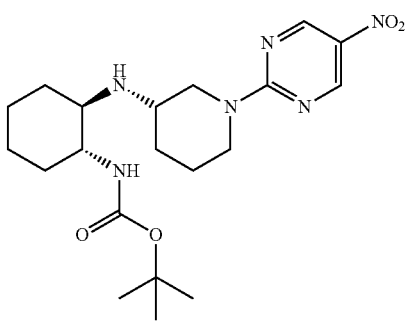

tert-Butyl (1R,2R)-2-((S)-1-(5-nitropyrimidin-2-yl)piperidin-3-ylamino)cyclohexylcarbamate (95 mg, 0.226 mmol) was synthesized as described in General Procedure F. The crude product was purified by silica gel chromatography (ISCO system) with the two diastereomers separating. The desired isomer was collected to give ISCO purification, two diastereomers were separated and the desired product was collected to give tert-butyl (1R,2R)-2-((S)-1-(5-nitropyrimidin-2-yl)piperidin-3-ylamino)cyclohexylcarbamate. Anal. Calcd. for C$_{20}$H$_{32}$N$_6$O$_4$ m/z 420.5, found: 421.3 (M+H)$^+$; $^1$H NMR (400 MHz, CDCl$_3$) δ ppm 9.05 (s, 2 H), 5.24-5.17 (m, 1 H), 4.92-4.75 (m, 1 H), 4.58-4.44 (m, 1 H), 3.88-3.74 (m, 1 H), 3.66-3.53 (m, 1 H), 3.48-3.40 (m, 1 H), 3.33-3.16 (m, 2 H), 2.26-2.11 (m, 2 H), 2.06-1.86 (m, 3 H), 1.85-1.77 (m, 1 H), 1.72-1.48 (m, 2 H), 1.41 (s, 9 H), 1.36-1.21 (m, 2 H).

D: (1R,2R)—N1-((S)-1-(5-Nitropyrimidin-2-yl)piperidin-3-yl)cyclohexane-1,2-diamine

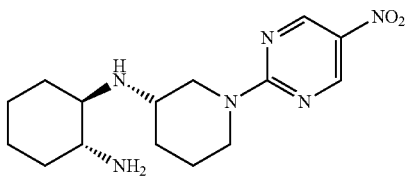

(1R,2R)—N1-((S)-1-(5-Nitropyrimidin-2-yl)piperidin-3-yl)cyclohexane-1,2-diamine bis-trifluoroacetate (220 mg, 0.388 mmol, 100% yield) was synthesized as described in General Procedure G using tert-butyl (1R,2R)-2-((S)-1-(4-(1H-pyrazol-1-yl)phenyl)piperidin-3-ylamino)cyclohexylcarbamate (149 mg, 0.272 mmol). Anal. Calcd. for C$_{15}$H$_{24}$N$_6$O$_2$ m/z 320.3, found: 321.1 (M+H)$^+$.

Intermediate 22

(1R,2R)—N1-(1-(4-(Oxazol-2-yl)phenyl)piperidin-3-yl)cyclohexane-1,2-diamine

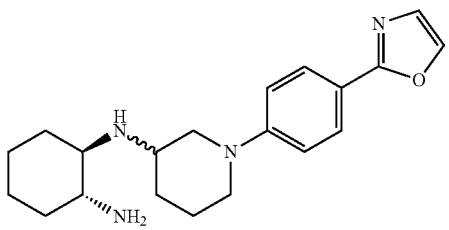 [SMILES: N[C@@H]1CCCC[C@H]1NC1CCCN(c2ccc(-c3ncco3)cc2)C1]

A: 1-(4-(Oxazol-2-yl)phenyl)piperidin-3-ol

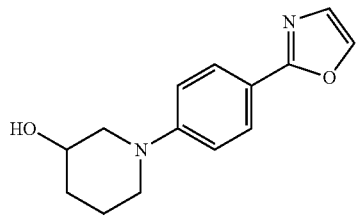 [SMILES: OC1CCCN(c2ccc(-c3ncco3)cc2)C1]

1-(4-(Oxazol-2-yl)phenyl)piperidin-3-ol (245 mg, 1.00 mmol) was synthesized in 45% yield, as described in General Procedure B using 2-(4-bromophenyl)oxazole (500 mg, 2.232 mmol) and piperidin-3-ol (451 mg, 4.46 mmol). Anal. Calcd. for $C_{14}H_{16}N_2O_2$ m/z 244.2, found: 245.0 (M+H)$^+$.

B: 1-(4-(Oxazol-2-yl)phenyl)piperidin-3-yl methanesulfonate

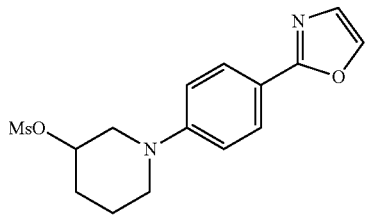 [SMILES: CS(=O)(=O)OC1CCCN(c2ccc(-c3ncco3)cc2)C1]

To a solution of 1-(4-(oxazol-2-yl)phenyl)piperidin-3-ol (85 mg, 0.348 mmol) in $CH_2Cl_2$ (2 mL) at 0° C. was added dropwise mesyl chloride (0.033 mL, 0.418 mmol), followed by $Et_3N$ (0.058 mL, 0.418 mmol). The reaction was stirred at 0° C. for 5 min, and then at rt for 30 min. After this time, HPLC and LC/MS showed that the desired product formed and there was no starting material remaining. The reaction mixture was concentrated. The residue was dissolved in EtOAc, washed with water, saturated aqueous $NaHCO_3$, and saturated aqueous NaCl. The organic layer was dried over $Na_2SO_4$, filtered and concentrated to give the desired product 1-(4-(oxazol-2-yl)phenyl)piperidin-3-yl methanesulfonate (110 mg, 0.341 mmol, 98% yield) as an off-white foam. Anal. Calcd. for $C_{15}H_{18}N_2O_4S$ m/z 322.3, found: 323.1 (M+H)$^+$.

C: tert-Butyl (1R,2R)-2-(1-(4-(oxazol-2-yl)phenyl)piperidin-3-ylamino)cyclohexylcarbamate

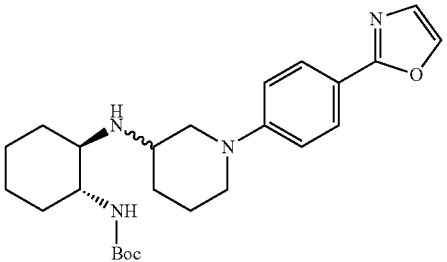 [SMILES: CC(C)(C)OC(=O)N[C@@H]1CCCC[C@H]1NC1CCCN(c2ccc(-c3ncco3)cc2)C1]

To a solution of 1-(4-(oxazol-2-yl)phenyl)piperidin-3-yl methane sulfonate (110 mg, 0.341 mmol) in acetonitrile (4 mL) was added tert-butyl (1R,2R)-2-aminocyclohexylcarbamate (110 mg, 0.512 mmol). The reaction was stirred in a microwave at 120° C. for 30 min. After this time, LC/MS showed two pairs of products formed. The reaction mixture was concentrated. The residue was diluted with EtOAc and washed with water. The remaining EtOAc organic layer was concentrated. The resulting residue was purified using silica gel chromatography (ISCO system) eluting with a gradient of 50-100% EtOAc/Hex. Under these conditions, the two diastereomers separated and the desired diastereomer tert-butyl (1R,2R)-2-((1-(4-(oxazol-2-yl)phenyl)pyrrolidin-2-yl)methylamino)cyclohexylcarbamate (156 mg total) as a white foam.

D: (1R,2R)—N1-(1-(4-(Oxazol-2-yl)phenyl)piperidin-3-yl)cyclohexane-1,2-diamine

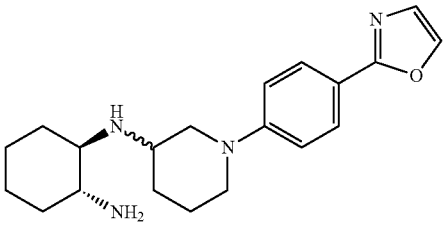 [SMILES: N[C@@H]1CCCC[C@H]1NC1CCCN(c2ccc(-c3ncco3)cc2)C1]

To a solution of tert-butyl (1R,2R)-2-(1-(4-(oxazol-2-yl)phenyl)piperidin-3-ylamino)cyclohexylcarbamate (32 mg, 0.073 mmol) and tert-butyl (1R,2R)-2-((1-(4-(oxazol-2-yl)phenyl)pyrrolidin-2-yl)methylamino)cyclohexylcarbamate (134.0 mg, 0.304 mmol) in $CH_2Cl_2$ (1.5 mL) was added trifluoroacetic acid (1.5 mL, 19.47 mmol). The reaction was stirred at rt for 1 h. After this time, LC/MS showed no SM remained and the desired product formed. The reaction was concentrated, and the resulting residue was reconcentrated from $CH_2Cl_2$ (2×5 mL). The residue was dried under high vacuum for 1 h to afford the desired product (1R,2R)—N1-(1-(4-(oxazol-2-yl)phenyl)piperidin-3-yl)cyclohexane-1,2-diamine bis-trifluoroacetate (41 mg, 0.072 mmol, 99% yield) and (1R,2S)—N1-((1-(4-(oxazol-2-yl)phenyl)pyrrolidin-2- yl)methyl)cyclohexane-1,2-diamine bis-trifluoroacetate (32 mg, 0.053 mmol, 100% yield) as an oil.

Intermediate 23

(1R,2R)—N1-(1-(4-(5-Methyl-1,3,4-oxadiazol-2-yl)phenyl)piperidin-3-yl)cyclohexane-1,2-diamine bis-trifluoromethyl acetate

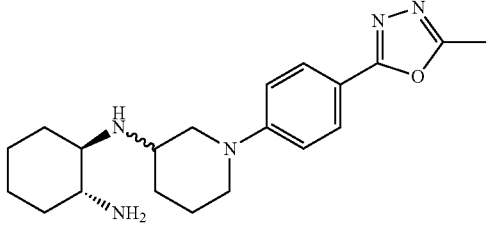 [SMILES: Cc1nnc(-c2ccc(N3CCCC(N[C@@H]4CCCC[C@H]4N)C3)cc2)o1]

A: 1-(4-(5-Methyl-1,3,4-oxadiazol-2-yl)phenyl)piperidin-3-ol

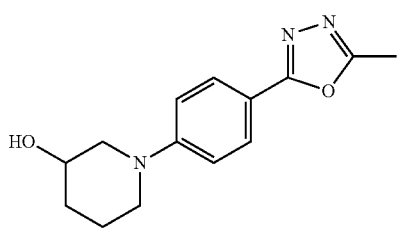 [SMILES: Cc1nnc(-c2ccc(N3CCCC(O)C3)cc2)o1]

1-(4-(5-Methyl-1,3,4-oxadiazol-2-yl)phenyl)piperidin-3-ol (400 mg, 1.543 mmol, 36.9% yield) was synthesized as described in General Procedure B using 2-(4-bromophenyl)-5-methyl-1,3,4-oxadiazole (1.0 g, 4.18 mmol) to give the title compound as a white solid. Anal. Calcd. for $C_{14}H_{17}N_3O_2$ m/z 259.3, found: 260.1 (M+H)$^+$.

B: 1-(4-(5-Methyl-1,3,4-oxadiazol-2-yl)phenyl)piperidin-3-one

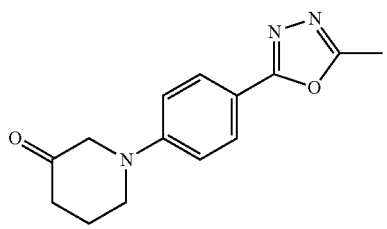 [SMILES: Cc1nnc(-c2ccc(N3CCCC(=O)C3)cc2)o1]

1-(4-(5-Methyl-1,3,4-oxadiazol-2-yl)phenyl)piperidin-3-one (334 mg, 1.298 mmol, 84% yield) was synthesized as described in General Procedure D using 1-(4-(5-methyl-1,3,4-oxadiazol-2-yl)phenyl)piperidin-3-ol (400 mg, 1.543 mmol) to give the title compound as a white solid. Anal. Calcd. for $C_{14}H_{15}N_3O_2$ m/z 257.2, found: 258.2 (M+H)$^+$.

C: tert-Butyl (1R,2R)-2-(1-(4-(5-methyl-1,3,4-oxadiazol-2-yl)phenyl)piperidin-3-ylamino)cyclohexylcarbamate

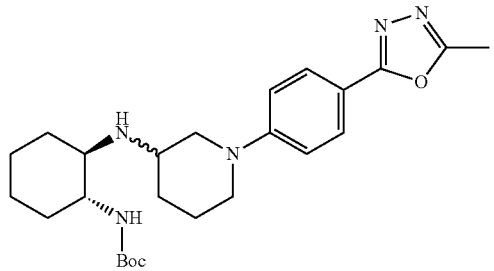 [SMILES: Cc1nnc(-c2ccc(N3CCCC(N[C@@H]4CCCC[C@H]4NC(=O)OC(C)(C)C)C3)cc2)o1]

tert-Butyl (1R,2R)-2-(1-(4-(5-methyl-1,3,4-oxadiazol-2-yl)phenyl)piperidin-3-ylamino)cyclohexylcarbamate (300 mg, 0.658 mmol, 51.3% yield) was synthesized as described in General Procedure F using 1-(4-(5-methyl-1,3,4-oxadiazol-2-yl)phenyl)piperidin-3-one (330 mg, 1.283 mmol) to give the title compound as a white solid. Anal. Calcd. for $C_{25}H_{37}N_5O_3$ m/z 455.5, found: 456.4 (M+H)$^+$.

D: (1R,2R)—N1-(1-(4-(5-Methyl-1,3,4-oxadiazol-2-yl)phenyl)piperidin-3-yl)cyclohexane-1,2-diamine bis-trifluoromethylacetate

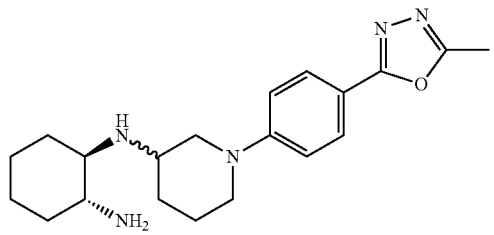 [SMILES: Cc1nnc(-c2ccc(N3CCCC(N[C@@H]4CCCC[C@H]4N)C3)cc2)o1]

(1R,2R)—N1-(1-(4-(5-methyl-1,3,4-oxadiazol-2-yl)phenyl)piperidin-3-yl)cyclohexane-1,2-diamine bis-trifluoromethylacetate (400 mg, 0.658 mmol, 100% yield) was synthesized as described in General Procedure F using tert-butyl (1R,2R)-2-(1-(4-(5-methyl-1,3,4-oxadiazol-2-yl)phenyl)piperidin-3-ylamino)cyclohexylcarbamate (300 mg, 0.658 mmol) to give the title compound as a light brown oil.

Intermediate 24

4-((S)-3-((1R,2R)-2-Aminocyclohexylamino)piperidin-1-yl)-3-fluorobenzonitrile

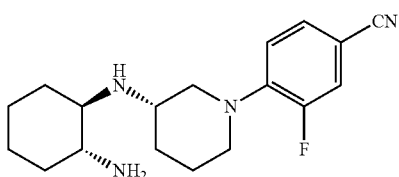

A: 3-Fluoro-4-(3-hydroxypiperidin-1-yl)benzonitrile

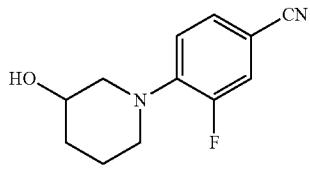 [SMILES: N#Cc1ccc(N2CCCC(O)C2)c(F)c1]

3-Fluoro-4-(3-hydroxypiperidin-1-yl)benzonitrile (2850 mg, 12.94 mmol, 90% yield) was synthesized as described in General Procedure A using 3,4-difluorobenzonitrile (2.0 g, 14.38 mmol) to give the title compound as a white solid. Anal. Calcd. for $C_{12}H_{13}FN_2O$ m/z 220.2, found: 221.1 $(M+H)^+$.

B: 3-Fluoro-4-(3-oxopiperidin-1-yl)benzonitrile

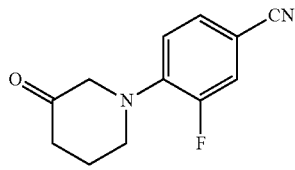 [SMILES: N#Cc1ccc(N2CCCC(=O)C2)c(F)c1]

To a solution of 3-fluoro-4-(3-hydroxypiperidin-1-yl)benzonitrile (2.4 g, 10.90 mmol) in $CH_2Cl_2$ (50 mL) was added Dess-Martin Periodinane (6.93 g, 16.35 mmol). The reaction was stirred at rt for 1 h. The reaction was then diluted with $CH_2Cl_2$, washed with aqueous 10% $Na_2S_2O_3$, saturated aqueous $Na_2CO_3$ and saturated aqueous NaCl. The organic layer was dried over $Na_2SO_4$, filtered and concentrated. The resulting residue was purified using silica gel chromatography (ISCO system) eluting with a gradient of 0-50% EtOAc/Hex to give the product, 3-fluoro-4-(3-oxopiperidin-1-yl)benzonitrile, (730 mg, 3.35 mmol, 30.7% yield) as a white foam. Anal. Calcd. for $C_{12}H_{11}FN_2O$ m/z 218.2, found: 219.1 $(M+H)^+$.

C: tert-Butyl (1R,2R)-2-((S)-1-(4-cyano-2-fluorophenyl)piperidin-3-ylamino)cyclohexylcarbamate

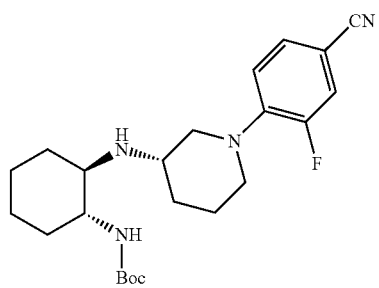 [SMILES: CC(C)(C)OC(=O)N[C@@H]1CCCC[C@H]1N[C@H]1CCCN(c2ccc(C#N)cc2F)C1]

tert-Butyl (1R,2R)-2-((S)-1-(4-cyano-2-fluorophenyl)piperidin-3-ylamino)cyclohexylcarbamate (670 mg, 1.609 mmol, 50.1% yield) was synthesized as described in General Procedure F using 3-fluoro-4-(3-oxopiperidin-1-yl)benzonitrile (700 mg, 21.12 mmol). The crude material was purified by silica gel chromatography (ISCO system) with the desired diastereomer eluted off the ISCO column behind the undesired diastereomer. The title compound was isolated as a white solid. Anal. Calcd. for $C_{23}H_{33}FN_4O_2$ m/z 416.5, found: 417.1 $(M+H)^+$.

D: 4-((S)-3-((1R,2R)-2-Aminocyclohexylamino)piperidin-1-yl)-3-fluorobenzonitrile

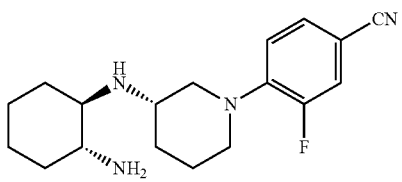 [SMILES: N#Cc1ccc(N2CCC[C@H](N[C@@H]3CCCC[C@H]3N)C2)c(F)c1]

4-((S)-3-((1R,2R)-2-Aminocyclohexylamino)piperidin-1-yl)-3-fluorobenzonitrile bis-trifluoromethylacetate (1,000 mg, 1.519 mmol, 100% yield) was synthesized as described in General Procedure G using tert-butyl (1R,2R)-2-((S)-1-(4-cyano-2-fluorophenyl)piperidin-3-ylamino)cyclohexylcarbamate (630 mg, 1.512 mmol) to give the title compound as a pink semi-solid. Anal. Calcd. for $C_{18}H_{25}FN_4$ m/z 316.4, found: 317.3 $(M+H)^+$.

Intermediate 25

(1R,2R)—N1-((S)-1-(4-(Trifluoromethoxy)phenyl)piperidin-3-yl)cyclohexane-1,2-diamine

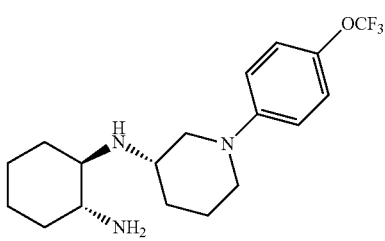 [SMILES: N[C@@H]1CCCC[C@H]1N[C@H]1CCCN(c2ccc(OC(F)(F)F)cc2)C1]

A: 1-(4-(Trifluoromethoxy)phenyl)piperidin-3-ol

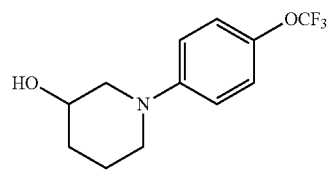 [SMILES: OC1CCCN(c2ccc(OC(F)(F)F)cc2)C1]

1-(4-(Trifluoromethoxy)phenyl)piperidin-3-ol (770 mg, 2.95 mmol, 54.6% yield) was synthesized as described in General Procedure B using 1-bromo-4-(trifluoromethoxy)benzene (1.3 g, 5.39 mmol) to give the title compound as an oil. Anal. Calcd. for $C_{12}H_{14}F_3NO_2$ m/z 261.2, found: 262.3 $(M+H)^+$.

B: 1-(4-(Trifluoromethoxy)phenyl)piperidin-3-one

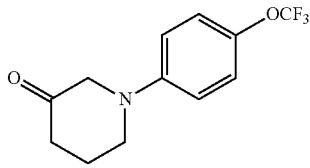 [SMILES: O=C1CCCN(c2ccc(OC(F)(F)F)cc2)C1]

1-(4-(Trifluoromethoxy)phenyl)piperidin-3-one (600 mg, 2.95 mmol, 80% yield) was synthesized as described in General Procedure C using 1-(4-(trifluoromethoxy)phenyl)piperidin-3-ol (760 mg, 2.315 mmol) to give the title compound as an off-white solid. Anal. Calcd. for $C_{12}H_{12}F_3NO_2$ m/z 259.2, found: 260.1 (M+H)+; $^1$H NMR (400 MHz, CDCl$_3$) δ ppm 7.13 (d, J=8.24 Hz, 2 H), 6.86-6.75 (m, 2 H), 3.80 (s, 2 H), 3.51-3.39 (m, 2 H), 2.56-2.47 (m, 2 H), 2.22-2.07 (m, 2 H).

C: tert-Butyl (1R,2R)-2-((S)-1-(4-(trifluoromethoxy)phenyl)piperidin-3-ylamino)cyclohexylcarbamate

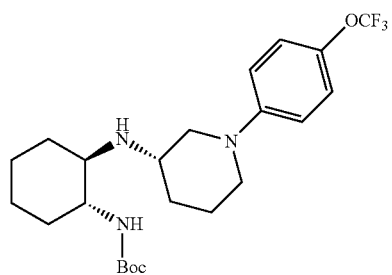 [SMILES: CC(C)(C)OC(=O)N[C@@H]1CCCC[C@H]1N[C@H]1CCCN(c2ccc(OC(F)(F)F)cc2)C1]

tert-Butyl (1R,2R)-2-((S)-1-(4-(trifluoromethoxy)phenyl)piperidin-3-ylamino)cyclohexylcarbamate (670 mg, 1.464 mmol, 63.3% yield) was synthesized as described in General Procedure F using 1-(4-(trifluoromethoxy)phenyl)piperidin-3-one (496 mg, 2.315 mmol). The crude material was purified by silica gel chromatography (ISCO system) with the desired diastereomer eluted off the ISCO column behind the undesired diastereomer. The title compound was isolated as an off-white foam. Anal. Calcd. for $C_{23}H_{34}F_3N_3O_2$ m/z 457.5, found: 458.2 (M+H)+.

D: (1R,2R)—N1-((S)-1-(4-(Trifluoromethoxy)phenyl)piperidin-3-yl)cyclohexane-1,2-diamine

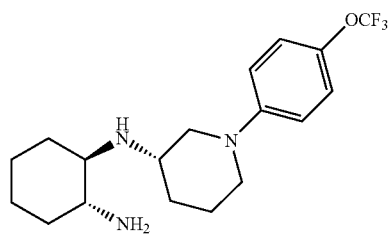

(1R,2R)—N1-((S)-1-(4-(Trifluoromethoxy)phenyl)piperidin-3-yl)cyclohexane-1,2-diamine bis-trifluoroacetate (950 mg, 1.168 mmol, 100% yield) was synthesized as described in General Procedure G using tert-butyl (1R,2R)-2-((S)-1-(4-(trifluoromethoxy)phenyl)piperidin-3-ylamino)cyclohexylcarbamate (520 mg, 1.137 mmol) to give the title compound as an off-white solid.

Intermediate 26

4-(3-((1R,2R)-2-Aminocyclohexylamino)piperidin-1-yl)-2-fluorobenzonitrile

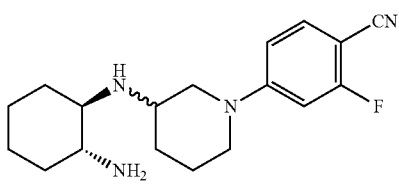 [SMILES: N#Cc1ccc(N2CCCC(N[C@@H]3CCCC[C@H]3N)C2)cc1F]

A: 2-Fluoro-4-(3-hydroxypiperidin-1-yl)benzonitrile

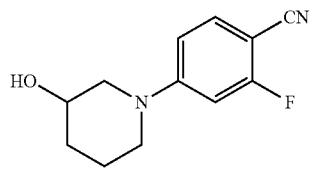 [SMILES: N#Cc1ccc(N2CCCC(O)C2)cc1F]

2-Fluoro-4-(3-hydroxypiperidin-1-yl)benzonitrile (770 mg, 3.50 mmol, 35% yield) was synthesized as described in General Procedure B using 4-bromo-2-fluorobenzonitrile (2,000 mg, 10.0 mmol) to give the title compound as an off-white foam. Anal. Calcd. for $C_{12}H_{13}FN_2O$ m/z 220.2, found: 221.1 (M+H)+.

B: 2-Fluoro-4-(3-oxopiperidin-1-yl)benzonitrile

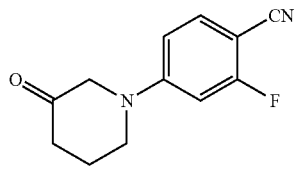 [SMILES: N#Cc1ccc(N2CCCC(=O)C2)cc1F]

To a solution of 2-fluoro-4-(3-hydroxypiperidin-1-yl)benzonitrile (1,000 mg, 4.54 mmol) in CH$_2$Cl$_2$ (2 mL) was added Dess-Martin Periodinane (231 mg, 0.545 mmol). The reaction was stirred at rt for 1 h. The reaction was diluted CH$_2$Cl$_2$, washed with saturated aqueous NaHCO$_3$ and saturated aqueous NaCl. The organic layer was dried over Na$_2$SO$_4$, filtered and concentrated. The resulting residue was purified using silica gel chromatography (ISCO system) eluting with a gradient of 0-50% EtOAc/Hex to give the product, 2-fluoro-4-(3-oxopiperidin-1-yl)benzonitrile, (600 mg, 2.75 mmol, 60.6% yield) as a white foam. Anal. Calcd. for $C_{12}H_{11}FN_2O$ m/z 218.2, found: 219.1 (M+H)⁺.

C: tert-Butyl (1R,2R)-2-(1-(4-cyano-3-fluorophenyl) piperidin-3-ylamino)cyclohexylcarbamate

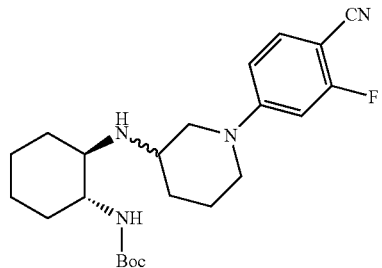 [SMILES: CC(C)(C)OC(=O)N[C@@H]1CCCC[C@H]1NC1CCCN(c2ccc(C#N)c(F)c2)C1]

tert-Butyl (1R,2R)-2-(1-(4-cyano-3-fluorophenyl)piperidin-3-ylamino)cyclohexylcarbamate (330 mg, 0.792 mmol, 43.2% yield) was synthesized as described in General Procedure F using 2-fluoro-4-(3-oxopiperidin-1-yl)benzonitrile (400 mg, 1.833 mmol) to give the title compound as an off-white foam. Anal. Calcd. for $C_{23}H_{33}F_3N_4O_2$ m/z 416.5, found: 417.2 (M+H)⁺.

D: 4-(3-((1R,2R)-2-Aminocyclohexylamino)piperidin-1-yl)-2-fluorobenzonitrile

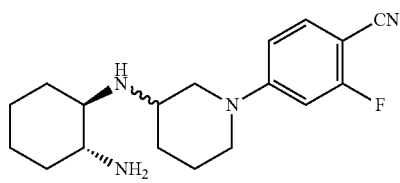 [SMILES: N#Cc1ccc(N2CCCC(N[C@@H]3CCCC[C@H]3N)C2)cc1F]

4-(3-((1R,2R)-2-Aminocyclohexylamino)piperidin-1-yl)-2-fluorobenzonitrile bis-trifluoroacetate (697 mg, 0.840 mmol, 100% yield) was synthesized as described in General Procedure G using tert-butyl (1R,2R)-2-(1-(4-cyano-3-fluorophenyl)piperidin-3-ylamino)cyclohexylcarbamate (350 mg, 0.840 mmol) to give the title compound as an oil. Anal. Calcd. for $C_{18}H_{25}FN_4$ m/z 316.4, found: 317.2 (M+H)⁺.

Intermediate 27

(1R,2R)—N1-(1-(4-(1H-1,2,4-Triazol-1-yl)phenyl) piperidin-3-yl)cyclohexane-1,2-diamine

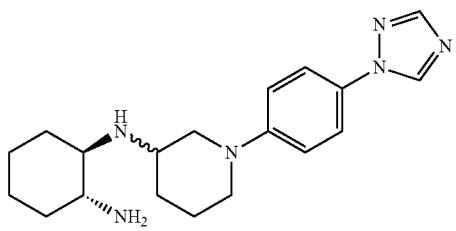 [SMILES: N[C@@H]1CCCC[C@H]1NC1CCCN(c2ccc(-n3cncn3)cc2)C1]

A: 1-(4-Iodophenyl)piperidin-3-ol

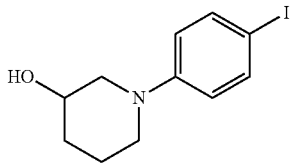 [SMILES: OC1CCCN(c2ccc(I)cc2)C1]

1-(4-Iodophenyl)piperidin-3-ol (1600 mg, 5.28 mmol, 26.7% yield) was synthesized as described in General Procedure B using 1,4-diiodobenzene (9780 mg, 29.7 mmol) to give the title compound as a yellow solid. Anal. Calcd. for $C_{11}H_{14}NO$ m/z 303.1, found: 304.0 (M+H)⁺.

B: 1-(4-(1H-1,2,4-Triazol-1-yl)phenyl)piperidin-3-ol

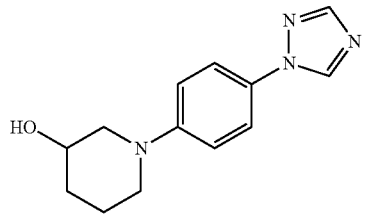 [SMILES: OC1CCCN(c2ccc(-n3cncn3)cc2)C1]

To a mixture of 1-(4-iodophenyl)piperidin-3-ol (920 mg, 3.03 mmol), 1H-1,2,4-triazole (272 mg, 3.95 mmol), (trans)-N1,N2-dimethylcyclohexane-1,2-diamine (43.2 mg, 0.303 mmol), $K_3PO_4$ (1288 mg, 6.07 mmol) and copper(I) iodide (28.9 mg, 0.152 mmol) in DMF (4 mL) was bubbled with Argon for 2 min. Then the reaction was stirred at 110° C. under Argon for 16 hrs. The reaction was diluted water and extracted with EtOAc (2×50 ml). Combined EtOAc extracts were washed with water (30 ml) and saturated aqueous NaCl (30 ml). The organic layer was dried over $Na_2SO_4$, filtered and concentrated. The resulting residue was purified using silica gel chromatography (ISCO system) eluting with a gradient of 0-100% EtOAc/Hex to give product 1-(4-(1H-1,2,4-triazol-1-yl)phenyl)piperidin-3-ol (453 mg, 1.854 mmol, 61.1% yield) as a foam. Anal. Calcd. for $C_{13}H_{16}N_4O$ m/z 244.2, found: 245.0 (M+H)⁺.

C: 1-(4-(1H-1,2,4-Triazol-1-yl)phenyl)piperidin-3-one

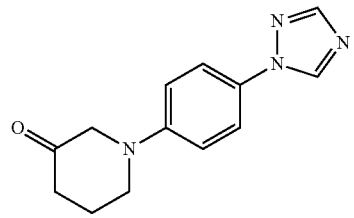 [SMILES: O=C1CCCN(c2ccc(-n3cncn3)cc2)C1]

1-(4-(1H-1,2,4-Triazol-1-yl)phenyl)piperidin-3-one (400 mg, 1.651 mmol, 94% yield) was synthesized as described in General Procedure D using 1-(4-(1H-1,2,4-triazol-1-yl)phenyl)piperidin-3-ol (430 mg, 1.76 mmol) to give the title compound as an off-white foam. Anal. Calcd. for C$_{13}$H$_{14}$N$_4$O m/z 242.2, found: 243.1 (M+H)$^+$.

D: tert-Butyl (1R,2R)-2-(1-(4-(1H-1,2,4-triazol-1-yl)phenyl)piperidin-3-ylamino)cyclohexylcarbamate

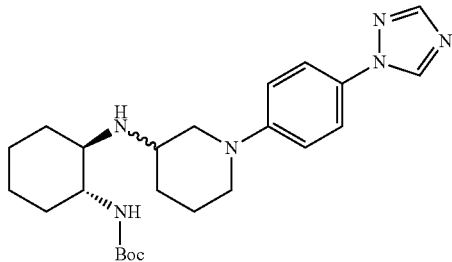 [SMILES: CC(C)(C)OC(=O)N[C@@H]1CCCC[C@H]1NC1CCCN(c2ccc(-n3cncn3)cc2)C1]

tert-Butyl (1R,2R)-2-(1-(4-(1H-1,2,4-triazol-1-yl)phenyl)piperidin-3-ylamino)cyclohexylcarbamate (415 mg, 0.942 mmol, 57.1% yield) was synthesized as described in General Procedure F using 1-(4-(1H-1,2,4-triazol-1-yl)phenyl)piperidin-3-one (400 mg, 1.651 mmol) to give the title compound as an off-white foam. Anal. Calcd. for C$_{24}$H$_{36}$N$_6$O$_2$ m/z 440.5, found: 441.3 (M+H)$^+$.

F: (1R,2R)—N1-(1-(4-(1H-1,2,4-Triazol-1-yl)phenyl)piperidin-3-yl)cyclohexane-1,2-diamine

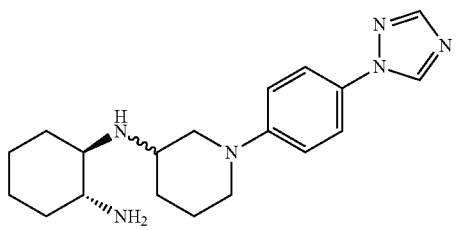 [SMILES: N[C@@H]1CCCC[C@H]1NC1CCCN(c2ccc(-n3cncn3)cc2)C1]

(1R,2R)—N1-(1-(4-(1H-1,2,4-Triazol-1-yl)phenyl)piperidin-3-yl)cyclohexane-1,2-diamine bis-trifluoroacetate (756 mg, 0.949 mmol, 100% yield) was synthesized as described in General Procedure G using tert-butyl (1R,2R)-2-(1-(4-(1H-1,2,4-triazol-1-yl)phenyl)piperidin-3-ylamino)cyclohexylcarbamate (415 mg, 0.949 mmol) to give the title compound as an oil. Anal. Calcd. for C$_{19}$H$_{28}$N$_6$ m/z 340.4, found: 341.2 (M+H)$^+$.

Intermediate 28

4-(3-((1R,2R)-2-Aminocyclohexylamino)piperidin-1-yl)-2-chlorobenzonitrile

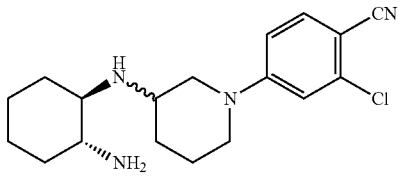

A: 2-Chloro-4-(3-hydroxypiperidin-1-yl)benzonitrile

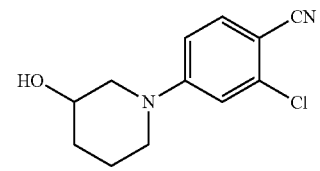 [SMILES: N#Cc1ccc(N2CCCC(O)C2)cc1Cl]

2-Chloro-4-(3-hydroxypiperidin-1-yl)benzonitrile (500 mg, 2.112 mmol, 21.4% yield) was synthesized as described in General Procedure A using 2-chloro-4-fluorobenzonitrile (1,846 mg, 11.86 mmol) to give the title compound as an oil. Anal. Calcd. for C$_{12}$H$_{13}$ClN$_2$O m/z 236.1, found: 237.1 (M+H)$^+$.

B: 2-Chloro-4-(3-oxopiperidin-1-yl)benzonitrile

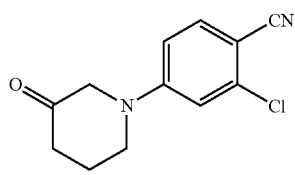 [SMILES: N#Cc1ccc(N2CCCC(=O)C2)cc1Cl]

2-Chloro-4-(3-oxopiperidin-1-yl)benzonitrile (360 mg, 1.534 mmol, 72.6% yield) was synthesized as described in General Procedure D using 2-chloro-4-(3-hydroxypiperidin-1-yl)benzonitrile (500 mg, 2.112 mmol) to give the title compound as an off-white foam. Anal. Calcd. for C$_{12}$H$_{11}$ClN$_2$O m/z 234.1, found: 235.0 (M+H)$^+$.

C: tert-Butyl (1R,2R)-2-(1-(3-chloro-4-cyanophenyl)piperidin-3-ylamino)cyclohexylcarbamate

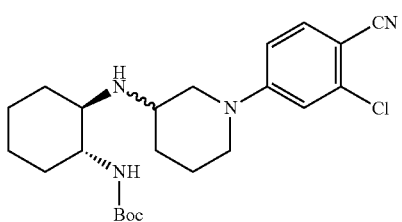 [SMILES: CC(C)(C)OC(=O)N[C@@H]1CCCC[C@H]1NC1CCCN(c2ccc(C#N)c(Cl)c2)C1]

tert-Butyl (1R,2R)-2-(1-(3-chloro-4-cyanophenyl)piperidin-3-ylamino)cyclohexylcarbamate (300 mg, 0.693 mmol, 45.8% yield) was synthesized as described in General Procedure F using 2-chloro-4-(3-oxopiperidin-1-yl)benzonitrile (355 mg, 1.513 mmol) to give the title compound as an off-white foam. Anal. Calcd. for C$_{23}$H$_{33}$ClN$_4$O$_2$ m/z 432.3, found: 433.2 (M+H)$^+$.

D: 4-(3-((1R,2R)-2-Aminocyclohexylamino)piperidin-1-yl)-2-chlorobenzonitrile

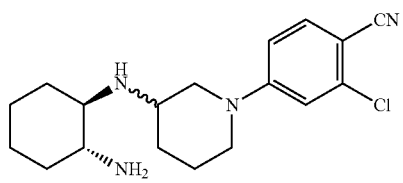

4-(3-((1R,2R)-2-Aminocyclohexylamino)piperidin-1-yl)-2-chlorobenzonitrile bis-trifluoroacetate (550 mg, 0.693 mmol, 100% yield) was synthesized as described in General Procedure G using tert-butyl (1R,2R)-2-(1-(3-chloro-4-cyanophenyl)piperidin-3-ylamino)cyclohexylcarbamate (300 mg, 0.693 mmol) to give the title compound as an off-white foam.

Intermediate 29

(1R,2R)—N1-(1-(3-Fluoro-4-(trifluoromethyl)phenyl)piperidin-3-yl)cyclohexane-1,2-diamine

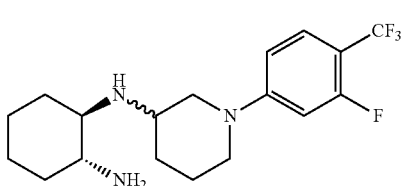

A: 1-(3-Fluoro-4-(trifluoromethyl)phenyl)piperidin-3-ol

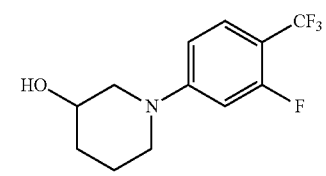 [SMILES: OC1CCCN(c2ccc(C(F)(F)F)c(F)c2)C1]

1-(3-Fluoro-4-(trifluoromethyl)phenyl)piperidin-3-ol (132 mg, 0.501 mmol, 14.5% yield) was synthesized as described in General Procedure B using 2-fluoro-4-iodo-1-(trifluoromethyl)benzene (1,000 mg, 3.45 mmol) to give the title compound as an oil. Anal. Calcd. for $C_{12}H_{13}F_4NO$ m/z 263.2, found: 264.2 (M+H)$^+$.

B: 1-(3-Fluoro-4-(trifluoromethyl)phenyl)piperidin-3-one

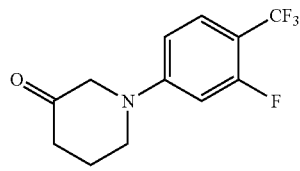 [SMILES: O=C1CCCN(c2ccc(C(F)(F)F)c(F)c2)C1]

1-(3-Fluoro-4-(trifluoromethyl)phenyl)piperidin-3-one (90 mg, 0.345 mmol, 69.8% yield) was synthesized as described in General Procedure D using 1-(3-fluoro-4-(trifluoromethyl)phenyl)piperidin-3-ol (130 mg, 0.494 mmol) to give the title compound as an off-white solid. Anal. Calcd. for $C_{12}H_{11}F_4NO$ m/z 261.2, found: 262.0 (M+H)$^+$.

C: tert-Butyl (1R,2R)-2-(1-(3-fluoro-4-(trifluoromethyl)phenyl)piperidin-3-ylamino)cyclohexylcarbamate

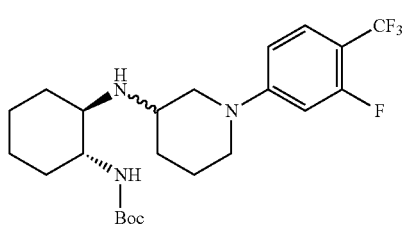 [SMILES: CC(C)(C)OC(=O)N[C@@H]1CCCC[C@H]1NC1CCCN(c2ccc(C(F)(F)F)c(F)c2)C1]

tert-Butyl (1R,2R)-2-(1-(3-fluoro-4-(trifluoromethyl)phenyl)piperidin-3-ylamino)cyclohexylcarbamate (42 mg, 0.091 mmol, 26.5% yield) was synthesized as described in General Procedure F using 1-(3-fluoro-4-(trifluoromethyl)phenyl)piperidin-3-one (90 mg, 0.345 mmol) to give the title compound as an off-white foam. Anal. Calcd. for $C_{23}H_{33}F_4N_3O_2$ m/z 459.5, found: 460.3 (M+H)$^+$.

D: (1R,2R)—N1-(1-(3-Fluoro-4-(trifluoromethyl)phenyl)piperidin-3-yl)cyclohexane-1,2-diamine

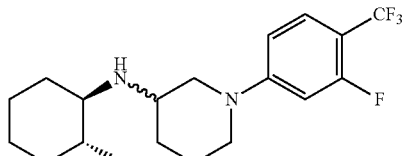

(1R,2R)—N1-(1-(3-Fluoro-4-(trifluoromethyl)phenyl)piperidin-3-yl)cyclohexane-1,2-diamine bis-trifluoroacetate (70 mg, 0.086 mmol, 99% yield) was synthesized as described in General Procedure G using tert-butyl (1R,2R)-

2-(1-(3-fluoro-4-(trifluoromethyl)phenyl)piperidin-3-ylamino)cyclohexylcarbamate (40 mg, 0.087 mmol) to give the title compound as an oil.

Intermediate 30

(1R,2R)—N1-((S)-1-(4-(4-Methyl-1H-pyrazol-1-yl)phenyl)piperidin-3-yl)cyclohexane-1,2-diamine

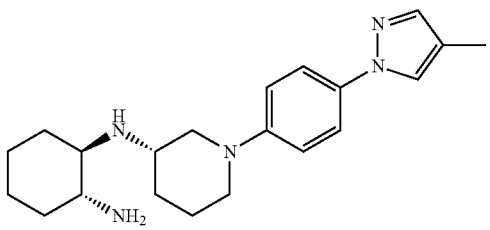 [SMILES: Cc1cnn(-c2ccc(N3CCC[C@H](N[C@@H]4CCCC[C@H]4N)C3)cc2)c1]

A: 1-(4-Iodophenyl)piperidin-3-one

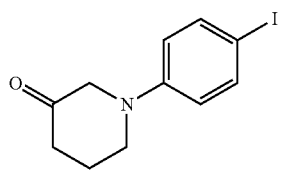 [SMILES: O=C1CCCN(c2ccc(I)cc2)C1]

1-(4-Iodophenyl)piperidin-3-one (1710 mg, 5.68 mmol, 86% yield) was synthesized as described in General Procedure D using 1-(4-iodophenyl)piperidin-3-ol (2.0 g, 6.6 mmol) to give the title compound as an off-white solid.

B: tert-Butyl (1R,2R)-2-((S)-1-(4-iodophenyl)piperidin-3-ylamino)cyclohexylcarbamate

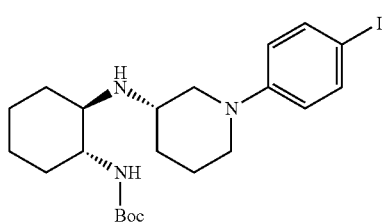 [SMILES: CC(C)(C)OC(=O)N[C@@H]1CCCC[C@H]1N[C@H]1CCCN(c2ccc(I)cc2)C1]

tert-Butyl (1R,2R)-2-((S)-1-(4-iodophenyl)piperidin-3-ylamino)cyclohexylcarbamate (1.45 g, 2.90 mmol, 51.4% yield) was synthesized as described in General Procedure F using 1-(4-iodophenyl)piperidin-3-one (1700 mg, 5.65 mmol) to give the title compound as an off-white solid. Anal. Calcd. for $C_{22}H_{34}IN_3O_2$ m/z 499.4, found: 501.5 (M+H)$^+$.

C: tert-Butyl (1R,2R)-2-((S)-1-(4-(4-methyl-1H-pyrazol-1-yl)phenyl)piperidin-3-ylamino)cyclohexylcarbamate

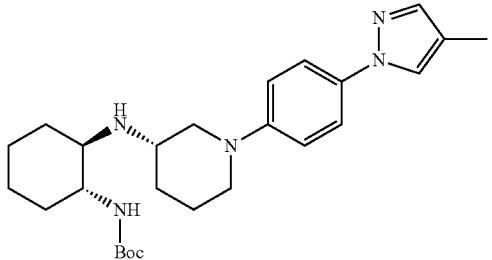 [SMILES: Cc1cnn(-c2ccc(N3CCC[C@H](N[C@@H]4CCCC[C@H]4NC(=O)OC(C)(C)C)C3)cc2)c1]

To a sealed tube was added tert-butyl (1R,2R)-2-((S)-1-(4-iodophenyl)piperidin-3-ylamino)cyclohexylcarbamate (150 mg, 0.300 mmol), 4-methyl-1H-pyrazole (29.6 mg, 0.360 mmol), (1R,2R)—N1,N2-dimethylcyclohexane-1,2-diamine (8.54 mg, 0.060 mmol), $K_2CO_3$ (87 mg, 0.631 mmol) and copper(I) iodide (5.72 mg, 0.030 mmol). The reaction was bubbled with argon for 2 min. The reaction vessel was sealed and the reaction was stirred at 100° C. for 16 hrs. After this time, the reaction was cooled to rt and diluted with water. The layers were separated and aqueous solution was extracted with EtOAc (2×30 ml). The combined organic layers were washed with saturated aqueous NaCl (30 ml), dried over $Na_2SO_4$, filtered and concentrated. The resulting residue was purified using silica gel chromatography (ISCO system) eluting with a gradient of 20-100% EtOAc/Hex to give tert-butyl (1R,2R)-2-((S)-1-(4-(4-methyl-1H-pyrazol-1-yl)phenyl)piperidin-3-ylamino)cyclohexylcarbamate (86 mg, 0.190 mmol, 63.1% yield). Anal. Calcd. for $C_{26}H_{39}N_5O_2$ m/z 453.5, found: 454.4 (M+H)$^+$.

D: (1R,2R)—N1-((S)-1-(4-(4-Methyl-1H-pyrazol-1-yl)phenyl)piperidin-3-yl)cyclohexane-1,2-diamine tetrakis-trifluoroacetate

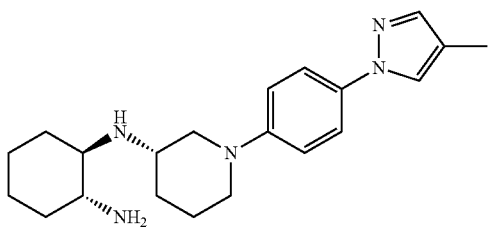 [SMILES: Cc1cnn(-c2ccc(N3CCC[C@H](N[C@@H]4CCCC[C@H]4N)C3)cc2)c1]

(1R,2R)—N1-((S)-1-(4-(4-Methyl-1H-pyrazol-1-yl)phenyl)piperidin-3-yl)cyclohexane-1,2-diamine tetrakis-trifluoroacetate (152 mg, 0.188 mmol, 100% yield) was synthesized as described in General Procedure G using tert-butyl (1R,2R)-2-((S)-1-(4-(4-methyl-1H-pyrazol-1-yl)phenyl)piperidin-3-ylamino)cyclohexylcarbamate (84 mg, 0.188 mmol) to give the title compound as an oil. Anal. Calcd. for $C_{21}H_{31}N_5$ m/z 353.5, found: 354.2 (M+H)$^+$.

Intermediate 31

(1R,2R)—N1-((S)-1-(4-(3-Methyl-1H-pyrazol-1-yl)phenyl)piperidin-3-yl)cyclohexane-1,2-diamine

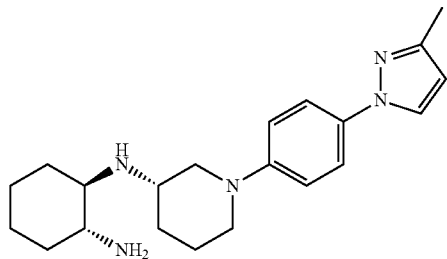 [SMILES: Cc1ccn(-c2ccc(N3CCC[C@H](N[C@@H]4CCCC[C@H]4N)C3)cc2)n1]

(1R,2R)—N1-((S)-1-(4-(3-Methyl-1H-pyrazol-1-yl)phenyl)piperidin-3-yl)cyclohexane-1,2-diamine (148 mg, 0.183 mmol) was synthesized as described for the synthesis of Intermediate 30 using 3-methyl-1H-pyrazole in step C.

Intermediate 32

(1R,2R)—N1-((S)-1-(4-(3-(Trifluoromethyl)-1H-pyrazol-1-yl)phenyl)piperidin-3-yl)cyclohexane-1,2-diamine

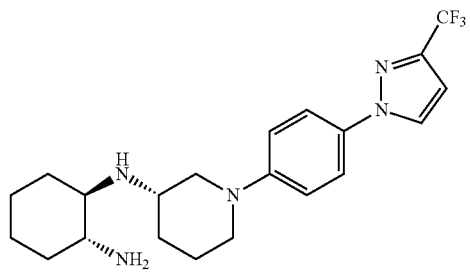 [SMILES: N[C@@H]1CCCC[C@H]1N[C@H]1CCCN(c2ccc(-n3ccc(C(F)(F)F)n3)cc2)C1]

(1R,2R)—N1-((S)-1-(4-(3-(Trifluoromethyl)-1H-pyrazol-1-yl)phenyl)piperidin-3-yl)cyclohexane-1,2-diamine (140 mg, 0.162 mmol) was synthesized as described for the synthesis of Intermediate 30 using 3-(trifluoromethyl)-1H-pyrazole in step C.

Intermediate 33

(1R,2R)—N1-((S)-1-(5-(Trifluoromethyl)pyrimidin-2-yl)piperidin-3-yl)cyclohexane-1,2-diamine

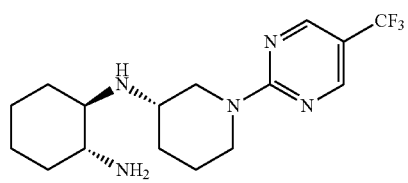

(1R,2R)—N1-((S)-1-(5-(Trifluoromethyl)pyrimidin-2-yl)piperidin-3-yl)cyclohexane-1,2-diamine was synthesized as described for the synthesis of Intermediate 21 using 2-(1H-imidazol-1-yl)-5-(trifluoromethyl)pyrimidine in step A.

Intermediate 34

2-((S)-3-((1R,2R)-2-Aminocyclohexylamino)piperidin-1-yl)pyrimidine-5-carbonitrile

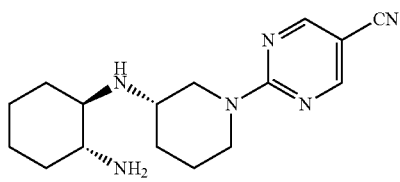

(1R,2R)—N1-((S)-1-(4-(3-(Trifluoromethyl)-1H-pyrazol-1-yl)phenyl)piperidin-3-yl)cyclohexane-1,2-diamine (85.7 mg, 0.162 mmol) was synthesized as described for the synthesis of Intermediate 21 using 2-chloropyrimidine-5-carbonitrile in step A.

Intermediate 35

(1R,2R)—N1-((S)-1-(4-Iodophenyl)piperidin-3-yl)cyclohexane-1,2-diamine

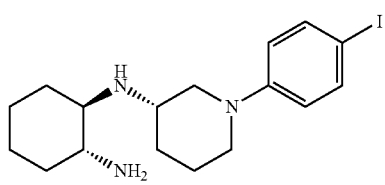 [SMILES: N[C@@H]1CCCC[C@H]1N[C@H]1CCCN(c2ccc(I)cc2)C1]

(1R,2R)—N1-((S)-1-(4-Iodophenyl)piperidin-3-yl)cyclohexane-1,2-diamine tetrakis-trifluoroacetate (140 mg, 0.164 mmol, 100% yield) was synthesized as described in General Procedure G using tert-butyl (1R,2R)-2-((S)-1-(4-iodophenyl)piperidin-3-ylamino)cyclohexylcarbamate from Intermediate 30 step B (80 mg, 0.160 mmol) to give the title compound as an oil. Anal. Calcd. for $C_{17}H_{26}IN_3$ m/z 399.3, found: 400.0 $(M+H)^+$.

Intermediate 36

4-((1R,4R,6S)-6-((1R,2R)-2-Aminocyclohexylamino)-2-azabicyclo[2.2.1]heptan-2-yl)benzonitrile

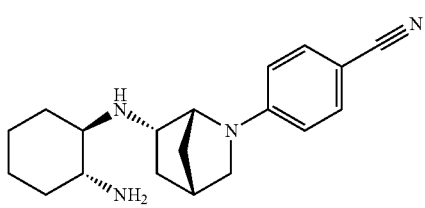 [SMILES: N#Cc1ccc(N2C[C@@H]3C[C@H](N[C@@H]4CCCC[C@H]4N)[C@H]2C3)cc1]

A: (1R,4S)-2-((S)-1-Phenylethyl)-2-azabicyclo[2.2.1]heptan-6-ol

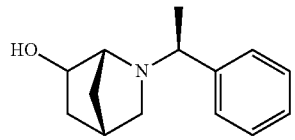 [SMILES: C[C@@H](c1ccccc1)N1C[C@@H]2CC(O)[C@H]1C2]

A solution of BH₃-THF (1.0 M in THF)(24.5 ml, 24.5 mmol) was added dropwise to a 0° C. solution of 2-((S)-1-phenylethyl)-2-azabicyclo[2.2.1]hept-5-ene in THF (90 mL). The reaction mixture was then stirred at rt. After 30 min the mixture was cooled to 0° C. and another 24.5 mL of BH₃-THF solution was added dropwise. The mixture was then stirred at rt once again. After 30 min the mixture was cooled to 0° C. and a solution of NaOH (3.9 g in 5 ml water) was carefully added dropwise. The white slurry was stirred at 0° C. for 10 min and then a solution of 30% H₂O₂ (2.7 mL) was slowly added. The mixture was then stirred at rt. After 45 min concentrated NH₄OH (31 mL) was added and the mixture was heated at 65° C. After 1.5 h heating was stopped. The mixture was cooled to rt and concentrated to ½ volume to remove some of the THF. The solution was then partitioned between EtOAc and water. The organic phase was isolated, washed with saturated aqueous NaCl, dried over MgSO₄, filtered and concentrated. The crude product was purified by silica gel chromatography (ISCO system) eluting with a gradient of 0-100% EtOAc/Hex to give the product (1R,4S)-2-((S)-1-phenylethyl)-2-azabicyclo[2.2.1]heptan-6-ol (3.37 gm, 15.54 mmol, 69.7% yield) as a colorless oil. Anal. Calcd. for C₁₄H₁₉NO m/z 217.3, found: 218.1 (M+H)⁺; ¹H NMR (400 MHz, CDCl₃) δ ppm 7.40-7.17 (5 H, m), 4.03 (1 H, d, J=7.1 Hz), 3.46 (1 H, q, J=6.2 Hz), 3.01 (1 H, s), 2.51 (1 H, dt, J=8.8, 3.0 Hz), 2.37 (1 H, br. s.), 2.25 (1 H, d, J=8.8 Hz), 1.86-1.78 (1 H, m), 1.54-1.38 (3 H, m), 1.37-1.21 (4 H, m).

B: (1R,4S)-2-Azabicyclo[2.2.1]heptan-6-ol

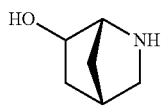

To a degassed solution of (1S,4R)-2-((S)-1-phenylethyl)-2-azabicyclo[2.2.1]heptan-6-ol in MeOH (18 ml) was added 5 drops of concentrated HCl followed by 20% Pd(OH)₂. The reaction mixture was placed under hydrogen at 50 p.s.i. and left to stir at rt. overnight. The reaction mixture was filtered through a CELITE® pad. The pad was rinsed with MeOH and the filtrate was concentrated to give (1R,4S)-2-azabicyclo[2.2.1]heptan-6-ol (1.60 g, 10.69 mmol, 89% yield) as a light yellow solid. ¹H NMR (400 MHz, CD₃OD) δ ppm 3.87 (1 H, d, J=7.1 Hz), 3.38-3.33 (1 H, m), 2.79 (1 H, dt, J=9.9, 3.0 Hz), 2.55-2.45 (2 H, m), 1.88-1.75 (2 H, m), 1.51-1.35 (2 H, m).

C: 4-((1R,4S)-6-Hydroxy-2-azabicyclo[2.2.1]heptan-2-yl)benzonitrile

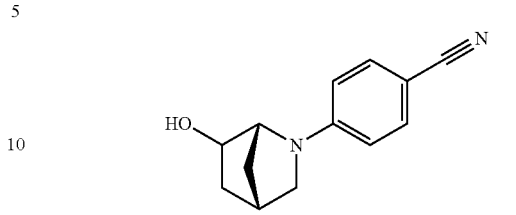

To a round bottom flask was added (1S,4R)-2-azabicyclo[2.2.1]heptan-6-ol (0.5 gm, 3.34 mmol), 4-fluorobenzonitrile (0.405 gm, 3.34 mmol), DMF (6 ml) and K₂CO₃ (1.386 gm, 10.03 mmol). The reaction was stirred at 80° C. for 5 hrs. After this time, the reaction was diluted with EtOAc. The resulting solution was washed with water (4×) and saturated aqueous NaCl. The organic layer was separated, dried over MgSO₄, filtered and concentrated. The resulting residue was purified using silica gel chromatography (ISCO system) eluting with a gradient of 0-100% EtOAc/Hex to give product 4-((1R,4S)-6-hydroxy-2-azabicyclo[2.2.1]heptan-2-yl)benzonitrile (338 mg, 1.578 mmol, 47.2% yield) as a white solid. Anal. Calcd. for C₁₃H₁₄N₂O m/z 214.2, found: 215.1 (M+H)⁺.

D: 4-((1R,4S)-6-Oxo-2-azabicyclo[2.2.1]heptan-2-yl)benzonitrile

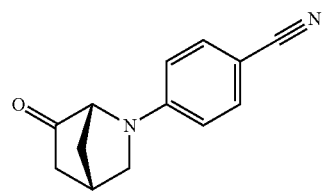 [SMILES: N#Cc1ccc(N2C[C@@H]3CC(=O)[C@H]2C3)cc1]

To a round bottom flask was added 4-((1S,4R)-6-hydroxy-2-azabicyclo[2.2.1]heptan-2-yl)benzonitrile (329 mg, 1.535 mmol), Et₃N (777 mg, 7.68 mmol) and CH₂Cl₂ (7.2 ml). The resulting solution was cooled to 0° C. In a separate vial, pyridine sulfur trioxide (1.22 gm, 7.68 mmol) and DMSO (2.4 gm, 30.7 mmol) were mixed until the solution turned clear. The resulting solution was then added to the reaction at 0° C. The reaction mixture was slowly warmed to rt and stirred for an additional 1 hr. After this time, the solution was diluted with CH₂Cl₂. The resulting solution was wash with water (2×) and saturated aqueous NaCl. The organic layer was separated, dried over MgSO₄, filtered and concentrated. The resulting residue was purified using silica gel chromatography (ISCO system) eluting with a gradient of 0-100% EtOAc/Hex to give product 4-((1R,4S)-6-oxo-2-azabicyclo[2.2.1]heptan-2-yl)benzonitrile (281 mg, 1.324 mmol, 86% yield) as colorless oil. Anal. Calcd. for C₁₃H₁₂N₂O m/z 212.2, found: 213.0 (M+H)⁺.

E: tert-Butyl (1R,2R)-2-((1R,4R,6S)-2-(4-cyanophenyl)-2-azabicyclo[2.2.1]heptan-6-ylamino)cyclohexylcarbamate

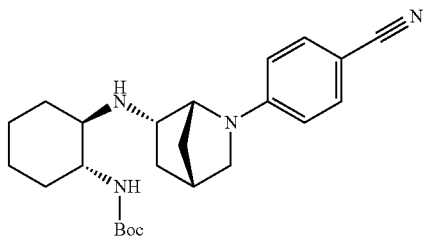 [SMILES: CC(C)(C)OC(=O)N[C@@H]1CCCC[C@H]1N[C@H]1C[C@@H]2C[C@H]1N(c1ccc(C#N)cc1)C2]

To a round bottom flask under argon was added 4-((1S,4R)-6-oxo-2-azabicyclo[2.2.1]heptan-2-yl)benzonitrile (272 mg, 1.282 mmol), tert-butyl (1R,2R)-2-aminocyclohexylcarbamate (330 mg, 1.538 mmol), $CH_2Cl_2$ (6.4 ml), solid anhydrous $Na_2SO_4$ (1 gm) and HOAc (1 drop). Argon was bubbled through the reaction mixture for 1 min and then the reaction was stirred under argon at rt for 1 hr. After this time, sodium triacetoxy borohydride (815 mg, 3.84 mmol) was added to the reaction which was then stirred at rt overnight. The reaction mixture was then diluted with $CH_2Cl_2$. The resulting solution was wash with saturated aqueous $NaHCO_3$, water and saturated aqueous NaCl. The organic layer was separated, dried over $MgSO_4$, filtered and concentrated. The resulting residue was purified using silica gel chromatography (ISCO system) eluting with a gradient of 0-100% EtOAc/Hex. The fractions containing the desired product were concentrated to give tert-butyl (1R,2R)-2-((1R,4R,6S)-2-(4-cyanophenyl)-2-azabicyclo[2.2.1]heptan-6-ylamino)cyclohexylcarbamate (466 mg, 1.135 mmol, 89% yield). Anal. Calcd. for $C_{24}H_{34}N_4O_2$ m/z 410.5, found: 411.3 (M+H)$^+$; $^1$H NMR (500 MHz, $CDCl_3$) δ ppm 7.45 (2 H, d, J=8.8 Hz), 6.55 (2 H, d, J=8.8 Hz), 4.26 (1 H, s), 3.65 (1 H, br. s.), 3.47-3.41 (1 H, m), 3.30 (1 H, dt, J=8.8, 3.0 Hz), 3.15 (1 H, d, J=8.8 Hz), 2.98 (1 H, d, J=8.2 Hz), 2.64 (1 H, s), 2.29-2.19 (2 H, m), 2.10-2.02 (1 H, m), 2.01-1.93 (1 H, m), 1.74-1.59 (4 H, m), 1.45-1.37 (1 H, m), 1.35 (9 H, s), 1.30-1.18 (2 H, m), 1.09- -0.93 (2 H, m), 0.90 (1 H, ddd, J=12.9, 3.8, 3.6 Hz).

F: 4-((1R,4R,6S)-6-((1R,2R)-2-Aminocyclohexylamino)-2-azabicyclo[2.2.1]heptan-2-yl)benzonitrile bishydrochloride

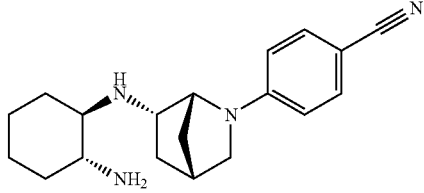 [SMILES: N#Cc1ccc(N2C[C@@H]3C[C@H](N[C@@H]4CCCC[C@H]4N)[C@H]2C3)cc1]

A solution of HCl (4.0 N in 1,4-dioxane, 2 ml)) was added to a mixture of tert-butyl (1R,2R)-2-((1S,4S,6S)-2-(4-cyanophenyl)-2-azabicyclo[2.2.1]heptan-6-ylamino)cyclohexylcarbamate (445 mg, 1.084 mmol) in 1,4-dioxane (2 ml). The starting material formed a gum. MeOH (1 mL) was then added. Eventually all solids went into solution. The reaction was stirred at rt for 2 hrs. The reaction mixture was concentrated to give 4-((1R,4R,6S)-6-((1R,2R)-2-aminocyclohexylamino)-2-azabicyclo[2.2.1]heptan-2-yl)benzonitrile bishydrochloride (440 mg, 1.084 mmol, 100% yield) of an off white solid. Calcd. for $C_{19}H_{26}N_4$ m/z 310.4, found: 311.2 (M+H)$^+$.

Intermediate 37

2-Chloro-5-phenylthiazole

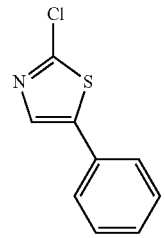 [SMILES: Clc1ncc(-c2ccccc2)s1]

A: 2-Bromo-2-phenylacetaldehyde

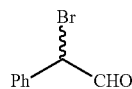

To a solution of phenyl-acetaldehyde (1 g, 8.3 mmol) in $CH_2Cl_2$ (3 mL) was added dropwise a solution of $Br_2$ (1.3 g, 8.3 mmol) in $CH_2Cl_2$ (3 mL) at −10° C. over 30 min. The resulting solution was allowed to warm to rt and then heated to reflux overnight. Aqueous $NaHCO_3$ was added to the cooled mixture and the solution was extracted with $CH_2Cl_2$. The organic layer was dried over anhydrous $Na_2SO_4$, filtered and concentrated to afford crude bromo-phenyl-acetaldehyde (1 g, 5.05 mmol, 61%) as a green liquid which was taken to the next step directly. Anal. Calcd. for $C_8H_7BrO$ m/z 198.0, found: 198.0 GC-MS (M)$^+$.

B: 5-Phenylthiazol-2-amine

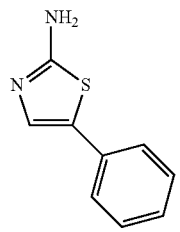 [SMILES: Nc1ncc(-c2ccccc2)s1]

A mixture of bromo-phenyl-acetaldehyde (1 g, 5 mmol), thiourea (0.64 g, 10 mmol) and ethanol (3.5 mL) was heated to reflux overnight. The mixture was then cooled to rt and the resulting yellow precipitate filtered. The precipitate was then washed with aqueous $NaHCO_3$ solution (10 mL) and dried. Recrystallization from 30% methanol gave 5-phenylthiazol- 2-amine (500 mg, 2.84 mmol, 56.5%) as a yellow solid. Anal. Calcd. for $C_9H_8N_2S$ m/z 176.2, found: 177.2 (M+H)$^+$; $^1H$ NMR (400 MHz, DMSO-$d_6$) δ ppm 7.41 (m, 3H), 7.33 (m, 2H), 7.18 (m, 1H), 7.13 (m, 2H).

C: 2-Chloro-5-phenylthiazole

To a mixture of 5-phenyl-thiazol-2-amine (100 mg, 0.57 mmol) and $CuCl_2.2H_2O$ (193 mg, 1.1 mmol) in $CH_3CN$ (3.8 mL) was added isoamyl nitrite (132.9 mg, 1.1 mmol) dropwise at rt. The mixture was then stirred overnight at ambient temperature and concentrated in vacuo to remove $CH_3CN$ and extracted with EtOAc. The organic layer was dried over anhydrous $Na_2SO_4$ and concentrated in vacuo to give crude title compound as a brown solid. The crude produce was purified by silica gel column chromatography eluting with Hex:EtOAc=100:1 to give 2-chloro-5-phenylthiazole (60 mg, 0.308 mmol, 54%) as a yellow solid. Anal. Calcd. for $C_9H_6ClNS$ m/z 195, found: 195 GC-MS (M)$^+$; $^1H$ NMR (400 MHz, DMSO-$d_6$) δ ppm 8.13 (s, 1H), 7.66 (m, 2H), 7.47-7.41 (m, 3H).

Intermediate 38

2-Chloro-5-(2-(trifluoromethoxy)phenyl)oxazole

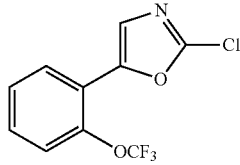

2-Chloro-5-(2-(trifluoromethoxy)phenyl)oxazole (4 g, 17.5 mmol) was synthesized as described for the preparation of Intermediate 2 using 2-(trifluoromethoxy)benzaldehyde in step A. Anal. Calcd. for $C_{10}H_5ClF_3NO_2$ m/z 263.0, found: 264.2 (M+H)$^+$; $^1H$ NMR (400 MHz, CDCl$_3$) δ ppm 7.52 (m, 1H), 7.47 (m, 1H), 7.44 (m, 1H), 7.33 (m, 1H), 7.21 (m, 1H).

Intermediate 39

(1R,2R)—N1-((S)-3-Methyl-1-(4-nitrophenyl)piperidin-3-yl)cyclohexane-1,2-diamine

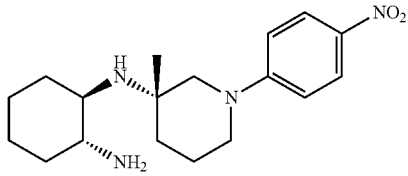 [SMILES: C[C@]1(N[C@@H]2CCCC[C@H]2N)CCCN(c2ccc([N+](=O)[O-])cc2)C1]

A: 1-Benzyl 3-ethyl piperidine-1,3-dicarboxylate

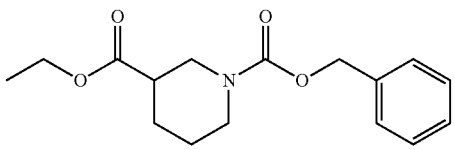 [SMILES: CCOC(=O)C1CCCN(C(=O)OCc2ccccc2)C1]

To a solution of ethyl piperidine-3-carboxylate (4 g, 25.4 mmol) in THF (30 mL) and water (30.0 mL) was added $Na_2CO_3$ (6.74 g, 63.6 mmol). The resulting suspension was stirred at rt for 20 min. After this time, benzyl carbonochloridate (4.12 g, 24.17 mmol) was added in dropwise. After addition, the stirring solution became milky, then white precipitates formed. After stirring at rt for 2 h, the reaction was partitioned between EtOAc and water. The separated aqueous phase was extracted with EtOAc (2×). The combined organics were washed with water and saturated aqueous NaCl. The organic layer was dried over $Na_2SO_4$, filtered and concentrated to dryness. The oily residue was purified using silica gel chromatography (ISCO system) eluting with a gradient of 0-40% EtOAc/Hex. The desired fractions were concentrated to afford the desired product, 1-benzyl 3-ethyl piperidine-1,3-dicarboxylate (5.68 g, 19.50 mmol, 77% yield) as a colorless oil. Anal. Calcd. for $C_{16}H_{21}NO_4$ m/z 291.3, found: 292.1 (M+H)$^+$; $^1H$ NMR (400 MHz, CDCl$_3$) δ ppm 7.41-7.28 (m, 5 H), 5.26-4.97 (m, 2 H), 4.34-4.06 (m, 3 H), 4.06-3.91 (m, 1 H), 3.13 (br. s., 1 H), 2.96-2.81 (m, 1 H), 2.46 (br. s., 1 H), 2.15-1.96 (m, 1 H), 1.78-1.56 (m, 2 H), 1.49 (br. s., 1 H), 1.33-1.17 (m, 3 H).

B: 1-Benzyl 3-ethyl 3-methylpiperidine-1,3-dicarboxylate

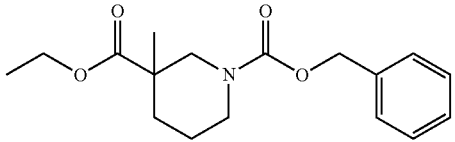 [SMILES: CCOC(=O)C1(C)CCCN(C(=O)OCc2ccccc2)C1]

To a solution of 1-benzyl 3-ethyl piperidine-1,3-dicarboxylate (2.107 g, 7.23 mmol) in dry THF (22 mL) and DMPU (1.4 mL, 1160 mmol) cooled at −78° C. was added dropwise lithium bis(trimethylsilyl)amide (1.271 g, 7.59 mmol, 7.60 mL of 1M solution in THF). After addition, the reaction mixture was stirred at −60° C. for 1 h. Then iodomethane (0.520 mL, 8.32 mmol) in DMPU (0.344 mL, 2.86 mmol was added dropwise. After addition, the reaction was stirred at −60° C. for 1.5 h, then slowly warmed up to −20° C. over approximately 1 hr. The reaction was quenched by the addition of saturated aqueous NH$_4$Cl. The reaction solution was extracted with EtOAc (2×). The combined organics were washed with saturated aqueous NH$_4$Cl and saturated aqueous NaCl. The organic layer was dried over $Na_2SO_4$, filtered and concentrated. The residue was purified using silica gel chromatography (ISCO system) eluting with a gradient of 0-30% EtOAc/Hex. The desired fractions were concentrated to give product, benzyl 3-ethyl 3-methylpiperidine-1,3-dicarboxylate (1.66 gm, 5.44 mmol, 75.2% yield) as a light brown oil. Anal. Calcd. for $C_{17}H_{23}NO_4$ m/z 305.3, found: 306.2 (M+H)$^+$; $^1H$ NMR (400 MHz, CDCl$_3$) δ ppm 7.44-7.27 (m, 5 H), 5.20-5.09 (m, 2 H), 4.24-4.04 (m, 2 H), 3.99 (d, J=13.19 Hz, 1 H), 3.59 (br. s., 1 H), 3.27 (d, J=7.15 Hz, 1 H), 3.13 (d, J=12.64 Hz, 1 H), 2.16-1.95 (m, 1 H), 1.74-1.52 (m, 2 H), 1.51-1.39 (m, 1 H), 1.25-1.07 (m, 6 H).

C: Ethyl 3-methylpiperidine-3-carboxylate

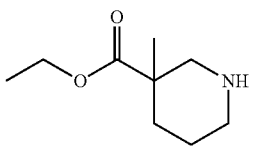

A suspension of 1-benzyl 3-ethyl 3-methylpiperidine-1,3-dicarboxylate (3.945 g, 12.92 mmol) and 5% Pd/C (800 mg) in ethyl acetate (20 mL) and methanol (20.00 mL) was vigorously stirred under a hydrogen balloon for 1.5 hr. The reaction mixture was filtered to remove the catalyst and the filtrate was concentrated to dryness to give the desired crude product ethyl 3-methylpiperidine-3-carboxylate (2.010 g, 11.74 mmol, 91% yield) as a colorless oily residue. Anal. Calcd. for $C_9H_{17}NO_2$ m/z 171.2, found: 172.2 (M+H)$^+$; $_1$H NMR (400 MHz, CDCl$_3$) δ ppm 4.25-4.06 (m, 2 H), 3.31 (d, J=13.19 Hz, 1 H), 2.93 (d, J=13.19 Hz, 1 H), 2.59 (d, J=10.44 Hz, 1 H), 2.41 (d, J=13.19 Hz, 1 H), 2.23-2.11 (m, 1 H), 1.68 (br. s., 1 H), 1.52 (t, J=3.85 Hz, 1 H), 1.46-1.31 (m, 2 H), 1.27 (t, J=7.15 Hz, 3 H), 1.10 (s, 3H).

D: Ethyl 3-methyl-1-(4-nitrophenyl)piperidine-3-carboxylate

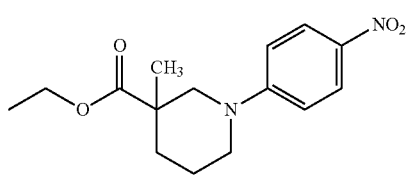 [SMILES: CCOC(=O)C1(C)CCCN(c2ccc([N+](=O)[O-])cc2)C1]

To a round bottom flask was added ethyl 3-methylpiperidine-3-carboxylate (2.040 g, 11.91 mmol), 1-fluoro-4-nitrobenzene (1.765 g, 12.51 mmol), DMF (20 ml) and K$_2$CO$_3$ (2.140 g, 15.49 mmol). The reaction was stirred at 65° C. for 6 hrs. After this time, the reaction was diluted with EtOAc. The resulting solution was washed with water (2×) and saturated aqueous NaCl. The organic layer was separated, dried over Na$_2$SO$_4$, filtered and concentrated. The resulting residue was purified using silica gel chromatography (ISCO system) eluting with a gradient of 0-30% EtOAc/Hex to give product, ethyl 3-methyl-1-(4-nitrophenyl)piperidine-3-carboxylate (2.922 g, 9.90 mmol, 83% yield) as a yellow oily residue. Anal. Calcd. for $C_{15}H_{20}N_2O_4$ m/z 292.3, found: 293.2 (M+H)$^+$; $_1$H NMR (400 MHz, CDCl$_3$) δ ppm 8.10 (d, J=9.34 Hz, 2 H), 6.87 (d, J=9.34 Hz, 2 H,) 4.18 (d, J=13.19 Hz, 1 H), 4.11 (q, J=7.15 Hz, 2 H), 3.80-3.58 (m, 1 H), 3.00 (s, 1 H), 2.90 (d, J=13.19 Hz, 1 H), 2.40-2.23 (m, 1 H), 1.75 (dd, J=8.52, 4.12 Hz, 2 H), 1.42 (s, 1 H), 1.26-1.14 (m, 6 H).

E: 3-Methyl-1-(4-nitrophenyl)piperidine-3-carboxylic acid

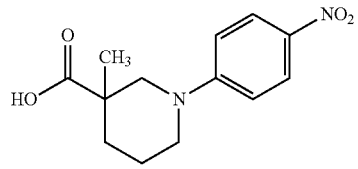 [SMILES: CC1(C(=O)O)CCCN(c2ccc([N+](=O)[O-])cc2)C1]

To a solution of ethyl 3-methyl-1-(4-nitrophenyl)piperidine-3-carboxylate (2.920 g, 9.99 mmol) in THF (12.50 mL) and MeOH (12.5 mL) was added 2 M aqueous solution of LiOH (25 mL, 50 mmol). The resulting yellow solution was stirred at rt for 22 hrs. The reaction was adjusted with 3N aqueous HCl to pH=5. The solution was extracted with EtOAc (3×). The combined EtOAc extracts were washed with saturated aqueous NaCl (2×), dried over Na$_2$SO$_4$, filtered and concentrated. The obtained yellow solid was dried in high vacuum to give the desired product, 3-methyl-1-(4-nitrophenyl)piperidine-3-carboxylic acid (2.650 g, 9.53 mmol, 95% yield) as a yellow solid. Anal. Calcd. for $C_{13}H_{16}N_2O_4$ m/z 264.2, found: 265.1 (M+H)$^+$; $^1$H NMR (400 MHz, CDCl$_3$) δ ppm 8.08 (d, J=9.34 Hz, 2 H), 6.89 (d, J=9.34 Hz, 2 H), 4.13 (d, J=12.64 Hz, 1 H), 3.64 (ddd, J=12.50, 4.53, 4.40 Hz, 1 H), 3.10-2.99 (m, 1 H), 2.94 (d, J=13.19 Hz, 1 H), 2.33-2.18 (m, 1 H), 1.88-1.69 (m, 2 H), 1.53-1.37 (m, 1 H), 1.25 (s, 3 H).

F: 3-Methyl-1-(4-nitrophenyl)piperidine-3-carboxamide

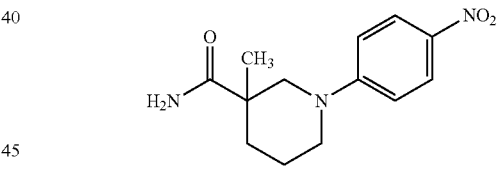

To a solution of 3-methyl-1-(4-nitrophenyl)piperidine-3-carboxylic acid (2.65 g, 10.03 mmol) in THF (45 ml) cooled at −5° C. (ice/NaCl bath) was added Et$_3$N (1.537 mL, 11.03 mmol), followed by dropwise addition of isobutyl carbonochloridate (1.443mL, 11.03 mmol). After addition, the resulting yellow suspension was stirred at −3° C. for 75 min before 6.25 mL of 28% ammonium hydroxide aqueous solution (50 mmol, 5.0 equiv.) was added. The reaction mixture was stirred at ~0° C. for 1.5 hrs. The reaction was quenched with water, the resulting mixture (pH>10) was extracted with EtOAc (3×). The combined organic phase was washed with water (2×), saturated aqueous NaCl (2×), dried over Na$_2$SO$_4$, filtered and concentrated. The crude product was crystallized from EtOAc to give title compound, 3-methyl-1-(4-nitrophenyl)piperidine-3-carboxamide (777 mg, 2.95 mmol, 29.4% yield) as a brown solid. Anal. Calcd. for $C_{13}H_{12}N_3O_3$ m/z 263.2, found: 264.2 (M+H)$^+$; $^1$H NMR (400 MHz, CDCl$_3$) δ ppm 8.20-8.02 (m, 2 H), 7.06-6.85 (m, 2 H), 3.91 (d, J=13.19 Hz, 1 H), 3.64-3.49 (m, 1 H), 3.16 (ddd, J=12.64, 8.25, 4.40

Hz, 1 H), 3.09 (s, 2 H), 3.06 (d, J=13.19 Hz, 1 H), 2.09 (d, J=13.74 Hz, 1 H), 1.91-1.72 (m, 2 H), 1.62-1.48 (m, 1 H), 1.25 (s, 3 H).

G: Benzyl 3-methyl-1-(4-nitrophenyl)piperidin-3-ylcarbamate

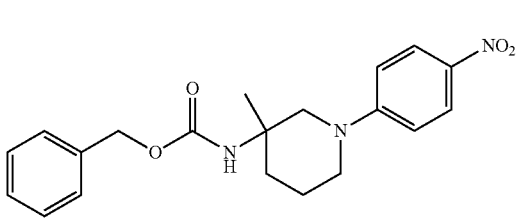 [SMILES: CC1(NC(=O)OCc2ccccc2)CCCN(c2ccc([N+](=O)[O-])cc2)C1]

To a solution of 3-methyl-1-(4-nitrophenyl)piperidine-3-carboxamide (1.8538 g, 7.04 mmol) and phenylmethanol (7.61 g, 70.4 mmol) in ClCH₂CH₂Cl (30 ml) cooled at 0° C. was added 1,8-diazabicyclo[5.4.0]undec-7-ene (3.18 mL, 21.12 mmol) dropwise, followed by 1-bromopyrrolidine-2,5-dione (1.378 g, 7.74 mmol) in portions. After addition, the resulting yellow mixture was stirred at 0° C. for 15 min, then at rt for 3.5 hrs, LCMS showed the reaction was not complete and 10% more of NBS (138 mg) was added and the reaction was allowed to stir for an additional 2.5 hrs. The reaction mixture was quenched by addition of water (50 mL) and then adjusted to pH=5 with 1N aqueous HCl. The solution was extracted with EtOAc (3×). The combined EtOAc extracts were washed with water, saturated aqueous NaCl, dried over Na₂SO₄, filtered and concentrated. The resulting residue was purified using silica gel chromatography (ISCO system) eluting with a gradient of 0-30% EtOAc/Hex to give product, benzyl 3-methyl-1-(4-nitrophenyl)piperidin-3-ylcarbamate (2.274 g, 6.16 mmol, 87% yield) as a yellow oil. Anal. Calcd. for $C_{20}H_{23}N_3O_4$ m/z 369.4, found: 370.1 (M+H)⁺; ¹H NMR (400 MHz, CDCl₃) δ ppm 8.06 (d, J=9.34 Hz, 2 H), 7.37 (d, J=4.40 Hz, 1 H), 7.34-7.27 (m, 4 H), 6.81 (d, J=9.34 Hz, 2 H), 5.09-4.93 (m, 2 H), 4.74 (s, 1 H), 4.18-4.07 (m, 1 H), 3.74-3.62 (m, 1 H), 3.11-3.02 (m, 2 H), 2.04-1.99 (m, 1 H), 1.81-1.68 (m, 2 H), 1.58-1.51 (m, 1 H), 1.44 (s, 3 H).

H: (S)-Benzyl 3-methyl-1-(4-nitrophenyl)piperidin-3-ylcarbamate

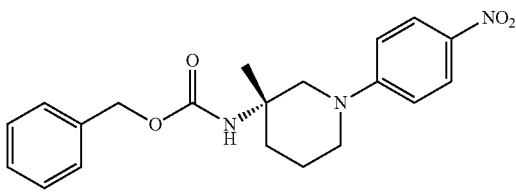 [SMILES: C[C@]1(NC(=O)OCc2ccccc2)CCCN(c2ccc([N+](=O)[O-])cc2)C1]

(S)-Benzyl 3-methyl-1-(4-nitrophenyl)piperidin-3-ylcarbamate (0.527 gm, 1.427 mmol) was separated from its enantiomer using chiral separation method C using benzyl 3-methyl-1-(4-nitrophenyl)piperidin-3-ylcarbamate (1.178 gm, 3.19 mmol). Anal. Calcd. for $C_{20}H_{23}N_3O_4$ m/z 369.4, found: 370.1 (M+H)⁺; ¹H NMR (400 MHz, CDCl₃) δ ppm 8.03 (d, J=9.89 Hz, 2 H), 7.39-7.16 (m, 5 H), 6.80 (d, J=8.79 Hz, 2 H), 5.12-4.91 (m, 2 H), 4.79 (br. s., 1 H), 4.13 (d, J=11.54 Hz, 1 H), 3.68 (d, J=13.19 Hz, 1 H), 3.14-2.94 (m, 2 H), 2.02 (d, J=13.19 Hz, 1 H), 1.87-1.63 (m, 2 H), 1.63-1.47 (m, 1 H), 1.43 (s, 3H).

I: (S)-3-Methyl-1-(4-nitrophenyl)piperidin-3-amine

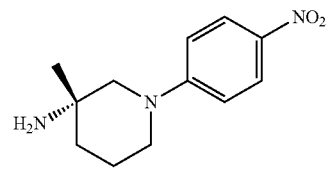 [SMILES: C[C@]1(N)CCCN(c2ccc([N+](=O)[O-])cc2)C1]

To a solution of (S)-benzyl 3-methyl-1-(4-nitrophenyl)piperidin-3-ylcarbamate (525 mg, 1.421 mmol) in CH₂Cl₂ (5 ml) cooled at 0° C. was added iodotrimethylsilane (0.290 mL, 2.132 mmol) dropwise. After addition, the orange colored solution was stirred at 0° C. for 15 min, then at rt for 1 hr. The reaction was quenched by addition of 4.3 mmol of HCl (1.1 mL of 4N HCl in dioxane) in MeOH (5 mL). The mixture was concentrated. The dark reddish residue was partitioned between ether and water. The ether phase was extracted with 0.2 N aqueous HCl. The combined acidic aqueous solution was extracted with ether (1×), then basified at 0° C. with 1N aqueous NaOH to pH=10. The aqueous phase was extracted with CH₂Cl₂ (3×). The combined CH₂Cl₂ extracts were washed with saturated aqueous NaCl, dried over Na₂SO₄, filtered and concentrated to give the desired product, (S)-3-methyl-1-(4-nitrophenyl)piperidin-3-amine (277 mg, 1.177 mmol, 83% yield) as a dark reddish oil. Anal. Calcd. for $C_{12}H_{17}N_3O_2$ m/z 235.2, found: 236.0 (M+H)⁺; ¹H NMR (400 MHz, chloroform-d) δ ppm 8.10 (d, J=9.34 Hz, 2 H), 6.83 (d, J=9.34 Hz, 2 H), 3.62-3.50 (m, 1 H), 3.32 (d, J=12.64 Hz, 1 H), 3.18 (s, 1 H), 3.12 (d, J=13.19 Hz, 1 H), 1.82 (d, J=4.95 Hz, 1 H), 1.75 (s, 1 H), 1.69-1.54 (m, 2 H), 1.18 (s, 3 H).

J: Benzyl (1R,2R)-2-((S)-3-methyl-1-(4-nitrophenyl)piperidin-3-ylamino)cyclohexylcarbamate

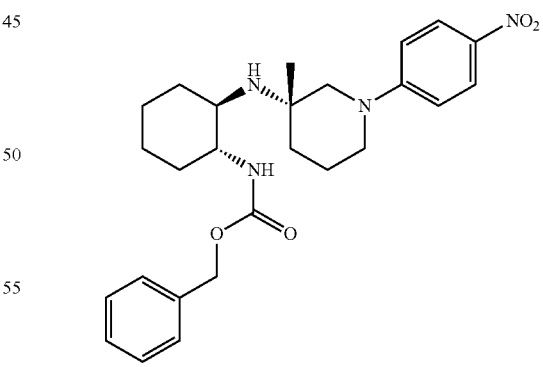

A solution of benzyl 7-azabicyclo[4.1.0]heptane-7-carboxylate (170 mg, 0.733 mmol) in CH₂Cl₂ (1 mL) was added to a 25 mL flask containing (S)-3-methyl-1-(4-nitrophenyl)piperidin-3-amine (115 mg, 0.489 mmol). Then lithium bis(trifluoromethylsulfonyl)amide (28.1 mg, 0.098 mmol) was added in one portion. The resulting greenish orange mixture was stirred at 45° C. under argon for 3 days. The reaction was cooled to rt and diluted with CH₂Cl₂. Then saturated aqueous NaHCO₃ solution (4 mL) was added to the reaction and the reaction was stirred at rt for 30 min. The separated aqueous layer was extracted with CH₂Cl₂ (3×). The combined organic layers were washed with saturated aqueous NaCl, dried over Na₂SO₄, filtered and concentrated. The residue was purified using ISCO column eluting with a gradient of 50-100% EtOAc/Hex. Two diastereomers were separated. The slower eluting fraction which had shorter Rf was the desired product. The fractions containing the desired product were concentrated to give title compound, benzyl (1R,2R)-2-((S)-3-methyl-1-(4-nitrophenyl)piperidin-3-ylamino)cyclohexylcarbamate (37 mg, 0.079 mmol, 16.2% yield) as a yellow oil. Anal. Calcd. for C₂₆H₃₄N₄O₄ m/z 466.5, found: 467.3 (M+H)⁺; ¹H NMR (400 MHz, CDCl₃) δ ppm 8.08-7.96 (m, 2 H), 7.39-7.29 (m, 5 H), 6.75 (d, J=9.34 Hz, 2 H), 5.13-5.01 (m, 2 H), 3.38-3.28 (m, 1 H), 3.24 (d, J=12.64 Hz, 1 H), 3.19-3.07 (m, 2 H), 2.98 (d, J=12.64 Hz, 1 H), 2.43-2.29 (m, 1 H), 2.21-2.09 (m, 1 H), 2.02-1.91 (m, 1 H), 1.88-1.77 (m, 1 H), 1.67-1.57 (m, 4 H), 1.55-1.44 (m, 3 H), 1.35-1.15 (m, 4 H), 1.07 (s, 3 H).

H: (1R,2R)—N1-((S)-3-Methyl-1-(4-nitrophenyl)piperidin-3-yl)cyclohexane-1,2-diamine

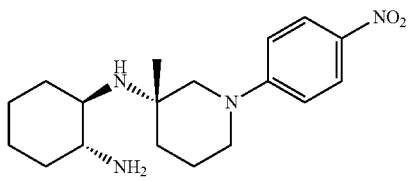

To a solution of benzyl (1R,2R)-2-((S)-3-methyl-1-(4-nitrophenyl)piperidin-3-ylamino)cyclohexylcarbamate (132 mg, 0.283 mmol) in CH₂Cl₂ (2 mL) cooled at 0° C. was added iodotrimethylsilane (0.058 mL, 0.424 mmol) dropwise. After addition, the orange colored suspension was stirred at 0° C. for 10 min, then at rt for 40 min. LCMS showed little reaction happened. Then more TMSI (0.060 mL) was added and the reaction was stirred for total 2 h. LCMS showed the reaction was about ~20% completed. More TMSI (0.070 mL) was added and the reaction was stirred at rt for total 7 h. LCMS showed the reaction was about ~60% completed. Additional amount of TMSI (0.060 mL, total 0.25 mL, 1.84 mmol) was added and the reaction was stirred at rt for total 9 h. LCMS showed the reaction was completed. The reaction was quenched by addition of 1.70 mmol of HCl (0.45 mL of 4N HCl in dioxane) in MeOH (3 mL), and then the mixture was concentrated. The dark reddish residue was partitioned between ether and water. The ether phase was extracted with 0.2 N aqueous HCl (3×). The combined acidic aqueous was cooled at 0° C. and then basified with 1N aqueous NaOH to pH ~10. The aqueous phase was extracted with CH₂Cl₂ (3×). The combined CH₂Cl₂ extracts were washed with saturated aqueous NaCl, dried over Na₂SO₄, filtered and concentrated to give the crude product. The crude product was purified using RP prep-HPLC (Method A). The desired fractions was neutralized and concentrated to give the desired product (1R, 2R)—N1-((S)-3-methyl-1-(4-nitrophenyl)piperidin-3-yl)cyclohexane-1,2-diamine (23 mg, 0.068 mmol, 24.21% yield) as a yellow oil. Anal. Calcd. for C₁₈H₂₈N₄O₂ m/z 332.4, found: 333.2 (M +H)⁺; ¹H NMR (400 MHz, CDCl₃) δ ppm 8.08 (d, J=9.34 Hz, 2H), 6.83 (d, J=9.34 Hz, 2 H), 3.35-3.46 (m, 1 H), 3.23-3.35 (m, 2 H), 3.16 (d, J=12.64 Hz, 1 H), 2.11-2.26 (m, 2 H), 1.88-2.00 (m, 2 H), 1.85 (ddd, J=8.11, 3.99, 3.85 Hz, 1 H), 1.65-1.75 (m, 4 H), 1.56 (ddd, J=17.31, 8.52, 8.25 Hz, 3 H), 1.21-1.33 (m, 3 H), 1.12 (s, 1 H).

Intermediate 40

(1R,2R)—N1-((S)-1-(5-(Trifluoromethyl)pyridin-2-yl)piperidin-3-yl)cyclohexane-1,2-diamine

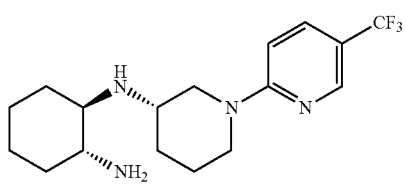 [SMILES: N[C@@H]1CCCC[C@H]1N[C@H]1CCCN(c2ccc(C(F)(F)F)cn2)C1]

(1R,2R)—N1-((S)-1-(5-(Trifluoromethyl)pyridin-2-yl)piperidin-3-yl)cyclohexane-1,2-diamine was synthesized as described in Intermediate 17 using 2-fluoro-5-(trifluoromethyl)pyridine in the step A.

Intermediate 41

3-(2-Chlorooxazole-5-yl)benzamide

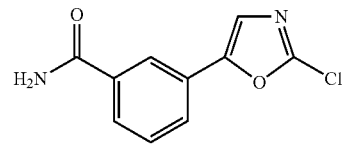 [SMILES: NC(=O)c1cccc(-c2cnc(Cl)o2)c1]

A: 3-(Oxazol-5-yl)benzonitrile

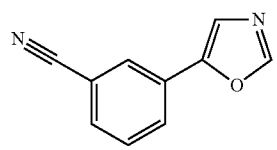 [SMILES: N#Cc1cccc(-c2cnco2)c1]

MeOH (28 mL) was added to a round bottom flask containing K₂CO₃ (4.22 gm, 30.50 mmol), 1-(isocyanomethylsulfonyl)-4-methylbenzene (3.28 gm, 16.78 mmol), and 3-formylbenzonitrile (2.00 gm, 15.25 mmol). The reaction mixture was refluxed for 2 h. After this time, the mixture was concentrated under reduced pressure. The remaining residue was dissolved in water (50 ml). The aqueous solution was extract with EtOAc (50 ml). The EtOAc layer was washed with saturated aqueous NaCl (30 ml), dried over MgSO₄, filtered and concentrated. The resulting residue was purified using silica gel chromatography eluting with a gradient of 0-100% EtOAc/Hexanes to give the product, 3-(oxazol-5-yl)

benzonitrile, (1.05 gm, 6.17 mmol, 41% yield) as a yellow solid. Anal. Calcd. for $C_{10}H_6N_2O$ m/z 170.1, found: 171.0 $(M+H)^+$.

B: 3-(2-Chlorooxazol-5-yl)benzonitrile

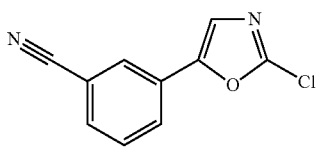 [SMILES: N#Cc1cccc(-c2cnc(Cl)o2)c1]

To a round bottom flask was added 3-(oxazol-5-yl)benzonitrile (1.93 gm, 11.34 mmol) and THF (45 mL). The reaction was cooled to −78° C. and 2.5 M nBuLi (4.99 mL, 12.48 mmol) was added dropwise. The reaction turned deep red color. After 30 min, a solution of hexachloroethane (4.03 gm, 17.01 mmol) in THF (10 mL) was slowly added. The reaction was slowly warmed to rt over 30 min. After 1 h at rt the reaction was quenched by slow addition of sat. $NH_4Cl$ (20 mL). The mixture was concentrated to remove most of the THF. The mixture was then partitioned between EtOAc (40 mL) and water (20 mL). The organic phase was isolated, washed with saturated aqueous NaCl, dried over $MgSO_4$, filtered and concentrated. The resulting residue was purified using silica gel chromatography eluting with a gradient of 0-100% EtOAc/Hexanes to give the product, 3-(2-chlorooxazol-5-yl)benzonitrile, (1.01 gm, 4.94 mmol, 44% yield) as a white solid. Anal. Calcd. for $C_{10}H_5ClN_2O$ m/z 204.0, found: 205.0 $(M+H)^+$.

C: 3-(2-Chlorooxazol-5-yl)benzamide

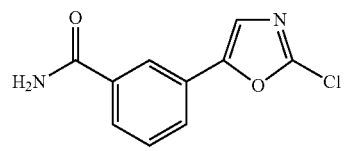 [SMILES: NC(=O)c1cccc(-c2cnc(Cl)o2)c1]

30% $H_2O_2$ (28.7 mL, 281.0 mmol) was slowly added to a 0° C. mixture of 3-(2-chlorooxazol-5-yl)benzonitrile (8.20 gm, 40.10 mmol) and $K_2CO_3$ (3.88 gm, 28.10 mmol) in DMSO (75 mL). The ice bath was removed and the reaction mixture was stirred at rt. After 24 h the reaction mixture was partitioned between EtOAc and water. The organic phase was isolated, washed with saturated aqueous NaCl (2×), dried over $MgSO_4$, filtered and concentrated to give the product, 3-(2-chlorooxazol-5-yl)benzamide, (7.00 gm, 31.40 mmol, 78% yield) as a light yellow solid. Anal. Calcd. for $C_{10}H_7ClN_2O_2$ m/z 222.0, found: 223.0 $(M+H)^+$. Crude product was used without purification.

Intermediate 42

3-(2-Chlorooxazole-5-yl)-N-methylbenzamide

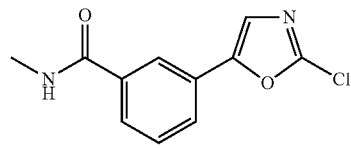 [SMILES: CNC(=O)c1cccc(-c2cnc(Cl)o2)c1]

A: 3-(Oxazol-5-yl)benzoic acid

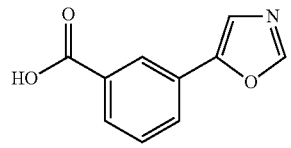

MeOH (54 mL) was added to a round bottom flask containing $K_2CO_3$ (6.74 gm, 48.70 mmol), 1-(isocyanomethylsulfonyl)-4-methylbenzene (5.00 gm, 25.60 mmol), and methyl 3-formylbenzoate (4.00 gm, 24.37 mmol). The reaction mixture was heated at 80° C. for 3 h and then stirred at rt overnight. The mixture was concentrated under reduced pressure. The remaining residue was partitioned between EtOAc and water. The aqueous solution was isolated and acidified using 1N HCl. The acidified aqueous phase was extracted with EtOAc (2×). The organic extracts were combined, washed with saturated aqueous NaCl, dried over $MgSO_4$, filtered and concentrated to give the product, 3-(oxazol-5-yl) benzoic acid, (4.00 gm, 21.15 mmol, 86% yield) as a white solid. Anal. Calcd. for $C_{10}H_7NO_3$ m/z 189.0, found: 190.1 $(M+H)^+$. Crude product was used without purification.

B: N-methyl-3-(Oxazol-5-yl)benzamide

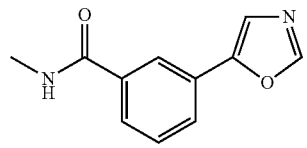

DMF (15.9 mL) was added to a round bottom flask containing 3-(oxazol-5-yl)benzoic acid (0.99 gm, 5.23 mmol), methylamine hydrochloride (0.39 gm, 5.76 mmol), EDC (1.10 gm, 5.76 mmol), and HOAt (0.78 gm, 5.76 mmol). DIPEA (2.29 mL, 13.08 mmol) was then added. The reaction mixture was stirred at rt overnight. After 24 h the mixture was partitioned between EtOAc and water. The organic phase was isolated, washed with saturated aqueous NaCl, dried over $MgSO_4$, filtered and concentrated. The resulting residue was purified using silica gel chromatography eluting with a gradient of 0-100% EtOAc/Hexanes then 15% MeOH in EtOAc to give the product, N-methyl-3-(oxazol-5-yl)benzamide, (0.50 gm, 2.49 mmol, 48% yield) as a white solid. Anal. Calcd. for $C_{11}H_{10}N_2O_2$ m/z 202.1, found: 203.1 (M+H)$^+$.

C: 3-(2-Chlorooxazol-5-yl)-N-methylbenzamide

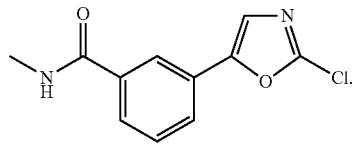 [SMILES: CNC(=O)c1cccc(-c2cnc(Cl)o2)c1]

To a round bottom flask was added N-methyl-3-(oxazol-5-yl)benzamide (0.50 gm, 2.47 mmol) and THF (25 mL). The reaction was cooled to −78° C. and 1.6 M nBuLi (3.86 mL, 6.18 mmol) was added dropwise. The reaction turned orange-red in color. After 60 min, a solution of hexachloroethane (0.88 gm, 3.71 mmol) in THF (5 mL) was slowly added. The reaction was slowly warmed to rt over 30 min. After 2 h at rt the reaction was quenched by slow addition of sat. NH$_4$Cl (10 mL). The mixture was concentrated to remove most of the THF. The mixture was then partitioned between EtOAc (40 mL) and water (20 mL). The organic phase was isolated, washed with saturated aqueous NaCl, dried over MgSO$_4$, filtered and concentrated. The resulting residue was purified using silica gel chromatography eluting with a gradient of 0-100% EtOAc/Hexanes to give the product, 3-(2-chlorooxazol-5-yl)-N-methylbenzamide, (123 mg, 0.52 mmol, 21% yield) as a light yellow solid. Anal. Calcd. for $C_{11}H_9ClN_2O_2$ m/z 236.0, found: 237.0 (M+H)$^+$.

Intermediate 43

Methyl 3-(2-chlorooxazole-5-yl)phenylcarbamate

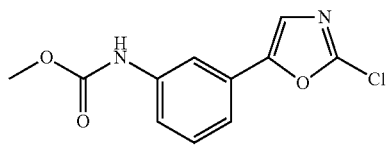

A: 5-(3-Nitrophenyl)oxazole

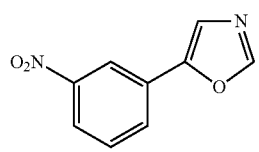

5-(3-Nitrophenyl)oxazole (5.80 gm, 30.50 mmol, 92% yield) was synthesized as described for the preparation of Intermediate A using 3-nitrobenzaldehyde in step A. Anal. Calcd. for $C_9H_6N_2O_3$ m/z 190.0, found: 191.0 (M+H)$^+$.

B: 3-(Oxazol-5-yl)aniline

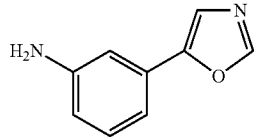 [SMILES: O=[N+]([O-])c1cccc(-c2cnco2)c1]

10% Pd/C (0.60 gm, 0.56 mmol) was added to a solution of 5-(3-Nitrophenyl)oxazole (5.80 gm, 30.50 mmol) in MeOH (122 mL). A H$_2$ atmosphere was then introduced via balloon. After 24 h the reaction mixture was filtered through Celite. The catalyst was rinsed with MeOH and the filtrate was concentrated to give the product 3-(oxazol-5-yl)aniline (4.82 gm, 30.10 mmol, 99% yield) as a white solid. Anal. Calcd. for $C_9H_6N_2O_3$ m/z 160.1, found: 161.1 (M+H)$^+$. Crude product was used without purification.

C: Methyl 3-(oxazol-5-yl)phenylcarbamate

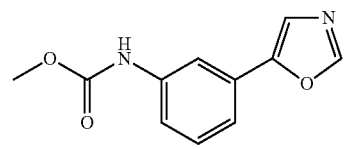 [SMILES: COC(=O)Nc1cccc(-c2cnco2)c1]

Methyl chloroformate (1.67 mL, 21.54 mmol) was slowly added to a 0° C. solution of 3-(oxazol-5-yl)aniline (2.30 gm, 14.36 mmol) and TEA (4.00 mL, 28.70 mmol) in THF (65 mL). The ice bath was removed and the reaction mixture was stirred at rt. After 2.5 h the reaction mixture was concentrated and the residue was partitioned between EtOAc and water. The organic phase was isolated, washed with 1 N HCl (2×) and saturated aqueous NaCl, dried over MgSO$_4$, filtered and concentrated. The resulting residue was purified using silica gel chromatography eluting with a gradient of 0-100% EtOAc/Hexanes to give the product, methyl 3-(oxazol-5-yl)phenylcarbamate, (1.34 gm, 6.14 mmol, 43% yield) as a white solid. Anal. Calcd. for $C_{11}H_{10}N_2O_3$ m/z 218.1, found: 219.1 (M+H)$^+$.

D: Methyl 3-(2-chlorooxazol-5-yl)phenylcarbamate

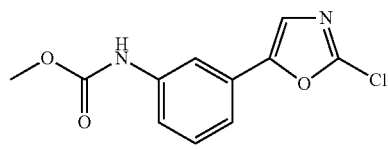 [SMILES: COC(=O)Nc1cccc(-c2cnc(Cl)o2)c1]

1.6 M nBuLi (9.60 mL, 15.35 mmol) was added dropwise to −78° C. solution of methyl 3-(oxazol-5-yl)phenylcarbamate (1.34 gm, 6.14 mmol) in THF (50 mL). Upon addition the reaction mixture turned red in color. After 60 min, a solution of hexachloroethane (2.18 gm, 9.21 mmol) in THF (10 mL) was slowly added. The reaction was slowly warmed to rt over 30 min. After 2 h at rt the reaction was quenched by slow addition of sat. NH₄Cl (20 mL). The mixture was concentrated to remove most of the THF. The mixture was then partitioned between EtOAc (80 mL) and water (30 mL). The organic phase was isolated, washed with saturated aqueous NaCl, dried over MgSO₄, filtered and concentrated. The resulting residue was purified using silica gel chromatography eluting with a gradient of 0-100% EtOAc/Hexanes to give the product, Methyl 3-(2-chlorooxazol-5-yl)phenylcarbamate, (1.20 gm, 4.75 mmol, 77% yield) as a light yeloow solid. Anal. Calcd. for $C_{11}H_9ClN_2O_3$ m/z 252.0, found: 253.0 (M+H)⁺.

Intermediate 44

Ethyl 3-(2-chlorooxazole-5-yl)phenylcarbamate

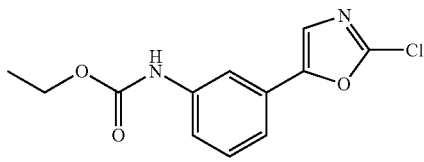 [SMILES: CCOC(=O)Nc1cccc(-c2cnc(Cl)o2)c1]

Ethyl 3-(2-chlorooxazol-5-yl)phenylcarbamate (1.72 gm, 6.45 mmol, 49% yield—2 steps) was synthesized as described for the preparation of Intermediate C using ethyl chloroformate in step C. Anal. Calcd. for $C_{12}K_1ClN_2O_3$ m/z 266.0, found: 267.1 (M+H)⁺.

Intermediate 45

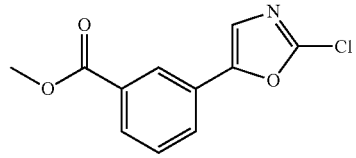 [SMILES: COC(=O)c1cccc(-c2cnc(Cl)o2)c1]

Methyl 3-(2-chlorooxazol-5-yl)benzoate (480 mg, 2.02 mmol, 35% yield) was synthesized as described for the preparation of Intermediate 2 using methyl 3-formylbenzaldehyde in step A. Anal. Calcd. for $C_{11}H_8ClNO_3$ m/z 237.64, found: 238.0 (M+H)⁺. ¹H NMR (400 MHz, Chloroform-d) δ ppm 8.31-8.19 (m, 1H), 8.01 (d, J=8.8 Hz, 1H), 7.77 (d, J=8.8 Hz, 1H), 7.51 (t, J=7.8 Hz, 1H), 7.37 (s, 1H), 3.97 (S, 3H).

Intermediate 46

(S)-Benzyl (3-methylpiperidin-3-yl)carbamate

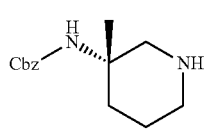

A: 1-tert-Butyl 3-ethyl piperidine-1,3-dicarboxylate

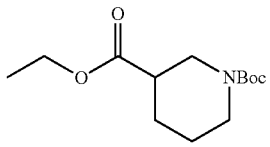 [SMILES: CCOC(=O)C1CCCN(C(=O)OC(C)(C)C)C1]

To a solution of ethyl piperidine-3-carboxylate (15 g, 95 mmol) in THF (159 mL) at RT was added Boc₂O (7.75 mL, 33.4 mmol), then stirred at RT for 16 h. The resultant reaction mass was diluted with water (50 mL), and then extracted with ethyl acetate (3×100 mL). Combined organic extracts was washed with saturated NaHCO₃ solution (1×200 mL), brine (20 mL), dried (Na₂SO₄), filtered and concentrated. The resulting residue was purified by ELSD ISCO on 120 g silica column, eluted the compound around 25% ethylacetate in hexanes, the pure fractions were collected and concentrated to give desired product 1-tert-butyl 3-ethyl piperidine-1,3-dicarboxylate (23.39 g, 91 mmol, 95% yield) as a colorless oil. Anal. Calcd. for $C_{13}H_{23}NO_4$ m/z 257.3, found: 158.2 (M-Boc+H)⁺; ¹HNMR (400 MHz, CDCl₃) ppm 4.13 (q, J=7.3 Hz, 2 H), 3.90 (d, J=13.1 Hz, 1H), 2.87-3.08 (m, 1H), 2.85-2.74 (m, 1H), 2.48-2.37 (m, 1H), 2.08-1.98 (m, 1H), 1.75-1.50 (s, 2 H), 1.48-1.40 (m, 11 H), 1.25 (t, J=7.15 Hz, 3 H).

B: 1-tert-Butyl 3-ethyl 3-methylpiperidine-1,3-dicarboxylate

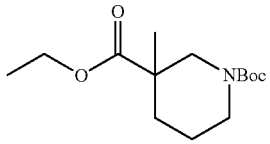 [SMILES: CCOC(=O)C1(C)CCCN(C(=O)OC(C)(C)C)C1]

To a flame-dried round bottom flask under Argon atmosphere was added THF (100 mL), then it was cooled to −30° C. To this cold solvent were added n-butyllithium (40.1 ml, 64.1 mmol), and diisopropylamine (10.80 ml, 76 mmol) drop wise. The resultant solution was stirred at −25° C. for 1 hour. To the above solution 1-tert-butyl 3-ethyl piperidine-1,3-dicarboxylate (15 g, 58.3 mmol) in THF (20 mL) was added drop wise at −78° C. (maintain temperature <−70° C.). After the addition, the reaction was stirred at −70° C. for 1 h, and then methyl iodide (4.74 mL, 76 mmol) was added drop wise. This reaction mixture was stirred at same temperature for 1 h, then slowly warmed to RT and stirred for 16 h. The reaction mixture was quenched with sat. aq. NH₄Cl (50 mL), extracted with EtOAc (2×200 mL), the combined organics extracts was washed with sat. NH₄Cl (100 mL), brine (50 mL), dried (Na₂SO₄) and concentrated to get crude compound. The crude residue was purified by ELSD ISCO on 120 g silica column, eluted the compound around 20% ethyl acetate in hexanes, the pure fractions were collected and concentrated to give desired product 1-tert-butyl 3-ethyl 3-methylpiperidine-1,3-dicarboxylate (15.14 g, 52.5 mmol, 90% yield) as a colorless oil. Anal. Calcd. for $C_{14}H_{25}NO_4$ m/z 271.3, found: 172.2 (M-Boc+H)⁺; ¹H NMR (400 MHz, CDCl₃) δ ppm 4.13 (q, J=7.0 Hz, 2 H), 3.82 (d, J=13.5 Hz, 1 H), 3.46-3.38 (m, 1

H), 3.32-3.19 (m, 1 H) 3.13 (d, J=13.2 Hz, 1 H) 2.07-1.97 (m, 1 H) 1.60-1.50 (m, 2 H) 1.48-1.40 (m, 10 H), 1.25 (t, J=7.15 Hz, 3 H), 1.15 (s, 3 H)

C: 1-(tert-Butoxycarbonyl)-3-methylpiperidine-3-carboxylic acid

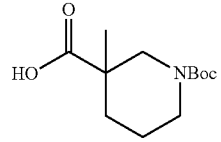 [SMILES: CC(C)(C)OC(=O)N1CCCC(C)(C(=O)O)C1]

To a solution of 1-tert-butyl 3-ethyl 3-methylpiperidine-1,3-dicarboxylate (15 g, 55.3 mmol) in THF (87 mL) and MeOH (87 mL) was added lithium hydroxide(2M in water) (172 mL, 345 mmol) at RT and stirred at same temperature for 15 h. The reaction mixture was cooled in an ice-bath, and adjusted to pH ~4 by adding 1N HCl solution. The aqueous layer was extracted with ethylacetate (3×200 mL) and the combined organic extracts was washed with brine (20 mL), dried (Na$_2$SO$_4$), filtered and concentrated to give desired 1-(tert-butoxycarbonyl)-3-methylpiperidine-3-carboxylic acid (13.45 g, 54.2 mmol, 98% yield) as a white solid. This material was directly used for next step with out any further purification. Anal. Calcd. for C$_{12}$H$_{21}$NO$_4$ m/z 243.3, found: 242.2 (M–H)$^+$; $^1$H NMR (400 MHz, DMSO-d$_6$) δ ppm 12.31 (s, 1 H) 3.68-3.52 (m, 1 H), 3.32-3.02 (m, 4 H), 1.89-1.82 (m, 1 H), 1.54-1.43 (m, 11 H) 1.06 (s, 3 H).

D: (S)-tert-Butyl 3-(((benzyloxy)carbonyl)amino)-3-methylpiperidine-1-carboxylate

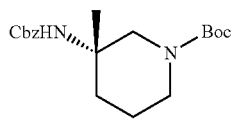 [SMILES: CC(C)(C)OC(=O)N1CCC[C@](C)(NC(=O)OCc2ccccc2)C1]

To a solution of 1-(tert-butoxycarbonyl)-3-methylpiperidine-3-carboxylic acid (10 g, 41.1 mmol) and triethylamine (5.73 mL, 41.1 mmol) in toluene (399 mL) was added diphenylphosphoryl azide (8.86 mL, 41.1 mmol) at RT, stirred for 1 h, then heated to reflux (115° C.) for 45 min. The reaction mass was cooled to 50° C. and then was added benzyl alcohol (42.7 mL, 411 mmol). The resultant solution was again heated to reflux for 16 h. Reaction was cooled to RT, concentrated under reduced pressure to get pale yellow oil. Bezylalcohol was removed from the resultant crude pale yellow oil by using Coughler distillation apparatus (150° C. at 7 mbar). The residue remained was purified over Silica cartridge by using ELSD ISCO. The pure fractions were collected and concentrated to get 10 g product as recemic mixture as a colorless oil. This recemic mixture was separated by SFC method 1 to give desired enantiomer (S)-tert-butyl 3-(((benzyloxy)carbonyl)amino)-3-methylpiperidine-1-carboxylate (4.5 g, 12.79 mmol, 31.1% yield) as off white solid.

Anal. Calcd. for C$_{19}$H$_{28}$N$_2$O$_4$ m/z 348.4, found: 349.2 (M+H)$^+$; $^1$H NMR (400 MHz, CDCl$_3$) δ ppm 7.37-7.29 (m, 5 H), 5.15-4.96 (m, 2 H), 3.89 (dd, J=14.3, 3.89 Hz, 2 H), 2.85 (t, J=6.2 Hz, 2 H), 1.67-1.20 (m, 16 H).

E: (S)-Benzyl (3-methylpiperidin-3-yl)carbamate

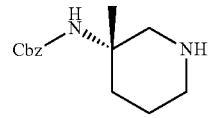 [SMILES: C[C@]1(NC(=O)OCc2ccccc2)CCCNC1]

To a solution of (S)-tert-butyl 3-(benzyloxycarbonylamino)-3-methylpiperidine-1-carboxylate (3.5 g, 10.04 mmol) in dioxane (14 mL) was added 4N HCl in dioxane (15 mL, 60 mmol) drop wise at 0° C. The resultant clear solution was stirred at room temperature for 2 h. The reaction mixture was concentrated, the pale yellow foam was dissolved in water (50 mL), washed with ethyl acetate (2×30 mL), the aqueous layer was basified with saturated NaHCO$_3$ (until reach pH ~9) at 0° C. The resultant aqueous layer was extracted with CHCl$_3$ (3×50 mL), the combined organic extracts was washed with water (50 mL), brine (10 mL), dried (Na$_2$SO$_4$), concentrated and dried in high vacuum to get the product (S)-benzyl (3-methylpiperidin-3-yl)carbamate (2.45 g, 9.85 mmol, 98% yield) as a light yellow solid. Anal. Calcd. for C$_{14}$H$_{20}$N$_2$O$_2$ m/z 248.3, found: 249.2 (M+H)$^+$; $^1$H NMR (400 MHz, CD$_3$OD) δ ppm 7.42-7.26 (m, 5 H), 5.13-4.97 (m, 2 H), 3.20 (d, J=13.2 Hz, 1 H), 2.93-2.82 (m, 1 H), 2.60-2.50 (m, 2 H), 2.13 (d, J=13.0 Hz, 1 H), 1.69-1.56 (m, 1 H), 1.54-1.37 (m, 2 H), 1.27 (s, 3 H).

Intermediate 47

(S)-3-Methyl-1-(4-(trifluoromethyl)phenyl)piperidin-3-amine

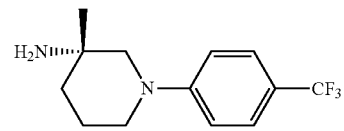

A: (S)-Benzyl (3-methyl-1-(4-(trifluoromethyl)phenyl)piperidin-3-yl)carbamate

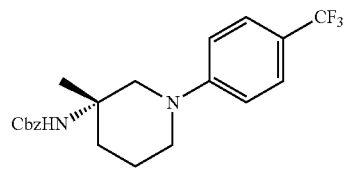 [SMILES: C[C@]1(NC(=O)OCc2ccccc2)CCCN(c2ccc(C(F)(F)F)cc2)C1]

To a pale yellow solution of Intermediate 46, (S)-benzyl (3-methylpiperidin-3-yl)carbamate (1.5 g, 6.04 mmol) and (4-(trifluoromethyl)phenyl)boronic acid (1.491 g, 7.85 mmol) in CH$_2$Cl$_2$ (7 mL) were added copper (II) acetate (1.207 g, 6.64 mmol) and pyridine (0.977 mL, 12.08 mmol) on stirring. The final resultant green solution was stirred under Oxygen atmosphere at RT for 18 h. The reaction mass was adsorbed on silica and purified on a 12 g silica cartridge by ISCO, eluted the compound around 5% of ethyl acetate in hexanes. The pure fractions were collected and concentrated to afford 1-(2-(trifluoromethyl)pyrimidin-5-yl)piperidin-3-ol (1.2 g, 3.04 mmol, 50.2% yield) as a pale yellow color solid. Anal. Calcd. for $C_{21}H_{23}F_3N_2O_2$ m/z 392.4, found: 393.4 (M+H)$^+$; $^1$H NMR (400 MHz, CDCl$_3$) δ ppm 7.51 (d, J=8.0 Hz, 2H), 7.43 (d, J=7.2 Hz, 1 H), 7.34-7.32 (m, 3 H), 6.94-6.89 (m, 3 H), 4.12 (d, J=13.0 Hz, 1 H), 3.54 (d, J=13.2 Hz, 1 H), 2.83-2.77 (m, 2H), 2.10 (d, J=11.2 Hz, 1 H), 1.84-1.64 (m, 2 H), 1.45 (s, 3 H), 1.43-1.35 (m, 1 H), B: (S)-3-Methyl-1-(4-(trifluoromethyl)phenyl)piperidin-3-amine

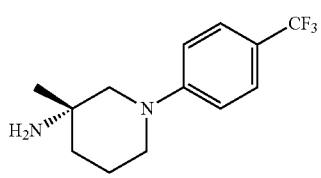 [SMILES: C[C@]1(N)CCCN(c2ccc(C(F)(F)F)cc2)C1]

To a solution of (S)-benzyl (3-methyl-1-(4-(trifluoromethyl)phenyl)piperidin-3-yl)carbamate (2.05 g, 5.22 mmol) in MeOH (20 mL) was added palladium on carbon (0.406 g, 3.81 mmol) under nitrogen atmosphere. The resultant black color suspension was stirred under hydrogen balloon pressure at rt for 2 hours. The reaction mass was filtered on Celite, the filter cake was washed with methanol (3×10 mL), and combined filtrate was concentrated and dried under vacuum to get 1.6 g of crude compound. This crude was purified on a 12 g silica cartridge by ISCO, eluted the compound around 5% methanol in chloroform. Pure fractions were collected and concentrated to get (S)-3-methyl-1-(4-(trifluoromethyl)phenyl)piperidin-3-amine (570 mg, 1.493 mmol, 28.6% yield) as pale yellow gummy solid.

Anal. Calcd. for $C_{13}H_{17}F_3N_2$ m/z 258.3, found: 259.2 (M+H)$^+$; $^1$H NMR (400 MHz, CD$_3$OD) δ ppm 7.47 (d, J=8.53 Hz, 2 H), 7.07 (d, J=8.78 Hz, 2 H), 3.48-3.39 (m, 1 H), 3.21 (d, J=12.05 Hz, 1 H), 3.06-3.00 (m, 1 H), 2.97 (d, J=12.30 Hz, 2 H), 1.92-1.81 (m, 1 H), 1.80-1.70 (m, 1 H), 1.65-1.52 (m, 2 H), 1.19 (s, 3 H).

Intermediate 48

(1R,2R)—N1-((S)-3-Methyl-1-(4-(trifluoromethyl)phenyl)piperidin-3-yl)cyclohexane-1,2-diamine

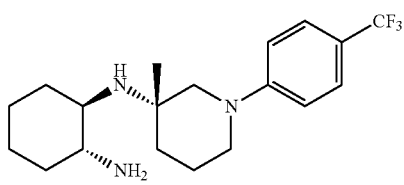 [SMILES: C[C@]1(N[C@@H]2CCCC[C@H]2N)CCCN(c2ccc(C(F)(F)F)cc2)C1]

A: Benzyl ((1R,2R)-2-(((S)-3-methyl-1-(4-(trifluoromethyl)phenyl)piperidin-3-yl)amino)cyclohexyl)carbamate

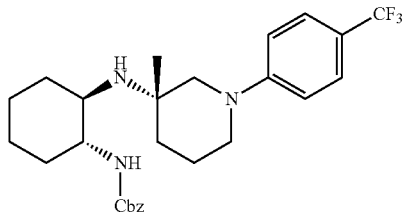 [SMILES: C[C@]1(N[C@@H]2CCCC[C@H]2NC(=O)OCc2ccccc2)CCCN(c2ccc(C(F)(F)F)cc2)C1]

To a solution of (S)-3-methyl-1-(4-(trifluoromethyl)phenyl)piperidin-3-amine (570 mg, 2.207 mmol) and benzyl 7-azabicyclo[4.1.0]heptane-7-carboxylate (715 mg, 3.09 mmol) in methylene chloride (1.5 mL) was added N-lithiotrifluoromethane-sulfonimide (317 mg, 1.103 mmol). The resultant pale brown solution was stirred at 45° C. for 3 days. The slurry reaction was allowed to cool to room temperature, then diluted with CH$_2$Cl$_2$ (30 mL), stirred with sat. NaHCO$_3$ (10 mL) for 30 min. The separated aqueous layer was extracted with CH$_2$Cl$_2$ (2×20 mL). The combined CH$_2$Cl$_2$ phase was washed with brine (10 mL), dried (Na$_2$SO$_4$) and concentrated to dryness. The dark orange oily residue was purified on a 12 g silica cartridge by ISCO, eluted the compound around 35% ethyl acetate in hexanes. Pure fractions were collected and concentrated to get 1.2 g of product as diastereomeric mixture. This diastereomeric mixture was separated by SFC method 2 to give desired diastereomer benzyl ((1R,2R)-2-(((S)-3-methyl-1-(4-(trifluoromethyl)phenyl)piperidin-3-yl)amino)cyclohexyl)carbamate (425 mg, 0.805 mmol, 36.5% yield) as pale brown oil. Anal. Calcd. for $C_{27}H_{34}F_3N_3O_2$ m/z 489.6, found: 490.4 (M+H)$^+$; $^1$H NMR (400 MHz, CDCl$_3$) δ ppm 7.39 (d, J=8.8 Hz, 2 H), 7.34-7.27 (m, 5 H), 6.87-6.90 (d, J=8.5 Hz, 2 H), 5.50 (bs, 1 H), 5.07-4.96 (m, 2 H), 3.34-3.21 (m, 2 H), 3.17-3.07 (m, 1 H), 2.83-2.75 (m, 1 H), 2.65 (d, J=12.8 Hz, 1 H), 2.38-2.28 (m, 1 H), 2.27-2.16 (m, 1 H), 2.04-1.84 (m, 2 H), 1.70-1.55 (m, 6 H), 1.33-1.20 (m, 5 H), 1.10 (s, 3 H).

B: (1R,2R)—N1-((S)-3-Methyl-1-(4-(trifluoromethyl)phenyl)piperidin-3-yl)cyclohexane-1,2-diamine

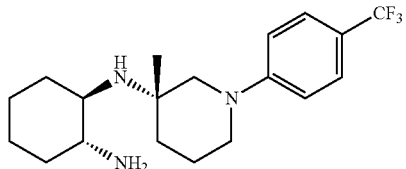

To a solution of benzyl ((1R,2R)-2-(((S)-3-methyl-1-(4-(trifluoromethyl)phenyl)piperidin-3-yl)amino)cyclohexyl)carbamate (420 mg, 0.858 mmol) in MeOH (4 mL) was added palladium on carbon (10%) (84 mg, 0.789 mmol) under nitrogen atmosphere. The resultant black color suspension was stirred under hydrogen balloon pressure at RT for 2 h. The reaction mass was filtered on Celite and the filter cake was washed with methanol (3×5 mL). The filtrate was concentrated and dried under vacuum to get (1R,2R)—N1-((S)-3- methyl-1-(4-(trifluoromethyl)phenyl)piperidin-3-yl)cyclohexane-1,2-diamine (300 mg, 0.667 mmol, 78% yield) as off white solid. This was directly used for next reaction with out any further purification. Anal. Calcd. for $C_{19}H_{28}F_3N_3$ m/z 355.4, found: 490.4 (M+H)$^+$; This was taken for next step with out any further characterization.

Intermediate 49

(1R,2R)—N1-(4-bromopyridin-2-yl)-N2-((S)-1-(4-(trifluoromethyl)phenyl)piperidin-3-yl)cyclohexane-1,2-diamine

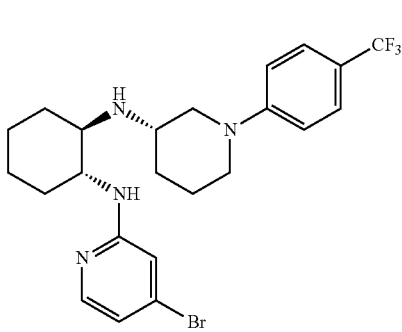 [SMILES: FC(F)(F)c1ccc(N2CCC[C@H](N[C@@H]3CCCC[C@H]3Nc3cc(Br)ccn3)C2)cc1]

To a 50 mL round-bottom flask equipped with a magnetic stir bar, were added 96% pure (1R,2R)—N1-((S)-1-(4-(trifluoromethyl)phenyl)piperidin-3-yl)cyclohexane-1,2-diamine (2.69 g, 7.56 mmol), 4-bromo-2-fluoropyridine (1.175 mL, 11.35 mmol), N-Methyl-2-pyrrolidinone (7.56 mL), and Hunig's Base (3.96 mL, 22.69 mmol). The flask was capped after being purged with argon, and it was placed in a sand bath at 95° C. The resulting homogeneous mixture was stirred. At 15 h, 0.59 mL more 4-bromo-2-fluoropyridine was added, and at 40 h, more Hunig's Base (1.32 mL) was added, and the temperature was increased to 120° C. After 4 h at 120° C., the reaction mixture was cooled to ambient temperature. Diethyl ether (30 mL) was added, and the resulting solution was washed with water (2×30 mL). The organic layer was saved, and the water washes were combined and extracted once with diethyl ether (60 mL). The organic extract was then washed twice with water (60 mL). The organic layer was saved, and all water washes were combined and extracted once with diethyl ether (120 mL). The organic extract was then washed twice with water (120 mL). The organic layer was saved. The three saved organic layers were combined for drying over anhydrous sodium sulfate. Evaporation under vacuum at 40° C. gave 3.3 g of a tan semi-solid. The crude product was dissolved in a small amount of dichloromethane and loaded to a slurry packed silica gel (150 g) column for flash chromatography, eluted with a step-wise gradient of 1.5% to 4% of (10% concentrated aqueous ammonia—methanol) in dichloromethane. Desired product fractions were divided into two sets based on the amount of a slightly higher Rf impurity. The early fractions were pooled and evaporated under vacuum to obtain a tan waxy solid (1.36 g), judged to be 89% pure title compound, the main impurity likely being the product of bromine rather than fluorine displacement. The late fractions were pooled and evaporated under vacuum to obtain a tan waxy solid (1.90 g), judged to be 98% pure title compound. The total purity-corrected yield is 82%. Anal. Calcd. for $C_{23}H_{28}BrFN_4$ m/z 496.1, found: 497.1, 499.0 (M+H)$^+$; $^1$H NMR (500 MHz, CDCl$_3$) δ ppm 7.90 (d, J=5.5 Hz, 1H), 7.48 (d, J=8.5 Hz, 2H), 6.86 (d, J=8.5 Hz, 2H), 6.73 (dd, J=5.5, 1.6 Hz, 1H), 6.55 (d, J=1.4 Hz, 1H), 4.45 (d, J=7.7 Hz, 1H), 3.57 (dd, J=12.4, 3.3 Hz, 1H), 3.39-3.50 (m, 2H), 2.95 (m, 1H), 2.85 (m, 1H), 2.72 (dd, J=12.1, 8.5 Hz, 1H), 2.49 (dt, J=3.7, 9.9 Hz, 1H), 2.19 (m, 1H), 2.11 (m, 1H), 1.90 (m, 1H), 1.73-1.82 (m, 3H), 1.65 (m, 1H), 1.17-1.45 (m, 5H); water at 1.57 ppm may obscure 1H.

Intermediate 50

(1R,2R)—N1-((S)-1-(6-(trifluoromethyl)pyridin-3-yl)piperidin-3-yl)cyclohexane-1,2-diamine

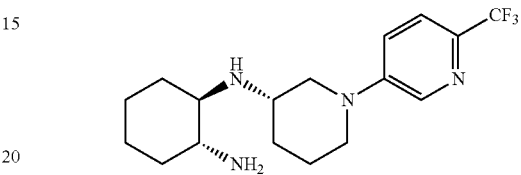

(1R,2R)—N1-((S)-1-(6-(trifluoromethyl)pyridin-3-yl)piperidin-3-yl)cyclohexane-1,2-diamine was synthesized as described in Intermediate 17 using 5-fluoro-2-(trifluoromethyl)pyridine in the step A.

Intermediate 51

(1R,2R)—N$^1$—((S)-1-(2-(trifluoromethyl)pyrimidin-5-yl)piperidin-3-yl)cyclohexane-1,2-diamine

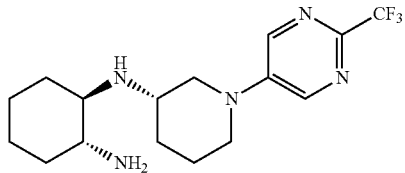 [SMILES: N[C@@H]1CCCC[C@H]1N[C@H]1CCCN(c2cnc(C(F)(F)F)nc2)C1]

A: Benzyl 3-((1R,2R)-2-(tert-butoxycarbonylamino)cyclohexylamino)piperidine-1-carboxylate

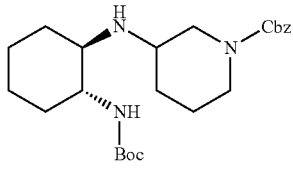 [SMILES: CC(C)(C)OC(=O)N[C@@H]1CCCC[C@H]1NC1CCCN(C(=O)OCc2ccccc2)C1]

MgSO$_4$ (0.25 gm) was added to a solution of tert-butyl ((1R,2R)-2-aminocyclohexyl)carbamate (1.49 gm, 6.97 mmol) and benzy 3-oxopiperidine-1-carboxylate (1.63 gm, 6.97 mmol) in CH$_2$Cl$_2$ (35 mL). After 1 h of stirring sodium triacetoxyborohydride (3.69 gm, 17.43 mmol) was added in portions. After 24 h the reaction mixture was diluted with CH$_2$Cl$_2$ and quenched by addition of water. The organic phase was isolated, dried over MgSO$_4$, filtered and concentrated. The resulting residue was purified using silica gel chromatography eluting with a gradient of 0-100% EtOAc/Hexanes holding at 100% EtOAc to give the product, benzyl 3-((1R,2R)-2-(tert-butoxycarbonylamino)cyclohexylamino)

piperidine-1-carboxylate, (1.73 gm, 4.01 mmol, 58% yield) as a taffy. Anal. Calcd. for $C_{24}H_{37}N_3O_4$ m/z 431.3, found: 432.3 (M+H)$^+$.

B: tert-Butyl (1R,2R)-2-(piperidin-3-ylamino)cyclohexylcarbamate

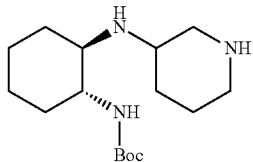 [SMILES: CC(C)(C)OC(=O)N[C@@H]1CCCC[C@H]1NC1CCCNC1]

10% Pd/C (0.20 gm, 0.19 mmol) was added to a solution of benzyl 3-((1R,2R)-2-(tert-butoxycarbonylamino)cyclohexylamino)piperidine-1-carboxylate, (1.73 gm, 4.01 mmol) in MeOH (14.6 mL) and AcOH (1.46 mL). A H$_2$ atmosphere was then introduced via balloon. After 1 h the reaction mixture was filtered through Celite. The catalyst was rinsed with MeOH and the filtrate was concentrated. The residue was partitioned between EtOAc and sat. NaHCO$_3$. The aqueous phase was isolated and extracted with EtOAc. All organic phases were combined, washed with saturated aqueous NaCl, dried over MgSO$_4$, filtered and concentrated to give the product tert-butyl (1R,2R)-2-(piperidin-3-ylamino)cyclohexylcarbamate (1.02 gm, 3.43 mmol, 86% yield) as a white foam. Anal. Calcd. for $C_{16}H_{31}N_3O_2$ m/z 297.2, found: 298.2 (M+H)$^+$. Crude product was used without purification.

C: tert-Butyl (1R,2R)-2-(1-(2-(trifluoromethyl)pyrimidin-5-yl)piperidin-3-ylamino)cyclohexylcarbamate

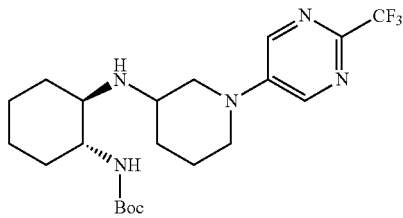 [SMILES: CC(C)(C)OC(=O)N[C@@H]1CCCC[C@H]1NC1CCCN(c2cnc(C(F)(F)F)nc2)C1]

Dimethylacetamide (5.25 mL) was added to a round bottom flask containing tert-butyl (1R,2R)-2-(piperidin-3-ylamino)cyclohexylcarbamate (0.47 gm, 1.58 mmol) and 5-bromo-2-(trifluoromethyl)pyrimidine (0.43 gm, 1.89 mmol). The reaction mixture was then heated at 100° C. After 48 h heating was stopped. The reaction mixture was partitioned between EtOAc and sat. NaHCO$_3$. The organic phase was isolated, washed with saturated aqueous NaCl, dried over MgSO$_4$, filtered and concentrated. The resulting residue was purified using silica gel chromatography eluting with a gradient of 0-100% EtOAc/Hexanes holding at 100% EtOAc to give the diastereomeric product, tert-butyl (1R,2R)-2-(1-(2-(trifluoromethyl)pyrimidin-5-yl)piperidin-3-ylamino)cyclohexylcarbamate, (0.31 gm, 0.70 mmol, 44% yield) as light yellow solid. Anal. Calcd. for $C_{21}H_{32}F_3N_5O_2$ m/z 443.3, found: 444.3 (M+H)$^+$.

D: t-Butyl (1R,2R)-2-((S)-1-(2-(trifluoromethyl)pyrimidin-5-yl)piperidin-3-ylamino)cyclohexylcarbamate

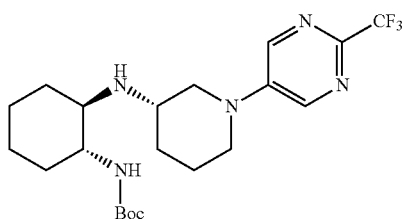 [SMILES: CC(C)(C)OC(=O)N[C@@H]1CCCC[C@H]1N[C@H]1CCCN(c2cnc(C(F)(F)F)nc2)C1]

t-Butyl (1R,2R)-2-(1-(2-(trifluoromethyl)pyrimidin-5-yl)piperidin-3-ylamino)cyclohexylcarbamate, (1.20 gm, 2.71 mmol) was purified by Chiral Preparative HPLC using method D:

Methanol solution of Peak 1 containing desired (S) isomer product was concentrated to give, tert-Butyl (1R,2R)-2-((S)-1-(2-(trifluoromethyl)pyrimidin-5-yl)piperidin-3-ylamino)cyclohexylcarbamate (0.58 gm, 1.30 mmol), 48%) as a foam. Anal. Calcd. for $C_{21}H_{32}F_3N_5O_2$ m/z 443.3, found: 444.3 (M+H)$^+$.

E: (1R,2R)—N$^1$—((S)-1-(2-(trifluoromethyl)pyrimidin-5-yl)piperidin-3-yl)cyclohexane-1,2-diamine

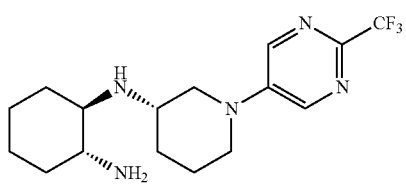

4 N HCl in dioxane (2.29 mL, 9.15 mmol) was slowly added to a solution of tert-butyl (1R,2R)-2-((S)-1-(2-(trifluoromethyl)pyrimidin-5-yl)piperidin-3-ylamino)cyclohexylcarbamate (0.58 gm, 1.31 mmol) in dioxane (3.52 mL) and MeOH (0.44 mL). After 1 h of stirring the reaction mixture was concentrated and the residue was partitioned between EtOAc and sat. NaHCO$_3$. The aqueous phase was isolated and extracted with EtOAc. All organic phases were combined, washed with saturated aqueous NaCl, dried over MgSO$_4$, filtered and concentrated to give the product (1R,2R)—N$^1$—((S)-1-(2-(trifluoromethyl)pyrimidin-5-yl)piperidin-3-yl)cyclohexane-1,2-diamine (0.44 gm, 1.29 mmol, 99% yield) as a syrup. Anal. Calcd. for $C_{16}H_{24}F_3N_5$ m/z 343.2, found: 344.2 (M+H)$^+$.

EXAMPLES

Example 1

(1R,2R)—N1-((S)-1-(4-Nitrophenyl)piperidin-3-yl)-N2-(5-(4-(trifluoromethoxy)phenyl)oxazol-2-yl)cyclohexane-1,2-diamine

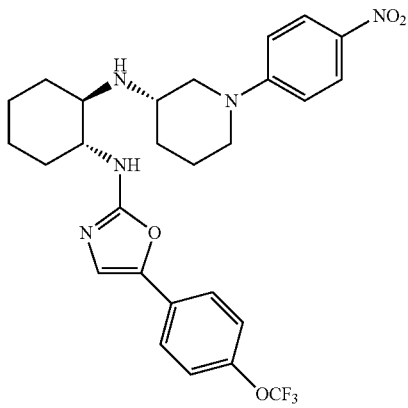 [SMILES: O=[N+]([O-])c1ccc(N2CCC[C@H](N[C@@H]3CCCC[C@H]3Nc3ncc(-c4ccc(OC(F)(F)F)cc4)o3)C2)cc1]

(1R,2R)—N1-((S)-1-(4-Nitrophenyl)piperidin-3-yl)-N2-(5-(4-(trifluoromethoxy)phenyl)oxazol-2-yl)cyclohexane-1,2-diamine (11 mg, 0.020 mmol, 41.5% yield) was synthesized as described in General Procedure H using Intermediate 2 (12.4 mg, 0.047 mmol) and Intermediate 17 (15 mg, 0.047 mmol). The product was purified using RP prep-HPLC method A to give the title compound as a yellow solid. Anal. Calcd. for $C_{27}H_{30}F_3N_5O_4$ m/z 545.5, found: 546.4 (M+H)$^+$; $^1$H NMR (500 MHz, CDCl$_3$) δ ppm 8.10 (d, J=9.35 Hz, 2 H), 7.48 (d, J=8.80 Hz, 2 H), 7.25 (d, 2 H), 7.03 (s, 1 H), 6.84 (d, J=9.35 Hz, 1 H), 4.13 (br. s., 1 H), 3.93 (br. s., 1 H), 3.74 (d, J=12.93 Hz, 1 H), 3.49 (s, 1 H), 3.44-3.35 (m, 1 H), 3.22 (dd, J=12.38, 10.18 Hz, 1 H), 3.03 (t, J=11.00 Hz, 1 H), 2.27 (dd, J=12.79, 2.34 Hz, 2 H), 2.21-2.13 (m, 1 H), 2.04-1.87 (m, 3 H), 1.78 (d, J=2.75 Hz, 1 H), 1.71-1.60 (m, 2 H), 1.48-1.39 (m, 2 H), 1.31-1.25 (m, 1 H); $^{13}$C NMR (126 MHz, CDCl$_3$) δ ppm 154.36, 145.13, 139.72, 126.00, 125.35, 123.69, 121.57, 114.25, 57.23, 55.72, 51.16, 48.71, 32.94, 29.72, 28.13, 27.38, 23.89, 23.76, 22.92.

Example 2

(1R,2R)—N1-((S)-1-(4-Nitrophenyl)piperidin-3-yl)-N2-(5-phenyloxazol-2-yl)cyclohexane-1,2-diamine

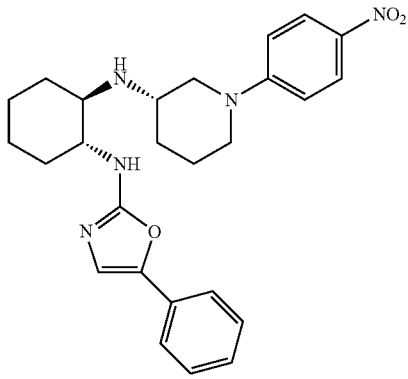 [SMILES: O=[N+]([O-])c1ccc(N2CCC[C@H](N[C@@H]3CCCC[C@H]3Nc3ncc(-c4ccccc4)o3)C2)cc1]

(1R,2R)—N1-((S)-1-(4-Nitrophenyl)piperidin-3-yl)-N2-(5-phenyloxazol-2-yl)cyclohexane-1,2-diamine (7 mg, 0.014 mmol, 30.6% yield) was synthesized as described in General Procedure H using Intermediate 1 (16.92 mg, 0.094 mmol) and Intermediate 17 (15 mg, 0.047 mmol). The crude product was purified using RP prep-HPLC method A to give the title compound as a yellow solid. Anal. Calcd. for $C_{26}H_{31}N_5O_4$ m/z 461.5, found: 426.4 (M+H)$^+$; $^1$H NMR (500 MHz, CDCl$_3$) δ ppm 8.07 (d, J=9.35 Hz, 2 H), 7.50-7.33 (m, 5 H), 7.00 (s, 1 H), 6.82 (d, J=9.35 Hz, 2 H), 4.09 (br. s., 1 H), 3.88 (br. s., 1 H), 3.68 (br. s., 1 H), 3.53-3.42 (m, 1 H), 3.42-3.32 (m, 1 H), 3.31-3.19 (m, 1 H), 3.13-2.97 (m, 1 H), 2.28 (d, J=3.85 Hz, 2 H), 2.16 (d, J=12.65 Hz, 2 H), 2.01-1.86 (m, 3 H), 1.82-1.60 (m, 3 H), 1.51-1.36 (m, 2 H).

Example 3

(1R,2R)—N1-(Benzo[d]oxazol-2-yl)-N2-((S)-1-(4-nitrophenyl)piperidin-3-yl)cyclohexane-1,2-diamine

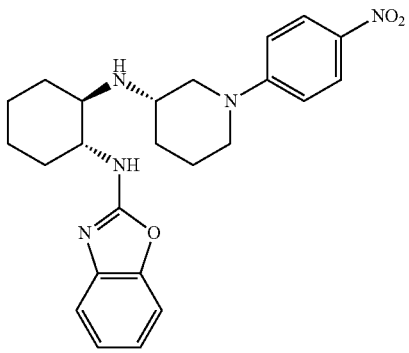 [SMILES: O=[N+]([O-])c1ccc(N2CCC[C@H](N[C@@H]3CCCC[C@H]3Nc3nc4ccccc4o3)C2)cc1]

To a 1 dram vial was added (1R,2R)—N1-(1-(4-nitrophenyl)piperidin-3-yl)cyclohexane-1,2-diamine (25 mg, 0.079 mmol), DMF (1 mL), diisopropyl ethyl amine (0.069 mL, 0.393 mmol) and 2-chlorobenzo[d]oxazole (0.013 mL, 0.118 mmol). The vial was capped and the reaction was stirred at 65° C. for 1 hr. After this time, the reaction was diluted with MeOH and purified using RP prep-HPLC. Two diastereomers were separated. The desired isomer had the shorter retention time. The fractions with the desired material were concentrated to give the product (1R,2R)—N1-(benzo[d]oxazol-2-yl)-N2-((S)-1-(4-nitrophenyl)piperidin-3-yl)cyclohexane-1,2-diamine (16 mg, 0.036 mmol, 45.4% yield) as yellow solid. Anal. Calcd. for $C_{24}H_{29}N_5O_3$ m/z 435.5, found: 436.3 (M+H)$^+$; $^1$H NMR (500 MHz, CDCl$_3$) δ ppm 8.06-7.92 (m, 2 H), 7.37 (d, J=7.70 Hz, 1 H), 7.25-7.15 (m, 2 H), 7.06 (t, J=7.70 Hz, 1H), 6.65 (d, J=9.35 Hz, 2 H), 5.33-5.15 (m, 1 H), 3.67 (d, J=9.08 Hz, 1 H), 3.59 (d, J=11.28 Hz, 1 H), 3.44 (br. s., 1 H), 3.16-3.03 (m, 1 H), 2.89 (br. s., 2 H), 2.63 (br. s., 1 H), 2.40 (br. s., 1 H), 2.16 (d, J=11.28 Hz, 1 H), 2.00-1.91 (m, 1 H), 1.82 (d, J=9.63 Hz, 4 H), 1.71-1.58 (m, 3 H), 1.44 (d, J=9.35 Hz, 2 H); $^{13}$C NMR (126 MHz, CDCl$_3$) δ ppm 162.09, 162.07, 154.71, 148.33, 126.15, 124.01, 121.2, 116.46, 112.55, 108.84, 59.37, 57.80, 53.01, 51.03, 48.07, 32.22, 31.92, 29.73, 24.84, 24.60, 22.91.

Example 4

(1R,2R)—N1-((S)-1-(4-Nitrophenyl)piperidin-3-yl)-N2-(5-(trifluoromethoxy)benzo[d]oxazol-2-yl)cyclohexane-1,2-diamine

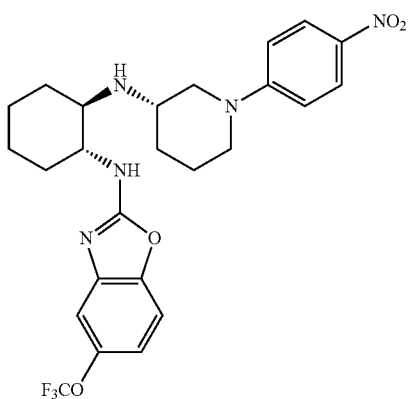 [SMILES: O=[N+]([O-])c1ccc(N2CCC[C@H](N[C@@H]3CCCC[C@H]3Nc3nc4cc(OC(F)(F)F)ccc4o3)C2)cc1]

(1R,2R)—N1-((S)-1-(4-Nitrophenyl)piperidin-3-yl)-N2-(5-(trifluoromethoxy)benzo[d]oxazol-2-yl)cyclohexane-1,2-diamine (8 mg, 0.014 mmol, 44.1% yield) was synthesized as described in General Procedure H using 2-chloro-5-(trifluoromethoxy)benzo[d]oxazole (7.46 mg, 0.031 mmol) and Intermediate 17 (10 mg, 0.031 mmol). The crude product was purified using RP prep-HPLC method A to give the title compound as a yellow oil. Anal. Calcd. for $C_{25}H_{28}F_3N_5O_4$ m/z 519.5, found: 520.4 (M+H)$^+$; $^1$H NMR (500 MHz, CDCl$_3$) δ ppm 7.96 (d, J=8.80 Hz, 2 H), 7.23-7.19 (m, 2 H), 7.01 (d, J=8.80 Hz, 1 H), 6.75 (d, J=9.35 Hz, 2 H), 4.07-3.99 (m, 1 H), 3.81-3.75 (m, 1 H), 3.64 (br. s., 1 H), 3.54-3.44 (m, 1 H), 3.31 (dd, J=12.65, 8.80 Hz, 1 H), 3.10 (t, J=9.90 Hz, 1 H), 2.31 (d, J=12.65 Hz, 1 H), 2.12 (d, J=12.65 Hz, 2 H), 2.04-1.93 (m, 3 H), 1.93-1.82 (m, 2 H), 1.79-1.69 (m, 2 H), 1.44 (t, J=9.90 Hz, 2H), 1.26 (t, J=7.15 Hz, 1 H).

Example 5

(1R,2R)—N1-((1R,4R,6S)-2-(4-Nitrophenyl)-2-azabicyclo[2.2.1]heptan-6-yl)-N2-(5-(4-(trifluoromethoxy)phenyl)oxazol-2-yl)cyclohexane-1,2-diamine

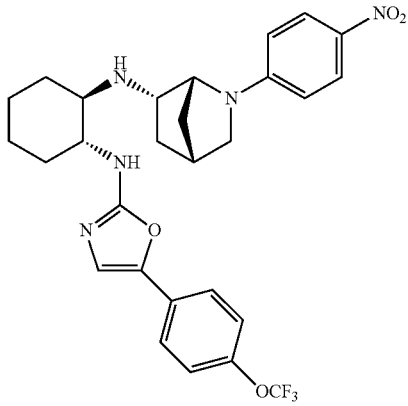 [SMILES: O=[N+]([O-])c1ccc(N2C[C@@H]3C[C@H](N[C@@H]4CCCC[C@H]4Nc4ncc(-c5ccc(OC(F)(F)F)cc5)o4)[C@H]2C3)cc1]

(1R,2R)—N1-((1R,4R,6S)-2-(4-Nitrophenyl)-2-azabicyclo[2.2.1]heptan-6-yl)-N2-(5-(4-(trifluoromethoxy)phenyl)oxazol-2-yl)cyclohexane-1,2-diamine (150 mg, 0.226 mmol, 49.8% yield) was synthesized as described in General Procedure H using Intermediate 2 (120 mg, 0.454 mmol) and Intermediate 16 (150 mg, 0.454 mmol). The product was purified using RP prep-HPLC method A to give the title compound as a yellow solid. Anal. Calcd. for $C_{28}H_{30}F_3N_5O_4$ m/z 557.5, found: 558.3 (M+H)$^+$; $^1$H NMR (500 MHz, CDCl$_3$) δ ppm 7.82 (d, J=9.34 Hz, 2 H), 7.50 (d, J=8.79 Hz, 2 H), 7.34-7.25 (m, 3 H), 6.74 (d, J=9.34 Hz, 2 H), 4.04 (dt, J=6.60, 3.30 Hz, 1 H), 3.84-3.75 (m, 1 H), 3.69-3.63 (m, 1 H), 3.339-3.33 (m, 2 H), 2.82 (br. s., 1 H), 2.47-2.32 (m, 2 H), 2.19-2.04 (m, 1 H), 1.96-1.76 (m, 5 H), 1.77-1.50 (m, 5 H), 1.49-1.36 (m, 2 H).

Example 6

(1R,2R)—N1-((1R,4R,6S)-2-(4-Nitrophenyl)-2-azabicyclo[2.2.1]heptan-6-yl)-N2-(5-phenyloxazol-2-yl)cyclohexane-1,2-diamine

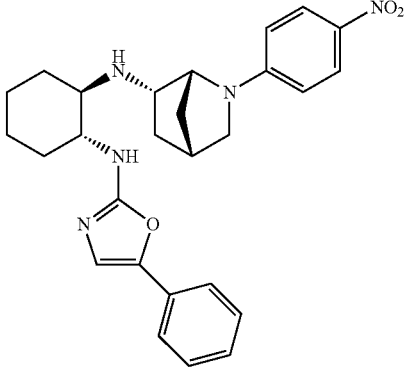 [SMILES: O=[N+]([O-])c1ccc(N2C[C@@H]3C[C@H](N[C@@H]4CCCC[C@H]4Nc4ncc(-c5ccccc5)o4)[C@H]2C3)cc1]

(1R,2R)—N1-((1R,4R,6S)-2-(4-Nitrophenyl)-2-azabicyclo[2.2.1]heptan-6-yl)-N2-(5-phenyloxazol-2-yl)cyclohexane-1,2-diamine (10 mg, 0.020 mmol, 44.2% yield) was synthesized as described in General Procedure H using Intermediate 1 (8.15 mg, 0.045 mmol) and Intermediate 16 (15 mg, 0.045 mmol). The product was purified using RP prep-HPLC method A to give the title compound as a yellow solid. Anal. Calcd. for $C_{27}H_{31}N_5O_3$ m/z 473.5, found: 474.3 (M+H)$^+$; $^1$H NMR (500 MHz, CDCl$_3$) δ ppm 7.74 (d, J=8.25 Hz, 2 H), 7.58-7.41 (m, 5 H), 6.72-6.63 (m, 2 H), 6.61 (s, 1 H), 5.06 (br. s., 1 H), 3.91 (dd, J=11.00, 3.85 Hz, 1 H), 3.59 (d, J=8.80 Hz, 2 H), 3.45-3.35 (m, 1 H), 3.31 (d, J=8.25 Hz, 1 H), 2.86 (br. s., 1 H), 2.24-2.14 (m, 1 H), 2.06 (d, J=9.90 Hz, 2 H), 2.00-1.95 (m, 1 H), 1.94-1.88 (m, 1 H), 1.83 (d, J=11.00 Hz, 2 H), 1.73 (d, J=10.45 Hz, 1 H), 1.67-1.46 (m, 2 H), 1.30 (t, J=11.00 Hz, 2 H).

Example 7

(1R,2R)—N1-((S)-1-(4-Nitrophenyl)piperidin-3-yl)-N2-(5-(4-(trifluoromethyl)phenyl)oxazol-2-yl)cyclohexane-1,2-diamine

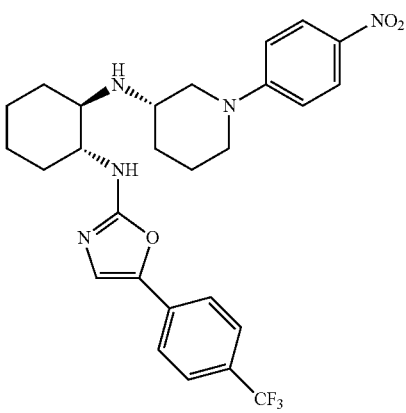 [SMILES: O=[N+]([O-])c1ccc(N2CCC[C@H](N[C@@H]3CCCC[C@H]3Nc3ncc(-c4ccc(C(F)(F)F)cc4)o3)C2)cc1]

(1R,2R)—N1-((S)-1-(4-Nitrophenyl)piperidin-3-yl)-N2-(5-(4-(trifluoromethyl)phenyl)oxazol-2-yl)cyclohexane-1,2-diamine (23 mg, 0.043 mmol, 69.1% yield) was synthesized as described in General Procedure H using Intermediate 3 (18.66 mg, 0.075 mmol) and Intermediate 17 (20 mg, 0.063 mmol). The product was purified using RP prep-HPLC method A to give the title compound as a yellow solid. Anal. Calcd. for $C_{27}H_{30}F_3N_5O_3$ m/z 529.2, found: 530.1 (M+H)$^+$; $^1$H NMR (400 MHz, CDCl$_3$) δ ppm 8.04 (2H, d, J=9.3 Hz), 7.62 (2 H, d, J=8.2 Hz), 7.47 (2 H, d, J=8.2 Hz), 7.05 (1 H, s), 6.81 (2 H, d, J=9.3 Hz), 4.00 (1 H, m), 3.77 (1 H, m), 3.57 (2 H, m), 3.43 (1 H, m), 3.35-3.25 (1 H, m), 3.13 (1 H, m), 2.27 (1 H, m), 2.23-1.84 (6 H, m), 1.59-1.84 (3 H, m), 1.44 (2 H, m).

Example 8

(1R,2R)—N1-(5-(3-Fluoro-4-(trifluoromethoxy)phenyl)oxazol-2-yl)-N2-((S)-1-(4-nitrophenyl)piperidin-3-yl)cyclohexane-1,2-diamine

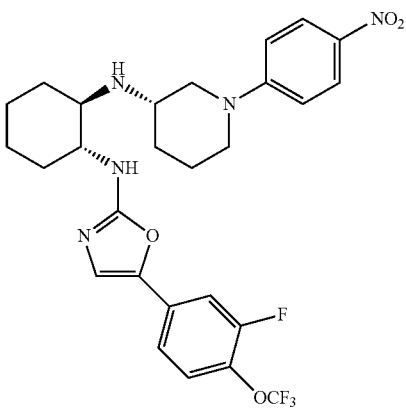 [SMILES: O=[N+]([O-])c1ccc(N2CCC[C@H](N[C@@H]3CCCC[C@H]3Nc3ncc(-c4ccc(OC(F)(F)F)c(F)c4)o3)C2)cc1]

(1R,2R)—N1-(5-(3-Fluoro-4-(trifluoromethoxy)phenyl)oxazol-2-yl)-N2-((S)-1-(4-nitrophenyl)piperidin-3-yl)cyclohexane-1,2-diamine (28 mg, 0.050 mmol, 79% yield) was synthesized as described in General Procedure H using Intermediate 4 (21.22 mg, 0.075 mmol) and Intermediate 17 (20 mg, 0.063 mmol). The product was purified using RP prep-HPLC method A to give the title compound as a yellow solid. Anal. Calcd. for $C_{27}H_{29}F_4N_5O_4$ m/z 563.2, found: 564.1 (M+H)$^+$; $^1$H NMR (400 MHz, CDCl$_3$) δ ppm 8.03 (2 H, d, J=9.3 Hz), 7.32 (1 H, t, J=7.4 Hz), 7.24-7.13 (2 H, m), 6.95 (1 H, s), 6.81 (2 H, d, J=9.3 Hz), 3.96 (1 H, m), 3.75 (1 H, m), 3.61-3.48 (2 H, m), 3.42 (1 H, m), 3.37-3.27 (1 H, m), 3.20-3.09 (1 H, m), 2.32-2.24 (1 H, m), 2.21-1.86 (6 H, m), 1.86-1.60 (3 H, m), 1.43 (2 H, m).

Example 9

(1R,2R)—N1-(5-(2-Fluorophenyl)oxazol-2-yl)-N2-((S)-1-(4-nitrophenyl)piperidin-3-yl)cyclohexane-1,2-diamine

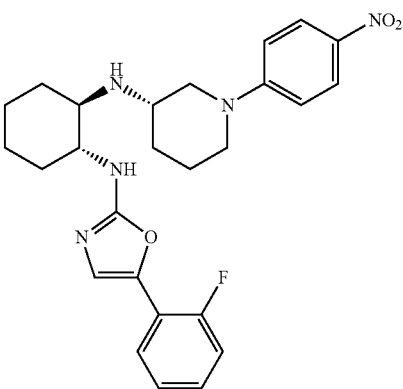 [SMILES: O=[N+]([O-])c1ccc(N2CCC[C@H](N[C@@H]3CCCC[C@H]3Nc3ncc(-c4ccccc4F)o3)C2)cc1]

(1R,2R)—N1-(5-(2-Fluorophenyl)oxazol-2-yl)-N2-((S)-1-(4-nitrophenyl)piperidin-3-yl)cyclohexane-1,2-diamine (17.5 mg, 0.036 mmol, 77% yield) was synthesized as described in General Procedure H using Intermediate 6 (11.17 mg, 0.057 mmol) and Intermediate 17 (15 mg, 0.047 mmol). The product was purified using RP prep-HPLC method A to give the title compound as a yellow solid. Anal. Calcd. for $C_{26}H_{30}FN_5O_3$ m/z 479.2, found: 480.1 (M+H)$^+$; $^1$H NMR (400 MHz, CDCl$_3$) δ ppm 8.12 (2 H, d), 7.60-7.53 (1 H, m), 7.45-7.35 (1 H, m), 7.29-7.23 (2 H, m), 7.18 (1 H, dd, J=11.0, 8.2 Hz), 6.87 (2 H, d, J=9.3 Hz), 4.23-4.11 (1 H, m), 4.02-3.92 (1 H, m), 3.76 (1 H, d, J=13.2 Hz), 3.56-3.39 (2 2.00-1.95 (m, 1 H), 1.94-1.88 (m, 1 H), 1.83 (d, J=11.00 Hz, 2 H), 1.73 (d, J=10.45 Hz, 1 H), 1.67-1.46 (m, 2 H), 1.30 (t, J=11.00 Hz, 2 H).

H, m), 3.27-3.14 (1 H, m), 3.50-2.94 (1 H, m), 2.36-2.20 (4 H, m), 2.08-1.90 (3 H, m), 1.90-1.60 (3 H, m), 1.56-1.36 (2 H, m).

Example 10

(1R,2R)—N1-(5-(3,4-Difluorophenyl)oxazol-2-yl)-N2-((S)-1-(4-nitrophenyl)piperidin-3-yl)cyclohexane-1,2-diamine

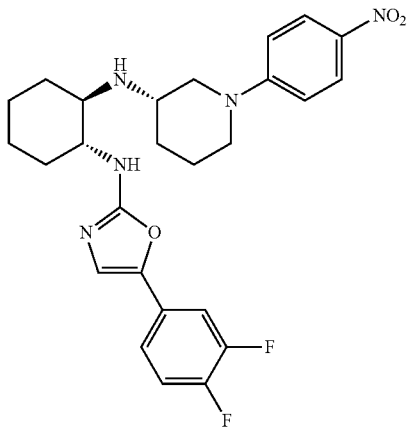 [SMILES: O=[N+]([O-])c1ccc(N2CCC[C@H](N[C@@H]3CCCC[C@H]3Nc3ncc(-c4ccc(F)c(F)c4)o3)C2)cc1]

(1R,2R)—N1-(5-(3,4-Difluorophenyl)oxazol-2-yl)-N2-((S)-1-(4-nitrophenyl)piperidin-3-yl)cyclohexane-1,2-diamine (17.9 mg, 0.036 mmol, 76% yield) was synthesized as described in General Procedure H using Intermediate 9 (12.19 mg, 0.057 mmol) and Intermediate 17 (15 mg, 0.047 mmol). The product was purified using RP prep-HPLC method A to give the title compound as a yellow solid. Anal. Calcd. for $C_{26}H_{29}F_2N_5O_3$ m/z 497.2, found: 498.0 (M+H)$^+$; $^1$H NMR (400 MHz, CDCl$_3$) δ ppm 8.12 (2 H, d, J=9.3 Hz), 7.34-7.20 (3 H, m), 7.08 (1 H, s), 6.86 (2 H, d, J=9.3 Hz), 4.19-4.08 (1 H, m), 4.04-3.95 (1 H, m), 3.77 (1 H, d, J=13.2 Hz), 3.54-3.39 (2 H, m), 3.25-3.14 (1 H, m), 3.06-2.92 (1 H, m), 2.37-2.16 (4 H, m), 2.09-1.57 (6 H, m), 1.53-1.32 (2 H, m).

Example 11

(1R,2R)—N1-(5-(2-Methyl-4-(trifluoromethoxy)phenyl)oxazol-2-yl)-N2-((S)-1-(4-nitrophenyl)piperidin-3-yl)cyclohexane-1,2-diamine

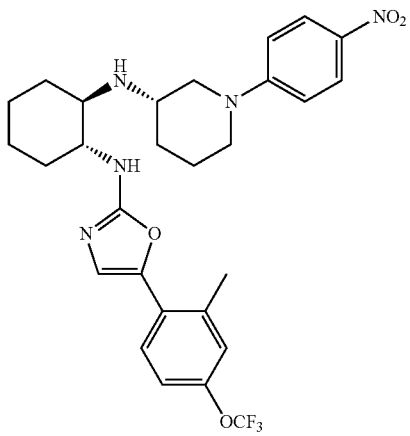 [SMILES: Cc1cc(OC(F)(F)F)ccc1-c1cnc(N[C@@H]2CCCC[C@H]2N[C@H]2CCCN(c3ccc([N+](=O)[O-])cc3)C2)o1]

(1R,2R)—N1-(5-(2-Methyl-4-(trifluoromethoxy)phenyl)oxazol-2-yl)-N2-((S)-1-(4-nitrophenyl)piperidin-3-yl)cyclohexane-1,2-diamine (6.0 mg, 0.011 mmol, 22.8% yield) was synthesized as described in General Procedure H using Intermediate 11 (15.69 mg, 0.057 mmol) and Intermediate 17 (15 mg, 0.047 mmol). The product was purified using RP prep-HPLC method A to give the title compound as a yellow solid. Anal. Calcd. for $C_{28}H_{32}F_3N_5O_4$ m/z 559.2, found: 560.0 (M+H)$^+$; $^1$H NMR (400 MHz, CDCl$_3$) δ ppm 8.14 (2 H, d, J=8.8 Hz), 7.57 (1 H, d, J=8.2 Hz), 7.20-7.13 (2 H, m), 7.01 (1 H, s), 6.87 (2 H, d, J=9.3 Hz), 4.21-4.07 (1 H, m), 4.04-3.96 (1 H, m), 3.79 (1 H, d, J=13.7 Hz), 3.53-3.39 (2 H, m), 3.25-3.15 (1 H, m), 3.04-2.93 (1 H, m), 2.42 (3 H, s), 2.35-2.19 (4 H, m), 2.08-1.56 (6 H, m), 1.53-1.36 (2 H, m).

Example 12

4-(2-((1R,2R)-2-((S)-1-(4-Nitrophenyl)piperidin-3-ylamino)cyclohexylamino)oxazol-5-yl)phenol

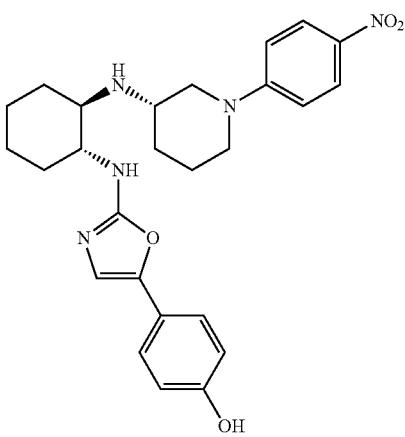 [SMILES: O=[N+]([O-])c1ccc(N2CCC[C@H](N[C@@H]3CCCC[C@H]3Nc3ncc(-c4ccc(O)cc4)o3)C2)cc1]

To a round bottom flask was added Example 14 (18 mg, 0.034 mmol), CH$_2$Cl$_2$ (0.3 ml) and TFA (0.3 ml). The reaction was stirred at rt for 2 hrs. The reaction was concentrated and the residue was purified by RP prep-HPLC method A to give 4-(2-((1R,2R)-2-((S)-1-(4-nitrophenyl)piperidin-3-ylamino)cyclohexylamino)oxazol-5-yl)phenol (12.7 mg, 0.027 mmol, 79% yield) as a yellow solid. Anal. Calcd. for $C_{26}H_{31}N_5O_4$ m/z 477.2, found: 478.0 (M+H)$^+$; $^1$H NMR (400 MHz, CDCl$_3$) δ ppm 8.13 (2 H, d, J=9.3 Hz), 7.26 (2 H, m), 6.89-6.80 (5 H, m), 4.20-4.08 (1 H, m), 4.03-3.92 (1 H, m), 3.83-3.74 (1 H, m), 3.52-3.40 (2 H, m), 3.27-3.17 (1 H, m), 3.04-2.94 (1 H, m), 2.34-1.55 (10 H, m), 1.51-1.39 (2H, m).

Example 13

(1R,2R)—N1-(5-(4-(Difluoromethoxy)phenyl)oxazol-2-yl)-N2-((S)-1-(4-nitrophenyl)piperidin-3-yl)cyclohexane-1,2-diamine

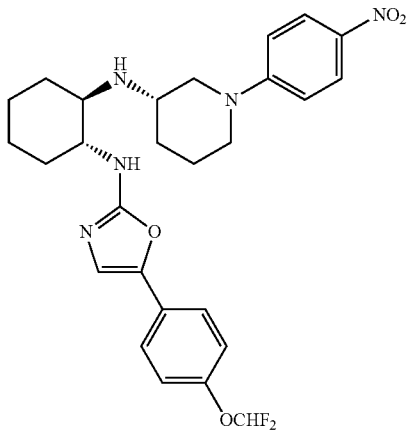 [SMILES: O=[N+]([O-])c1ccc(N2CCC[C@H](N[C@@H]3CCCC[C@H]3Nc3ncc(-c4ccc(OC(F)F)cc4)o3)C2)cc1]

(1R,2R)—N1-(5-(4-(Difluoromethoxy)phenyl)oxazol-2-yl)-N2-((S)-1-(4-nitrophenyl)piperidin-3-yl)cyclohexane-1,2-diamine (4 mg, 0.0076 mmol, 16% yield) was synthesized as described in General Procedure H using Intermediate 10 (13.98 mg, 0.057 mmol) and Intermediate 17 (15.1 mg, 0.047 mmol). The product was purified using RP prep-HPLC method A to give the title compound as a yellow solid. Anal. Calcd. for $C_{27}H_{31}F_2N_5O_4$ m/z 527.2, found: 528.0 (M+H)$^+$; $^1$H NMR (400 MHz, CDCl$_3$) δ ppm 8.13 (2 H, d, J=9.3 Hz), 7.48 (2 H, d, J=8.8 Hz), 7.19 (2H, d, J=8.2 Hz), 7.07 (1 H, s), 6.87 (2 H, d, J=9.3 Hz), 6.77-6.36 (1 H, t), 4.14 (1 H, m), 3.54-3.39 (2 H, m), 3.25-3.15 (1 H, m), 3.05-2.93 (1 H, m), 2.36-2.16 (3 H, m), 2.08-1.55 (7 H, m), 1.53-1.37 (2 H, m).

Example 14

(1R,2R)—N1-(5-(4-tert-Butoxyphenyl)oxazol-2-yl)-N2-((S)-1-(4-nitrophenyl)piperidin-3-yl)cyclohexane-1,2-diamine

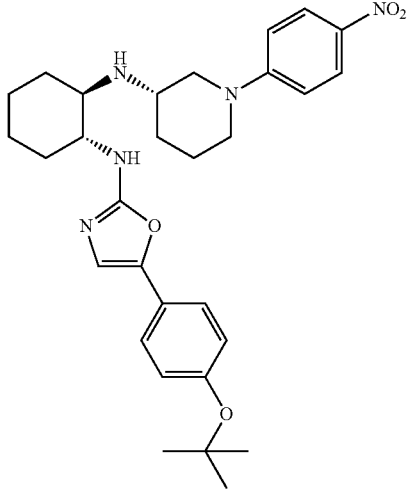 [SMILES: CC(C)(C)Oc1ccc(-c2cnc(N[C@@H]3CCCC[C@H]3N[C@H]3CCCN(c4ccc([N+](=O)[O-])cc4)C3)o2)cc1]

(1R,2R)—N1-(5-(4-tert-Butoxyphenyl)oxazol-2-yl)-N2-((S)-1-(4-nitrophenyl)piperidin-3-yl)cyclohexane-1,2-diamine (15.25 mg, 0.029 mmol, 39.7% yield) was synthesized as described in General Procedure H using Intermediate 5 (21.72 mg, 0.086 mmol) and Intermediate 17 (22.9 mg, 0.072 mmol). The product was purified using RP prep-HPLC method A to give the title compound as a yellow solid. Anal. Calcd. for $C_{30}H_{39}N_5O_4$ m/z 533.3, found: 534.3 (M+H)$^+$; $^1$H NMR (400 MHz, CDCl$_3$) δ ppm 8.06 (2 H, d, J=9.3 Hz), 7.35 (2 H, d, J=8.8 Hz), 6.99 (2 H, d, J=8.8 Hz), 6.92 (1 H, s), 6.77 (2 H, d, J=9.3 Hz), 4.99 (1 H, d, J=4.9 Hz), 3.84-3.75 (1 H, m), 3.73-3.64 (1H, m), 3.29-3.17 (1 H, m), 3.11-3.00 (1 H, m), 2.90-2.78 (2 H, m), 2.57-2.46 (1 H, m), 2.41 (1 H, d, J=11.5 Hz), 2.14 (1 H, d, J=12.6 Hz), 1.93 (1 H, dd, J=12.1, 3.8 Hz), 1.87-1.69 (3 H, m), 1.69-1.52 (2 H, m), 1.48-1.22 (11 H, m), 1.21-1.09 (1 H, m).

Example 15

(1R,2R)—N1-(5-(2-Fluorophenyl)oxazol-2-yl)-N2-((1R,4R,6S)-2-(4-nitrophenyl)-2-azabicyclo[2.2.1]heptan-6-yl)cyclohexane-1,2-diamine

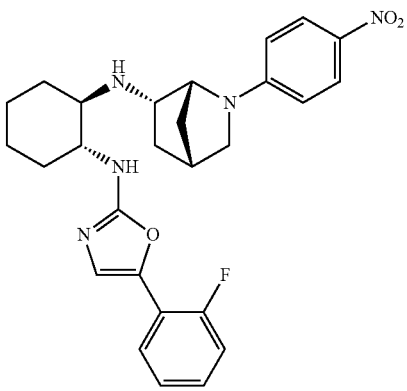 [SMILES: O=[N+]([O-])c1ccc(N2C[C@@H]3C[C@H](N[C@@H]4CCCC[C@H]4Nc4ncc(-c5ccccc5F)o4)[C@H]2C3)cc1]

(1R,2R)—N1-(5-(2-Fluorophenyl)oxazol-2-yl)-N2-((1R,4R,6S)-2-(4-nitrophenyl)-2-azabicyclo[2.2.1]heptan-6-yl)cyclohexane-1,2-diamine (12.4 mg, 0.025 mmol, 91% yield) was synthesized as described in General Procedure H using Intermediate 6 (6.03 mg, 0.031 mmol) and Intermediate 16 (15.5 mg, 0.028 mmol). The product was purified using RP prep-HPLC method A to give the title compound as a yellow solid. Anal. Calcd. for $C_{27}H_{30}FN_5O_3$ m/z 491.2, found: 492.3 (M+H)$^+$; $^1$H NMR (400 MHz, CDCl$_3$) δ ppm 10.77 (1 H, d, J=10.4 Hz), 9.42 (1 H, br. s.), 8.53 (1 H, br. s.), 7.75 (2 H, d, J=9.3 Hz), 7.59 (1 H, t, J=7.4 Hz), 7.49-7.40 (1 H, m), 7.31 (1 H, t), 7.28-7.21 (1H, m), 6.81 (1 H, d, J=2.2 Hz), 6.66 (2 H, d, J=9.3 Hz), 5.00 (1 H, s), 3.98-3.86 (1 H, m), 3.68-3.58 (2H, m), 3.42 (1 H, br. s.), 3.31 (1 H, d, J=8.8 Hz), 2.88 (1 H, br. s.), 2.27-2.15 (1 H, m), 2.15-2.04 (2H, m), 2.04-1.78 (4 H, m), 1.78-1.70 (1 H, m), 1.69-1.45 (2 H, m), 1.40-1.25 (2H, m).

Example 16

4-(2-((1R,2R)-2-((1R,4R,6S)-2-(4-Nitrophenyl)-2-azabicyclo[2.2.1]heptan-6-ylamino)cyclohexy-lamino)oxazol-5-yl)phenol

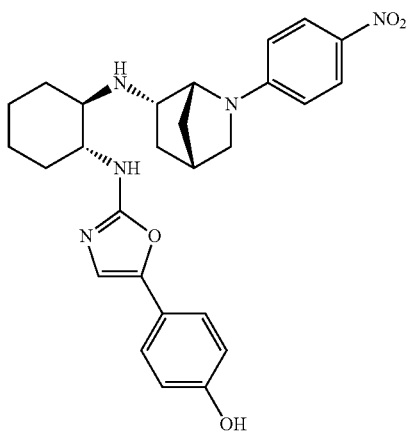 [SMILES: O=[N+]([O-])c1ccc(N2C[C@@H]3C[C@H](N[C@@H]4CCCC[C@H]4Nc4ncc(-c5ccc(O)cc5)o4)[C@H]2C3)cc1]

4-(2-((1R,2R)-2-((1R,4R,6S)-2-(4-Nitrophenyl)-2-azabicyclo[2.2.1]heptan-6-ylamino)cyclohexylamino)oxazol-5-yl)phenol was synthesized according to the method of Example 12 to give the title compound (10.6 mg, 70% yield) as a yellow solid. Anal. Calcd. for $C_{27}H_{31}N_5O_4$ m/z 489.2, found: 490.3 $(M+H)^+$; $^1H$ NMR (400 MHz, $CDCl_3$) δ ppm 10.37 (1 H, d, J=9.9 Hz), 9.63 (1 H, br. s.), 8.37 (1 H, br. s.), 7.78 (2 H, d, J=9.3 Hz), 7.39 (2 H, d, J=8.8 Hz), 6.96 (2 H, d, J=8.8 Hz), 6.64 (2 H, d, J=9.3 Hz), 6.50 (1H, s), 5.00 (1H, s), 3.88 (1H, d, J=6.6 Hz), 3.54-3.52 (1H, m), 3.54 (1H, d, J=8.8 Hz), 3.09-3.07 (1H, m), 3.07 (1H, d, J=8.8 Hz), 2.87 (1H, s), 2.28-2.17 (1H, m), 2.16-2.02 (2 H, m), 2.02-1.88 (2H, m), 1.88-1.70 (2H, m), 1.68-1.47 (32 H, m), 1.39-1.21 (2 H, m).

Example 17

(1R,2R)—N1-((6S)-2-(4-Nitrophenyl)-2-azabicyclo[2.2.2]octan-6-yl)-N2-(5-(4-(trifluoromethoxy)phenyl)oxazol-2-yl)cyclohexane-1,2-diamine

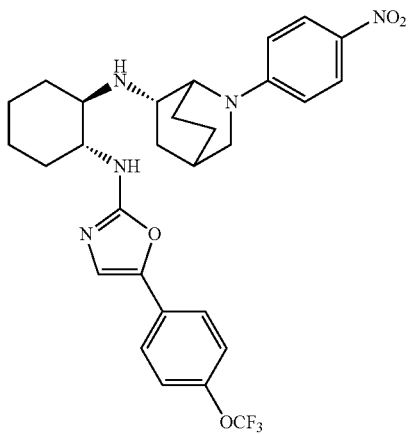 [SMILES: O=[N+]([O-])c1ccc(N2CC3CCC2[C@@H](N[C@@H]2CCCC[C@H]2Nc2ncc(-c4ccc(OC(F)(F)F)cc4)o2)C3)cc1]

A: 3-((2R,5S)-1-Benzyl-5-(tert-butoxycarbonyl)pyrrolidin-2-yl)propanoic acid

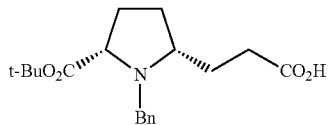

To a degassed solution of (S)-dibenzyl 2-(1-benzyl-5-(tert-butoxycarbonyl)pyrrolidin-2-ylidene)succinate (1500 mg, 2.70 mmol) was added 10% Pd/C (900 mg, 0.846 mmol) and ammonium formate (2,550 mg, 40.5 mmol) in MeOH (20 ml). The reaction mixture was then heated to reflux under argon. After 12 hrs, heating was stopped and the reaction mixture was left to stand at rt overnight. The next day another 0.5 g of ammonium formate was added to the reaction and reaction was heated for another 5 hrs. The reaction mixture was diluted with MeOH and filtered. The catalyst was rinsed with MeOH and the filtrate was concentrated to give a yellow solid. $CH_2Cl_2$ was added to the residue and the mixture was stirred for 5 min. The mixture was then filtered to remove ammonium formate. The filtrate was concentrated to give 3-((2R,5S)-1-benzyl-5-(tert-butoxycarbonyl)pyrrolidin-2-yl)propanoic acid (200 mg, 0.60 mmol, 22.2% yield) as a yellow syrup. $^1H$ NMR (400 MHz, $CDCl_3$) δ ppm 8.20 (2 H, d, J=13.7 Hz), 7.36-7.26 (5 H, m), 3.97 (1 H, d, J=13.7 Hz), 3.75 (1 H, d, J=13.7Hz), 3.36 (1 H, t, J=7.4 Hz), 3.14-3.05 (1 H, m), 2.61-2.52 (1 H, m), 2.40-2.31 (1 H, m), 2.10-1.98 (1 H, m), 1.96-1.77 (4 H, m), 1.77-1.65 (1 H, m), 1.34 (9 H, s).

B: (2S,5R)-Methyl 1-benzyl-5-(3-methoxy-3-oxopropyl)pyrrolidine-2-carboxylate

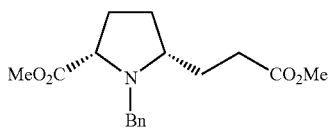

Acetyl chloride (1.50 ml, 21.10 mmol) was added dropwise to MeOH (7.5 mL) at 0° C. After 15 min of stirring a solution of 3-((2R,5S)-1-benzyl-5-(tert-butoxycarbonyl)pyrrolidin-2-yl)propanoic acid (200 mg, 0.600 mmol) in MeOH (7.5 mL) was slowly added to the reaction. The reaction mixture was then heated at reflux overnight. The reaction was concentrated. The residue was partitioned between EtOAc and 10% $Na_2CO_3$. The organic phase was separated, washed with saturated aqueous NaCl solution, dried over $MgSO_4$, filtered and concentrated. The resulting residue was purified using silica gel chromatography (ISCO system) to give the product (2S,5R)-methyl 1-benzyl-5-(3-methoxy-3-oxopropyl)pyrrolidine-2-carboxylate (126 mg, 0.413 mmol, 68.8% yield) as colorless syrup. $^1HNMR$ (400 MHz, $CDCl_3$) δ ppm 7.35-7.17 (5 H, m), 3.95 (1 H, d, J=13.7 Hz), 3.71-3.61 (4 H, m), 3.47 (3 H, s), 3.37-3.26 (1 H, m), 2.86-2.73 (1 H, m), 2.53-2.41 (1 H, m), 2.38-2.25 (1 H, m), 2.08-1.79 (4 H, m), 1.79-1.66 (1 H, m), 1.66-1.53 (1 H, m).

C: Methyl 8-benzyl-2-hydroxy-8-azabicyclo[3.2.1]oct-2-ene-3-carboxylate

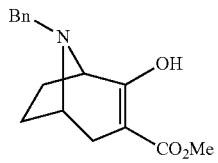 [SMILES: COC(=O)C1=C(O)C2CCC(C1)N2Cc1ccccc1]

A solution of LiHMDS (1.0 M in THF, 0.908 ml, 0.980 mmol) was slowly added to a solution of (2S,5R)-methyl 1-benzyl-5-(3-methoxy-3-oxopropyl)pyrrolidine-2-carboxylate (126, mg, 0.413 mmol) in THF (4 ml) at −78° C. The reaction mixture was stir at −78° C. for 6 hrs. Then the reaction mixture was poured into a 0° C. stirring mixture of EtOAc (10 mL) and pH 7.0 aqueous phosphate buffer. The organic phase was separated, washed with saturated aqueous NaCl solution, dried over MgSO$_4$, filtered and concentrated. The resulting residue was purified using silica gel chromatography (ISCO system) to give the product methyl 8-benzyl-2-hydroxy-8-azabicyclo[3.2.1]oct-2-ene-3-carboxylate (74 mg, 0.271 mmol) as a syrup. Anal. Calcd. for C$_{16}$H$_{19}$NO$_3$ m/z 273.1, found: 274.1 (M+H)$^+$; $^1$H NMR (400 MHz, CDCl$_3$) δ ppm 7.40-7.21 (5 H, m), 3.80-3.73 (4 H, m), 3.70 (2 H, d, J=3.0 Hz), 3.36 (1 H, t, J=5.2 Hz), 3.32 (1 H, d, J=5.6 Hz), 2.63 (1 H, dd, J=15.9, 4.8 Hz), 2.18-2.11 (2 H, m), 2.02-1.95 (1 H, m), 1.85 (1 H, d, J=15.9 Hz), 1.59-1.48 (1 H, m).

D: 8-Benzyl-8-azabicyclo[3.2.1]octan-2-one

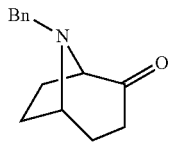

To a solution of methyl 8-benzyl-2-hydroxy-8-azabicyclo[3.2.1]oct-2-ene-3-carboxylate (68 mg, 0.249 mmol) in pyridine (2.5 ml) was added NaI (746 mg, 4.98 mmol). The reaction mixture was then reflux at 120° C. for 7.5 hr. The reaction mixture was concentrated and placed under vacuum. The residue was then partitioned between EtOAc and water. The aqueous phase was separated and extracted with EtOAc. All organic phases were combined, washed with saturated aqueous Na$_2$S$_2$O$_3$ solution, dried over MgSO$_4$, filtered and concentrated. The resulting residue was purified using silica gel chromatography (ISCO system) eluting with a gradient of 0-40% EtOAc/Hex to give the product 8-benzyl-8-azabicyclo[3.2.1]octan-2-one (39.4 mg, 0.183 mmol) as a syrup. Anal. Calcd. for C$_{14}$H$_{17}$NO m/z 215.1, found: 216.1 (M+H)$^+$; $^1$H NMR (400 MHz, CDCl$_3$) δ ppm 7.35-7.21 (5 H, m), 3.68 (2 H, s), 3.36 (2 H, d, J=5.5 Hz), 2.45-2.28 (2 H, m), 2.27-2.16 (3 H, m), 1.81-1.70 (3 H, m).

E: (1R,2R)—N1-((5S)-8-Benzyl-8-azabicyclo[3.2.1]octan-2-yl)cyclohexane-1,2-diamine

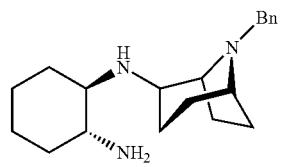

(1R,2R)—N1-((5S)-8-Benzyl-8-azabicyclo[3.2.1]octan-2-yl)cyclohexane-1,2-diamine was synthesized as described in General Procedure E using 8-benzyl-8-azabicyclo[3.2.1]octan-2-one (26 mg, 0.121 mmol) to give an orange syrup (38, mg, 100% yield). Anal. Calcd. for C$_{20}$H$_{13}$N$_3$ m/z 313.4, found: 314.3 (M+H)$^+$.

F: (1R,2R)—N1-((5S)-8-Benzyl-8-azabicyclo[3.2.1]octan-2-yl)-N2-(5-(4-(trifluoromethoxy)phenyl)oxazol-2-yl)cyclohexane-1,2-diamine

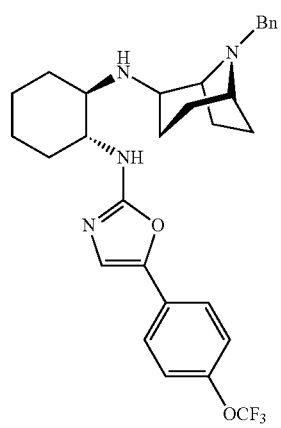

(1R,2R)—N1-((5S)-8-Benzyl-8-azabicyclo[3.2.1]octan-2-yl)-N2-(5-(4-(trifluoromethoxy)phenyl)oxazol-2-yl)cyclohexane-1,2-diamine (34 mg, 0.063 mmol, 51.9% yield) was synthesized as described in General Procedure H using Intermediate 2 (35.1 mg, 0.133 mmol) and (1R,2R)—N1-((5S)-8-benzyl-8-azabicyclo[3.2.1]octan-2-yl)cyclohexane-1,2-diamine (38 mg, 0.121 mmol). The crude material was purified using RP HPLC method A to give the product as an oil. Anal. Calcd. for C$_{30}$H$_{35}$F$_3$N$_4$O$_2$ m/z 540.2, found: 541.0 (M+H)$^+$.

G: (1R,2R)—N1-((5R)-8-Azabicyclo[3.2.1]octan-2-yl)-N2-(5-(4-(trifluoromethoxy)phenyl)oxazol-2-yl)cyclohexane-1,2-diamine

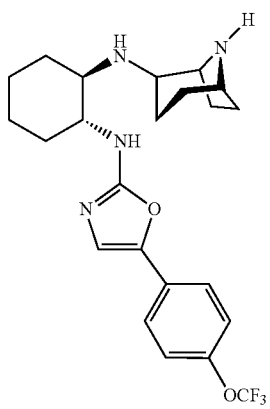

(1R,2R)—N1-((5S)-8-Benzyl-8-azabicyclo[3.2.1]octan-2-yl)cyclohexane-1,2-diamine (34 mg, 0.063 mmol) was dissolved in argon degassed MeOH (0.5 ml). Ammonium formate (15.86 mg, 0.252 mmol) was added followed by 10% Pd/C (15 mg, 0.014 mmol). The reaction mixture was then heated at 63° C. under argon for 1.5 hrs. The reaction mixture was diluted with MeOH and filtered. The catalyst was rinsed several times with MeOH. The filtrated was concentrated and placed under vacuum to give (1R,2R)—N1-((5R)-8-zzabicyclo[3.2.1]octan-2-yl)-N2-(5-(4-(trifluoromethoxy)phenyl)oxazol-2-yl)cyclohexane-1,2-diamine (28 mg, 0.062 mmol, 99% yield).

H: (1R,2R)—N1-((6S)-2-(4-Nitrophenyl)-2-azabicyclo[2.2.2]octan-6-yl)-N2-(5-(4-(trifluoromethoxy)phenyl)oxazol-2-yl)cyclohexane-1,2-diamine

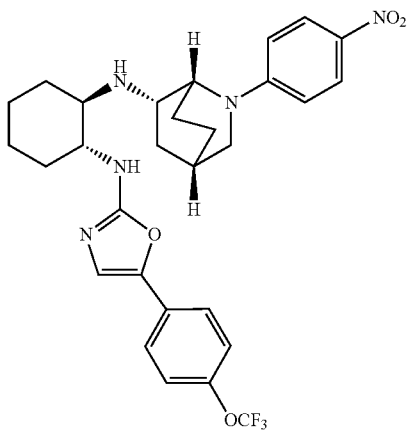 [SMILES: O=[N+]([O-])c1ccc(N2C[C@H]3CC[C@@H]2[C@@H](N[C@@H]2CCCC[C@H]2Nc2ncc(-c4ccc(OC(F)(F)F)cc4)o2)C3)cc1]

To a solution of (1R,2R)—N1-((5R)-8-azabicyclo[3.2.1]octan-2-yl)-N2-(5-(4-(trifluoromethoxy)phenyl)oxazol-2-yl)cyclohexane-1,2-diamine (28 mg, 0.062 mmol) and 4-fluoronitrobenzene (9.65 mg, 0.069 mmol) in DMF (0.38 ml) was added $K_2CO_3$. The reaction mixture was then heated at 80° C. for 4 hrs. The reaction mixture was partitioned between EtOAc and water. The organic phase was separated, dried over $MgSO_4$, filtered and concentrated. The residue was purified by RP prep-HPLC using method A with two isomers were separating. The fractions with the desired product, which eluted later than the undesired isomer, were concentrated to give (1R,2R)—N1-((6S)-2-(4-nitrophenyl)-2-azabicyclo[2.2.2]octan-6-yl)-N2-(5-(4-(trifluoromethoxy)phenyl)oxazol-2-yl)cyclohexane-1,2-diamine (5.82 mg, 0.0102 mmol, 16.4% yield) as a yellow solid. Anal. Calcd. for $C_{29}H_{32}F_3N_5O_4$ m/z 571.2, found: 572.2 $(M+H)^+$; $^1H$ NMR (400 MHz, $CDCl_3$) δ ppm 11.04 (1 H, br. s.), 7.88 (2 H, d, J=9.3 Hz), 7.55 (2 H, d, J=8.2 Hz), 7.30 (2 H, d, J=8.2 Hz), 7.02 (1 H, s), 6.78 (2 H, d, J=9.3 Hz), 6.38 (1 H, br. s.), 4.65 (1 H, d, J=6.0 Hz), 4.36 (1 H, d, J=6.0 Hz), 4.33-4.20 (1 H, m), 3.80-3.73 (1 H, m), 3.40-3.27 (1 H, m), 2.26-1.65 (13 H, m), 1.65-1.30 (3 H, m).

Example 18

(1R,2R)—N1-(5-(4-Fluorophenyl)oxazol-2-yl)-N2-((S)-1-(4-nitrophenyl)piperidin-3-yl)cyclohexane-1,2-diamine

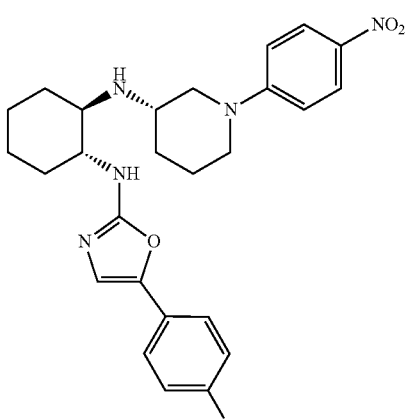

(1R,2R)—N1-(5-(4-Fluorophenyl)oxazol-2-yl)-N2-((S)-1-(4-nitrophenyl)piperidin-3-yl)cyclohexane-1,2-diamine (18.36 mg, 0.038 mmol, 51.6% yield) was synthesized as described in General Procedure H using Intermediate 8 (16.13 mg, 0.082 mmol) and Intermediate 17 (23.63 mg, 0.074 mmol). The product was purified using RP prep-HPLC method A to give the title compound as a yellow solid. Anal. Calcd. for $C_{26}H_{30}FN_5O_3$ m/z 479.2, found: 480.0 $(M+H)^+$; $^1H$ NMR (400 MHz, $CDCl_3$) δ ppm 8.13 (2 H, d, J=9.3 Hz), 7.45 (2 H, dd, J=8.8, 5.5 Hz), 7.11 (2 H, dd, J=8.5 Hz), 7.02 (1 H, s), 6.85 (2 H, d, J=9.3 Hz), 4.26-4.11 (1 H, m), 4.06-3.95 (1 H, m), 3.80 (1 H, d, J=13.2 Hz), 3.56-3.36 (2 H, m), 3.18 (1 H, t, J=11.5 Hz), 2.97 (1 H, t, J=11.0 Hz), 2.36-2.14 (3 H, m), 2.09-1.84 (4 H, m), 1.83-1.55 (3 H, m), 1.55-1.35 (2 H, m).

Example 19

(1R,2R)—N1-(5-(3-Fluorophenyl)oxazol-2-yl)-N2-((S)-1-(4-nitrophenyl)piperidin-3-yl)cyclohexane-1,2-diamine

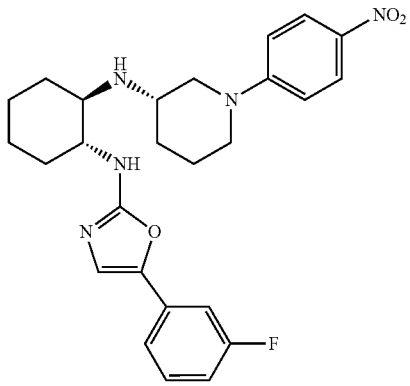

(1R,2R)—N1-(5-(3-Fluorophenyl)oxazol-2-yl)-N2-((S)-1-(4-nitrophenyl)piperidin-3-yl)cyclohexane-1,2-diamine (12.5 mg, 0.03 mmol, 8.3% yield) was synthesized as described in General Procedure H using Intermediate 7 (74 mg, 0.31 mmol) and Intermediate 17 (100 mg, 0.31 mmol). The product was purified using RP prep-HPLC method C to give the title compound as a yellow solid. Anal. Calcd. for $C_{26}H_{30}FN_5O_3$ m/z 479.2, found: 480.2 (M+H)$^+$; $^1$H NMR (400 MHz, CD$_3$OD) δ ppm 7.82 (m, 2H), 7.30 (m, 1H), 7.10 (m, 2H), 7.07 (m, 1H), 6.99-6.90 (m, 3H), 4.08 (m, 1H), 4.02 (m, 1H), 3.72 (m, 1H), 3.64 (m, 2H), 3.47 (m, 1 H), 3.40 (m, 1H), 3.09 (m, 1H), 2.34 (m, 2H), 2.19 (m, 1H), 2.08 (m, 2H), 1.92 (m, 4H), 1.60 (m, 3H), 1.45 (m, 2H), 1.31 (m, 6H).

Example 20

(1R,2R)—N1-(5-(2,4-Difluorophenyl)oxazol-2-yl)-N2-((S)-1-(4-nitrophenyl)piperidin-3-yl)cyclohexane-1,2-diamine

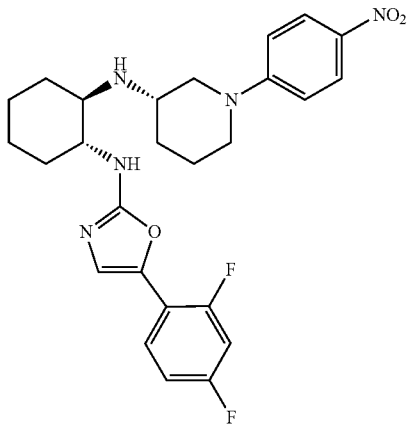 [SMILES: O=[N+]([O-])c1ccc(N2CCC[C@H](N[C@@H]3CCCC[C@H]3Nc3ncc(-c4ccc(F)cc4)o3)C2)cc1]

(1R,2R)—N1-(5-(2,4-Difluorophenyl)oxazol-2-yl)-N2-((S)-1-(4-nitrophenyl)piperidin-3-yl)cyclohexane-1,2-diamine (20.2 mg, 0.041 mmol, 65.8% yield) was synthesized as described in General Procedure H using Intermediate 13 (14.63 mg, 0.068 mmol) and Intermediate 17 (19.64 mg, 0.062 mmol). The product was purified using RP prep-HPLC method A to give the title compound as a yellow solid. Anal. Calcd. for $C_{26}H_{29}F_2N_5O_3$ m/z 497.2, found: 498.1 (M+H)$^+$; $^1$H NMR (400 MHz, CDCl$_3$) δ ppm 8.11 (2 H, d, J=9.3 Hz), 7.64-7.49 (1 H, m), 7.25-7.20 (1 H, d), 7.05-6.92 (2 H, m), 6.87 (2 H, d, J=9.3 Hz), 4.21-4.09 (1 H, m), 4.01-3.92 (1 H, m), 3.75 (1 H, d, J=12.6 Hz), 3.60-3.40 (2 H, m), 3.20 (1 H, t, J=11.3 Hz), 3.00 (1 H, t, J=10.7 Hz), 2.40-2.15 (3 H, m), 2.11-1.88 (3 H, m), 1.88-1.55 (4 H, m), 1.55-1.34 (2 H, m).

Example 21

(1R,2R)—N1-(5-(2-fluoro-4-methoxyphenyl)oxazol-2-yl)-N2-((S)-1-(4-nitrophenyl)piperidin-3-yl)cyclohexane-1,2-diamine

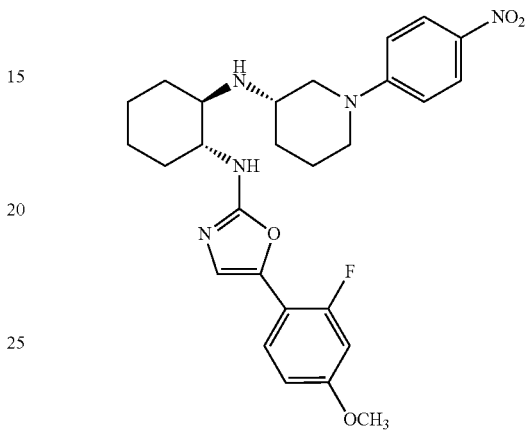

(1R,2R)—N1-(5-(2-Fluoro-4-methoxyphenyl)oxazol-2-yl)-N2-((S)-1-(4-nitrophenyl)piperidin-3-yl)cyclohexane-1,2-diamine (60 mg, 0.118 mmol, 93% yield) was synthesized as described in General Procedure H using Intermediate 12 (31.8 mg, 0.140 mmol) and Intermediate 17 (40.43 mg, 0.127 mmol). The product was purified using RP prep-HPLC method A to give the title compound as a yellow solid. Anal. Calcd. for $C_{27}H_{32}FN_5O_4$ m/z 509.2, found: 510.2 (M+H)$^+$; $^1$H NMR (400 MHz, CDCl$_3$) δ ppm 8.12 (2 H, d, J=9.3 Hz), 7.45 (1 H, t, J=8.5 Hz), 7.11 (1 H, d, J=2.7 Hz), 6.87 (2 H, d, J=9.3 Hz), 6.79 (1 H, dd, J=8.8, 2.2 Hz), 6.72 (1 H, dd), 4.21-4.07 (1 H, m), 4.00-3.92 (1 H, m), 3.85 (3 H, s), 3.74 (1 H, d, J=13.7 Hz), 3.54-3.42 (2 H, m), 3.27-3.16 (1 H, m), 3.04-2.95 (1 H, m), 2.36-2.18 (3 H, m), 2.05-1.57 (7 H, m), 1.54-1.35 (2 H, m).

Example 22

(1R,2R)—N1-((S)-1-(4-Nitrophenyl)piperidin-3-yl)-N2-(5-(3-(trifluoromethoxy)phenyl)oxazol-2-yl)cyclohexane-1,2-diamine

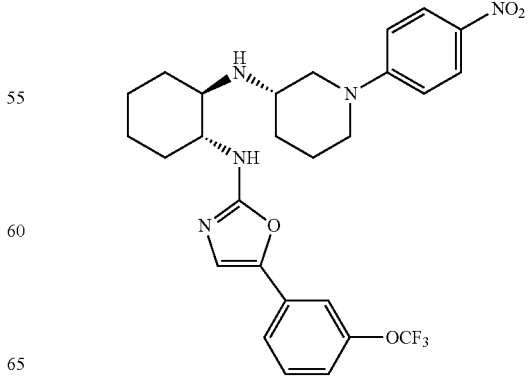

(1R,2R)—N1-((S)-1-(4-Nitrophenyl)piperidin-3-yl)-N2-(5-(3-(trifluoromethoxy)phenyl)oxazol-2-yl)cyclohexane-1,2-diamine (10 mg, 0.02 mmol, 11.7% yield) was synthesized as described in General Procedure H using Intermediate 14 (41.3 mg, 0.16 mmol) and Intermediate 17 (50 mg, 0.16 mmol). The product was purified using RP prep-HPLC method D to give the title compound as a yellow solid. Anal. Calcd. for $C_{27}H_{30}F_3N_5O_4$ m/z 545.2, found: 546.2 (M+H)$^+$; $^1$H NMR (400 MHz, DMSO-$d_6$) δ ppm 7.13 (d, J=3.1 Hz, 2H), 6.62 (d, J=4Hz, 2H), 6.51 (m, 1H), 6.42 (s, 1H), 6.29 (m, 1H), 6.07 (m, 2H), 2.94 (m, 1H), 2.83 (m, 1H), 2.61 (m, 1H), 2.35 (m, 1H), 2.21 (m, 1H), 2.11 (m, 1H), 1.90 (m, 1H), 1.31 (m, 2 H), 1.17 (m, 1H), 1.02 (m, 3H), 0.86 (m, 1H), 0.61 (m, 6H).

Example 23

(1R,2R)—N1-((S)-1-(4-Nitrophenyl)piperidin-3-yl)-N2-(4-(3-(trifluoromethoxy)phenyl)pyridin-2-yl)cyclohexane-1,2-diamine

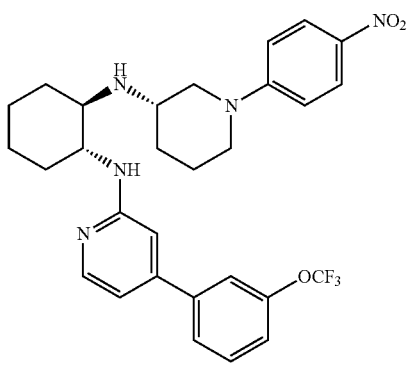

A: (1R,2R)—N1-(4-Bromopyridin-2-yl)-N2-((S)-1-(4-nitrophenyl)piperidin-3-yl)cyclohexane-1,2-diamine

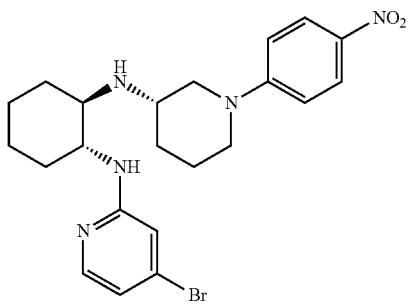 [SMILES: O=[N+]([O-])c1ccc(N2CCC[C@H](N[C@@H]3CCCC[C@H]3Nc3cc(Br)ccn3)C2)cc1]

(1R,2R)—N1-(4-Bromopyridin-2-yl)-N2-((S)-1-(4-nitrophenyl)piperidin-3-yl)cyclohexane-1,2-diamine (50 mg, 0.105 mmol, 19.7% yield) was synthesized as described in General Procedure H using 4-bromo-2-fluoropyridine (95 mg, 0.54 mmol) and Intermediate 17 (171 mg, 0.54 mmol). The product was purified using RP prep-HPLC method A to give the title compound as a pale yellow solid.

B: (1R,2R)—N1-((S)-1-(4-Nitrophenyl)piperidin-3-yl)-N2-(4-(3-(trifluoromethoxy)phenyl)pyridin-2-yl)cyclohexane-1,2-diamine

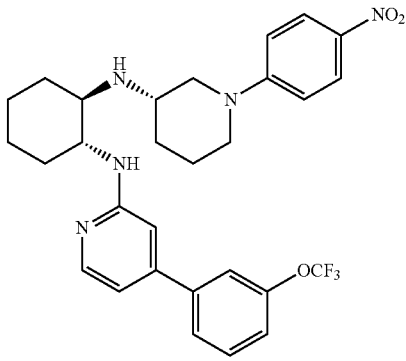

(1R,2R)—N1-((S)-1-(4-Nitrophenyl)piperidin-3-yl)-N2-(4-(3-(trifluoromethoxy)phenyl)pyridin-2-yl)cyclohexane-1,2-diamine (1.6 mg, 0.003 mmol, 6.8% yield) was synthesized as described in General Procedure I using (1R,2R)—N1-(4-bromopyridin-2-yl)-N2-((S)-1-(4-nitrophenyl)piperidin-3-yl)cyclohexane-1,2-diamine (20 mg, 0.04 mmol) and 3-(trifluoromethoxy)phenylboronic acid (12.2 mg, 0.04 mmol). The desired fraction from RP prep-HPLC method D was concentrated to give the title compound as a pale yellow solid. Anal. Calcd. for $C_{29}H_{32}F_3N_5O_3$ m/z 555.2, found: 556.2 (M+H)$^+$; $^1$H NMR (400 MHz, CD$_3$OD) δ ppm 8.05 (d, J=2.0 Hz, 1H), 7.80 (m, 2H), 7.51 (m, 1H), 7.39 (m, 1H), 7.33 (m, 2H), 6.89 (dd, J=5.6 Hz, J=1.6 Hz, 1H), 6.77 (m, 2H), 6.47 (m, 1H), 4.09 (m, 1H), 3.70 (m, 3H), 3.23 (m, 1H), 3.11 (m, 1H), 2.92 (m, 1H), 2.36 (m, 1H), 2.11 (m, 3H), 1.92 (m, 4H), 1.64 (m, 2H), 1.44 (m, 2H).

Example 24

(1R,2R)—N1-((S)-1-(4-Nitrophenyl)piperidin-3-yl)-N2-(4-(4-(trifluoromethoxy)phenyl)pyridin-2-yl)cyclohexane-1,2-diamine

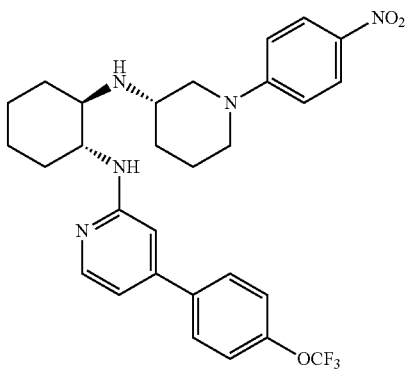 [SMILES: O=[N+]([O-])c1ccc(N2CCC[C@H](N[C@@H]3CCCC[C@H]3Nc3cc(-c4ccc(OC(F)(F)F)cc4)ccn3)C2)cc1]

(1R,2R)—N1-((S)-1-(4-Nitrophenyl)piperidin-3-yl)-N2-(4-(4-(trifluoromethoxy)phenyl)pyridin-2-yl)cyclohexane-1,2-diamine (1.4 mg, 0.003 mmol, 6.0% yield) was synthesized as described in General Procedure I using Intermediate A from Example 23 (20 mg, 0.04 mmol) and 4-(trifluoromethoxy)phenylboronic acid (12.2 mg, 0.04 mmol). The desired fraction from RP prep-HPLC method D was concentrated to give the title compound as a pale yellow solid. Anal. Calcd. for $C_{29}H_{32}F_3N_5O_3$ m/z 555.2, found: 556.2 (M+H)$^+$; $^1$H NMR (400 MHz, CD$_3$OD) δ ppm 8.11 (d, J=5.6 Hz, 1H), 8.01 (d, J=9.2 Hz, 2H), 7.57 (d, J=4.4 Hz, 2H), 7.30 (d, J=8 Hz, 2H), 6.78 (d, J=5.6 Hz, 1H), 6.66 (d, J=9.3 Hz, 2H), 6.51 (s, 1H), 4.7 (bs, 1H), 3.72 (m, 1H), 3.62 (m, 2H), 3.54 (m, 1H), 3.05 (m, 1H), 2.9 (m, 2H), 2.53 (m, 1H), 2.14 (m, 3H), 1.96 (m, 1H), 1.78 (m, 4H), 1.27 (m, 6H).

Example 25

(1R,2R)—N1-((S)-1-(4-Nitrophenyl)piperidin-3-yl)-N2-(4-phenylpyridin-2-yl)cyclohexane-1,2-diamine

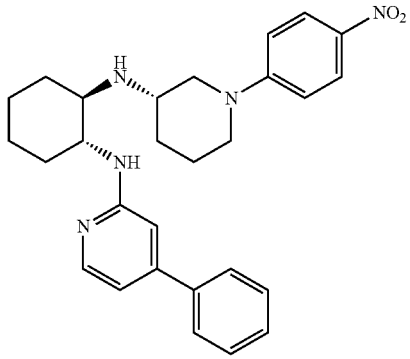

(1R,2R)—N1-((S)-1-(4-Nitrophenyl)piperidin-3-yl)-N2-(4-phenylpyridin-2-yl)cyclohexane-1,2-diamine (13.5 mg, 0.029 mmol, 9.1% yield) was synthesized as described in General Procedure H using Intermediate 18 (100 mg, 0.314 mmol) and 2-bromo-4-phenylpyridine (73.3 mg, 0.314 mmol). The desired fraction from RP prep-HPLC method C was concentrated to give the title compound as a pale yellow solid. Anal. Calcd. for $C_{28}H_{33}N_5O_2$ m/z 471.3, found: 472.2 (M+H)$^+$; $^1$H NMR (400 MHz, CD$_3$OD) δ ppm 8.02 (d, J=5.2 Hz, 1H), 7.84 (d, J=7.2 Hz, 2H), 7.42 (m, 5H), 6.88 (dd, J=5.6 Hz, 1H), 6.77 (dd, J=7.2 Hz, 2H), 6.52 d, J=0.8 Hz, 1H), 3.9 (m, 1H), 3.7 (m, 1H), 3.54 (m, 1H), 3.21 (m, 1H), 3.07 (m, 2H), 2.31 (m, 1H), 2.15 (m, 1H), 2.03 (m, 2H), 1.88 (m, 4H), 1.58 (m, 2H), 1.45 (m, 2H).

Example 26

(1R,2R)—N1-((S)-1-(4-Nitrophenyl)piperidin-3-yl)-N2-(5-phenylthiazol-2-yecyclohexane-1,2-diamine

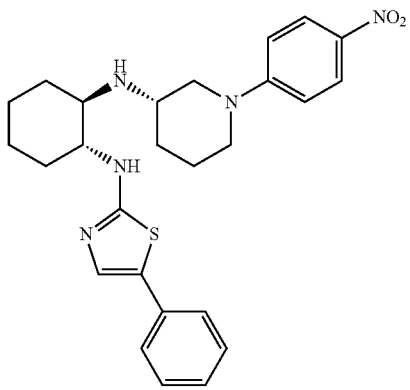

(1R,2R)—N1-((S)-1-(4-Nitrophenyl)piperidin-3-yl)-N2-(5-phenylthiazol-2-yl)cyclohexane-1,2-diamine (9.5 mg, 0.02 mmol, 15.9% yield) was synthesized as described in General Procedure H using Intermediate 37 (24.5 mg, 0.13 mmol) and Intermediate 17 (40 mg, 0.13 mmol). The product was purified using RP prep-HPLC method C to give the title compound as a yellow solid. Anal. Calcd. for $C_{26}H_{31}N_5O_2S$ m/z 477.2, found: 478.4 (M+H)$^+$; $^1$H NMR (400 MHz, CD$_3$OD) δ ppm 7.83 (m, 2H), 7.32 (m, 6H), 6.82 (m, 2H), 4.00 (m, 1H), 3.75-3.68 (m, 4H), 3.25 (m, 2H), 3.06 (m, 1H), 2.35 (m, 1H), 2.13 (m, 3H), 1.94 (m, 4H), 1.59 (m, 2H), 1.43 (m, 1H), 1.31 (m, 1H).

Example 27

(1R,2R)—N1-((S)-1-(4-Nitrophenyl)piperidin-3-yl)-N2-(5-phenyl-1,3,4-oxadiazol-2-yl)cyclohexane-1,2-diamine

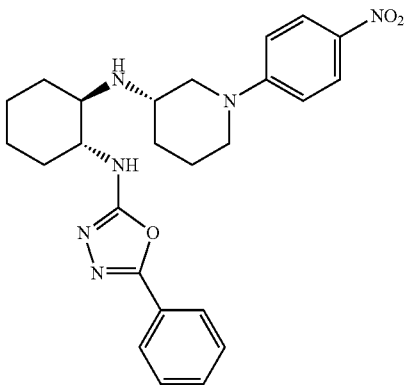 [SMILES: O=[N+]([O-])c1ccc(N2CCC[C@H](N[C@@H]3CCCC[C@H]3Nc3ncc(-c4ccccc4)s3)C2)cc1]

(1R,2R)—N1-((S)-1-(4-Nitrophenyl)piperidin-3-yl)-N2-(5-phenyl-1,3,4-oxadiazol-2-yl)cyclohexane-1,2-diamine (15 mg, 0.031 mmol, 83% yield) was synthesized as described in General Procedure H using 2-chloro-5-phenyl-1,3,4-oxadiazole (6.81 mg, 0.038 mmol) and Intermediate 17 (12 mg, 0.038 mmol). The product was purified using RP prep-HPLC method A to give the title compound as a yellow solid. Anal. Calcd. for $C_{25}H_{30}N_6O_3$ m/z 462.5, found: 463.3 (M+H)$^+$; $^1$H NMR (500 MHz, CDCl$_3$) δ ppm 7.99 (d, J=8.80 Hz, 2 H), 7.70 (d, J=7.15 Hz, 2 H), 7.49-7.43 (m, 1 H), 7.39 (t, J=7.70 Hz, 2 H), 6.83 (d, J=9.35 Hz, 2 H), 3.89-3.68 (m, 3 H), 3.54-3.43 (m, 2H), 3.40 (dd, J=12.37, 8.52 Hz, 1 H), 3.25-3.15 (m, 1H), 2.29 (d, J=12.65 Hz, 1 H), 2.19-2.02 (m, 3 H), 2.02-1.84 (m, 4 H), 1.82-1.64 (m, 2 H), 1.42 (br. s., 2H).

Example 28

(1R,2R)—N1-((S)-1-(4-Nitrophenyl)piperidin-3-yl)-N2-(4-(4-(trifluoromethoxy)phenyl)pyrimidin-2-yl)cyclohexane-1,2-diamine

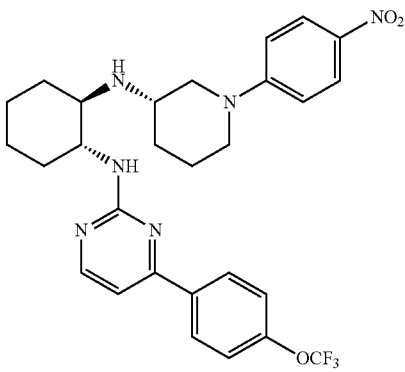

(1R,2R)—N1-((S)-1-(4-Nitrophenyl)piperidin-3-yl)-N2-(4-(4-(trifluoromethoxy)phenyl)pyrimidin-2-yl)cyclohexane-1,2-diamine (16 mg, 0.020 mmol, 33% yield) was synthesized as described in General Procedure H using 2-chloro-4-(4-(trifluoromethoxy)phenyl)pyrimidine (24.95 mg, 0.091 mmol) and Intermediate 17 (40 mg, 0.061 mmol). The product was purified using RP prep-HPLC method A to give the title compound as a yellow solid. Anal. Calcd. for $C_{28}H_{31}F_3N_6O_3$ m/z 556.5, found: 557.4 (M+H)+; $^1$H NMR (400 MHz, CDCl$_3$) δ ppm 8.33-7.93 (m, 5H), 7.39 (d, J=8.4 Hz, 2H), 7.22 (d, J=6.5 Hz, 1H), 6.87 (d, J=9.2 Hz, 2H), 4.50 (s, 1H), 4.06 (d, J=12.2 Hz, 1H), 3.83-3.60 (m, 1H), 3.55-3.39 (m, 2H), 3.28 (dd, J=12.5, 9.9 Hz, 1H), 3.05-2.90 (m, 1H), 2.42-2.26 (m, 2H), 2.26-2.16 (m, 1H), 2.09-1.95 (m, 1H), 1.96-1.63 (m, 5H), 1.62-1.37 (m, 3H).

Example 29

(1R,2R)—N1-((S)-1-(4-Nitrophenyl)piperidin-3-yl)-N2-(4-(3-(trifluoromethoxy)phenyl)pyrimidin-2-yl)cyclohexane-1,2-diamine

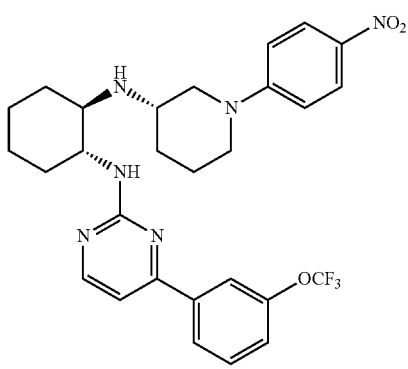 [SMILES: O=[N+]([O-])c1ccc(N2CCC[C@H](N[C@@H]3CCCC[C@H]3Nc3nccc(-c4cccc(OC(F)(F)F)c4)n3)C2)cc1]

(1R,2R)—N1-((S)-1-(4-Nitrophenyl)piperidin-3-yl)-N2-(4-(3-(trifluoromethoxy)phenyl)pyrimidin-2-yl)cyclohexane-1,2-diamine (10 mg, 0.012 mmol, 20.3% yield) was synthesized as described in General Procedure H using 2-chloro-4-(3-(trifluoromethoxy)phenyl)pyrimidine (24.95 mg, 0.091 mmol) and Intermediate 17 (40 mg, 0.061 mmol). The product was purified using RP prep-HPLC method A to give the title compound as a yellow solid. Anal. Calcd. for $C_{28}H_{31}F_3N_6O_3$ m/z 556.5, found: 557.4 (M+H)+; $^1$H NMR (400 MHz, CDCl$_3$) δ ppm 8.13 (d, J=8.6 Hz, 2H), 8.01 (d, J=7.9 Hz, 1H), 7.90 (s, 1H), 7.62 (t, J=7.9 Hz, 1H), 7.51 (d, J=8.1 Hz, 1H), 7.29-7.18 (m, 2H), 6.89 (d, J=8.8 Hz, 2H), 4.46 (s, 1H), 4.18-4.00 (m, 1H), 3.74 (d, J=13.0 Hz, 1H), 3.53-3.36 (m, 2H), 3.36-3.20 (m, 1H), 3.06-2.88 (m, 1H), 2.33 (d, J=9.2 Hz, 2H), 2.28-2.14 (m, 1H), 2.03 (d, J=12.0 Hz, 1H), 1.97-1.65 (m, 5H), 1.58-1.37 (m, 3H).

Example 30

(1R,2R)—N1-(4-(3-Methoxyphenyl)pyrimidin-2-yl)-N2-((S)-1-(4-nitrophenyl)piperidin-3-yl)cyclohexane-1,2-diamine

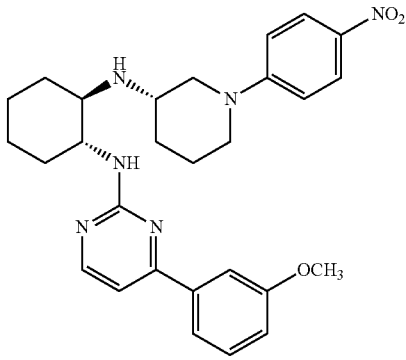

(1R,2R)—N1-(4-(3-Methoxyphenyl)pyrimidin-2-yl)-N2-((S)-1-(4-nitrophenyl)piperidin-3-yl)cyclohexane-1,2-diamine (8 mg, 0.0107 mmol, 14.1% yield) was synthesized as described in General Procedure H using 2-chloro-4-(3-methoxyphenyl)pyrimidine (25.06 mg, 0.113 mmol) and Intermediate 17 (50 mg, 0.076 mmol). The product was purified using RP prep-HPLC method A to give the title compound as a yellow solid. Anal. Calcd. for $C_{28}H_{34}N_6O_3$ m/z 502.6, found: 503.4 (M+H)+; $^1$H NMR (400 MHz, CDCl$_3$) δ ppm 8.10 (d, J=9.1 Hz, 2H), 8.05 (d, J=6.5 Hz, 1H), 7.66 (d, J=7.6 Hz, 1H), 7.59 (s, 1H), 7.47 (t, J=8.0 Hz, 1H), 7.24-7.14 (m, 2H), 6.85 (d, J=9.3 Hz, 2H), 4.49 (s, 1H), 4.03 (d, J=12.2 Hz, 1H), 3.90 (s, 3H), 3.76-3.63 (m, 1H), 3.55-3.37 (m, 2H), 3.29 (dd, J=12.5, 10.0 Hz, 1H), 2.96 (t, J=10.9 Hz, 1H), 2.43-2.27 (m, 2H), 2.27-2.15 (m, 1H), 2.07-1.96 (m, 1H), 1.96-1.77 (m, 4H), 1.77-1.64 (m, 1H), 1.59-1.34 (m, 3H).

Example 31

(1R,2R)—N1-(4-(4-Methoxyphenyl)pyrimidin-2-yl)-N2-((S)-1-(4-nitrophenyl)piperidin-3-yl)cyclohexane-1,2-diamine

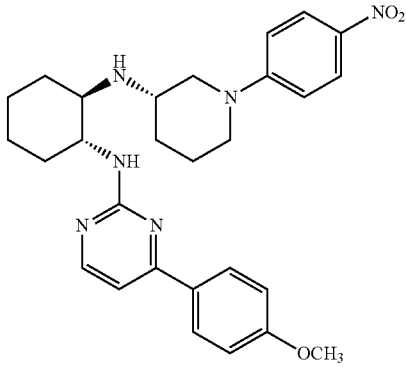

(1R,2R)—N1-(4-(4-Methoxyphenyl)pyrimidin-2-yl)-N2-((S)-1-(4-nitrophenyl)piperidin-3-yl)cyclohexane-1,2-diamine (4 mg, 0.0054 mmol, 14.8% yield) was synthesized as described in General Procedure H using 2-chloro-4-(4-methoxyphenyl)pyrimidine (8.08 mg, 0.037 mmol) and Intermediate 17 (20 mg, 0.037 mmol). The product was purified using RP prep-HPLC method A to give the title compound as a yellow solid. Anal. Calcd. for $C_{28}H_{34}N_6O_3$ m/z 502.6, found: 503.4 (M+H)$^+$; $^1$H NMR (400 MHz, CDCl$_3$) δ ppm 8.08 (d, J=9.1 Hz, 2H), 8.05 (d, J=6.5 Hz, 1H), 7.96 (d, J=7.6 Hz, 2H), 7.24-7.10 (m, 3H), 6.92 (d, J=9.1 Hz, 2H), 4.49 (s, 1H), 4.03 (d, J=12.2 Hz, 1H), 3.85 (s, 3H), 3.76-3.63 (m, 1H), 3.55-3.37 (m, 2H), 3.29 (dd, J=12.5, 10.0 Hz, 1H), 2.96 (t, J=10.9 Hz, 1H), 2.43-2.27 (m, 2H), 2.27-2.15 (m, 1H), 2.07-1.96 (m, 1H), 1.96-1.77 (m, 4H), 1.77-1.64 (m, 1H), 1.59-1.34 (m, 3H).

Example 32

(1R,2R)—N1-((S)-1-(4-Nitrophenyl)piperidin-3-yl)-N2-(4-phenylpyrimidin-2-yl)cyclohexane-1,2-diamine

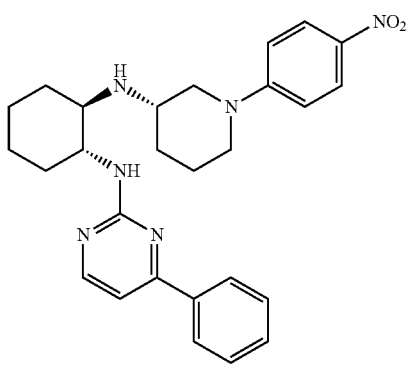 [SMILES: O=[N+]([O-])c1ccc(N2CCC[C@H](N[C@@H]3CCCC[C@H]3Nc3nccc(-c4ccccc4)n3)C2)cc1]

(1R,2R)—N1-((S)-1-(4-Nitrophenyl)piperidin-3-yl)-N2-(4-phenylpyrimidin-2-yl)cyclohexane-1,2-diamine (14 mg, 0.023 mmol, 38.2% yield) was synthesized as described in General Procedure H using 2-chloro-4-phenylpyrimidine (17.32 mg, 0.091 mmol) and Intermediate 17 (40 mg, 0.061 mmol). The product was purified using RP prep-HPLC method A to give the title compound as a yellow solid. Anal. Calcd. for $C_{27}H_{32}N_6O_2$ m/z 472.5, found: 473.3 (M+H)$^+$; $^1$H NMR (400 MHz, CDCl$_3$) δ ppm 8.17-7.98 (m, 5H), 7.65 (d, J=7.4 Hz, 1H), 7.57 (t, J=7.7 Hz, 2H), 7.22 (d, J=5.5 Hz, 1H), 6.84 (d, J=9.1 Hz, 2H), 4.51 (s, 1H), 4.04-3.91 (m, 2H), 3.67 (d, J=13.0 Hz, 1H), 3.43 (s, 2H), 3.34-3.25 (m, 1H), 2.96 (s, 1H), 2.39-2.26 (m, 1H), 2.26-2.16 (m, 1H), 2.06-1.79 (m, 5H), 1.77-1.61 (m, 1H), 1.59-1.32 (m, 3H).

Example 33

4-((S)-3-((1R,2R)-2-(4-(1H-Pyrazol-3-yl)pyridin-2-ylamino)cyclohexylamino)piperidin-1-yl)benzonitrile tris-trifluoroacetate

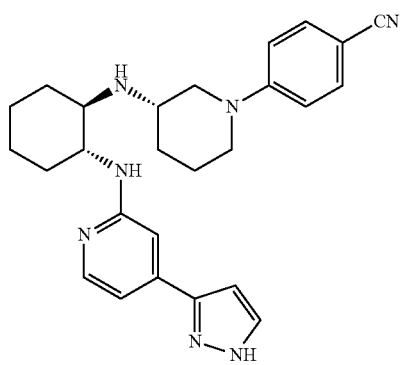 [SMILES: N#Cc1ccc(N2CCC[C@H](N[C@@H]3CCCC[C@H]3Nc3cc(-c4cc[nH]n4)ccn3)C2)cc1]

4-((S)-3-((1R,2R)-2-(4-(1H-Pyrazol-3-yl)pyridin-2-ylamino)cyclohexylamino)piperidin-1-yl)benzonitrile tris-trifluoroacetate (4.88 mg, 0.00623 mmol, 9.42% yield) was synthesized as described in General Procedure I using Example 50 (30 mg, 0.066 mmol) and 1H-pyrazol-3-ylboronic acid (8.86 mg, 0.079 mmol). The desired fraction from RP prep-HPLC method A was concentrated to give the title compound as an off-white solid. Anal. Calcd. for $C_{26}H_{31}N_7$ m/z 441.5, found: 442.2 (M+H)$^+$; $^1$H NMR (400 MHz, CDCl$_3$) δ ppm 7.66-7.43 (m, 6 H), 7.03-6.90 (m, 3 H), 6.67 (br. s., 1 H), 4.30-4.06 (m, 1 H), 3.89 (d, J=9.34 Hz, 1 H), 3.59-3.42 (m, 2 H), 3.42-3.27 (m, 2 H), 3.02 (br. s., 1 H), 2.30 (d, J=12.09 Hz, 1 H), 2.26-2.10 (m, 2 H), 1.99-1.86 (m, 3 H), 1.85-1.72 (m, 2 H), 1.43 (br. s., 3 H), 1.30-1.21 (m, 1 H).

Example 34

4-((S)-3-((1R,2R)-2-(4-(1-Methyl-1H-pyrazol-5-yl)pyridin-2-ylamino)cyclohexylamino)piperidin-1-yl)benzonitrile tris-trifluoroacetate

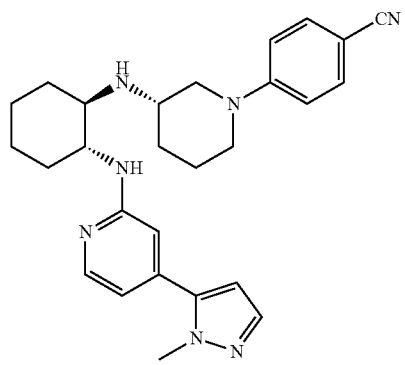 [SMILES: Cn1nccc1-c1ccnc(N[C@@H]2CCCC[C@H]2N[C@H]2CCCN(c3ccc(C#N)cc3)C2)c1]

4-((S)-3-((1R,2R)-2-(4-(1-Methyl-1H-pyrazol-5-yl)pyridin-2-ylamino)cyclohexylamino)piperidin-1-yl)benzonitrile tris-trifluoroacetate (6.80 mg, 0.00844 mmol, 13.7% yield) was synthesized as described in General Procedure I using Example 50 (28 mg, 0.062 mmol) and 1-methyl-5-(4,4,5,5-tetramethyl-1,3,2-dioxaborolan-2-yl)-1H-pyrazole (25.6 mg, 0.123 mmol). The desired fraction from RP prep-HPLC method A was concentrated to give the title compound as an off-white solid. Anal. Calcd. for $C_{27}H_{33}N_7$ m/z 455.5, found: 456.2 (M+H)$^+$; $^1$H NMR (400 MHz, CDCl$_3$) δ ppm 7.81 (br. s., 1 H), 7.62 (d, J=2.20 Hz, 1 H), 7.52 (d, J=8.79 Hz, 2 H), 7.00 (br. s., 1H), 6.90 (d, J=6.60 Hz, 4 H), 6.63 (br. s., 1 H), 4.13-3.93 (m, 4 H), 3.82 (d, J=10.99 Hz, 1 H), 3.71-3.24 (m, 4 H), 3.11-2.79 (m, 1 H), 2.29 (br. s., 1 H), 2.18 (br. s., 3 H), 2.02 (br. s., 1 H), 1.99-1.69 (m, 5 H), 1.45 (d, J=9.34 Hz, 2 H).

Example 35

4-((S)-3-((1R,2R)-2-(5-(3-Fluorophenyl)oxazol-2-ylamino)cyclohexylamino)piperidin-1-yl)benzonitrile

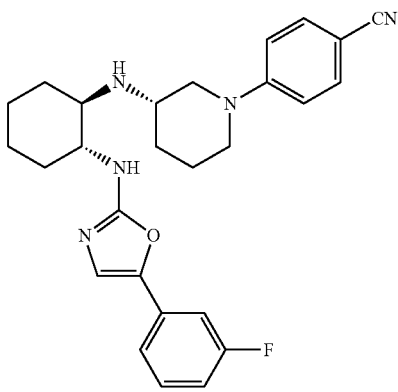 [SMILES: N#Cc1ccc(N2CCC[C@H](N[C@@H]3CCCC[C@H]3Nc3ncc(-c4cccc(F)c4)o3)C2)cc1]

4-((S)-3-((1R,2R)-2-(5-(3-Fluorophenyl)oxazol-2-ylamino)cyclohexylamino)piperidin-1-yl)benzonitrile (9 mg, 0.02 mmol, 12.3% yield) was synthesized as described in General Procedure H using Intermediate 7 (57 mg, 0.29 mmol) and Intermediate 18 (50 mg, 0.15 mmol). The product was purified using RP prep-HPLC method D to give the title compound as a yellow solid. Anal. Calcd. for $C_{27}H_{30}FN_5O$ m/z 459.2, found: 460.2 $(M+H)^+$; $^1H$ NMR (400 MHz, $CD_3OD$) δ ppm 7.40 (m, 1H), 7.27 (d, J=9 Hz, 2H), 7.17 (t, J=3.8 Hz, 2H), 7.09 (dd, J=10 Hz, 1H), 7.0 (dt, J=8.4 Hz, J=2.4 Hz, 1H), 6.93 (d, J=9 Hz, 2H), 3.83 (dd, J=10 Hz, J=4Hz, 1H), 3.67 (m, 2H), 3.54 (m, 1H), 3.41 (m, 1H), 3.30 (m, 1H), 2.35 (m, 1H), 2.19 (m, 1H), 2.07 (m, 2H), 1.91 (m, 4H), 1.61 (m, 2H), 1.44 (m, 2H).

Example 36

4-((S)-3-((1R,2R)-2-(4-(3-Fluorophenyl)pyridin-2-ylamino)cyclohexylamino)piperidin-1-yl)benzonitrile tris-trifluoroacetate

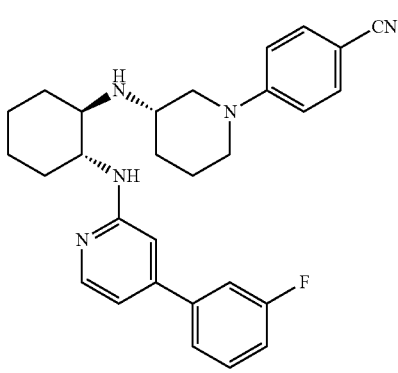 [SMILES: N#Cc1ccc(N2CCC[C@H](N[C@@H]3CCCC[C@H]3Nc3cc(-c4cccc(F)c4)ccn3)C2)cc1]

4-((S)-3-((1R,2R)-2-(4-(3-Fluorophenyl)pyridin-2-ylamino)cyclohexylamino)piperidin-1-yl)benzonitrile tris-trifluoroacetate (40.35 mg, 0.049 mmol, 55.3% yield) was synthesized as described in General Procedure I using Example 50 (40 mg, 0.088 mmol) and 3-fluorophenylboronic acid (13.55 mg, 0.097 mmol). The desired fraction from RP prep-HPLC method A was concentrated to give the title compound as an off-white solid. Anal. Calcd. for $C_{29}H_{32}FN_5$ m/z 469.5, found: 470.4 $(M+H)^+$; $^1H$ NMR (400 MHz, $CDCl_3$) δ ppm 7.74 (d, J=6.60 Hz, 1 H), 7.61-7.45 (m, 4H), 7.28-7.20 (m, 3 H), 7.01 (d, J=5.50 Hz, 1 H), 6.90 (d, J=8.25 Hz, 2 H), 4.24 (br. s., 1 H), 3.68 (d, J=9.34 Hz, 2 H), 3.47 (br. s., 3 H), 3.14 (br. s., 1 H), 2.28 (d, J=11.54 Hz, 1 H), 2.20-2.07 (m, 2 H), 2.02-1.83 (m, 4 H), 1.86-1.70 (m, 2 H), 1.56-1.34 (m, 4 H).

Example 37

4-((S)-3-((1R,2R)-2-(4-(2-Fluorophenyl)pyridin-2-ylamino)cyclohexylamino)piperidin-1-yl)benzonitrile tris-trifluoroacetate

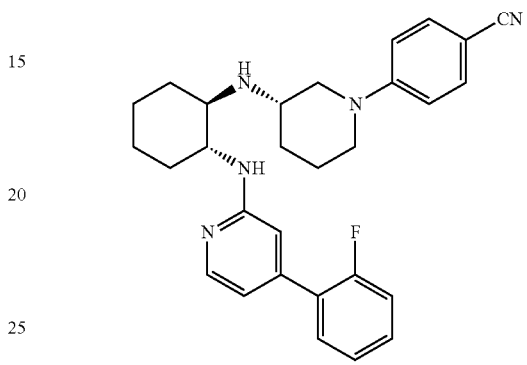

4-((S)-3-((1R,2R)-2-(4-(2-Fluorophenyl)pyridin-2-ylamino)cyclohexylamino)piperidin-1-yl)benzonitrile tris-trifluoroacetate (37.6 mg, 0.046 mmol, 60.4% yield) was synthesized as described in General Procedure I using Example 50 (34.5 mg, 0.076 mmol) and 2-fluorophenylboronic acid (11.69 mg, 0.084 mmol). The desired fraction from RP prep-HPLC method A was concentrated to give the title compound as an off-white solid. Anal. Calcd. for $C_{29}H_{32}FN_5$ m/z 469.5, found: 470.3 $(M+H)^+$; $^1H$ NMR (400 MHz, $CDCl_3$) δ ppm 7.71 (d, J=6.60 Hz, 1 H), 7.57-7.44 (m, 3 H), 7.32 (t, J=7.15 Hz, 1 H), 7.22 (dd, J=10.99, 8.79 Hz, 2 H), 7.18-7.12 (m, 1 H), 7.07 (br. s., 1 H), 6.90 (d, J=8.79 Hz, 2 H), 4.34-4.05 (m, 1 H), 3.72 (br. s., 2 H), 3.45 (br. s., 3 H), 3.20-2.98 (m, 1 H), 2.34-2.23 (m, 1 H), 2.16 (br. s., 2 H), 2.05-1.83 (m, 5 H), 1.83-1.70 (m, 2 H), 1.52-1.37 (m, 2 H).

Example 38

2-Chloro-4-((S)-3-((1R,2R)-2-(5-(4-(trifluoromethoxy)phenyl)oxazol-2-ylamino)cyclohexylamino)piperidin-1-yl)benzonitrile bis-trifluoroacetate

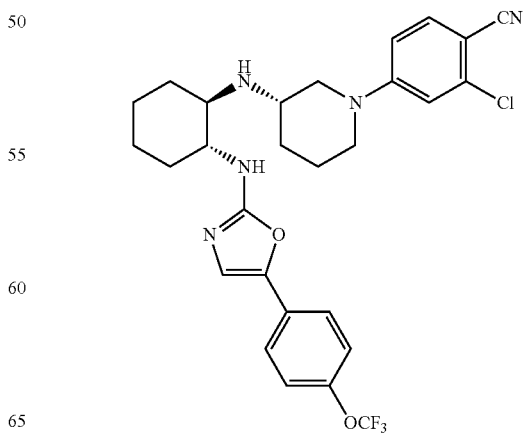

2-Chloro-4-((S)-3-((1R,2R)-2-(5-(4-(trifluoromethoxy)phenyl)oxazol-2-ylamino)cyclohexylamino)piperidin-1-yl)benzonitrile bis-trifluoroacetate (17 mg, 0.021 mmol, 21.1% yield) was synthesized as described in General Procedure H using Intermediate 2 (40.1 mg, 0.152 mmol) and Intermediate 28 (80 mg, 0.101 mmol). The desired fraction from RP prep-HPLC method A was concentrated to give the title compound as an off-white solid. Anal. Calcd. for $C_{28}H_{29}ClFN_5O_2$ m/z 549.5, found: 560.3 (M+H)$^+$; $^1$H NMR (400 MHz, CDCl$_3$) δ ppm 7.45 (dd, J=8.8, 2.4 Hz, 2H), 7.26-7.21 (m, 3H), 7.03 (s, 1H), 6.86 (d, J=2.4 Hz, 1H), 6.75 (dd, J=8.8, 2.4 Hz, 1H), 4.11 (s, 1H), 3.83 (d, J=12.0 Hz, 1H), 3.64 (d, J=13.0 Hz, 1H), 3.49 (s, 1H), 3.39 (s, 1H), 3.22-3.11 (m, 1H), 2.99 (d, J=11.1 Hz, 1H), 2.35-2.09 (m, 3H), 2.06-1.84 (m, 4H), 1.83-1.56 (m, 3H), 1.53-1.35 (m, 2H).

Example 39

2-Chloro-4-((S)-3-((1R,2R)-2-(5-(2-fluorophenyl)oxazol-2-ylamino)cyclohexylamino)piperidin-1-yl)benzonitrile bis-trifluoroacetate

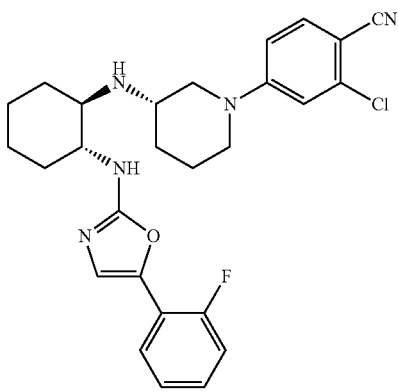 [SMILES: N#Cc1ccc(N2CCC[C@H](N[C@@H]3CCCC[C@H]3Nc3ncc(-c4ccccc4F)o3)C2)cc1Cl]

2-Chloro-4-((S)-3-((1R,2R)-2-(5-(2-fluorophenyl)oxazol-2-ylamino)cyclohexylamino)piperidin-1-yl)benzonitrile bis-trifluoroacetate (14 mg, 0.019 mmol, 18.8% yield) was synthesized as described in General Procedure H using Intermediate 6 (30.1 mg, 0.152 mmol) and Intermediate 28 (80 mg, 0.101 mmol). The desired fraction from RP prep-HPLC method A was concentrated to give the title compound as an off-white solid. Anal. Calcd. for $C_{27}H_{29}ClFN_5O$ m/z 493.5, found: 494.1 (M+H)$^+$; $^1$H NMR (400 MHz, CDCl$_3$) δ ppm 7.57 (t, J=6.8 Hz, 1H), 7.47 (d, J=8.8 Hz, 1H), 7.42-7.33 (m, 1H), 7.28-7.21 (m, 2H), 7.17 (dd, J=10.8, 8.4 Hz, 1H), 6.87 (d, J=2.5 Hz, 1H), 6.76 (dd, J=8.8, 2.4 Hz, 1H), 4.28-4.14 (m, 1H), 3.88 (d, J=12.8 Hz, 1H), 3.76-3.64 (m, 1H), 3.54-3.43 (m, 1H), 3.43-3.33 (m, 1H), 3.22-3.11 (m, 1H), 3.01-2.90 (m, 1H), 2.33-2.13 (m, 3H), 2.07-1.84 (m, 4H), 1.82-1.54 (m, 3H), 1.52-1.38 (m, 2H).

Example 40

2-Chloro-4-((S)-3-((1R,2R)-2-(4-phenylpyrimidin-2-ylamino)cyclohexylamino)piperidin-1-yl)benzonitrile bis-trifluoroacetate

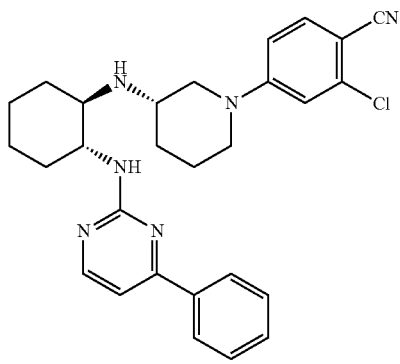 [SMILES: N#Cc1ccc(N2CCC[C@H](N[C@@H]3CCCC[C@H]3Nc3nccc(-c4ccccc4)n3)C2)cc1Cl]

2-Chloro-4-((S)-3-((1R,2R)-2-(4-phenylpyrimidin-2-ylamino)cyclohexylamino)piperidin-1-yl)benzonitrile bis-trifluoroacetate (13 mg, 0.018 mmol, 17.8% yield) was synthesized as described in General Procedure H using 2-chloro-4-phenylpyrimidine (29 mg, 0.152 mmol) and Intermediate 28 (80 mg, 0.101 mmol). The desired fraction from RP prep-HPLC method A was concentrated to give the title compound as an off-white solid. Anal. Calcd. for $C_{28}H_{31}ClN_6$ m/z 486.5, found: 487.0 (M+H)$^+$; $^1$H NMR (400 MHz, CDCl$_3$) δ ppm 8.15-7.95 (m, 3H), 7.69-7.60 (m, 1H), 7.56 (t, J=7.6 Hz, 2H), 7.45-7.33 (m, 1H), 7.16 (d, J=6.2 Hz, 1H), 6.76-6.70 (m, 1H), 6.68-6.60 (m, 1H), 4.48 (br.s, 1H), 3.80-3.64 (m, 1H), 3.47-3.33 (m, 2H), 3.33-3.16 (m, 2H), 2.91-2.73 (m, 1H), 2.37-2.23 (m, 2H), 2.22-2.09 (m, 1H), 2.04-1.69 (m, 5H), 1.68-1.31 (m, 4H).

Example 41

4-((S)-3-((1R,2R)-2-(5-Phenyl-1,2,4-oxadiazol-3-ylamino)cyclohexylamino)piperidin-1-ylbenzonitrile bis-trifluoroacetate

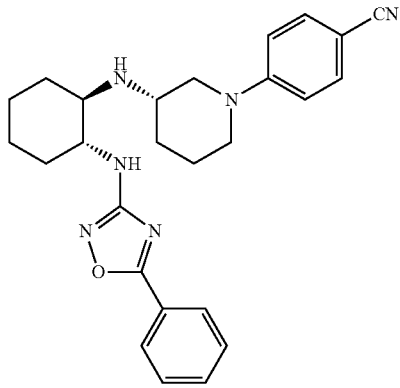 [SMILES: N#Cc1ccc(N2CCC[C@H](N[C@@H]3CCCC[C@H]3Nc3noc(-c4ccccc4)n3)C2)cc1]

4-((S)-3-((1R,2R)-2-(5-Phenyl-1,2,4-oxadiazol-3-ylamino)cyclohexylamino)piperidin-1-yl)benzonitrile bis-trifluoroacetate (12 mg, 0.017 mmol, 9.14% yield) was synthesized as described in General Procedure H using 3-chloro-5-phenyl-1,2,4-oxadiazole (68.6 mg, 0.380 mmol) and Intermediate 18 (100 mg, 0.190 mmol). The desired fraction from RP prep-HPLC method A was concentrated to give the title compound as a beige solid. Anal. Calcd. for $C_{26}H_{30}N_6O$ m/z 442.5, found: 443.2 (M+H)$^+$; $^1$H NMR (400 MHz, CDCl$_3$) δ ppm 8.06 (d, J=7.6 Hz, 2H), 7.64 (t, J=7.4 Hz, 1H), 7.55-7.46 (m, 4H), 6.88 (d, J=8.9 Hz, 2H), 3.89-3.72 (m, 2H), 3.40-3.26 (m, 1H), 3.24-3.12 (m, 1H), 3.07-2.95 (m, 1H), 2.89-2.77 (m, 2H), 2.31 (d, J=10.5 Hz, 1H), 2.14 (d, J=9.8 Hz, 1H), 2.05-1.81 (m, 2H), 2.04-1.81 (m, 3H), 1.78-1.64 (m, 2H), 1.51-1.29 (m, 3H).

Example 42

4-((S)-3-((1R,2R)-2-(5-Phenylthiazol-2-ylamino)cyclohexylamino)piperidin-1-yl)benzonitrile

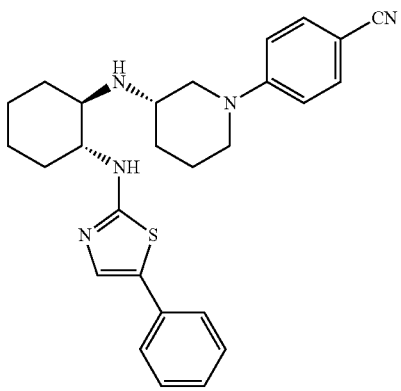 [SMILES: N#Cc1ccc(N2CCC[C@H](N[C@@H]3CCCC[C@H]3Nc3ncc(-c4ccccc4)s3)C2)cc1]

4-((S)-3-((1R,2R)-2-(5-Phenylthiazol-2-ylamino)cyclohexylamino)piperidin-1-yl)benzonitrile (11 mg, 0.02 mmol, 17.9% yield) was synthesized as described in General Procedure H using Intermediate 37 (26.2 mg, 0.13 mmol) and Intermediate 18 (40 mg, 0.13 mmol). The product was purified using RP prep-HPLC method A to give the title compound as a yellow solid. Anal. Calcd. for $C_{27}H_{31}N_5S$ m/z 457.2, found: 458.4 (M+H)$^+$; $^1$H NMR (400 MHz, CD$_3$OD) δ ppm 7.37 (m, 4H), 7.26 (m, 4H), 6.85 (d, J=9 Hz, 2H), 3.82 (m, 1H), 3.73 (m, 1H), 3.66 (m, 1H), 3.58 (m, 1H), 3.29 (m, 2H), 3.25 (m, 1H), 3.03 (m, 1H), 2.34 (m, 1H), 2.17 (m, 1H), 2.06 (m, 2H), 1.90 (m, 4H), 1.60 (m, 2H), 1.43 (m, 2H), 1.34 (m, 1H), 1.31 (m, 1H).

Example 43

4-((S)-3-((1R,2R)-2-(4-(4-(Difluoromethoxy)phenyl)pyridin-2-ylamino)cyclohexylamino)piperidin-1-yl)benzonitrile tris-trifluoroacetate

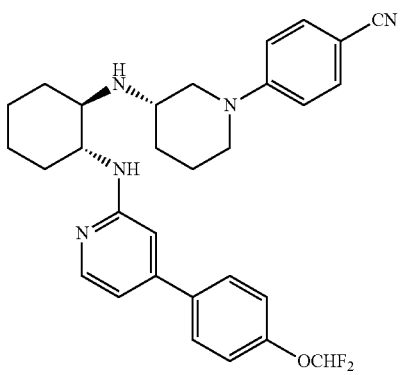 [SMILES: N#Cc1ccc(N2CCC[C@H](N[C@@H]3CCCC[C@H]3Nc3cc(-c4ccc(OC(F)F)cc4)ccn3)C2)cc1]

4-((S)-3-((1R,2R)-2-(4-(4-(Difluoromethoxy)phenyl)pyridin-2-ylamino)cyclohexylamino)piperidin-1-yl)benzonitrile tris-trifluoroacetate (31 mg, 0.035 mmol, 50.7% yield) was synthesized as described in General Procedure I using Example 50 (31 mg, 0.068 mmol) and 2-(4-(difluoromethoxy)phenyl)-4,4,5,5-tetramethyl-1,3,2-dioxaborolane (19.35 mg, 0.072 mmol). The desired fraction from RP prep-HPLC method A was concentrated to give the title compound as an off-white solid. Anal. Calcd. for $C_{30}H_{33}F_2N_5O$ m/z 517.5, found: 518.5 (M+H)$^+$; $^1$H NMR (400 MHz, CDCl$_3$) δ ppm 7.85 (br. s., 1 H), 7.70 (d, J=4.40 Hz, 1H), 7.50 (d, J=9.34 Hz, 2 H), 7.32-7.23 (m, 4 H), 7.00 (br. s., 1 H), 6.90 (d, J=7.70 Hz, 2 H), 6.81-6.37 (m, 1 H), 4.42-4.19 (m, 1 H), 3.49 (br. s., 3 H), 3.39-3.10 (m, 3 H), 2.27 (d, J=10.99 Hz, 2 H), 2.18-2.07 (m, 2 H), 1.96 (br. s., 5 H), 1.78 (ddd, J=9.21, 4.53, 4.40 Hz, 1 H), 1.45 (br. s., 2 H).

Example 44

4-((S)-3-((1R,2R)-2-(4-(4-Fluorophenyl)pyridin-2-ylamino)cyclohexylamino)piperidin-1-yl)benzonitrile tris-trifluoroacetate

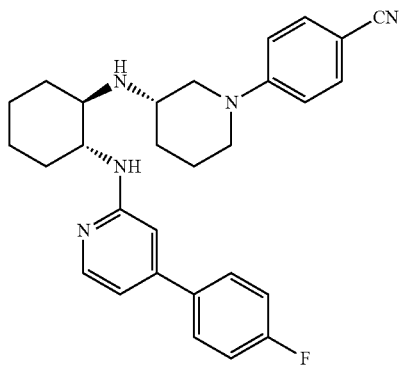

4-((S)-3-((1R,2R)-2-(4-(4-Fluorophenyl)pyridin-2-ylamino)cyclohexylamino)piperidin-1-yl)benzonitrile tris-trifluoroacetate (38.8 mg, 0.045 mmol, 54.3% yield) was synthesized as described in General Procedure I using Example 50 (38 mg, 0.084 mmol) and 2-(4-fluorophenyl)-4,4,5,5-tetramethyl-1,3,2-dioxaborolane (19.5 mg, 0.088 mmol). The desired fraction from RP prep-HPLC method A was concentrated to give the title compound as an off-white solid. Anal. Calcd. for $C_{29}H_{32}FN_5$ m/z 469.5, found: 470.3 (M+H)$^+$; $^1$H NMR (400 MHz, CDCl$_3$) δ ppm 7.82 (s, 1H), 7.69 (d, J=5.3 Hz, 1H), 7.51 (d, J=7.2 Hz, 2H), 7.39-7.28 (m, 1H), 7.26-7.17 (m, 3H), 7.08-6.95 (m, 1H), 6.90 (d, J=8.3 Hz, 2H), 4.66-4.15 (m, 2H), 3.96-2.77 (m, 5H), 2.28 (d, J=11.0 Hz, 1H), 2.20-2.06 (m, 2H), 2.06-1.68 (m, 5H), 1.70-1.31 (m, 4H).

Example 45

4-((S)-3-((1R,2R)-2-(4-(4-Hydroxyphenyl)pyridin-2-ylamino)cyclohexylamino)piperidin-1-yl)benzonitrile tris-trifluoroacetate

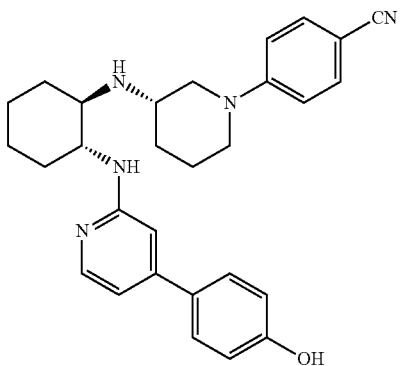 [SMILES: N#Cc1ccc(N2CCC[C@H](N[C@@H]3CCCC[C@H]3Nc3cc(-c4ccc(O)cc4)ccn3)C2)cc1]

4-((S)-3-((1R,2R)-2-(4-(4-Hydroxyphenyl)pyridin-2-ylamino)cyclohexylamino)piperidin-1-yl)benzonitrile tris-trifluoroacetate (45 mg, 0.055 mmol, 60.5% yield) was synthesized as described in General Procedure I using Example 50 (41 mg, 0.090 mmol) and 4-(4,4,5,5-tetramethyl-1,3,2-dioxaborolan-2-yl)phenol (20.85 mg, 0.095 mmol). The desired fraction from RP prep-HPLC method A was concentrated to give the title compound as an off-white solid. Anal. Calcd. for $C_{29}H_{33}N_5O$ m/z 467.5, found: 468.2 (M+H)$^+$; $^1$H NMR (400 MHz, CDCl$_3$) δ ppm 7.61 (d, J=6.6 Hz, 1H), 7.55-7.39 (m, 4H), 7.04 (s, 1H), 6.98-6.79 (m, 6H), 4.30 (s, 1H), 3.72 (d, J=11.2 Hz, 1H), 3.62-3.29 (m, 5H), 3.15-2.97 (m, 1H), 2.28 (d, J=10.2 Hz, 1H), 2.17 (s, 2H), 2.06-1.64 (m, 5H), 1.61-1.33 (m, 3H).

Example 46

4-((S)-3-((1R,2R)-2-(4-(4-Chlorophenyl)pyridin-2-ylamino)cyclohexylamino)piperidin-1-yl)benzonitrile tris-trifluoroacetate

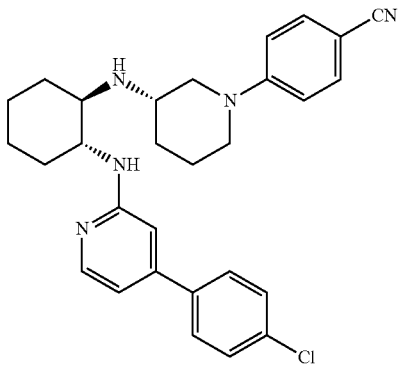

4-((S)-3-((1R,2R)-2-(4-(4-Chlorophenyl)pyridin-2-ylamino)cyclohexylamino)piperidin-1-yl)benzonitrile tris-trifluoroacetate (41 mg, 0.049 mmol, 49.5% yield) was synthesized as described in General Procedure I using Example 50 (45 mg, 0.099 mmol) and 2-(4-chlorophenyl)-4,4,5,5-tetramethyl-1,3,2-dioxaborolane (23.6 mg, 0.099 mmol). The desired fraction from RP prep-HPLC method A was concentrated to give the title compound as an off-white solid. Anal. Calcd. for $C_{29}H_{32}ClN_5$ m/z 485.5, found: 486.2 (M+H)$^+$; $^1$H NMR (400 MHz, CDCl$_3$) δ ppm 7.70 (d, J=6.6 Hz, 2H), 7.57-7.45 (m, 5H), 7.26 (s, 1H), 7.00 (d, J=5.6 Hz, 1H), 6.90 (d, J=8.6 Hz, 2H), 4.97-3.94 (m, 2H), 3.90-2.78 (m, 6H), 2.36-2.23 (m, 1H), 2.11 (d, J=10.0 Hz, 2H), 2.06-1.66 (m, 5H), 1.65-1.33 (m, 3H).

Example 47

2-Fluoro-4-((S)-3-((1R,2R)-2-(4-phenylpyrimidin-2-ylamino)cyclohexylamino)piperidin-1-yl)benzonitrile bis-trifluoroacetate

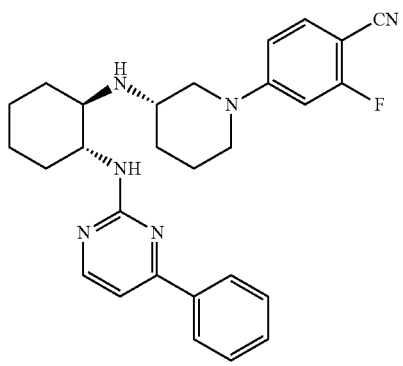 [SMILES: N#Cc1ccc(N2CCC[C@H](N[C@@H]3CCCC[C@H]3Nc3nccc(-c4ccccc4)n3)C2)cc1F]

2-Fluoro-4-((S)-3-((1R,2R)-2-(4-phenylpyrimidin-2-ylamino)cyclohexylamino)piperidin-1-yl)benzonitrile bis-trifluoroacetate (31 mg, 0.044 mmol, 18.0% yield) was synthesized as described in General Procedure H using 2-chloro-4-phenylpyrimidine (46.3 mg, 0.243 mmol) and Intermediate 26 (160 mg, 0.243 mmol). The desired fraction from RP prep-HPLC method A was concentrated to give the title compound as an off-white solid. Anal. Calcd. for $C_{28}H_{31}FN_6$ m/z 470.5, found: 471.0 (M+H)$^+$; $^1$H NMR (400 MHz, CDCl$_3$) δ ppm 8.16-7.93 (m, 3H), 7.65 (t, J=7.3 Hz, 1H), 7.56 (t, J=7.6 Hz, 2H), 7.33 (t, J=8.0 Hz, 1H), 7.14 (d, J=6.5 Hz, 1H), 6.54 (d, J=8.7 Hz, 1H), 6.43 (dd, J=12.6, 2.3 Hz, 1H), 4.48 (s, 1H), 3.83 (d, J=11.9 Hz, 1H), 3.53-3.26 (m, 3H), 3.20-3.04 (m, 1H), 2.83-2.60 (m, 1H), 2.36-2.12 (m, 3H), 2.05-1.70 (m, 5H), 1.67-1.31 (m, 4H).

Example 48

2-Fluoro-4-((S)-3-((1R,2R)-2-(5-phenyloxazol-2-ylamino)cyclohexylamino)piperidin-1-yl)benzonitrile bis-trifluoroacetate

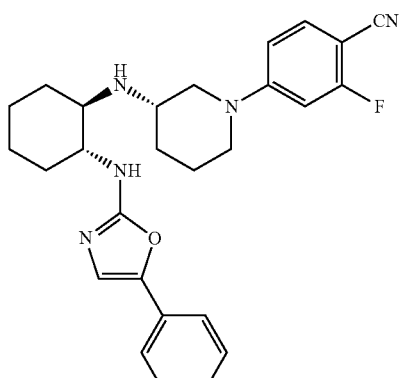

2-Fluoro-4-((S)-3-((1R,2R)-2-(5-phenyloxazol-2-ylamino)cyclohexylamino)piperidin-1-yl)benzonitrile bis-trifluoroacetate (35 mg, 0.050 mmol, 20.6% yield) was synthesized as described in General Procedure H using Intermediate 1 (43.6 mg, 0.242 mmol) and Intermediate 26 (160 mg, 0.243 mmol). The desired fraction from RP prep-HPLC method A was concentrated to give the title compound as an off-white solid. Anal. Calcd. for $C_{27}H_{30}FN_5O$ m/z 459.5, found: 460.2 (M+H)$^+$; $^1$H NMR (400 MHz, CDCl$_3$) δ ppm 7.52-7.33 (m, 6H), 7.05 (s, 1H), 6.64 (dd, J=8.8, 2.0 Hz, 1H), 6.56 (dd, J=12.5, 2.0 Hz, 1H), 4.27-4.11 (m, 1H), 3.93 (d, J=12.1 Hz, 1H), 3.71 (d, J=13.2 Hz, 1H), 3.53-3.25 (m, 2H), 3.18-3.07 (m, 1H), 2.91 (t, J=11.5 Hz, 1H), 2.35-2.13 (m, 3H), 2.05-1.80 (m, 4H), 1.80-1.54 (m, 3H), 1.53-1.36 (m, 2H).

Example 49

2-Fluoro-4-((S)-3-((1R,2R)-2-(5-(4-(trifluoromethoxy)phenyl)oxazol-2-ylamino)cyclohexylamino)piperidin-1-yl)benzonitrile bis-trifluoroacetate

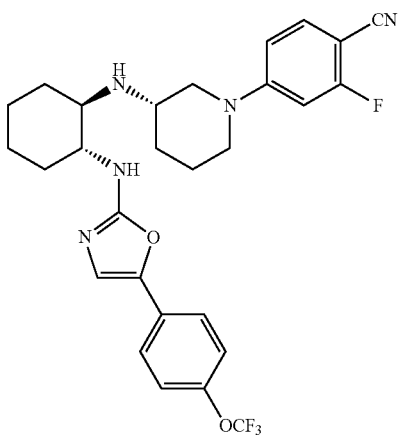

2-Fluoro-4-((S)-3-((1R,2R)-2-(5-(4-(trifluoromethoxy)phenyl)oxazol-2-ylamino)cyclohexylamino)piperidin-1-yl)benzonitrile bis-trifluoroacetate (28 mg, 0.036 mmol, 17.4% yield) was synthesized as described in General Procedure H using Intermediate 2 (54.6 mg, 0.207 mmol) and Intermediate 26 (160 mg, 0.207 mmol). The desired fraction from RP prep-HPLC method A was concentrated to give the title compound as an off-white solid. Anal. Calcd. for $C_{28}H_{29}F_4N_5O_2$ m/z 543.5, found: 544.2 (M+H)$^+$; $^1$H NMR (400 MHz, CDCl$_3$) δ ppm 7.45 (d, J=8.7 Hz, 2H), 7.39 (d, J=7.9 Hz, 1H), 7.23 (d, J=8.4 Hz, 2H), 7.04 (s, 1H), 6.68-6.48 (m, 2H), 4.13 (s, 1H), 3.89 (d, J=13.0 Hz, 1H), 3.68 (d, J=12.8 Hz, 1H), 3.48 (t, J=9.2 Hz, 1H), 3.44-3.32 (m, 1H), 3.25-3.07 (m, 1H), 3.04-2.85 (m, 1H), 2.36-2.09 (m, 3H), 2.08-1.82 (m, 4H), 1.82-1.56 (m, 3H), 1.56-1.35 (m, 2H).

Example 50

4-((S)-3-((1R,2R)-2-(4-Bromopyridin-2-ylamino)cyclohexylamino)piperidin-1-yl)benzonitrile

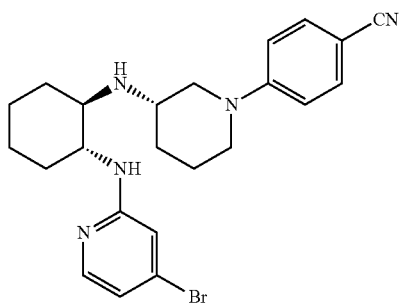 [SMILES: N#Cc1ccc(N2CCC[C@H](N[C@@H]3CCCC[C@H]3Nc3cc(Br)ccn3)C2)cc1]

4-((S)-3-((1R,2R)-2-(4-Bromopyridin-2-ylamino)cyclohexylamino)piperidin-1-yl)benzonitrile (160 mg, 0.340 mmol, 46.1% yield) was synthesized as described in General Procedure H using 4-bromo-2-fluoropyridine (130 mg, 0.739 mmol) and Intermediate 18 (220 mg, 0.0739 mmol). The product was purified using RP prep-HPLC method A to give the title compound as an off-white solid. Anal. Calcd. for $C_{23}H_{28}BrN_5$ m/z 453.4, found: 454.1 (M+H)$^+$; $^1$H NMR (400 MHz, CDCl$_3$) δ ppm 7.87 (d, J=5.4 Hz, 1H), 7.51-7.42 (m, 2H), 6.74 (d, J=8.9 Hz, 2H), 6.71 (dd, J=5.4, 1.5 Hz, 1H), 6.51 (d, J=1.4 Hz, 1H), 4.40 (d, J=7.9 Hz, 1H), 3.57 (d, J=10.2 Hz, 1H), 3.55-3.47 (m, 1H), 3.47-3.35 (m, 1H), 3.03-2.92 (m, 1H), 2.84-2.69 (m, 2H), 2.50-2.39 (m, 1H), 2.19-2.02 (m, 1H), 1.96-1.86 (m, 1H), 1.82-1.67 (m, 2H), 1.66-1.47 (m, 3H), 1.43-1.30 (m, 2H), 1.29-1.14 (m, 2H).

Example 51

3-Fluoro-4-((S)-3-((1R,2R)-2-(5-phenyloxazol-2-ylamino)cyclohexylamino)piperidin-1-yl)benzonitrile

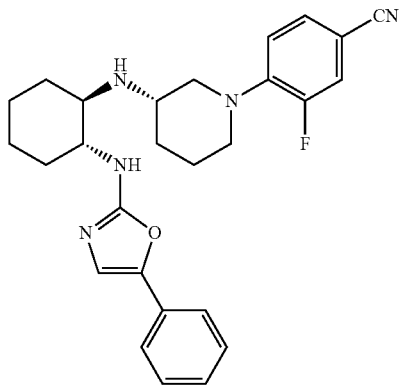 [SMILES: N#Cc1ccc(N2CCC[C@H](N[C@@H]3CCCC[C@H]3Nc3ncc(-c4ccccc4)o3)C2)c(F)c1]

3-Fluoro-4-((S)-3-((1R,2R)-2-(5-phenyloxazol-2-ylamino)cyclohexylamino)piperidin-1-yl)benzonitrile (19 mg, 0.040 mmol, 52.8% yield) was synthesized as described in General Procedure H using Intermediate 1 (27.3 mg, 0.152 mmol) and Intermediate 24 (50 mg, 0.076 mmol). The product was purified using RP prep-HPLC method A to give the title compound as a white solid. Anal. Calcd. for $C_{27}H_{30}FN_5O$ m/z 459.5, found: 460.2 (M+H)$^+$; $^1$H NMR (400 MHz, CDCl$_3$) δ ppm 7.44 (d, J=8.1 Hz, 2H), 7.35 (t, J=7.7 Hz, 2H), 7.28 (d, J=8.5 Hz, 1H), 7.25-7.16 (m, 2H), 6.99 (s, 1H), 6.89 (t, J=8.5 Hz, 1H), 5.15 (d, J=5.5 Hz, 1H), 3.46 (d, J=11.6 Hz, 1H), 3.38-3.29 (m, 1H), 3.29-3.18 (m, 1H), 2.98-2.88 (m, 1H), 2.88-2.79 (m, 1H), 2.66 (dd, J=11.5, 8.6 Hz, 1H), 2.55-2.38 (m, 2H), 2.18 (d, J=12.5 Hz, 1H), 1.92-1.64 (m, 4H), 1.49-1.21 (m, 4H), 1.20-1.06 (m, 1H).

Example 52

3-Fluoro-4-((S)-3-((1R,2R)-2-(5-(4-(trifluoromethoxy)phenyl)oxazol-2-ylamino)cyclohexylamino)piperidin-1-yl)benzonitrile

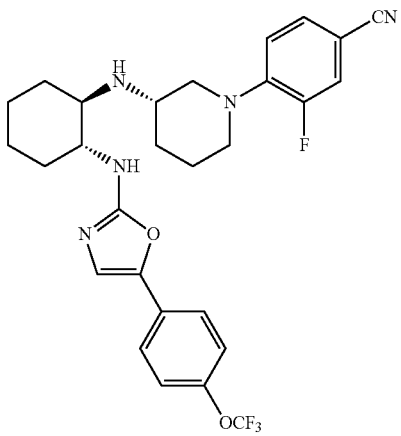 [SMILES: N#Cc1ccc(N2CCC[C@H](N[C@@H]3CCCC[C@H]3Nc3ncc(-c4ccc(OC(F)(F)F)cc4)o3)C2)c(F)c1]

3-Fluoro-4-((S)-3-((1R,2R)-2-(5-(4-(trifluoromethoxy)phenyl)oxazol-2-ylamino)cyclohexylamino)piperidin-1-yl)benzonitrile (21 mg, 0.038 mmol, 49.9% yield) was synthesized as described in General Procedure H using Intermediate 2 (40 mg, 0.152 mmol) and Intermediate 24 (50 mg, 0.076 mmol). The product was purified using RP prep-HPLC method A to give the title compound as an off-white solid. Anal. Calcd. for $C_{28}H_{29}F_4N_5O_2$ m/z 543.5, found: 544.3 (M+H)$^+$; $^1$H NMR (400 MHz, CDCl$_3$) δ ppm 7.44 (d, J=5.7 Hz, 2H), 7.32 (dd, J=8.5, 1.5 Hz, 1H), 7.25-7.16 (m, 3H), 6.99 (s, 1H), 6.91 (t, J=8.6 Hz, 1H), 5.17 (d, J=5.3 Hz, 1H), 3.47 (dd, J=11.7, 2.8 Hz, 1H), 3.39-3.29 (m, 1H), 3.29-3.17 (m, 1H), 3.01-2.79 (m, 2H), 2.68 (dd, J=11.6, 8.4 Hz, 1H), 2.56-2.37 (m, 2H), 2.19 (d, J=12.1 Hz, 1H), 1.94-1.64 (m, 3H), 1.53-1.22 (m, 5H), 1.21-1.03 (m, 1H).

Example 53

4-((S)-3-((1R,2R)-2-(4-Phenylpyridin-2-ylamino)cyclohexylamino)piperidin-1-yl)benzonitrile bis-trifluoroacetate

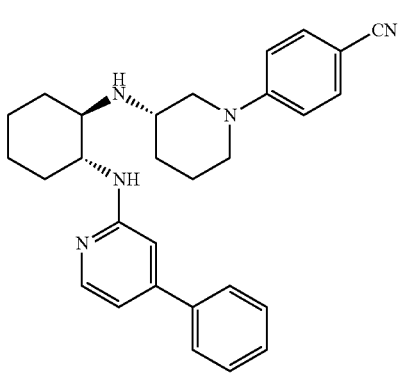

To a sealed tube was added Intermediate 18 (50 mg, 0.168 mmol), 2-bromo-4-phenylpyridine (39.2 mg, 0.168 mmol), BINAP (41.7 mg, 0.067 mmol), sodium tert-butoxide (56.4 mg, 0.586 mmol) and Pd$_2$(dba)$_3$ (61.4 mg, 0.067 mmol). The reaction was purged with argon and then was sealed. The sealed reaction was stirred at 120° C. for 16 hrs. After this time, the reaction was cooled to rt and filtered through CELITE®. The CELITE® pad was washed with EtOAc (2×10 ml). The combined organic layers were washed with water and concentrated. The resulting residue was purified by RP prep-HPLC method A. The desired fractions which contained TFA from eluting solvent were concentrated to give 4-((S)-3-((1R,2R)-2-(4-phenylpyridin-2-ylamino)cyclohexylamino) piperidin-1-yl)benzonitrile bis-trifluoroacetate (10 mg, 0.015 mmol, 8.69% yield) as a pink solid. Anal. Calcd. for $C_{29}H_{33}N_5$ m/z 451.5, found: 452.1 (M+H)$^+$; $^1$H NMR (400 MHz, CDCl$_3$) δ ppm 7.80-7.59 (m, 3H), 7.59-7.45 (m, 5H), 7.17 (s, 1H), 7.07 (d, J=6.3 Hz, 1H), 6.91 (d, J=8.7 Hz, 2H), 3.98 (s, 1H), 3.75 (d, J=11.8 Hz, 1H), 3.65-3.18 (m, 4H), 3.18-2.88 (m, 1H), 2.29 (d, J=11.8 Hz, 1H), 2.24-2.07 (m, 2H), 2.06-1.66 (m, 6H), 1.62-1.32 (m, 3H).

Example 54

4-((S)-3-((1R,2R)-2-(5-Phenyl-1,3,4-oxadiazol-2-ylamino)cyclohexylamino)piperidin-1-yl)benzonitrile trifluoroacetate

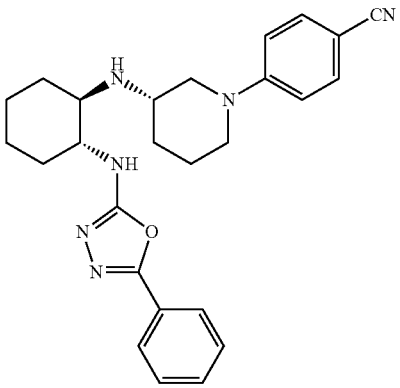 [SMILES: N#Cc1ccc(N2CCC[C@H](N[C@@H]3CCCC[C@H]3Nc3nnc(-c4ccccc4)o3)C2)cc1]

4-((S)-3-((1R,2R)-2-(5-Phenyl-1,3,4-oxadiazol-2-ylamino)cyclohexylamino)piperidin-1-yl)benzonitrile trifluoroacetate (16 mg, 0.028 mmol, 45.5% yield) was synthesized as described in General Procedure H using 2-chloro-5-phenyl-1,3,4-oxadiazole (22.56 mg, 0.125 mmol) and Intermediate 18 (40 mg, 0.062 mmol). The desired fraction from RP prep-HPLC method A was concentrated to give the title compound as a white solid. Anal. Calcd. for $C_{26}H_{30}N_6O$ m/z 442.5, found: 443.3 (M+H)$^+$; $^1$H NMR (400 MHz, CDCl$_3$) δ ppm 7.71 (d, J=8.9 Hz, 2H), 7.51-7.31 (m, 5H), 6.84 (d, J=8.9 Hz, 2H), 3.94-3.62 (m, 3H), 3.54-3.35 (m, 2H), 3.28 (dd, J=12.4, 8.7 Hz, 1H), 3.03 (t, J=9.9 Hz, 1H), 2.28 (d, J=12.9 Hz, 1H), 2.20-2.11 (m, 1H), 2.11-1.80 (m, 6H), 1.79-1.62 (m, 2H), 1.50-1.33 (m, 2H).

Example 55

4-((S)-3-((1R,2R)-2-(Benzo[d]oxazol-2-ylamino)cyclohexylamino)piperidin-1-yl)benzonitrile

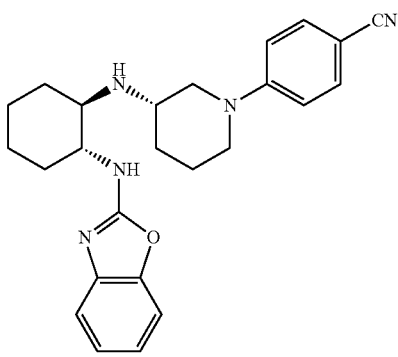 [SMILES: N#Cc1ccc(N2CCC[C@H](N[C@@H]3CCCC[C@H]3Nc3nc4ccccc4o3)C2)cc1]

4-((S)-3-((1R,2R)-2-(Benzo[d]oxazol-2-ylamino)cyclohexylamino)piperidin-1-yl)benzonitrile (12 mg, 0.026 mmol, 78% yield) was synthesized as described in General Procedure H using 2-chlorobenzo[d]oxazole (5.15 mg, 0.034 mmol) and Intermediate 17 (10 mg, 0.034 mmol). The product was purified using RP prep-HPLC method A to give the title compound as an off-white solid. Anal. Calcd. for $C_{25}H_{29}N_5O$ m/z 415.5, found: 416.5 (M+H)$^+$; $^1$H NMR (500 MHz, CDCl$_3$) δ ppm 7.47 (d, J=8.80 Hz, 2 H), 7.37-7.33 (m, 2 H), 7.28 (d, J=7.70 Hz, 2 H), 6.85 (d, J=9.35 Hz, 2 H), 4.33-4.21 (m, 1 H), 3.85 (d, J=11.00 Hz, 1 H), 3.64 (d, J=13.20 Hz, 1 H), 3.52-3.36 (m, 2 H), 3.12 (dd, J=12.37, 10.17 Hz, 1 H), 2.94-2.84 (m, 1 H), 2.33-2.25 (m, 1 H), 2.25-2.16 (m, 2 H), 1.99 (d, J=12.10 Hz, 1 H), 1.96-1.82 (m, 3 H), 1.79-1.64 (m, 3 H), 1.53-1.37 (m, 2 H).

Example 56

4-((S)-3-((1R,2R)-2-(5-(4-(Trifluoromethoxy)phenyl)oxazol-2-ylamino)cyclohexylamino)piperidin-1-yl)benzonitrile

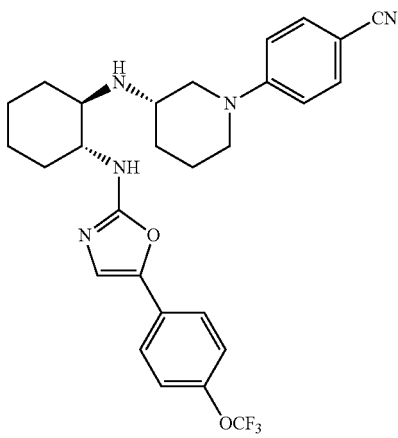 [SMILES: N#Cc1ccc(N2CCC[C@H](N[C@@H]3CCCC[C@H]3Nc3ncc(-c4ccc(OC(F)(F)F)cc4)o3)C2)cc1]

4-((S)-3-((1R,2R)-2-(5-(4-(Trifluoromethoxy)phenyl)oxazol-2-ylamino)cyclohexylamino)piperidin-1-yl)benzonitrile (12 mg, 0.022 mmol, 43.2% yield) was synthesized as described in General Procedure H using Intermediate 2 (15.9 mg, 0.060 mmol) and Intermediate 18 (15 mg, 0.050 mmol). The product was purified using RP prep-HPLC method A to give the title compound as an off-white solid. Anal. Calcd. for $C_{28}H_{30}F_3N_5O_2$ m/z 525.5, found: 526.4 (M+H)$^+$; $^1$H NMR (500 MHz, CDCl$_3$) δ ppm 7.55-7.49 (m, 4 H), 7.28 (d, 2 H), 7.08 (s, 1 H), 6.89 (d, J=8.80 Hz, 2 H), 4.18 (br. s., 1 H), 3.85 (d, J=11.55 Hz, 1 H), 3.67 (d, J=13.20 Hz, 1 H), 3.49-3.38 (m, 2 H), 3.15-3.07 (m, 1 H), 2.97-2.86 (m, 1 H), 2.33-2.16 (m, 3 H), 2.01 (d, J=11.00 Hz, 1 H), 1.96-1.86 (m, 3 H), 1.81-1.73 (m, 1 H), 1.69-1.59 (m, 2 H), 1.51-1.35 (m, 2 H).

Example 57

4-((S)-3-((1R,2R)-2-(5-Phenyloxazol-2-ylamino)cyclohexylamino)piperidin-1-yl)benzonitrile

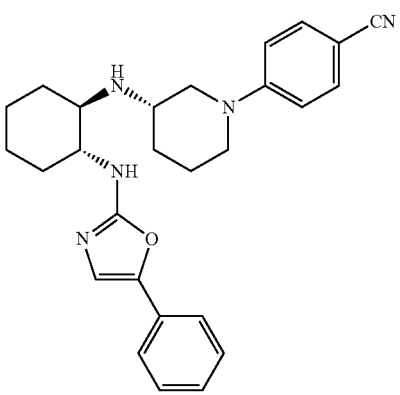

4-((S)-3-((1R,2R)-2-(5-Phenyloxazol-2-ylamino)cyclohexylamino)piperidin-1-yl)benzonitrile (6 mg, 0.013 mmol, 38.5% yield) was synthesized as described in General Procedure H using Intermediate 1 (7.22 mg, 0.040 mmol) and Intermediate 18 (10 mg, 0.034 mmol). The product was purified using RP prep-HPLC method A to give the title compound as a light brown solid. Anal. Calcd. for $C_{27}H_{31}N_5O$ m/z 441.5, found: 442.5 (M+H)$^+$; $^1$H NMR (500 MHz, CDCl$_3$) δ ppm 7.52 (d, J=8.80 Hz, 2 H), 7.50-7.47 (m, 2 H), 7.47-7.40 (m, 3 H), 7.07 (s, 1 H), 6.90 (d, J=8.80 Hz, 2 H), 4.18 (br. s., 1 H), 3.86 (d, J=11.55 Hz, 1 H), 3.67 (d, J=13.20 Hz, 1 H), 3.49-3.39 (m, 2 H), 3.13 (t, J=11.00 Hz, 1 H), 2.96-2.85 (m, 1 H), 2.32-2.18 (m, 3 H), 2.00 (d, J=11.00 Hz, 1 H), 1.97-1.90 (m, 2 H), 1.90-1.83 (m, 1 H), 1.76 (d, J=13.20 Hz, 1 H), 1.71-1.60 (m, 2 H), 1.49-1.40 (m, 2 H).

Example 58

4-((S)-3-((1R,2R)-2-(4-(4-Methoxyphenyl)pyrimidin-2-ylamino)cyclohexylamino)piperidin-1-yl)benzonitrile trifluoroacetate

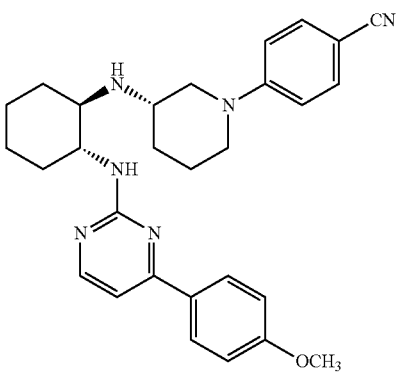

4-((S)-3-((1R,2R)-2-(4-(4-Methoxyphenyl)pyrimidin-2-ylamino)cyclohexylamino)piperidin-1-yl)benzonitrile trifluoroacetate (6 mg, 0.0083 mmol, 17.7% yield) was synthesized as described in General Procedure H using 2-chloro-4-(4-methoxyphenyl)pyrimidine (15.50 mg, 0.070 mmol) and Intermediate 18 (30 mg, 0.047 mmol). The desired fraction from RP prep-HPLC method A was concentrated to give the title compound as a light brown solid. Anal. Calcd. for $C_{29}H_{34}N_6O$ m/z 482.5, found: 483.4 (M+H)$^+$; $^1$H NMR (400 MHz, CDCl$_3$) δ ppm 8.10 (d, J=8.8 Hz, 2H), 7.95 (d, J=6.7 Hz, 1H), 7.50 (d, J=8.7 Hz, 2H), 7.15 (d, J=6.8 Hz, 1H), 7.05 (d, J=8.8 Hz, 2H), 6.88 (d, J=8.8 Hz, 2H), 4.50 (s, 1H), 3.94 (s, 3H), 3.76 (d, J=12.6 Hz, 1H), 3.58-3.36 (m, 3H), 3.36-3.26 (m, 1H), 3.01-2.91 (m, 1H), 2.39-2.22 (m, 2H), 2.09 (s, 1H), 1.91 (ddd, J=41.0, 30.1, 17.3 Hz, 5H), 1.76-1.61 (m, 1H), 1.61-1.34 (m, 3H).

Example 59

4-((S)-3-((1R,2R)-2-(4-(4-(Trifluoromethoxy)phenyl)pyrimidin-2-ylamino)cyclohexylamino)piperidin-1-yl)benzonitrile bis-trifluoroacetate

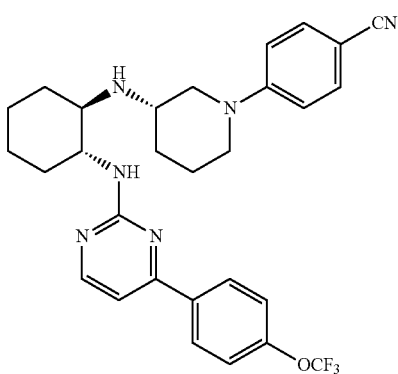 [SMILES: N#Cc1ccc(N2CCC[C@H](N[C@@H]3CCCC[C@H]3Nc3nccc(-c4ccc(OC(F)(F)F)cc4)n3)C2)cc1]

4-((S)-3-((1R,2R)-2-(4-(4-(Trifluoromethoxy)phenyl)pyrimidin-2-ylamino)cyclohexylamino)piperidin-1-yl)benzonitrile bis-trifluoroacetate (5 mg, 0.0065 mmol, 13.8% yield) was synthesized as described in General Procedure H using Intermediate 15 (19.29 mg, 0.070 mmol) and Intermediate 18 (30 mg, 0.047 mmol). The desired fraction from RP prep-HPLC method A was concentrated to give the title compound as a beige oil. Anal. Calcd. for $C_{29}H_{31}F_3N_6O$ m/z 536.5, found: 537.4 (M+H)$^+$; $^1$H NMR (400 MHz, CDCl$_3$) δ ppm 8.20-8.06 (m, 3H), 7.51 (d, J=8.8 Hz, 2H), 7.39 (d, J=8.4 Hz, 2H), 7.21 (d, J=5.9 Hz, 1H), 6.91 (d, J=8.8 Hz, 2H), 4.50 (s, 1H), 3.87 (d, J=10.5 Hz, 1H), 3.62-3.32 (m, 3H), 3.24 (dd, J=12.2, 9.4 Hz, 1H), 2.94 (t, J=10.2 Hz, 1H), 2.40-2.24 (m, 2H), 2.23-2.09 (m, 1H), 2.01 (d, J=11.5 Hz, 1H), 1.95-1.62 (m, 5H), 1.47 (dd, J=29.4, 11.0 Hz, 3H).

Example 60

4-((S)-3-((1R,2R)-2-(4-Phenylpyrimidin-2-ylamino)cyclohexylamino)piperidin-1-yl)benzonitrile bis-trifluoroacetate

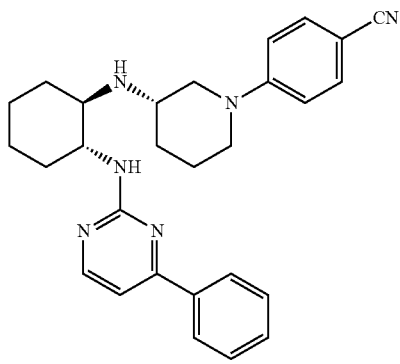 [SMILES: N#Cc1ccc(N2CCC[C@H](N[C@@H]3CCCC[C@H]3Nc3nccc(-c4ccccc4)n3)C2)cc1]

4-((S)-3-((1R,2R)-2-(4-Phenylpyrimidin-2-ylamino)cyclohexylamino)piperidin-1-yl)benzonitrile bis-trifluoroacetate (5 mg, 0.0073 mmol, 7.5% yield) was synthesized as described in General Procedure H using 2-chloro-4-phenylpyrimidine (27.7 mg, 0.145 mmol) and Intermediate 18 (40 mg, 0.097 mmol). The desired fraction from RP prep-HPLC method A was concentrated to give the title compound as a yellow solid. Anal. Calcd. for $C_{28}H_{32}N_6$ m/z 452.5, found: 453.3 (M+H)$^+$; $^1$H NMR (400 MHz, CDCl$_3$) δ ppm 8.09 (d, J=7.5 Hz, 2H), 8.01 (d, J=6.2 Hz, 1H), 7.66 (t, J=7.4 Hz, 1H), 7.57 (t, J=7.6 Hz, 2H), 7.50 (d, J=7.9 Hz, 2H), 7.21 (d, J=6.6 Hz, 1H), 6.87 (d, J=8.8 Hz, 2H), 4.53 (s, 1H), 3.81 (d, J=12.6 Hz, 1H), 3.60-3.31 (m, 3H), 3.31-3.18 (m, 1H), 2.99-2.84 (m, 1H), 2.31 (d, J=10.8 Hz, 2H), 2.21-2.07 (m, 1H), 2.07-1.77 (m, 5H), 1.77-1.62 (m, 1H), 1.60-1.32 (m, 3H).

Example 61

4-((S)-3-((1R,2R)-2-(4-(3-(Trifluoromethoxy)phenyl)pyrimidin-2-ylamino)cyclohexylamino)piperidin-1-yl)benzonitrile bis-trifluoroacetate

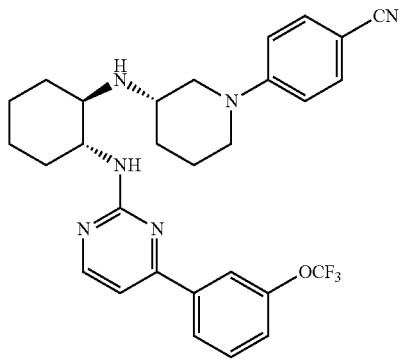 [SMILES: N#Cc1ccc(N2CCC[C@H](N[C@@H]3CCCC[C@H]3Nc3nccc(-c4cccc(OC(F)(F)F)c4)n3)C2)cc1]

4-((S)-3-((1R,2R)-2-(4-(3-(Trifluoromethoxy)phenyl)pyrimidin-2-ylamino)cyclohexylamino)piperidin-1-yl)benzonitrile bis-trifluoroacetate (24.23 mg, 0.031 mmol, 31.7% yield) was synthesized as described in General Procedure H using 2-chloro-4-(3-(trifluoromethoxy)phenyl)pyrimidine (40 mg, 0.145 mmol) and Intermediate 18 (40 mg, 0.097 mmol). The desired fraction from RP prep-HPLC method A was concentrated to give the title compound as a beige oil. Anal. Calcd. for $C_{29}H_{31}F_3N_6O$ m/z 536.5, found: 537.4 (M+H)+; $^1$H NMR (400 MHz, CDCl$_3$) δ ppm 10.55 (d, J=7.3 Hz, 1H), 8.15 (d, J=6.5 Hz, 1H), 8.01 (d, J=7.7 Hz, 1H), 7.89 (s, 1H), 7.63 (dd, J=17.7, 9.7 Hz, 1H), 7.57-7.46 (m, 3H), 7.23 (d, J=6.6 Hz, 1H), 6.92 (d, J=8.7 Hz, 2H), 4.46 (s, 1H), 3.90 (d, J=12.2 Hz, 1H), 3.68-3.54 (m, 1H), 3.54-3.35 (m, 2H), 3.29-3.17 (m, 1H), 3.03-2.86 (m, 1H), 2.41-2.26 (m, 2H), 2.24-2.10 (m, 1H), 2.08-1.97 (m, 1H), 1.94-1.62 (m, 5H), 1.59-1.38 (m, 3H).

Example 62

(1R,2R)—N1-((S)-1-(4-(1H-Pyrazol-1-yl)phenyl)piperidin-3-yl)-N2-(5-phenyloxazol-2-yl)cyclohexane-1,2-diamine trifluoroacetate

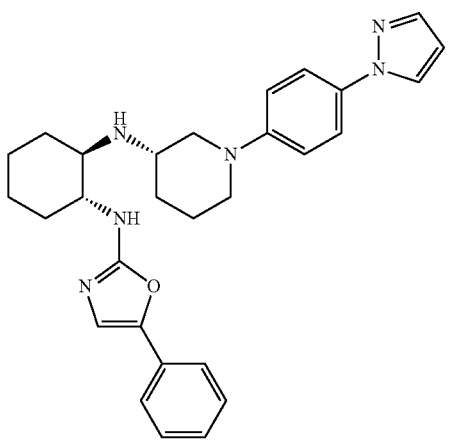 [SMILES: c1ccc(-c2cnc(N[C@@H]3CCCC[C@H]3N[C@H]3CCCN(c4ccc(-n5cccn5)cc4)C3)o2)cc1]

(1R,2R)—N1-((S)-1-(4-(1H-Pyrazol-1-yl)phenyl)piperidin-3-yl)-N2-(5-phenyloxazol-2-yl)cyclohexane-1,2-diamine trifluoroacetate (11 mg, 0.018 mmol, 25.6% yield) was synthesized as described in General Procedure H using Intermediate 1 (25.3 mg, 0.141 mmol) and Intermediate 19 (40 mg, 0.070 mmol). The desired fraction from RP prep-HPLC method A was concentrated to give the title compound as a white solid. Anal. Calcd. for $C_{29}H_{34}N_6O$ m/z 482.5, found: 483.3 (M+H)+; $^1$H NMR (400 MHz, CDCl$_3$) δ ppm 7.84 (d, J=2.4 Hz, 1H), 7.80 (d, J=1.6 Hz, 1H), 7.56 (d, J=8.8 Hz, 2H), 7.53-7.47 (m, 2H), 7.46-7.38 (m, 3H), 7.12 (d, J=8.9 Hz, 2H), 7.08 (s, 1H), 6.50 (t, J=2.1 Hz, 1H), 4.16 (s, 1H), 3.80-3.65 (m, 1H), 3.55 (d, J=10.8 Hz, 1H), 3.49-3.22 (m, 3H), 3.05 (d, J=8.8 Hz, 1H), 2.37 (d, J=10.9 Hz, 1H), 2.29-2.07 (m, 2H), 2.05-1.82 (m, 5H), 1.74 (d, J=12.5 Hz, 1H), 1.61 (d, J=12.0 Hz, 1H), 1.42 (dd, J=27.6, 13.5 Hz, 2H).

Example 63

(1R,2R)—N1-((S)-1-(4-(1H-Pyrazol-1-yl)phenyl)piperidin-3-yl)-N2-(5-(4-(trifluoromethoxy)phenyl)oxazol-2-yl)cyclohexane-1,2-diamine trifluoroacetate

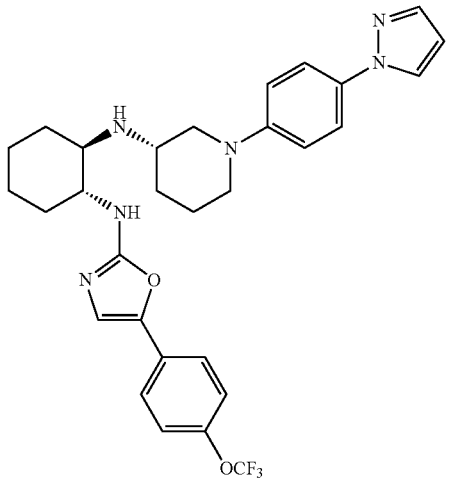 [SMILES: FC(F)(F)Oc1ccc(-c2cnc(N[C@@H]3CCCC[C@H]3N[C@H]3CCCN(c4ccc(-n5cccn5)cc4)C3)o2)cc1]

(1R,2R)—N1-((S)-1-(4-(1H-Pyrazol-1-yl)phenyl)piperidin-3-yl)-N2-(5-(4-(trifluoromethoxy)phenyl)oxazol-2-yl)cyclohexane-1,2-diamine trifluoroacetate was synthesized as described in General Procedure H using Intermediate 2 (37.2 mg, 0.141 mmol) and Intermediate 19 (40 mg, 0.070 mmol). The desired fraction from RP prep-HPLC method A was concentrated to give the title compound as a beige oil. Anal. Calcd. for $C_{30}H_{33}F_3N_6O_2$ m/z 566.5, found: 567.4 (M+H)+; $^1$H NMR (400 MHz, CDCl$_3$) δ ppm 7.92-7.80 (m, 2H), 7.60 (d, J=8.9 Hz, 2H), 7.54 (d, J=8.7 Hz, 2H), 7.29 (d, J=8.4 Hz, 2H), 7.23 (d, J=8.9 Hz, 2H), 7.15 (s, 1H), 6.54 (t, J=2.2 Hz, 1H), 4.13 (s, 1H), 3.92-3.78 (m, 1H), 3.65 (d, J=10.5 Hz, 1H), 3.57-3.47 (m, 1H), 3.46-3.31 (m, 2H), 3.21-3.08 (m, 1H), 2.40 (d, J=10.6 Hz, 1H), 2.29-2.09 (m, 2H), 2.08-1.81 (m, 5H), 1.81-1.66 (m, 1H), 1.66-1.52 (m, 1H), 1.52-1.31 (m, 2H).

Example 64

(1R,2R)—N1-((S)-1-(4-(1H-Pyrazol-1-yl)phenyl)piperidin-3-yl)-N2-(4-phenylpyrimidin-2-yl)cyclohexane-1,2-diamine bis-trifluoroacetate

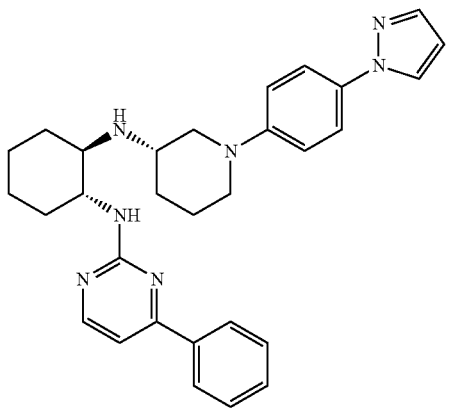 [SMILES: c1ccc(-c2ccnc(N[C@@H]3CCCC[C@H]3N[C@H]3CCCN(c4ccc(-n5cccn5)cc4)C3)n2)cc1]

(1R,2R)—N1-((S)-1-(4-(1H-Pyrazol-1-yl)phenyl)piperidin-3-yl)-N2-(4-phenylpyrimidin-2-yl)cyclohexane-1,2-diamine bis-trifluoroacetate (12 mg, 0.016 mmol, 35% yield) was synthesized as described in General Procedure H using 2-chloro-4-phenylpyrimidine (17.9 mg, 0.094 mmol) and Intermediate 19 (32 mg, 0.047 mmol). The desired fraction from RP prep-HPLC method A was concentrated to give the title compound as a beige oil. Anal. Calcd. for $C_{30}H_{35}N_7$ m/z 493.5, found: 494.3 (M+H)$^+$; $^1$H NMR (400 MHz, CDCl$_3$) δ ppm 8.24-8.02 (m, 3H), 7.91-7.77 (m, 2H), 7.74 (s, 1H), 7.70-7.63 (m, 1H), 7.62-7.46 (m, 3H), 7.15 (d, J=6.3 Hz, 1H), 6.89 (d, J=8.9 Hz, 2H), 6.47 (s, 1H), 4.78-4.06 (m, 1H), 3.64-3.40 (m, 2H), 3.40-3.11 (m, 2H), 3.09-2.85 (m, 2H), 2.38-2.28 (m, 1H), 2.27-2.02 (m, 3H), 2.02-1.74 (m, 3H), 1.74-1.44 (m, 4H), 1.44-1.27 (m, 1H).

Example 65

(1R,2R)—N1-((S)-1-(4-(4-Methyl-1H-pyrazol-1-yl)phenyl)piperidin-3-yl)-N2-(4-phenylpyrimidin-2-yl)cyclohexane-1,2-diamine bis-trifluoroacetate

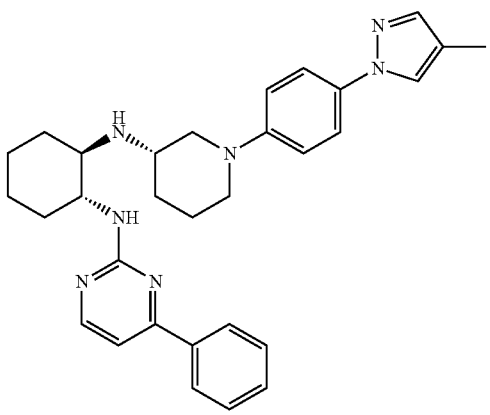 [SMILES: Cc1cnn(-c2ccc(N3CCC[C@H](N[C@@H]4CCCC[C@H]4Nc4nccc(-c5ccccc5)n4)C3)cc2)c1]

(1R,2R)—N1-((S)-1-(4-(4-Methyl-1H-pyrazol-1-yl)phenyl)piperidin-3-yl)-N2-(4-phenylpyrimidin-2-yl)cyclohexane-1,2-diamine bis-trifluoroacetate (25 mg, 0.034 mmol, 37.4% yield) was synthesized as described in General Procedure H using 2-chloro-4-phenylpyrimidine (25.7 mg, 0.135 mmol) and Intermediate 30 (31.8 mg, 0.09 mmol). The desired fraction from RP prep-HPLC method A was concentrated to give the title compound as a yellow solid. Anal. Calcd. for $C_{31}H_{37}N_7$ m/z 507.5, found: 508.3 (M+H)$^+$; $^1$H NMR (400 MHz, CDCl$_3$) δ ppm 8.15 (d, J=7.70 Hz, 2 H), 7.84 (d, J=6.05 Hz, 1 H), 7.70-7.61 (m, 2 H), 7.61-7.51 (m, 3 H), 7.46 (d, J=8.79 Hz, 2 H), 7.16 (d, J=6.05 Hz, 1 H), 6.92 (d, J=9.34 Hz, 2 H), 4.58 (d, J=6.60 Hz, 1 H,) 3.66-3.50 (m, 2 H), 3.36-3.17 (m, 2 H), 3.09-2.90 (m, 2 H), 2.33 (d, J=10.99 Hz, 1 H), 2.24 (d, J=10.99 Hz, 1 H), 2.17 (s, 3 H), 2.12 (d, J=6.05 Hz, 1 H), 2.06-1.78 (m, 4 H), 1.70-1.24 (m, 5 H).

Example 66

(1R,2R)—N1-((S)-1-(4-(4-Methyl-1H-pyrazol-1-yl)phenyl)piperidin-3-yl)-N2-(5-(4-(trifluoromethoxy)phenyl)oxazol-2-yl)cyclohexane-1,2-diamine bis-trifluoroacetate

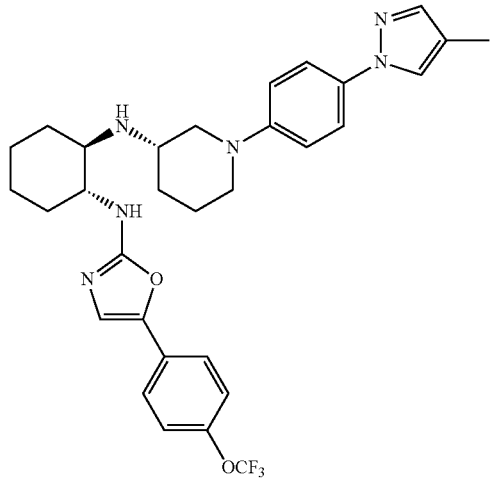 [SMILES: Cc1cnn(-c2ccc(N3CCC[C@H](N[C@@H]4CCCC[C@H]4Nc4ncc(-c5ccc(OC(F)(F)F)cc5)o4)C3)cc2)c1]

(1R,2R)—N1-((S)-1-(4-(4-Methyl-1H-pyrazol-1-yl)phenyl)piperidin-3-yl)-N2-(5-(4-(trifluoromethoxy)phenyl)oxazol-2-yl)cyclohexane-1,2-diamine bis-trifluoroacetate (25 mg, 0.030 mmol, 33.3% yield) was synthesized as described in General Procedure H using Intermediate 2 (35.6 mg, 0.135 mmol) and Intermediate 30 (31.8 mg, 0.09 mmol). The desired fraction from RP prep-HPLC method A was concentrated to give the title compound as a beige oil. Anal. Calcd. for $C_{31}H_{35}F_3N_6O_2$ m/z 580.5, found: 581.3 (M+H)$^+$; $^1$H NMR (400 MHz, CDCl$_3$) δ ppm 7.69 (s, 1H), 7.64 (s, 1H), 7.61-7.41 (m, 3H), 7.32-7.23 (m, 3H), 7.19 (d, J=8.2 Hz, 2H), 7.15 (s, 1H), 4.13 (s, 1H), 3.87-3.76 (m, 1H), 3.62 (d, J=11.3 Hz, 1H), 3.53-3.30 (m, 3H), 3.19-3.09 (m, 1H), 2.39 (d, J=11.0 Hz, 1H), 2.27-2.07 (m, 5H), 2.06-1.81 (m, 5H), 1.81-1.67 (m, 1H), 1.67-1.52 (m, 1H), 1.52-1.31 (m, 2H).

Example 67

(1R,2R)—N1-((S)-1-(4-(3-Methyl-1H-pyrazol-1-yl)phenyl)piperidin-3-yl)-N2-(4-phenylpyrimidin-2-yl)cyclohexane-1,2-diamine bis-trifluoroacetate

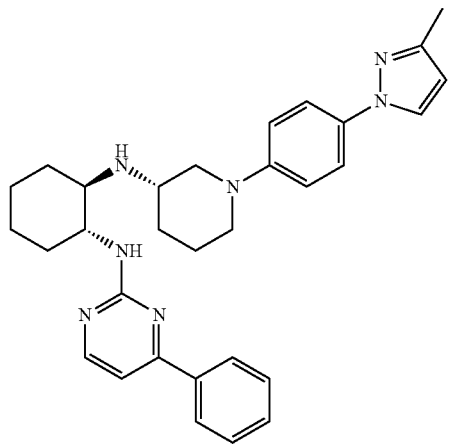 [SMILES: Cc1ccn(-c2ccc(N3CCC[C@H](N[C@@H]4CCCC[C@H]4Nc4nccc(-c5ccccc5)n4)C3)cc2)n1]

(1R,2R)—N1-((S)-1-(4-(3-Methyl-1H-pyrazol-1-yl)phenyl)piperidin-3-yl)-N2-(4-phenylpyrimidin-2-yl)cyclohexane-1,2-diamine bis-trifluoroacetate (22 mg, 0.030 mmol, 32.9% yield) was synthesized as described in General Procedure H using 2-chloro-4-phenylpyrimidine (25.7 mg, 0.135 mmol) and Intermediate 31 (31.8 mg, 0.09 mmol). The desired fraction from RP prep-HPLC method A was concentrated to give the title compound as a yellow foam. Anal. Calcd. for $C_{31}H_{37}N_7$ m/z 507.5, found: 508.3 (M+H)$^+$; $^1$H NMR (400 MHz, CDCl$_3$) δ ppm 8.13 (d, J=7.6 Hz, 2H), 7.93 (d, J=6.3 Hz, 1H), 7.75 (s, 1H), 7.67 (t, J=7.2 Hz, 1H), 7.57 (t, J=7.5 Hz, 2H), 7.48 (d, J=8.6 Hz, 2H), 7.20 (d, J=6.4 Hz, 1H), 6.99 (d, J=8.6 Hz, 2H), 6.30 (s, 1H), 4.54 (s, 1H), 3.76-3.53 (m, 2H), 3.39-3.20 (m, 2H), 3.11-2.93 (m, 2H), 2.44-2.30 (m, 4H), 2.31-2.20 (m, 1H), 2.18-2.05 (m, 1H), 2.04-1.78 (m, 4H), 1.75-1.27 (m, 5H).

Example 68

(1R,2R)—N1-((S)-1-(4-(3-Methyl-1H-pyrazol-1-yl)phenyl)piperidin-3-yl)-N2-(5-(4-(trifluoromethoxy)phenyl)oxazol-2-yl)cyclohexane-1,2-diamine bis-trifluoroacetate

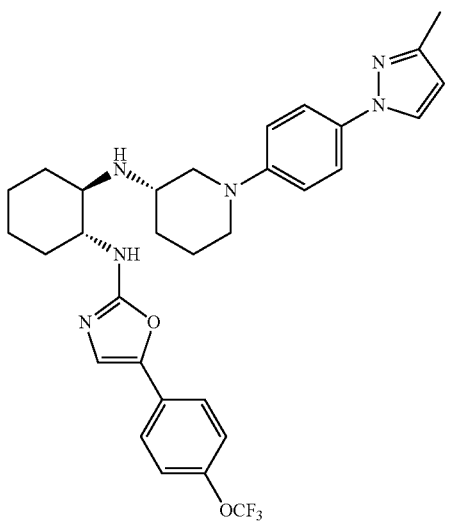 [SMILES: Cc1ccn(-c2ccc(N3CCC[C@H](N[C@@H]4CCCC[C@H]4Nc4ncc(-c5ccc(OC(F)(F)F)cc5)o4)C3)cc2)n1]

(1R,2R)—N1-((S)-1-(4-(3-Methyl-1H-pyrazol-1-yl)phenyl)piperidin-3-yl)-N2-(5-(4-(trifluoromethoxy)phenyl)oxazol-2-yl)cyclohexane-1,2-diamine bis-trifluoroacetate (15 mg, 0.018 mmol, 20.3% yield) was synthesized as described in General Procedure H using Intermediate 2 (35.6 mg, 0.135 mmol) and Intermediate 31 (31.8 mg, 0.09 mmol). The desired fraction from RP prep-HPLC method A was concentrated to the title compound as a beige oil. Anal. Calcd. for $C_{31}H_{35}F_3N_6O_2$ m/z 580.5, found: 581.3 (M+H)$^+$; $^1$H NMR (400 MHz, CDCl$_3$) δ ppm 7.74 (d, J=2.3 Hz, 1H), 7.60-7.46 (m, 4H), 7.34-7.22 (m, 2H), 7.21-7.11 (m, 3H), 6.34 (d, J=2.3 Hz, 1H), 4.22-4.05 (m, 1H), 3.86-3.73 (m, 1H), 3.64 (d, J=11.3 Hz, 1H), 3.54-3.30 (m, 3H), 3.20-3.06 (m, 1H), 2.50-2.30 (m, 4H), 2.27-2.08 (m, 2H), 2.05-1.81 (m, 5H), 1.80-1.66 (m, 1H), 1.65-1.53 (m, 1H), 1.52-1.30 (m, 2H).

Example 69

(1R,2R)—N1-(4-Phenylpyrimidin-2-yl)-N2-((S)-1-(4-(3-(trifluoromethyl)-1H-pyrazol-1-yl)phenyl)piperidin-3-yl)cyclohexane-1,2-diamine bis-trifluoroacetate

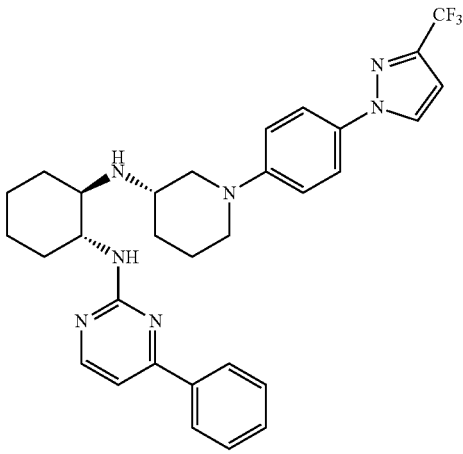 [SMILES: FC(F)(F)c1ccn(-c2ccc(N3CCC[C@H](N[C@@H]4CCCC[C@H]4Nc4nccc(-c5ccccc5)n4)C3)cc2)n1]

(1R,2R)—N1-(4-Phenylpyrimidin-2-yl)-N2-((S)-1-(4-(3-(trifluoromethyl)-1H-pyrazol-1-yl)phenyl)piperidin-3-yl)cyclohexane-1,2-diamine bis-trifluoroacetate (15 mg, 0.019 mmol, 22.9% yield) was synthesized as described in General Procedure H using 2-chloro-4-phenylpyrimidine (23.45 mg, 0.123 mmol) and Intermediate 32 (33.4 mg, 0.082 mmol). The desired fraction from RP prep-HPLC method A was concentrated to give the title compound as a beige oil. Anal. Calcd. for $C_{31}H_{34}F_3N_7$ m/z 561.5, found: 562.3 (M+H)$^+$; $^1$H NMR (400 MHz, CDCl$_3$) δ ppm 8.11 (d, J=7.7 Hz, 2H), 8.00 (d, J=6.5 Hz, 1H), 7.91 (s, 1H), 7.68 (t, J=7.3 Hz, 1H), 7.63-7.51 (m, 4H), 7.25 (d, J=6.6 Hz, 1H), 7.09 (d, J=9.0 Hz, 2H), 6.73 (d, J=2.1 Hz, 1H), 4.53 (s, 1H), 3.81-3.67 (m, 1H), 3.64-3.54 (m, 1H), 3.50-3.43 (m, 1H), 3.42-3.32 (m, 1H), 3.24-3.03 (m, 2H), 2.37 (d, J=12.7 Hz, 1H), 2.32-2.19 (m, 1H), 2.09-1.83 (m, 5H), 1.83-1.72 (m, 2H), 1.60-1.28 (m, 3H).

Example 70

(1R,2R)—N1-(5-(4-(Trifluoromethoxy)phenyl)oxazol-2-yl)-N2-((S)-1-(4-(3-(trifluoromethyl)-1H-pyrazol-1-yl)phenyl)piperidin-3-yl)cyclohexane-1,2-diamine bis-trifluoroacetate

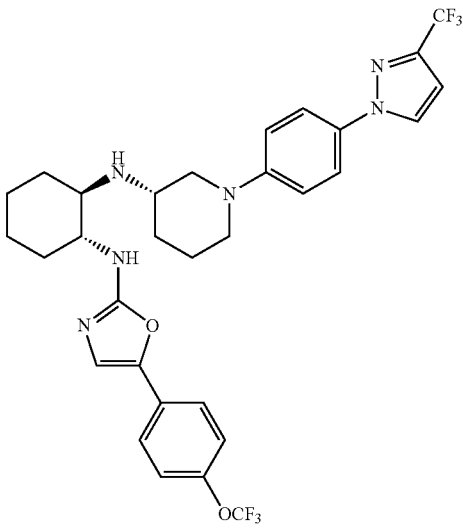 [SMILES: FC(F)(F)Oc1ccc(-c2cnc(N[C@@H]3CCCC[C@H]3N[C@H]3CCCN(c4ccc(-n5ccc(C(F)(F)F)n5)cc4)C3)o2)cc1]

(1R,2R)—N1-(5-(4-(Trifluoromethoxy)phenyl)oxazol-2-yl)-N2-((S)-1-(4-(3-(trifluoromethyl)-1H-pyrazol-1-yl)phenyl)piperidin-3-yl)cyclohexane-1,2-diamine bis-trifluoroacetate (22 mg, 0.025 mmol, 30.8% yield) was synthesized as described in General Procedure H using Intermediate 2 (32.4 mg, 0.123 mmol) and Intermediate 32 (33.4 mg, 0.082 mmol). The desired fraction from RP prep-HPLC method A was concentrated the title compound as to give a white solid. Anal. Calcd. for $C_{31}H_{32}F_6N_6O_2$ m/z 634.5, found: 635.2 (M+H)$^+$; $^1$H NMR (400 MHz, CDCl$_3$) δ ppm 7.66 (s, 1H), 7.43 (d, J=8.7 Hz, 2H), 7.37 (d, J=8.5 Hz, 2H), 7.12 (d, J=8.3 Hz, 2H), 6.92 (d, J=8.9 Hz, 2H), 6.82 (s, 1H), 6.65 (d, J=2.2 Hz, 1H), 3.97 (s, 1H), 3.66-3.46 (m, 2H), 3.39-3.22 (m, 2H), 3.20-3.05 (m, 2H), 2.28 (d, J=10.4 Hz, 1H), 2.17-1.91 (m, 5H), 1.78 (dd, J=35.9, 14.9 Hz, 4H), 1.41 (dd, J=26.8, 13.5 Hz, 2H).

Example 71

(1R,2R)—N1-(5-(4-(Trifluoromethoxy)phenyl)oxazol-2-yl)-N2-((S)-1-(4-(trifluoromethyl)phenyl)piperidin-3-yl)cyclohexane-1,2-diamine

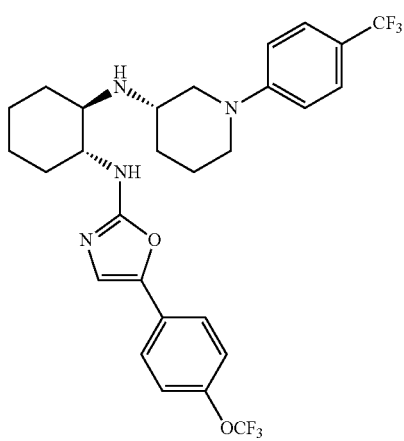 [SMILES: FC(F)(F)Oc1ccc(-c2cnc(N[C@@H]3CCCC[C@H]3N[C@H]3CCCN(c4ccc(C(F)(F)F)cc4)C3)o2)cc1]

(1R,2R)—N1-(5-(4-(Trifluoromethoxy)phenyl)oxazol-2-yl)-N2-((S)-1-(4-(trifluoromethyl)phenyl)piperidin-3-yl)cyclohexane-1,2-diamine (42 mg, 0.072 mmol, 61.2% yield) was synthesized as described in General Procedure H using Intermediate 2 (37.1 mg, 0.141 mmol) and Intermediate 20 (40 mg, 0.117 mmol). The product was purified using RP prep-HPLC method A to give the title compound as a beige solid. Anal. Calcd. for $C_{28}H_{30}F_6N_4O_2$ m/z 568.5, found: 569.3 (M+H)$^+$; $^1$H NMR (500 MHz, CDCl$_3$) δ ppm 7.51-7.38 (m, 4 H), 7.22 (d, J=8.25 Hz, 2 H), 6.93-6.86 (m, 3 H), 4.07 (br. s., 1 H), 3.61-3.42 (m, 3 H), 3.42-3.33 (m, 1 H), 3.20 (br. s., 1 H), 3.03 (br. s., 1 H), 2.27 (d, J=12.10 Hz, 1 H), 2.11 (d, J=11.55 Hz, 2 H), 2.07-1.91 (m, 3 H), 1.88 (d, J=12.10 Hz, 1 H), 1.83-1.63 (m, 3 H), 1.52-1.35 (m, 2 H).

Example 72

(1R,2R)—N1-(5-Phenylthiazol-2-yl)-N2-((S)-1-(4-(trifluoromethyl)phenyl)piperidin-3-yl)cyclohexane-1,2-diamine

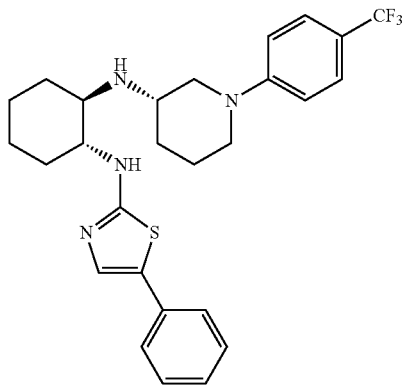 [SMILES: FC(F)(F)c1ccc(N2CCC[C@H](N[C@@H]3CCCC[C@H]3Nc3ncc(-c4ccccc4)s3)C2)cc1]

(1R,2R)—N1-(5-Phenylthiazol-2-yl)-N2-((S)-1-(4-(trifluoromethyl)phenyl)piperidin-3-yl)cyclohexane-1,2-diamine (2 mg, 0.004 mmol, 13.6% yield) was synthesized as described in General Procedure H using Intermediate 37 (5.7 mg, 0.03 mmol) and Intermediate 20 (10 mg, 0.03 mmol). The product was purified using RP prep-HPLC method C to give the title compound as a beige solid. Anal. Calcd. for $C_{27}H_{31}F_3N_4S$ m/z 500.2, found: 501.2 (M+H)$^+$; $^1$H NMR (400 MHz, CDCl$_3$) δ ppm 7.49 (d, J=8.6 Hz, 2H), 7.41 (m, 3H), 7.36 (m, 2H), 7.16 (s, 1H), 6.96 (d, J=8.6 Hz, 2H), 3.64 (m, 1H), 3.46 (m, 4H), 3.25 (m, 1H), 2.97 (m, 1H), 2.24 (m, 2H), 1.93 (m, 1H), 1.79 (m, 4H), 1.56 (m, 2H), 1.51 (m, 1H). 1.42 (m, 2H).

Example 73

(1R,2R)—N1-((S)-1-(3-Fluoro-4-(trifluoromethyl)phenyl)piperidin-3-yl)-N2-(5-(4-(trifluoromethoxy)phenyl)oxazol-2-yl)cyclohexane-1,2-diamine bis-trifluoroacetate

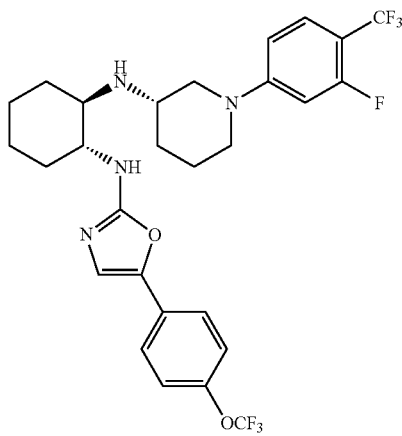 [SMILES: Fc1cc(N2CCC[C@H](N[C@@H]3CCCC[C@H]3Nc3ncc(-c4ccc(OC(F)(F)F)cc4)o3)C2)ccc1C(F)(F)F]

(1R,2R)—N1-((S)-1-(3-Fluoro-4-(trifluoromethyl)phenyl)piperidin-3-yl)-N2-(5-(4-(trifluoromethoxy)phenyl)oxazol-2-yl)cyclohexane-1,2-diamine bis-trifluoroacetate (8 mg, 0.00943 mmol, 22.0% yield) was synthesized as described in General Procedure H using Intermediate 2 (16.97 mg, 0.064 mmol) and Intermediate 29 (35 mg, 0.043 mmol). The desired fraction from RP prep-HPLC method A was concentrated to give the title compound as a beige oil. Anal. Calcd. for $C_{28}H_{29}F_7N_4O_2$ m/z 586.4, found: 587.2 (M+H)$^+$; $^1$H NMR (400 MHz, CDCl$_3$) δ ppm 7.53 (d, J=8.7 Hz, 2H), 7.44 (t, J=8.4 Hz, 1H), 7.29 (d, J=8.2 Hz, 2H), 7.12 (s, 1H), 6.66 (t, J=11.2 Hz, 2H), 4.23-4.05 (m, 1H), 3.74 (d, J=12.1 Hz, 1H), 3.62-3.35 (m, 3H), 3.24-3.05 (m, 1H), 3.03-2.85 (m, 1H), 2.40-2.12 (m, 3H), 2.10-1.54 (m, 7H), 1.55-1.34 (m, 2H).

Example 74

(1R,2R)—N1-((S)-1-(3-Fluoro-4-(trifluoromethyl)phenyl)piperidin-3-yl)-N2-(4-phenylpyrimidin-2-yl)cyclohexane-1,2-diamine bis-trifluoroacetate

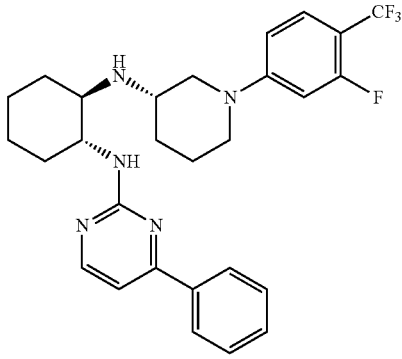 [SMILES: Fc1cc(N2CCC[C@H](N[C@@H]3CCCC[C@H]3Nc3nccc(-c4ccccc4)n3)C2)ccc1C(F)(F)F]

(1R,2R)—N1-((S)-1-(3-Fluoro-4-(trifluoromethyl)phenyl)piperidin-3-yl)-N2-(4-phenylpyrimidin-2-yl)cyclohexane-1,2-diamine bis-trifluoroacetate (10 mg, 0.013 mmol, 30.8% yield) was synthesized as described in General Procedure H using 2-chloro-4-phenylpyrimidine (12.27 mg, 0.064 mmol) and Intermediate 29 (35 mg, 0.043 mmol). The desired fraction from RP prep-HPLC method A was concentrated to give the title compound as a beige oil. Anal. Calcd. for $C_{28}H_{31}F_4N_5$ m/z 513.4, found: 514.2 (M+H)$^+$; $^1$H NMR (400 MHz, CDCl$_3$) δ ppm 8.20-7.96 (m, 3H), 7.68 (t, J=7.1 Hz, 1H), 7.57 (t, J=7.4 Hz, 2H), 7.42 (t, J=8.2 Hz, 1H), 7.27-7.21 (m, 1H), 6.66 (d, J=8.4 Hz, 1H), 6.58 (d, J=13.3 Hz, 1H), 4.51 (s, 1H), 3.66 (d, J=11.7 Hz, 1H), 3.58-3.45 (m, 1H), 3.35 (d, J=12.1 Hz, 3H), 3.06-2.86 (m, 1H), 2.46-2.22 (m, 2H), 2.15-1.83 (m, 5H), 1.82-1.59 (m, 2H), 1.59-1.33 (m, 3H).

Example 75

(1R,2R)—N1-(4-Phenylpyridin-2-yl)-N2-((S)-1-(4-(trifluoromethyl)phenyl)piperidin-3-yl)cyclohexane-1,2-diamine

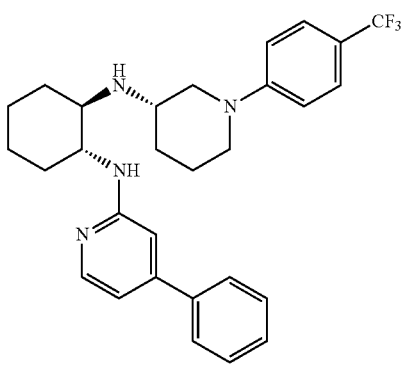 [SMILES: FC(F)(F)c1ccc(N2CCC[C@H](N[C@@H]3CCCC[C@H]3Nc3cc(-c4ccccc4)ccn3)C2)cc1]

(1R,2R)—N1-(4-Phenylpyridin-2-yl)-N2-((S)-1-(4-(trifluoromethyl)phenyl)piperidin-3-yl)cyclohexane-1,2-diamine (5 mg, 0.01 mmol, 3.5% yield) was synthesized as described in General Procedure H using Intermediate 20 (100 mg, 0.293 mmol) and 2-bromo-4-phenylpyridine (68.3 mg, 0.293 mmol). The desired fraction from RP prep-HPLC method C was concentrated to give the title compound as a pale yellow solid. Anal. Calcd. for $C_{29}H_{33}F_3N_4$ m/z 494.3, found: 495.2 (M+H)$^+$; $^1$H NMR (400 MHz, DMSO-d$_6$) δ ppm 8.09 (d, J=5.6 Hz, 1H), 7.49 (m, 4H), 7.34 (d, J=8.7 Hz, 1H), 6.95 (m, 1H), 6.90 (d, J=8.6 Hz, 2H), 6.71 (m, 1H), 3.83 (m, 2H), 3.49 (m, 4H), 3.28 (m, 2H), 3.03 (m, 1H), 2.23 (m, 1H), 2.02 (m, 2H), 1.86 (m, 1H), 1.76 (m, 3H), 1.62 (m, 2H), 1.43 (m, 1H), 1.33 (m, 2H).

Example 76

(1R,2R)—N1-(5-(3-Fluorophenyl)oxazol-2-yl)-N2-((S)-1-(4-(trifluoromethyl)phenyl)piperidin-3-yl)cyclohexane-1,2-diamine

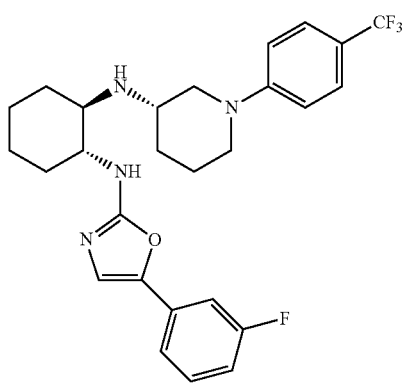 [SMILES: Fc1cccc(-c2cnc(N[C@@H]3CCCC[C@H]3N[C@H]3CCCN(c4ccc(C(F)(F)F)cc4)C3)o2)c1]

(1R,2R)—N1-(5-(3-Fluorophenyl)oxazol-2-yl)-N2-((S)-1-(4-(trifluoromethyl)phenyl)piperidin-3-yl)cyclohexane-1,2-diamine (17 mg, 0.04 mmol, 23% yield) was synthesized as described in General Procedure H using Intermediate 7 (66 mg, 0.34 mmol) and Intermediate 20 (50 mg, 0.17 mmol) The product was purified using RP prep-HPLC method A to give the title compound as a brown oil. Anal. Calcd. for $C_{27}H_{30}F_4N_4O$ m/z 502.2, found: 503.2 (M+H)$^+$; $^1$H NMR (400 MHz, CD$_3$OD) δ ppm 7.35 (m, 1H), 7.25 (d, J=8.6 Hz, 2H), 7.20 (s, 1H), 7.16 (dt, J=8.4 Hz, J=0.8 Hz), 7.05 (dt, J=4Hz, J=2.4 Hz, 1H), 6.99 (m, 1H), 6.94 (m, 3H), 3.80 (m, 1H), 3.72 (m, 1H), 3.66 (m, 1H), 3.52 (m, 1H), 3.38 (m, 1H), 3.18 (dd, J=2 Hz, 1H), 2.96 (m, 1H), 2.36 (m, 1H), 2.17 (m, 1H), 2.04 (m, 2H), 1.91 (m, 4H), 1.61 (m, 2H), 1.45 (m, 2H).

Example 77

(1R,2R)—N1-((S)-1-(5-Nitropyrimidin-2-yl)piperidin-3-yl)-N2-(5-phenyloxazol-2-yl)cyclohexane-1,2-diamine bis-trifluoroacetate

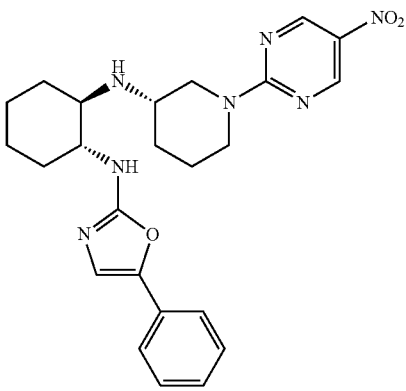 [SMILES: O=[N+]([O-])c1cnc(N2CCC[C@H](N[C@@H]3CCCC[C@H]3Nc3ncc(-c4ccccc4)o3)C2)nc1]

(1R,2R)—N1-((S)-1-(5-Nitropyrimidin-2-yl)piperidin-3-yl)-N2-(5-phenyloxazol-2-yl)cyclohexane-1,2-diamine bis-trifluoroacetate (17.53 mg, 0.024 mmol, 30.7% yield) was synthesized as described in General Procedure H using Intermediate 1 (28.5 mg, 0.159 mmol) and Intermediate 21 (43.5 mg, 0.079 mmol). The desired fraction from RP prep-HPLC method A was concentrated to give the title compound as a yellow solid. Anal. Calcd. for $C_{24}H_{29}N_7O_3$ m/z 463.4, found: 464.4 (M+H)$^+$; $^1$H NMR (400 MHz, CDCl$_3$) δ ppm 9.09 (s, 2H), 7.51-7.34 (m, 5H), 7.09 (s, 1H), 5.17 (d, J=12.2 Hz, 1H), 4.92 (d, J=12.7 Hz, 1H), 4.16 (s, 1H), 3.63-3.49 (m, 1H), 3.30 (t, J=10.9 Hz, 1H), 3.24-3.14 (m, 1H), 3.03 (t, J=11.8 Hz, 1H), 2.61-2.39 (m, 1H), 2.28 (d, J=11.9 Hz, 1H), 2.20 (d, J=13.1 Hz, 1H), 2.13-1.78 (m, 4H), 1.73-1.57 (m, 2H), 1.57-1.41 (m, 3H).

Example 78

(1R,2R)—N1-((S)-1-(5-Nitropyrimidin-2-yl)piperidin-3-yl)-N2-(5-(4-(trifluoromethoxy)phenyl)oxazol-2-yl)cyclohexane-1,2-diamine bis-trifluoroacetate

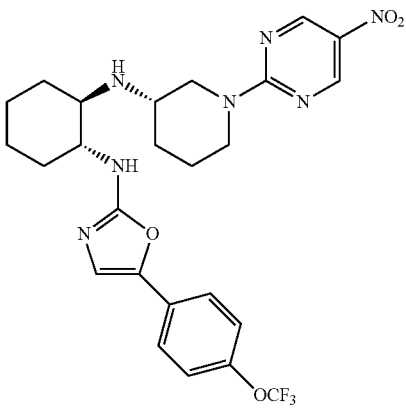 [SMILES: O=[N+]([O-])c1cnc(N2CCC[C@H](N[C@@H]3CCCC[C@H]3Nc3ncc(-c4ccc(OC(F)(F)F)cc4)o3)C2)nc1]

(1R,2R)—N1-((S)-1-(5-Nitropyrimidin-2-yl)piperidin-3-yl)-N2-(5-(4-(trifluoromethoxy)phenyl)oxazol-2-yl)cyclohexane-1,2-diamine bis-trifluoroacetate (19.50 mg, 0.025 mmol, 31.4% yield) was synthesized as described in General Procedure H using Intermediate 2 (41.3 mg, 0.157 mmol) and Intermediate 21 (43 mg, 0.078 mmol). The desired fraction from RP prep-HPLC method A was concentrated to a give the title compound as yellow solid. Anal. Calcd. for $C_{25}H_{28}F_3N_7O_4$ m/z 547.5, found: 548.5 (M+H)$^+$; $^1$H NMR (400 MHz, CDCl$_3$) δ ppm 9.09 (s, 2H), 7.43 (d, J=8.8 Hz, 2H), 7.21 (d, J=8.4 Hz, 2H), 7.09 (s, 1H), 5.17 (d, J=12.2 Hz, 1H), 4.92 (d, J=12.7 Hz, 1H), 4.16 (s, 1H), 3.63-3.49 (m, 1H), 3.30 (t, J=10.9 Hz, 1H), 3.24-3.14 (m, 1H), 3.03 (t, J=11.8 Hz, 1H), 2.61-2.39 (m, 1H), 2.28 (d, J=11.9 Hz, 1H), 2.20 (d, J=13.1 Hz, 1H), 2.13-1.78 (m, 4H), 1.73-1.57 (m, 2H), 1.57-1.41 (m, 3H).

Example 79

(1R,2R)—N1-(5-Phenyloxazol-2-yl)-N2-((S)-1-(5-(trifluoromethyl)pyrimidin-2-yl)piperidin-3-yl)cyclohexane-1,2-diamine bis-trifluoroacetate

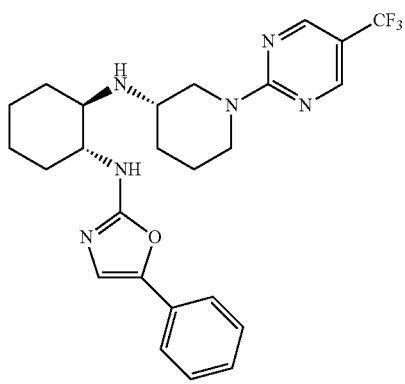 [SMILES: FC(F)(F)c1cnc(N2CCC[C@H](N[C@@H]3CCCC[C@H]3Nc3ncc(-c4ccccc4)o3)C2)nc1]

(1R,2R)—N1-(5-Phenyloxazol-2-yl)-N2-((S)-1-(5-(trifluoromethyl)pyrimidin-2-yl)piperidin-3-yl)cyclohexane-1,2-diamine bis-trifluoroacetate (32.4 mg, 0.045 mmol, 45.5% yield) was synthesized as described in General Procedure H using Intermediate 1 (35.8 mg, 0.199 mmol) and Intermediate 33 (57 mg, 0.100 mmol). The crude product was purified by RP prep-HPLC method A to give the title compound as a light yellow solid. Anal. Calcd. for $C_{25}H_{29}F_3N_6O$ m/z 486.5, found: 487.4 (M+H)$^+$; $^1$H NMR (400 MHz, CDCl$_3$) δ ppm 8.51 (s, 2H), 7.51-7.34 (m, 5H), 7.09 (s, 1H), 5.07 (d, J=12.6 Hz, 1H), 4.80 (d, J=12.9 Hz, 1H), 4.26-4.07 (m, 1H), 3.59-3.46 (m, 1H), 3.37-3.23 (m, 1H), 3.20-3.08 (m, 1H), 3.00-2.89 (m, 1H), 2.52 (d, J=10.2 Hz, 1H), 2.33-2.16 (m, 2H), 2.09-1.97 (m, 1H), 1.97-1.82 (m, 3H), 1.74-1.33 (m, 5H).

Example 80

(1R,2R)—N1-(5-(4-(Trifluoromethoxy)phenyl)oxazol-2-yl)-N2-((S)-1-(5-(trifluoromethyl)pyrimidin-2-yl)piperidin-3-yl)cyclohexane-1,2-diamine bis-trifluoroacetate

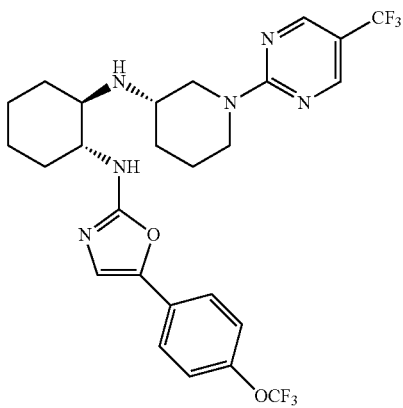 [SMILES: FC(F)(F)Oc1ccc(-c2cnc(N[C@@H]3CCCC[C@H]3N[C@H]3CCCN(c4ncc(C(F)(F)F)cn4)C3)o2)cc1]

(1R,2R)—N1-(5-(4-(Trifluoromethoxy)phenyl)oxazol-2-yl)-N2-((S)-1-(5-(trifluoromethyl)pyrimidin-2-yl)piperidin-3-yl)cyclohexane-1,2-diamine bis-trifluoroacetate (43.95 mg, 0.055 mmol, 54.9% yield) was synthesized as described in General Procedure H using Intermediate 2 (52.6 mg, 0.199 mmol) and Intermediate 33 (57 mg, 0.100 mmol). The desired fraction from RP prep-HPLC method A was concentrated to give the title compound as a light yellow solid. Anal. Calcd. for $C_{25}H_{28}F_6N_6O_2$ m/z 570.5, found: 487.4 (M+H)$^+$; $^1$H NMR (400 MHz, CDCl$_3$) δ ppm 8.51 (s, 2H), 7.41 (d, J=8.8 Hz, 2H), 7.18 (d, J=8.4 Hz, 2H), 7.08 (s, 1H), 5.10 (d, J=12.4 Hz, 1H), 4.83 (d, J=12.9 Hz, 1H), 4.15 (s, 1H), 3.62-3.50 (m, 1H), 3.34-3.17 (m, 1H), 3.15-3.02 (m, 1H), 2.94 (t, J=11.8 Hz, 1H), 2.61-2.44 (m, 1H), 2.31-2.13 (m, 2H), 2.11-1.83 (m, 4H), 1.71-1.39 (m, 5H).

Example 81

2-((S)-3-((1R,2R)-2-(5-(4-(Trifluoromethoxy)phenyl)oxazol-2-ylamino)cyclohexylamino)piperidin-1-yl)pyrimidine-5-carbonitrile bis-trifluoroacetate

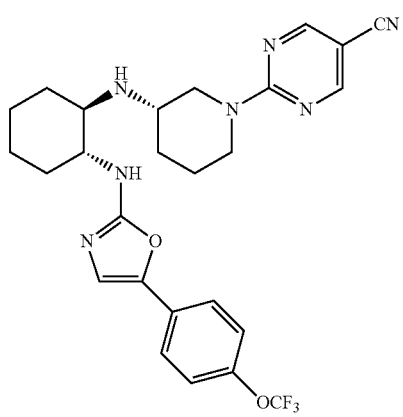 [SMILES: N#Cc1cnc(N2CCC[C@H](N[C@@H]3CCCC[C@H]3Nc3ncc(-c4ccc(OC(F)(F)F)cc4)o3)C2)nc1]

2-((S)-3-((1R,2R)-2-(5-(4-(Trifluoromethoxy)phenyl)oxazol-2-ylamino)cyclohexylamino)piperidin-1-yl)pyrimidine-5-carbonitrile bis-trifluoroacetate (10 mg, 0.013 mmol, 15.8% yield) was synthesized as described in General Procedure H using Intermediate 2 (42.9 mg, 0.163 mmol) and Intermediate 34 (43 mg, 0.081 mmol). The desired fraction from RP prep-HPLC method A was concentrated to give the title compound as a white solid. Anal. Calcd. for $C_{26}H_{28}F_3N_7O_2$ m/z 527.5, found: 528.3 (M+H)$^+$; $^1$H NMR (400 MHz, CDCl$_3$) δ ppm 8.53 (s, 2H), 7.48 (dd, J=22.6, 8.8 Hz, 2H), 7.29 (d, J=8.5 Hz, 2H), 7.15 (s, 1H), 5.08 (d, J=12.3 Hz, 1H), 4.87-4.72 (m, 1H), 4.24-4.04 (m, 1H), 3.57-3.43 (m, 1H), 3.41-3.28 (m, 1H), 3.27-3.06 (m, 1H), 2.98 (t, J=12.3 Hz, 1H), 2.45 (d, J=10.7 Hz, 1H), 2.22 (d, J=18.5 Hz, 2H), 2.12-1.76 (m, 4H), 1.73-1.37 (m, 5H).

Example 82

2-((S)-3-((1R,2R)-2-(5-Phenyloxazol-2-ylamino)cyclohexylamino)piperidin-1-yl)pyrimidine-5-carbonitrile

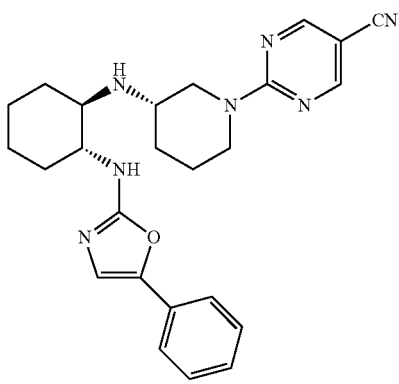 [SMILES: N#Cc1cnc(N2CCC[C@H](N[C@@H]3CCCC[C@H]3Nc3ncc(-c4ccccc4)o3)C2)nc1]

2-((S)-3-((1R,2R)-2-(5-Phenyloxazol-2-ylamino)cyclohexylamino)piperidin-1-yl)pyrimidine-5-carbonitrile (5.05 mg, 0.011 mmol, 15.4% yield) was synthesized as described in General Procedure H using Intermediate 1 (26.2 mg, 0.146 mmol) and Intermediate 34 (38.5 mg, 0.073 mmol). The product was purified using RP prep-HPLC method A to give the title compound as a white solid. Anal. Calcd. for $C_{25}H_{29}N_7O$ m/z 443.4, found: 444.2 (M+H)$^+$; $^1$H NMR (400 MHz, CDCl$_3$) δ ppm 8.52 (s, 2H), 7.52-7.36 (m, 5H), 7.08 (s, 1H), 5.07 (d, J=12.4 Hz, 1H), 4.81 (d, J=12.7 Hz, 1H), 4.25-4.06 (m, 1H), 3.56-3.24 (m, 2H), 3.21-3.08 (m, 1H), 3.03-2.89 (m, 1H), 2.54-2.37 (m, 1H), 2.35-2.09 (m, 2H), 2.08-1.79 (m, 4H), 1.74-1.32 (m, 5H).

Example 83

(1R,2R)—N1-((S)-1-(4-(5-Methyl-1,3,4-oxadiazol-2-yl)phenyl)piperidin-3-yl)-N2-(5-phenyloxazol-2-yl)cyclohexane-1,2-diamine bis-trifluoroacetate

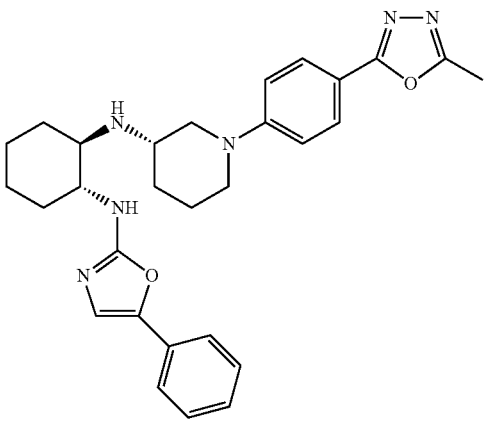 [SMILES: Cc1nnc(-c2ccc(N3CCC[C@H](N[C@@H]4CCCC[C@H]4Nc4ncc(-c5ccccc5)o4)C3)cc2)o1]

(1R,2R)—N1-((S)-1-(4-(5-Methyl-1,3,4-oxadiazol-2-yl)phenyl)piperidin-3-yl)-N2-(5-phenyloxazol-2-yl)cyclohexane-1,2-diamine bis-trifluoroacetate (3 mg, 0.0038 mmol, 7.47% yield) was synthesized as described in General Procedure H using Intermediate 1 18.47 mg, 0.103 mmol) and Intermediate 23 (30 mg, 0.051 mmol). The crude material was purified by RP prep-HPLC method A to give the title compound as a beige oil. Anal. Calcd. for $C_{29}H_{34}N_6O_2$ m/z 498.5, found: 499.3 (M+H)$^+$; $^1$H NMR (400 MHz, CDCl$_3$) δ ppm 7.89 (d, J=8.6 Hz, 2H), 7.48 (d, J=6.8 Hz, 2H), 7.46-7.38 (m, 3H), 7.07 (s, 1H), 6.98 (d, J=8.7 Hz, 2H), 4.17 (s, 1H), 3.77 (d, J=11.5 Hz, 1H), 3.66-3.38 (m, 3H), 3.23 (d, J=10.0 Hz, 1H), 3.06-2.89 (m, 1H), 2.62 (s, 3H), 2.32 (d, J=11.7 Hz, 1H), 2.21 (d, J=12.1 Hz, 2H), 2.09-1.55 (m, 7H), 1.54-1.32 (m, 2H).

Example 84

(1R,2R)—N1-((S)-1-(4-(5-Methyl-1,3,4-oxadiazol-2-yl)phenyl)piperidin-3-yl)-N2-(4-phenylpyrimidin-2-yl)cyclohexane-1,2-diamine bis-trifluoroacetate

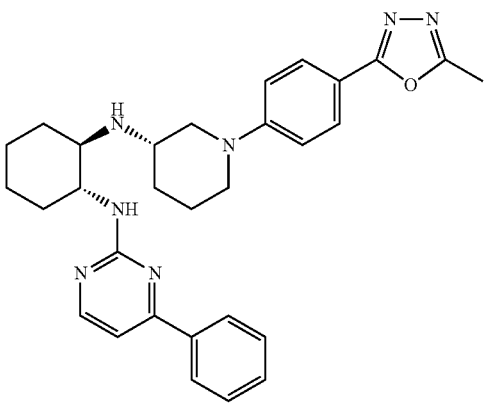 [SMILES: Cc1nnc(-c2ccc(N3CCC[C@H](N[C@@H]4CCCC[C@H]4Nc4nccc(-c5ccccc5)n4)C3)cc2)o1]

(1R,2R)—N1-((S)-1-(4-(5-Methyl-1,3,4-oxadiazol-2-yl)phenyl)piperidin-3-yl)-N2-(4-phenylpyrimidin-2-yl)cyclohexane-1,2-diamine bis-trifluoroacetate (5 mg, 0.0064 mmol, 12.4% yield) was synthesized as described in General Procedure H using 2-chloro-4-phenylpyrimidine (9.80 mg, 0.051 mmol) and Intermediate 23 (30 mg, 0.051 mmol). The crude material was purified by RP prep-HPLC method A to give the title compound as a light yellow solid. Anal. Calcd. for $C_{30}H_{35}N_7O$ m/z 509.5, found: 510.3 (M+H)$^+$; $^1$H NMR (400 MHz, CDCl$_3$) δ ppm 8.14 (s, 1H), 7.93-7.75 (m, 3H), 7.72-7.62 (m, 1H), 7.62-7.49 (m, 3H), 7.15 (d, J=6.3 Hz, 1H), 6.86 (d, J=8.7 Hz, 2H), 4.72-4.47 (m, 1H), 4.16-3.36 (m, 5H), 3.36-3.09 (m, 2H), 3.06-2.96 (m, 1H), 2.59 (s, 3H), 2.38-2.16 (m, 2H), 2.16-1.90 (m, 3H), 1.86 (d, J=10.3 Hz, 1H), 1.71-1.45 (m, 3H), 1.45-1.27 (m, 1H).

Example 85

(1R,2R)—N1-((S)-1-(4-(5-Methyl-1,3,4-oxadiazol-2-yl)phenyl)piperidin-3-yl)-N2-(5-(4-(trifluoromethoxy)phenyl)oxazol-2-yl)cyclohexane-1,2-diamine

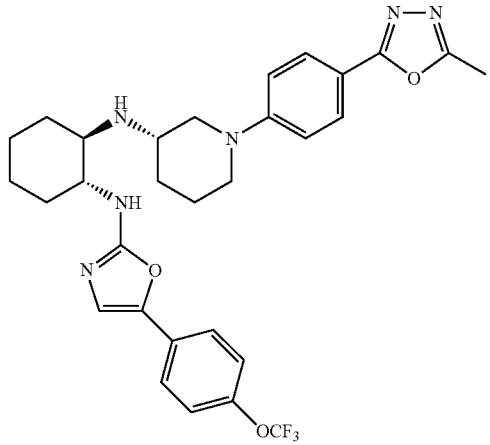 [SMILES: Cc1nnc(-c2ccc(N3CCC[C@H](N[C@@H]4CCCC[C@H]4Nc4ncc(-c5ccc(OC(F)(F)F)cc5)o4)C3)cc2)o1]

(1R,2R)—N1-((S)-1-(4-(5-Methyl-1,3,4-oxadiazol-2-yl)phenyl)piperidin-3-yl)-N2-(5-(4-(trifluoromethoxy)phenyl)oxazol-2-yl)cyclohexane-1,2-diamine (3 mg, 0.0051 mmol, 9.92% yield) was synthesized as described in General Procedure H using Intermediate 2 (27.1 mg, 0.103 mmol) and Intermediate 23 (30 mg, 0.051 mmol). The crude material was purified by RP prep-HPLC method A to give the title compound as an off-white solid. Anal. Calcd. for $C_{30}H_{33}F_3N_6O_3$ m/z 582.5, found: 583.3 (M+H)$^+$; $^1$H NMR (400 MHz, CDCl$_3$) δ ppm 7.84 (d, J=8.8 Hz, 2H), 7.44 (d, J=8.8 Hz, 2H), 7.18 (d, J=8.4 Hz, 2H), 7.01 (s, 1H), 6.92 (d, J=8.9 Hz, 2H), 5.15 (d, J=5.1 Hz, 1H), 3.68 (d, J=10.3 Hz, 1H), 3.61-3.49 (m, 1H), 3.32-3.14 (m, 1H), 3.05-2.93 (m, 1H), 2.91-2.83 (m, 1H), 2.82-2.72 (m, 1H), 2.63-2.39 (m, 4H), 2.18 (d, J=12.4 Hz, 1H), 1.97-1.74 (m, 2H), 1.73-1.44 (m, 3H), 1.46-1.08 (m, 5H).

Example 86

(1R,2R)—N1-(5-Phenyloxazol-2-yl)-N2-((S)-1-(4-(trifluoromethoxy)phenyl)piperidin-3-yl)cyclohexane-1,2-diamine

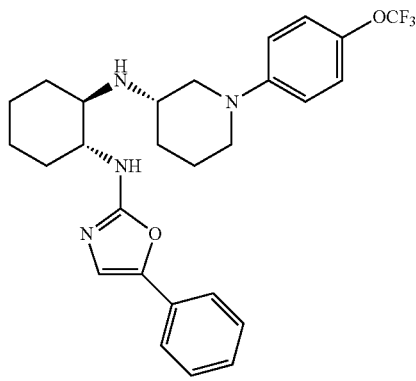 [SMILES: FC(F)(F)Oc1ccc(N2CCC[C@H](N[C@@H]3CCCC[C@H]3Nc3ncc(-c4ccccc4)o3)C2)cc1]

(1R,2R)—N1-(5-Phenyloxazol-2-yl)-N2-((S)-1-(4-(trifluoromethoxy)phenyl)piperidin-3-yl)cyclohexane-1,2-diamine (8 mg, 0.015 mmol, 20.6% yield) was synthesized as described in General Procedure H using Intermediate 1 (26.5 mg, 0.148 mmol) and Intermediate 25 (60 mg, 0.074 mmol). T The crude material was purified by RP prep-HPLC method A to give the title compound as an off-white solid. Anal. Calcd. for $C_{27}H_{31}F_3N_4O_2$ m/z 500.4, found: 501.2 (M+H)$^+$; $^1$H NMR (400 MHz, CDCl$_3$) δ ppm 7.45 (d, J=7.70 Hz, 2 H), 7.34 (t, J=7.70 Hz, 2 H), 7.21 (t, J=7.42 Hz, 1 H), 7.04 (d, J=8.79 Hz, 2 H), 7.00 (s, 1 H), 6.87 (d, J=8.79 Hz, 2 H), 5.23 (d, J=3.85 Hz, 1 H), 3.50 (dd, J=10.99, 2.20 Hz, 1 H), 3.35 (d, J=12.09 Hz, 1 H), 3.27-3.17 (m, 1 H), 2.97-2.85 (m, 1 H), 2.85-2.73 (m, 1 H), 2.64-2.39 (m, 2 H), 2.16 (br. s., 1 H) 1.90-1.72 (m, 4 H), 1.72-1.62 (m, 1 H), 1.46-1.23 (m, 4 H), 1.23-1.10 (m, 1 H).

Example 87

(1R,2R)—N1-(5-(4-(Trifluoromethoxy)phenyl)oxazol-2-yl)-N2-((S)-1-(4-(trifluoromethoxy)phenyl)piperidin-3-yl)cyclohexane-1,2-diamine

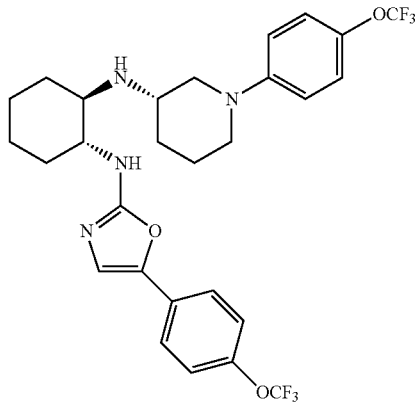 [SMILES: FC(F)(F)Oc1ccc(-c2cnc(N[C@@H]3CCCC[C@H]3N[C@H]3CCCN(c4ccc(OC(F)(F)F)cc4)C3)o2)cc1]

(1R,2R)—N1-(5-(4-(Trifluoromethoxy)phenyl)oxazol-2-yl)-N2-((S)-1-(4-(trifluoromethoxy)phenyl)piperidin-3-yl)cyclohexane-1,2-diamine (12 mg, 0.020 mmol, 27.3% yield) was synthesized as described in General Procedure H using Intermediate 2 (38.9 mg, 0.148 mmol) and Intermediate 25 (60 mg, 0.074 mmol). T The crude material was purified by RP prep-HPLC method A to give the title compound as an off-white solid. Anal. Calcd. for $C_{28}H_{30}F_6N_4O_3$ m/z 584.4, found: 585.2 (M+H)$^+$; $^1$H NMR (400 MHz, CDCl$_3$) δ ppm 7.45 (d, J=8.79 Hz, 2 H), 7.19 (d, J=8.24 Hz, 2 H), 7.05 (d, J=8.79 Hz, 2 H), 7.00 (s, 1 H), 6.88 (d, J=8.79 Hz, 2 H), 5.26 (d, J=3.30 Hz, 1 H), 3.47 (d, J=2.20 Hz, 1 H), 3.34 (br. s., 1 H), 3.21 (br. s., 1 H), 2.88 (s, 1 H), 2.86-2.76 (m, 1 H), 2.65-2.55 (m, 1H), 2.50 (br. s., 1 H), 2.20 (br. s., 1 H), 1.88-1.74 (m, 4 H), 1.69 (d, J=9.89 Hz, 1 H), 1.44-1.25 (m, 4 H), 1.21-1.07 (m, 1 H).

Example 88

(1R,2R)—N1-(4-Phenylpyrimidin-2-yl)-N2-((S)-1-(4-(trifluoromethoxy)phenyl)piperidin-3-yl)cyclohexane-1,2-diamine

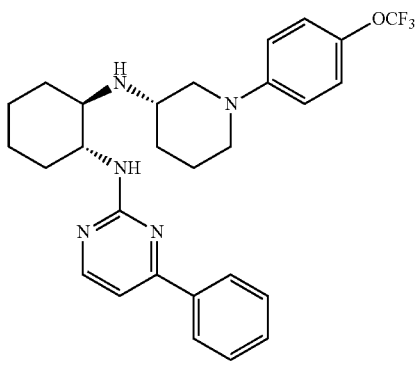 [SMILES: FC(F)(F)Oc1ccc(N2CCC[C@H](N[C@@H]3CCCC[C@H]3Nc3nccc(-c4ccccc4)n3)C2)cc1]

(1R,2R)—N1-(4-Phenylpyrimidin-2-yl)-N2-((S)-1-(4-(trifluoromethoxy)phenyl)piperidin-3-yl)cyclohexane-1,2-diamine (21 mg, 0.039 mmol, 40.1% yield) was synthesized as described in General Procedure H using 2-chloro-4-phenylpyrimidine (37.5 mg, 0.197 mmol) and Intermediate 25 (80 mg, 0.098 mmol). The crude material was purified by RP prep-HPLC method A to give the title compound as an off-white solid. Anal. Calcd. for $C_{28}H_{32}F_3N_5O$ m/z 511.5, found: 512.3 (M+H)$^+$; $^1$H NMR (400 MHz, CDCl$_3$) δ ppm 8.31 (d, J=5.3 Hz, 1H), 8.08-7.95 (m, 2H), 7.54-7.40 (m, 3H), 7.05-6.92 (m, 3H), 6.83-6.74 (m, 2H), 5.13 (d, J=8.1 Hz, 1H), 3.93-3.74 (m, 1H), 3.46 (d, J=9.7 Hz, 1H), 3.40-3.28 (m, 1H), 2.96-2.76 (m, 1H), 2.74-2.64 (m, 1H), 2.63-2.52 (m, 1H), 2.24 (d, J=11.2 Hz, 1H), 2.17-2.01 (m, 1H), 1.96-1.83 (m, 1H), 1.81-1.52 (m, 5H), 1.51-1.12 (m, 4H).

Example 89

(1R,2R)—N1-((S)-1-(4-(1H-1,2,4-Triazol-1-yl)phenyl)piperidin-3-yl)-N2-(5-(4-(trifluoromethoxy)phenyl)oxazol-2-yl)cyclohexane-1,2-diamine bis-trifluoroacetate

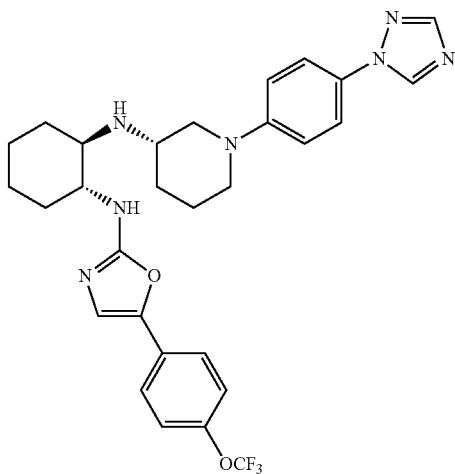 [SMILES: FC(F)(F)Oc1ccc(-c2cnc(N[C@@H]3CCCC[C@H]3N[C@H]3CCCN(c4ccc(-n5cncn5)cc4)C3)o2)cc1]

(1R,2R)—N1-((S)-1-(4-(1H-1,2,4-Triazol-1-yl)phenyl)piperidin-3-yl)-N2-(5-(4-(trifluoromethoxy)phenyl)oxazol-2-yl)cyclohexane-1,2-diamine bis-trifluoroacetate (28 mg, 0.035 mmol, 34.7% yield) was synthesized as described in General Procedure H using Intermediate 2 (39.7 mg, 0.151 mmol) and Intermediate 27 (80 mg, 0.100 mmol). The crude material was purified by RP prep-HPLC method A to give the title compound as an off-white solid. Anal. Calcd. for $C_{29}H_{32}F_3N_7O_2$ m/z 567.5, found: 568.2 (M+H)$^+$; $^1$H NMR (400 MHz, CDCl$_3$) δ ppm 8.40 (s, 1H), 8.07 (s, 1H), 7.47 (d, J=8.8 Hz, 2H), 7.42 (d, J=8.7 Hz, 2H), 7.17 (d, J=8.4 Hz, 2H), 7.02-6.89 (m, 3H), 4.09 (s, 1H), 3.62-3.40 (m, 3H), 3.34-3.14 (m, 2H), 3.10-2.97 (m, 1H), 2.29 (d, J=10.7 Hz, 1H), 2.17-1.93 (m, 4H), 1.93-1.59 (m, 4H), 1.55-1.30 (m, 3H).

Example 90

(1R,2R)—N1-((S)-1-(4-(1H-1,2,4-Triazol-1-yl)phenyl)piperidin-3-yl)-N2-(5-phenyloxazol-2-yl)cyclohexane-1,2-diamine bis-trifluoroacetate

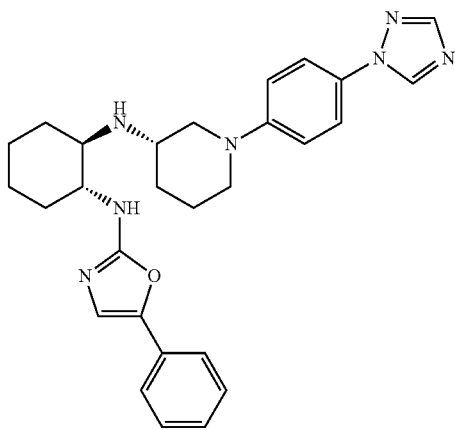 [SMILES: c1ccc(-c2cnc(N[C@@H]3CCCC[C@H]3N[C@H]3CCCN(c4ccc(-n5cncn5)cc4)C3)o2)cc1]

(1R,2R)—N1-((S)-1-(4-(1H-1,2,4-Triazol-1-yl)phenyl)piperidin-3-yl)-N2-(5-phenyloxazol-2-yl)cyclohexane-1,2-diamine bis-trifluoroacetate (10 mg, 0.014 mmol, 13.9% yield) was synthesized as described in General Procedure H using Intermediate 1 (27.1 mg, 0.151 mmol) and Intermediate 27 (80 mg, 0.100 mmol). The crude material was purified by RP prep-HPLC method A to give the title compound as an off-white solid. Anal. Calcd. for $C_{28}H_{33}N_7O$ m/z 483.5, found: 484.2 (M+H)$^+$; $^1$H NMR (400 MHz, CDCl$_3$) δ ppm 8.50 (s, 1H), 8.10 (s, 1H), 7.52 (d, J=6.0 Hz, 2H), 7.48-7.41 (m, 2H), 7.41-7.32 (m, 3H), 7.07-6.92 (m, 3H), 4.20 (s, 1H), 3.61 (d, J=11.8 Hz, 1H), 3.57-3.36 (m, 3H), 3.21-3.09 (m, 1H), 2.92 (t, J=10.1 Hz, 1H), 2.30 (d, J=10.2 Hz, 1H), 2.25-2.10 (m, 2H), 2.06-1.56 (m, 7H), 1.55-1.30 (m, 2H).

Example 91

(1R,2R)—N1-((S)-1-(4-(1H-1,2,4-Triazol-1-yl)phenyl)piperidin-3-yl)-N2-(4-phenylpyrimidin-2-yl)cyclohexane-1,2-diamine bis-trifluoroacetate

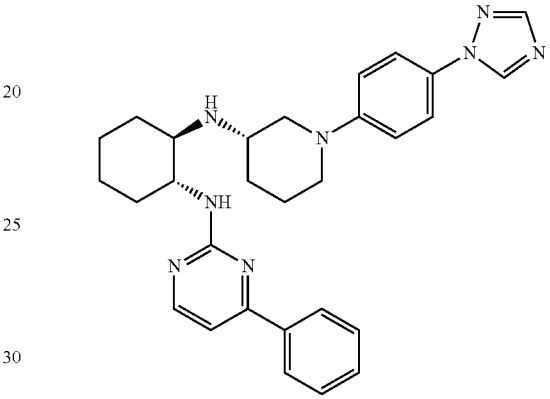

((1R,2R)—N1-((S)-1-(4-(1H-1,2,4-Triazol-1-yl)phenyl)piperidin-3-yl)-N2-(4-phenylpyrimidin-2-yl)cyclohexane-1,2-diamine bis-trifluoroacetate (12 mg, 0.016 mmol, 16.0% yield) was synthesized as described in General Procedure H using 2-chloro-4-phenylpyrimidine (28.7 mg, 0.151 mmol) and Intermediate 27 (80 mg, 0.100 mmol). The crude material was purified by RP prep-HPLC method A to give the title compound as a light yellow solid. Anal. Calcd. for $C_{29}H_{34}N_8$ m/z 494.5, found: 495.3 (M+H)$^+$; $^1$H NMR (400 MHz, CDCl$_3$) δ ppm 8.53 (s, 1H), 8.24-8.00 (m, 3H), 7.87 (s, 1H), 7.71-7.39 (m, 5H), 7.17 (s, 1H), 6.92 (d, J=8.0 Hz, 2H), 4.75-4.50 (m, 1H), 3.61-3.38 (m, 2H), 3.38-3.18 (m, 2H), 3.15-2.96 (m, 2H), 2.37-2.20 (m, 2H), 2.20-2.03 (m, 2H), 2.03-1.91 (m, 2H), 1.91-1.79 (m, 1H), 1.79-1.60 (m, 2H), 1.60-1.46 (m, 2H), 1.46-1.29 (m, 1H).

Example 92

(1R,2R)—N1-((S)-1-(4-Iodophenyl)piperidin-3-yl)-N2-(4-phenylpyrimidin-2-yl)cyclohexane-1,2-diamine bis-trifluoroacetate

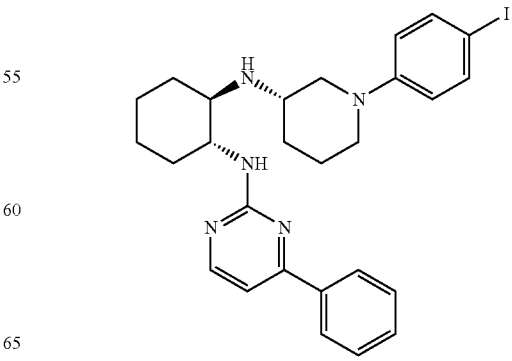

(1R,2R)—N1-((S)-1-(4-Iodophenyl)piperidin-3-yl)-N2-(4-phenylpyrimidin-2-yl)cyclohexane-1,2-diamine bis-trifluoroacetate (22 mg, 0.028 mmol, 31.3% yield) was synthesized as described in General Procedure H using 2-chloro-4-phenylpyrimidine (25.7 mg, 0.135 mmol) and Intermediate 35 (35.9 mg, 0.09 mmol). The crude material was purified by RP prep-HPLC method A to give the title compound as a beige oil. Anal. Calcd. for $C_{27}H_{32}IN_5$ m/z 553.3, found: 554.2 (M+H)$^+$; $^1$H NMR (400 MHz, CDCl$_3$) δ ppm 8.09 (d, J=7.7 Hz, 2H), 8.03 (d, J=6.5 Hz, 1H), 7.72-7.64 (m, 1H), 7.62-7.51 (m, 4H), 7.23 (d, J=6.6 Hz, 1H), 6.79 (d, J=8.6 Hz, 2H), 4.49 (s, 1H), 3.82-3.67 (m, 1H), 3.62-3.26 (m, 3H), 3.23-3.09 (m, 1H), 3.08-2.95 (m, 1H), 2.36 (d, J=12.8 Hz, 1H), 2.31-2.21 (m, 1H), 2.10-1.67 (m, 7H), 1.59-1.28 (m, 3H).

Example 93

(1R,2R)—N1-((S)-1-(4-Iodophenyl)piperidin-3-yl)-N2-(5-(4-(trifluoromethoxy)phenyl)oxazol-2-yl)cyclohexane-1,2-diamine bis-trifluoroacetate

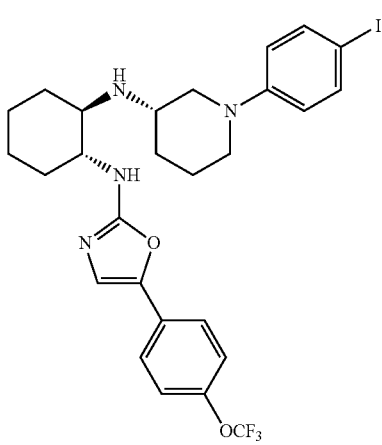 [SMILES: FC(F)(F)Oc1ccc(-c2cnc(N[C@@H]3CCCC[C@H]3N[C@H]3CCCN(c4ccc(I)cc4)C3)o2)cc1]

(1R,2R)—N1-((S)-1-(4-Iodophenyl)piperidin-3-yl)-N2-(5-(4-(trifluoromethoxy)phenyl)oxazol-2-yl)cyclohexane-1,2-diamine bis-trifluoroacetate (35 mg, 0.040 mmol, 44.4% yield) was synthesized as described in General Procedure H using Intermediate 2 (35.6 mg, 0.135 mmol) and Intermediate 35 (77 mg, 0.192 mmol). The crude material was purified by RP prep-HPLC method A to give the title compound as a beige oil. Anal. Calcd. for $C_{27}H_{30}F_3IN_4O_2$ m/z 626.3, found: 627.2 (M+H)$^+$; $^1$H NMR (400 MHz, CDCl$_3$) δ ppm 7.66 (d, J=8.7 Hz, 2H), 7.54 (d, J=8.7 Hz, 2H), 7.30 (d, J=8.5 Hz, 2H), 7.15 (s, 1H), 6.91 (d, J=8.8 Hz, 2H), 4.11 (s, 1H), 3.90-3.76 (m, 1H), 3.63 (d, J=10.1 Hz, 1H), 3.48-3.31 (m, 3H), 3.13-2.99 (m, 1H), 2.38 (d, J=10.2 Hz, 1H), 2.25-2.10 (m, 2H), 2.05-1.94 (m, 3H), 1.93-1.81 (m, 2H), 1.78-1.52 (m, 2H), 1.51-1.29 (m, 2H).

Example 94

(1R,2R)—N1-(5-(4-(Trifluoromethoxy)phenyl)oxazol-2-yl)-N2-((S)-1-(5-(trifluoromethyl)pyridin-2-yl)piperidin-3-yl)cyclohexane-1,2-diamine

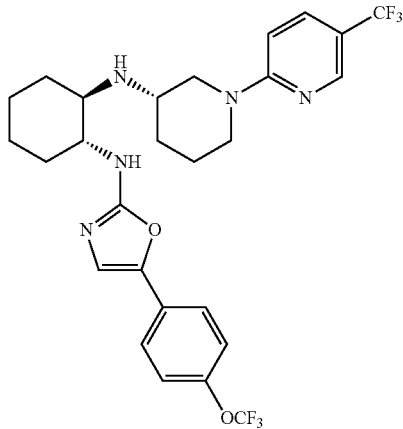

(1R,2R)—N1-(5-(4-(Trifluoromethoxy)phenyl)oxazol-2-yl)-N2-((S)-1-(5-(trifluoromethyl)pyridin-2-yl)piperidin-3-yl)cyclohexane-1,2-diamine (30 mg, 0.053 mmol, 9% yield) was synthesized as described in General Procedure H using Intermediate 2 (169.2 mg, 0.643 mmol) and Intermediate 40 (200 mg, 0.584 mmol). The crude material was purified by RP prep-HPLC method C to give the title compound as a beige solid. Anal. Calcd. for $C_{27}H_{29}F_6N_5O_2$ m/z 569.2, found: 570.2 (M+H)$^+$; $^1$H NMR (400 MHz, CDCl$_3$) δ ppm 8.38 (s, 1H), 7.53 (m, 1H), 7.36 (m, 1H), 7.17 (d, J=8.1 Hz, 2H), 6.95 (s, 1H), 6.60 (d, J=9 Hz, 1H), 5.32 (m, 1H), 3.86 (m, 1H), 3.62 (m, 2H), 3.40 (m, 1H), 3.29 (m, 1H), 2.97 (m, 1H), 2.74 (m, 1H), 2.37 (m, 1H), 2.20 (m, 1H), 1.90 (m, 2H), 1.79 (m, 4H), 1.37 (m, 4H).

Example 95

4-((1R,4R)-6-((1R,2R)-2-(5-(4-(Trifluoromethoxy)phenyl)oxazol-2-ylamino)cyclohexylamino)-2-azabicyclo[2.2.1]heptan-2-yl)benzonitrile

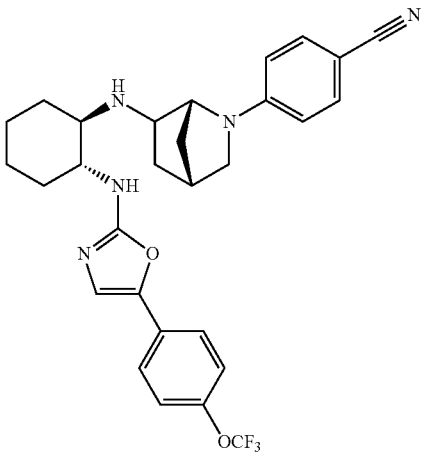 [SMILES: N#Cc1ccc(N2C[C@@H]3CC(N[C@@H]4CCCC[C@H]4Nc4ncc(-c5ccc(OC(F)(F)F)cc5)o4)[C@H]2C3)cc1]

4-((1R,4R)-6-((1R,2R)-2-(5-(4-(Trifluoromethoxy)phenyl)oxazol-2-ylamino)cyclohexylamino)-2-azabicyclo[2.2.1]heptan-2-yl)benzonitrile (14.9 mg, 0.028 mmol, 66.4% yield) was synthesized as described in General Procedure H using Intermediate 2 (12.1 mg, 0.046 mmol) and Intermediate 36 (16 mg, 0.42 mmol). The crude material was purified by RP prep-HPLC method A to give the title compound as a beige solid. Anal. Calcd. for $C_{29}H_{30}F_3N_5O_2$ m/z 537.2, found: 538.3 (M+H)$^+$; $^1$H NMR (400 MHz, CDCl$_3$) δ ppm 11.84 (1 H, d, J=9.9 Hz), 9.25 (1 H, br. s.), 8.97 (1 H, br. s.), 7.68 (2 H, d, J=8.8 Hz), 7.36 (2 H, d, J=8.2 Hz), 7.05 (2 H, d, J=8.8 Hz), 6.82 (1 H, s), 6.68 (2 H, d, J=8.8 Hz), 4.99 (1 H, s), 3.98-3.84 (1 H, m), 3.60-3.48 (2 H, m), 3.43-3.30 (1 H, m), 3.27 (1 H, d, J=8.8 Hz), 2.84 (1 H, s), 2.22-2.11 (1 H, m), 2.06 (2 H, d, J=10.4 Hz), 1.88-1.98 (2 H, m), 1.87-1.76 (2 H, m), 1.74-1.67 (1 H, m), 1.66-1.46 (2 H, m), 1.30 (2 H, m).

Example 96

(1R,2R)—N1-((S)-3-Methyl-1-(4-nitrophenyl)piperidin-3-yl)-N2-(5-(4-(trifluoromethoxy)phenyl)oxazol-2-yl)cyclohexane-1,2-diamine bis-trifluoroacetate

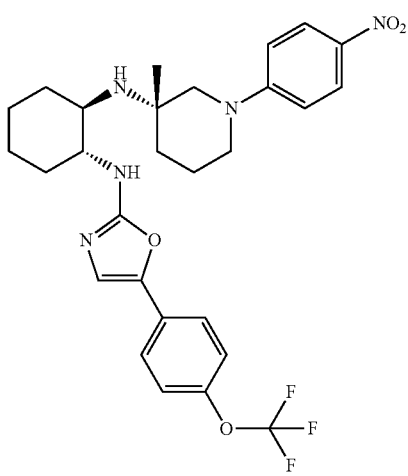 [SMILES: C[C@]1(N[C@@H]2CCCC[C@H]2Nc2ncc(-c3ccc(OC(F)(F)F)cc3)o2)CCCN(c2ccc([N+](=O)[O-])cc2)C1]

(1R,2R)—N1-((S)-3-Methyl-1-(4-nitrophenyl)piperidin-3-yl)-N2-(5-(4-(trifluoromethoxy)phenyl)oxazol-2-yl)cyclohexane-1,2-diamine bis-trifluoroacetate. (32 mg, 0.040 mmol, 66.2% yield) was synthesized as described in General Procedure H using Intermediate 2 (31.7 mg, 0.120 mmol) and Intermediate 39 (20 mg, 0.06 mmol). The crude material was purified by RP prep-HPLC method A to give the title compound as a beige solid. Anal. Calcd. for $C_{28}H_{32}F_3N_5O_4$ m/z 559.4, found: 560.3 (M+H)$^+$; $^1$H NMR (400 MHz, CDCl$_3$) δ ppm 8.02 (d, J=8.79 Hz, 2 H), 7.55 (d, J=8.79 Hz, 2 H), 7.30 (d, J=8.25 Hz, 2 H), 7.06 (s, 1 H), 6.84 (d, J=9.34 Hz, 2 H), 4.12 (d, J=6.05 Hz, 1 H), 3.68 (d, J=13.74 Hz, 1 H), 3.55-3.41 (m, 2 H), 3.37 (d, J=13.74 Hz, 1 H), 3.25 (ddd, J=8.11, 3.99, 3.85 Hz, 1 H), 2.35 (d, J=11.54 Hz, 1 H), 2.24-2.12 (m, 2 H), 2.08-1.81 (m, 6 H), 1.75-1.59 (m, 1 H), 1.55 (s, 3 H), 1.49-1.38 (m, 2 H).

Example 97

3-(2-(((1R,2R)-2-(((S)-1-(2-(trifluoromethyl)pyrimidin-5-yl)piperidin-3-yl)amino)cyclohexyl)amino)oxazol-5-yl)benzamide

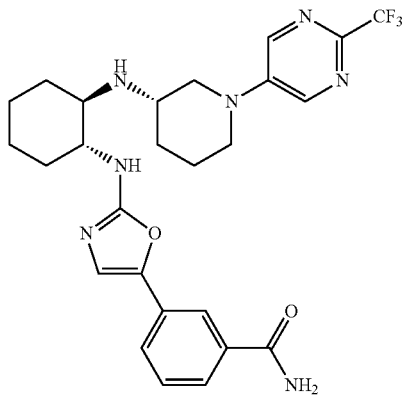 [SMILES: NC(=O)c1cccc(-c2cnc(N[C@@H]3CCCC[C@H]3N[C@H]3CCCN(c4cnc(C(F)(F)F)nc4)C3)o2)c1]

3-(2-(((1R,2R)-2-(((S)-1-(2-(trifluoromethyl)pyrimidin-5-yl)piperidin-3-yl)amino)cyclohexyl)amino)oxazol-5-yl)benzamide (270 mg, 0.51 mmol, 42% yield) was synthesized as described in General Procedure H using Intermediate 51 (0.41 gm, 1.19 mmol) and Intermediate 41 (0.35 gm, 1.55 mmol). The product was purified using RP prep-HPLC method E to give the product as a TFA salt. The product was taken up in EtOAc, washed with sat. NaHCO$_3$ (2×), dried over MgSO$_4$, filtered and concentrated to give the title product as the free amine. Anal. Calcd. for $C_{26}H_{30}F_3N_7O_2$ m/z 529.2, found: 530.3 (M+H)$^+$; $^1$H NMR (400 MHz, CDCl$_3$) δ ppm 8.36 (s, 2H), 8.01-7.82 (m, 1H), 7.65 (dt, J=7.7, 1.4 Hz, 1H), 7.60-7.49 (m, 1H), 7.46-7.33 (m, 1H), 7.05 (s, 1H), 6.78 (br. s., 1H), 6.01 (br. s., 1H), 5.31 (d, J=6.0 Hz, 1H), 3.64-3.52 (m, 1H), 3.51-3.39 (m, 1H), 3.35-3.18 (m, 1H), 3.11 (ddd, J=12.5, 9.2, 3.0 Hz, 1H), 3.00-2.77 (m, 2H), 2.46 (td, J=10.3, 3.6 Hz, 1H), 2.41-2.26 (m, 1H), 2.11 (d, J=12.6 Hz, 1H), 1.98-1.82 (m, 2H), 1.80-1.54 (m, 6H), 1.47-1.30 (m, 3H), 1.21-1.09 (m, 1H).

Example 98

Ethyl 3-(2-((1R,2R)-2-((S)-1-(5-(trifluoromethyl)pyrazin-2-yl)piperidin-3-ylamino)cyclohexylamino)oxazol-5-yl)phenylcarbamate

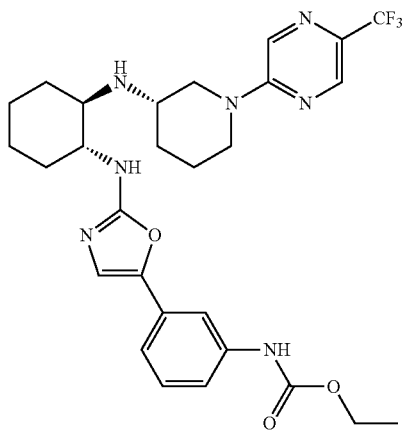 [SMILES: CCOC(=O)Nc1cccc(-c2cnc(N[C@@H]3CCCC[C@H]3N[C@H]3CCCN(c4cnc(C(F)(F)F)cn4)C3)o2)c1]

167

A: 1-(5-(Trifluoromethyl)pyrazin-2-yl)piperidin-3-ol

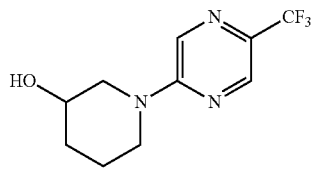 [SMILES: OC1CCCN(c2cnc(C(F)(F)F)cn2)C1]

1-(5-(Trifluoromethyl)pyrazin-2-yl)piperidin-3-ol (1.11 gm, 4.93 mmol, 94% yield) was synthesized as described in General Procedure B using 2-chloro-5-(trifluoromethyl)pyrazine (1.00 gm, 5.50 mmol) to give the title compound as a yellow solid. Anal. Calcd. for $C_{10}H_{12}F_3N_3O$ m/z 247.1, found: 248.1 $(M+H)^+$.

B: 1-(5-(Trifluoromethyl)pyrazin-2-yl)piperidin-3-one

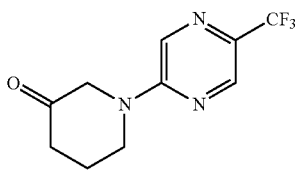 [SMILES: O=C1CCCN(c2cnc(C(F)(F)F)cn2)C1]

1-(5-(Trifluoromethyl)pyrazin-2-yl)piperidin-3-one (0.68 gm, 2.77 mmol, 56% yield) was synthesized as described in General Procedure D using 1-(5-(trifluoromethyl)pyrazin-2-yl)piperidin-3-ol (1.22 gm, 4.93 mmol) to give the title compound as a yellow syrup. Anal. Calcd. for $C_{10}H_{10}F_3N_3O$ m/z 245.1, found: 246.1 $(M+H)^+$.

C: tert-Butyl (1R,2R)-2-(1-(5-(trifluoromethyl)pyrazin-2-yl)piperidin-3-ylamino)cyclohexylcarbamate

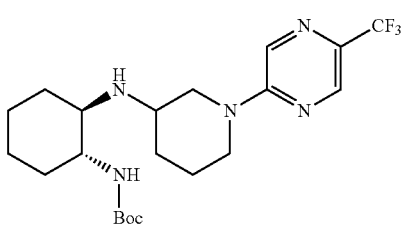 [SMILES: CC(C)(C)OC(=O)N[C@@H]1CCCC[C@H]1NC1CCCN(c2cnc(C(F)(F)F)cn2)C1]

tert-Butyl (1R,2R)-2-(1-(5-(trifluoromethyl)pyrazin-2-yl)piperidin-3-ylamino)cyclohexylcarbamate (387 mg, 0.87 mmol, 31% yield) was synthesized as described in General Procedure F using 1-(5-(Trifluoromethyl)pyrazin-2-yl)piperidin-3-one (0.68 gm, 2.77 mmol) to give the title compound as a syrup. Anal. Calcd. for $C_{21}H_{32}F_3N_5O_2$ m/z 443.3, found: 444.4 $(M+H)^+$.

168

D: (1R,2R)—N1-(1-(5-(trifluoromethyl)pyrazin-2-yl)piperidin-3-yl)cyclohexane-1,2-diamine

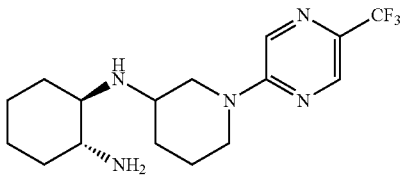

(1R,2R)—N1-(1-(5-(trifluoromethyl)pyrazin-2-yl)piperidin-3-yl)cyclohexane-1,2-diamine (275 mg, 0.80 mmol, 92% yield) was synthesized as described in Example 97 step E using tert-butyl (1R,2R)-2-(1-(5-(trifluoromethyl)pyrazin-2-yl)piperidin-3-ylamino)cyclohexylcarbamate (387 mg, 0.87 mmol) to give the title compound (diastereomeric mixture) as a syrup. Anal. Calcd. for $C_{16}H_{24}F_3N_5$ m/z 343.2, found: 344.2 $(M+H)^+$.

E: (1R,2R)—N1-((S)-1-(5-(trifluoromethyl)pyrazin-2-yl)piperidin-3-yl)cyclohexane-1,2-diamine

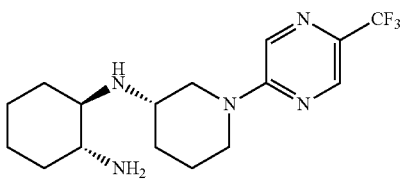

(1R,2R)—N1-(1-(5-(Trifluoromethyl)pyrazin-2-yl)piperidin-3-yl)cyclohexane-1,2-diamine, (387 mg, 0.87 mmol) was purified by Chiral Preparative HPLC method E:

An ethanol solution of Peak 1 containing the desired (S) isomer product was concentrated to give, (1R,2R)—$N^1$—((S)-1-(5-(trifluoromethyl)pyrazin-2-yl)piperidin-3-yl)cyclohexane-1,2-diamine (129 mg, 0.77 mmol), 43%) as a syrup. Anal. Calcd. for $C_{16}H_{24}F_3N_5$ m/z 343.2, found: 344.2 $(M+H)^+$.

F: Ethyl 3-(2-((1R,2R)-2-((S)-1-(5-(trifluoromethyl)pyrazin-2-yl)piperidin-3-ylamino)cyclohexylamino)oxazol-5-yl)phenylcarbamate

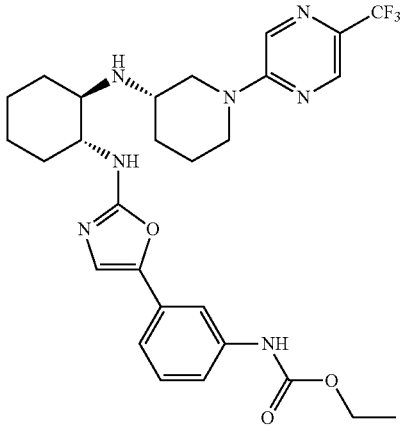 [SMILES: CCOC(=O)Nc1cccc(-c2cnc(N[C@@H]3CCCC[C@H]3N[C@H]3CCCN(c4cnc(C(F)(F)F)cn4)C3)o2)c1]

Ethyl 3-(2-((1R,2R)-2-((S)-1-(5-(trifluoromethyl)pyrazin-2-yl)piperidin-3-ylamino)cyclohexylamino)oxazol-5-yl)phenylcarbamate (7.13 mg, 0.012 mmol, 21% yield) was synthesized as described in General Procedure H using (1R,2R)—N1-((S)-1-(5-(trifluoromethyl)pyrazin-2-yl)piperidin-3-yl)cyclohexane-1,2-diamine (19.86 mg, 0.058 mmol) and Intermediate 44, ethyl 3-(2-chlorooxazol-5-yl)phenylcarbamate (15.42 mg, 0.058 mmol). The product was purified via preparative LC/MS with the following conditions: Column. Waters XBridge C18, 19×100 mm, 5-μm particles; Guard Column: Waters XBridge C18, 19×10 mm, 5-μm particles; Mobile Phase A: 5:95 acetonitrile:water with 0.1% ammonium hydroxide; Mobile Phase B: 95:5 acetonitrile:water with 0.1% ammonium hydroxide; Gradient: 35-75% B over 10 minutes, then a 7-minute hold at 75% B; Flow rate: 20 mL/min. Anal. Calcd. for $C_{28}H_{34}F_3N_7O_3$ m/z 573.3, found: 574.3 (M+H)$^+$; $^1$H NMR (500 MHz, DMSO-d$_6$) δ ppm 9.64 (s, 1H), 8.40 (d, J=1.1 Hz, 1H), 8.36 (s, 1H), 7.96 (s, 1H), 7.69 (s, 1H), 7.27-7.18 (m, 3H), 7.15-7.10 (m, 2H), 4.41 (d, J=10.7 Hz, 1H), 4.21 (d, J=12.9 Hz, 1H), 4.13 (q, J=7.2 Hz, 2H), 3.25 (td, J=9.3, 4.0 Hz, 1H), 3.06-2.99 (m, 1H), 2.76-2.69 (m, 1H), 2.66-2.54 (m, 2H), 2.06-1.96 (m, 2H), 1.89-1.82 (m, 1H), 1.75-1.61 (m, 3H), 1.45 (d, J=13.2 Hz, 1H), 1.37-1.28 (m, 2H), 1.28-2.21 (m, 5H), 1.09 (d, J=12.4 Hz, 1H).

Example 99

N-cyclopropyl-(3-(2-((1R,2R)-2((S)-1-(6-trifluoromethyl)pyridin-3yl)piperidin-3-ylamino)cyclohexylamino)oxazol-5-yl)benzamide

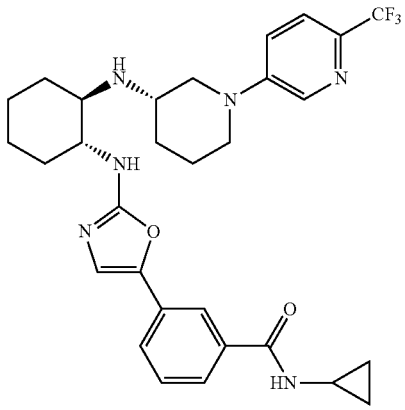 [SMILES: O=C(NC1CC1)c1cccc(-c2cnc(N[C@@H]3CCCC[C@H]3N[C@H]3CCCN(c4ccc(C(F)(F)F)nc4)C3)o2)c1]

A: Methyl 3-(2-((1R,2R)-2-((S)-1-(6-(trifluoromethyl)pyridin-3-yl)piperidin-3-ylamino)cyclohexylamino)oxazol-5-yl)benzoate

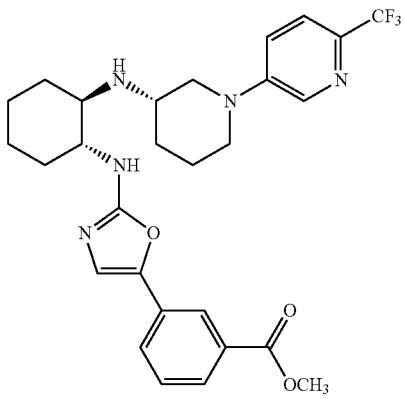 [SMILES: COC(=O)c1cccc(-c2cnc(N[C@@H]3CCCC[C@H]3N[C@H]3CCCN(c4ccc(C(F)(F)F)nc4)C3)o2)c1]

Methyl 3-(2-((1R,2R)-2-((S)-1-(6-(trifluoromethyl)pyridin-3-yl)piperidin-3-ylamino)cyclohexylamino)oxazol-5-yl)benzoate (73 mg, 0.134 mmol, 60.7% yield) was synthesized as described in General Procedure H using Intermediate 50 (100 mg, 0.221 mmol) and Intermediate 45 (79 mg, 0.332 mmol). The product was purified using chromatography (12 g silica gel cartridge) eluting with EtOAc/hexanes (50-100%) to give the title compound as a white foam. Anal. Calcd. for $C_{28}H_{32}F_3N_5O_3$ m/z 543.24, found: 544.2.

B: 3-(2-((1R,2R)-2((S)-1-(6-trifluoromethyl)pyridin-3yl)piperidin-3-ylamino)cyclohexylamino)oxazol-5-yl)benzoic acid

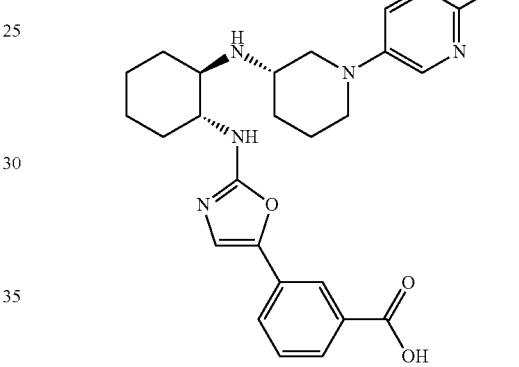

To a solution of methyl 3-(2-((1R,2R)-2-((S)-1-(6-trifluoromethyl)pyridin-3yl)piperidin-3-ylamino)cyclohexylamino) oxazol-5-yl)benzoate (69 mg, 0.127 mmol) in THF (0.5 mL) and MeOH (0.5 mL) was added 2M LiOH (1 mL, 2 mmol) in H$_2$O. The reaction mixture was allowed to stir at rt overnight. The reaction mixture was cooled in an ice bath, 1M HCl was added dropwise to pH ~3. The reaction mixture was concentrated. The resulting residue was purified using RP prep-HPLC method A. The desired fractions were concentrated and then lyophilized with water to give the desired product, 3-(2-((1R,2R)-2((S)-1-(6-trifluoromethyl)pyridin-3yl)piperidin-3-ylamino)cyclohexylamino)oxazol-5-yl)benzoic acid 3TFA salt (86 mg, 0.094 mmol, 74% yield) as a white foam. Anal. Calcd. for $C_{22}H_{30}F_3N_5O_3$ m/z 529.23, found: 530.2 (M+H)$^+$; $^1$H NMR (400 MHz, METHANOL-D$_3$) δ ppm 8.26 (d, J=2.7 Hz, 1H), 7.98 (s, 1H), 7.88 (d, J=7.7 Hz, 1H), 7.52 (d, J=8.2 Hz, 1H), 7.47-7.40 (m, 1H), 7.34 (dd, J=8.8, 2.7 Hz, 1H), 7.28-7.21 (m, 2H), 3.85 (dd, J=13.5, 4.7 Hz, 1H), 3.77-3.61 (m, 2H), 3.52 (dt, J=12.4, 4.5 Hz, 1H), 3.46-3.38 (m, 1H), 3.38-3.26 (m, 1H), 3.14-3.01 (m, 1H), 2.19 (d, J=12.6 Hz, 1H), 2.10-2.00 (m, 2H), 2.00-1.82 (m, 4H), 1.62-1.61 (m, 1H), 1.70-1.53 (m, 2H), 1.52-1.39 (m, 2H).

C: N-Cyclopropyl-(3-(2-((1R,2R)-2((S)-1-(6-trifluoromethyl)pyridin-3yl)piperidin-3-ylamino)cyclohexylamino)oxazol-5-yl)benzamide

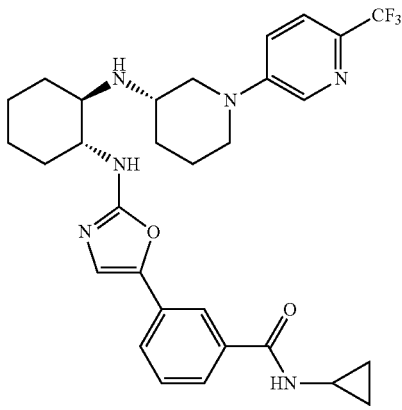 [SMILES: O=C(NC1CC1)c1cccc(-c2cnc(N[C@@H]3CCCC[C@H]3N[C@H]3CCCN(c4ccc(C(F)(F)F)nc4)C3)o2)c1]

To a solution of intermediate X 3TFA salt (40 mg, 0.046 mmol) in DMF (0.5 mL) was added cyclopropylamine (3.93 mg, 0.069 mmol), followed by BOP (20.3 mg, 0.046 mmol) and Et$_3$N (27.9 mg, 0.275 mmol). The reaction was allowed to stir at rt overnight. The reaction was diluted with water (4 mL), and then extracted with EtOAc (2×4 mL). Combined organics were concentrated. The resulting residue was purified using RP prep-HPLC method A to give the title compound, N-cyclopropyl-(3-(2-((1R,2R)-2((S)-1-(6-trifluoromethyl)pyridin-3yl)piperidin-3-ylamino) cyclohexylamino)oxazol-5-yl)benzamide 3TFA salt (17 mg, 0.018 mmol, 40% yield) as a white foam. Anal. Calcd. for C$_{30}$H$_{35}$F$_3$N$_6$O$_2$ m/z 568.28, found: 569.2 (M+H)$^+$; $^1$H NMR (400 MHz, METHANOL-D$_3$) δ ppm 8.25 (d, J=3.3 Hz, 1H), 7.80 (s, 1H), 7.69-7.55 (m, 1H), 7.45-7.36 (m, 2H), 7.32 (dd, J=8.8, 2.7 Hz, 1H), 7.26-7.20 (m, 1H), 7.19 (s, 1H), 3.86 (dd, J=13.5, 4.7 Hz, 1H), 3.72 (br. s., 1H), 3.65 (td, J=10.9, 4.7 Hz, 1H), 3.56-3.46 (m, 1H), 3.46-3.36 (m, 1H), 3.34 (s, 1H), 3.06 (ddd, J=12.6, 9.1, 3.6 Hz, 1H), 2.93-2.72 (m, 1H), 2.34 (d, J=13.2 Hz, 1H), 2.17 (d, J=14.3 Hz, 1H), 2.09-1.99 (m, 2H), 1.89 (dt, J=9.1, 4.8 Hz, 4H), 1.71-1.53 (m, 2H), 1.52-1.33 (m, 2H), 0.87-0.77 (m, 2H), 0.69-0.59 (m, 2H).

Example 100

Methyl (3-(2-((1R,2R)-2(S)-1-(4-trifluoromethyl)phenylpiperidin-3-ylamino)cyclohexylamino)oxazol-5-yl)phenylcarbamate

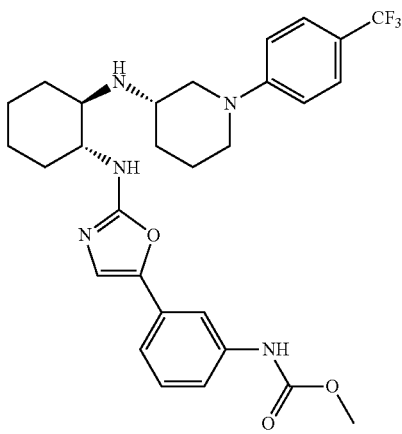 [SMILES: COC(=O)Nc1cccc(-c2cnc(N[C@@H]3CCCC[C@H]3N[C@H]3CCCN(c4ccc(C(F)(F)F)cc4)C3)o2)c1]

Methyl (3-(2-((1R,2R)-2(S)-1-(4-trifluoromethyl)phenylpiperidin-3-ylamino)cyclohexylamino)oxazol-5-yl)phenylcarbamate (16 mg, 0.028 mmol, 32%) was synthesized as described in General Procedure H using Intermediate 20 (30 mg, 0.088 mmol) and intermediate 43 (33 mg, 0.132 mmol). The product was purified using RP prep-HPLC method A, followed by neutralization using NaHCO$_3$ to give the title compound as an off-white powder. Anal. Calcd. for C$_{29}$H$_{34}$F$_3$N$_5$O$_3$ m/z 557.26, found: 558.3 (M+H)$^+$; $^1$H NMR (400 MHz, Methanol-d4) δ ppm 7.85 (s, 1H), 7.51 (s, 1H), 7.40 (d, J=8.7 Hz, 2H), 7.36-7.24 (m, 2H), 7.20 (dt, J=7.5, 1.5 Hz, 1H), 7.07 (d, J=8.7 Hz, 2H), 3.88 (td, J=10.9, 4.4 Hz, 1H), 3.81-3.57 (m, 6H), 3.54-3.38 (m, 2H), 3.20-3.05 (m, 1H), 2.38 (d, J=13.3 Hz, 1H), 2.28-2.11 (m, 2H), 2.06-1.76 (m, 5H), 1.75-1.56 (m, 2H), 1.49 (t, J=10.3 Hz, 2H).

Example 101

Methyl (3-(2-((1R,2R)-2(S)-1-(4-trifluoromethyl)phenylpiperidin-3-ylamino)cyclohexylamino)oxazol-5-yl)phenylcarbamate

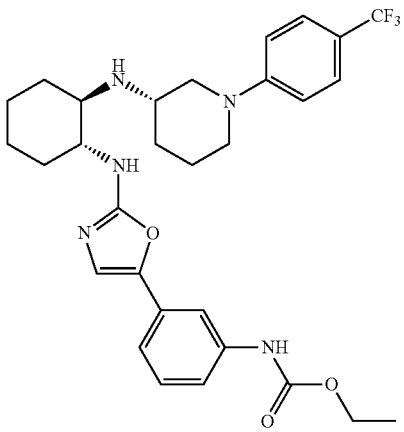 [SMILES: CCOC(=O)Nc1cccc(-c2cnc(N[C@@H]3CCCC[C@H]3N[C@H]3CCCN(c4ccc(C(F)(F)F)cc4)C3)o2)c1]

Ethyl (3-(2-((1R,2R)-2(S)-1-(4-trifluoromethyl)phenylpiperidin-3-ylamino)cyclohexylamino)oxazol-5-yl)phenylcarbamate (88 mg, 0.439 mmol, 35%) was synthesized as described in General Procedure H using Intermediate 20 (150 mg, 0.088 mmol) and intermediate 44 (164 mg, 0.615 mmol). The product was purified using RP prep-HPLC method A, followed by neutralization using NaHCO$_3$ to give the title compound as an off-white powder. Anal. Calcd. for C$_{30}$H$_{36}$F$_3$N$_5$O$_3$ m/z 571.28, found: 572.2 (M+H)$^+$; $^1$H NMR (400 MHz, Methanol-d4) δ ppm 7.68 (s, 1H), 7.32 (d, J=8.7 Hz, 2H), 7.26-7.17 (m, 2H), 7.12 (dd, J=7.1, 1.7 Hz, 1H), 7.07 (s, 1H), 6.92 (d, J=8.8 Hz, 2H), 4.18 (q, J=7.0 Hz, 2H), 3.58 (d, J=12.2 Hz, 1H), 3.50-3.35 (m, 2H), 3.05-2.86 (m, 2H), 2.86-2.64 (m, 2H), 2.18-2.03 (m, 2H), 1.99-1.86 (m, 1H), 1.84-1.71 (m, 3H), 1.70-1.57 (m, 1H), 1.53-1.18 (m, 8H).

Example 102

(Ethyl (3-(2-((1R,2R)-2((S)-1-(6-trifluoromethyl)pyridin-3-yl)piperidin-3-ylamino)cyclohexylamino)oxazol-5-yl)phenylcarbamate

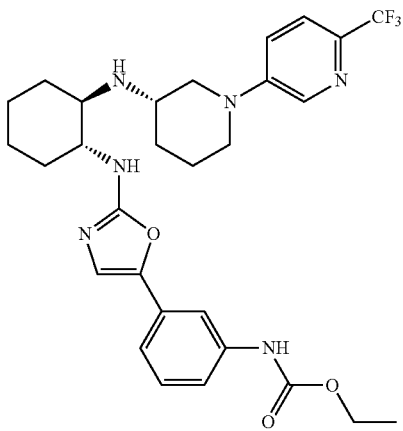 [SMILES: CCOC(=O)Nc1cccc(-c2cnc(N[C@@H]3CCCC[C@H]3N[C@H]3CCCN(c4ccc(C(F)(F)F)nc4)C3)o2)c1]

Methyl (3-(2-((1R,2R)-2(S)-1-(4-trifluoromethyl)phenylpiperidin-3-ylamino)cyclohexylamino)oxazol-5-yl)phenylcarbamate (16 mg, 0.028 mmol, 32%) was synthesized as described in General Procedure H using Intermediate 50 (30 mg, 0.088 mmol) and intermediate 44 (33 mg, 0.132 mmol). The product was purified using RP prep-HPLC method A, followed by neutralization using NaHCO$_3$ to give the title compound as an off-white powder. Anal. Calcd. for C$_{29}$H$_{34}$F$_3$N$_5$O$_3$ m/z 572.27, found: 573.3 (M+H)$^+$; $^1$H NMR (400 MHz, METHANOL-d$_4$) δ ppm 8.26 (d, J=2.8 Hz, 1H), 7.65 (s, 1H), 7.40 (d, J=8.8 Hz, 1H), 7.33-7.16 (m, 3H), 7.10 (dt, J=6.9, 1.7 Hz, 1H), 7.06 (s, 1H), 4.18 (q, J=7.1 Hz, 2H), 3.66 (d, J=10.9 Hz, 1H), 3.59-3.46 (m, 1H), 3.43-3.33 (m, 1H), 3.08-2.95 (m, 1H), 2.93-2.78 (m, 2H), 2.74-2.62 (m, 1H), 2.10 (d, J=10.6 Hz, 2H), 2.01-1.89 (m, 1H), 1.87-1.72 (m, 3H), 1.72-1.58 (m, 1H), 1.52-1.20 (m, 8H)

Example 103

Methyl (3-(2-((1R,2R)-2((S)-1-(2-trifluoromethyl)pyrimidin-5-yl)piperidin-3-ylamino)cyclohexylamino)oxazol-5-yl)phenylcarbamate

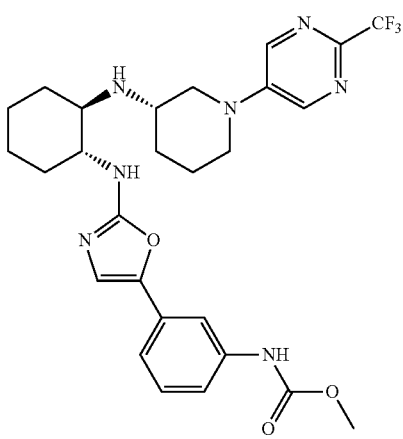 [SMILES: COC(=O)Nc1cccc(-c2cnc(N[C@@H]3CCCC[C@H]3N[C@H]3CCCN(c4cnc(C(F)(F)F)nc4)C3)o2)c1]

Methyl (3-(2-((1R,2R)-2((S)-1-(2-trifluoromethyl)pyrimidin-5-yl)piperidin-3-ylamino)cyclohexylamino)oxazol-5-yl)phenylcarbamate.TFA salt (16 mg, 32%) was synthesized as described in General Procedure H using Intermediate 51 (30 mg, 0.088 mmol) and intermediate 43 (33 mg, 0.132 mmol). The product was purified using RP prep-HPLC method A to give the title compound as an off-white foam. Anal. Calcd. for C$_{29}$H$_{34}$F$_3$N$_5$O$_3$ m/z 559.25, found: 560.3 (M+H)$^+$; $^1$H NMR (400 MHz, CHLOROFORM-d) δ ppm 8.45 (s, 2H), 7.57-7.37 (m, 2H), 7.36-7.21 (m, 1H), 7.10 (d, J=7.1 Hz, 1H), 7.05 (s, 1H), 4.19 (br. s., 1H), 4.01 (d, J=11.0 Hz, 1H), 3.87-3.65 (m, 4H), 3.56-3.39 (m, 2H), 3.31-3.16 (m, 1H), 2.94 (t, J=10.7 Hz, 1H), 2.38-2.13 (m, 4H), 2.06-1.84 (m, 4H), 1.83-1.55 (m, 2H), 1.54-1.32 (m, 2H).

Example 104

(3-(2-((1R,2R)-2((S)-1-(4-trifluoromethyl)phenyl)piperidin-3-ylamino)cyclohexylamino)oxazol-5-yl)benzamide

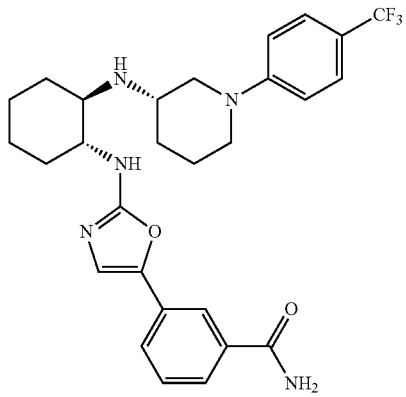 [SMILES: NC(=O)c1cccc(-c2cnc(N[C@@H]3CCCC[C@H]3N[C@H]3CCCN(c4ccc(C(F)(F)F)cc4)C3)o2)c1]

(3-(2-((1R,2R)-2((S)-1-(4-trifluoromethyl)phenyl)piperidin-3-ylamino)cyclohexylamino)oxazol-5-yl)benzamide was synthesized as described in General Procedure H using Intermediate 20 (200 mg, 0.586 mmol) and Intermediate 41 (163 mg, 0.732 mmol). The product was purified using chromatography (24 g silica gel cartridge) eluting with EtOAc/hexanes (0-100%, 15 min; 100%, 5 min; 5% MeOH/EtOAc, 15 min) to give the title compound as a white solid. Anal. Calcd. for C$_{28}$H$_{32}$F$_3$N$_5$O$_2$ m/z 527.25, found: 528.2 (M+H)$^+$; $^1$H NMR (400 MHz, Methanol-d4) δ ppm 8.06 (s, 1H), 7.82 (d, J=7.6 Hz, 1H), 7.62 (d, J=7.6 Hz, 1H), 7.54-7.45 (m, 2H), 7.34 (d, J=8.6 Hz, 2H), 7.04 (d, J=8.6 Hz, 2H), 3.87 (br. s., 1H), 3.77-3.56 (m, 3H), 3.52-3.40 (m, 2H), 3.27-3.16 (m, 1H), 2.38 (d, J=12.9 Hz, 1H), 2.22 (d, J=13.9 Hz, 1H), 2.14 (d, J=4.0 Hz, 1H), 2.03-1.78 (m, 5H), 1.75-1.56 (m, 2H), 1.55-1.42 (m, 2H).

Example 105

N-Methyl (3-(2-((1R,2R)-2((S)-1-(4-trifluoromethyl)phenyl)piperidin-3-ylamino)cyclohexylamino)oxazol-5-yl)benzamide

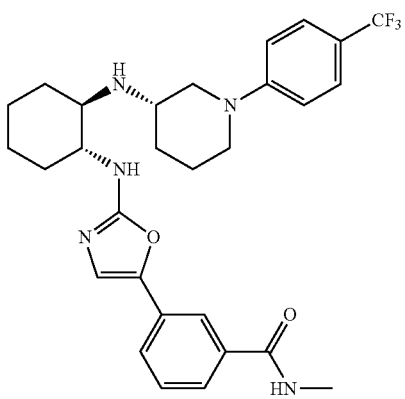 [SMILES: CNC(=O)c1cccc(-c2cnc(N[C@@H]3CCCC[C@H]3N[C@H]3CCCN(c4ccc(C(F)(F)F)cc4)C3)o2)c1]

A: Methyl 3-(2-((1R,2R)-2-((S)-1-(4-trifluoromethyl)phenyl)piperidin-3-ylamino)cyclohexylamino)oxazol-5-yl)benzoate

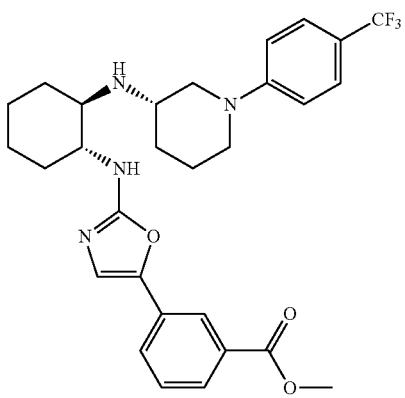 [SMILES: COC(=O)c1cccc(-c2cnc(N[C@@H]3CCCC[C@H]3N[C@H]3CCCN(c4ccc(C(F)(F)F)cc4)C3)o2)c1]

Methyl 3-(2-((1R,2R)-2-((S)-1-(4-(trifluoromethyl)phenyl)piperidin-3-ylamino)cyclohexylamino)oxazol-5-yl)benzoate (472 mg, 0.818 mmol, 68% yield) was synthesized as described in General Procedure H using Intermediate 20 (410 mg, 1.20 mmol) and Intermediate 45 (358 mg, 1.506 mmol). The product was purified using chromatography (40 g silica gel cartridge) eluting with EtOAc/hexanes (30-100%) to give the title compound as a pale yellow oil. Anal. Calcd. for $C_{29}H_{33}F_3N_4O_3$ m/z 542.25, found: 543.2

B: 3-(2-(((1R,2R)-2-((S)-1-(4-(Trifluoromethyl)phenyl)piperidin-3-ylamino)cyclohexylamino)oxazol-5-yl)benzoic acid

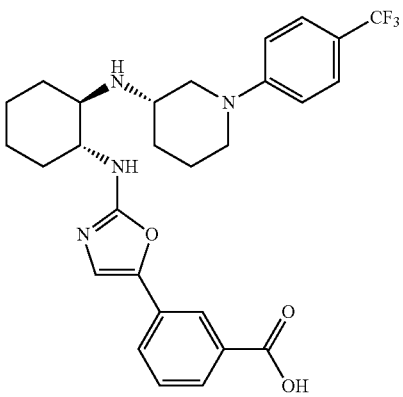 [SMILES: O=C(O)c1cccc(-c2cnc(N[C@@H]3CCCC[C@H]3N[C@H]3CCCN(c4ccc(C(F)(F)F)cc4)C3)o2)c1]

Methyl 3-(2-(((1R,2R)-2-(((S)-1-(4-(trifluoromethyl)phenyl)piperidin-3-yl)amino)cyclohexyl)amino)oxazol-5-yl)benzoate (470 mg, 0.866 mmol) was dissolved in a mixed solvent of MeOH (3.5 mL) and THF (3.5 mL), then 2 M of aqueous LiOH (7 mL, 14 mmol) was added. The resultant mixture was stirred at rt for 16 h. LC/MS check showed the reaction was completed. The reaction was cooled in an ice-bath, 3 M HCl was added dropwise to adjust pH ~3. The reaction mixture was concentrated. The resulting residue was purified using prep HPLC (Phenomenex Luna Axia, 5μ, 30×100 mm, 40-80% B, gradient over 10 min, hold at 80% B for 2 min). The desired fractions were concentraed to almost dryness, and the residue was lyophilized in CH$_3$CN—H$_2$O to afford the title compound (2 TFA salt) as a beign colored powder (465 mg, 0.615 mmol, 71.0% yield). Anal. Calcd. for $C_{28}H_{31}F_3N_4O_3$ m/z 528.2, found: 529.1.

C: N-Methyl (3-(2-((1R,2R)-2((S)-1-(4-trifluoromethyl)phenyl)piperidin-3-ylamino)cyclohexylamino)oxazol-5-yl)benzamide

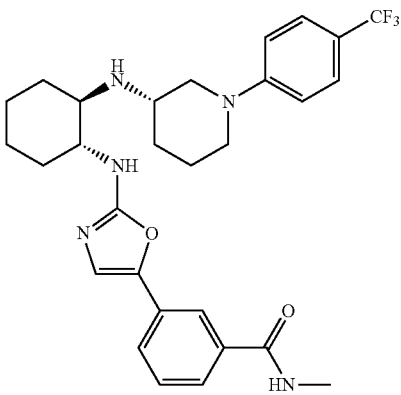 [SMILES: CNC(=O)c1cccc(-c2cnc(N[C@@H]3CCCC[C@H]3N[C@H]3CCCN(c4ccc(C(F)(F)F)cc4)C3)o2)c1]

N-Methyl (3-(2-((1R,2R)-2((S)-1-(4-trifluoromethyl)phenyl)piperidin-3-ylamino)cyclohexylamino)oxazol-5-yl)benzamide (123 mg, 0.224 mmol, 81% yield) was synthesized as described in Scheme 8 using Intermediate 3-(2-(((1R,2R)-2-((S)-1-(4-(Trifluoromethyl)phenyl)piperidin-3-ylamino)cyclohexylamino)oxazol-5-yl)benzoic acid (210 mg, 0.5278 mmol) and methylamine (17.3 mg, 0.555 mmol). The product was purified using chromatography (24 g silica gel cartridge) eluting with EtOAc/hexanes (50-100%) to give the title compound as a white solid. Anal. Calcd. for $C_{29}H_{34}F_3N_5O_2$ m/z 541.27, found: 542.1 (M+H); $^1$H NMR (400 MHz, METHANOL-$D_3$) δ ppm 7.88 (s, 1H), 7.67 (d, J=7.7 Hz, 1H), 7.51-7.38 (m, 2H), 7.30-7.19 (m, 3H), 6.94 (d, J=7.1 Hz, 2H), 3.76-3.60 (m, 3H), 3.43-3.33 (m, 2H), 3.33-3.25 (m, 1H), 3.12-2.99 (m, 1H), 2.94 (d, J=2.7 Hz, 3H), 2.34 (d, J=11.5 Hz, 1H), 2.17 (d, J=12.6 Hz, 1H), 2.08-1.78 (m, 6H), 1.70-1.51 (m, 2H), 1.51-1.36 (m, 2H).

Example 106

3-(2-(((1R,2R)-2-(((S)-3-Methyl-1-(4-(trifluoromethyl)phenyl)piperidin-3-yl)amino)cyclohexyl)amino)oxazol-5-yl)benzamide

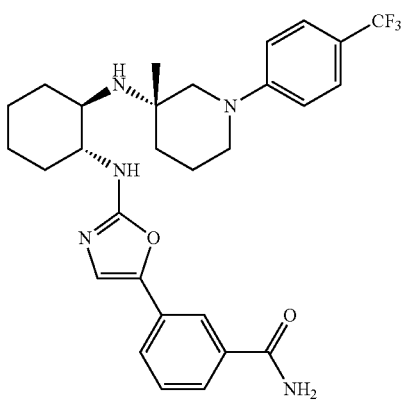 [SMILES: C[C@]1(N[C@@H]2CCCC[C@H]2Nc2ncc(-c3cccc(C(N)=O)c3)o2)CCCN(c2ccc(C(F)(F)F)cc2)C1]

3-(2-(((1R,2R)-2-(((S)-3-Methyl-1-(4-(trifluoromethyl)phenyl)piperidin-3-yl)amino)cyclohexyl)amino)oxazol-5-yl)benzamide was synthesized as described in General Procedure H using Intermediate 48 (300 mg, 0.844 mmol) and Intermediate 41 (207 mg, 0.928 mmol)). The product was purified using ISCO chromatography (24 g silica gel cartridge) eluting with 10% methanol in chloroform followed by normal phase HPLC (method:column Chiral Pak IA (19×250 mm), 5 uM, mobile phase nHexane:Ethanol (60:40)) to give the title compound (73 mg, 0.133 mmol, 15.7 yields) as a off white solid. Anal. Calcd. for $C_{29}H_{34}F_3N_5O_2$ m/z 541.2, found: 542.2 (M+H)$^+$; $^1$H NMR (400 MHz, CD$_3$OD) δ ppm 7.89 (t, J=1.5 Hz, 1 H), 7.70 (dt, J=7.5 Hz, 1.5 Hz, 1 H), 7.49-7.39 (m, 2 H), 7.33 (d, J=8.8 Hz, 2 H), 7.18 (s, 1 H), 6.99 (d, J=8.8 Hz, 2 H), 3.35-3.29 (m, 3 H), 2.89 (t, J=9.5 Hz, 2 H), 2.79 (d, J=12.3 Hz, 1 H), 2.74-2.63 (m, 1 H), 2.21-2.06 (m, 2 H), 1.95-1.84 (m, 1 H), 1.82-1.63 (m, 4 H), 1.55-1.29 (m, 5 H), 1.18 (s, 3 H).

Example 107

Ethyl (3-(2-(((1R,2R)-2-(((S)-1-(2-(trifluoromethyl)pyrimidin-5-yl)piperidin-3-yl)amino)cyclohexyl)amino)oxazol-5-yl)phenyl)carbamate

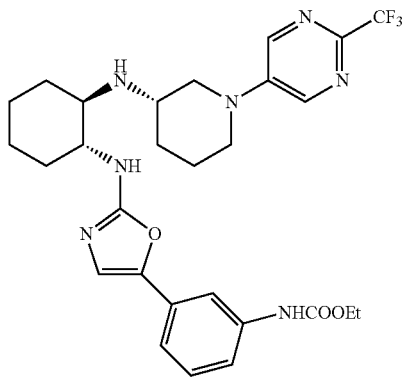

Ethyl (3-(2-(((1R,2R)-2-(((S)-1-(2-(trifluoromethyl)pyrimidin-5-yl)piperidin-3-yl)amino)cyclohexyl)amino)oxazol-5-yl)phenyl)carbamate was synthesized as described in General Procedure H using Intermediate 51 (250 mg, 0.728 mmol) and Intermediate 44 (194 mg, 0.728 mmol). The product was purified using ISCO chromatography (12 g silica gel cartridge) eluting with 10% methanol in chloroform followed by RP Prep-HPLC method 2 to give the title compound (161 mg, 0.281 mmol, 38.6% yield) as off white solid. Anal. Calcd. for $C_{28}H_{34}F_3N_7O_3$ m/z 573.3, found: 574.2 (M+H)$^+$; $^1$H NMR (400 MHz, CD$_3$OD) δ ppm 8.49 (s, 2 H), 7.69 (s, 1H), 7.28-7.21 (m, 2H), 7.15 (dt, J=6.8 Hz, 1.8 Hz, 1H), 7.07 (s, 1H), 4.21 (q, J=7.3 Hz, 2H), 3.80 (d, J=9 Hz, 1H), 3.69-3.61 (m, 1 H), 3.44-3.34 (m, 1H), 3.10-3.01 (m, 1H), 2.93-2.82 (m, 2 H), 2.71-2.63 (m, 1 H), 2.19-2.09 (m, 2 H), 2.01-1.92 (m, 1 H), 1.90-1.63 (m, 4H), 1.51-1.36 (m, 4 H), 1.33 (t, J=7 Hz, 3H); $^{19}$F NMR (400 MHz, CD$_3$OD) δ ppm-70.31 (s, 3 F).

Example 108 and Example 109

(Z)-tert-butyl 3-(2-(((1R,2R)-2-(((S)-1-(4-cyanophenyl)piperidin-3-yl)amino)cyclohexyl)amino)pyridin-4-yl)acrylate and (E)-tert-butyl 3-(2-(((1R,2R)-2-(((S)-1-(4-cyanophenyl)piperidin-3-yl)amino)cyclohexyl)amino)pyridin-4-yl)acrylate

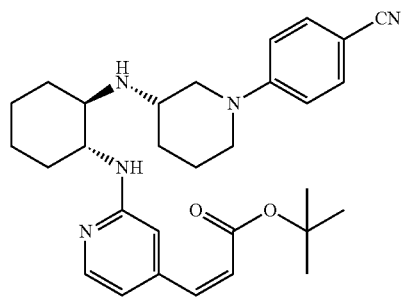

-continued

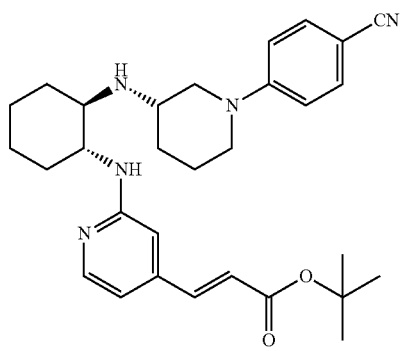

A: 4-((S)-3-(((1R,2R)-2-((4-formylpyridin-2-yl)amino)cyclohexyl)amino)piperidin-1-yl)benzonitrile

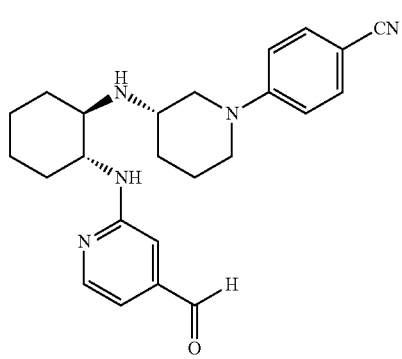 [SMILES: N#Cc1ccc(N2CCC[C@H](N[C@@H]3CCCC[C@H]3Nc3cc(C=O)ccn3)C2)cc1]

To a pressure apparatus was added 4-((S)-3-(1R,2R)-2-((4-bromopyridin-2-yl)amino)cyclohexyl)amino)piperidin-1-yl)benzonitrile (600 mg, 1.320 mmol), dichloro[1,3-bis(diphenylphosphino)propane]palladium(II) (23.36 mg, 0.040 mmol), triethylsilane (0.422 mL, 2.64 mmol), Na$_2$CO$_3$ (140 mg, 1.320 mmol) and DMF (2.5 mL). The apparatus was sealed and equipped with CO gas pressure line. The reaction was stirred under CO gas 30 psi at 80° C. overnight. The reaction was cooled and the reaction was diluted with EtOAc (30 ml). The organic layer was washed with water (3×10 ml) and saturated NaCl solution (10 ml), dried over MgSO$_4$, filtered and concentrated. The crude product was purified using ISCO system (0-80% EtOAc/Hex) to give 4-((S)-3-(((1R,2R)-2-((4-formylpyridin-2-yl)amino)cyclohexyl)amino)piperidin-1-yl)benzonitrile (520 mg, 1.289 mmol, 98% yield) as a yellow semi solid. Anal. Calcd. for C$_{24}$H$_{29}$N$_5$O m/z 403.2, found: 404.4 (M+H)$^+$; $^1$H NMR (400 MHz, CHLOROFORM-d) δ ppm 9.88 (s, 1H), 8.24 (d, J=4.9 Hz, 1H), 7.45-7.38 (m, 2H), 6.93 (dd, J=4.9, 1.1 Hz, 1H), 6.75-6.69 (m, 3H), 4.64 (d, J=7.7 Hz, 1H), 3.63-3.53 (m, 1H), 3.52-3.43 (m, 2H), 2.98-2.89 (m, 1H), 2.83-2.75 (m, 1H), 2.74-2.65 (m, 1H), 2.47 (td, J=9.9, 3.8 Hz, 1H), 2.22-2.02 (m, 2H), 1.93-1.82 (m, 1H), 1.80-1.67 (m, 3H), 1.39-1.18 (m, 5H).

B: (Z)-tert-butyl 3-(2-(((1R,2R)-2-(((S)-1-(4-cyanophenyl)piperidin-3-yl)amino)cyclohexyl)amino)pyridin-4-yl)acrylate and (E)-tert-butyl 3-(2-(((1R,2R)-2-(((S)-1-(4-cyanophenyl)piperidin-3-yl)amino)cyclohexyl)amino)pyridin-4-yl)acrylate

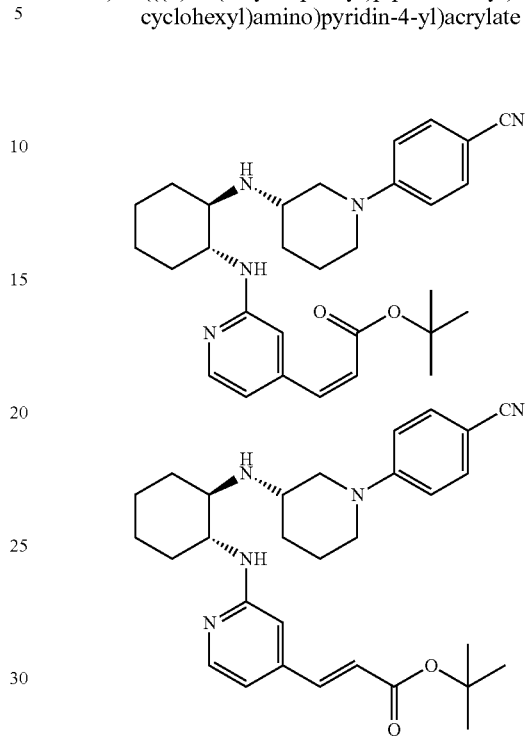

To a round bottom flask was added (2-(tert-butoxy)-2-oxoethyl)triphenylphosphonium chloride (98 mg, 0.238 mmol) and diethyl ether (1 mL). The reaction was cooled to −78° C. and nBuLi (0.119 mL, 0.297 mmol) was added to the reaction. The reaction was stirred at −78° C. for 30 mins before 4-((S)-3-(1R,2R)-2-((4-formylpyridin-2-yl)amino)cyclohexyl)amino)piperidin-1-yl)benzonitrile (80 mg, 0.198 mmol) was added to the reaction. The reaction was slowly warmed up to rt over 2 hrs. The reaction was concentrated and purified by RP Prep-HPLC to give (Z)-tert-butyl 3-(2-(((1R,2R)-2-(((S)-1-(4-cyanophenyl)piperidin-3-yl)amino)cyclohexyl)amino)pyridin-4-yl)acrylate (30 mg, 0.046 mmol, 23.5% yield) as a beige solid and (E)-tert-butyl 3-(2-(((1R,2R)-2-(((S)-1-(4-cyanophenyl)piperidin-3-yl)amino)cyclohexyl)amino)pyridin-4-yl)acrylate (60 mg, 0.093 mmol, 46.7% yield) as an off white solid. (Z)-tert-butyl 3-(2-(((1R,2R)-2-(((S)-1-(4-cyanophenyl)piperidin-3-yl)amino)cyclohexyl)amino)pyridin-4-yl)acrylate: Anal. Calcd. for C$_{30}$H$_{39}$N$_5$O$_2$ m/z 501.3, found: 502.5 (M+H)$^+$; $^1$H NMR (400 MHz, CHLOROFORM-d) δ ppm 7.61 (d, J=6.6 Hz, 1H), 7.53-7.43 (m, 2H), 6.98 (s, 1H), 6.92-6.80 (m, 3H), 6.71 (d, J=6.6 Hz, 1H), 6.14 (d, J=12.1 Hz, 1H), 3.74 (d, J=12.1 Hz, 1H), 3.59-3.18 (m, 4H), 3.07-2.86 (m, 1H), 2.24 (d, J=13.2 Hz, 1H), 2.13 (br. s., 2H), 2.00-1.79 (m, 4H), 1.78-1.67 (m, 1H), 1.49-1.33 (m, 12H), 1.31-1.26 (m, 1H)

(E)-tert-butyl 3-(2-(((1R,2R)-2-(((S)-1-(4-cyanophenyl)piperidin-3-yl)amino)cyclohexyl)amino)pyridin-4-yl)acrylate: Anal. Calcd. for C$_{30}$H$_{39}$N$_5$O$_2$ m/z 501.3, found: 502.5 (M+H)$^+$; $^1$H NMR (400 MHz, METHANOL-D$_3$) δ ppm 7.93 (d, J=6.0 Hz, 1H), 7.35-7.28 (m, 2H), 7.18 (dt, J=16.1, 3.0 Hz, 1H), 6.81-6.69 (m, 3H), 6.46-6.35 (m, 1H), 6.29 (br. s., 1H), 3.85 (br. s., 1H), 3.75-3.63 (m, 1H), 3.62-3.56 (m, 1H), 3.47 (dt, J=3.3, 1.6 Hz, 1H), 3.21-3.03 (m, 2H), 2.86 (br. s., 1H), 2.32 (d, J=13.2 Hz, 1H), 2.11 (d, J=13.7 Hz, 1H), 2.00 (d, J=18.1 Hz, 2H), 1.93-1.80 (m, 4H), 1.66-1.57 (m, 1H), 1.54 (s, 9H), 1.45-1.36 (m, 2H), 1.34-1.30 (m, 1H)

Example 110

(Z)-3-(2-(((1R,2R)-2-(((S)-1-(4-cyanophenyl)piperidin-3-yl)amino)cyclohexyl)amino)pyridin-4-yl)acrylamide

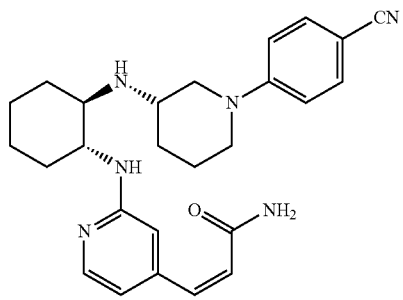

A: (Z)-3-(2-(((1R,2R)-2-(((S)-1-(4-cyanophenyl)piperidin-3-yl)amino)cyclohexyl)amino) pyridin-4-yl)acrylic acid

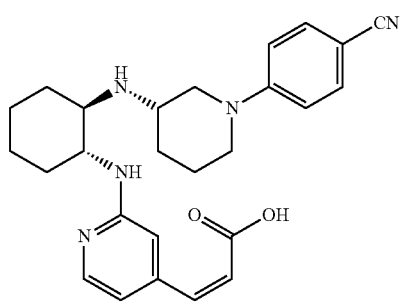

To a round bottom flask was aded (Z)-tert-butyl 3-(2-(((1R,2R)-2-(((S)-1-(4-cyanophenyl)piperidin-3-yl)amino)cyclohexyl)amino)pyridin-4-yl)acrylate (30 mg, 0.060 mmol), TFA (1 mL) and CH$_2$Cl$_2$ (1 mL). The reaction was stirred at rt overnight. The reaction was concentrated and dried to give (Z)-3-(2-(((1R,2R)-2-(((S)-1-(4-cyanophenyl)piperidin-3-yl)amino)cyclohexyl)amino)pyridin-4-yl)acrylic acid (29 mg, 0.049 mmol, 82% yield) as a beige solid. Anal. Calcd. for C$_{26}$H$_{31}$N$_5$O$_2$ m/z 445.5, found: 446.4 (M+H)$^+$.

B: (Z)-3-(2-(((1R,2R)-2-(((S)-1-(4-cyanophenyl)piperidin-3-yl)amino)cyclohexyl)amino) pyridin-4-yl)acrylamide

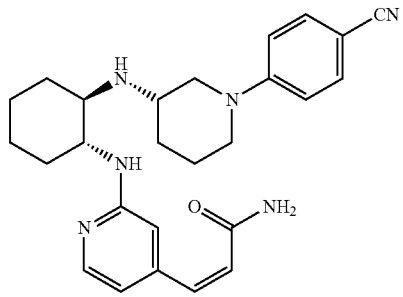

To a round bottom flask was added (Z)-3-(2-(((1R,2R)-2-(((S)-1-(4-cyanophenyl)piperidin-3-yl)amino)cyclohexyl)

amino)pyridin-4-yl)acrylic acid (35 mg, 0.063 mmol), THF (0.8 mL) and Et3N (0.026 mL, 0.188 mmol). The reaction was cooled to 0° C. Then isobutyl chloroformate (9.04 µl, 0.069 mmol) was added to the reaction and the reaction was stirred at 0° C. for 15 mins before ammonia (0.045 mL, 0.313 mmol) in methanol was added to the reaction. The reaction was stirred at 0° C. for 30 mins. The reaction was concentrated and purified using RP prep-HPLC. The desired fraction was concentrated to give (Z)-3-(2-(((1R,2R)-2-(((S)-1-(4-cyanophenyl)piperidin-3-yl)amino)cyclohexyl)amino)pyridin-4-yl)acrylamide (8 mg, 0.014 mmol, 21.98% yield) as a light brown film. Anal. Calcd. for C$_{26}$H$_{32}$N$_6$O m/z 444.3, found: 445.5 (M+H)$^+$; $^1$H NMR (400 MHz, METHANOL-D$_4$) δ ppm 7.87 (d, J=6.6 Hz, 1H), 7.47 (d, J=8.8 Hz, 2H), 7.00-6.89 (m, 3H), 6.84 (br. s., 1H), 6.67 (d, J=12.6 Hz, 1H), 6.35 (d, J=12.6 Hz, 1H), 3.88-3.67 (m, 2H), 3.63-3.52 (m, 1H), 3.50-3.42 (m, 1H), 3.40-3.33 (m, 2H), 3.18-3.08 (m, 1H), 2.34 (d, J=12.6 Hz, 1H), 2.14 (dd, J=9.6, 3.0 Hz, 2H), 1.91-1.72 (m, 4H), 1.66-1.53 (m, 1H), 1.52-1.40 (m, 3H), 1.33-1.26 (m, 1H)

Example 111

(2-(((1R,2R)-2-(((S)-1-(4-cyanophenyl)piperidin-3-yl)amino)cyclohexyl)amino)pyridin-4-yl)methyl pivalate

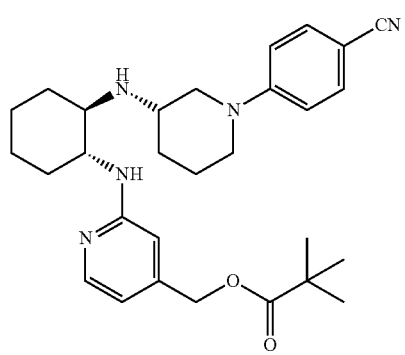

A: 4-((S)-3-(((1R,2R)-2-((4-(hydroxymethyl)pyridin-2-yl)amino)cyclohexyl)amino) piperidin-1-yl) benzonitrile

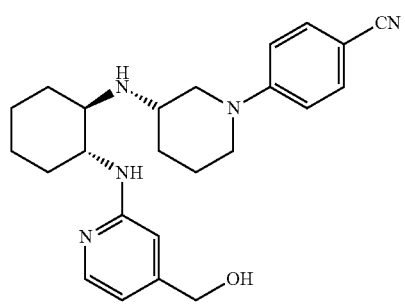

To a round bottom flask was added 4-((S)-3-(((1R,2R)-2-((4-formylpyridin-2-yl)amino)cyclohexyl)amino)piperidin-1-yl)benzonitrile (100 mg, 0.248 mmol) and THF (1 mL). The reaction was cooled to 0° C. and NaBH$_4$ (9.38 mg, 0.248 mmol) was added to the reaction. The reaction was stirred at 0° C. for 2 hrs. The reaction was quenched with 1N NH$_4$Cl (0.5 ml) and then diluted with EtOAc (30 ml). The organics was washed with water (2×15 ml) and saturated NaCl solution (15 ml). The organic layer dried over MgSO$_4$, filtered and concentrated. The residue was purified using ISCO system (0-100% EtOAc/Hex) to give 4-((S)-3-(((1R,2R)-2-((4-(hydroxymethyl)pyridin-2-yl)amino)cyclohexyl)amino)piperidin-1-yl)benzonitrile (23 mg, 0.054 mmol, 21.74% yield) as white solid. Anal. Calcd. for C$_{24}$H$_{31}$N$_5$O m/z 405.3, found: 406.2 (M+H)$^+$; $^1$H NMR (400 MHz, METHANOL-D$_4$) δ ppm 8.07-7.97 (m, 1H), 7.45 (d, J=8.8 Hz, 2H), 6.93 (d, J=9.3 Hz, 3H), 6.62-6.51 (m, 1H), 4.60 (s, 2H), 3.86-3.75 (m, 1H), 3.71-3.62 (m, 1H), 3.37-3.33 (m, 1H), 2.95-2.84 (m, 1H), 2.83-2.59 (m, 3H), 2.16-2.04 (m, 2H), 2.01-1.92 (m, 1H), 1.82-1.72 (m, 2H), 1.68-1.55 (m, 1H), 1.45-1.23 (m, 6H).

B: (2-(((1R,2R)-2-(((S)-1-(4-cyanophenyl)piperidin-3-yl)amino)cyclohexyl)amino) pyridin-4-yl)methyl pivalate

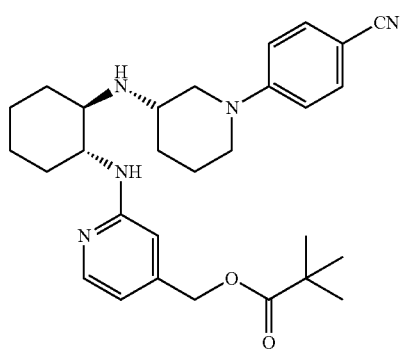

To a round bottom flask was added 4-((S)-3-(1R,2R)-2-((4-(hydroxymethyl)pyridin-2-yl)amino)cyclohexyl)amino)piperidin-1-yl)benzonitrile (10 mg, 0.025 mmol), pivaloyl chloride (3.64 μl, 0.030 mmol), DMAP (3.01 mg, 0.025 mmol), Et3N (6.87 μl, 0.049 mmol) and CH$_2$Cl$_2$ (0.5 mL). The reaction was stirred at rt overnight. The reaction was concentrated and purified using RP prep-HPLC to give (2-(((1R,2R)-2-(((S)-1-(4-cyanophenyl)piperidin-3-yl)amino)cyclohexyl)amino)pyridin-4-yl)methyl pivalate (3.4 mg, 0.0069 mmol, 27.6% yield) as a clear film. Anal. Calcd. for C$_{29}$H$_{39}$N$_5$O$_2$ m/z 489.3, found: 490 (M+H)$^+$; $^1$H NMR (400 MHz, METHANOL-D$_4$) δ ppm 7.44 (d, J=8.8 Hz, 2H), 6.79 (d, J=8.8 Hz, 2H), 6.51 (d, J=5.5 Hz, 1H), 6.36 (s, 1H), 4.97 (s, 2H), 3.62 (d, J=9.6 Hz, 1H), 3.57-3.47 (m, 2H), 3.06-2.94 (m, 1H), 2.89-2.78 (m, 2H), 2.63-2.52 (m, 1H), 2.14-2.01 (m, 2H), 1.95 (s, 1H), 1.77 (d, J=12.1 Hz, 3H), 1.68-1.55 (m, 1H), 1.47-1.28 (m, 5H), 1.25 (s, 9H).

Example 112

N-(1,3,4-thiadiazol-2-yl)-2-(1R,2R)-2-(((S)-1-(4-(trifluoromethyl)phenyl)piperidin-3-yl)amino)cyclohexyl)amino)isonicotinamide

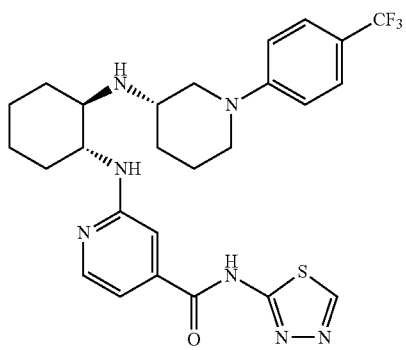 [SMILES: O=C(Nc1nncs1)c1ccnc(N[C@@H]2CCCC[C@H]2N[C@H]2CCCN(c3ccc(C(F)(F)F)cc3)C2)c1]

A: 2-(((1R,2R)-2-(((S)-1-(4-(trifluoromethyl)phenyl)piperidin-3-yl)amino)cyclohexyl)amino)isonicotinic acid

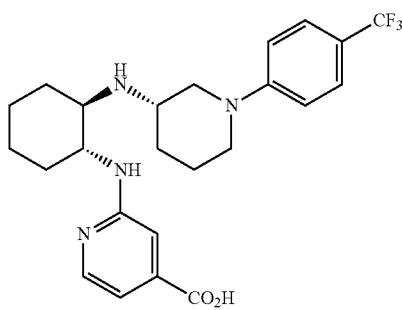 [SMILES: O=C(O)c1ccnc(N[C@@H]2CCCC[C@H]2N[C@H]2CCCN(c3ccc(C(F)(F)F)cc3)C2)c1]

A mixture of (1R,2R)—N1-(4-bromopyridin-2-yl)-N2-((S)-1-(4-(trifluoromethyl)phenyl)piperidin-3-yl)cyclohexane-1,2-diamine (40 mg, 0.080 mmol), potassium acetate (31.6 mg, 0.322 mmol), palladium(II) acetate (3.6 mg, 0.016 mmol) and 1,1'-bis(diphenylphosphino)ferrocene (35.7 mg, 0.064 mmol) in DMSO (0.5 mL) was purged with carbon monoxide for 5 min, then stirred under a CO balloon at 60° C. for 14 hr. DMSO was removed by vacuum and the residue was dissolved in acetonitrile, filtered, and the filtrate was concentrated. The residue was purified by RP prep-HPLC (method C) to afford 2-(((1R,2R)-2-(((S)-1-(4-(trifluoromethyl)phenyl)piperidin-3-yl)amino)cyclohexyl)amino)isonicotinic acid (32 mg, 0.056 mmol, 69% yield).

B: N-(1,3,4-thiadiazol-2-yl)-2-(1R,2R)-2-(((S)-1-(4-(trifluoromethyl)phenyl)piperidin-3-yl)amino)cyclohexyl)amino)isonicotinamide

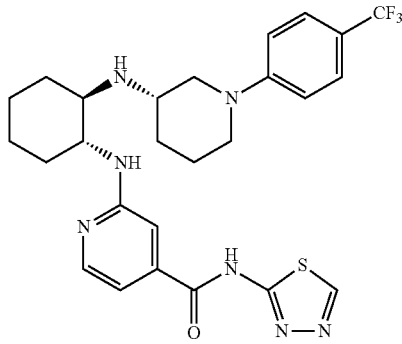 [SMILES: O=C(Nc1nncs1)c1ccnc(N[C@@H]2CCCC[C@H]2N[C@H]2CCCN(c3ccc(C(F)(F)F)cc3)C2)c1]

A solution of 2-(((1R,2R)-2-(((S)-1-(4-(trifluoromethyl)phenyl)piperidin-3-yl)amino)cyclohexyl)amino)isonicotinic acid, TFA (32 mg, 0.056 mmol) and 1,3,4-thiadiazol-2-amine (11.8 mg, 0.117 mmol) in DMF (0.4 mL) was treated with N,N-Diisopropylethylamine (0.02 mL, 0.111 mmol) and HATU (21.1 mg, 0.056 mmol), then stirred at rt for 16 hr. The reaction mixture was concentrated and purified by RP prep-HPLC (Method C) to afford N-(1,3,4-thiadiazol-2-yl)-2-(((1R,2R)-2-(((S)-1-(4-(trifluoromethyl)phenyl)piperidin-3-yl)amino)cyclohexyl)amino)isonicotinamide, TFA (11 mg, 0.016 mmol, 28% yield) as a tan solid. Anal. Calcd. for $C_{26}H_{30}F_3N_7OS$ m/z 545.2, found: 546.2 $(M+H)^+$; $^1H$ NMR (400 MHz, $CDCl_3$) δ ppm 8.80 (s, 1H), 7.67-7.61 (m, 1H), 7.51 (d, J=8.5 Hz, 2H), 7.46 (d, J=8.3 Hz, 1H), 7.29 (br. s., 1H), 7.01 (d, J=8.5 Hz, 2H), 4.37 (br. s., 1H), 3.97 (br. s., 1H), 3.60-3.51 (m, 4H), 3.34 (br. s., 1H), 2.98-2.85 (m, 1H), 2.39 (d, J=10.8 Hz, 1H), 2.29 (br. s., 2H), 2.04-1.98 (m, 2H), 1.86-1.89 (m, 5H), 1.47 (m, 3H)

Example 113

2-(((1R,2R)-2-(((S)-1-(4-(trifluoromethyl)phenyl)piperidin-3-yl)amino)cyclohexyl)amino)oxazole-5-carbonitrile

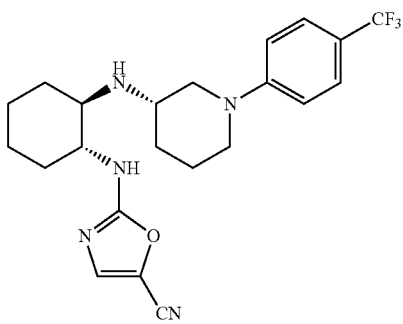 [SMILES: N#Cc1cnc(N[C@@H]2CCCC[C@H]2N[C@H]2CCCN(c3ccc(C(F)(F)F)cc3)C2)o1]

To ethyl 2-(((1R,2R)-2-(((S)-1-(4-(trifluoromethyl)phenyl)piperidin-3-yl)amino)cyclohexyl)amino)oxazole-5-carboxylate (Example 184) (0.279 g, 0.58 mmol) added THF (3 mL) and 1 N aqueous NaOH solution (0.580 mL, 0.580 mmol). The resulting mixture was stirred at RT for 1 d. Due to incomplete reaction (as judged by HPLC/MS), LiOH monohydrate (0.028 g, 1.160 mmol) was then added, and the resulting mixture was stirred at RT for 16 h before the bulk of the THF was evaporated under vacuum. The resulting mixture was acidified with 1 N aqueous HCl solution before extraction 3× with dichloromethane. The extracts were combined and dried over anhydrous $MgSO_4$ before evaporation under vacuum to obtain crude 2-(((1R,2R)-2-(S)-1-(4-(trifluoromethyl)phenyl)piperidin-3-yl)amino)cyclohexyl)amino)oxazole-5-carboxylic acid (Anal. Calcd. for $C_{22}H_{27}F_3N_4O_3$ m/z 452.2, found: 453.2 $(M+H)^+$). To this crude carboxylic acid were added DMF (2 mL), 0.5 M ammonia in 1,4-dioxane solution (11.60 mL, 5.80 mmol), EDC (222 mg, 1.160 mmol), and lastly HOBT (178 mg, 1.160 mmol). The resulting reaction mixture was stirred at RT for 16 h under argon. The solvent was then evaporated under vacuum, and the resulting residue was dissolved in methanol. Purification by RP preparative HPLC (Method A) provided a yellow oil, 2-(((1R,2R)-2-(((S)-1-(4-(trifluoromethyl)phenyl)piperidin-3-yl)amino)cyclohexyl)amino)-oxazole-5-carboxamide, probably as a bis TFA salt (58 mg, 15% yield, Anal. Calcd. for $C_{22}H_{28}F_3N_5O_2$ m/z 451.2, found: 452.2 $(M+H)^+$). This carboxamide bis TFA salt (36 mg, 0.053 mmol) dissolved in 1,4-dioxane (1 mL) under argon, and pyridine (0.086 mL, 1.060 mmol) and then trifluoroacetic anhydride (0.015 mL, 0.106 mmol) were added. The resulting mixture was stirred at RT for 30 min. HPLC/MS indicated formation of both desired product and trifluoroacetylated desired product. Purification of half of the reaction mixture by reversed phase preparative HPLC (Waters XBridge C18, 19×100 mm, 5 μm, Solvent A: 5:95 acetonitrile:water with 0.1% ammonium hydroxide, Solvent B: 95:5 acetonitrile:water with 0.1% ammonium hydroxide), gradient 35-75% B) provided 3.9 mg (34% yield considering that only half of the reaction mixture was purified) of pure title compound. Anal. Calcd. for $C_{22}H_{26}F_3N_5O$ m/z 433.2, found: 434.2 $(M+H)^+$; $^1H$ NMR (500 MHz, 1:1 $CD_3OD$-$CDCl_3$) δ ppm 7.50 (s, 1H), 7.46 (d, J=8.8 Hz, 2H), 6.94 (d, J=8.8 Hz, 2H), 3.62 (dd, J=12.2, 3.4 Hz, 1H), 3.48 (dt, J=12.6, 4.4 Hz, 1H), 3.40 (dt, J=3.6, 10.2 Hz, 1H), 2.93 (m, 1H), 2.83 (m, 1H), 2.68 (dd, J=11.4, 8.7 Hz, 1H), 2.61 (dt, J=3.8, 10.4 Hz, 1H), 2.03-2.15 (m, 2H), 1.89 (m, 1H), 1.74-1.84 (m, 3H), 1.67 (m, 1H), 1.16-1.45 (m, 5H).

Example 114

2-(((1R,2R)-2-(((S)-1-(4-(trifluoromethyl)phenyl)piperidin-3-yl)amino)cyclohexyl)amino)isonicotinonitrile, bis trifluoroacetic acid salt

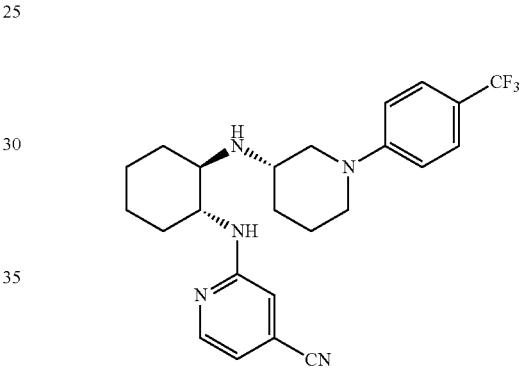

To a 1 dram vial equipped with a magnetic stirbar were added 98% pure (1R,2R)—N1-(4-bromopyridin-2-yl)-N2-((S)-1-(4-(trifluoromethyl)phenyl)piperidin-3-yl)cyclohexane-1,2-diamine (Intermediate 49) (29 mg, 0.057 mmol), tetrakis(triphenylphosphine)palladium(0) (9.90 mg, 8.57 μmol) zinc cyanide (16.77 mg, 0.143 mmol), and N-Methyl-2-pyrrolidinone (286 μL). The vial was promptly purged with argon, capped, and placed in a 130° C. sand bath. The reaction mixture was stirred for 30 min before cooling to ambient temperature. Methanol (2 mL), water (1 mL) and TFA (0.015 mL, 0.2 mmol) were added. The resulting acidic, heterogeneous mixture was centrifuged, and the supernatant was injected to reversed-phase preparative HPLC (Phenomenex Axia 5 μm C18 21.2×100 mm, Solvent A: 90% $H_2O$ and 10% MeOH with 0.1% TFA, Solvent B: 90% MeOH and 10% $H_2O$ with 0.1% TFA, gradient 40% to 100% B) Uninjected solid was stirred in methanol (1.0 mL) and water (0.5 mL) was added. The resulting heterogeneous mixture was centrifuged and the supernatant was injected to preparative HPLC. Desired product containing fractions were evaporated under vacuum to obtain 37 mg of tan solid, 97% pure title compound (94% yield). Anal. Calcd. for $C_{24}H_{28}F_3N_5$ m/z 443.2, found: 444.2 $(M+H)^+$; $^1H$ NMR (400 MHz, $CD_3SOCD_3$) δ ppm 8.1-8.9 (bm, 2H), 8.19 (d, J=5.3 Hz, 1H), 7.48 (d, J=8.5 Hz, 2H), 7.16 (d, J=8.0 Hz, 1H), 6.98 (d, J=8.5 Hz, 2H), 6.87 (d, J=5.3 Hz, 1H), 6.69 (s, 1H), 3.87 (m, 1H), 3.62 (bd, J=12.3 Hz, 1H), 3.50 (bs, 1H), 3.25-3.42 (m, 3H), 3.00 (m, 1H), 2.23 (bd, J=11.0 Hz, 1H), 1.94-2.04 (m, 2H), 1.68-1.88 (m, 4H), 1.65 (m, 1H), 1.54 (m, 1H), 1.21-1.44 (m, 3H).

Table 1 includes additional compounds of the invention wherein R² is Phenyl—CF₃.

TABLE 1

| Example | Structure | hY4 CAMP EC50 (nM) | HPLC retention time (Method) | Mass (M + H) | Synthesis Method |
|---|---|---|---|---|---|
| 115 | 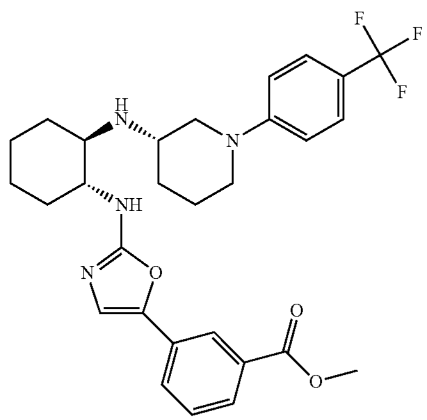 [SMILES: COC(=O)c1cccc(-c2cnc(N[C@@H]3CCCC[C@H]3N[C@H]3CCCN(c4ccc(C(F)(F)F)cc4)C3)o2)c1] | 67 | 3.62 (A) | 543.3 | Scheme 8 |
| 116 | 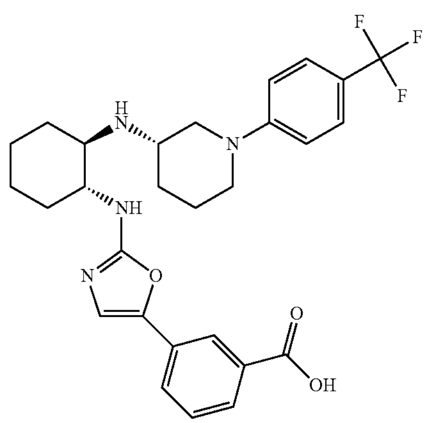 [SMILES: O=C(O)c1cccc(-c2cnc(N[C@@H]3CCCC[C@H]3N[C@H]3CCCN(c4ccc(C(F)(F)F)cc4)C3)o2)c1] | 886 | 3.35 (A) | 529.3 | Scheme 8 |
| 117 | 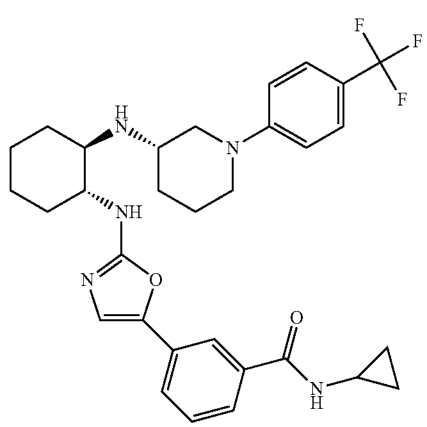 [SMILES: O=C(NC1CC1)c1cccc(-c2cnc(N[C@@H]3CCCC[C@H]3N[C@H]3CCCN(c4ccc(C(F)(F)F)cc4)C3)o2)c1] | 1 | 3.31 (A) | 568.3 | Scheme 8 |

TABLE 1-continued

| Example | Structure | hY4 CAMP EC50 (nM) | HPLC retention time (Method) | Mass (M + H) | Synthesis Method |
|---------|-----------|--------------------|------------------------------|--------------|------------------|
| 118 | 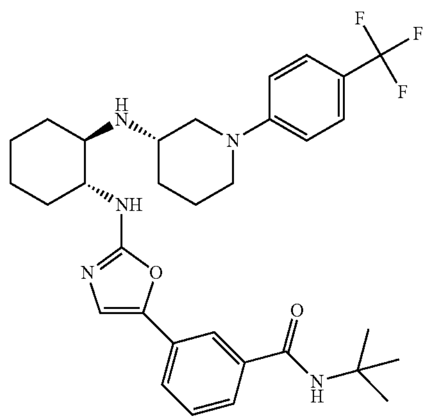 [SMILES: CC(C)(C)NC(=O)c1cccc(-c2cnc(N[C@@H]3CCCC[C@H]3N[C@H]3CCCN(c4ccc(C(F)(F)F)cc4)C3)o2)c1] | 38 | 3.59 (A) | 584.3 | Scheme 8 |
| 119 | 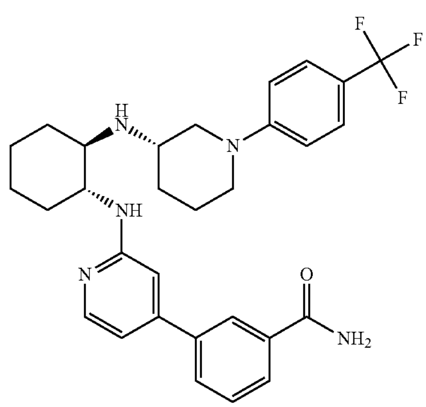 [SMILES: NC(=O)c1cccc(-c2ccnc(N[C@@H]3CCCC[C@H]3N[C@H]3CCCN(c4ccc(C(F)(F)F)cc4)C3)c2)c1] | 4 | 6.446 (J) | 539.2 | Scheme 3 |
| 120 | 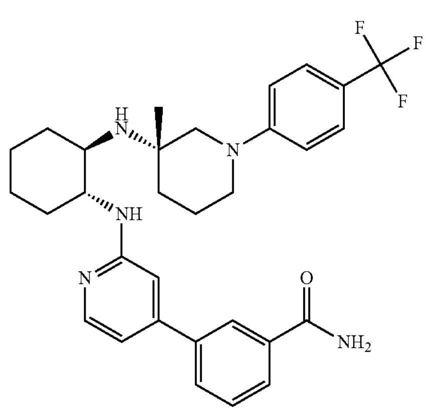 [SMILES: C[C@]1(N[C@@H]2CCCC[C@H]2Nc2cc(-c3cccc(C(N)=O)c3)ccn2)CCCN(c2ccc(C(F)(F)F)cc2)C1] | 3 | 6.962 (J) | 552.2 | Scheme 4 |

TABLE 1-continued
| Example | Structure | hY4 cAMP EC50 (nM) | HPLC retention time (Method) | Mass (M + H) | Synthesis Method |
|---|---|---|---|---|---|
| 121 | 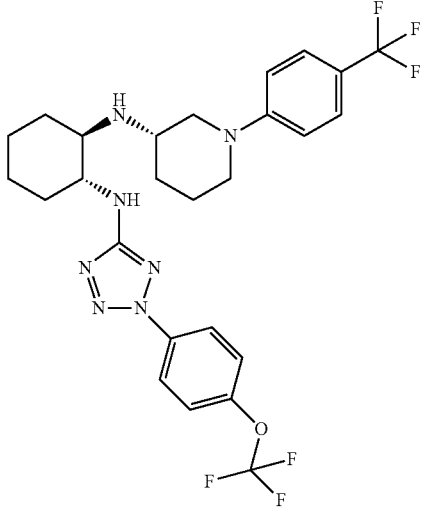 [SMILES: FC(F)(F)Oc1ccc(-n2nnc(N[C@@H]3CCCC[C@H]3N[C@H]3CCCN(c4ccc(C(F)(F)F)cc4)C3)n2)cc1] | 922 | 14.664 (K) | 570.2 | Scheme 1 |
| 122 | 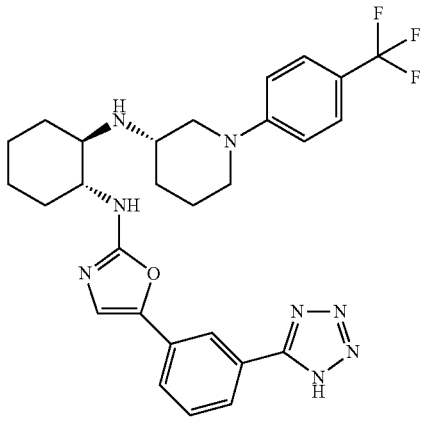 [SMILES: FC(F)(F)c1ccc(N2CCC[C@H](N[C@@H]3CCCC[C@H]3Nc3ncc(-c4cccc(-c5nnn[nH]5)c4)o3)C2)cc1] | 319 | 6.756 (J) | 553.2 | Scheme 1 |
| 123 | 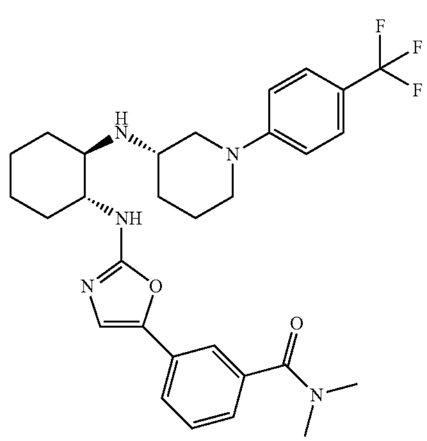 [SMILES: CN(C)C(=O)c1cccc(-c2cnc(N[C@@H]3CCCC[C@H]3N[C@H]3CCCN(c4ccc(C(F)(F)F)cc4)C3)o2)c1] | 234 | 7.027 (J) | 556.2 | Scheme 1 |

TABLE 1-continued

| Example | Structure | hY4 cAMP EC50 (nM) | HPLC retention time (Method) | Mass (M + H) | Synthesis Method |
|---------|-----------|--------------------|------------------------------|--------------|------------------|
| 124 | 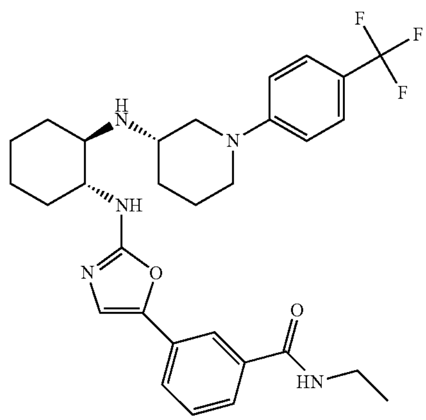 [SMILES: CCNC(=O)c1cccc(-c2cnc(N[C@@H]3CCCC[C@H]3N[C@H]3CCCN(c4ccc(C(F)(F)F)cc4)C3)o2)c1] | 2 | 1.504 (C) | 556.4 | Scheme 8 |
| 125 | 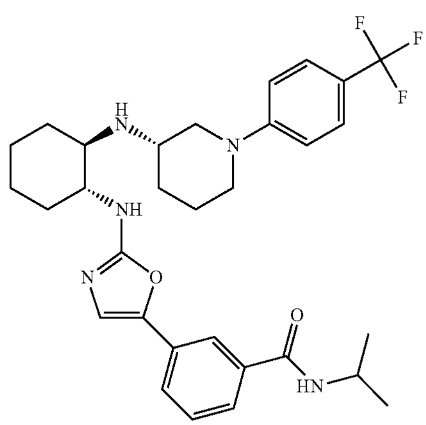 [SMILES: CC(C)NC(=O)c1cccc(-c2cnc(N[C@@H]3CCCC[C@H]3N[C@H]3CCCN(c4ccc(C(F)(F)F)cc4)C3)o2)c1] | 11 | 1.603 (C) | 570.4 | Scheme 8 |
| 126 | 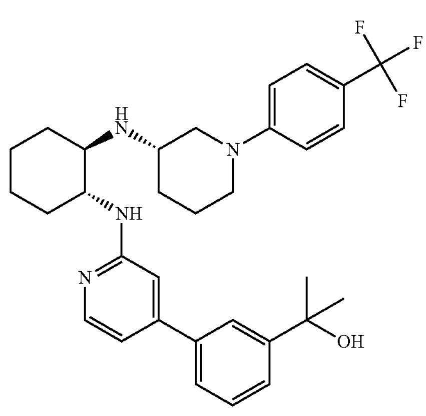 [SMILES: CC(C)(O)c1cccc(-c2ccnc(N[C@@H]3CCCC[C@H]3N[C@H]3CCCN(c4ccc(C(F)(F)F)cc4)C3)c2)c1] | 48 | 1.56 (C) | 553 | Scheme 3 |

TABLE 1-continued

| Example | Structure | hY4 cAMP EC50 (nM) | HPLC retention time (Method) | Mass (M + H) | Synthesis Method |
|---------|-----------|--------------------|------------------------------|--------------|------------------|
| 127 | 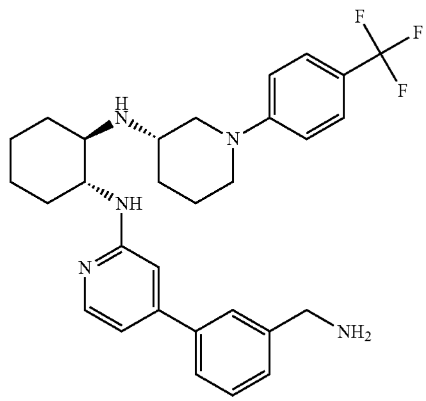 [SMILES: NCc1cccc(-c2ccnc(N[C@@H]3CCCC[C@H]3N[C@H]3CCCN(c4ccc(C(F)(F)F)cc4)C3)c2)c1] | 79 | 1.18 (C) | 524 | Scheme 3 |
| 128 | 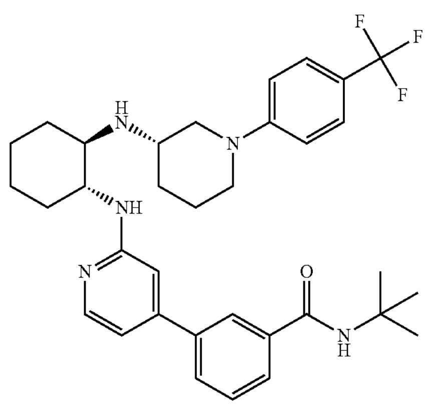 [SMILES: CC(C)(C)NC(=O)c1cccc(-c2ccnc(N[C@@H]3CCCC[C@H]3N[C@H]3CCCN(c4ccc(C(F)(F)F)cc4)C3)c2)c1] | 227 | 1.71 (C) | 594 | Scheme 3 |
| 129 | 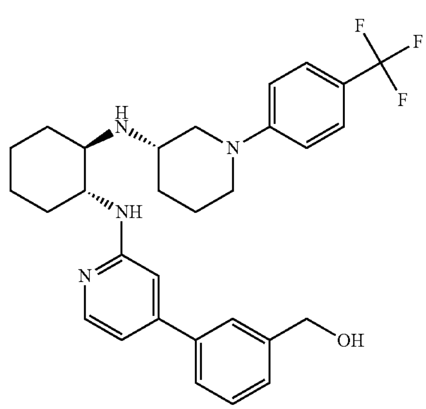 [SMILES: OCc1cccc(-c2ccnc(N[C@@H]3CCCC[C@H]3N[C@H]3CCCN(c4ccc(C(F)(F)F)cc4)C3)c2)c1] | 41 | 1.41 (C) | 525 | Scheme 3 |

TABLE 1-continued

| Example | Structure | hY4 cAMP EC50 (nM) | HPLC retention time (Method) | Mass (M + H) | Synthesis Method |
|---|---|---|---|---|---|
| 130 | 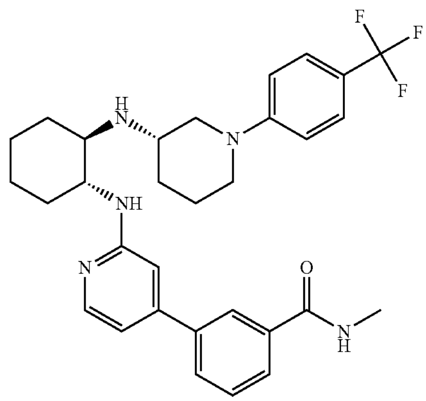 [SMILES: CNC(=O)c1cccc(-c2ccnc(N[C@@H]3CCCC[C@H]3N[C@H]3CCCN(c4ccc(C(F)(F)F)cc4)C3)c2)c1] | 1 | 1.39 (C) | 552 | Scheme 3 |
| 131 | 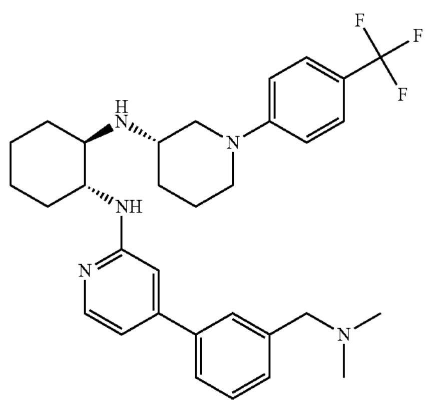 [SMILES: CN(C)Cc1cccc(-c2ccnc(N[C@@H]3CCCC[C@H]3N[C@H]3CCCN(c4ccc(C(F)(F)F)cc4)C3)c2)c1] | 1110 | 1.21 (C) | 552 | Scheme 3 |
| 132 | 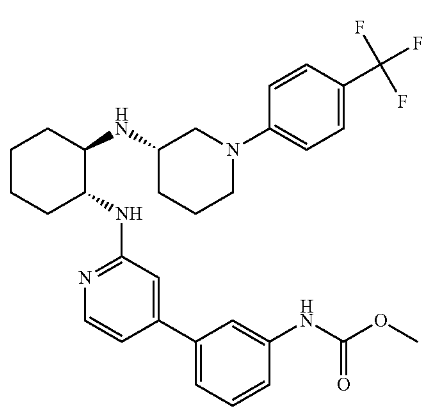 [SMILES: COC(=O)Nc1cccc(-c2ccnc(N[C@@H]3CCCC[C@H]3N[C@H]3CCCN(c4ccc(C(F)(F)F)cc4)C3)c2)c1] | 3 | 3.28 (A) | 568.2 | Scheme 3 |

TABLE 1-continued

| Example | Structure | hY4 CAMP EC50 (nM) | HPLC retention time (Method) | Mass (M + H) | Synthesis Method |
|---|---|---|---|---|---|
| 133 | 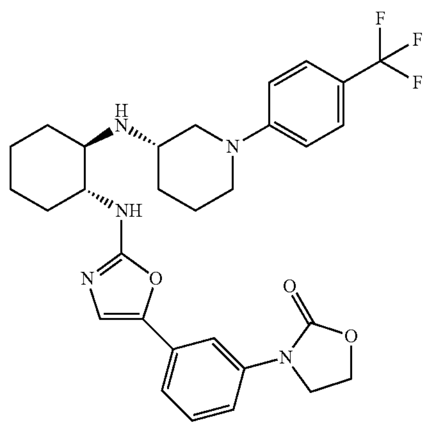 | 8 | 7.518 (J) | 570.2 | Scheme 1 |
| 134 | 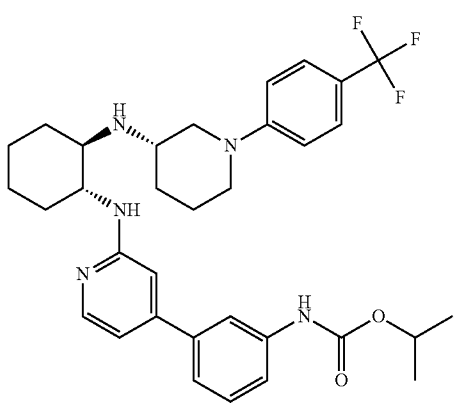 [SMILES: CC(C)OC(=O)Nc1cccc(-c2ccnc(N[C@@H]3CCCC[C@H]3N[C@H]3CCCN(c4ccc(C(F)(F)F)cc4)C3)c2)c1] | 13 | 3.63 (A) | 596.3 | Scheme 3 |
| 135 | 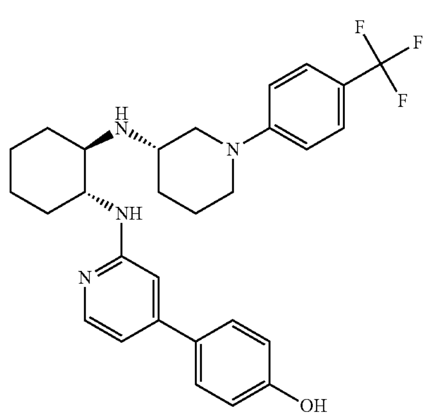 [SMILES: Oc1ccc(-c2ccnc(N[C@@H]3CCCC[C@H]3N[C@H]3CCCN(c4ccc(C(F)(F)F)cc4)C3)c2)cc1] | 27 | 3.16 (A) | 511.2 | Scheme 3 |

TABLE 1-continued

| Example | Structure | hY4 CAMP EC50 (nM) | HPLC retention time (Method) | Mass (M + H) | Synthesis Method |
|---------|-----------|---------------------|------------------------------|--------------|------------------|
| 136 | 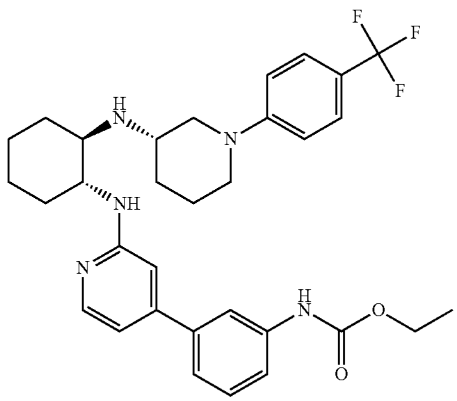 [SMILES: CCOC(=O)Nc1cccc(-c2ccnc(N[C@@H]3CCCC[C@H]3N[C@H]3CCCN(c4ccc(C(F)(F)F)cc4)C3)c2)c1] | 2 | 3.52 (A) | 582.3 | Scheme 3 |
| 137 | 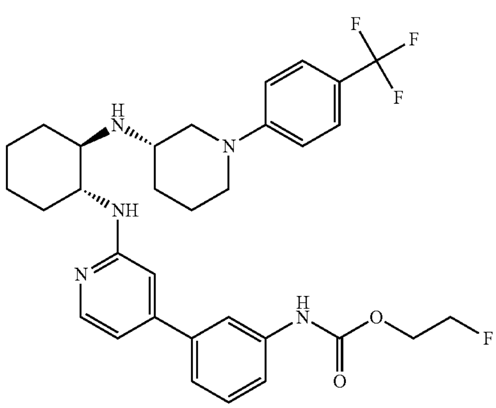 [SMILES: O=C(Nc1cccc(-c2ccnc(N[C@@H]3CCCC[C@H]3N[C@H]3CCCN(c4ccc(C(F)(F)F)cc4)C3)c2)c1)OCCF] | 2 | 3.48 (A) | 600.3 | Scheme 3 |
| 138 | 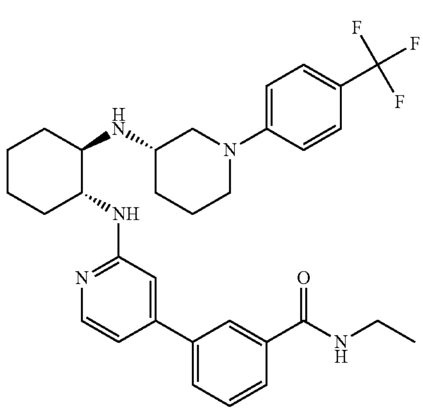 [SMILES: CCNC(=O)c1cccc(-c2ccnc(N[C@@H]3CCCC[C@H]3N[C@H]3CCCN(c4ccc(C(F)(F)F)cc4)C3)c2)c1] | 9 | 1.46 (C) | 566 | Scheme 3 |

TABLE 1-continued

| Example | Structure | hY4 cAMP EC50 (nM) | HPLC retention time (Method) | Mass (M + H) | Synthesis Method |
|---------|-----------|--------------------|-----------------------------|--------------|------------------|
| 139 | 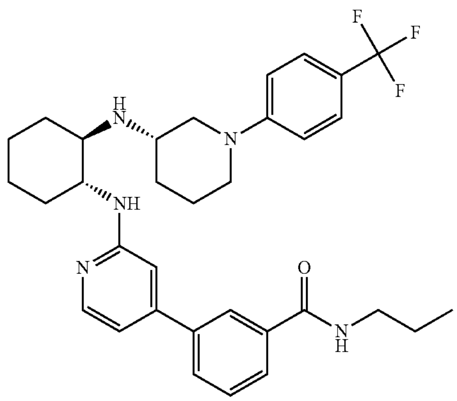 [SMILES: CCCNC(=O)c1cccc(-c2ccnc(N[C@@H]3CCCC[C@H]3N[C@H]3CCCN(c4ccc(C(F)(F)F)cc4)C3)c2)c1] | 29 | 1.56 (C) | 580 | Scheme 3 |
| 140 | 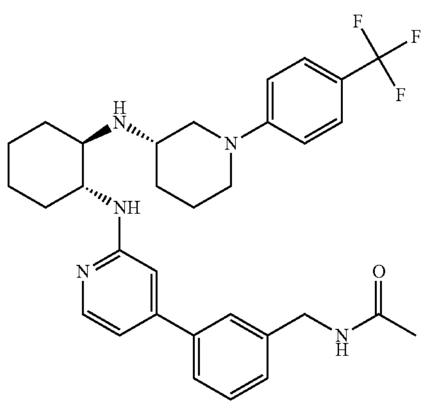 [SMILES: CC(=O)NCc1cccc(-c2ccnc(N[C@@H]3CCCC[C@H]3N[C@H]3CCCN(c4ccc(C(F)(F)F)cc4)C3)c2)c1] | 1 | 1.55 (D) | 566 | Scheme 3 |
| 141 | 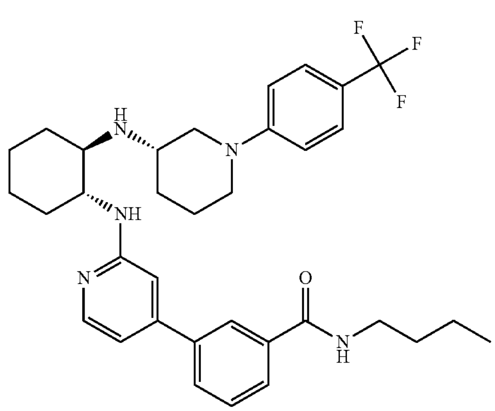 [SMILES: CCCCNC(=O)c1cccc(-c2ccnc(N[C@@H]3CCCC[C@H]3N[C@H]3CCCN(c4ccc(C(F)(F)F)cc4)C3)c2)c1] | 227 | 1.66 (C) | 594 | Scheme 3 |

TABLE 1-continued

| Example | Structure | hY4 cAMP EC50 (nM) | HPLC retention time (Method) | Mass (M + H) | Synthesis Method |
|---------|-----------|--------------------|------------------------------|--------------|------------------|
| 142 | 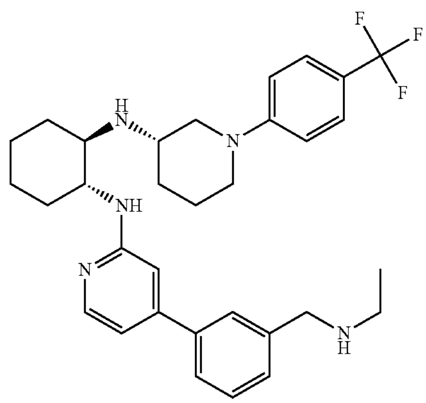 [SMILES: CCNCc1cccc(-c2ccnc(N[C@@H]3CCCC[C@H]3N[C@H]3CCCN(c4ccc(C(F)(F)F)cc4)C3)c2)c1] | 58 | 2.83 (A) | 552 | Scheme 3 |
| 143 | 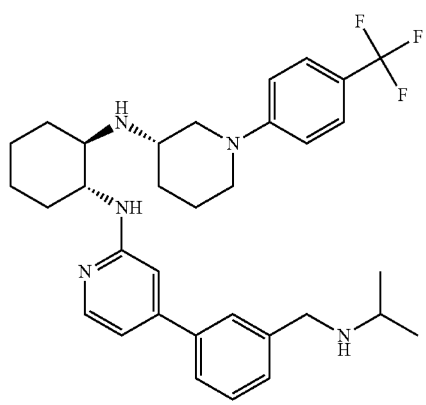 [SMILES: CC(C)NCc1cccc(-c2ccnc(N[C@@H]3CCCC[C@H]3N[C@H]3CCCN(c4ccc(C(F)(F)F)cc4)C3)c2)c1] | 107 | 2.89 (A) | 566 | Scheme 3 |
| 144 | 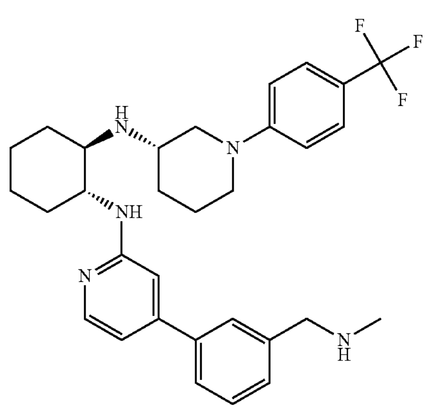 [SMILES: CNCc1cccc(-c2ccnc(N[C@@H]3CCCC[C@H]3N[C@H]3CCCN(c4ccc(C(F)(F)F)cc4)C3)c2)c1] | 26 | 2.78 (A) | 538 | Scheme 3 |

TABLE 1-continued

| Example | Structure | hY4 cAMP EC50 (nM) | HPLC retention time (Method) | Mass (M + H) | Synthesis Method |
|---------|-----------|--------------------|------------------------------|--------------|------------------|
| 145 | 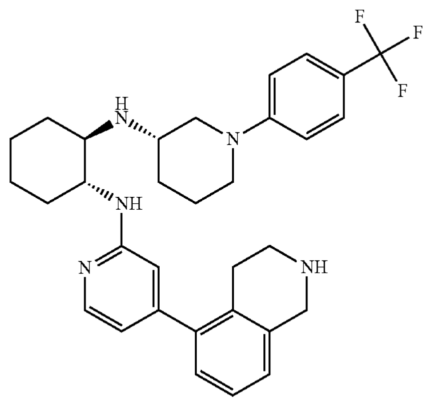 [SMILES: FC(F)(F)c1ccc(N2CCC[C@H](N[C@@H]3CCCC[C@H]3Nc3cc(-c4cccc5c4CCNC5)ccn3)C2)cc1] | 905 | 2.81 (A) | 550 | Scheme 3 |
| 146 | 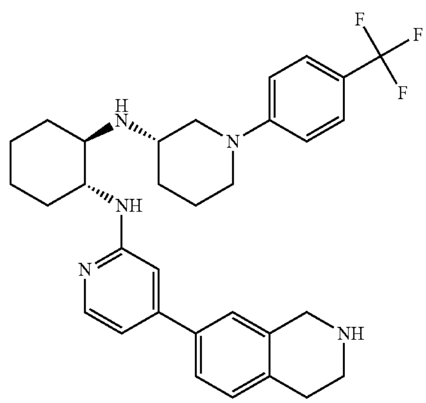 [SMILES: FC(F)(F)c1ccc(N2CCC[C@H](N[C@@H]3CCCC[C@H]3Nc3cc(-c4ccc5c(c4)CNCC5)ccn3)C2)cc1] | 726 | 2.71 (A) | 550 | Scheme 3 |
| 147 | 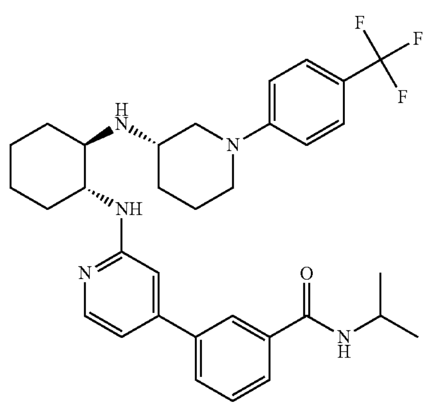 [SMILES: CC(C)NC(=O)c1cccc(-c2ccnc(N[C@@H]3CCCC[C@H]3N[C@H]3CCCN(c4ccc(C(F)(F)F)cc4)C3)c2)c1] | 20 | 1.55 (C) | 580 | Scheme 3 |

TABLE 1-continued

| Example | Structure | hY4 cAMP EC50 (nM) | HPLC retention time (Method) | Mass (M + H) | Synthesis Method |
|---------|-----------|--------------------|------------------------------|--------------|------------------|
| 148 | 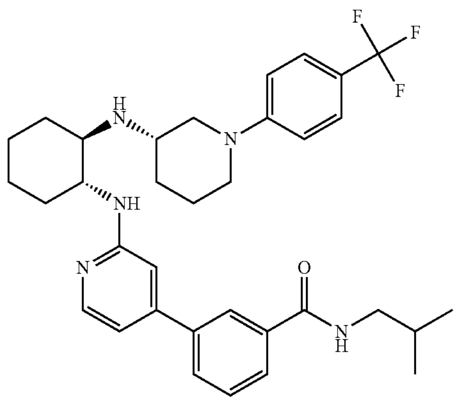 [SMILES: CC(C)CNC(=O)c1cccc(-c2ccnc(N[C@@H]3CCCC[C@H]3N[C@H]3CCCN(c4ccc(C(F)(F)F)cc4)C3)c2)c1] | 205 | 1.80 (D) | 594 | Scheme 3 |
| 149 | 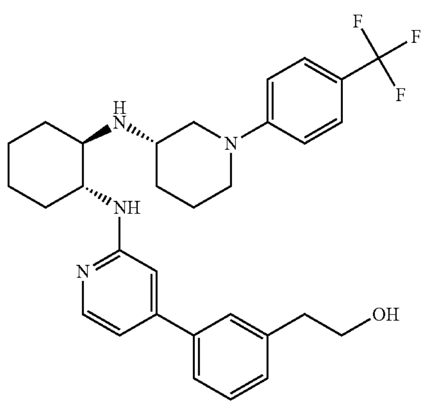 [SMILES: OCCc1cccc(-c2ccnc(N[C@@H]3CCCC[C@H]3N[C@H]3CCCN(c4ccc(C(F)(F)F)cc4)C3)c2)c1] | 30 | 1.42 (C) | 539 | Scheme 3 |
| 150 | 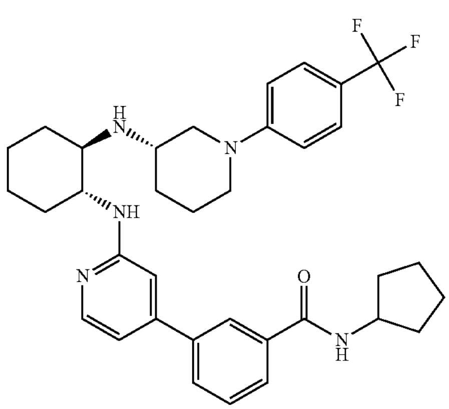 [SMILES: O=C(NC1CCCC1)c1cccc(-c2ccnc(N[C@@H]3CCCC[C@H]3N[C@H]3CCCN(c4ccc(C(F)(F)F)cc4)C3)c2)c1] | 192 | 1.68 (C) | 606 | Scheme 3 |

TABLE 1-continued

| Example | Structure | hY4 cAMP EC50 (nM) | HPLC retention time (Method) | Mass (M + H) | Synthesis Method |
|---|---|---|---|---|---|
| 151 | 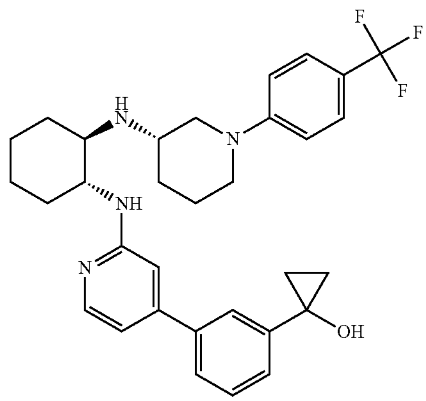 [SMILES: OC1(c2cccc(-c3ccnc(N[C@@H]4CCCC[C@H]4N[C@H]4CCCN(c5ccc(C(F)(F)F)cc5)C4)c3)c2)CC1] | 292 | 3.51 (A) | 551.2 | Scheme 3 |
| 152 | 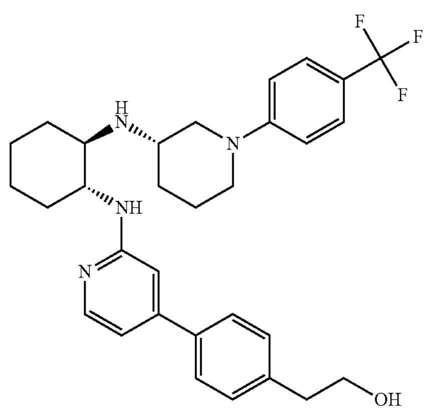 [SMILES: OCCc1ccc(-c2ccnc(N[C@@H]3CCCC[C@H]3N[C@H]3CCCN(c4ccc(C(F)(F)F)cc4)C3)c2)cc1] | 508 | 1.34 (C) | 539 | Scheme 3 |
| 153 | 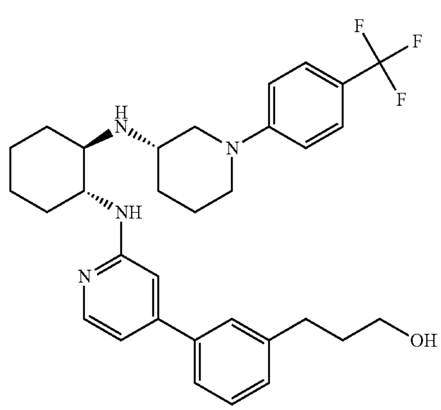 [SMILES: OCCCc1cccc(-c2ccnc(N[C@@H]3CCCC[C@H]3N[C@H]3CCCN(c4ccc(C(F)(F)F)cc4)C3)c2)c1] | 31 | 1.70 (D) | 553 | Scheme 3 |

TABLE 1-continued
| Example | Structure | hY4 CAMP EC50 (nM) | HPLC retention time (Method) | Mass (M + H) | Synthesis Method |
|---|---|---|---|---|---|
| 154 | 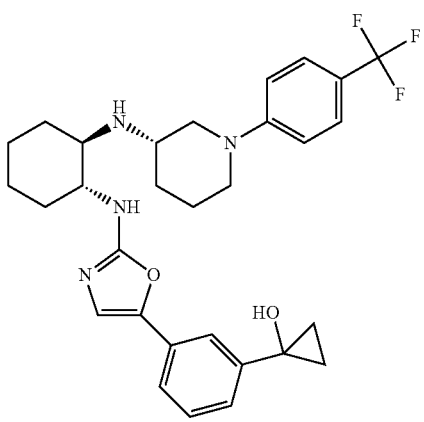 [SMILES: OC1(c2cccc(-c3cnc(N[C@@H]4CCCC[C@H]4N[C@H]4CCCN(c5ccc(C(F)(F)F)cc5)C4)o3)c2)CC1] | 36 | 3.36 (A) | 541.2 | Scheme 1 |
| 155 | 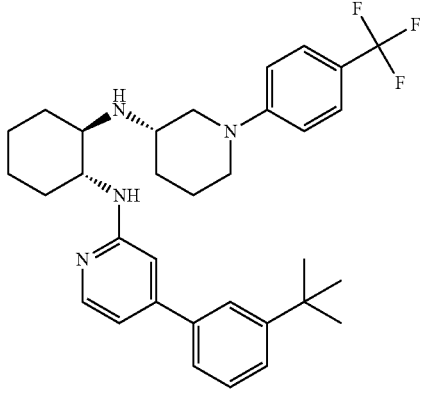 [SMILES: CC(C)(C)c1cccc(-c2ccnc(N[C@@H]3CCCC[C@H]3N[C@H]3CCCN(c4ccc(C(F)(F)F)cc4)C3)c2)c1] | 235 | 2.03 (C) | 551 | Scheme 3 |
| 156 | 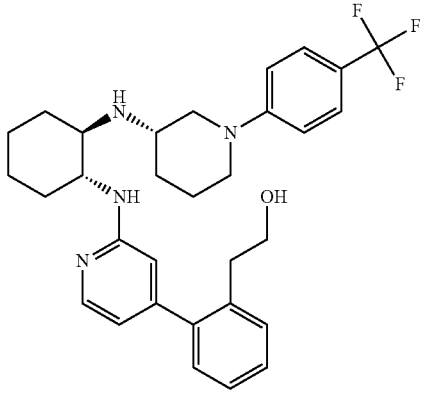 [SMILES: OCCc1ccccc1-c1ccnc(N[C@@H]2CCCC[C@H]2N[C@H]2CCCN(c3ccc(C(F)(F)F)cc3)C2)c1] | 50 | 1.40 (C) | 539 | Scheme 3 |

TABLE 1-continued

| Example | Structure | hY4 cAMP EC50 (nM) | HPLC retention time (Method) | Mass (M + H) | Synthesis Method |
|---------|-----------|--------------------|------------------------------|--------------|------------------|
| 157 | 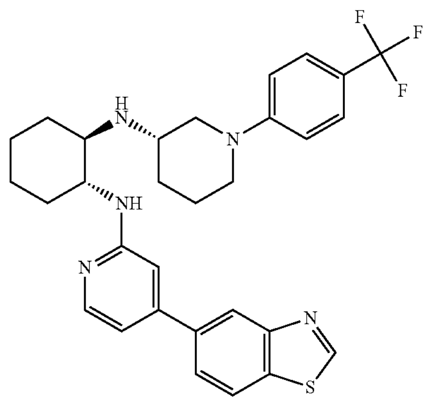 [SMILES: FC(F)(F)c1ccc(N2CCC[C@H](N[C@@H]3CCCC[C@H]3Nc3cc(-c4ccc5scnc5c4)ccn3)C2)cc1] | 194 | 1.48 (C) | 552 | Scheme 3 |
| 158 | 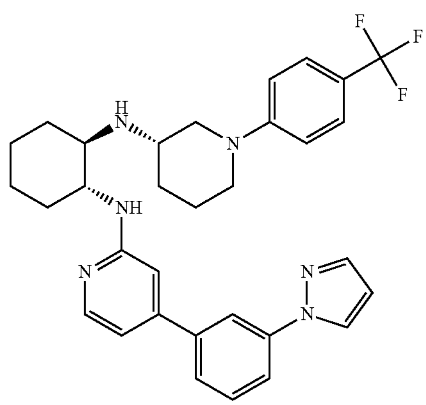 [SMILES: FC(F)(F)c1ccc(N2CCC[C@H](N[C@@H]3CCCC[C@H]3Nc3cc(-c4cccc(-n5cccn5)c4)ccn3)C2)cc1] | 53 | 1.59 (C) | 561 | Scheme 3 |
| 159 | 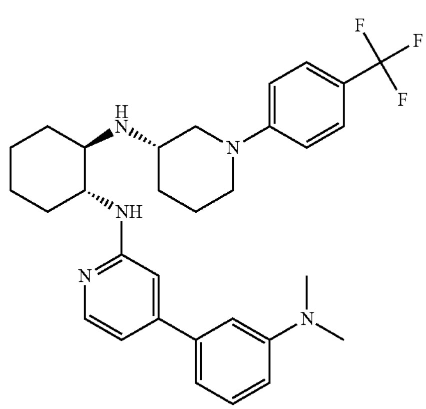 [SMILES: CN(C)c1cccc(-c2ccnc(N[C@@H]3CCCC[C@H]3N[C@H]3CCCN(c4ccc(C(F)(F)F)cc4)C3)c2)c1] | 239 | 1.40 (C) | 538 | Scheme 3 |

TABLE 1-continued
| Example | Structure | hY4 CAMP EC50 (nM) | HPLC retention time (Method) | Mass (M + H) | Synthesis Method |
|---------|-----------|--------------------|------------------------------|--------------|------------------|
| 160 | 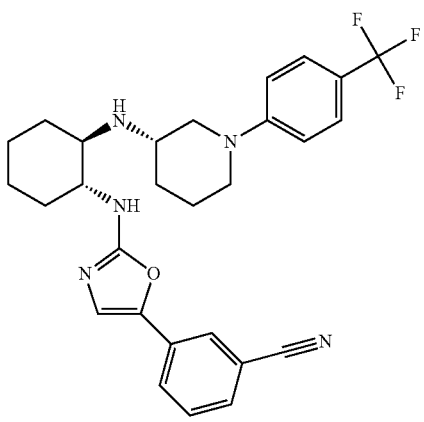 [SMILES: N#Cc1cccc(-c2cnc(N[C@@H]3CCCC[C@H]3N[C@H]3CCCN(c4ccc(C(F)(F)F)cc4)C3)o2)c1] | 548 | 1.578 (C) | 510.3 | Scheme 1 |
| 161 | 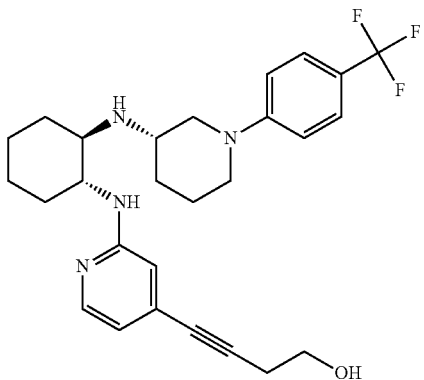 [SMILES: OCCC#Cc1ccnc(N[C@@H]2CCCC[C@H]2N[C@H]2CCCN(c3ccc(C(F)(F)F)cc3)C2)c1] | 31 | 1.27 (C) | 487 | Scheme 3 |
| 162 | 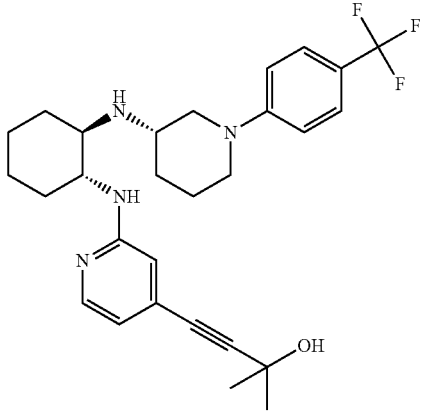 [SMILES: CC(C)(O)C#Cc1ccnc(N[C@@H]2CCCC[C@H]2N[C@H]2CCCN(c3ccc(C(F)(F)F)cc3)C2)c1] | 546 | 1.43 (C) | 501 | Scheme 3 |

TABLE 1-continued

| Example | Structure | hY4 CAMP EC50 (nM) | HPLC retention time (Method) | Mass (M + H) | Synthesis Method |
|---|---|---|---|---|---|
| 163 | 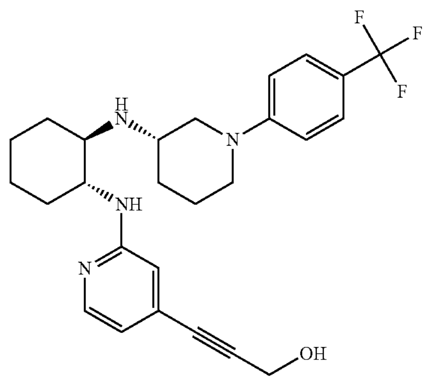 [SMILES: OCC#Cc1ccnc(N[C@@H]2CCCC[C@H]2N[C@H]2CCCN(c3ccc(C(F)(F)F)cc3)C2)c1] | 74 | 1.25 (C) | 473 | Scheme 3 |
| 164 | 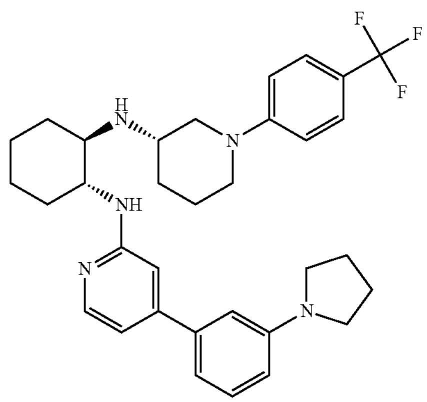 [SMILES: FC(F)(F)c1ccc(N2CCC[C@H](N[C@@H]3CCCC[C@H]3Nc3cc(-c4cccc(N5CCCC5)c4)ccn3)C2)cc1] | 104 | 1.76 (C) | 564 | Scheme 3 |
| 165 | 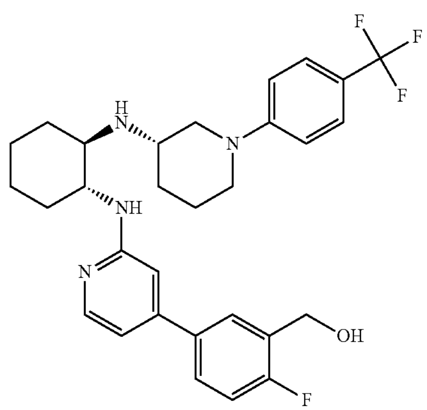 [SMILES: OCc1cc(-c2ccnc(N[C@@H]3CCCC[C@H]3N[C@H]3CCCN(c4ccc(C(F)(F)F)cc4)C3)c2)ccc1F] | 38 | 1.37 (C) | 543 | Scheme 3 |
| 166 | 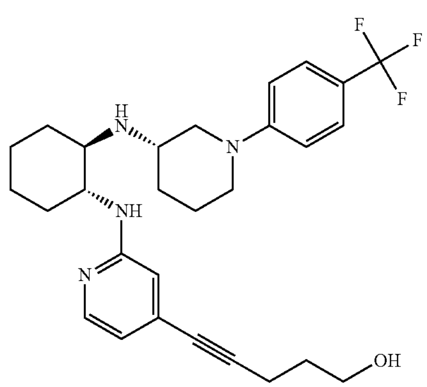 [SMILES: OCCCC#Cc1ccnc(N[C@@H]2CCCC[C@H]2N[C@H]2CCCN(c3ccc(C(F)(F)F)cc3)C2)c1] | 17 | 1.31 (C) | 501 | Scheme 3 |

TABLE 1-continued

| Example | Structure | hY4 cAMP EC50 (nM) | HPLC retention time (Method) | Mass (M + H) | Synthesis Method |
|---------|-----------|--------------------|------------------------------|--------------|------------------|
| 167 | 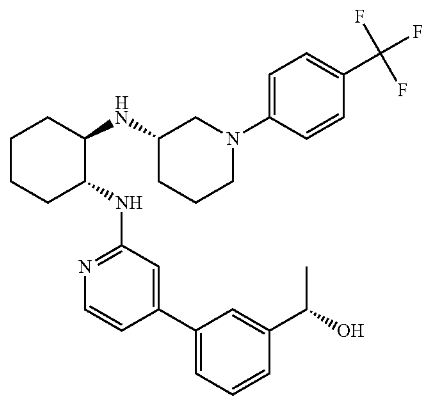 [SMILES: C[C@H](O)c1cccc(-c2ccnc(N[C@@H]3CCCC[C@H]3N[C@H]3CCCN(c4ccc(C(F)(F)F)cc4)C3)c2)c1] | 6 | 3.24 (A) | 539 | Scheme 3 |
| 168 | 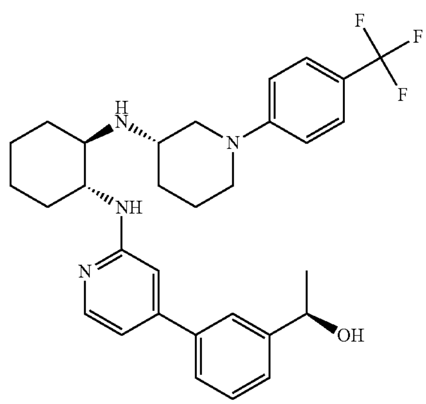 [SMILES: C[C@@H](O)c1cccc(-c2ccnc(N[C@@H]3CCCC[C@H]3N[C@H]3CCCN(c4ccc(C(F)(F)F)cc4)C3)c2)c1] | 14 | 3.24 (A) | 539 | Scheme 3 |
| 169 | 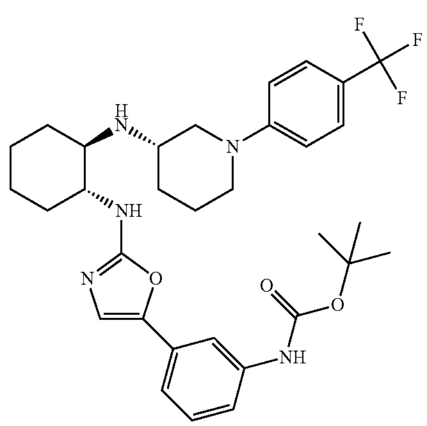 [SMILES: CC(C)(C)OC(=O)Nc1cccc(-c2cnc(N[C@@H]3CCCC[C@H]3N[C@H]3CCCN(c4ccc(C(F)(F)F)cc4)C3)o2)c1] | 32 | 3.66 (A) | 600.3 | Scheme 3 |

TABLE 1-continued

| Example | Structure | hY4 CAMP EC50 (nM) | HPLC retention time (Method) | Mass (M + H) | Synthesis Method |
|---|---|---|---|---|---|
| 170 | 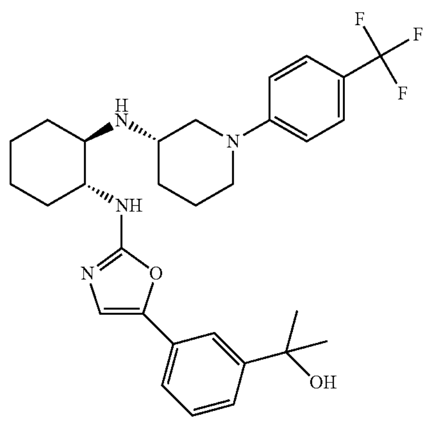 [SMILES: CC(C)(O)c1cccc(-c2cnc(N[C@@H]3CCCC[C@H]3N[C@H]3CCCN(c4ccc(C(F)(F)F)cc4)C3)o2)c1] | 48 | 3.40 (A) | 543.2 | Scheme 1 |
| 171 | 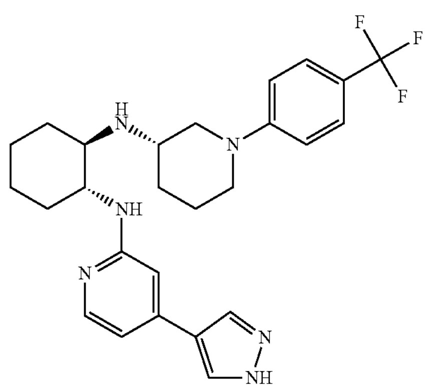 [SMILES: FC(F)(F)c1ccc(N2CCC[C@H](N[C@@H]3CCCC[C@H]3Nc3cc(-c4cn[nH]c4)ccn3)C2)cc1] | 142 | 1.14 (C) | 485 | Scheme 3 |
| 172 | 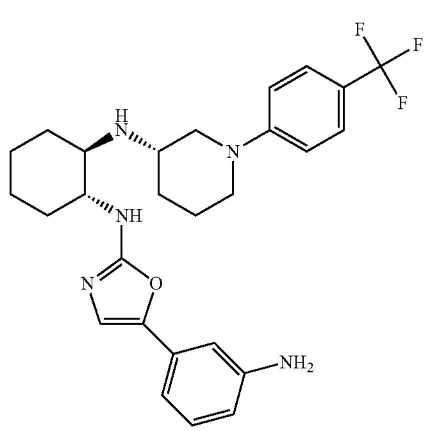 [SMILES: Nc1cccc(-c2cnc(N[C@@H]3CCCC[C@H]3N[C@H]3CCCN(c4ccc(C(F)(F)F)cc4)C3)o2)c1] | 5 | 2.68 (A) | 500.2 | Scheme 1 |

TABLE 1-continued

| Example | Structure | hY4 cAMP EC50 (nM) | HPLC retention time (Method) | Mass (M + H) | Synthesis Method |
|---------|-----------|---------------------|------------------------------|--------------|------------------|
| 173 | 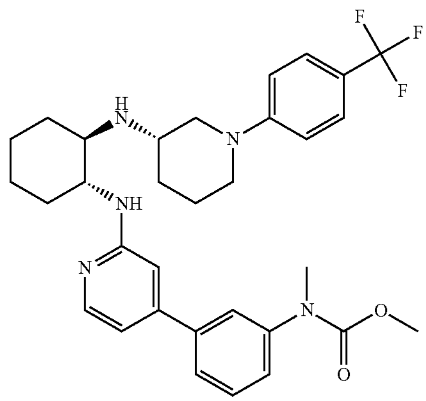 [SMILES: COC(=O)N(C)c1cccc(-c2ccnc(N[C@@H]3CCCC[C@H]3N[C@H]3CCCN(c4ccc(C(F)(F)F)cc4)C3)c2)c1] | 920 | 1.53 (C) | 582 | Scheme 3 |
| 174 | 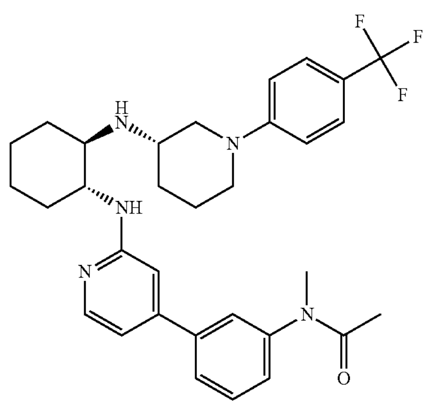 [SMILES: CC(=O)N(C)c1cccc(-c2ccnc(N[C@@H]3CCCC[C@H]3N[C@H]3CCCN(c4ccc(C(F)(F)F)cc4)C3)c2)c1] | 363 | 1.38 (C) | 566 | Scheme 3 |
| 175 | 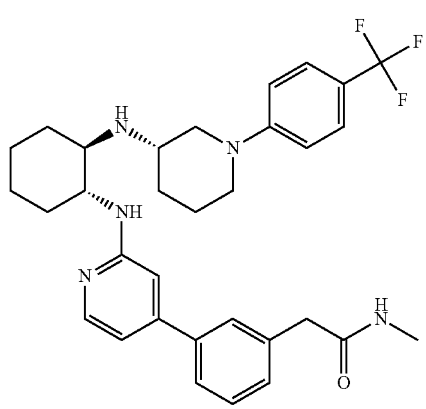 [SMILES: CNC(=O)Cc1cccc(-c2ccnc(N[C@@H]3CCCC[C@H]3N[C@H]3CCCN(c4ccc(C(F)(F)F)cc4)C3)c2)c1] | 2 | 3.12 (A) | 566.3 | Scheme 3 |

TABLE 1-continued

| Example | Structure | hY4 cAMP EC50 (nM) | HPLC retention time (Method) | Mass (M + H) | Synthesis Method |
|---|---|---|---|---|---|
| 176 | 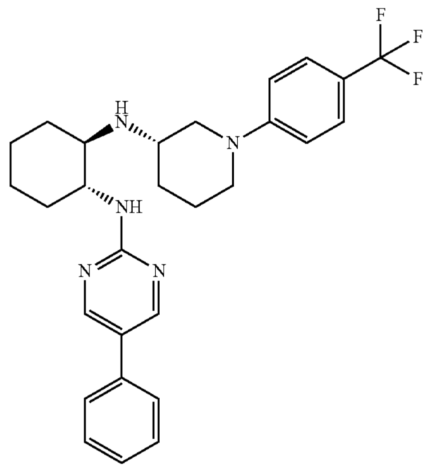 [SMILES: FC(F)(F)c1ccc(N2CCC[C@H](N[C@@H]3CCCC[C@H]3Nc3ncc(-c4ccccc4)cn3)C2)cc1] | 579 | 8.146 (J) | 496.2 | Scheme 1 |
| 177 | 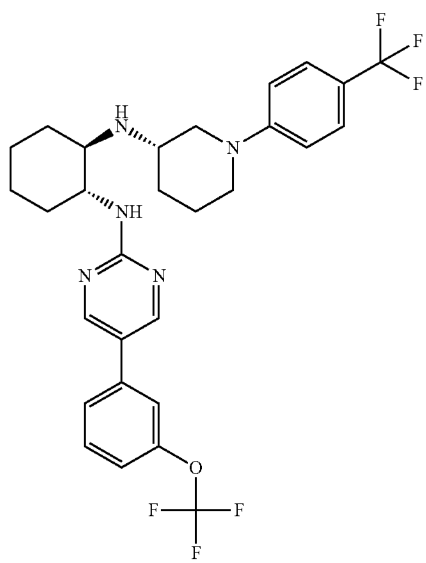 [SMILES: FC(F)(F)Oc1cccc(-c2cnc(N[C@@H]3CCCC[C@H]3N[C@H]3CCCN(c4ccc(C(F)(F)F)cc4)C3)nc2)c1] | 781 | 8.774 (J) | 580.2 | Scheme 3 |
| 178 | 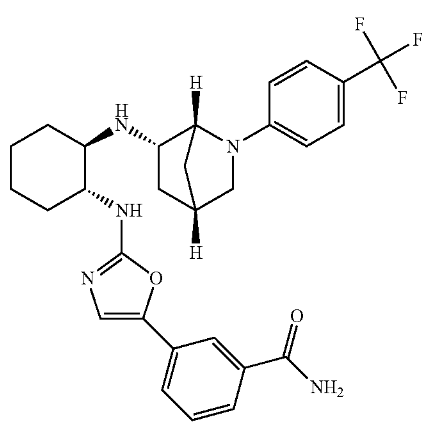 [SMILES: NC(=O)c1cccc(-c2cnc(N[C@@H]3CCCC[C@H]3N[C@H]3C[C@@H]4C[C@H]3N(c3ccc(C(F)(F)F)cc3)C4)o2)c1] | 2 | 6.656 (J) | 540.2 | Scheme 5 |

TABLE 1-continued
| Example | Structure | hY4 cAMP EC50 (nM) | HPLC retention time (Method) | Mass (M + H) | Synthesis Method |
|---|---|---|---|---|---|
| 179 | 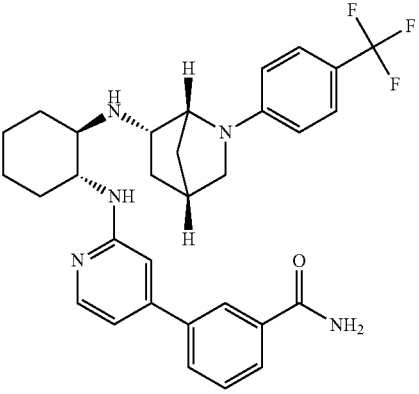 [SMILES: NC(=O)c1cccc(-c2ccnc(N[C@@H]3CCCC[C@H]3N[C@H]3C[C@@H]4C[C@H]3N(c3ccc(C(F)(F)F)cc3)C4)c2)c1] | 7 | 6.213 (J) | 550.2 | Scheme 5 |
| 180 | 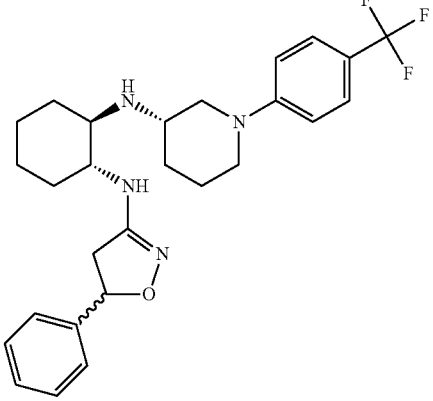 | 54 | 1.726 (G) | 487.2 | Scheme 1 |
| 181 | 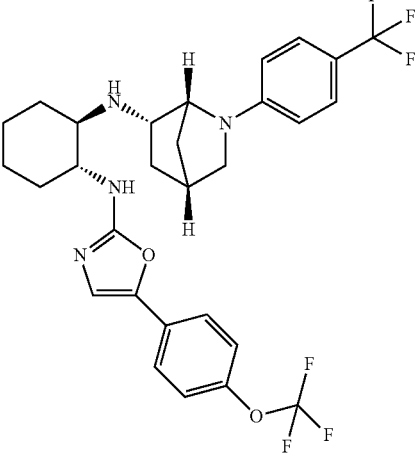 | 126 | 9.292 (J) | 581.2 | Scheme 5 |

TABLE 1-continued

| Example | Structure | hY4 CAMP EC50 (nM) | HPLC retention time (Method) | Mass (M + H) | Synthesis Method |
|---|---|---|---|---|---|
| 182 | 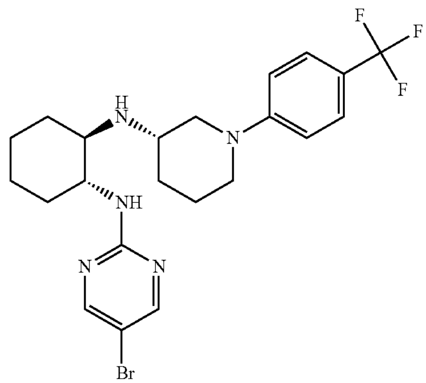 [SMILES: FC(F)(F)c1ccc(N2CCC[C@H](N[C@@H]3CCCC[C@H]3Nc3ncc(Br)cn3)C2)cc1] | 258 | | 500 | Scheme 1 |
| 183 | 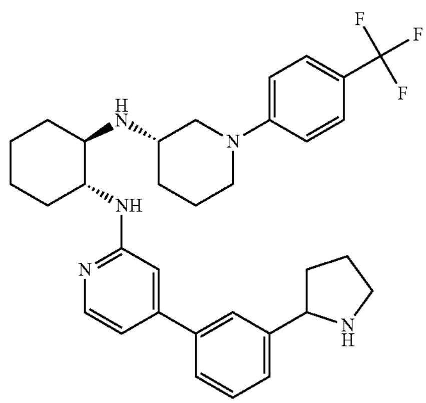 [SMILES: FC(F)(F)c1ccc(N2CCC[C@H](N[C@@H]3CCCC[C@H]3Nc3cc(-c4cccc(C5CCCN5)c4)ccn3)C2)cc1] | 153 | 1.27 (C) | 564 | Scheme 3 |
| 184 | 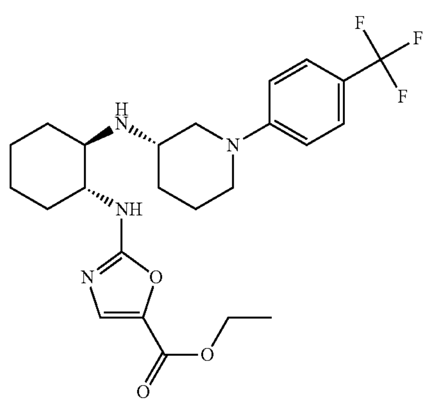 [SMILES: CCOC(=O)c1cnc(N[C@@H]2CCCC[C@H]2N[C@H]2CCCN(c3ccc(C(F)(F)F)cc3)C2)o1] | 764 | 3.296 (B) | 481.3 | Scheme 1 |
| 185 | 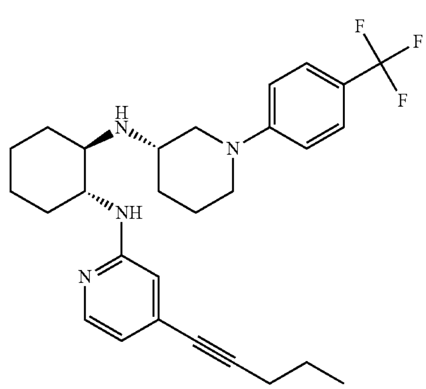 [SMILES: CCCC#Cc1ccnc(N[C@@H]2CCCC[C@H]2N[C@H]2CCCN(c3ccc(C(F)(F)F)cc3)C2)c1] | 218 | 1.91 (C) | 485 | Scheme 3 |

TABLE 1-continued
| Example | Structure | hY4 CAMP EC50 (nM) | HPLC retention time (Method) | Mass (M + H) | Synthesis Method |
|---|---|---|---|---|---|
| 186 | 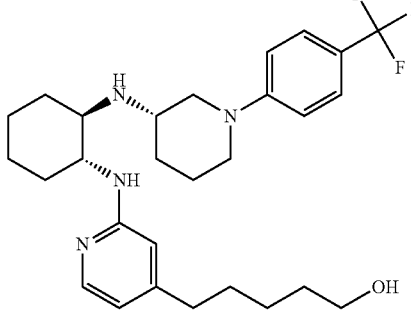 | 115 | 3.08 (A) | 505 | Hydrogenation of Example 166 with Pd/C and hydrogen balloon |
| 187 | 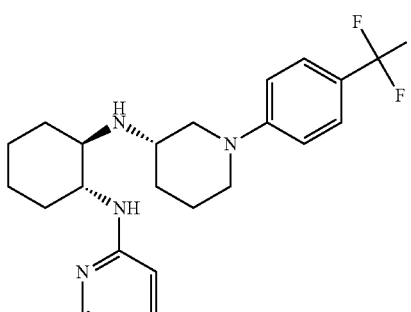 | 42 | 2.99 (A) | 491 | Hydrogenation of Example 161 with Pd/C and hydrogen balloon |
| 188 | 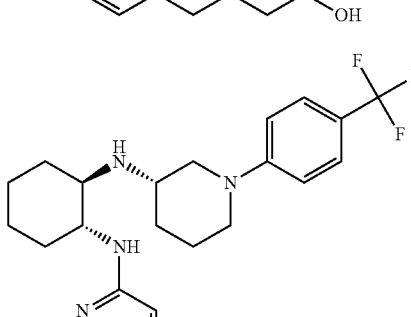 | 1037 | 1.31 (C) | 499 | Scheme 3 |
| 189 | 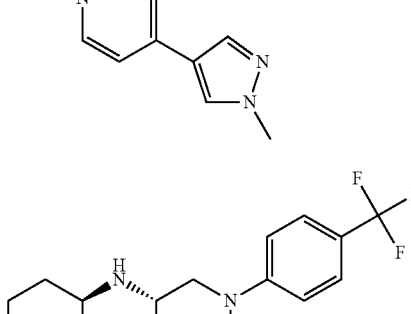 | 27 | 1.57 (C) | 567 | Scheme 3 |

TABLE 1-continued

| Example | Structure | hY4 CAMP EC50 (nM) | HPLC retention time (Method) | Mass (M + H) | Synthesis Method |
|---------|-----------|--------------------|-----------------------------|--------------|------------------|
| 190 | 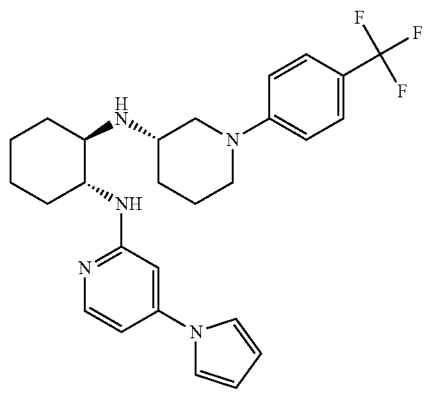 [SMILES: FC(F)(F)c1ccc(N2CCC[C@H](N[C@@H]3CCCC[C@H]3Nc3cc(-n4cccc4)ccn3)C2)cc1] | 51 | 2.881 (B) | 484.1 | Scheme 3 |
| 191 | 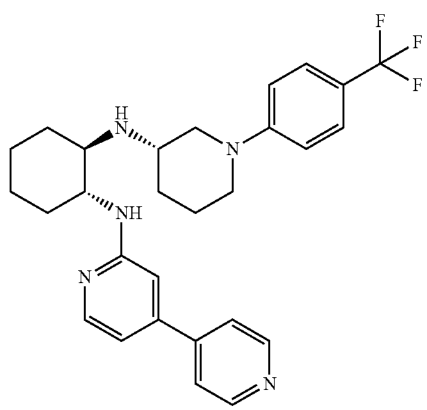 [SMILES: FC(F)(F)c1ccc(N2CCC[C@H](N[C@@H]3CCCC[C@H]3Nc3cc(-c4ccncc4)ccn3)C2)cc1] | 48 | | 496.2 | Scheme 3 |
| 192 | 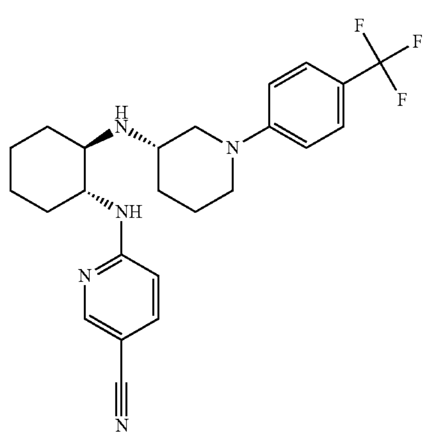 [SMILES: N#Cc1ccc(N[C@@H]2CCCC[C@H]2N[C@H]2CCCN(c3ccc(C(F)(F)F)cc3)C2)nc1] | 284 | 1.472 (C) | 444.1 | Scheme 1 |

TABLE 1-continued

| Example | Structure | hY4 CAMP EC50 (nM) | HPLC retention time (Method) | Mass (M + H) | Synthesis Method |
|---|---|---|---|---|---|
| 193 | 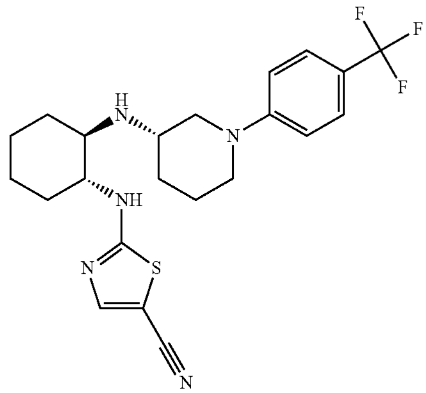 [SMILES: N#Cc1cnc(N[C@@H]2CCCC[C@H]2N[C@H]2CCCN(c3ccc(C(F)(F)F)cc3)C2)s1] | 70 | 3.06 (A) | 450.2 | Scheme 1 |
| 194 | 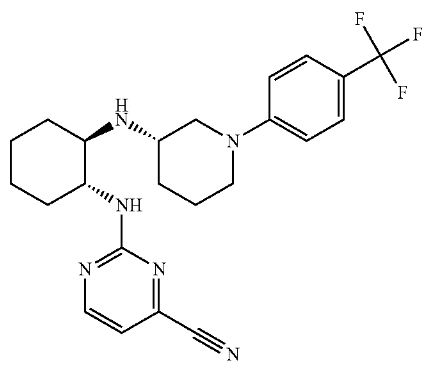 [SMILES: N#Cc1ccnc(N[C@@H]2CCCC[C@H]2N[C@H]2CCCN(c3ccc(C(F)(F)F)cc3)C2)n1] | 606 | 2.443 (B) | 445.3 | Scheme 1 |
| 195 | 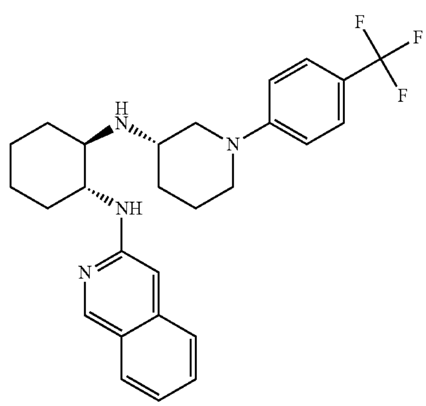 [SMILES: FC(F)(F)c1ccc(N2CCC[C@H](N[C@@H]3CCCC[C@H]3Nc3cc4ccccc4cn3)C2)cc1] | 48 | 1.275 (C) | 441.1 | Scheme 1 |
| 196 | 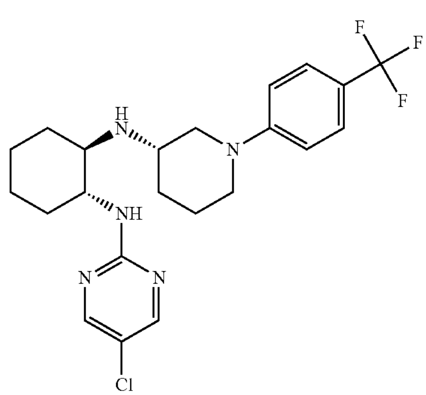 [SMILES: FC(F)(F)c1ccc(N2CCC[C@H](N[C@@H]3CCCC[C@H]3Nc3ncc(Cl)cn3)C2)cc1] | 809 | | 454.2 | Scheme 1 |

TABLE 1-continued
| Example | Structure | hY4 CAMP EC50 (nM) | HPLC retention time (Method) | Mass (M + H) | Synthesis Method |
|---|---|---|---|---|---|
| 197 | 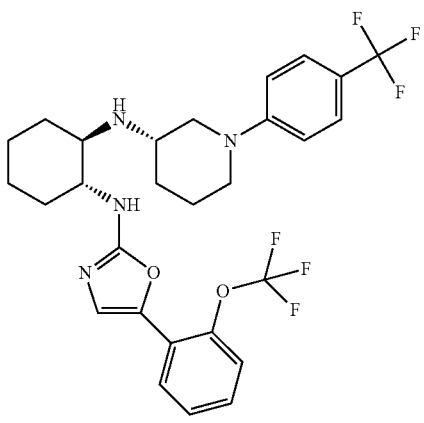 [SMILES: FC(F)(F)Oc1ccccc1-c1cnc(N[C@@H]2CCCC[C@H]2N[C@H]2CCCN(c3ccc(C(F)(F)F)cc3)C2)o1] | 12 | 2.014 (G) | 569.2 | Scheme 3 |
| 198 | 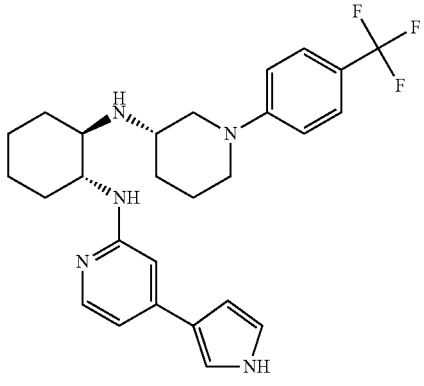 [SMILES: FC(F)(F)c1ccc(N2CCC[C@H](N[C@@H]3CCCC[C@H]3Nc3cc(-c4cc[nH]c4)ccn3)C2)cc1] | 67 | 1.36 (C) | 484 | Scheme 3 |
Table 2 includes additional compounds of the invention wherein $R^2$ is Phenyl-CN.
TABLE 2
| Example | Structure | hY4 CAMP EC50 (nM) | HPLC retention time (Method) | Mass (M + H) | Synthesis Method |
|---|---|---|---|---|---|
| 199 | 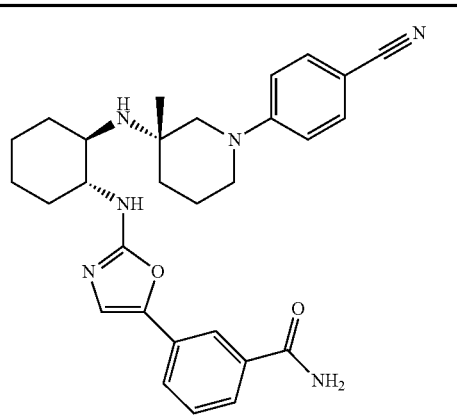 | 2 | 5.597 (J) | 499.2 | Scheme 4 |

TABLE 2-continued

| Example | Structure | hY4 cAMP EC50 (nM) | HPLC retention time (Method) | Mass (M + H) | Synthesis Method |
|---|---|---|---|---|---|
| 200 | 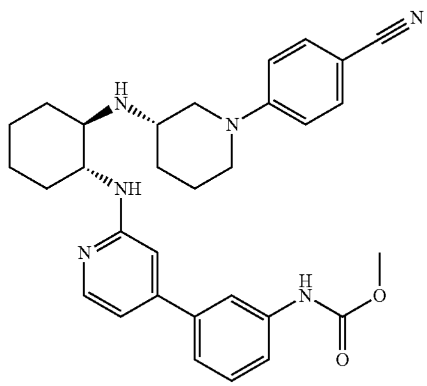 [SMILES: COC(=O)Nc1cccc(-c2ccnc(N[C@@H]3CCCC[C@H]3N[C@H]3CCCN(c4ccc(C#N)cc4)C3)c2)c1] | 3 | 2.728 (A) | 525.4 | Scheme 3 |
| 201 | 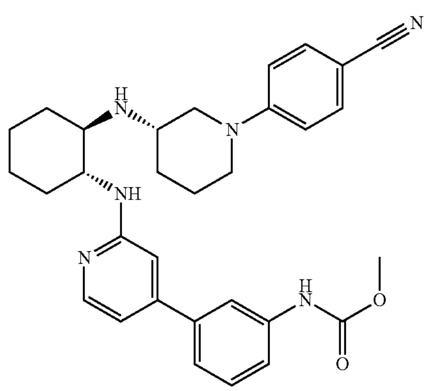 [SMILES: COC(=O)Nc1cccc(-c2ccnc(N[C@@H]3CCCC[C@H]3N[C@H]3CCCN(c4ccc(C#N)cc4)C3)c2)c1] | 5 | 1.55 (L) | 525.3 | Scheme 3 |
| 202 | 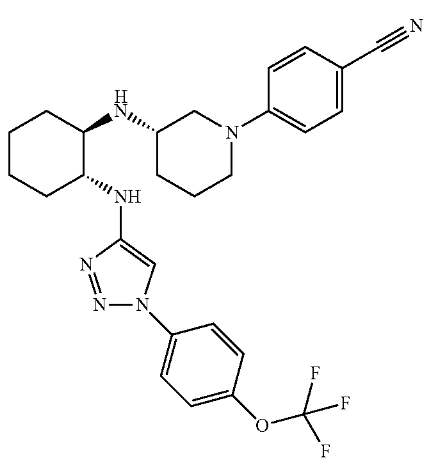 [SMILES: N#Cc1ccc(N2CCC[C@H](N[C@@H]3CCCC[C@H]3Nc3cn(-c4ccc(OC(F)(F)F)cc4)nn3)C2)cc1] | 774 | 7.791 (J) | 526.2 | Scheme 1 |

TABLE 2-continued
| Example | Structure | hY4 cAMP EC50 (nM) | HPLC retention time (Method) | Mass (M + H) | Synthesis Method |
|---------|-----------|--------------------|------------------------------|--------------|------------------|
| 203 | 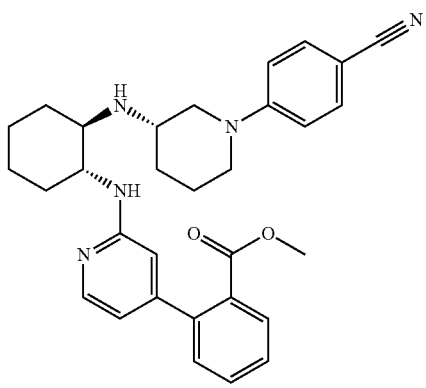 [SMILES: COC(=O)c1ccccc1-c1ccnc(N[C@@H]2CCCC[C@H]2N[C@H]2CCCN(c3ccc(C#N)cc3)C2)c1] | 211 | 1.309 (C) | 510.4 | Scheme 3 |
| 204 | 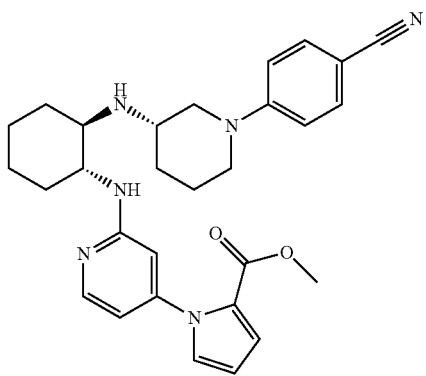 [SMILES: COC(=O)c1cccn1-c1ccnc(N[C@@H]2CCCC[C@H]2N[C@H]2CCCN(c3ccc(C#N)cc3)C2)c1] | 147 | 2.318 (B) | 499.2 | Scheme 3 |
| 205 | 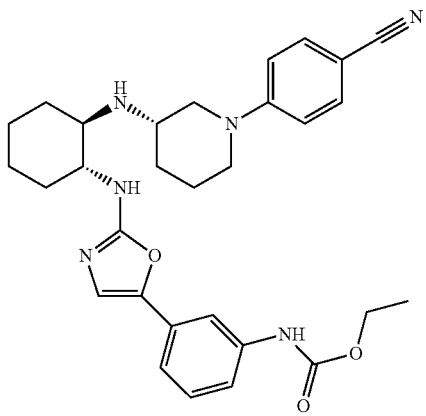 [SMILES: CCOC(=O)Nc1cccc(-c2cnc(N[C@@H]3CCCC[C@H]3N[C@H]3CCCN(c4ccc(C#N)cc4)C3)o2)c1] | 0.2 | 1.38 (C) | 529.3 | Scheme 1 |

TABLE 2-continued

| Example | Structure | hY4 CAMP EC50 (nM) | HPLC retention time (Method) | Mass (M + H) | Synthesis Method |
|---------|-----------|---------------------|------------------------------|--------------|------------------|
| 206 | 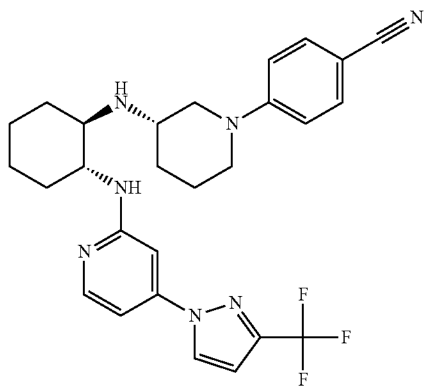 [SMILES: N#Cc1ccc(N2CCC[C@H](N[C@@H]3CCCC[C@H]3Nc3cc(-n4ccc(C(F)(F)F)n4)ccn3)C2)cc1] | 440 | 3.10 (A) | 510.2 | Scheme 3 |
| 207 | 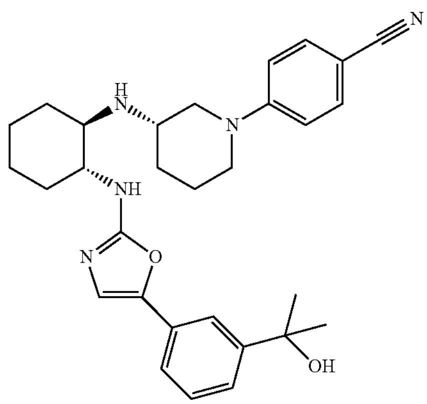 [SMILES: CC(C)(O)c1cccc(-c2cnc(N[C@@H]3CCCC[C@H]3N[C@H]3CCCN(c4ccc(C#N)cc4)C3)o2)c1] | 39 | 2.89 (A) | 500.2 | Scheme 1 |
| 208 | 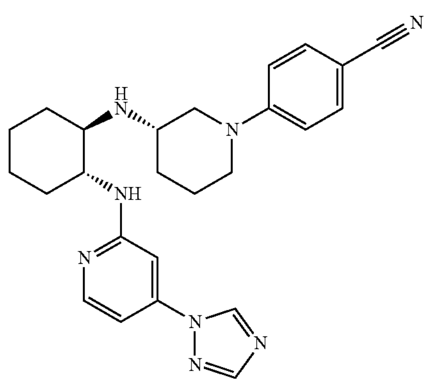 [SMILES: N#Cc1ccc(N2CCC[C@H](N[C@@H]3CCCC[C@H]3Nc3cc(-n4cncn4)ccn3)C2)cc1] | 231 | 2.32 (A) | 443.2 | Scheme 3 |
| 209 | 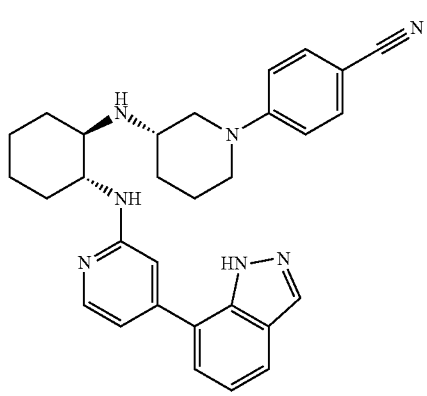 [SMILES: N#Cc1ccc(N2CCC[C@H](N[C@@H]3CCCC[C@H]3Nc3cc(-c4cccc5cn[nH]c45)ccn3)C2)cc1] | 83 | 2.163 (B) | 492.2 | Scheme 3 |

TABLE 2-continued
| Example | Structure | hY4 cAMP EC50 (nM) | HPLC retention time (Method) | Mass (M + H) | Synthesis Method |
|---|---|---|---|---|---|
| 210 | 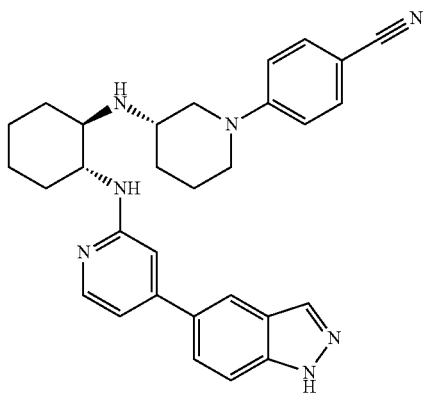 [SMILES: N#Cc1ccc(N2CCC[C@H](N[C@@H]3CCCC[C@H]3Nc3cc(-c4ccc5[nH]ncc5c4)ccn3)C2)cc1] | 640 | 1.865 (B) | 492.2 | Scheme 3 |
| 211 | 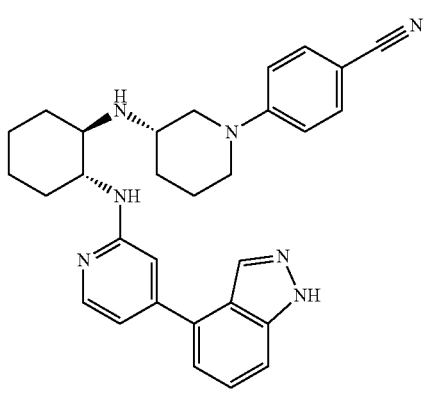 [SMILES: N#Cc1ccc(N2CCC[C@H](N[C@@H]3CCCC[C@H]3Nc3cc(-c4cccc5[nH]ncc45)ccn3)C2)cc1] | 22 | 2.045 (B) | 492.3 | Scheme 3 |
| 212 | 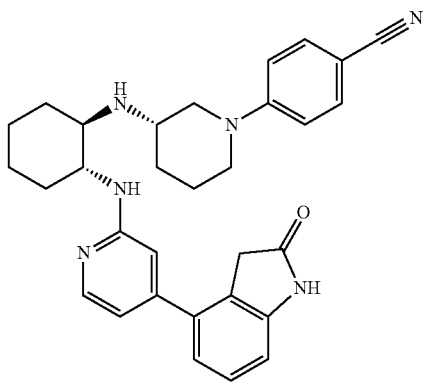 [SMILES: N#Cc1ccc(N2CCC[C@H](N[C@@H]3CCCC[C@H]3Nc3cc(-c4cccc5c4CC(=O)N5)ccn3)C2)cc1] | 13 | 1.895 (B) | 507.3 | Scheme 3 |

TABLE 2-continued

| Example | Structure | hY4 cAMP EC50 (nM) | HPLC retention time (Method) | Mass (M + H) | Synthesis Method |
|---------|-----------|--------------------|------------------------------|--------------|------------------|
| 213 | 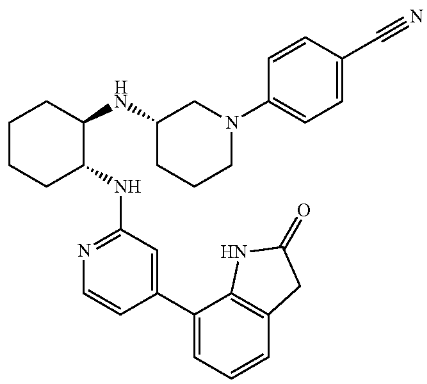 [SMILES: N#Cc1ccc(N2CCC[C@H](N[C@@H]3CCCC[C@H]3Nc3cc(-c4cccc5c4NC(=O)C5)ccn3)C2)cc1] | 183 | 1.982 (B) | 507.3 | Scheme 3 |
| 214 | 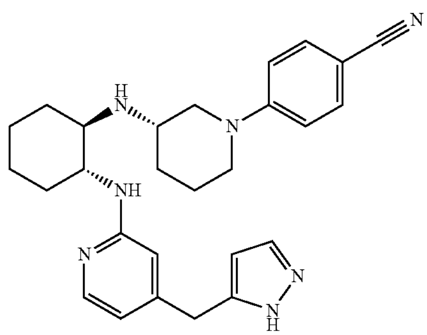 [SMILES: N#Cc1ccc(N2CCC[C@H](N[C@@H]3CCCC[C@H]3Nc3cc(Cc4ccn[nH]4)ccn3)C2)cc1] | 964 | 1.367 (B) | 456.4 | Scheme 3 |
| 215 | 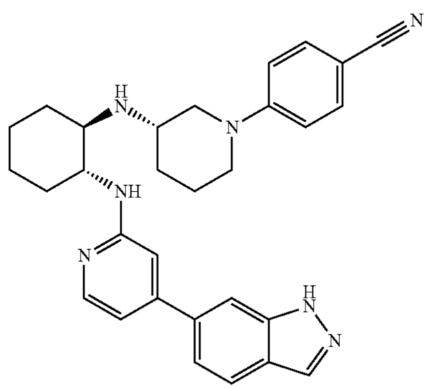 [SMILES: N#Cc1ccc(N2CCC[C@H](N[C@@H]3CCCC[C@H]3Nc3cc(-c4ccc5cn[nH]c5c4)ccn3)C2)cc1] | 215 | 2.098 (B) | 492.3 | Scheme 3 |
| 216 | 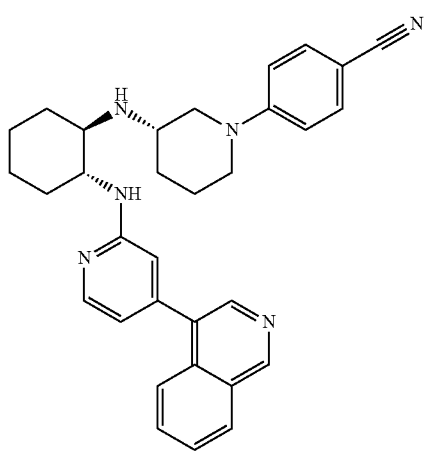 [SMILES: N#Cc1ccc(N2CCC[C@H](N[C@@H]3CCCC[C@H]3Nc3cc(-c4cncc5ccccc45)ccn3)C2)cc1] | 189 | 2.31 (A) | 503.3 | Scheme 3 |

TABLE 2-continued
| Example | Structure | hY4 CAMP EC50 (nM) | HPLC retention time (Method) | Mass (M + H) | Synthesis Method |
|---------|-----------|--------------------|-----------------------------|--------------|------------------|
| 217 | 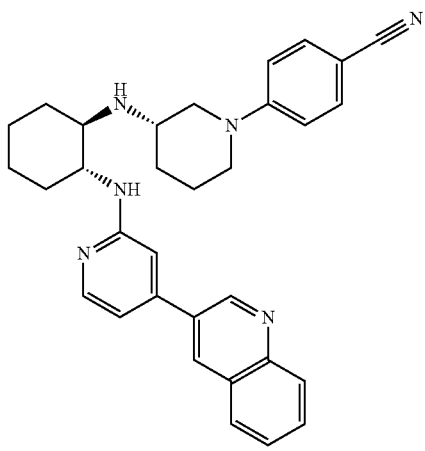 [SMILES: N#Cc1ccc(N2CCC[C@H](N[C@@H]3CCCC[C@H]3Nc3cc(-c4cnc5ccccc5c4)ccn3)C2)cc1] | 478 | 2.59 (A) | 503.3 | Scheme 3 |
| 218 | 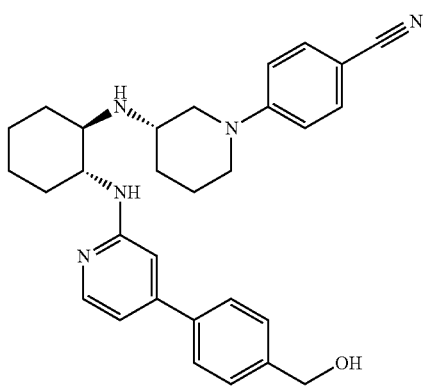 [SMILES: N#Cc1ccc(N2CCC[C@H](N[C@@H]3CCCC[C@H]3Nc3cc(-c4ccc(CO)cc4)ccn3)C2)cc1] | 302 | 2.54 (A) | 482.3 | Scheme 3 |
| 219 | 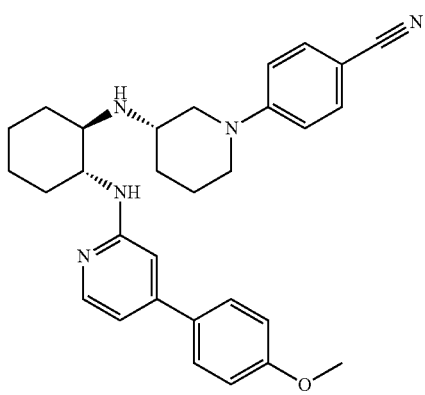 [SMILES: COc1ccc(-c2ccnc(N[C@@H]3CCCC[C@H]3N[C@H]3CCCN(c4ccc(C#N)cc4)C3)c2)cc1] | 45 | 5.540 (H) | 482.5 | Scheme 3 |

TABLE 2-continued
| Example | Structure | hY4 CAMP EC50 (nM) | HPLC retention time (Method) | Mass (M + H) | Synthesis Method |
|---------|-----------|--------------------|------------------------------|--------------|------------------|
| 220 | 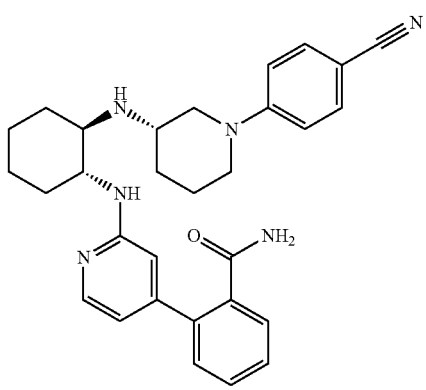 [SMILES: N#Cc1ccc(N2CCC[C@H](N[C@@H]3CCCC[C@H]3Nc3cc(-c4ccccc4C(N)=O)ccn3)C2)cc1] | 696 | 6.360 (H) | 466.6 | Scheme 3 |
| 221 | 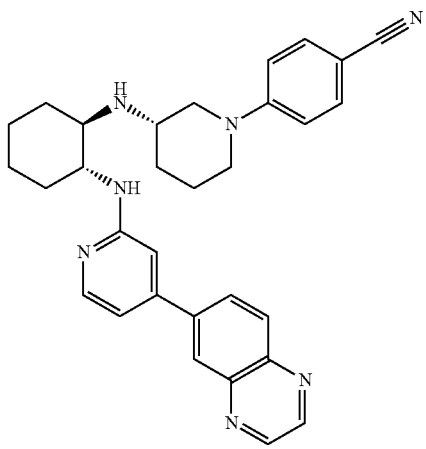 [SMILES: N#Cc1ccc(N2CCC[C@H](N[C@@H]3CCCC[C@H]3Nc3cc(-c4ccc5nccnc5c4)ccn3)C2)cc1] | 77 | 4.010 (H) | 504.5 | Scheme 3 |
| 222 | 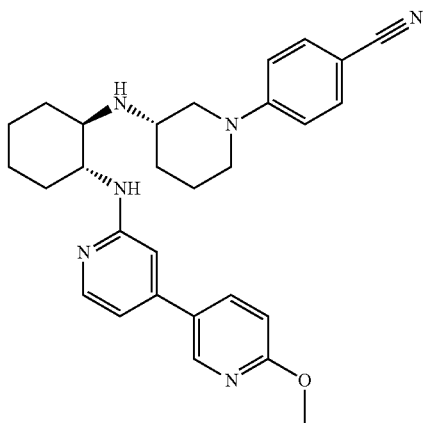 [SMILES: COc1ccc(-c2ccnc(N[C@@H]3CCCC[C@H]3N[C@H]3CCCN(c4ccc(C#N)cc4)C3)c2)cn1] | 46 | 4.86 (H) | 483.5 | Scheme 3 |

TABLE 2-continued
| Example | Structure | hY4 CAMP EC50 (nM) | HPLC retention time (Method) | Mass (M + H) | Synthesis Method |
|---|---|---|---|---|---|
| 223 | 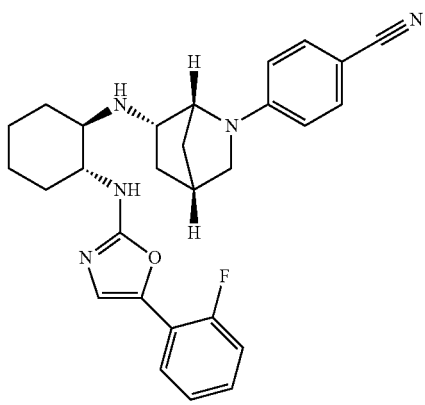 [SMILES: N#Cc1ccc(N2C[C@@H]3C[C@H](N[C@@H]4CCCC[C@H]4Nc4ncc(-c5ccccc5F)o4)[C@H]2C3)cc1] | 5 | 1.72 (L) | 472.3 | Scheme 5 |
| 224 | 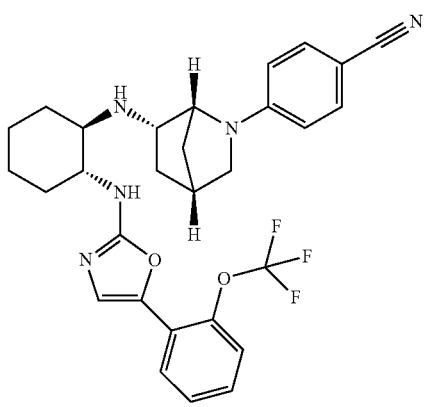 [SMILES: N#Cc1ccc(N2C[C@@H]3C[C@H](N[C@@H]4CCCC[C@H]4Nc4ncc(-c5ccccc5OC(F)(F)F)o4)[C@H]2C3)cc1] | 2 | 1.85 (L) | 538.2 | Scheme 5 |
| 225 | 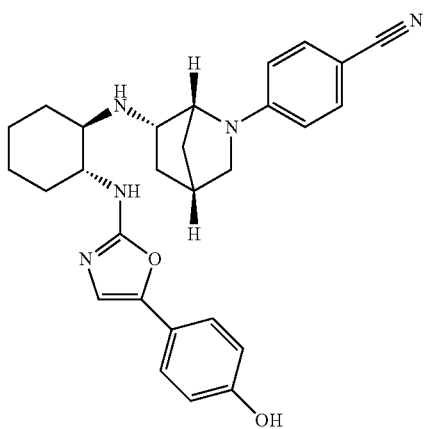 [SMILES: N#Cc1ccc(N2C[C@@H]3C[C@H](N[C@@H]4CCCC[C@H]4Nc4ncc(-c5ccc(O)cc5)o4)[C@H]2C3)cc1] | 54 | 2.50 (A) | 470.3 | Scheme 5 |

TABLE 2-continued
| Example | Structure | hY4 CAMP EC50 (nM) | HPLC retention time (Method) | Mass (M + H) | Synthesis Method |
|---------|-----------|--------------------|------------------------------|--------------|------------------|
| 226 | 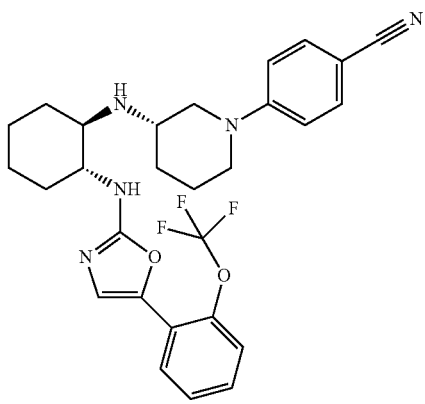 [SMILES: N#Cc1ccc(N2CCC[C@H](N[C@@H]3CCCC[C@H]3Nc3ncc(-c4ccccc4OC(F)(F)F)o3)C2)cc1] | 5 | 1.816 (G) | 526.2 | Scheme 1 |
| 227 | 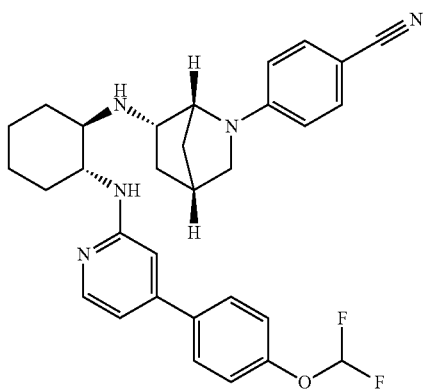 [SMILES: N#Cc1ccc(N2C[C@@H]3C[C@H](N[C@@H]4CCCC[C@H]4Nc4cc(-c5ccc(OC(F)F)cc5)ccn4)[C@H]2C3)cc1] | 16 | 1.74 (L) | 530.4 | Scheme 5 |
| 228 | 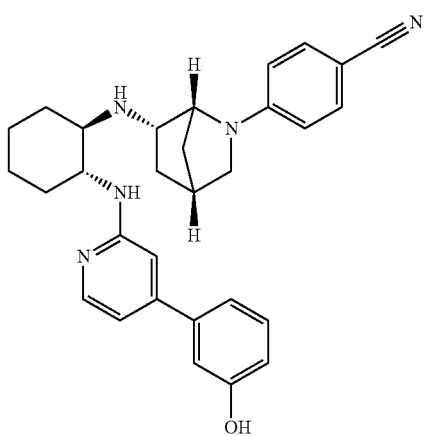 [SMILES: N#Cc1ccc(N2C[C@@H]3C[C@H](N[C@@H]4CCCC[C@H]4Nc4cc(-c5cccc(O)c5)ccn4)[C@H]2C3)cc1] | 1 | 1.50 (L) | 480.4 | Scheme 5 |

TABLE 2-continued

| Example | Structure | hY4 CAMP EC50 (nM) | HPLC retention time (Method) | Mass (M + H) | Synthesis Method |
|---------|-----------|--------------------|------------------------------|--------------|------------------|
| 229 | 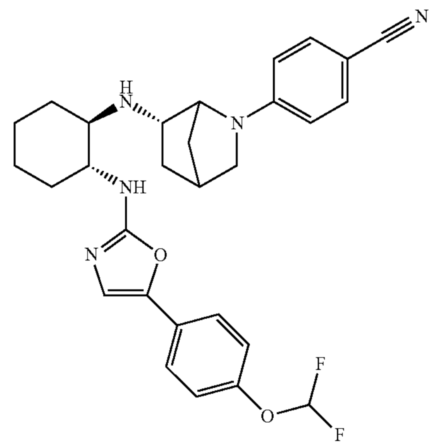 [SMILES: N#Cc1ccc(N2CC3CC2[C@@H](N[C@@H]2CCCC[C@H]2Nc2ncc(-c4ccc(OC(F)F)cc4)o2)C3)cc1] | 3 | 1.71 (L) | 520.4 | Scheme 5 |
| 230 | 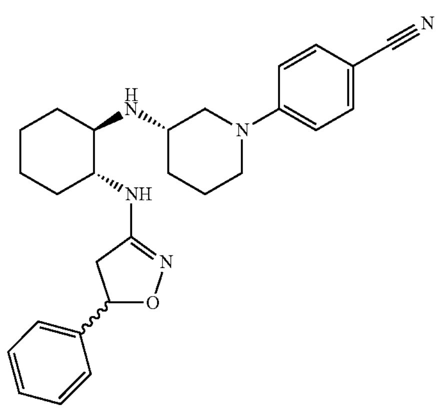 [SMILES: N#Cc1ccc(N2CCC[C@H](N[C@@H]3CCCC[C@H]3NC3=NOC(c4ccccc4)C3)C2)cc1] | 378 | 1.487 (G) | 444.2 | Scheme 1 |
| 231 | 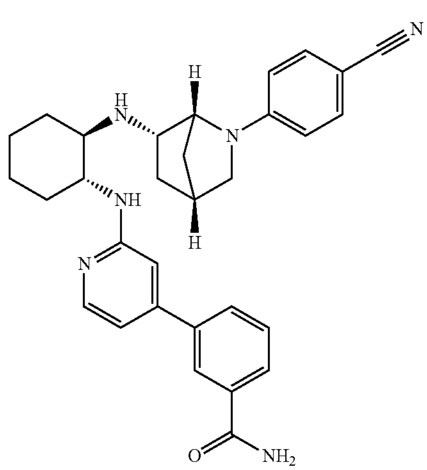 [SMILES: N#Cc1ccc(N2C[C@@H]3C[C@H](N[C@@H]4CCCC[C@H]4Nc4cc(-c5cccc(C(N)=O)c5)ccn4)[C@H]2C3)cc1] | 8 | 1.39 (L) | 507.4 | Scheme 5 |

TABLE 2-continued

| Example | Structure | hY4 CAMP EC50 (nM) | HPLC retention time (Method) | Mass (M + H) | Synthesis Method |
|---|---|---|---|---|---|
| 232 | 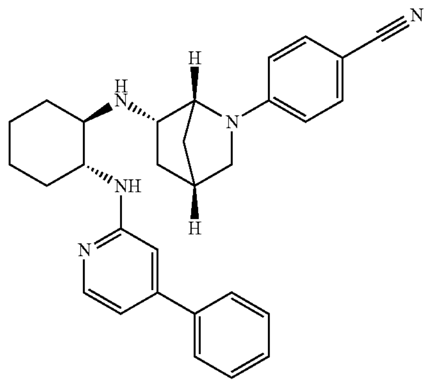 [SMILES: N#Cc1ccc(N2C[C@@H]3C[C@H](N[C@@H]4CCCC[C@H]4Nc4cc(-c5ccccc5)ccn4)[C@H]2C3)cc1] | 37 | 1.63 (L) | 464.3 | Scheme 5 |
| 233 | 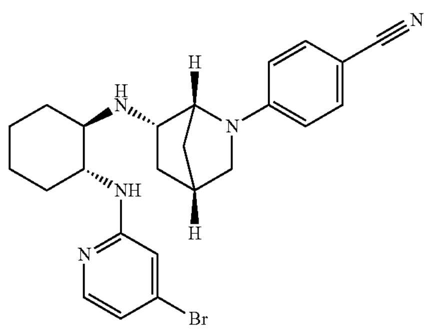 [SMILES: N#Cc1ccc(N2C[C@@H]3C[C@H](N[C@@H]4CCCC[C@H]4Nc4cc(Br)ccn4)[C@H]2C3)cc1] | 196 | 1.58 (L) | 466.3 | Scheme 5 |
| 234 | 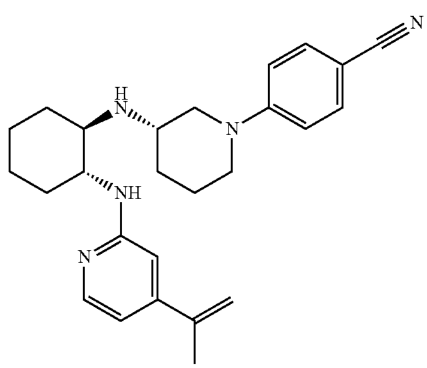 [SMILES: C=C(C)c1ccnc(N[C@@H]2CCCC[C@H]2N[C@H]2CCCN(c3ccc(C#N)cc3)C2)c1] | 299 | 2.68 (A) | 416.4 | Scheme 3 |
| 235 | 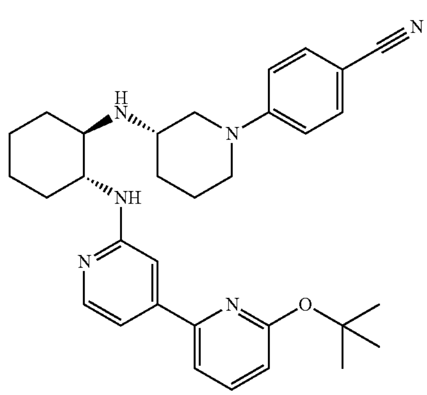 [SMILES: CC(C)(C)Oc1cccc(-c2ccnc(N[C@@H]3CCCC[C@H]3N[C@H]3CCCN(c4ccc(C#N)cc4)C3)c2)n1] | 355 | 2.37 (A) | 469.3 | Scheme 3 |

TABLE 2-continued

| Example | Structure | hY4 CAMP EC50 (nM) | HPLC retention time (Method) | Mass (M + H) | Synthesis Method |
|---------|-----------|--------------------|-----------------------------|--------------|------------------|
| 236 | 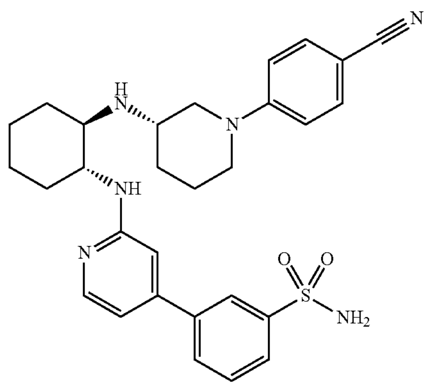 [SMILES: N#Cc1ccc(N2CCC[C@H](N[C@@H]3CCCC[C@H]3Nc3cc(-c4cccc(S(N)(=O)=O)c4)ccn3)C2)cc1] | 40 | 2.43 (A) | 531.3 | Scheme 3 |
| 237 | 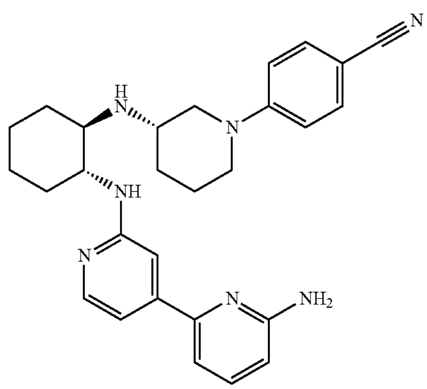 [SMILES: N#Cc1ccc(N2CCC[C@H](N[C@@H]3CCCC[C@H]3Nc3cc(-c4cccc(N)n4)ccn3)C2)cc1] | 9 | 2.13 (A) | 468.3 | Scheme 3 |
| 238 | 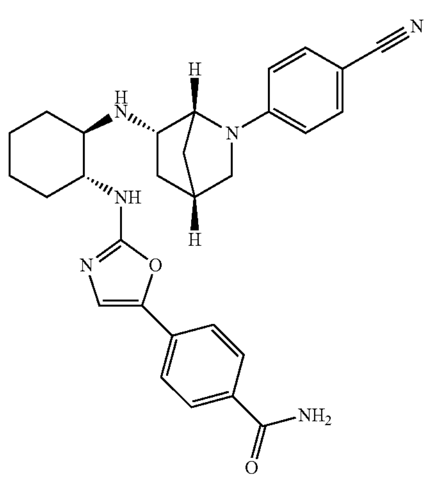 [SMILES: N#Cc1ccc(N2C[C@@H]3C[C@H](N[C@@H]4CCCC[C@H]4Nc4ncc(-c5ccc(C(N)=O)cc5)o4)[C@H]2C3)cc1] | 272 | 1.39 (L) | 497.4 | Scheme 5 |

TABLE 2-continued
| Example | Structure | hY4 CAMP EC50 (nM) | HPLC retention time (Method) | Mass (M + H) | Synthesis Method |
|---------|-----------|--------------------|------------------------------|--------------|------------------|
| 239 | 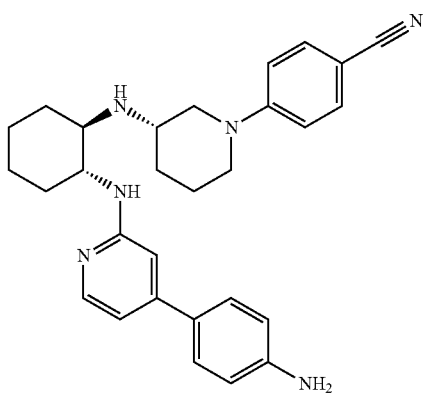 [SMILES: N#Cc1ccc(N2CCC[C@H](N[C@@H]3CCCC[C@H]3Nc3cc(-c4ccc(N)cc4)ccn3)C2)cc1] | 290 | 3.150 (H) | 467.2 | Scheme 3 |
| 240 | 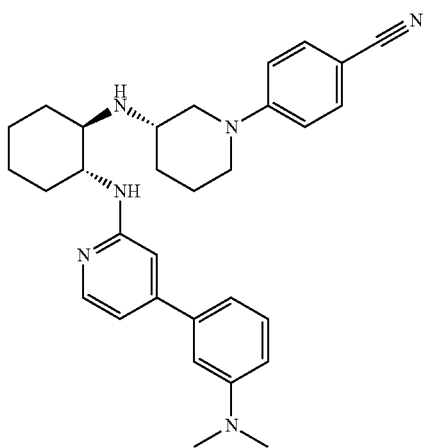 [SMILES: CN(C)c1cccc(-c2ccnc(N[C@@H]3CCCC[C@H]3N[C@H]3CCCN(c4ccc(C#N)cc4)C3)c2)c1] | 72 | 4.470 (H) | 495.3 | Scheme 3 |
| 241 | 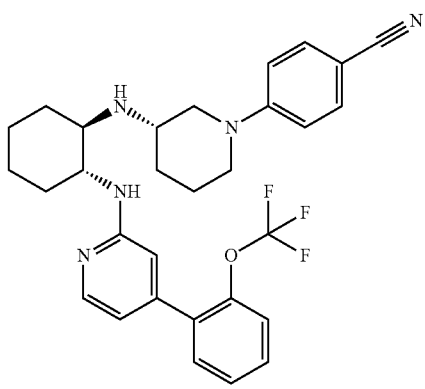 [SMILES: N#Cc1ccc(N2CCC[C@H](N[C@@H]3CCCC[C@H]3Nc3cc(-c4ccccc4OC(F)(F)F)ccn3)C2)cc1] | 289 | 4.690 (H) | 536.2 | Scheme 3 |

TABLE 2-continued

| Example | Structure | hY4 cAMP EC50 (nM) | HPLC retention time (Method) | Mass (M + H) | Synthesis Method |
|---------|-----------|--------------------|------------------------------|--------------|------------------|
| 242 | 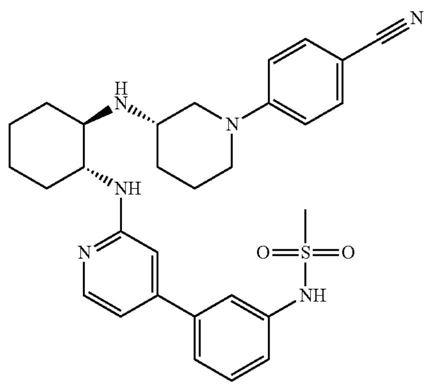 [SMILES: CS(=O)(=O)Nc1cccc(-c2ccnc(N[C@@H]3CCCC[C@H]3N[C@H]3CCCN(c4ccc(C#N)cc4)C3)c2)c1] | 3 | 3.180 (H) | 545.2 | Scheme 3 |
| 243 | 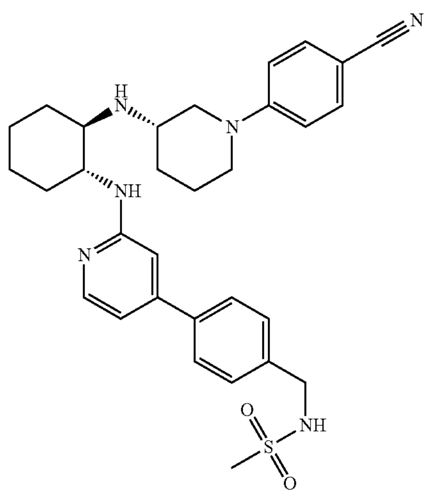 [SMILES: CS(=O)(=O)NCc1ccc(-c2ccnc(N[C@@H]3CCCC[C@H]3N[C@H]3CCCN(c4ccc(C#N)cc4)C3)c2)cc1] | 602 | 3.220 (H) | 559.2 | Scheme 3 |
| 244 | 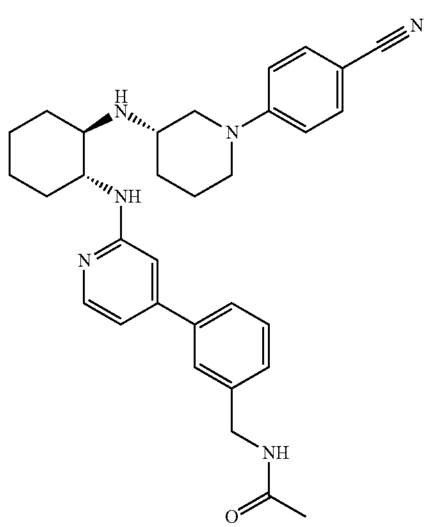 [SMILES: CC(=O)NCc1cccc(-c2ccnc(N[C@@H]3CCCC[C@H]3N[C@H]3CCCN(c4ccc(C#N)cc4)C3)c2)c1] | 7 | 2.960 (H) | 522.7 | Scheme 3 |

TABLE 2-continued

| Example | Structure | hY4 CAMP EC50 (nM) | HPLC retention time (Method) | Mass (M + H) | Synthesis Method |
|---------|-----------|-------------------|------------------------------|--------------|------------------|
| 245 | 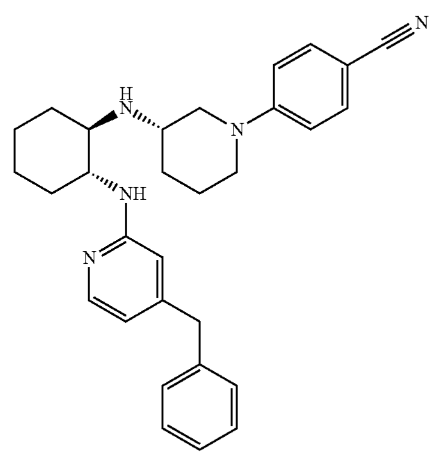 [SMILES: N#Cc1ccc(N2CCC[C@H](N[C@@H]3CCCC[C@H]3Nc3cc(Cc4ccccc4)ccn3)C2)cc1] | 299 | 4.510 (H) | 466.3 | Scheme 3 |
| 246 | 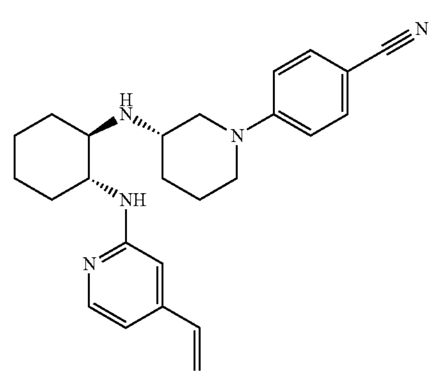 [SMILES: C=Cc1ccnc(N[C@@H]2CCCC[C@H]2N[C@H]2CCCN(c3ccc(C#N)cc3)C2)c1] | 379 | 3.520 (H) | 402.2 | Scheme 3 |
| 247 | 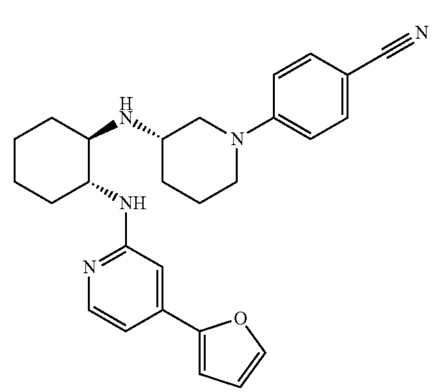 [SMILES: N#Cc1ccc(N2CCC[C@H](N[C@@H]3CCCC[C@H]3Nc3cc(-c4ccco4)ccn3)C2)cc1] | 15 | 3.560 (H) | 442.2 | Scheme 3 |

TABLE 2-continued
| Example | Structure | hY4 CAMP EC50 (nM) | HPLC retention time (Method) | Mass (M + H) | Synthesis Method |
|---|---|---|---|---|---|
| 248 | 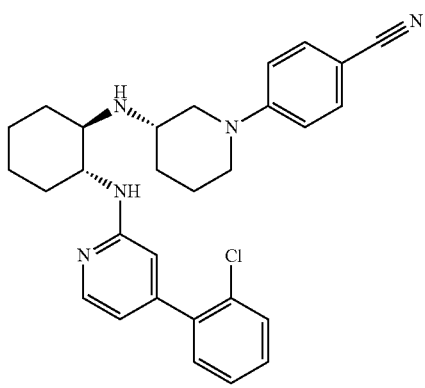 [SMILES: N#Cc1ccc(N2CCC[C@H](N[C@@H]3CCCC[C@H]3Nc3cc(-c4ccccc4Cl)ccn3)C2)cc1] | 557 | 4.410 (H) | 486.2 | Scheme 3 |
| 249 | 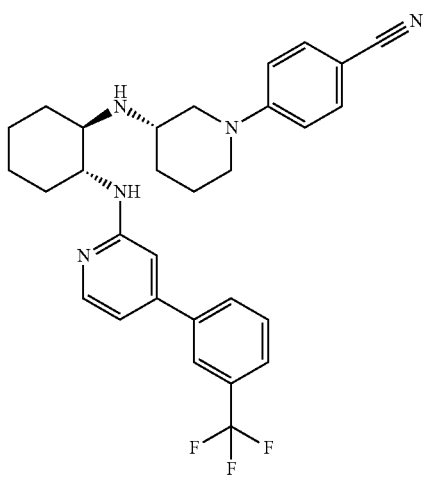 [SMILES: N#Cc1ccc(N2CCC[C@H](N[C@@H]3CCCC[C@H]3Nc3cc(-c4cccc(C(F)(F)F)c4)ccn3)C2)cc1] | 537 | 4.500 (H) | 520.1 | Scheme 3 |
| 250 | 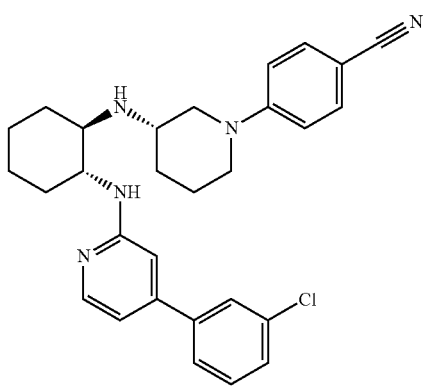 [SMILES: N#Cc1ccc(N2CCC[C@H](N[C@@H]3CCCC[C@H]3Nc3cc(-c4cccc(Cl)c4)ccn3)C2)cc1] | 559 | 4.520 (H) | 486.2 | Scheme 3 |

TABLE 2-continued

| Example | Structure | hY4 cAMP EC50 (nM) | HPLC retention time (Method) | Mass (M + H) | Synthesis Method |
|---------|-----------|--------------------|------------------------------|--------------|------------------|
| 251 | 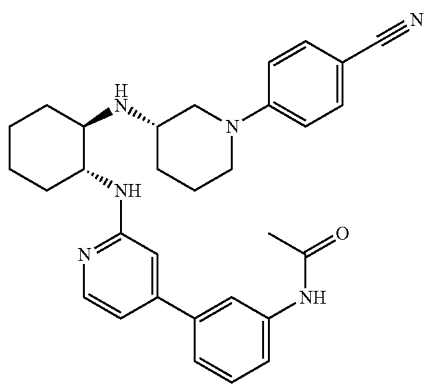 [SMILES: CC(=O)Nc1cccc(-c2ccnc(N[C@@H]3CCCC[C@H]3N[C@H]3CCCN(c4ccc(C#N)cc4)C3)c2)c1] | 1 | 3.030 (H) | 509.3 | Scheme 3 |
| 252 | 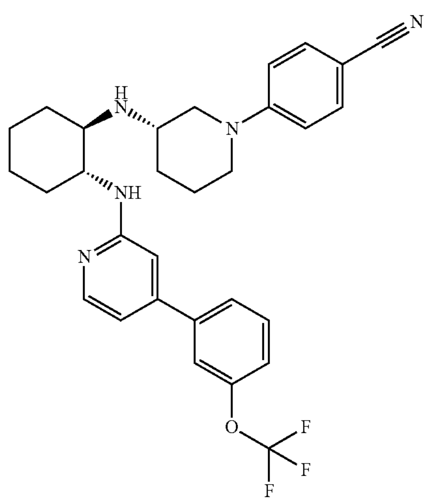 [SMILES: N#Cc1ccc(N2CCC[C@H](N[C@@H]3CCCC[C@H]3Nc3cc(-c4cccc(OC(F)(F)F)c4)ccn3)C2)cc1] | 313 | 4.770 (H) | 539.2 | Scheme 3 |
| 253 | 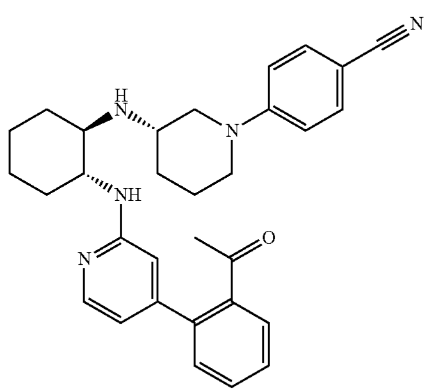 [SMILES: CC(=O)c1ccccc1-c1ccnc(N[C@@H]2CCCC[C@H]2N[C@H]2CCCN(c3ccc(C#N)cc3)C2)c1] | 70 | 3.750 (H) | 494.2 | Scheme 3 |

TABLE 2-continued
| Example | Structure | hY4 CAMP EC50 (nM) | HPLC retention time (Method) | Mass (M + H) | Synthesis Method |
|---|---|---|---|---|---|
| 254 | 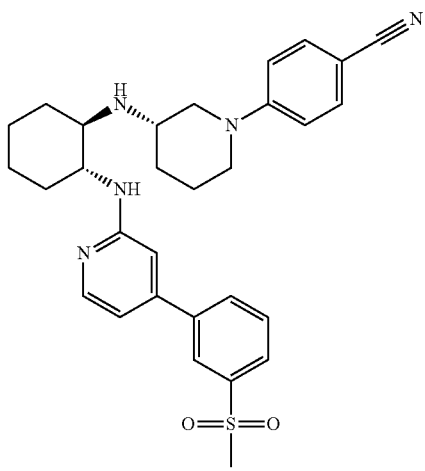 [SMILES: CS(=O)(=O)c1cccc(-c2ccnc(N[C@@H]3CCCC[C@H]3N[C@H]3CCCN(c4ccc(C#N)cc4)C3)c2)c1] | 381 | 3.070 (H) | 530.2 | Scheme 3 |
| 255 | 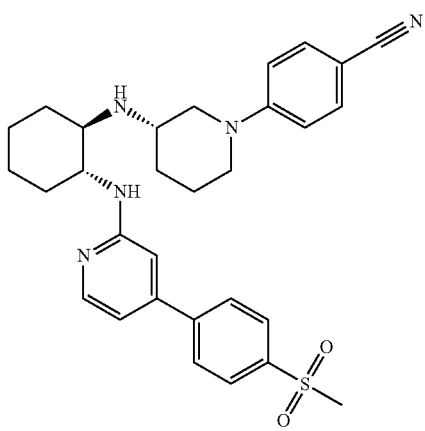 [SMILES: CS(=O)(=O)c1ccc(-c2ccnc(N[C@@H]3CCCC[C@H]3N[C@H]3CCCN(c4ccc(C#N)cc4)C3)c2)cc1] | 922 | 3.160 (H) | 530.2 | Scheme 3 |
| 256 | 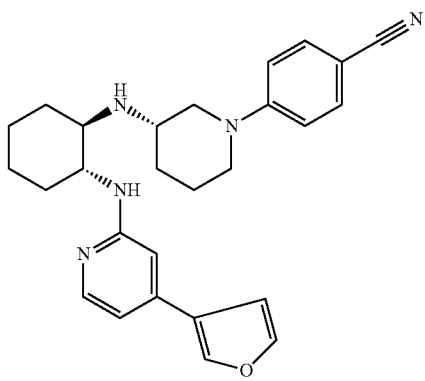 [SMILES: N#Cc1ccc(N2CCC[C@H](N[C@@H]3CCCC[C@H]3Nc3cc(-c4ccoc4)ccn3)C2)cc1] | 38 | 3.380 (H) | 494.2 | Scheme 3 |

TABLE 2-continued

| Example | Structure | hY4 cAMP EC50 (nM) | HPLC retention time (Method) | Mass (M + H) | Synthesis Method |
|---|---|---|---|---|---|
| 257 | 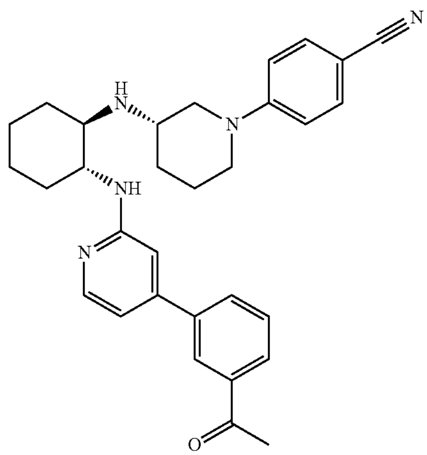 [SMILES: CC(=O)c1cccc(-c2ccnc(N[C@@H]3CCCC[C@H]3N[C@H]3CCCN(c4ccc(C#N)cc4)C3)c2)c1] | 100 | 3.410 (H) | 494.2 | Scheme 3 |
| 258 | 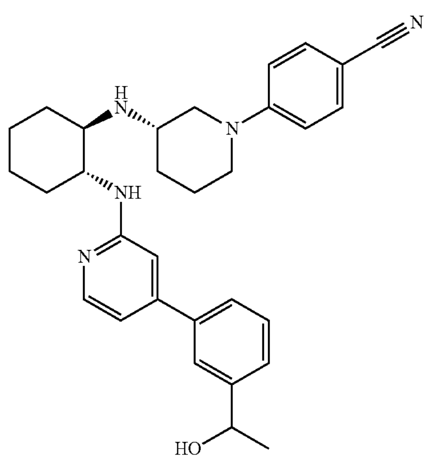 [SMILES: CC(O)c1cccc(-c2ccnc(N[C@@H]3CCCC[C@H]3N[C@H]3CCCN(c4ccc(C#N)cc4)C3)c2)c1] | 10 | 3.040 (H) | 456.2 | Scheme 3 |
| 259 | 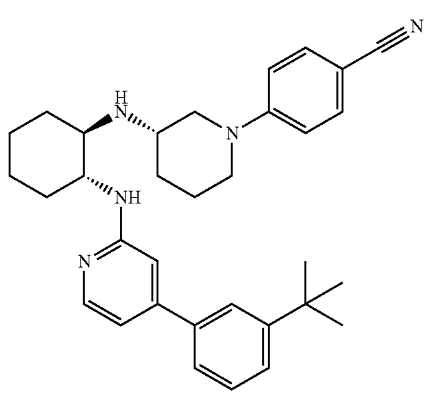 [SMILES: CC(C)(C)c1cccc(-c2ccnc(N[C@@H]3CCCC[C@H]3N[C@H]3CCCN(c4ccc(C#N)cc4)C3)c2)c1] | 59 | 5.290 (H) | 508.3 | Scheme 3 |

TABLE 2-continued

| Example | Structure | hY4 cAMP EC50 (nM) | HPLC retention time (Method) | Mass (M + H) | Synthesis Method |
|---|---|---|---|---|---|
| 260 | 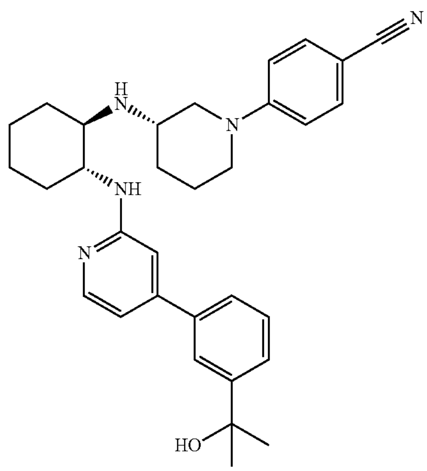 [SMILES: CC(C)(O)c1cccc(-c2ccnc(N[C@@H]3CCCC[C@H]3N[C@H]3CCCN(c4ccc(C#N)cc4)C3)c2)c1] | 11 | 3.430 (H) | 510.3 | Scheme 3 |
| 261 | 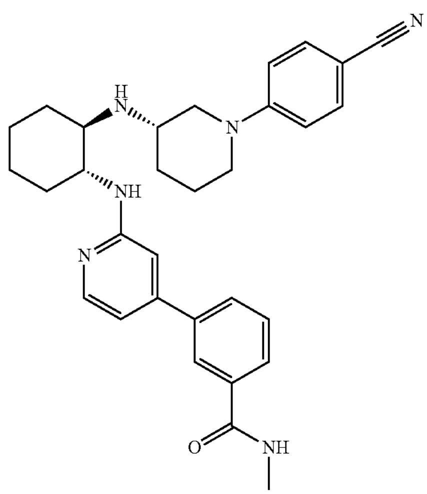 [SMILES: CNC(=O)c1cccc(-c2ccnc(N[C@@H]3CCCC[C@H]3N[C@H]3CCCN(c4ccc(C#N)cc4)C3)c2)c1] | 9 | 2.790 (H) | 509.2 | Scheme 3 |
| 262 | 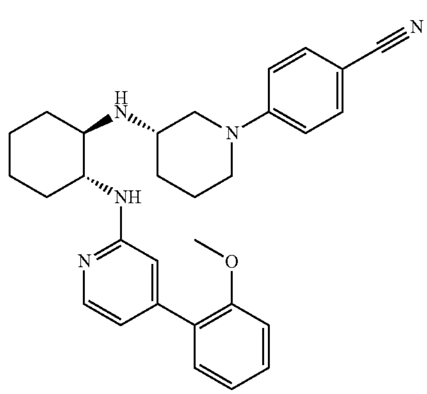 [SMILES: COc1ccccc1-c1ccnc(N[C@@H]2CCCC[C@H]2N[C@H]2CCCN(c3ccc(C#N)cc3)C2)c1] | 116 | 4.000 (H) | 482.2 | Scheme 3 |

TABLE 2-continued

| Example | Structure | hY4 CAMP EC50 (nM) | HPLC retention time (Method) | Mass (M + H) | Synthesis Method |
|---------|-----------|--------------------|------------------------------|--------------|------------------|
| 263 | 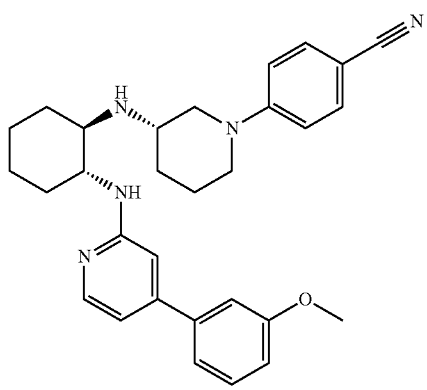 [SMILES: COc1cccc(-c2ccnc(N[C@@H]3CCCC[C@H]3N[C@H]3CCCN(c4ccc(C#N)cc4)C3)c2)c1] | 87 | 4.060 (H) | 482.2 | Scheme 3 |
| 264 | 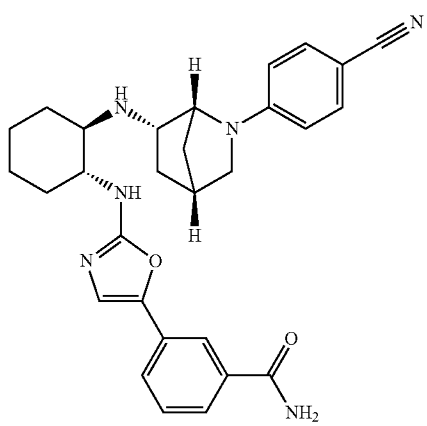 [SMILES: N#Cc1ccc(N2C[C@@H]3C[C@H](N[C@@H]4CCCC[C@H]4Nc4ncc(-c5cccc(C(N)=O)c5)o4)[C@H]2C3)cc1] | 7 | 1.39 (L) | 497.4 | Scheme 5 |
| 265 | 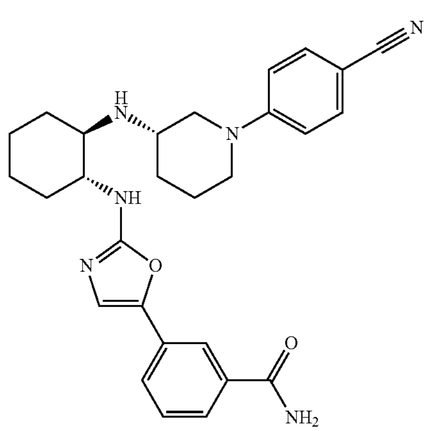 [SMILES: N#Cc1ccc(N2CCC[C@H](N[C@@H]3CCCC[C@H]3Nc3ncc(-c4cccc(C(N)=O)c4)o3)C2)cc1] | 2 | 1.37 (L) | 485.4 | Scheme 1 |

TABLE 2-continued
| Example | Structure | hY4 cAMP EC50 (nM) | HPLC retention time (Method) | Mass (M + H) | Synthesis Method |
|---|---|---|---|---|---|
| 266 | 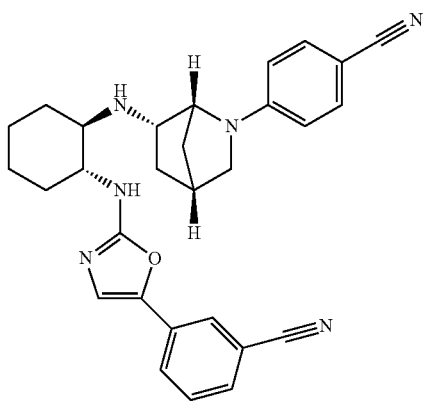 [SMILES: N#Cc1ccc(N2C[C@@H]3C[C@H](N[C@@H]4CCCC[C@H]4Nc4ncc(-c5cccc(C#N)c5)o4)[C@H]2C3)cc1] | 181 | 1.55 (L) | 479.3 | Scheme 5 |
| 267 | 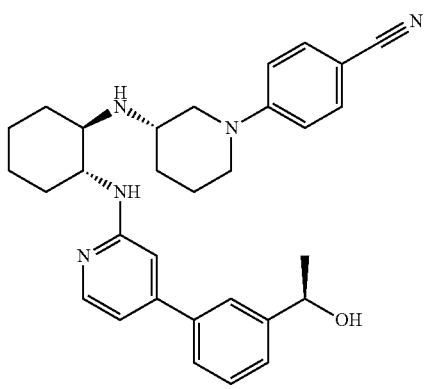 [SMILES: C[C@@H](O)c1cccc(-c2ccnc(N[C@@H]3CCCC[C@H]3N[C@H]3CCCN(c4ccc(C#N)cc4)C3)c2)c1] | 3 | 2.79 (A) | 496.2 | Scheme 3 |
| 268 | 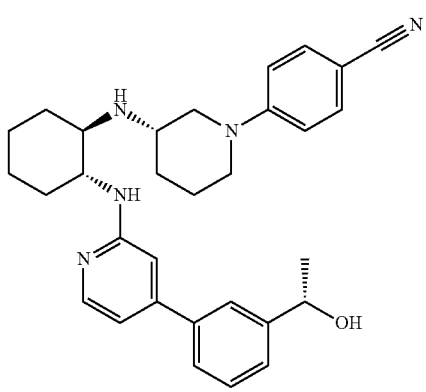 [SMILES: C[C@H](O)c1cccc(-c2ccnc(N[C@@H]3CCCC[C@H]3N[C@H]3CCCN(c4ccc(C#N)cc4)C3)c2)c1] | 8 | 2.79 (A) | 496.2 | Scheme 3 |

TABLE 2-continued
| Example | Structure | hY4 CAMP EC50 (nM) | HPLC retention time (Method) | Mass (M + H) | Synthesis Method |
|---------|-----------|--------------------|------------------------------|--------------|------------------|
| 269 | 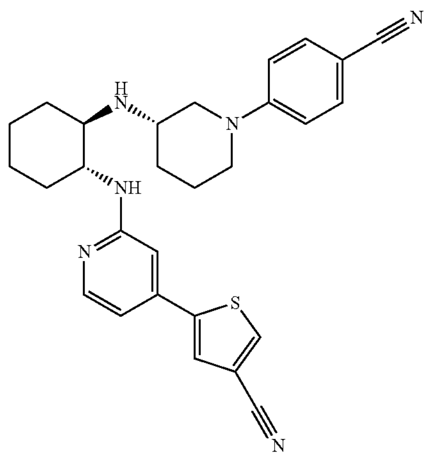 [SMILES: N#Cc1ccc(N2CCC[C@H](N[C@@H]3CCCC[C@H]3Nc3cc(-c4cc(C#N)cs4)ccn3)C2)cc1] | 223 | 4.020 (I) | 483.2 | Scheme 3 |
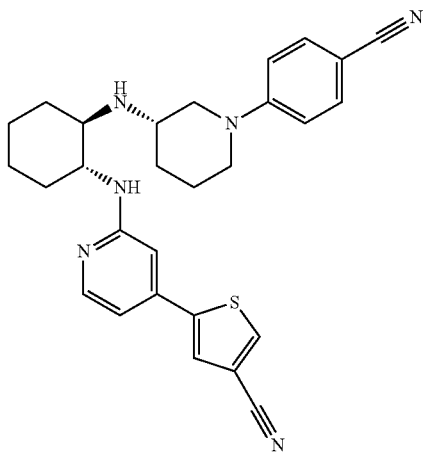
| 270 | | 468 | 3.330 (I) | 453.2 | Scheme 3 |
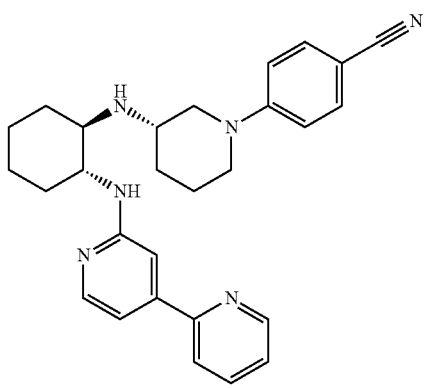 [SMILES: N#Cc1ccc(N2CCC[C@H](N[C@@H]3CCCC[C@H]3Nc3cc(-c4ccccn4)ccn3)C2)cc1]
| 271 | | 461 | 4.060 (I) | 466.3 | Scheme 3 |
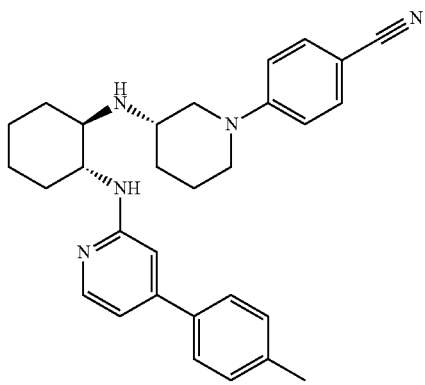 [SMILES: Cc1ccc(-c2ccnc(N[C@@H]3CCCC[C@H]3N[C@H]3CCCN(c4ccc(C#N)cc4)C3)c2)cc1]

TABLE 2-continued
| Example | Structure | hY4 CAMP EC50 (nM) | HPLC retention time (Method) | Mass (M + H) | Synthesis Method |
|---|---|---|---|---|---|
| 272 | 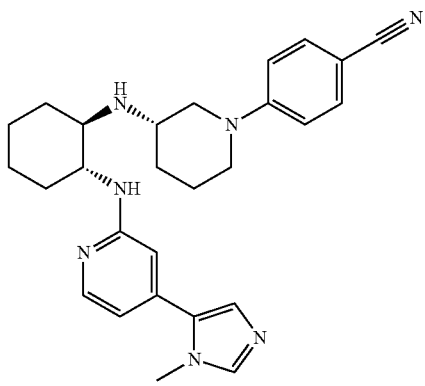 [SMILES: Cn1cncc1-c1ccnc(N[C@@H]2CCCC[C@H]2N[C@H]2CCCN(c3ccc(C#N)cc3)C2)c1] | 537 | 3.970 (I) | 454.1 | Scheme 3 |
| 273 | 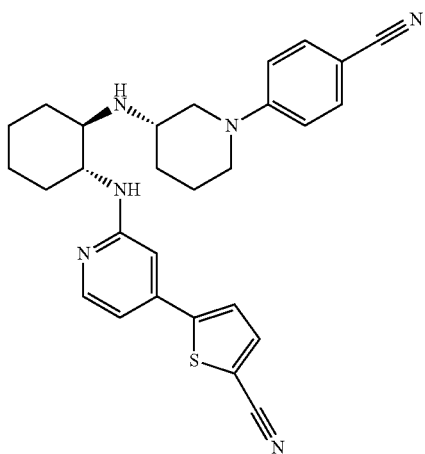 [SMILES: N#Cc1ccc(N2CCC[C@H](N[C@@H]3CCCC[C@H]3Nc3cc(-c4ccc(C#N)s4)ccn3)C2)cc1] | 542 | 4.060 (I) | 483.2 | Scheme 3 |
| 274 | 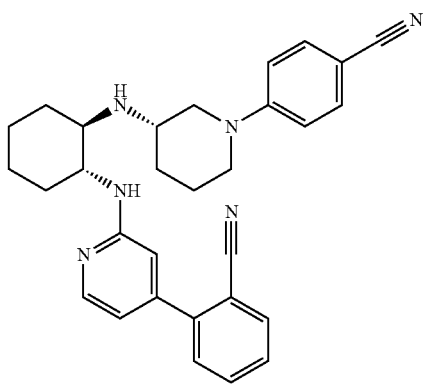 [SMILES: N#Cc1ccc(N2CCC[C@H](N[C@@H]3CCCC[C@H]3Nc3cc(-c4ccccc4C#N)ccn3)C2)cc1] | 272 | 3.870 (I) | 477.2 | Scheme 3 |

TABLE 2-continued

| Example | Structure | hY4 CAMP EC50 (nM) | HPLC retention time (Method) | Mass (M + H) | Synthesis Method |
|---|---|---|---|---|---|
| 275 | 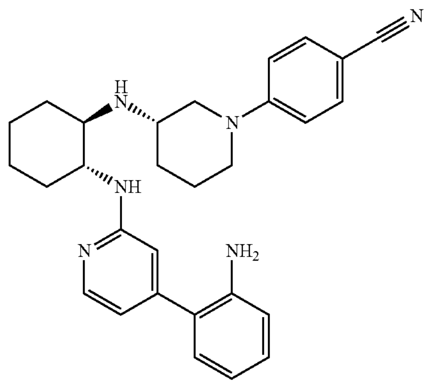 [SMILES: N#Cc1ccc(N2CCC[C@H](N[C@@H]3CCCC[C@H]3Nc3cc(-c4ccccc4N)ccn3)C2)cc1] | 872 | 3.690 (I) | 467.2 | Scheme 3 |
| 276 | 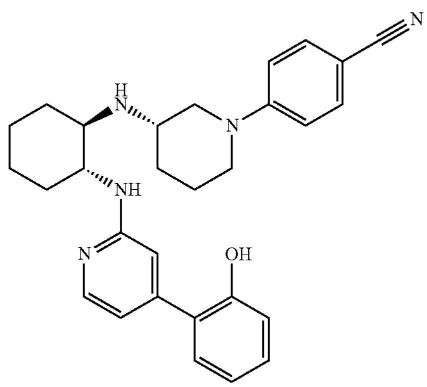 [SMILES: N#Cc1ccc(N2CCC[C@H](N[C@@H]3CCCC[C@H]3Nc3cc(-c4ccccc4O)ccn3)C2)cc1] | 120 | 3.610 (I) | 468.2 | Scheme 3 |
| 277 | 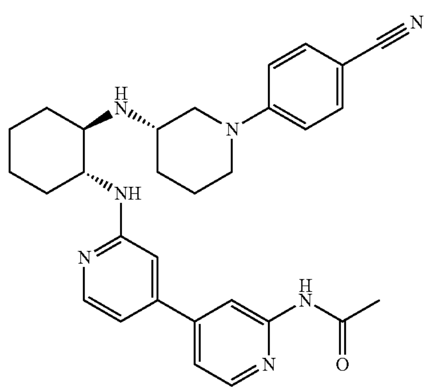 [SMILES: CC(=O)Nc1cc(-c2ccnc(N[C@@H]3CCCC[C@H]3N[C@H]3CCCN(c4ccc(C#N)cc4)C3)c2)ccn1] | 8 | 3.130 (I) | 510.2 | Scheme 3 |
| 278 | 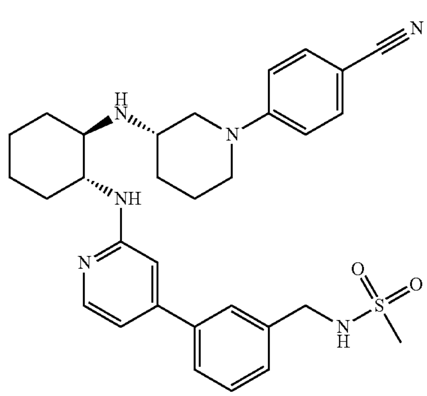 [SMILES: CS(=O)(=O)NCc1cccc(-c2ccnc(N[C@@H]3CCCC[C@H]3N[C@H]3CCCN(c4ccc(C#N)cc4)C3)c2)c1] | 24 | 3.580 (I) | 559.2 | Scheme 3 |

TABLE 2-continued

| Example | Structure | hY4 CAMP EC50 (nM) | HPLC retention time (Method) | Mass (M + H) | Synthesis Method |
|---|---|---|---|---|---|
| 279 | 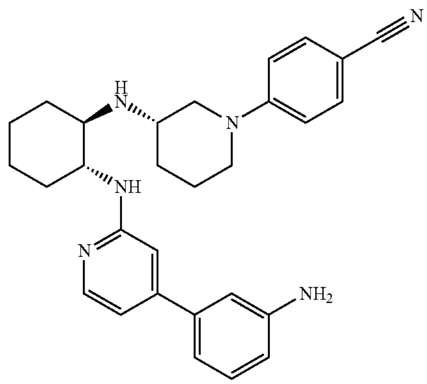 [SMILES: N#Cc1ccc(N2CCC[C@H](N[C@@H]3CCCC[C@H]3Nc3cc(-c4cccc(N)c4)ccn3)C2)cc1] | 12 | 3.100 (I) | 467.2 | Scheme 2 |
| 280 | 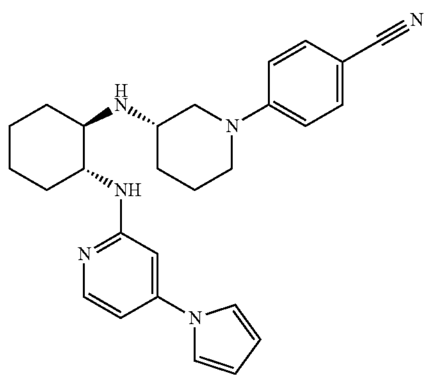 [SMILES: N#Cc1ccc(N2CCC[C@H](N[C@@H]3CCCC[C@H]3Nc3cc(-n4cccc4)ccn3)C2)cc1] | 43 | 1.275 (C) | 441.1 | Scheme 2 |
| 281 | 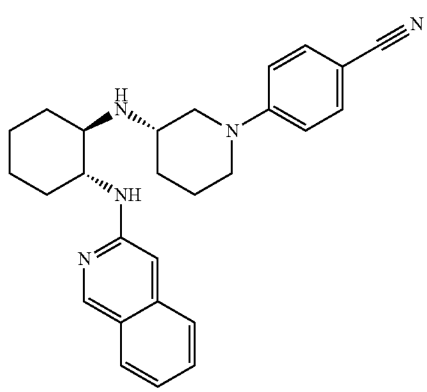 [SMILES: N#Cc1ccc(N2CCC[C@H](N[C@@H]3CCCC[C@H]3Nc3cc4ccccc4cn3)C2)cc1] | 152 | 2.425 (B) | 426.3 | Scheme 1 |
| 282 | 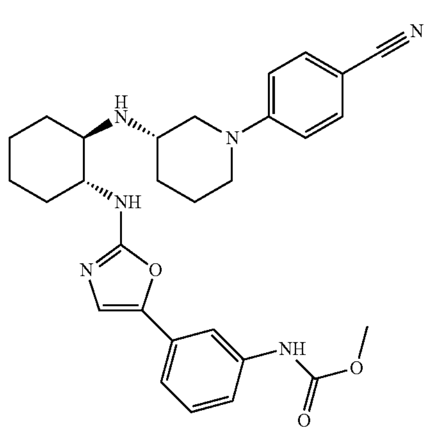 [SMILES: COC(=O)Nc1cccc(-c2cnc(N[C@@H]3CCCC[C@H]3N[C@H]3CCCN(c4ccc(C#N)cc4)C3)o2)c1] | 1 | 1.34 (C) | 515.3 | Scheme 1 |

TABLE 2-continued

| Example | Structure | hY4 CAMP EC50 (nM) | HPLC retention time (Method) | Mass (M + H) | Synthesis Method |
|---|---|---|---|---|---|
| 283 | 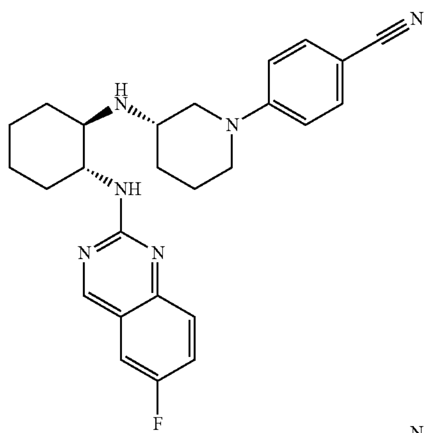 [SMILES: N#Cc1ccc(N2CCC[C@H](N[C@@H]3CCCC[C@H]3Nc3ncc4cc(F)ccc4n3)C2)cc1] | 308 | 1.285 (C) | 445.3 | Scheme 1 |
| 284 | 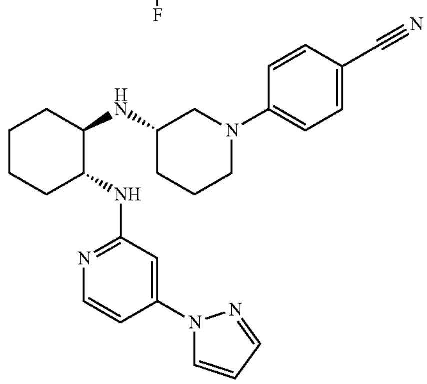 | 176 | 1.161 (C) | 442.1 | Scheme 3 |

Table 3 includes additional compounds of the invention wherein $R^2$ is Phenyl-$NO_2$.

TABLE 3

| Example | Structure | hY4 CAMP EC50 (nM) | HPLC retention time (Method) | Mass (M + H) | Synthesis Method |
|---|---|---|---|---|---|
| 285 | 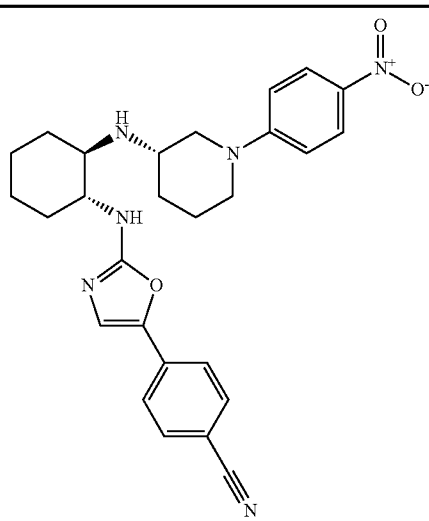 | 26 | 1.60 (L) | 487.4 | Scheme 1 |

TABLE 3-continued

| Example | Structure | hY4 CAMP EC50 (nM) | HPLC retention time (Method) | Mass (M + H) | Synthesis Method |
|---------|-----------|--------------------|------------------------------|--------------|------------------|
| 286 | 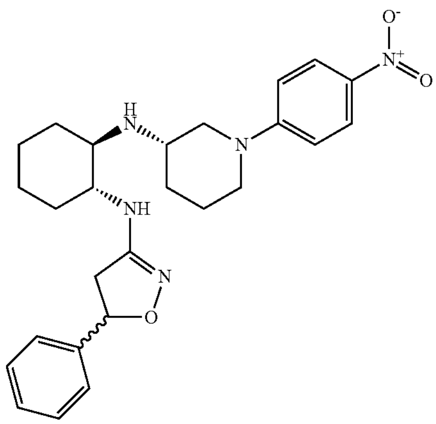 [SMILES: O=[N+]([O-])c1ccc(N2CCC[C@H](N[C@@H]3CCCC[C@H]3NC3=NOC(c4ccccc4)C3)C2)cc1] | 74 | 1.559 (G) | 464.2 | Scheme 1 |
| 287 | 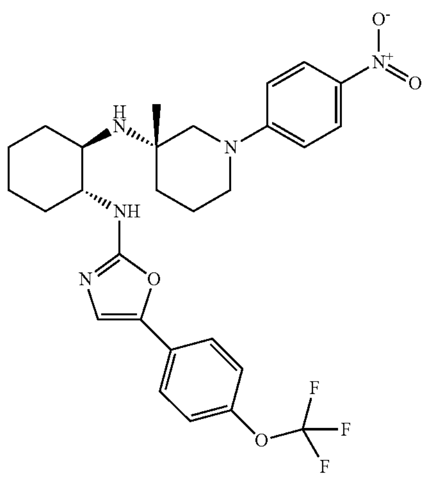 [SMILES: C[C@]1(N[C@@H]2CCCC[C@H]2Nc2ncc(-c3ccc(OC(F)(F)F)cc3)o2)CCCN(c2ccc([N+](=O)[O-])cc2)C1] | 1 | 3.53 (A) | 560.3 | Scheme 5 |
| 293 | 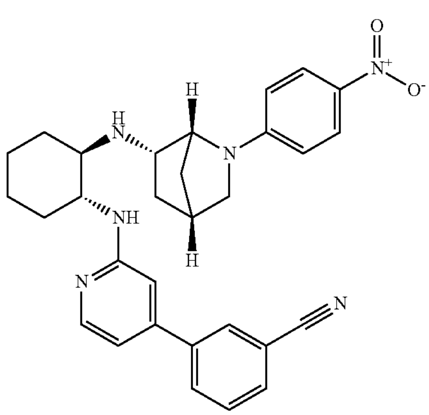 [SMILES: N#Cc1cccc(-c2ccnc(N[C@@H]3CCCC[C@H]3N[C@H]3C[C@@H]4C[C@H]3N(c3ccc([N+](=O)[O-])cc3)C4)c2)c1] | 163 | 9.836 (M) | | Scheme 5 |

TABLE 3-continued
| Example | Structure | hY4 CAMP EC50 (nM) | HPLC retention time (Method) | Mass (M + H) | Synthesis Method |
|---------|-----------|---------------------|------------------------------|--------------|------------------|
| 294 | 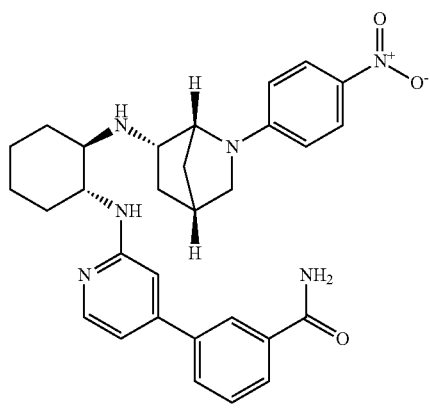 [SMILES: NC(=O)c1cccc(-c2ccnc(N[C@@H]3CCCC[C@H]3N[C@H]3C[C@@H]4C[C@H]3N(c3ccc([N+](=O)[O-])cc3)C4)c2)c1] | 41 | 6.511 (M) | | Scheme 5 |
| 295 | 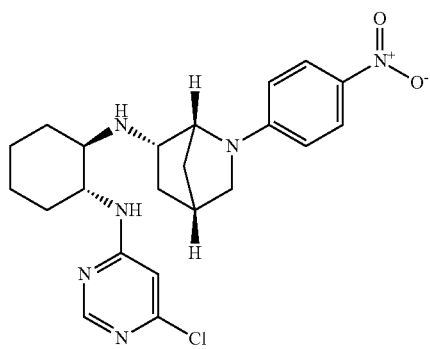 [SMILES: O=[N+]([O-])c1ccc(N2C[C@@H]3C[C@H](N[C@@H]4CCCC[C@H]4Nc4cc(Cl)ncn4)[C@H]2C3)cc1] | 122 | 5.940 (J) | 443.2 | Scheme 5 |
| 296 | 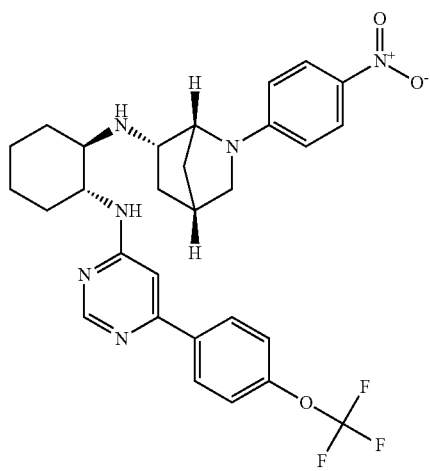 [SMILES: O=[N+]([O-])c1ccc(N2C[C@@H]3C[C@H](N[C@@H]4CCCC[C@H]4Nc4cc(-c5ccc(OC(F)(F)F)cc5)ncn4)[C@H]2C3)cc1] | 68 | 7.517 (J) | 569.2 | Scheme 5 |

TABLE 3-continued
| Example | Structure | hY4 CAMP EC50 (nM) | HPLC retention time (Method) | Mass (M + H) | Synthesis Method |
|---|---|---|---|---|---|
| 297 | 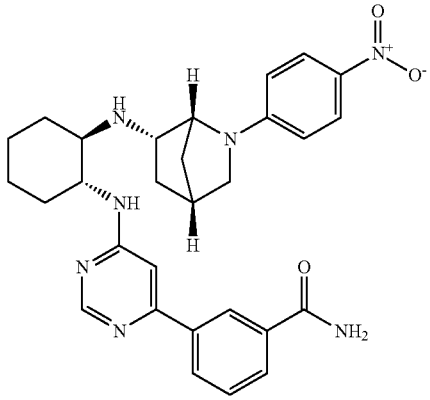 [SMILES: NC(=O)c1cccc(-c2cc(N[C@@H]3CCCC[C@H]3N[C@H]3C[C@@H]4C[C@H]3N(c3ccc([N+](=O)[O-])cc3)C4)ncn2)c1] | 163 | | 528.2 | Scheme 5 |
Table 4 includes additional compounds of the invention wherein $R^2$ is Pyridinyl-CN.
TABLE 4
| Example | Structure | hY4 CAMP EC50 (nM) | HPLC retention time (Method) | Mass (M + H) | Synthesis Method |
|---|---|---|---|---|---|
| 298 | 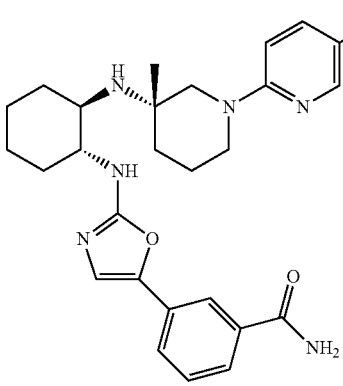 | 23 | 3.09 (A) | 500.1 | Scheme 4 |
| 299 | 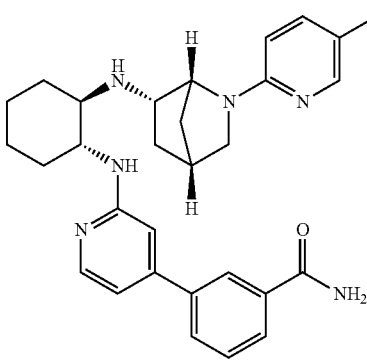 | 392 | | 508.2 | Scheme 5 |

TABLE 4-continued

| Example | Structure | hY4 CAMP EC50 (nM) | HPLC retention time (Method) | Mass (M + H) | Synthesis Method |
|---------|-----------|---------------------|------------------------------|--------------|------------------|
| 300 | 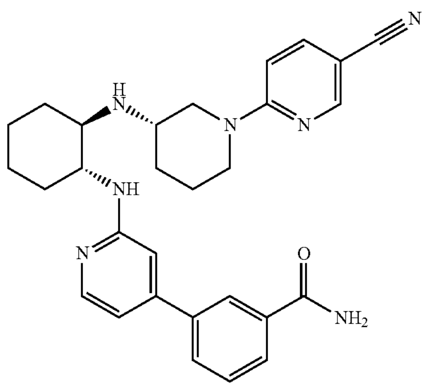 [SMILES: N#Cc1ccc(N2CCC[C@H](N[C@@H]3CCCC[C@H]3Nc3cc(-c4cccc(C(N)=O)c4)ccn3)C2)nc1] | 130 | | 496.2 | Scheme 3 |
| 301 | 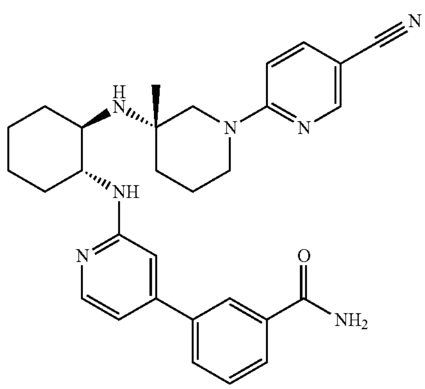 [SMILES: C[C@]1(N[C@@H]2CCCC[C@H]2Nc2cc(-c3cccc(C(N)=O)c3)ccn2)CCCN(c2ccc(C#N)cn2)C1] | 66 | 5.675 (J) | 510.2 | Scheme 4 |
| 302 | 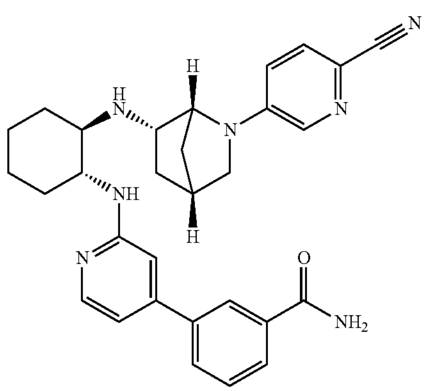 [SMILES: N#Cc1ccc(N2C[C@@H]3C[C@H](N[C@@H]4CCCC[C@H]4Nc4cc(-c5cccc(C(N)=O)c5)ccn4)[C@H]2C3)cn1] | 1215 | | 508.2 | Scheme 5 |
| 303 | 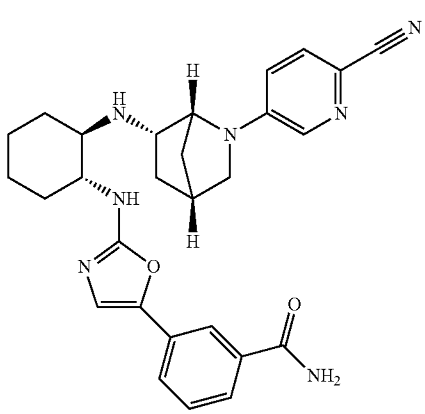 [SMILES: N#Cc1ccc(N2C[C@@H]3C[C@H](N[C@@H]4CCCC[C@H]4Nc4ncc(-c5cccc(C(N)=O)c5)o4)[C@H]2C3)cn1] | 221 | 5.756 (J) | 498.2 | Scheme 5 |

TABLE 4-continued
| Example | Structure | hY4 CAMP EC50 (nM) | HPLC retention time (Method) | Mass (M + H) | Synthesis Method |
|---------|-----------|---------------------|------------------------------|--------------|------------------|
| 304 | 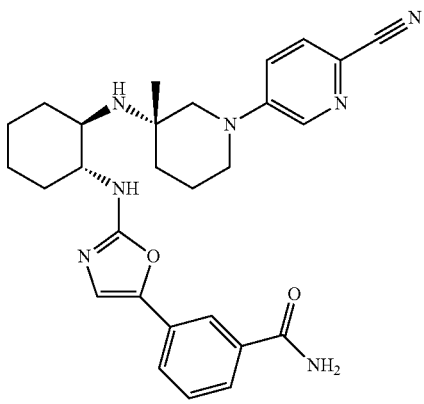 [SMILES: C[C@]1(N[C@@H]2CCCC[C@H]2Nc2ncc(-c3cccc(C(N)=O)c3)o2)CCCN(c2ccc(C#N)nc2)C1] | 3 | 2.30 (A) | 500.1 | Scheme 4 |
| 305 | 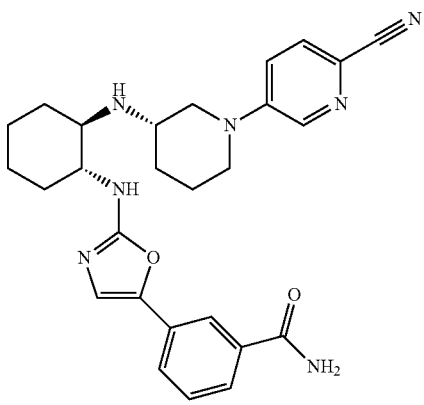 [SMILES: N#Cc1ccc(N2CCC[C@H](N[C@@H]3CCCC[C@H]3Nc3ncc(-c4cccc(C(N)=O)c4)o3)C2)cn1] | 7 | 1.30 (L) | 486.2 | Scheme 1 |
| 306 | 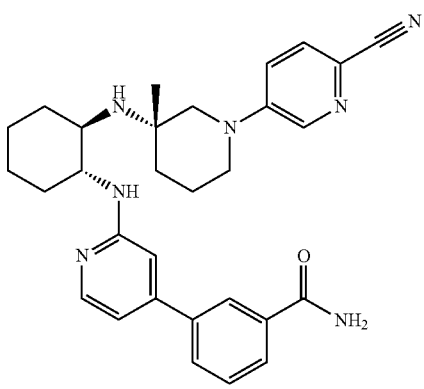 [SMILES: C[C@]1(N[C@@H]2CCCC[C@H]2Nc2cc(-c3cccc(C(N)=O)c3)ccn2)CCCN(c2ccc(C#N)nc2)C1] | 141 | 2.40 (A) | 510.1 | Scheme 4 |

TABLE 4-continued

| Example | Structure | hY4 CAMP EC50 (nM) | HPLC retention time (Method) | Mass (M + H) | Synthesis Method |
|---|---|---|---|---|---|
| 307 | 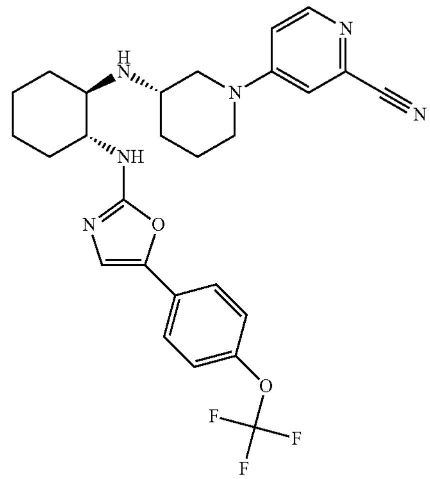 [SMILES: N#Cc1cc(N2CCC[C@H](N[C@@H]3CCCC[C@H]3Nc3ncc(-c4ccc(OC(F)(F)F)cc4)o3)C2)ccn1] | 7 | 7.169 (J) | 527.2 | Scheme 1 |
| 308 | 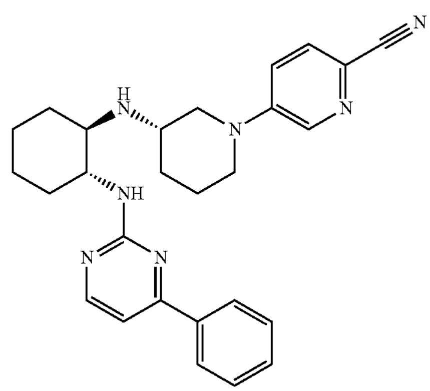 [SMILES: N#Cc1ccc(N2CCC[C@H](N[C@@H]3CCCC[C@H]3Nc3nccc(-c4ccccc4)n3)C2)cn1] | 135 | 2.68 (A) | 454.3 | Scheme 1 |
| 309 | 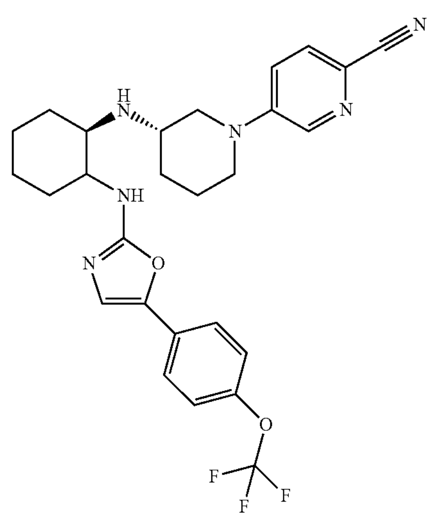 [SMILES: N#Cc1ccc(N2CCC[C@H](N[C@@H]3CCCCC3Nc3ncc(-c4ccc(OC(F)(F)F)cc4)o3)C2)cn1] | 10 | 3.24 (A) | 527.3 | Scheme 1 |

TABLE 4-continued

| Example | Structure | hY4 cAMP EC50 (nM) | HPLC retention time (Method) | Mass (M + H) | Synthesis Method |
|---|---|---|---|---|---|
| 310 | 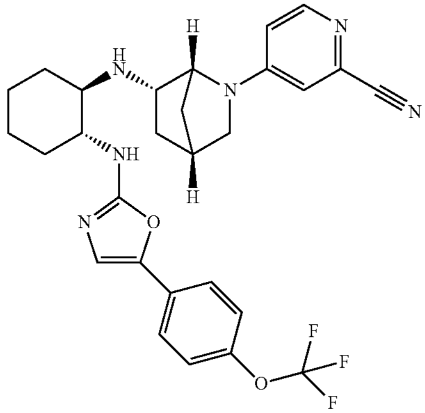 [SMILES: N#Cc1cc(N2C[C@@H]3C[C@H](N[C@@H]4CCCC[C@H]4Nc4ncc(-c5ccc(OC(F)(F)F)cc5)o4)[C@H]2C3)ccn1] | 124 | 1.664 (G) | 539.2 | Scheme 5 |
| 311 | 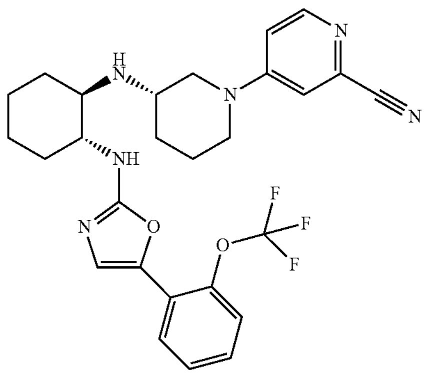 [SMILES: N#Cc1cc(N2CCC[C@H](N[C@@H]3CCCC[C@H]3Nc3ncc(-c4ccccc4OC(F)(F)F)o3)C2)ccn1] | 9 | 1.722 (G) | 527.2 | Scheme 1 |
| 312 | 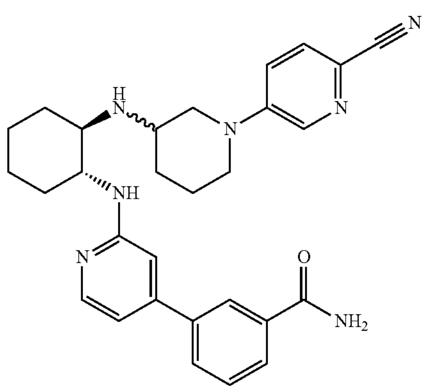 [SMILES: N#Cc1ccc(N2CCCC(N[C@@H]3CCCC[C@H]3Nc3cc(-c4cccc(C(N)=O)c4)ccn3)C2)cn1] | 124 | 2.21 (A) | 496.3 | Scheme 3 |
| 313 | 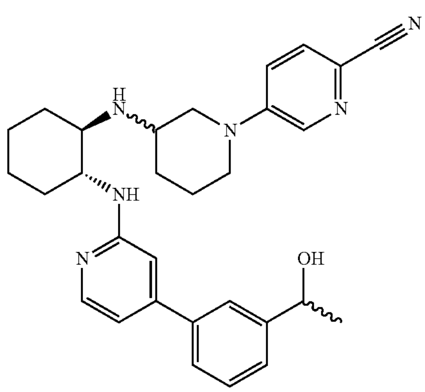 [SMILES: CC(O)c1cccc(-c2ccnc(N[C@@H]3CCCC[C@H]3NC3CCCN(c4ccc(C#N)nc4)C3)c2)c1] | 68 | 2.52 (A) | 497.3 | Scheme 3 |

TABLE 4-continued
| Example | Structure | hY4 CAMP EC50 (nM) | HPLC retention time (Method) | Mass (M + H) | Synthesis Method |
|---|---|---|---|---|---|
| 314 | 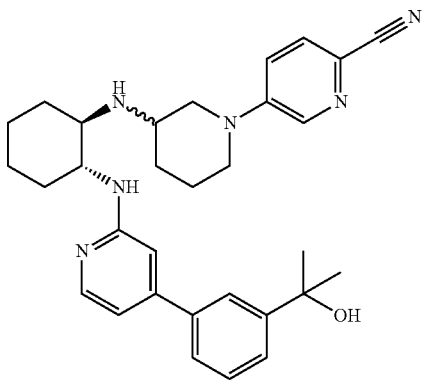 [SMILES: CC(C)(O)c1cccc(-c2ccnc(N[C@@H]3CCCC[C@H]3NC3CCCN(c4ccc(C#N)nc4)C3)c2)c1] | 67 | 2.70 (A) | 511.4 | Scheme 3 |
| 315 | 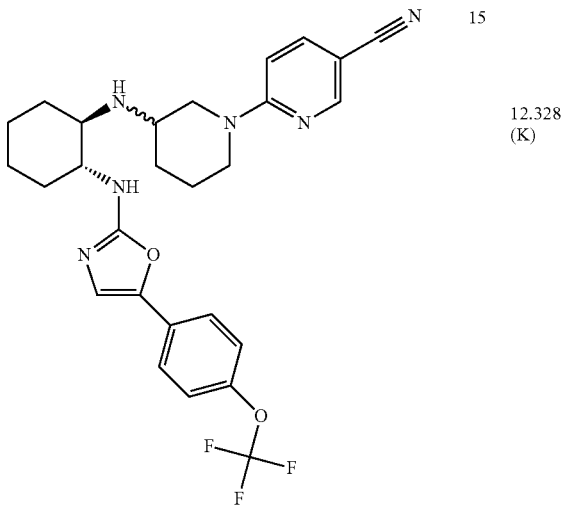 | 15 | 12.328 (K) | 527.2 | Scheme 1 |
| 316 | 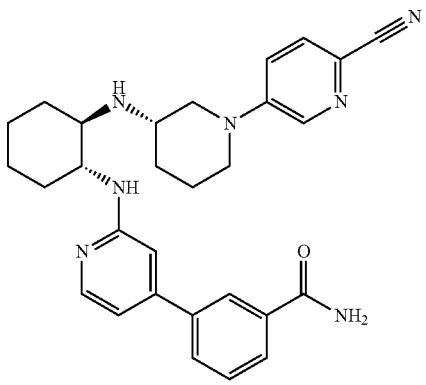 [SMILES: N#Cc1ccc(N2CCC[C@H](N[C@@H]3CCCC[C@H]3Nc3cc(-c4cccc(C(N)=O)c4)ccn3)C2)cn1] | 165 | 2.26 (A) | 496.3 | Scheme 3 |

TABLE 4-continued

| Example | Structure | hY4 CAMP EC50 (nM) | HPLC retention time (Method) | Mass (M + H) | Synthesis Method |
|---------|-----------|--------------------|-----------------------------|--------------|------------------|
| 317 | 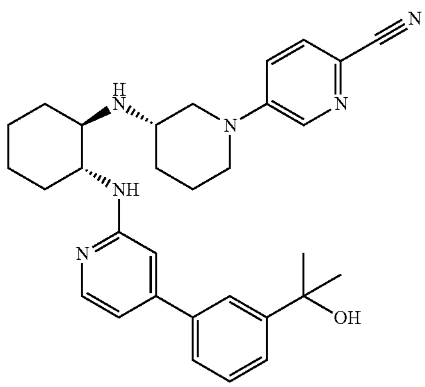 [SMILES: CC(C)(O)c1cccc(-c2ccnc(N[C@@H]3CCCC[C@H]3N[C@H]3CCCN(c4ccc(C#N)nc4)C3)c2)c1] | 105 | 2.71 (A) | 511.4 | Scheme 3 |

Table 5 includes additional compounds of the invention wherein $R^2$ is Pyridinyl-$CF_3$.

TABLE 5

| Example | Structure | hY4 CAMP EC50 (nM) | HPLC retention time (Method) | Mass (M + H) | Synthesis Method |
|---------|-----------|--------------------|-----------------------------|--------------|------------------|
| 318 | 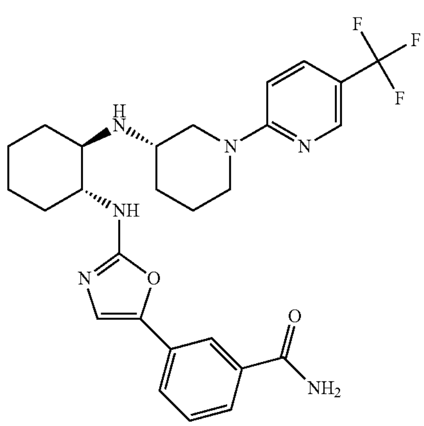 [SMILES: NC(=O)c1cccc(-c2cnc(N[C@@H]3CCCC[C@H]3N[C@H]3CCCN(c4ccc(C(F)(F)F)cn4)C3)o2)c1] | 1 | 2.81 (A) | 529.1 | Scheme 1 |
| 319 | 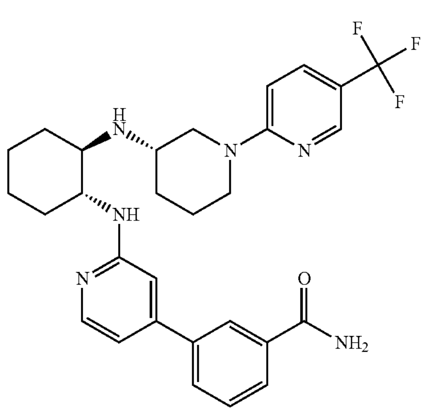 [SMILES: NC(=O)c1cccc(-c2ccnc(N[C@@H]3CCCC[C@H]3N[C@H]3CCCN(c4ccc(C(F)(F)F)cn4)C3)c2)c1] | 10 | 2.84 (A) | 539.1 | Scheme 3 |

TABLE 5-continued
| Example | Structure | hY4 cAMP EC50 (nM) | HPLC retention time (Method) | Mass (M + H) | Synthesis Method |
|---|---|---|---|---|---|
| 320 | 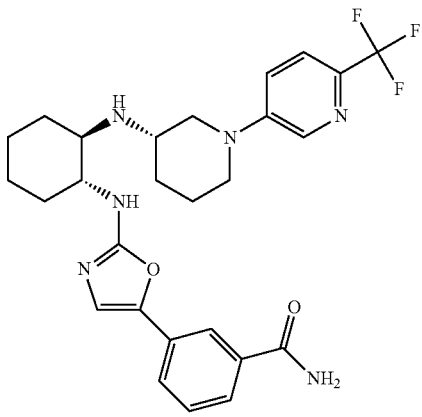 [SMILES: NC(=O)c1cccc(-c2cnc(N[C@@H]3CCCC[C@H]3N[C@H]3CCCN(c4ccc(C(F)(F)F)nc4)C3)o2)c1] | 1 | 2.66 (A) | 529.1 | Scheme 1 |
| 321 | 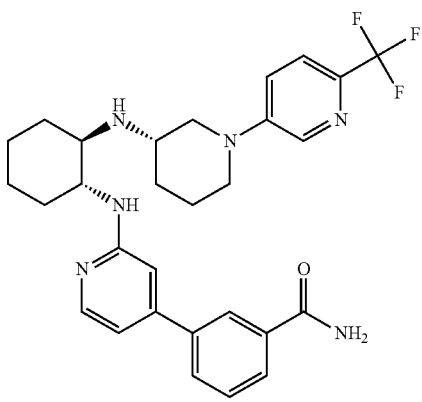 [SMILES: NC(=O)c1cccc(-c2ccnc(N[C@@H]3CCCC[C@H]3N[C@H]3CCCN(c4ccc(C(F)(F)F)nc4)C3)c2)c1] | 16 | 2.63 (A) | 539.1 | Scheme 3 |
| 322 | 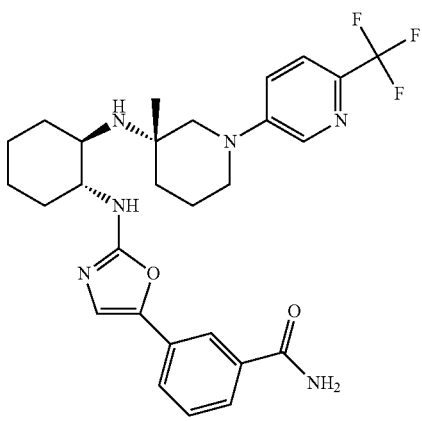 [SMILES: C[C@]1(N[C@@H]2CCCC[C@H]2Nc2ncc(-c3cccc(C(N)=O)c3)o2)CCCN(c2ccc(C(F)(F)F)nc2)C1] | 2 | 1.52 (D) | 543.3 | Scheme 4 |

TABLE 5-continued
| Example | Structure | hY4 cAMP EC50 (nM) | HPLC retention time (Method) | Mass (M + H) | Synthesis Method |
|---|---|---|---|---|---|
| 323 | 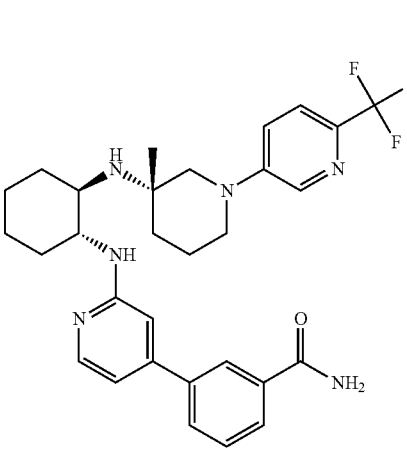 | 17 | 2.76 (A) | 553.1 | Scheme 4 |
| 324 | 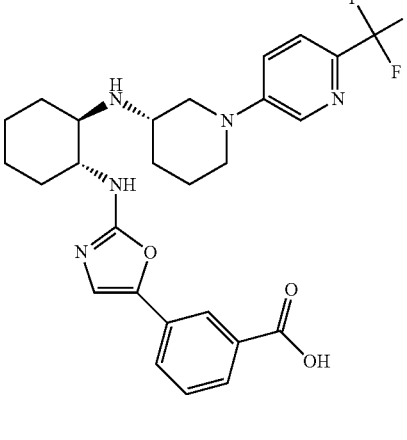 | 52 | 3.00 (A) | 530.2 | Scheme 8 |
| 325 | 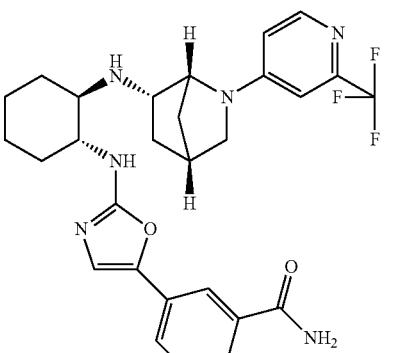 | 567 | 9.649 (J) | 541.2 | Scheme 5 |

TABLE 5-continued

| Example | Structure | hY4 CAMP EC50 (nM) | HPLC retention time (Method) | Mass (M + H) | Synthesis Method |
|---------|-----------|--------------------|-----------------------------|--------------|-----------------|
| 326 | 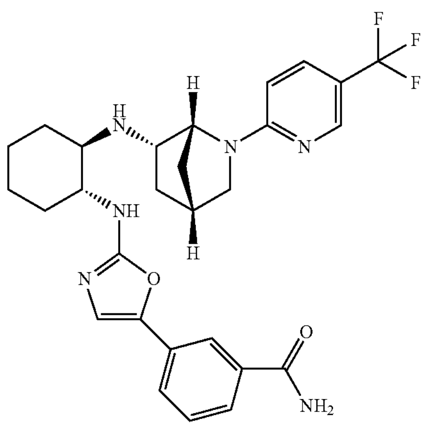 [SMILES: NC(=O)c1cccc(-c2cnc(N[C@@H]3CCCC[C@H]3N[C@H]3C[C@@H]4C[C@H]3N(c3ccc(C(F)(F)F)cn3)C4)o2)c1] | 9 | 6.452 (J) | 541.2 | Scheme 5 |
| 327 | 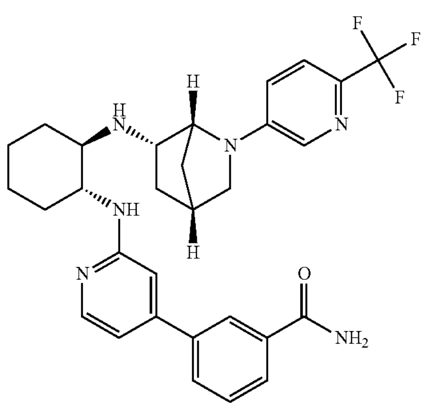 [SMILES: NC(=O)c1cccc(-c2ccnc(N[C@@H]3CCCC[C@H]3N[C@H]3C[C@@H]4C[C@H]3N(c3ccc(C(F)(F)F)nc3)C4)c2)c1] | 180 | 5.690 (J) | 551.2 | Scheme 5 |
| 328 | 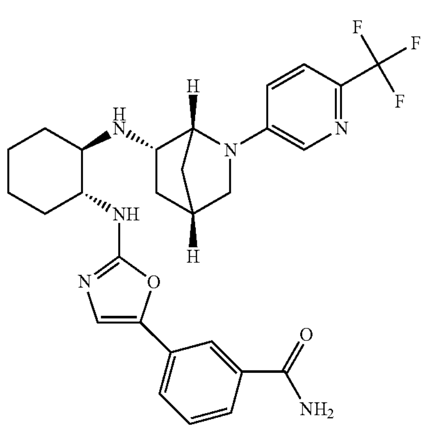 [SMILES: NC(=O)c1cccc(-c2cnc(N[C@@H]3CCCC[C@H]3N[C@H]3C[C@@H]4C[C@H]3N(c3ccc(C(F)(F)F)nc3)C4)o2)c1] | 31 | 5.498 (J) | 541.2 | Scheme 5 |

TABLE 5-continued

| Example | Structure | hY4 CAMP EC50 (nM) | HPLC retention time (Method) | Mass (M + H) | Synthesis Method |
|---------|-----------|---------------------|------------------------------|--------------|------------------|
| 329 | 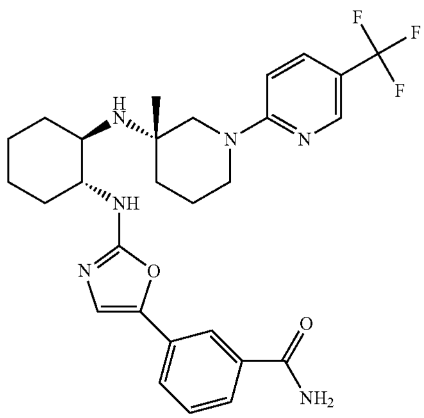 [SMILES: C[C@]1(N[C@@H]2CCCC[C@H]2Nc2ncc(-c3cccc(C(N)=O)c3)o2)CCCN(c2ccc(C(F)(F)F)cn2)C1] | 1 | 8.339 (K) | 543.2 | Scheme 4 |
| 330 | 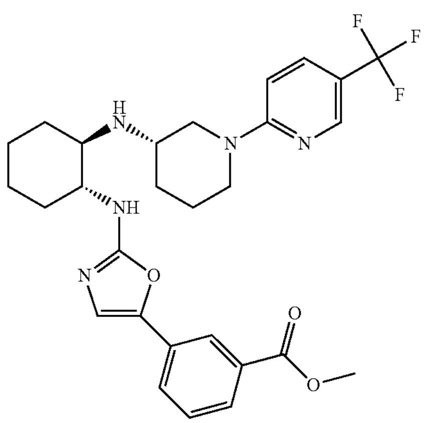 | 166 | 3.53 (A) | 544.3 | Scheme 1 |
| 331 | 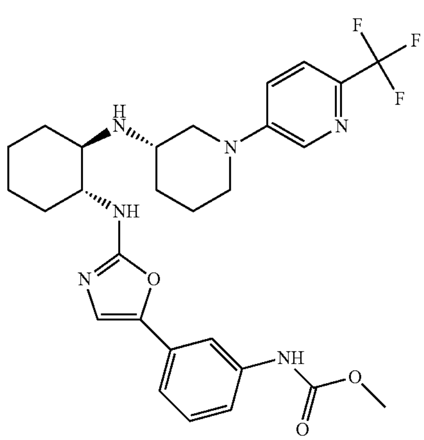 [SMILES: COC(=O)Nc1cccc(-c2cnc(N[C@@H]3CCCC[C@H]3N[C@H]3CCCN(c4ccc(C(F)(F)F)nc4)C3)o2)c1] | 5 | 3.14 (A) | 559.3 | Scheme 1 |

TABLE 5-continued
| Example | Structure | hY4 CAMP EC50 (nM) | HPLC retention time (Method) | Mass (M + H) | Synthesis Method |
|---|---|---|---|---|---|
| 332 | 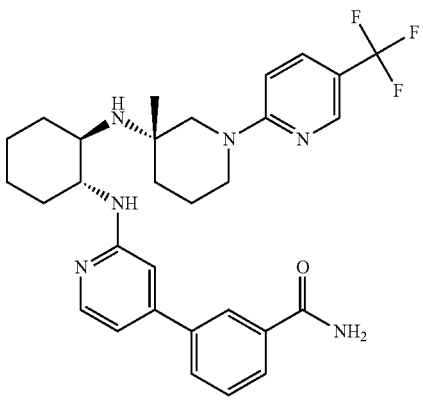 [SMILES: C[C@]1(N[C@@H]2CCCC[C@H]2Nc2cc(-c3cccc(C(N)=O)c3)ccn2)CCCN(c2ccc(C(F)(F)F)cn2)C1] | 24 | 6.703 (J) | 553.2 | Scheme 4 |
| 333 | 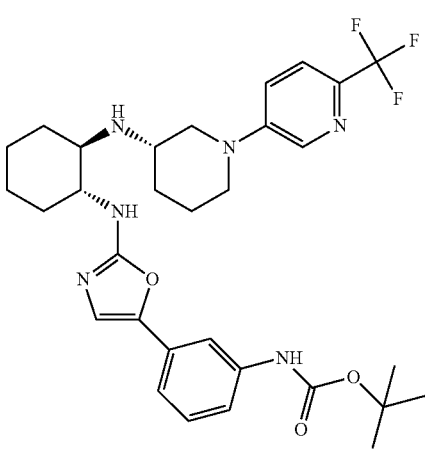 [SMILES: CC(C)(C)OC(=O)Nc1cccc(-c2cnc(N[C@@H]3CCCC[C@H]3N[C@H]3CCCN(c4ccc(C(F)(F)F)nc4)C3)o2)c1] | 95 | 3.40 (A) | 601.4 | Scheme 1 |
| 334 | 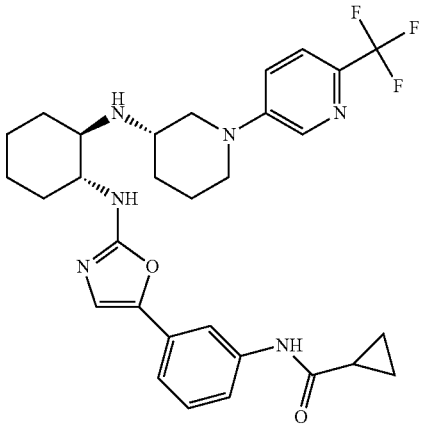 [SMILES: O=C(Nc1cccc(-c2cnc(N[C@@H]3CCCC[C@H]3N[C@H]3CCCN(c4ccc(C(F)(F)F)nc4)C3)o2)c1)C1CC1] | 3 | 3.01 (A) | 569.4 | Scheme 1 |

TABLE 5-continued

| Example | Structure | hY4 CAMP EC50 (nM) | HPLC retention time (Method) | Mass (M + H) | Synthesis Method |
|---------|-----------|--------------------|------------------------------|--------------|------------------|
| 335 | 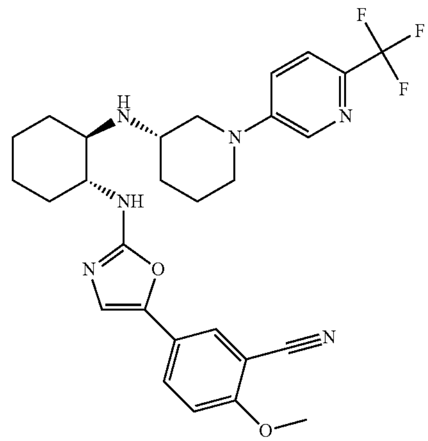 [SMILES: COc1ccc(-c2cnc(N[C@@H]3CCCC[C@H]3N[C@H]3CCCN(c4ccc(C(F)(F)F)nc4)C3)o2)cc1C#N] | 1599 | 2.92 (A) | 541.1 | Scheme 1 |
| 336 | 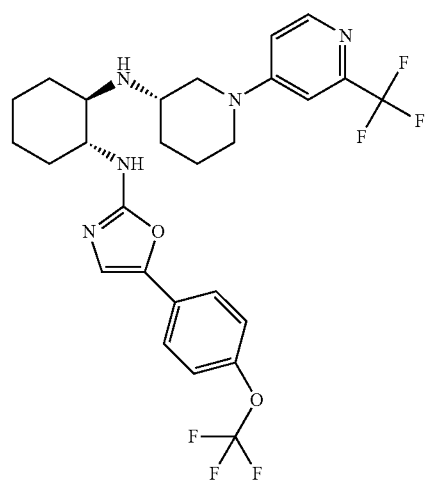 [SMILES: FC(F)(F)Oc1ccc(-c2cnc(N[C@@H]3CCCC[C@H]3N[C@H]3CCCN(c4ccnc(C(F)(F)F)c4)C3)o2)cc1] | 212 | 12.124 (K) | 570.2 | Scheme 1 |
| 337 | 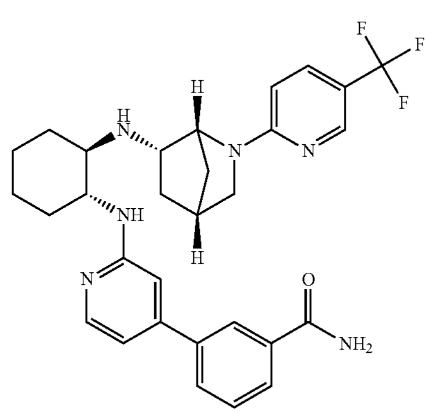 | 26 | 5.794 (J) | 551.2 | Scheme 5 |

TABLE 5-continued
| Example | Structure | hY4 CAMP EC50 (nM) | HPLC retention time (Method) | Mass (M + H) | Synthesis Method |
|---|---|---|---|---|---|
| 338 | 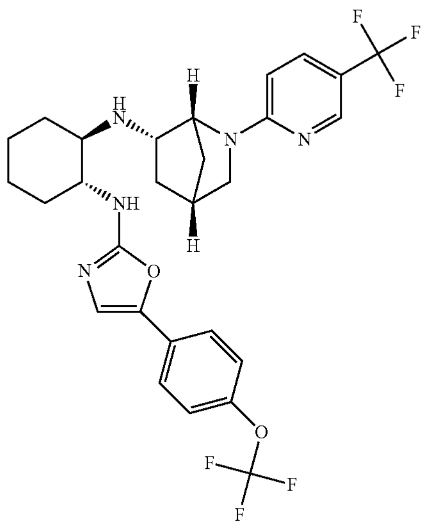 | 226 | 9.005 (J) | 582.2 | Scheme 5 |
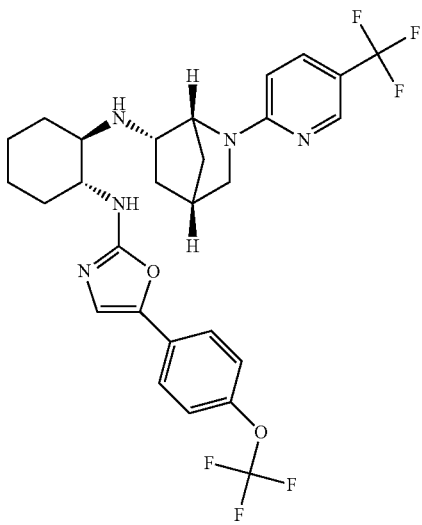 [SMILES: FC(F)(F)Oc1ccc(-c2cnc(N[C@@H]3CCCC[C@H]3N[C@H]3C[C@@H]4C[C@H]3N(c3ccc(C(F)(F)F)cn3)C4)o2)cc1]
Table 6 includes additional compounds of the invention wherein $R^2$ is Phenyl-oxadiazole-$CH_3$.
TABLE 6
| Example | Structure | hY4 CAMP EC50 (nM) | HPLC retention time (Method) | Mass (M + H) | Synthesis Method |
|---|---|---|---|---|---|
| 339 | 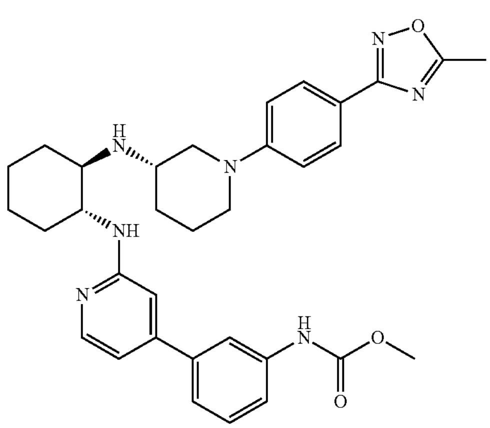 [SMILES: COC(=O)Nc1cccc(-c2ccnc(N[C@@H]3CCCC[C@H]3N[C@H]3CCCN(c4ccc(-c5noc(C)n5)cc4)C3)c2)c1] | 0.1 | 1.26 (C) | 582.3 | Scheme 9 |
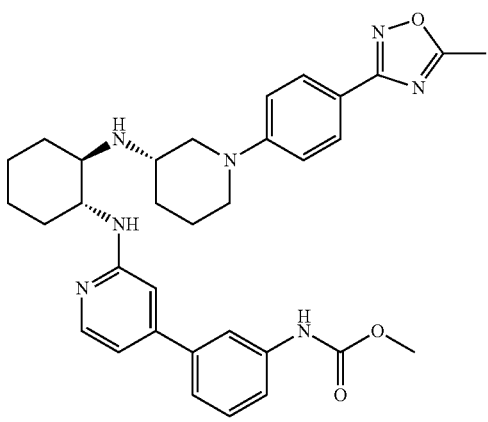

TABLE 6-continued

| Example | Structure | hY4 CAMP EC50 (nM) | HPLC retention time (Method) | Mass (M + H) | Synthesis Method |
|---------|-----------|--------------------|------------------------------|--------------|------------------|
| 340 | 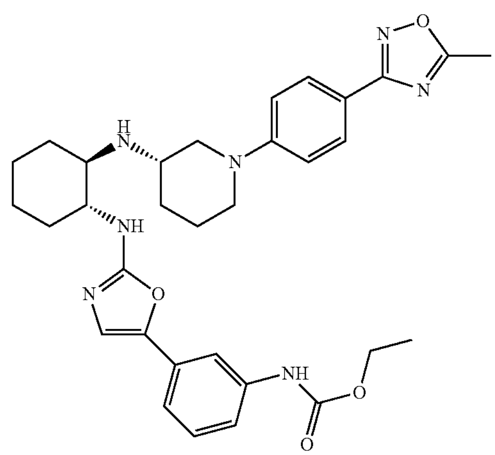 [SMILES: CCOC(=O)Nc1cccc(-c2cnc(N[C@@H]3CCCC[C@H]3N[C@H]3CCCN(c4ccc(-c5noc(C)n5)cc4)C3)o2)c1] | 3 | 1.36 (C) | 586.3 | Scheme 9 |
| 341 | 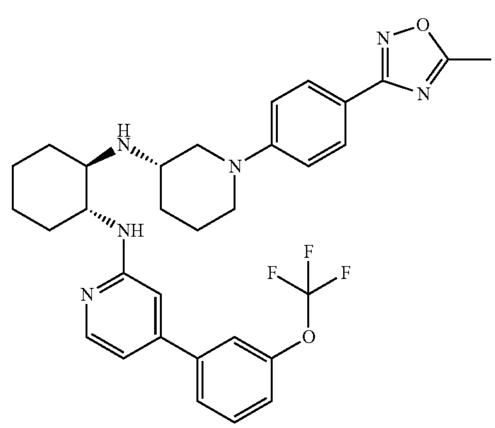 [SMILES: Cc1nc(-c2ccc(N3CCC[C@H](N[C@@H]4CCCC[C@H]4Nc4cc(-c5cccc(OC(F)(F)F)c5)ccn4)C3)cc2)no1] | 123 | 1.66 (C) | 593.3 | Scheme 3 |
| 342 | 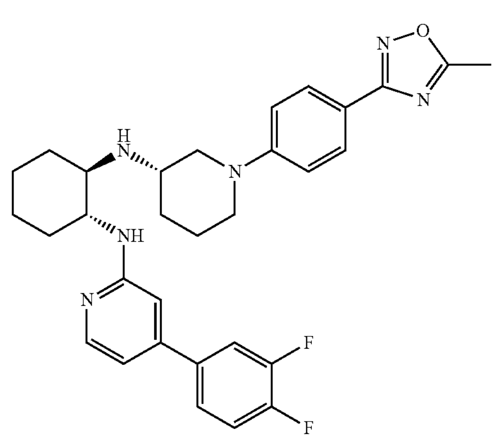 [SMILES: Cc1nc(-c2ccc(N3CCC[C@H](N[C@@H]4CCCC[C@H]4Nc4cc(-c5ccc(F)c(F)c5)ccn4)C3)cc2)no1] | 8 | 1.48 (C) | 545.3 | Scheme 3 |

TABLE 6-continued

| Example | Structure | hY4 CAMP EC50 (nM) | HPLC retention time (Method) | Mass (M + H) | Synthesis Method |
|---|---|---|---|---|---|
| 343 | 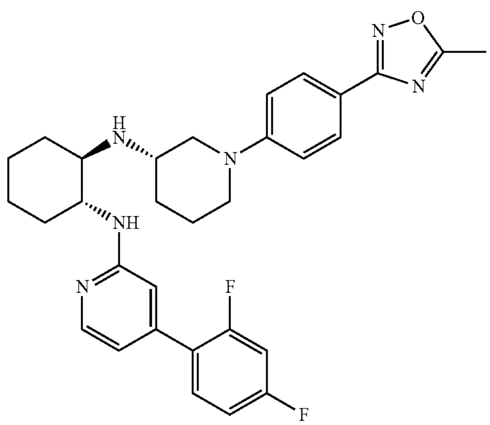 [SMILES: Cc1nc(-c2ccc(N3CCC[C@H](N[C@@H]4CCCC[C@H]4Nc4cc(-c5ccc(F)cc5F)ccn4)C3)cc2)no1] | 11 | 1.46 (C) | 545.3 | Scheme 3 |
| 344 | 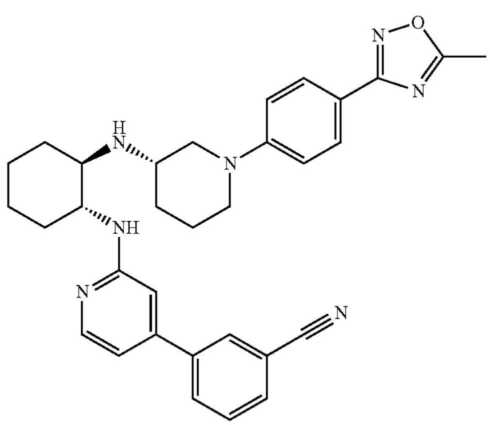 [SMILES: Cc1nc(-c2ccc(N3CCC[C@H](N[C@@H]4CCCC[C@H]4Nc4cc(-c5cccc(C#N)c5)ccn4)C3)cc2)no1] | 22 | | 535.4 | Scheme 3 |
| 345 | 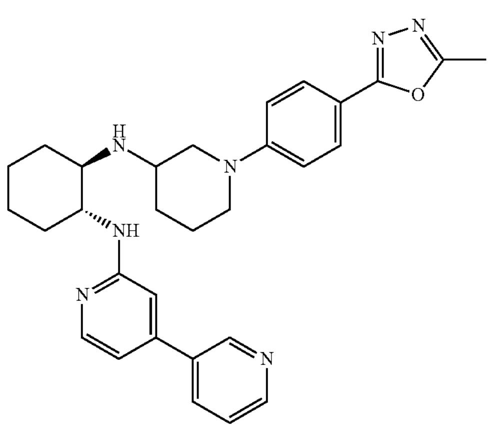 [SMILES: Cc1nnc(-c2ccc(N3CCCC(N[C@@H]4CCCC[C@H]4Nc4cc(-c5cccnc5)ccn4)C3)cc2)o1] | 64 | | 510.2 | Scheme 3 |

TABLE 6-continued

| Example | Structure | hY4 cAMP EC50 (nM) | HPLC retention time (Method) | Mass (M + H) | Synthesis Method |
|---------|-----------|---------------------|------------------------------|--------------|------------------|
| 346 | 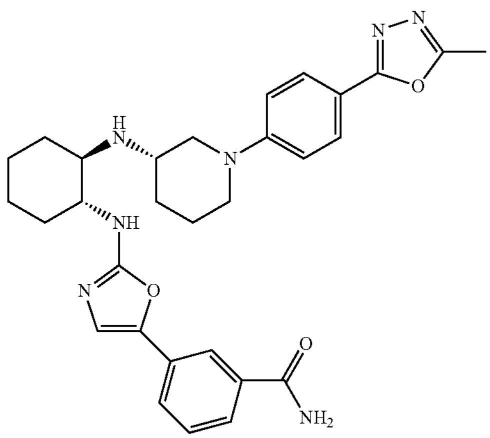 [SMILES: Cc1nnc(-c2ccc(N3CCC[C@H](N[C@@H]4CCCC[C@H]4Nc4ncc(-c5cccc(C(N)=O)c5)o4)C3)cc2)o1] | 306 | 5.409 (J) | 542.2 | Scheme 6 |
| 347 | 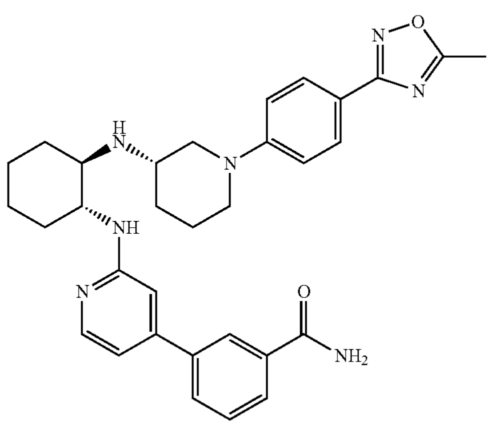 [SMILES: Cc1nc(-c2ccc(N3CCC[C@H](N[C@@H]4CCCC[C@H]4Nc4cc(-c5cccc(C(N)=O)c5)ccn4)C3)cc2)no1] | 0.2 | 2.50 (A) | 552.4 | Scheme 3 |
| 348 | 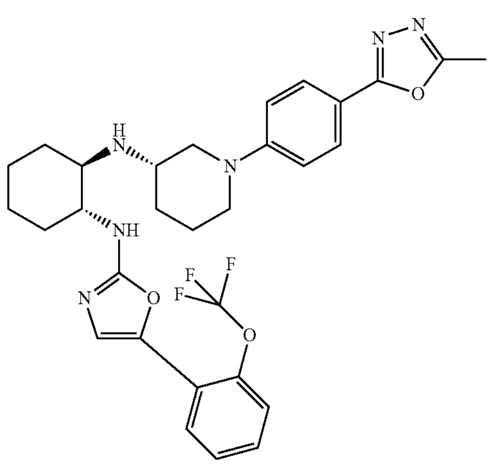 [SMILES: Cc1nnc(-c2ccc(N3CCC[C@H](N[C@@H]4CCCC[C@H]4Nc4ncc(-c5ccccc5OC(F)(F)F)o4)C3)cc2)o1] | 3 | 1.791 (G) | 583.2 | Scheme 1 |

TABLE 6-continued

| Example | Structure | hY4 CAMP EC50 (nM) | HPLC retention time (Method) | Mass (M + H) | Synthesis Method |
|---|---|---|---|---|---|
| 349 | 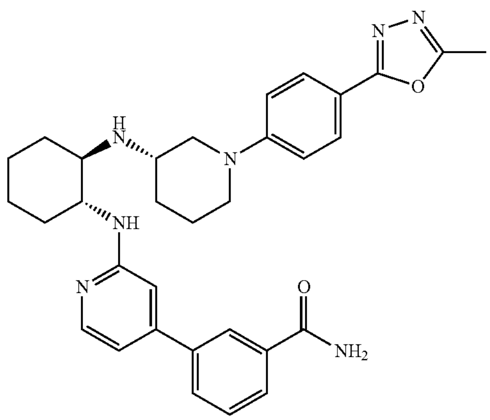 [SMILES: Cc1nnc(-c2ccc(N3CCC[C@H](N[C@@H]4CCCC[C@H]4Nc4cc(-c5cccc(C(N)=O)c5)ccn4)C3)cc2)o1] | 1 | 9.294 (K) | | Scheme 3 |
| 350 | 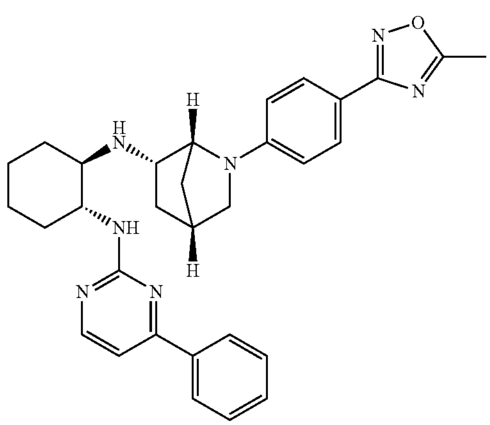 [SMILES: Cc1nc(-c2ccc(N3C[C@@H]4C[C@H](N[C@@H]5CCCC[C@H]5Nc5nccc(-c6ccccc6)n5)[C@H]3C4)cc2)no1] | 9 | 3.06 (A) | 522.4 | Scheme 5 |
| 351 | 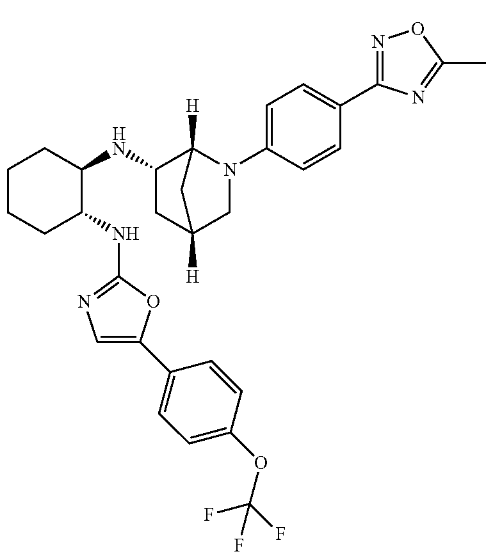 [SMILES: Cc1nc(-c2ccc(N3C[C@@H]4C[C@H](N[C@@H]5CCCC[C@H]5Nc5ncc(-c6ccc(OC(F)(F)F)cc6)o5)[C@H]3C4)cc2)no1] | 448 | 3.59 (A) | 595.4 | Scheme 5 |

TABLE 6-continued
| Example | Structure | hY4 cAMP EC50 (nM) | HPLC retention time (Method) | Mass (M + H) | Synthesis Method |
|---|---|---|---|---|---|
| 352 | 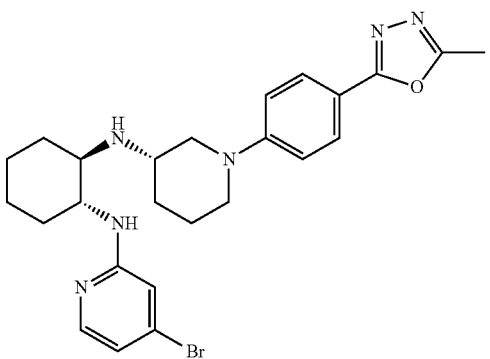 [SMILES: Cc1nnc(-c2ccc(N3CCC[C@H](N[C@@H]4CCCC[C@H]4Nc4cc(Br)ccn4)C3)cc2)o1] | 318 | 7.318 (M) | 511.1 | Scheme 3 |
| 353 | 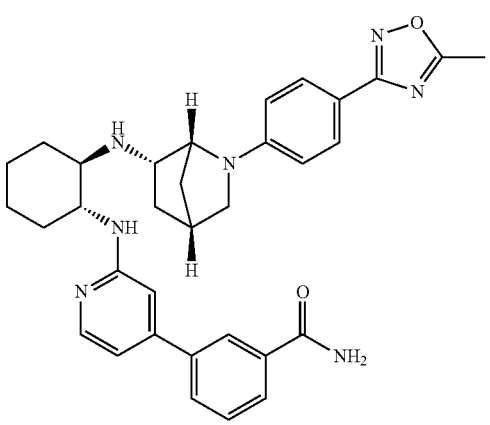 [SMILES: Cc1nc(-c2ccc(N3C[C@@H]4C[C@H](N[C@@H]5CCCC[C@H]5Nc5cc(-c6cccc(C(N)=O)c6)ccn5)[C@H]3C4)cc2)no1] | 1 | 2.56 (A) | 564.4 | Scheme 5 |
| 354 | 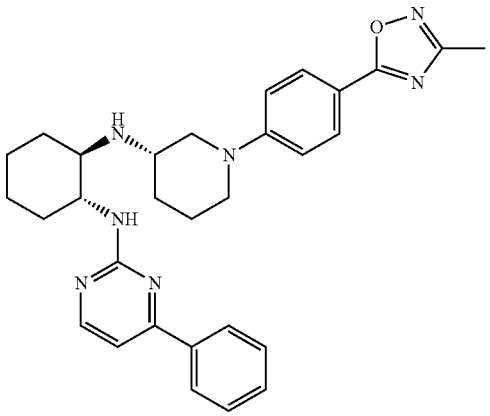 [SMILES: Cc1noc(-c2ccc(N3CCC[C@H](N[C@@H]4CCCC[C@H]4Nc4nccc(-c5ccccc5)n4)C3)cc2)n1] | 15 | 3.11 (A) | 510.4 | Scheme 1 |

TABLE 6-continued
| Example | Structure | hY4 cAMP EC50 (nM) | HPLC retention time (Method) | Mass (M + H) | Synthesis Method |
|---------|-----------|--------------------|------------------------------|--------------|------------------|
| 355 | 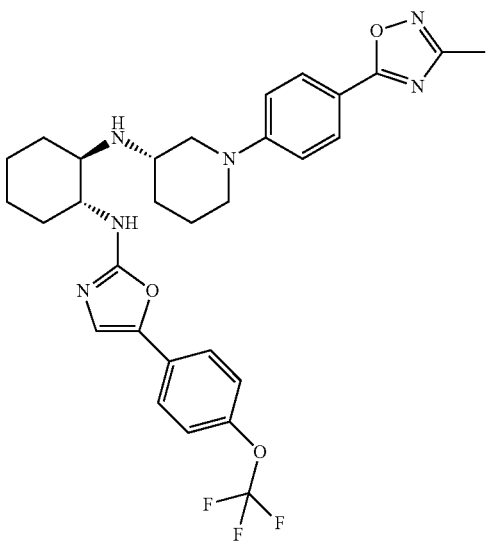 [SMILES: Cc1noc(-c2ccc(N3CCC[C@H](N[C@@H]4CCCC[C@H]4Nc4ncc(-c5ccc(OC(F)(F)F)cc5)o4)C3)cc2)n1] | 225 | 3.51 (A) | 583.3 | Scheme 1 |
| 356 | 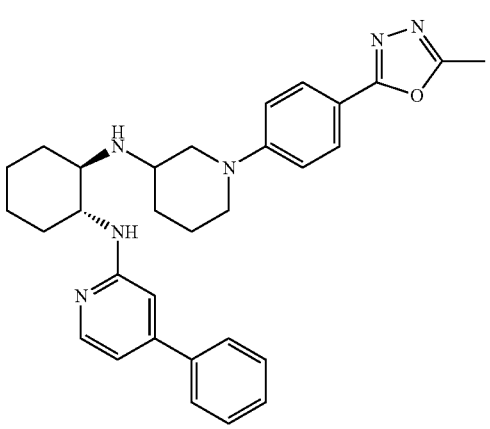 [SMILES: Cc1nnc(-c2ccc(N3CCCC(N[C@@H]4CCCC[C@H]4Nc4cc(-c5ccccc5)ccn4)C3)cc2)o1] | 3 | | 509.2 | Scheme 3 |
| 357 | 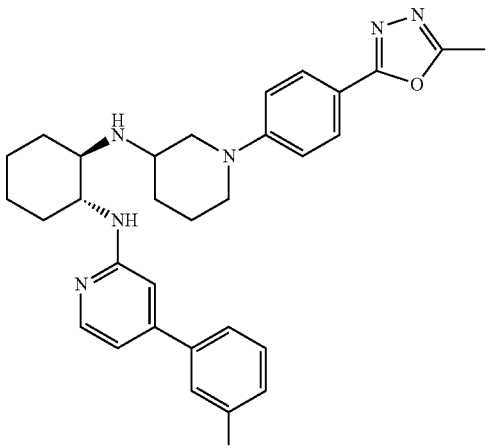 | 0.4 | | 525.2 | Scheme 3 |

TABLE 6-continued
| Example | Structure | hY4 CAMP EC50 (nM) | HPLC retention time (Method) | Mass (M + H) | Synthesis Method |
|---------|-----------|--------------------|-----------------------------|--------------|------------------|
| 358 | 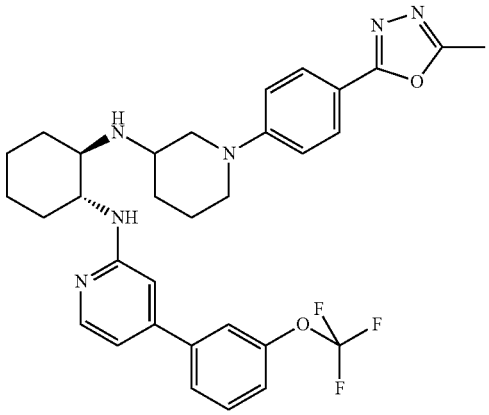 [SMILES: Cc1nnc(-c2ccc(N3CCCC(N[C@@H]4CCCC[C@H]4Nc4cc(-c5cccc(OC(F)(F)F)c5)ccn4)C3)cc2)o1] | 17 | | 593.2 | Scheme 3 |
| 359 | 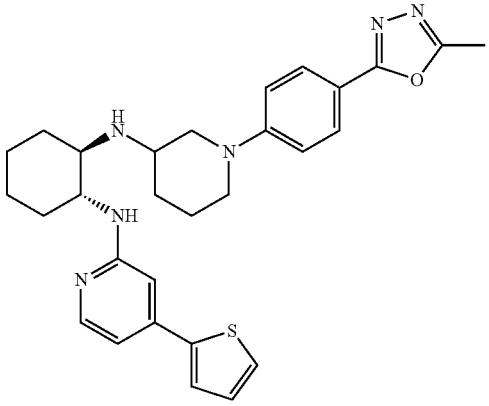 [SMILES: Cc1nnc(-c2ccc(N3CCCC(N[C@@H]4CCCC[C@H]4Nc4cc(-c5cccs5)ccn4)C3)cc2)o1] | 757 | | 515.2 | Scheme 3 |
| 360 | 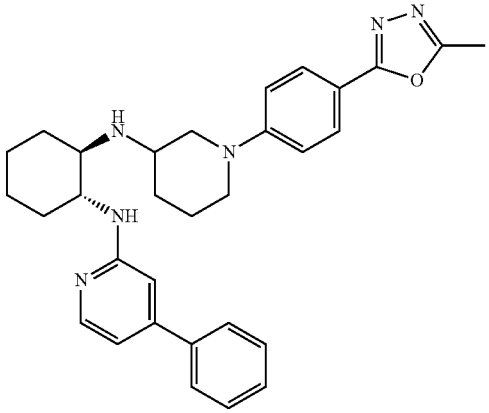 | 635 | | 509.2 | Scheme 3 |

TABLE 6-continued
| Example | Structure | hY4 CAMP EC50 (nM) | HPLC retention time (Method) | Mass (M + H) | Synthesis Method |
|---------|-----------|--------------------|-----------------------------|--------------|------------------|
| 361 | 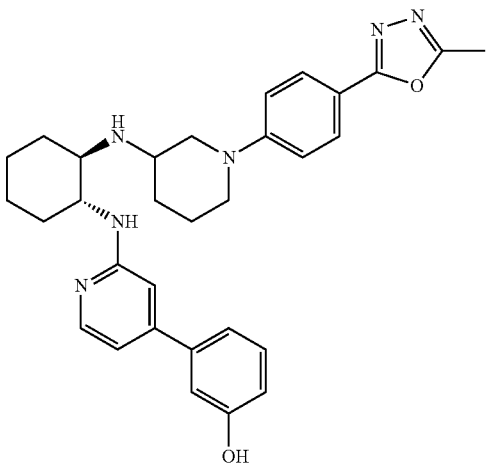 [SMILES: Cc1nnc(-c2ccc(N3CCCC(N[C@@H]4CCCC[C@H]4Nc4cc(-c5cccc(O)c5)ccn4)C3)cc2)o1] | 286 | | 525.2 | Scheme 3 |
| 362 | 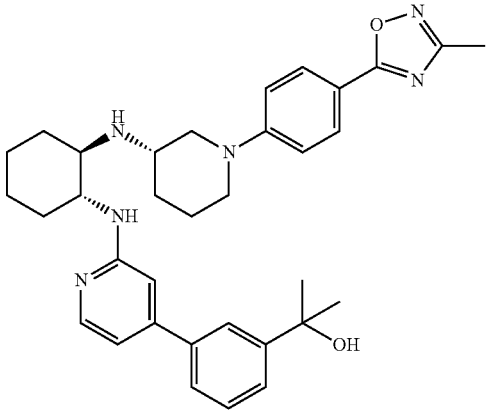 [SMILES: Cc1noc(-c2ccc(N3CCC[C@H](N[C@@H]4CCCC[C@H]4Nc4cc(-c5cccc(C(C)(C)O)c5)ccn4)C3)cc2)n1] | 23 | 3.01 (A) | 567.4 | Scheme 3 |
| 363 | 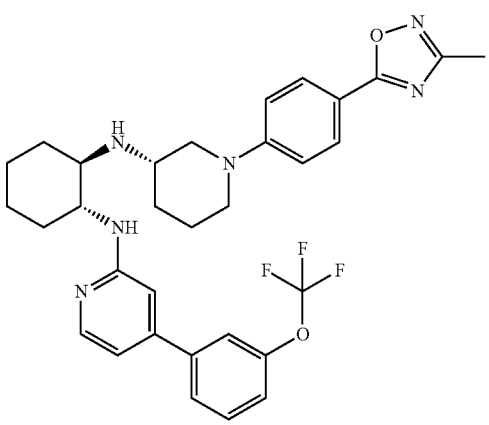 [SMILES: Cc1noc(-c2ccc(N3CCC[C@H](N[C@@H]4CCCC[C@H]4Nc4cc(-c5cccc(OC(F)(F)F)c5)ccn4)C3)cc2)n1] | 314 | 3.51 (A) | 593.4 | Scheme 3 |

TABLE 6-continued
| Example | Structure | hY4 CAMP EC50 (nM) | HPLC retention time (Method) | Mass (M + H) | Synthesis Method |
|---------|-----------|--------------------|------------------------------|--------------|------------------|
| 364 | 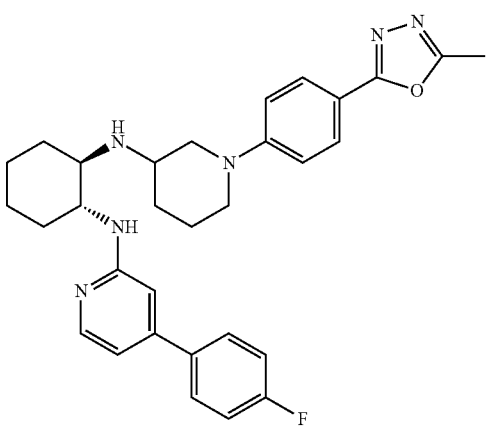 [SMILES: Cc1nnc(-c2ccc(N3CCCC(N[C@@H]4CCCC[C@H]4Nc4cc(-c5ccc(F)cc5)ccn4)C3)cc2)o1] | 3 | | 527.2 | Scheme 3 |
| 365 | 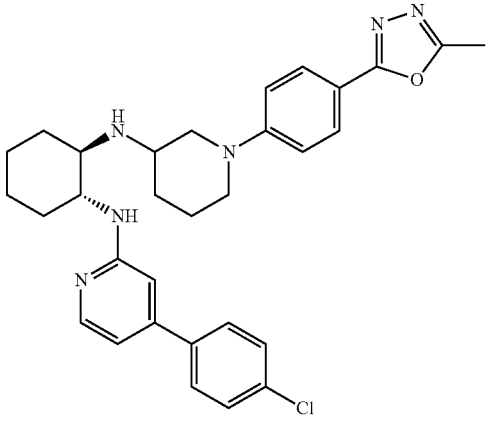 | 52 | | 543.2 | Scheme 3 |
| 366 | 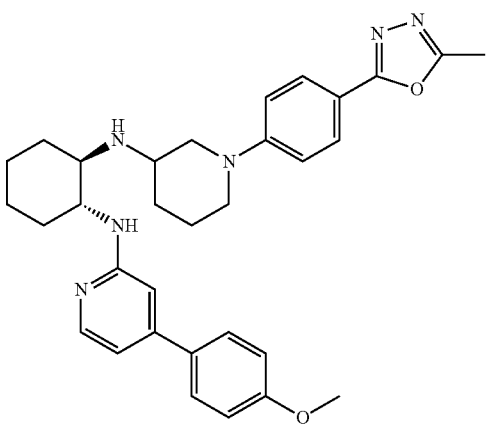 [SMILES: COc1ccc(-c2ccnc(N[C@@H]3CCCC[C@H]3NC3CCCN(c4ccc(-c5nnc(C)o5)cc4)C3)c2)cc1] | 323 | | 539.2 | Scheme 3 |

TABLE 6-continued

| Example | Structure | hY4 CAMP EC50 (nM) | HPLC retention time (Method) | Mass (M + H) | Synthesis Method |
|---------|-----------|---------------------|-------------------------------|--------------|------------------|
| 367 | 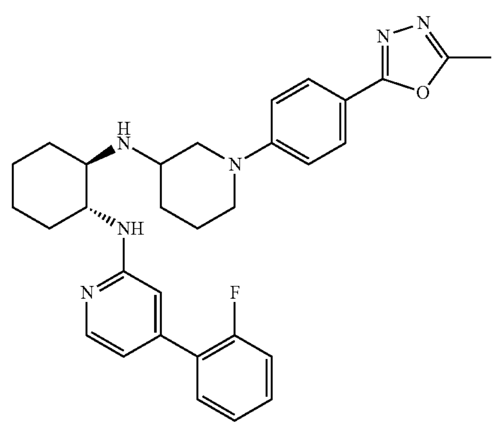 [SMILES: Cc1nnc(-c2ccc(N3CCCC(N[C@@H]4CCCC[C@H]4Nc4cc(-c5ccccc5F)ccn4)C3)cc2)o1] | 9 | | 527.2 | Scheme 3 |
| 368 | 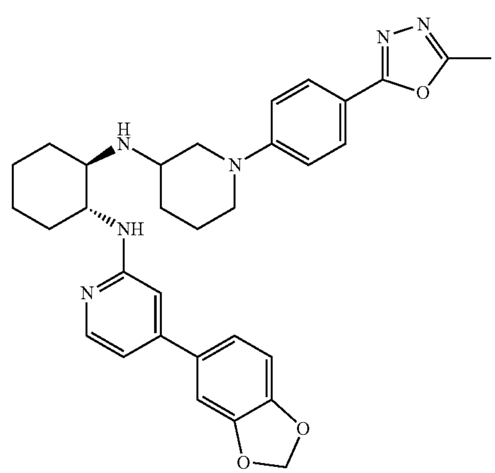 [SMILES: Cc1nnc(-c2ccc(N3CCCC(N[C@@H]4CCCC[C@H]4Nc4cc(-c5ccc6c(c5)OCO6)ccn4)C3)cc2)o1] | 39 | | 553.2 | Scheme 3 |
| 369 | 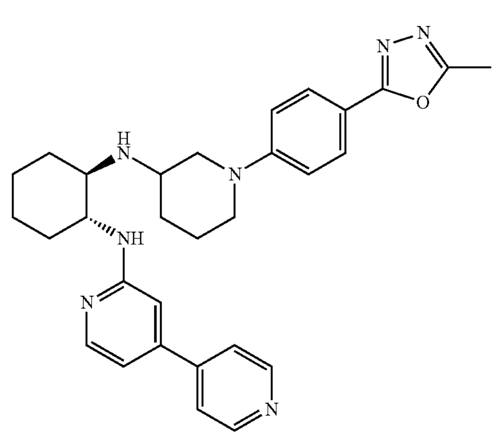 [SMILES: Cc1nnc(-c2ccc(N3CCCC(N[C@@H]4CCCC[C@H]4Nc4cc(-c5ccncc5)ccn4)C3)cc2)o1] | 5 | | 510.2 | Scheme 3 |

TABLE 6-continued
| Example | Structure | hY4 CAMP EC50 (nM) | HPLC retention time (Method) | Mass (M + H) | Synthesis Method |
|---------|-----------|---------------------|------------------------------|--------------|------------------|
| 370 | 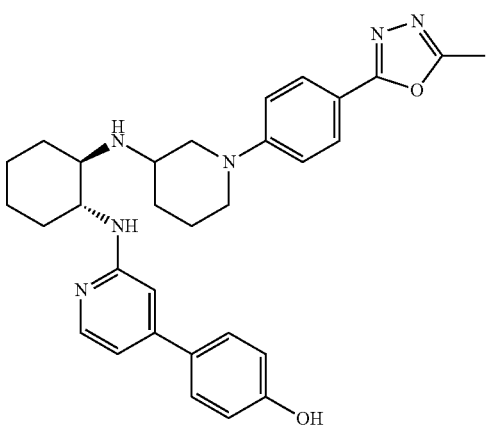 [SMILES: Cc1nnc(-c2ccc(N3CCCC(N[C@@H]4CCCC[C@H]4Nc4cc(-c5ccc(O)cc5)ccn4)C3)cc2)o1] | 3 | | 525.2 | Scheme 3 |
| 371 | 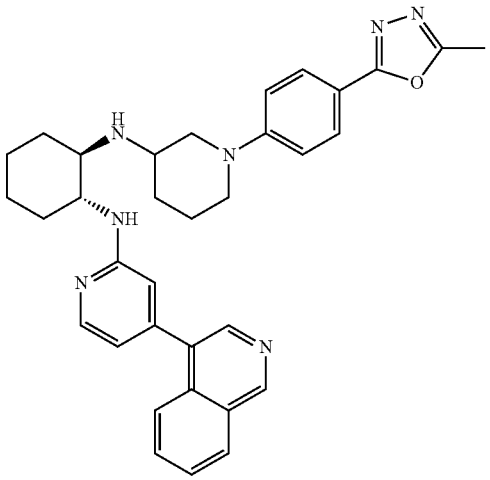 [SMILES: Cc1nnc(-c2ccc(N3CCCC(N[C@@H]4CCCC[C@H]4Nc4cc(-c5cncc6ccccc56)ccn4)C3)cc2)o1] | 18 | | 560.2 | Scheme 3 |
| 372 | 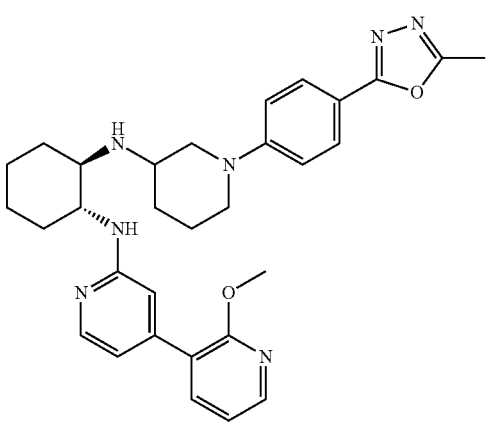 [SMILES: COc1ncccc1-c1ccnc(N[C@@H]2CCCC[C@H]2NC2CCCN(c3ccc(-c4nnc(C)o4)cc3)C2)c1] | 59 | | 539.2 | Scheme 3 |

TABLE 6-continued
| Example | Structure | hY4 CAMP EC50 (nM) | HPLC retention time (Method) | Mass (M + H) | Synthesis Method |
|---|---|---|---|---|---|
| 373 | 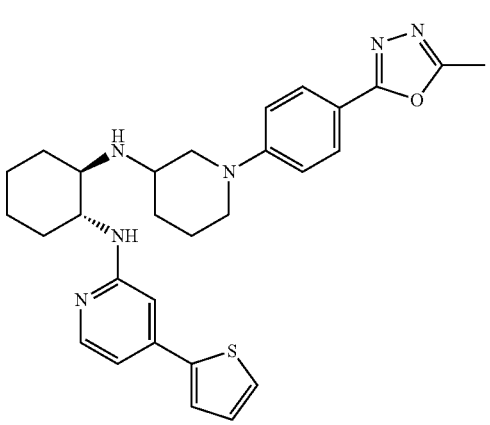 [SMILES: Cc1nnc(-c2ccc(N3CCCC(N[C@@H]4CCCC[C@H]4Nc4cc(-c5cccs5)ccn4)C3)cc2)o1] | 1 | | 515.2 | Scheme 3 |
| 374 | 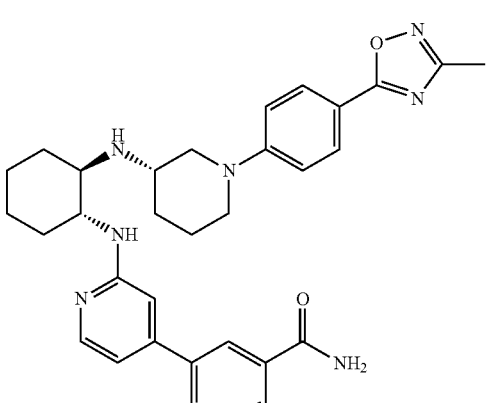 | 2 | 2.60 (A) | 552.4 | Scheme 3 |
| 375 | 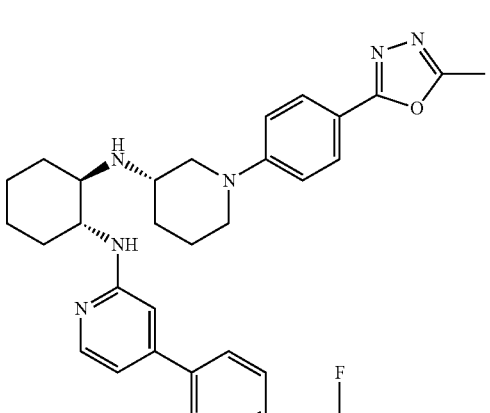 | 217 | 6.685 (J) | 575.2 | Scheme 3 |

TABLE 6-continued
| Example | Structure | hY4 CAMP EC50 (nM) | HPLC retention time (Method) | Mass (M + H) | Synthesis Method |
|---------|-----------|---------------------|------------------------------|--------------|------------------|
| 376 | 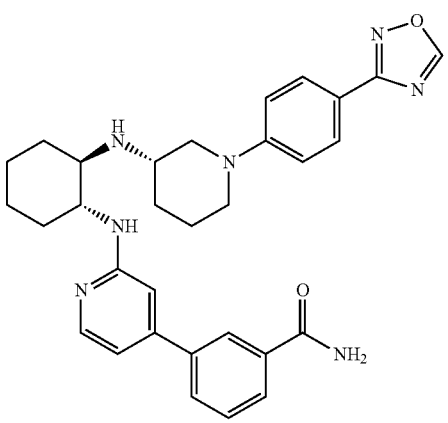 [SMILES: NC(=O)c1cccc(-c2ccnc(N[C@@H]3CCCC[C@H]3N[C@H]3CCCN(c4ccc(-c5ncon5)cc4)C3)c2)c1] | 15 | 2.50 (A) | 538.2 | Scheme 9 |
| 377 | 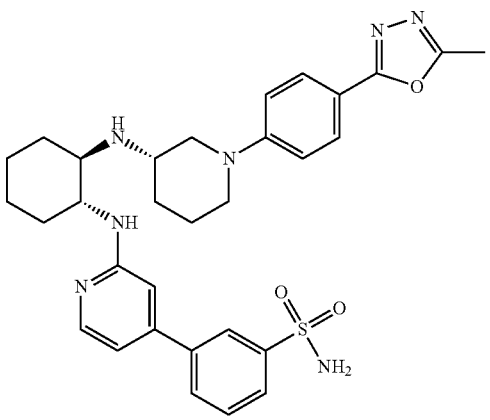 [SMILES: Cc1nnc(-c2ccc(N3CCC[C@H](N[C@@H]4CCCC[C@H]4Nc4cc(-c5cccc(S(N)(=O)=O)c5)ccn4)C3)cc2)o1] | 93 | 5.398 (J) | 588.2 | Scheme 3 |
| 378 | 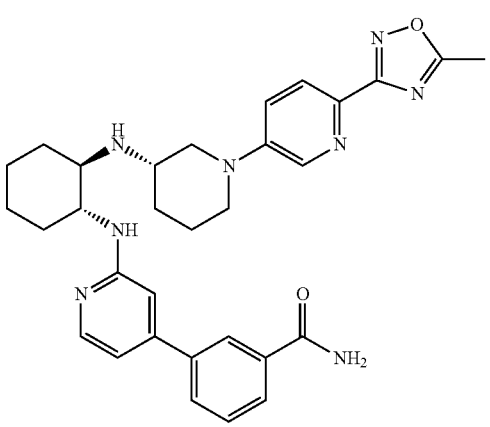 [SMILES: Cc1nc(-c2ccc(N3CCC[C@H](N[C@@H]4CCCC[C@H]4Nc4cc(-c5cccc(C(N)=O)c5)ccn4)C3)cn2)no1] | 4 | 2.43 (A) | 553.2 | Scheme 3 |

TABLE 6-continued

| Example | Structure | hY4 CAMP EC50 (nM) | HPLC retention time (Method) | Mass (M + H) | Synthesis Method |
|---|---|---|---|---|---|
| 379 | 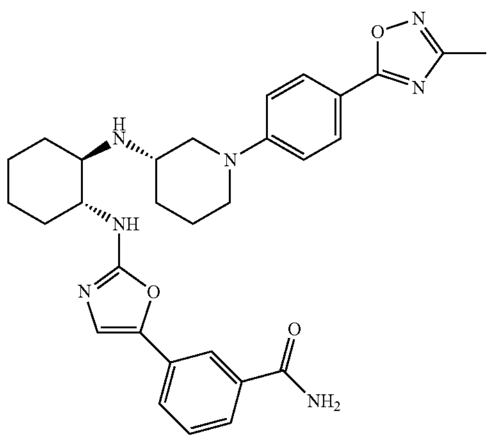 [SMILES: Cc1noc(-c2ccc(N3CCC[C@H](N[C@@H]4CCCC[C@H]4Nc4ncc(-c5cccc(C(N)=O)c5)o4)C3)cc2)n1] | 1 | 1.44 (D) | 542.4 | Scheme 1 |
| 380 | 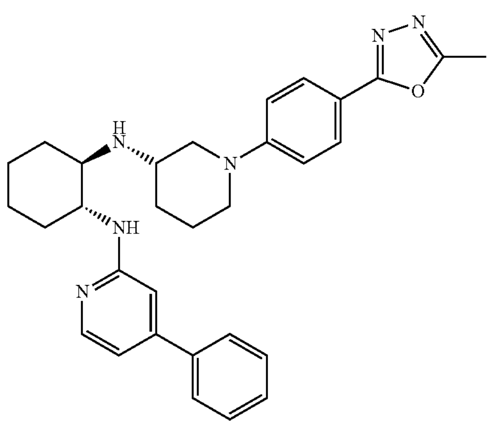 | 4 | 5.830 (J) | 509.3 | Scheme 3 |

Table 7 includes additional compounds of the invention wherein $R^2$ is Pyridinyl-oxadiazole-$CH_3$.

TABLE 7

| Example | Structure | hY4 CAMP EC50 (nM) | HPLC retention time (Method) | Mass (M + H) | Synthesis Method |
|---|---|---|---|---|---|
| 381 | 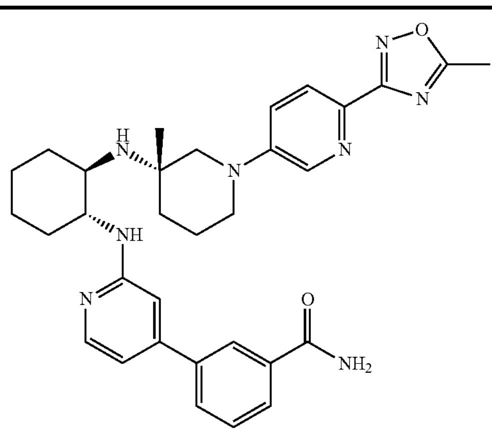 | 5 | 2.50 (A) | 567.3 | Scheme 4 |

TABLE 7-continued

| Example | Structure | hY4 CAMP EC50 (nM) | HPLC retention time (Method) | Mass (M + H) | Synthesis Method |
|---------|-----------|--------------------|------------------------------|--------------|------------------|
| 382 | 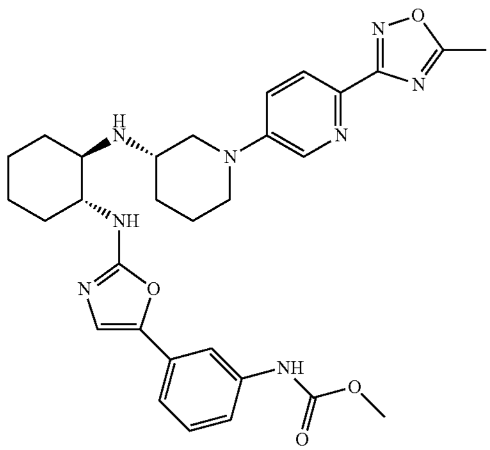 [SMILES: COC(=O)Nc1cccc(-c2cnc(N[C@@H]3CCCC[C@H]3N[C@H]3CCCN(c4ccc(-c5noc(C)n5)nc4)C3)o2)c1] | 1 | 2.64 (A) | 573.4 | Scheme 1 |
| 383 | 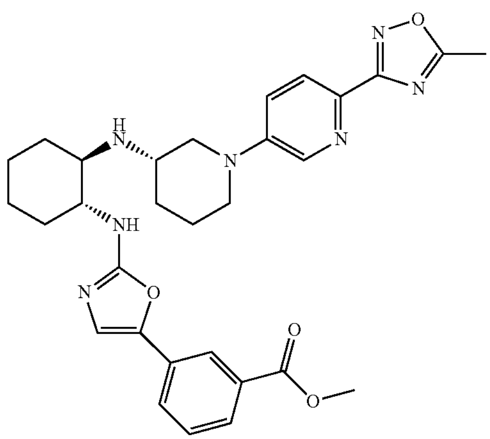 [SMILES: COC(=O)c1cccc(-c2cnc(N[C@@H]3CCCC[C@H]3N[C@H]3CCCN(c4ccc(-c5noc(C)n5)nc4)C3)o2)c1] | 14 | 2.86 (A) | 558.3 | Scheme 1 |
| 384 | 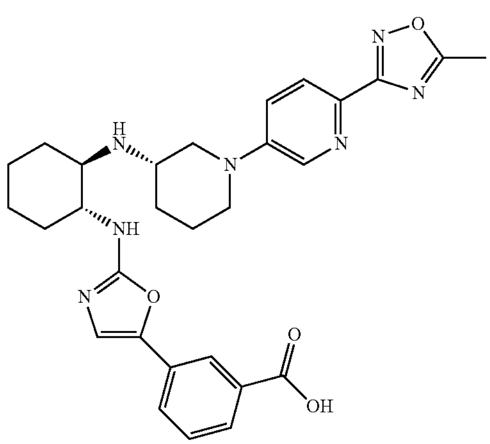 | 606 | 2.55 (A) | 544.3 | Scheme 8 |

TABLE 7-continued

| Example | Structure | hY4 CAMP EC50 (nM) | HPLC retention time (Method) | Mass (M + H) | Synthesis Method |
|---------|-----------|--------------------|-----------------------------|--------------|------------------|
| 385 | 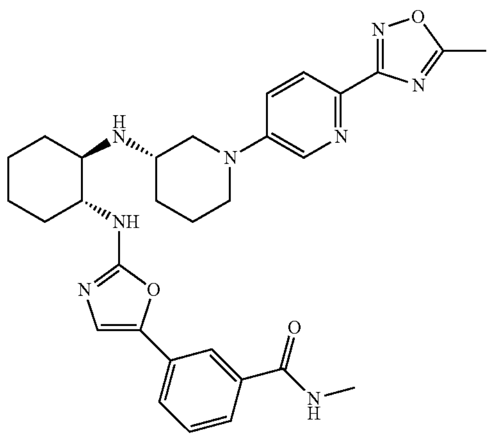 [SMILES: CNC(=O)c1cccc(-c2cnc(N[C@@H]3CCCC[C@H]3N[C@H]3CCCN(c4ccc(-c5noc(C)n5)nc4)C3)o2)c1] | 9 | 1.46 (D) | 557 | Scheme 8 |
| 386 | 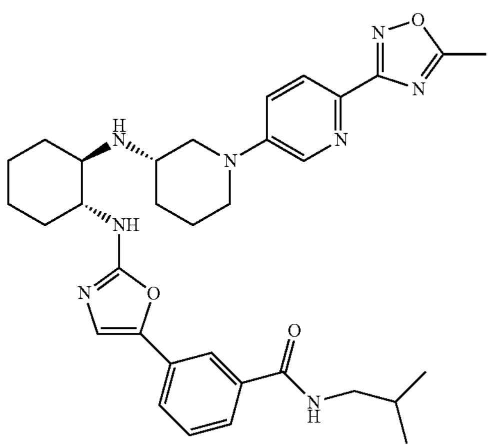 [SMILES: Cc1nc(-c2ccc(N3CCC[C@H](N[C@@H]4CCCC[C@H]4Nc4ncc(-c5cccc(C(=O)NCC(C)C)c5)o4)C3)cn2)no1] | 243 | 1.88 (D) | 599 | Scheme 8 |
| 387 | 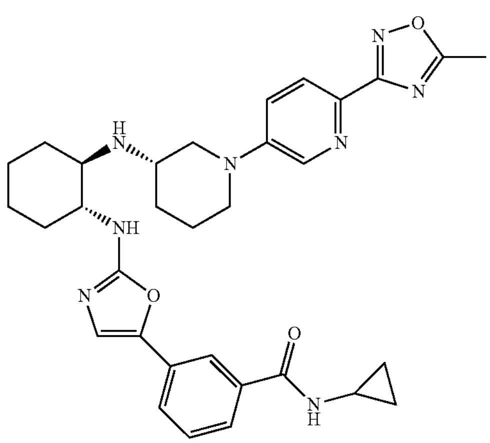 [SMILES: Cc1nc(-c2ccc(N3CCC[C@H](N[C@@H]4CCCC[C@H]4Nc4ncc(-c5cccc(C(=O)NC6CC6)c5)o4)C3)cn2)no1] | 78 | 1.57 (D) | 583 | Scheme 8 |

TABLE 7-continued

| Example | Structure | hY4 cAMP EC50 (nM) | HPLC retention time (Method) | Mass (M + H) | Synthesis Method |
|---------|-----------|---------------------|------------------------------|--------------|------------------|
| 388 | 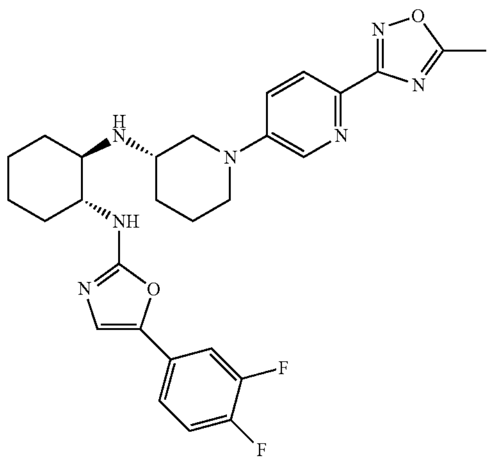 [SMILES: Cc1nc(-c2ccc(N3CCC[C@H](N[C@@H]4CCCC[C@H]4Nc4ncc(-c5ccc(F)c(F)c5)o4)C3)cn2)no1] | 10 | 2.50 (A) | 531.4 | Scheme 1 |
| 389 | 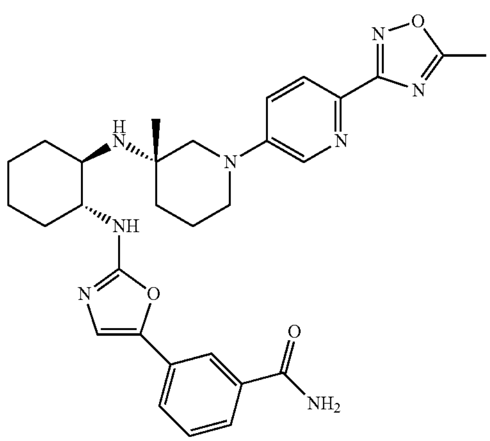 [SMILES: Cc1nc(-c2ccc(N3CCC[C@](C)(N[C@@H]4CCCC[C@H]4Nc4ncc(-c5cccc(C(N)=O)c5)o4)C3)cn2)no1] | 13 | 2.43 (A) | 557.1 | Scheme 4 |
| 390 | 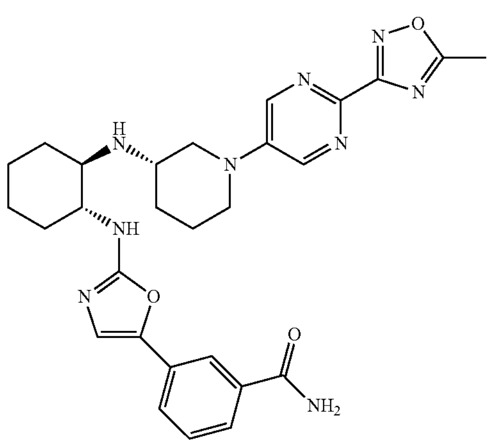 [SMILES: Cc1nc(-c2ncc(N3CCC[C@H](N[C@@H]4CCCC[C@H]4Nc4ncc(-c5cccc(C(N)=O)c5)o4)C3)cn2)no1] | 3 | 1.31 (L) | 544.4 | Scheme 9 |

TABLE 7-continued

| Example | Structure | hY4 CAMP EC50 (nM) | HPLC retention time (Method) | Mass (M + H) | Synthesis Method |
|---|---|---|---|---|---|
| 391 | 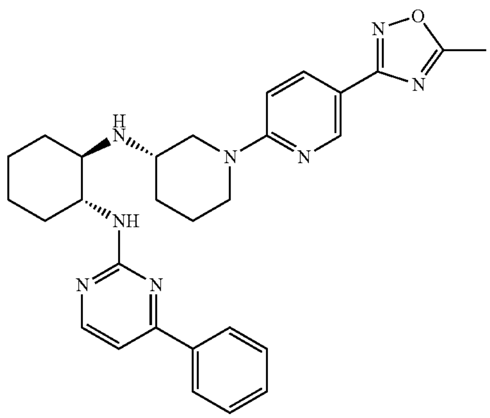 [SMILES: Cc1nc(-c2ccc(N3CCC[C@H](N[C@@H]4CCCC[C@H]4Nc4nccc(-c5ccccc5)n4)C3)nc2)no1] | 2 | 2.88 (A) | 511.4 | Scheme 1 |
| 392 | 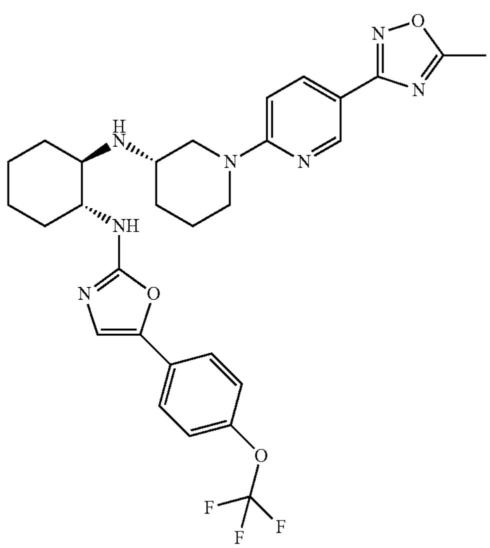 [SMILES: Cc1nc(-c2ccc(N3CCC[C@H](N[C@@H]4CCCC[C@H]4Nc4ncc(-c5ccc(OC(F)(F)F)cc5)o4)C3)nc2)no1] | 194 | 3.39 (A) | 584.4 | Scheme 1 |
| 393 | 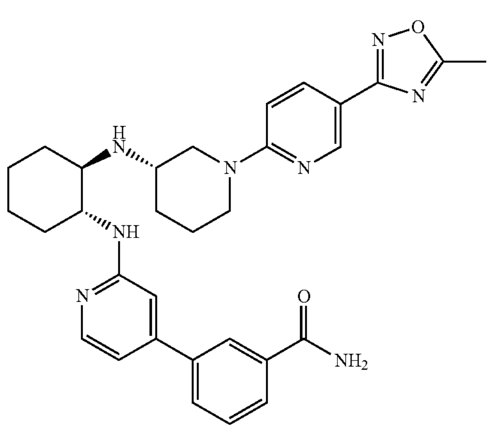 [SMILES: Cc1nc(-c2ccc(N3CCC[C@H](N[C@@H]4CCCC[C@H]4Nc4cc(-c5cccc(C(N)=O)c5)ccn4)C3)nc2)no1] | 1 | 2.43 (A) | 553.4 | Scheme 3 |

TABLE 7-continued

| Example | Structure | hY4 cAMP EC50 (nM) | HPLC retention time (Method) | Mass (M + H) | Synthesis Method |
|---------|-----------|---------------------|------------------------------|--------------|-------------------|
| 394 | 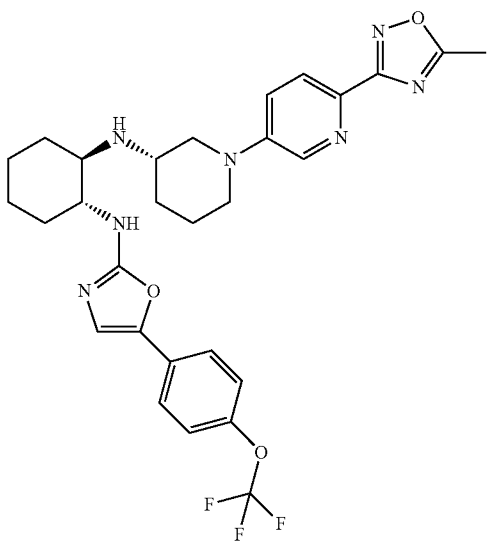 [SMILES: Cc1nc(-c2ccc(N3CCC[C@H](N[C@@H]4CCCC[C@H]4Nc4ncc(-c5ccc(OC(F)(F)F)cc5)o4)C3)cn2)no1] | 427 | 3.39 (A) | 584.2 | Scheme 1 |
| 395 | 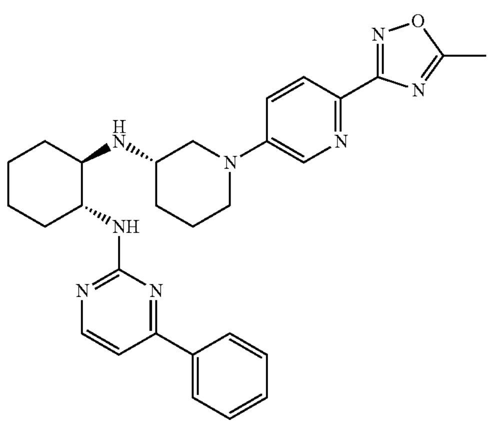 [SMILES: Cc1nc(-c2ccc(N3CCC[C@H](N[C@@H]4CCCC[C@H]4Nc4nccc(-c5ccccc5)n4)C3)cn2)no1] | 5 | 2.83 (A) | 511.2 | Scheme 1 |
| 396 | 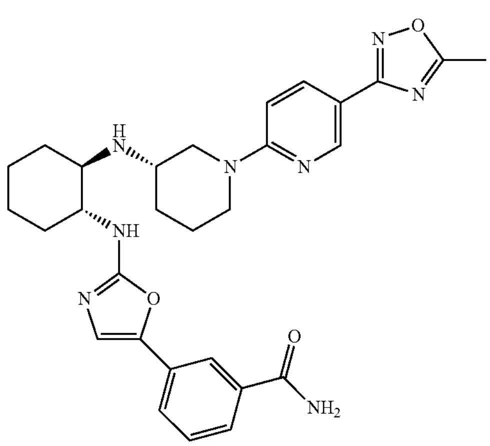 [SMILES: Cc1nc(-c2ccc(N3CCC[C@H](N[C@@H]4CCCC[C@H]4Nc4ncc(-c5cccc(C(N)=O)c5)o4)C3)nc2)no1] | 0.2 | 2.60 (A) | 543.2 | Scheme 1 |

TABLE 7-continued

| Example | Structure | hY4 CAMP EC50 (nM) | HPLC retention time (Method) | Mass (M + H) | Synthesis Method |
|---|---|---|---|---|---|
| 397 | 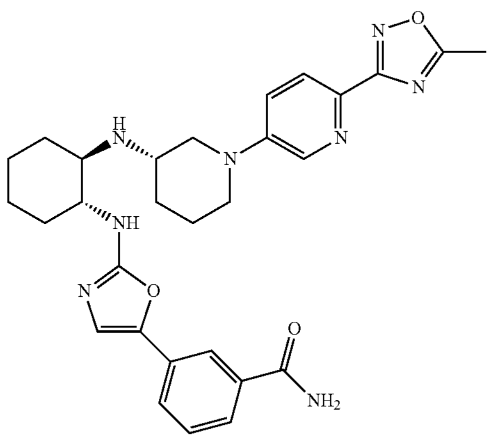 | 3 | 2.35 (A) | 543.2 | Scheme 1 |

Table 8 includes additional compounds of the invention wherein $R^2$ is Pyrimidinyl-$CF_3$.

TABLE 8

| Example | Structure | hY4 CAMP EC50 (nM) | HPLC retention time (Method) | Mass (M + H) | Synthesis Method |
|---|---|---|---|---|---|
| 398 | 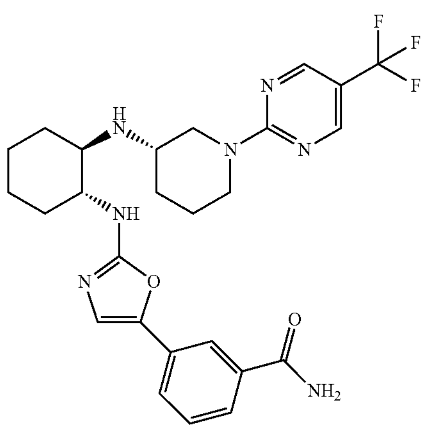 [SMILES: NC(=O)c1cccc(-c2cnc(N[C@@H]3CCCC[C@H]3N[C@H]3CCCN(c4ncc(C(F)(F)F)cn4)C3)o2)c1] | 5 | 8.022 (K) | 530.2 | Scheme 1 |
| 399 | 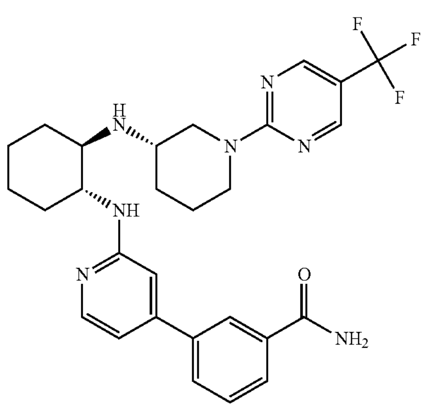 [SMILES: NC(=O)c1cccc(-c2ccnc(N[C@@H]3CCCC[C@H]3N[C@H]3CCCN(c4ncc(C(F)(F)F)cn4)C3)c2)c1] | 22 | 5.675 (J) | 540.2 | Scheme 2 |

TABLE 8-continued
| Example | Structure | hY4 CAMP EC50 (nM) | HPLC retention time (Method) | Mass (M + H) | Synthesis Method |
|---|---|---|---|---|---|
| 400 | 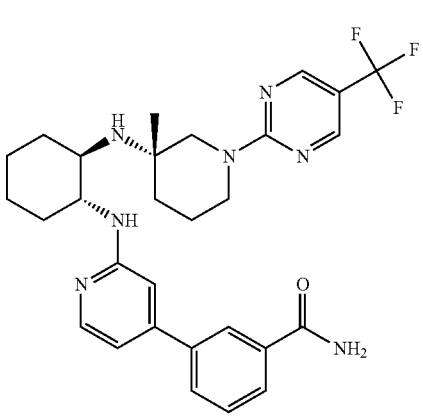 [SMILES: C[C@]1(N[C@@H]2CCCC[C@H]2Nc2cc(-c3cccc(C(N)=O)c3)ccn2)CCCN(c2ncc(C(F)(F)F)cn2)C1] | 28 | 6.356 (J) | 554.2 | Scheme 5 |
| 401 | 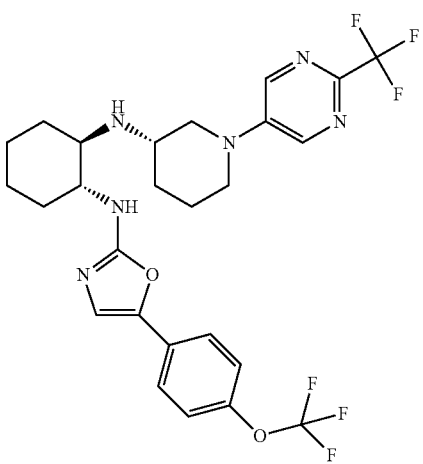 [SMILES: FC(F)(F)Oc1ccc(-c2cnc(N[C@@H]3CCCC[C@H]3N[C@H]3CCCN(c4cnc(C(F)(F)F)nc4)C3)o2)cc1] | 1478 | 3.086 (B) | 571.5 | Scheme 1 |
| 402 | 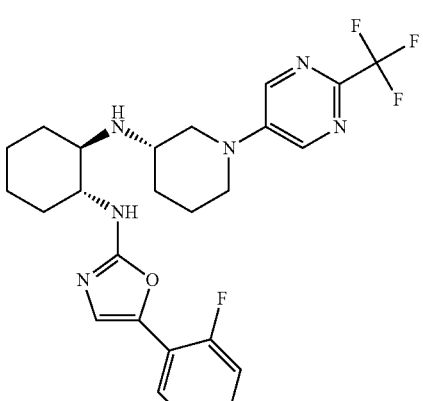 | 161 | 1.727 (C) | 505.1 | Scheme 1 |

TABLE 8-continued

| Example | Structure | hY4 CAMP EC50 (nM) | HPLC retention time (Method) | Mass (M + H) | Synthesis Method |
|---|---|---|---|---|---|
| 403 | 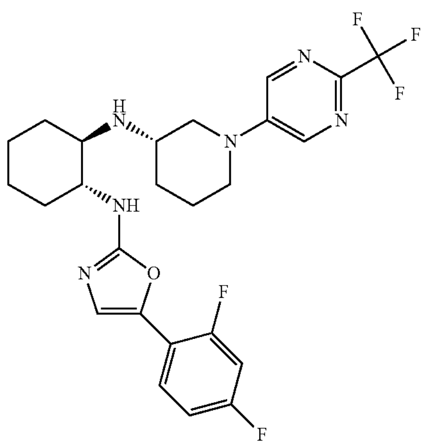 [SMILES: Fc1ccc(-c2cnc(N[C@@H]3CCCC[C@H]3N[C@H]3CCCN(c4cnc(C(F)(F)F)nc4)C3)o2)c(F)c1] | 264 | 1.775 (C) | 523.1 | Scheme 1 |
| 404 | 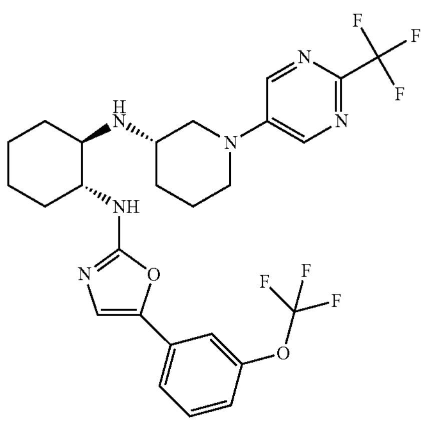 [SMILES: FC(F)(F)Oc1cccc(-c2cnc(N[C@@H]3CCCC[C@H]3N[C@H]3CCCN(c4cnc(C(F)(F)F)nc4)C3)o2)c1] | 954 | 2.033 (C) | 571.1 | Scheme 1 |
| 405 | 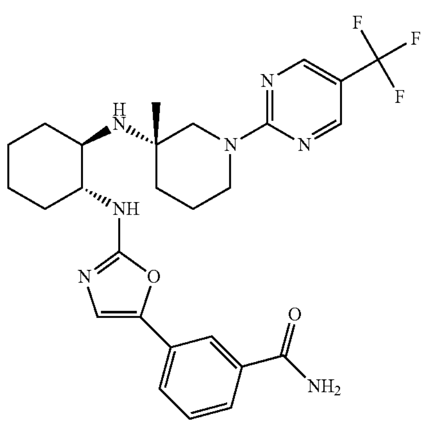 [SMILES: C[C@]1(N[C@@H]2CCCC[C@H]2Nc2ncc(-c3cccc(C(N)=O)c3)o2)CCCN(c2ncc(C(F)(F)F)cn2)C1] | 4 | 6.532 (J) | 544.2 | Scheme 4 |

TABLE 8-continued

| Example | Structure | hY4 CAMP EC50 (nM) | HPLC retention time (Method) | Mass (M + H) | Synthesis Method |
|---------|-----------|--------------------|-----------------------------|--------------|------------------|
| 406 | 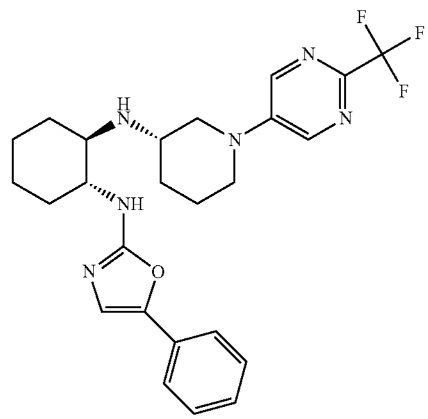 [SMILES: FC(F)(F)c1ncc(N2CCC[C@H](N[C@@H]3CCCC[C@H]3Nc3ncc(-c4ccccc4)o3)C2)cn1] | 66 | 2.010 (C) | 487.3 | Scheme 1 |
| 407 | 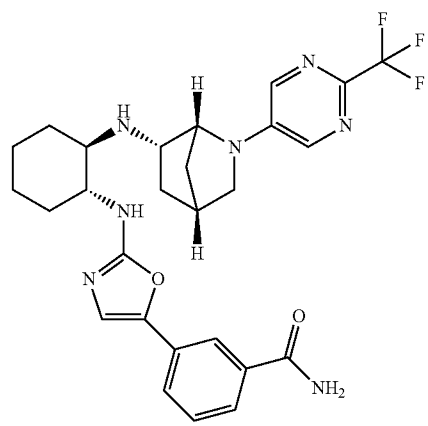 [SMILES: NC(=O)c1cccc(-c2cnc(N[C@@H]3CCCC[C@H]3N[C@H]3C[C@@H]4C[C@H]3N(c3cnc(C(F)(F)F)nc3)C4)o2)c1] | 329 | 5.506 (J) | 542.2 | Scheme 5 |
| 408 | 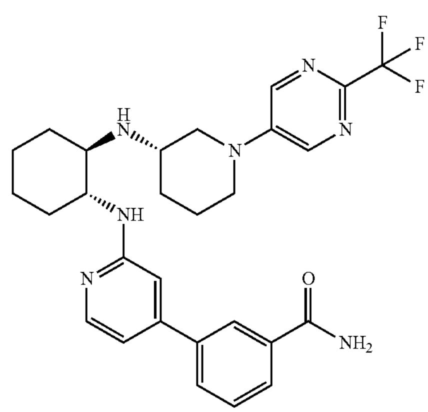 [SMILES: NC(=O)c1cccc(-c2ccnc(N[C@@H]3CCCC[C@H]3N[C@H]3CCCN(c4cnc(C(F)(F)F)nc4)C3)c2)c1] | 121 | 5.198 (J) | 540.3 | Scheme 1 |

TABLE 8-continued
| Example | Structure | hY4 CAMP EC50 (nM) | HPLC retention time (Method) | Mass (M + H) | Synthesis Method |
|---|---|---|---|---|---|
| 409 | 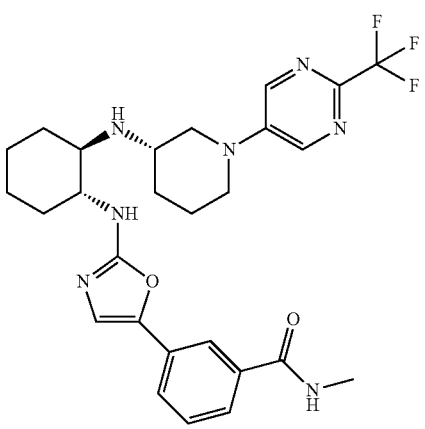 [SMILES: CNC(=O)c1cccc(-c2cnc(N[C@@H]3CCCC[C@H]3N[C@H]3CCCN(c4cnc(C(F)(F)F)nc4)C3)o2)c1] | 4 | 5.951 (J) | 544.2 | Scheme 1 |
| 410 | 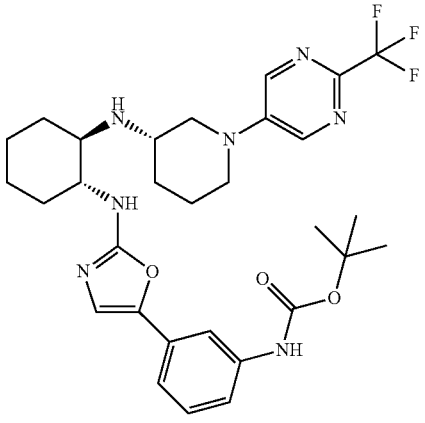 [SMILES: CC(C)(C)OC(=O)Nc1cccc(-c2cnc(N[C@@H]3CCCC[C@H]3N[C@H]3CCCN(c4cnc(C(F)(F)F)nc4)C3)o2)c1] | 320 | 7.649 (J) | 603.2 | Scheme 1 |
| 411 | 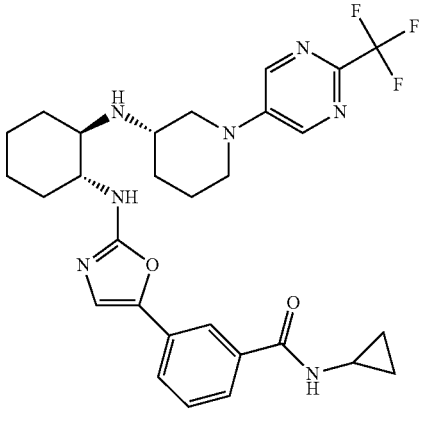 [SMILES: O=C(NC1CC1)c1cccc(-c2cnc(N[C@@H]3CCCC[C@H]3N[C@H]3CCCN(c4cnc(C(F)(F)F)nc4)C3)o2)c1] | 10 | 6.353 (J) | 570.2 | Scheme 1 |

TABLE 8-continued

| Example | Structure | hY4 cAMP EC50 (nM) | HPLC retention time (Method) | Mass (M + H) | Synthesis Method |
|---|---|---|---|---|---|
| 412 | 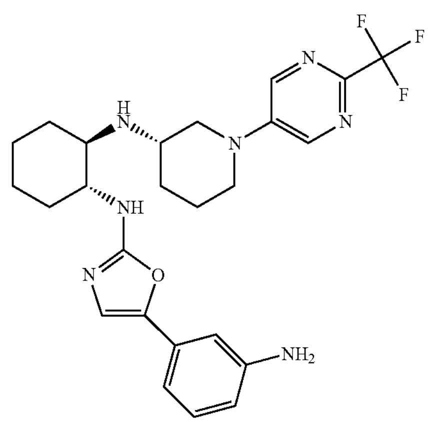 [SMILES: Nc1cccc(-c2cnc(N[C@@H]3CCCC[C@H]3N[C@H]3CCCN(c4cnc(C(F)(F)F)nc4)C3)o2)c1] | 69 | | 502.2 | Scheme 1 |
| 413 | 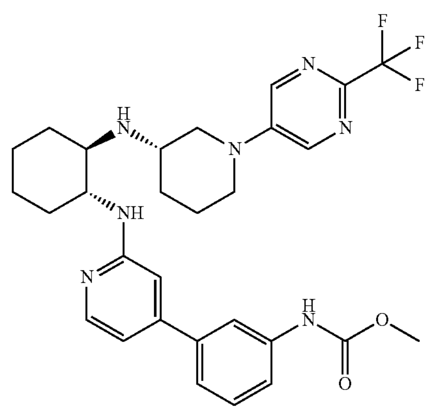 [SMILES: COC(=O)Nc1cccc(-c2ccnc(N[C@@H]3CCCC[C@H]3N[C@H]3CCCN(c4cnc(C(F)(F)F)nc4)C3)c2)c1] | 6 | 5.642 (J) | 570.2 | Scheme 3 |
| 414 | 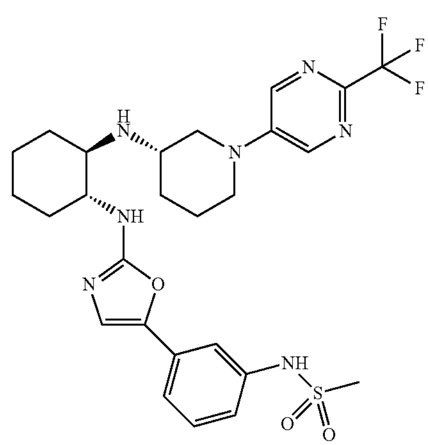 [SMILES: CS(=O)(=O)Nc1cccc(-c2cnc(N[C@@H]3CCCC[C@H]3N[C@H]3CCCN(c4cnc(C(F)(F)F)nc4)C3)o2)c1] | 5 | 6.455 (J) | 580.2 | Scheme 1 |

TABLE 8-continued

| Example | Structure | hY4 CAMP EC50 (nM) | HPLC retention time (Method) | Mass (M + H) | Synthesis Method |
|---|---|---|---|---|---|
| 415 | 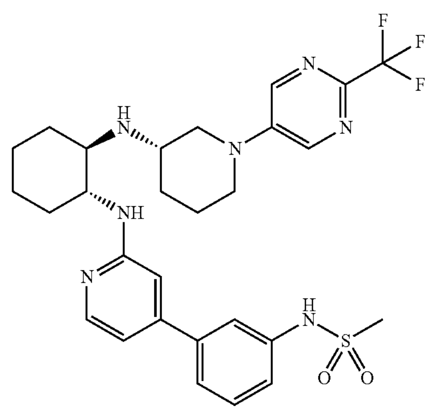 [SMILES: CS(=O)(=O)Nc1cccc(-c2ccnc(N[C@@H]3CCCC[C@H]3N[C@H]3CCCN(c4cnc(C(F)(F)F)nc4)C3)c2)c1] | 19 | 6.022 (J) | 590.2 | Scheme 3 |
| 416 | 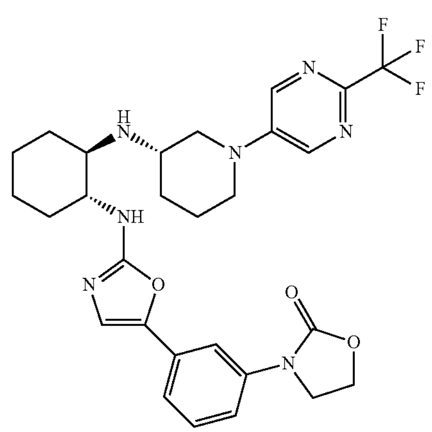 [SMILES: O=C1OCCN1c1cccc(-c2cnc(N[C@@H]3CCCC[C@H]3N[C@H]3CCCN(c4cnc(C(F)(F)F)nc4)C3)o2)c1] | 49 | 6.180 (J) | 572.2 | Scheme 1 |
| 417 | 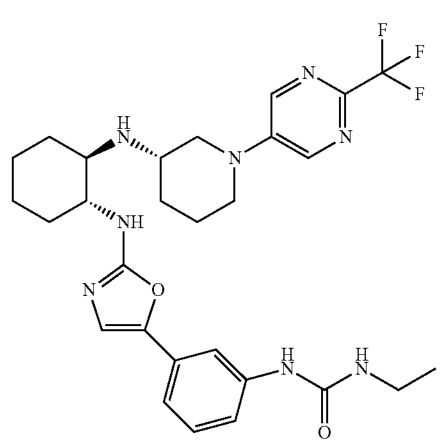 [SMILES: CCNC(=O)Nc1cccc(-c2cnc(N[C@@H]3CCCC[C@H]3N[C@H]3CCCN(c4cnc(C(F)(F)F)nc4)C3)o2)c1] | 6 | 5.938 (J) | 573.2 | Scheme 1 |

TABLE 8-continued
| Example | Structure | hY4 cAMP EC50 (nM) | HPLC retention time (Method) | Mass (M + H) | Synthesis Method |
|---|---|---|---|---|---|
| 418 | 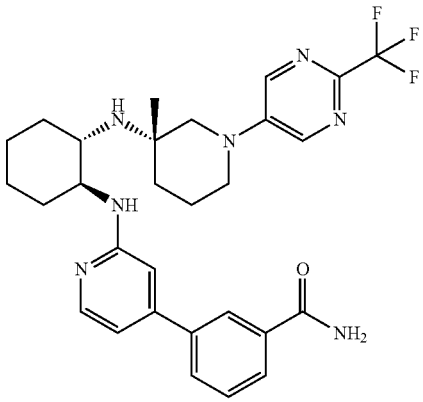 [SMILES: C[C@]1(N[C@H]2CCCC[C@@H]2Nc2cc(-c3cccc(C(N)=O)c3)ccn2)CCCN(c2cnc(C(F)(F)F)nc2)C1] | 48 | 5.354 (J) | 554.4 | Scheme 4 |
| 419 | 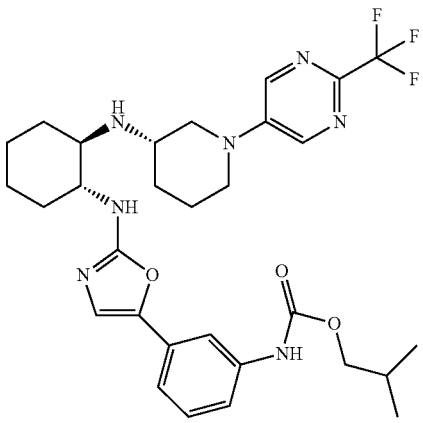 [SMILES: CC(C)COC(=O)Nc1cccc(-c2cnc(N[C@@H]3CCCC[C@H]3N[C@H]3CCCN(c4cnc(C(F)(F)F)nc4)C3)o2)c1] | 7 | 7.593 (J) | 602.2 | Scheme 1 |
| 420 | 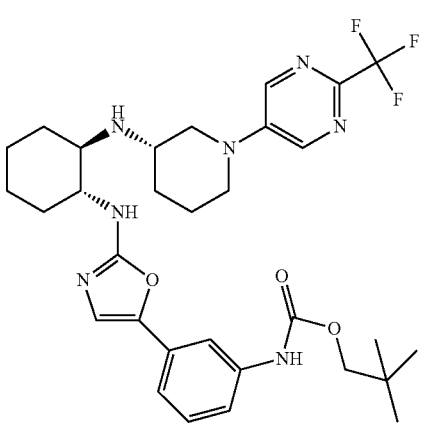 [SMILES: CC(C)(C)COC(=O)Nc1cccc(-c2cnc(N[C@@H]3CCCC[C@H]3N[C@H]3CCCN(c4cnc(C(F)(F)F)nc4)C3)o2)c1] | 212 | 7.969 (J) | 616.2 | Scheme 1 |

TABLE 8-continued

| Example | Structure | hY4 CAMP EC50 (nM) | HPLC retention time (Method) | Mass (M + H) | Synthesis Method |
|---|---|---|---|---|---|
| 421 | 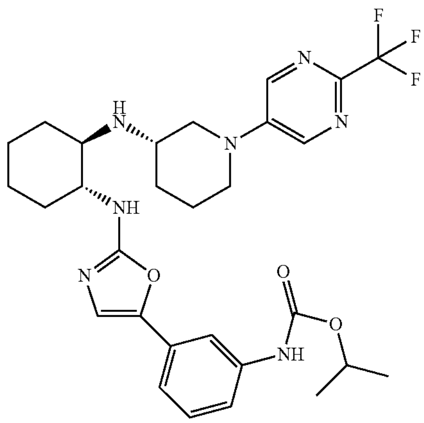 [SMILES: CC(C)OC(=O)Nc1cccc(-c2cnc(N[C@@H]3CCCC[C@H]3N[C@H]3CCCN(c4cnc(C(F)(F)F)nc4)C3)o2)c1] | 23 | 7.145 (J) | 588.2 | Scheme 1 |
| 422 | 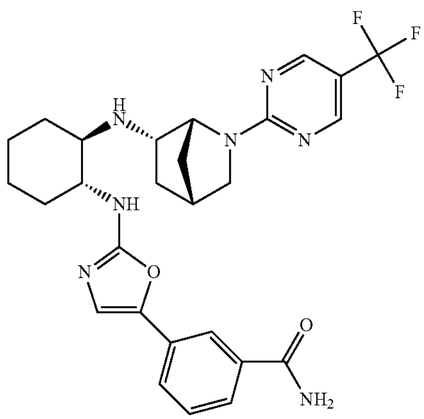 [SMILES: NC(=O)c1cccc(-c2cnc(N[C@@H]3CCCC[C@H]3N[C@H]3C[C@@H]4C[C@H]3N(c3ncc(C(F)(F)F)cn3)C4)o2)c1] | 41 | 6.204 (K) | 542 | Scheme 5 |
| 423 | 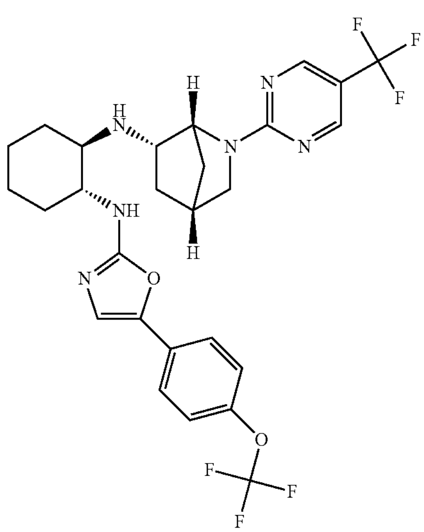 [SMILES: FC(F)(F)Oc1ccc(-c2cnc(N[C@@H]3CCCC[C@H]3N[C@H]3C[C@@H]4C[C@H]3N(c3ncc(C(F)(F)F)cn3)C4)o2)cc1] | 222 | 8.517 (J) | 583.2 | Scheme 5 |

TABLE 8-continued
| Example | Structure | hY4 cAMP EC50 (nM) | HPLC retention time (Method) | Mass (M + H) | Synthesis Method |
|---|---|---|---|---|---|
| 424 | 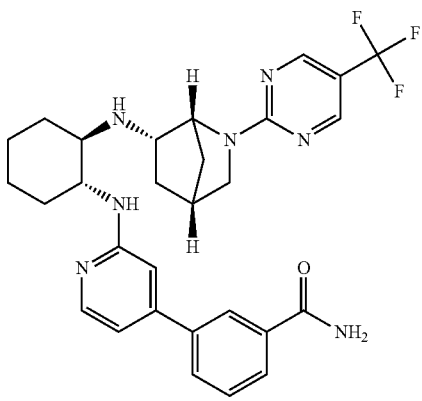 [SMILES: NC(=O)c1cccc(-c2ccnc(N[C@@H]3CCCC[C@H]3N[C@H]3C[C@@H]4C[C@H]3N(c3ncc(C(F)(F)F)cn3)C4)c2)c1] | 69 | 5.513 (J) | 552.2 | Scheme 5 |
| 425 | 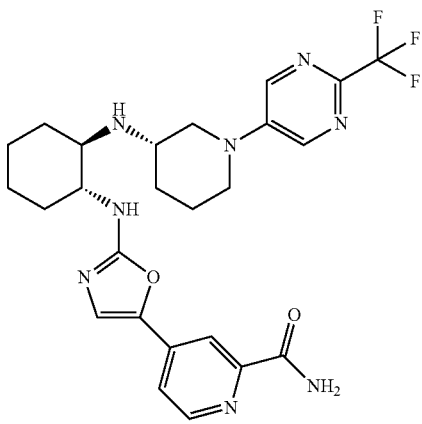 [SMILES: NC(=O)c1cc(-c2cnc(N[C@@H]3CCCC[C@H]3N[C@H]3CCCN(c4cnc(C(F)(F)F)nc4)C3)o2)ccn1] | 15 | 5.206 (J) | 531.2 | Scheme 1 |
| 426 | 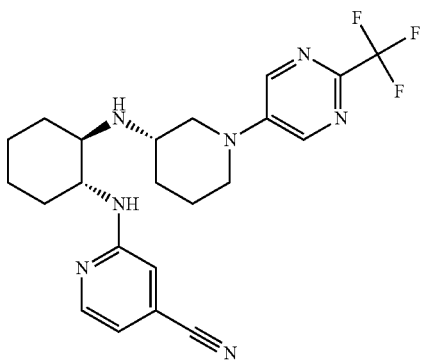 [SMILES: N#Cc1ccnc(N[C@@H]2CCCC[C@H]2N[C@H]2CCCN(c3cnc(C(F)(F)F)nc3)C2)c1] | 600 | 2.30 (A) | 446.2 | Scheme 1 |

TABLE 8-continued

| Example | Structure | hY4 CAMP EC50 (nM) | HPLC retention time (Method) | Mass (M + H) | Synthesis Method |
|---------|-----------|--------------------|------------------------------|--------------|------------------|
| 427 | 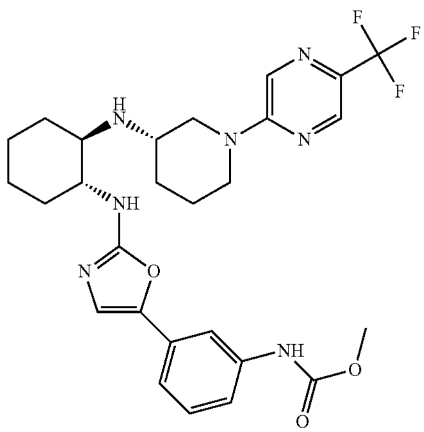 [SMILES: COC(=O)Nc1cccc(-c2cnc(N[C@@H]3CCCC[C@H]3N[C@H]3CCCN(c4cnc(C(F)(F)F)cn4)C3)o2)c1] | 1 | 1.41 (C) | 560.3 | Scheme 1 |
| 428 | 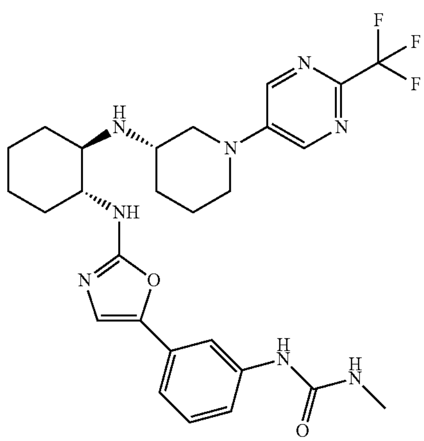 [SMILES: CNC(=O)Nc1cccc(-c2cnc(N[C@@H]3CCCC[C@H]3N[C@H]3CCCN(c4cnc(C(F)(F)F)nc4)C3)o2)c1] | 4 | 5.933 (J) | 559.2 | Scheme 1 |
| 429 | 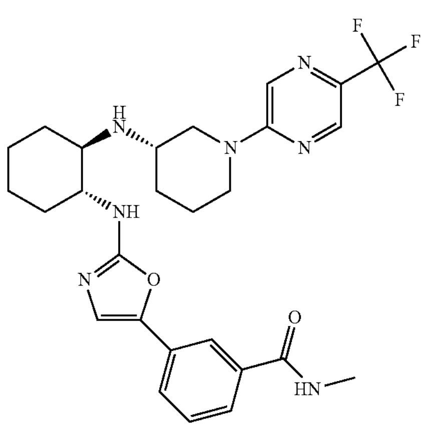 [SMILES: CNC(=O)c1cccc(-c2cnc(N[C@@H]3CCCC[C@H]3N[C@H]3CCCN(c4cnc(C(F)(F)F)cn4)C3)o2)c1] | 2 | 1.286 (C) | 544.4 | Scheme 1 |

Table 9 includes additional compounds of the invention wherein $R^2$ is pyrimidinyl-CN.
TABLE 9
| Example | Structure | hY4 CAMP EC50 (nM) | HPLC retention time (Method) | Mass (M + H) | Synthesis Method |
|---|---|---|---|---|---|
| 430 | 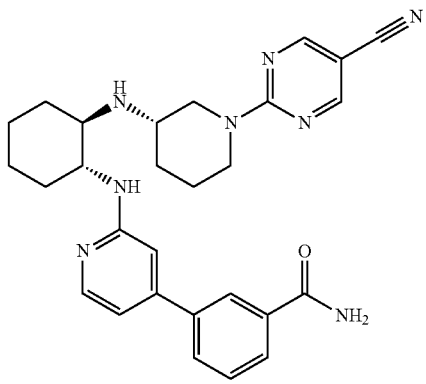 [SMILES: N#Cc1cnc(N2CCC[C@H](N[C@@H]3CCCC[C@H]3Nc3cc(-c4cccc(C(N)=O)c4)ccn3)C2)nc1] | 142 | | 497.2 | Scheme 3 |
| 431 | 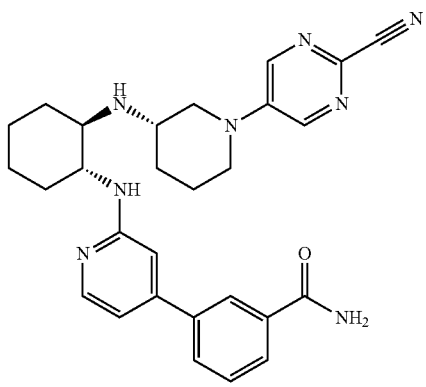 [SMILES: N#Cc1ncc(N2CCC[C@H](N[C@@H]3CCCC[C@H]3Nc3cc(-c4cccc(C(N)=O)c4)ccn3)C2)cn1] | 171 | 1.31 (C) | 497 | Scheme 3 |
| 432 | 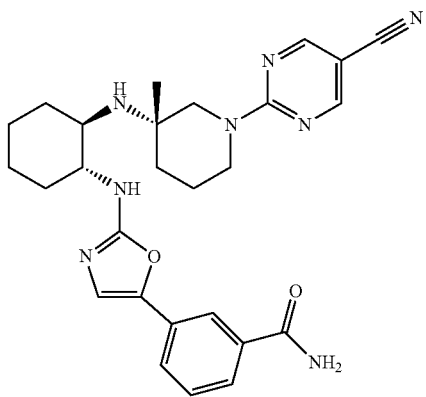 [SMILES: C[C@]1(N[C@@H]2CCCC[C@H]2Nc2ncc(-c3cccc(C(N)=O)c3)o2)CCCN(c2ncc(C#N)cn2)C1] | 29 | 5.328 (J) | 501.2 | Scheme 4 |

TABLE 9-continued
| Example | Structure | hY4 CAMP EC50 (nM) | HPLC retention time (Method) | Mass (M + H) | Synthesis Method |
|---|---|---|---|---|---|
| 433 | 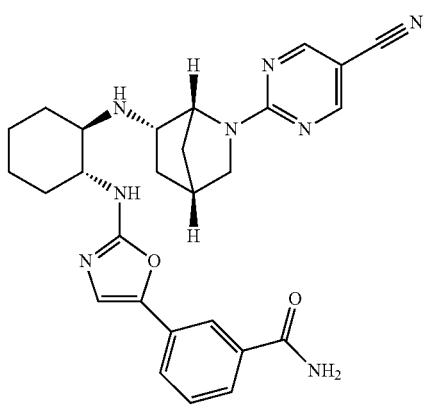 [SMILES: N#Cc1cnc(N2C[C@@H]3C[C@H](N[C@@H]4CCCC[C@H]4Nc4ncc(-c5cccc(C(N)=O)c5)o4)[C@H]2C3)nc1] | 144 | 5.325 (J) | | Scheme 5 |
| 434 | 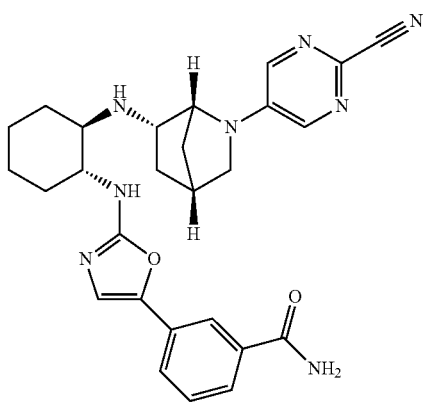 [SMILES: N#Cc1ncc(N2C[C@@H]3C[C@H](N[C@@H]4CCCC[C@H]4Nc4ncc(-c5cccc(C(N)=O)c5)o4)[C@H]2C3)cn1] | 129 | 5.756 (J) | 499.2 | Scheme 5 |
| 435 | 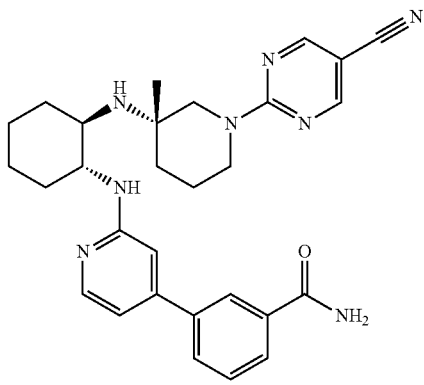 [SMILES: C[C@]1(N[C@@H]2CCCC[C@H]2Nc2cc(-c3cccc(C(N)=O)c3)ccn2)CCCN(c2ncc(C#N)cn2)C1] | 400 | | 511.2 | Scheme 4 |

TABLE 9-continued
| Example | Structure | hY4 CAMP EC50 (nM) | HPLC retention time (Method) | Mass (M + H) | Synthesis Method |
|---|---|---|---|---|---|
| 436 | 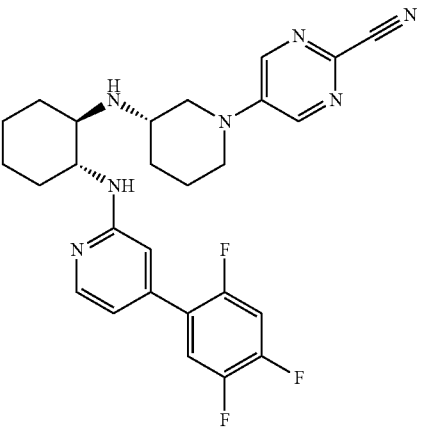 [SMILES: N#Cc1ncc(N2CCC[C@H](N[C@@H]3CCCC[C@H]3Nc3cc(-c4cc(F)c(F)cc4F)ccn3)C2)cn1] | 756 | 1.39 (C) | 508.3 | Scheme 2 |
| 437 | 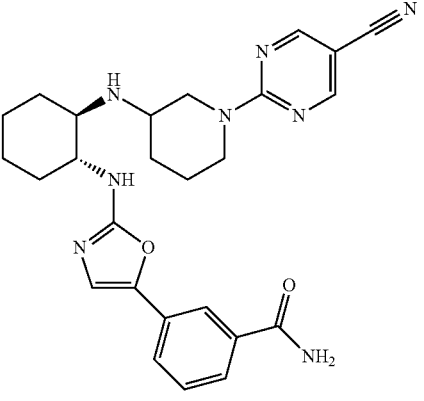 [SMILES: N#Cc1cnc(N2CCCC(N[C@@H]3CCCC[C@H]3Nc3ncc(-c4cccc(C(N)=O)c4)o3)C2)nc1] | 35 | 5.150 (J) | 487.2 | Scheme 6 |
| 438 | 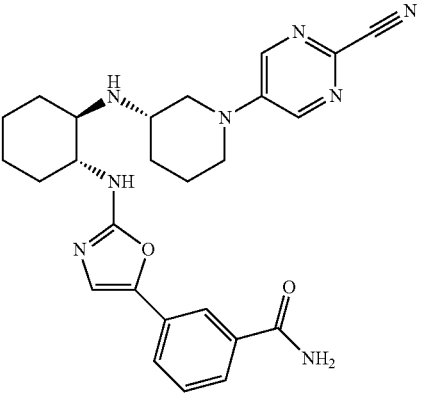 [SMILES: N#Cc1ncc(N2CCC[C@H](N[C@@H]3CCCC[C@H]3Nc3ncc(-c4cccc(C(N)=O)c4)o3)C2)cn1] | 5 | 1.25 (L) | 487.3 | Scheme 1 |

TABLE 9-continued

| Example | Structure | hY4 CAMP EC50 (nM) | HPLC retention time (Method) | Mass (M + H) | Synthesis Method |
|---|---|---|---|---|---|
| 439 | 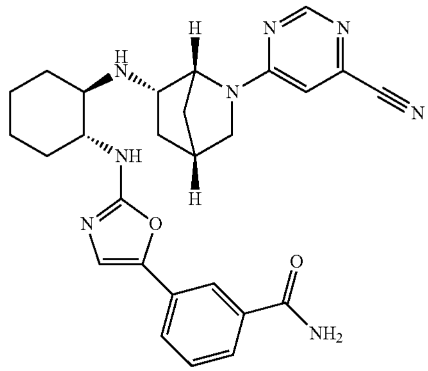 [SMILES: N#Cc1cc(N2C[C@@H]3C[C@H](N[C@@H]4CCCC[C@H]4Nc4ncc(-c5cccc(C(N)=O)c5)o4)[C@H]2C3)ncn1] | 578 | 5.718 (K) | 499.2 | Scheme 6 |
| 440 | 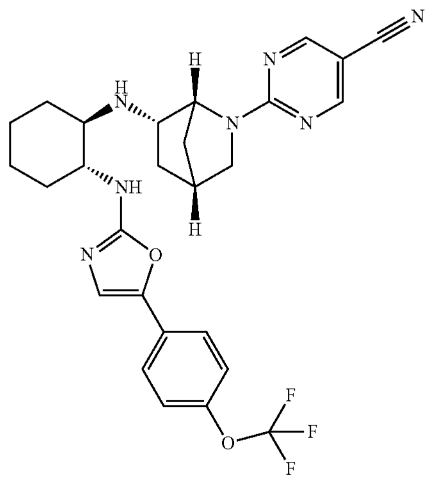 [SMILES: N#Cc1cnc(N2C[C@@H]3C[C@H](N[C@@H]4CCCC[C@H]4Nc4ncc(-c5ccc(OC(F)(F)F)cc5)o4)[C@H]2C3)nc1] | 15 | 3.38 (A) | 540.3 | Scheme 5 |
| 441 | 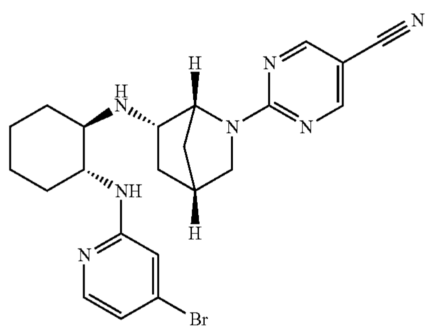 | 803 | 2.52 (A) | 468.1 | Scheme 5 |
| 442 | 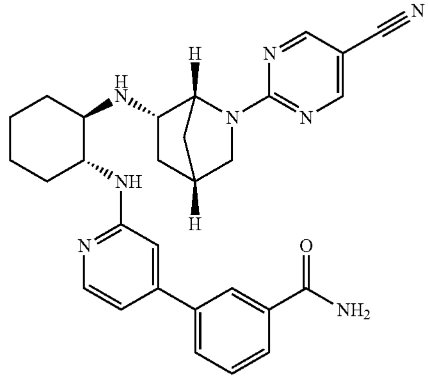 | 228 | 2.26 (A) | 509.3 | Scheme 5 |

TABLE 9-continued
| Example | Structure | hY4 CAMP EC50 (nM) | HPLC retention time (Method) | Mass (M + H) | Synthesis Method |
|---|---|---|---|---|---|
| 443 | 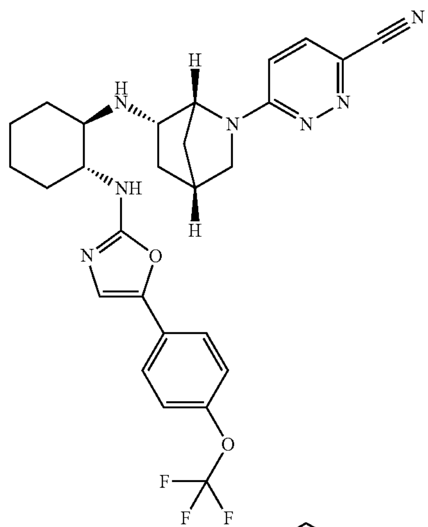 [SMILES: N#Cc1ccc(N2C[C@@H]3C[C@H](N[C@@H]4CCCC[C@H]4Nc4ncc(-c5ccc(OC(F)(F)F)cc5)o4)[C@H]2C3)nn1] | 482 | 1.79 (L) | 540.3 | Scheme 5 |
| 444 | 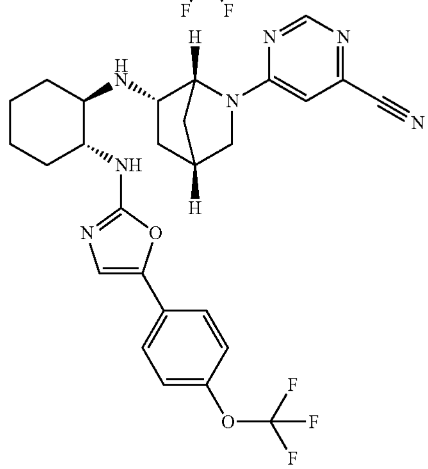 | 378 | 8.195 (M) | 540.1 | Scheme 5 |
Table 10 includes other compounds of the invention.
TABLE 10
| Example | Structure | hY4 CAMP EC50 (nM) | HPLC retention time (Method) | Mass (M + H) | Synthesis Method |
|---|---|---|---|---|---|
| 445 | 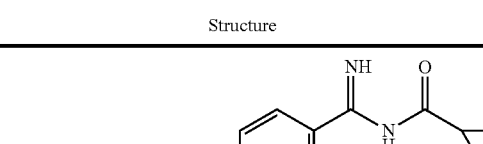 | 4 | 2.25 (A) | 585.3 | Scheme 4 |

TABLE 10-continued
| Example | Structure | hY4 CAMP EC50 (nM) | HPLC retention time (Method) | Mass (M + H) | Synthesis Method |
|---|---|---|---|---|---|
| 446 | 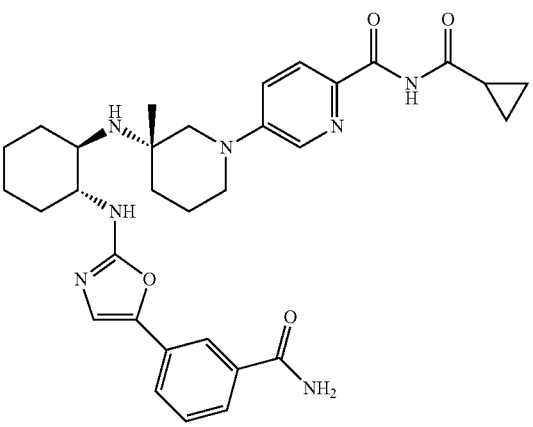 [SMILES: C[C@]1(N[C@@H]2CCCC[C@H]2Nc2ncc(-c3cccc(C(N)=O)c3)o2)CCCN(c2ccc(C(=O)NC(=O)C3CC3)nc2)C1] | 6 | 2.64 (A) | 586.2 | Scheme 4 |
| 447 | 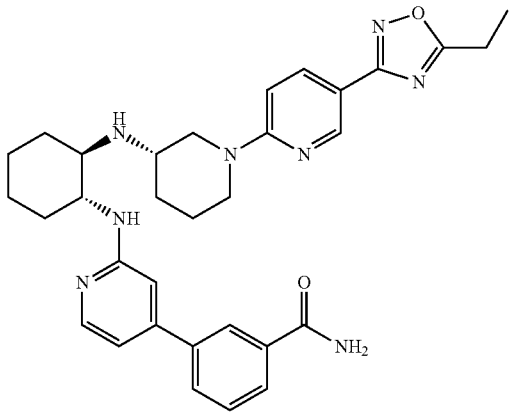 [SMILES: CCc1nc(-c2ccc(N3CCC[C@H](N[C@@H]4CCCC[C@H]4Nc4cc(-c5cccc(C(N)=O)c5)ccn4)C3)nc2)no1] | 8 | 2.68 (A) | 567.2 | Scheme 3 |
| 448 | 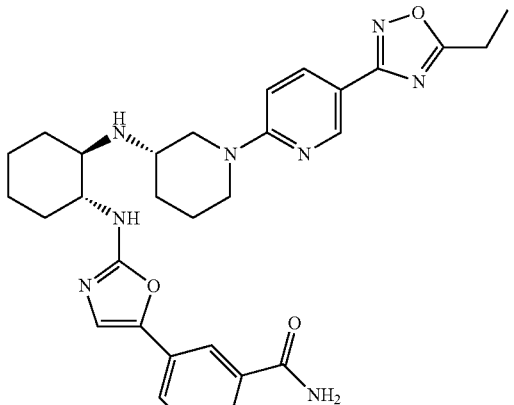 | 2 | 2.67 (A) | 557.2 | Scheme 1 |

TABLE 10-continued

| Example | Structure | hY4 CAMP EC50 (nM) | HPLC retention time (Method) | Mass (M + H) | Synthesis Method |
|---|---|---|---|---|---|
| 449 | 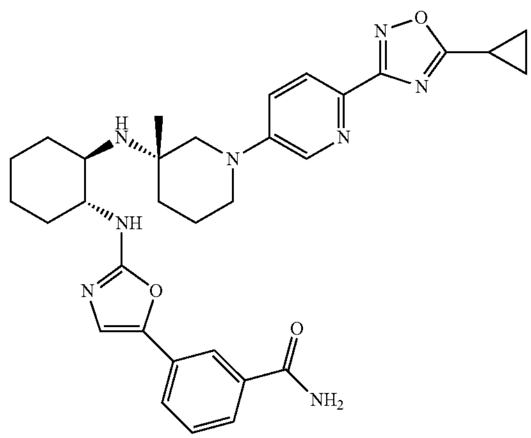 [SMILES: C[C@]1(N[C@@H]2CCCC[C@H]2Nc2ncc(-c3cccc(C(N)=O)c3)o2)CCCN(c2ccc(-c3noc(C4CC4)n3)nc2)C1] | 5 | 2.72 (A) | 583.3 | Scheme 4 |
| 450 | 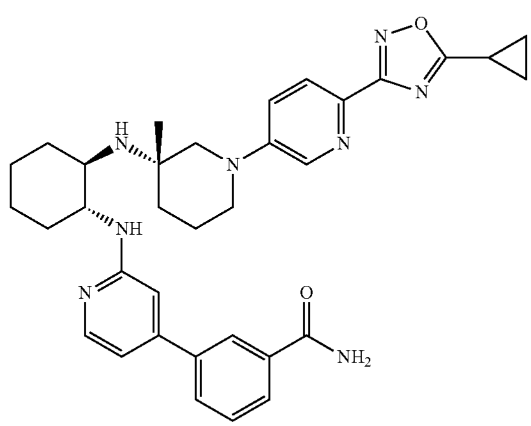 [SMILES: C[C@]1(N[C@@H]2CCCC[C@H]2Nc2cc(-c3cccc(C(N)=O)c3)ccn2)CCCN(c2ccc(-c3noc(C4CC4)n3)nc2)C1] | 10 | 2.71 (A) | 593.4 | Scheme 4 |
| 451 | 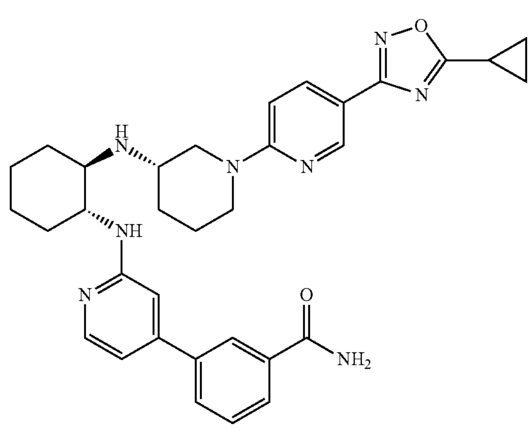 [SMILES: NC(=O)c1cccc(-c2ccnc(N[C@@H]3CCCC[C@H]3N[C@H]3CCCN(c4ccc(-c5noc(C6CC6)n5)cn4)C3)c2)c1] | 4 | 2.74 (A) | 579.2 | Scheme 3 |

TABLE 10-continued

| Example | Structure | hY4 CAMP EC50 (nM) | HPLC retention time (Method) | Mass (M + H) | Synthesis Method |
|---------|-----------|--------------------|------------------------------|--------------|------------------|
| 452 | 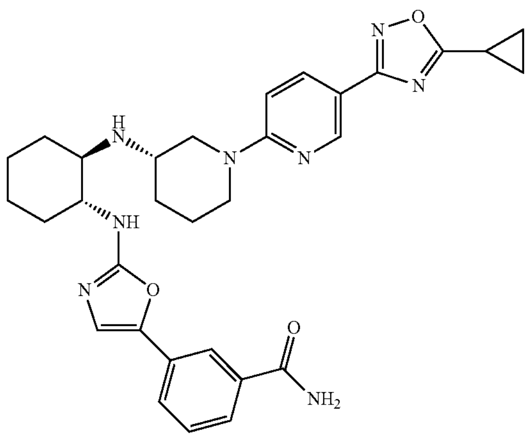 [SMILES: NC(=O)c1cccc(-c2cnc(N[C@@H]3CCCC[C@H]3N[C@H]3CCCN(c4ccc(-c5noc(C6CC6)n5)cn4)C3)o2)c1] | 3 | 2.76 (A) | 569.2 | Scheme 1 |
| 453 | 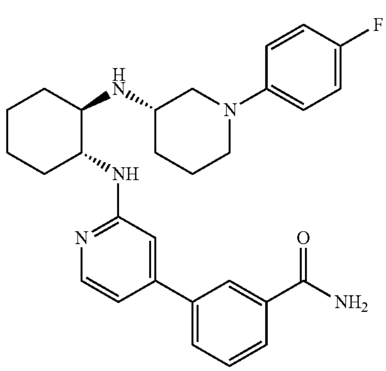 [SMILES: NC(=O)c1cccc(-c2ccnc(N[C@@H]3CCCC[C@H]3N[C@H]3CCCN(c4ccc(F)cc4)C3)c2)c1] | 41 | 1.480 (B) | 488.3 | Scheme 3 |
| 454 | 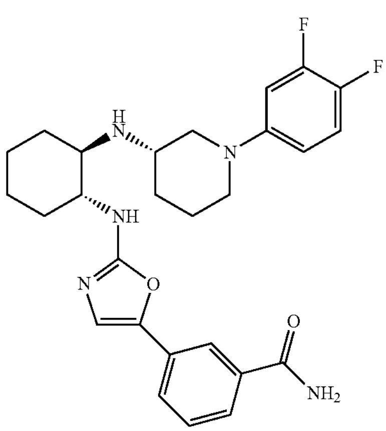 [SMILES: NC(=O)c1cccc(-c2cnc(N[C@@H]3CCCC[C@H]3N[C@H]3CCCN(c4ccc(F)c(F)c4)C3)o2)c1] | 3 | 6.120 (J) | | Scheme 1 |

TABLE 10-continued

| Example | Structure | hY4 CAMP EC50 (nM) | HPLC retention time (Method) | Mass (M + H) | Synthesis Method |
|---|---|---|---|---|---|
| 455 | 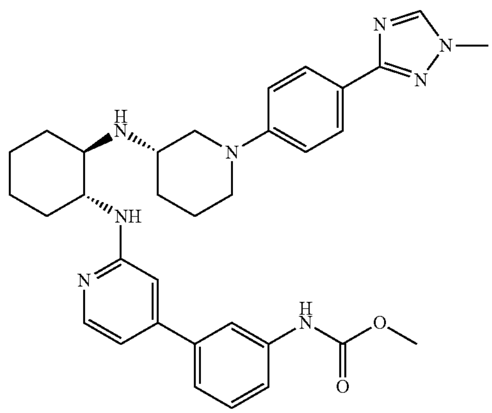 [SMILES: COC(=O)Nc1cccc(-c2ccnc(N[C@@H]3CCCC[C@H]3N[C@H]3CCCN(c4ccc(-c5ncn(C)n5)cc4)C3)c2)c1] | 2 | 2.61 (A) | 581.3 | Scheme 3 |
| 456 | 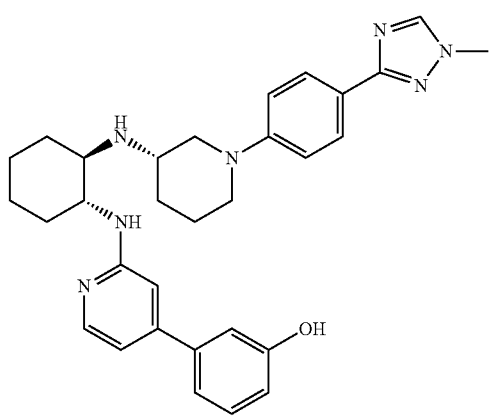 [SMILES: Cn1cnc(-c2ccc(N3CCC[C@H](N[C@@H]4CCCC[C@H]4Nc4cc(-c5cccc(O)c5)ccn4)C3)cc2)n1] | 28 | 2.37 (A) | 524.2 | Scheme 3 |
| 457 | 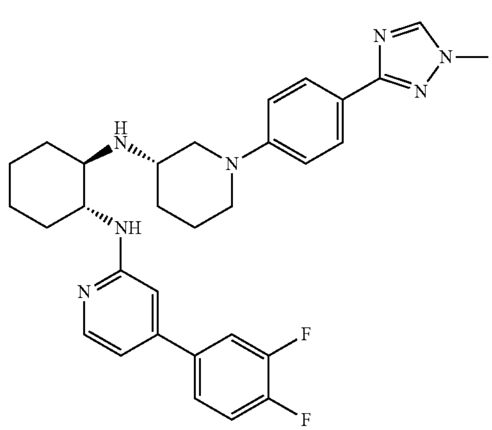 [SMILES: Cn1cnc(-c2ccc(N3CCC[C@H](N[C@@H]4CCCC[C@H]4Nc4cc(-c5ccc(F)c(F)c5)ccn4)C3)cc2)n1] | 26 | 2.90 (A) | 544.3 | Scheme 3 |

TABLE 10-continued

| Example | Structure | hY4 CAMP EC50 (nM) | HPLC retention time (Method) | Mass (M + H) | Synthesis Method |
|---|---|---|---|---|---|
| 458 | 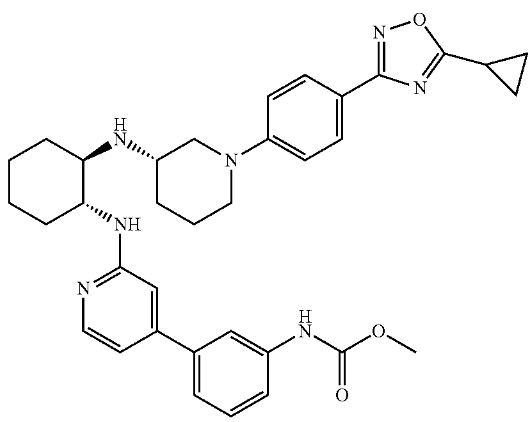 [SMILES: COC(=O)Nc1cccc(-c2ccnc(N[C@@H]3CCCC[C@H]3N[C@H]3CCCN(c4ccc(-c5noc(C6CC6)n5)cc4)C3)c2)c1] | 0.2 | 1.40 (C) | 608.3 | Scheme 9 |
| 459 | 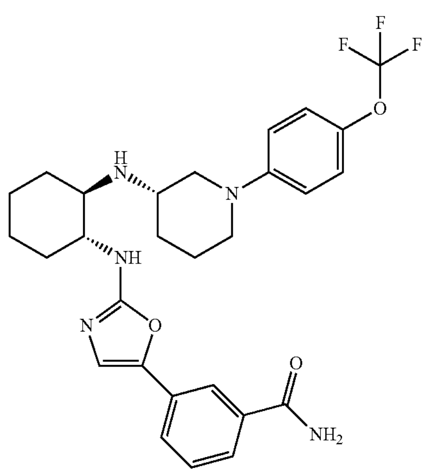 [SMILES: NC(=O)c1cccc(-c2cnc(N[C@@H]3CCCC[C@H]3N[C@H]3CCCN(c4ccc(OC(F)(F)F)cc4)C3)o2)c1] | 1 | 2.542 (B) | 544.2 | Scheme 1 |
| 460 | 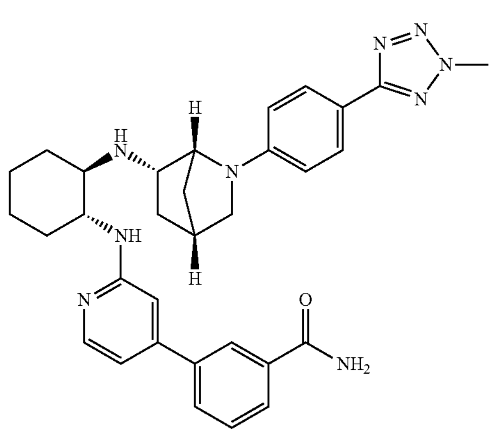 [SMILES: Cn1nnc(-c2ccc(N3C[C@@H]4C[C@H](N[C@@H]5CCCC[C@H]5Nc5cc(-c6cccc(C(N)=O)c6)ccn5)[C@H]3C4)cc2)n1] | 4 | 1.44 (L) | 564.3 | Scheme 5 |

TABLE 10-continued
| Example | Structure | hY4 CAMP EC50 (nM) | HPLC retention time (Method) | Mass (M + H) | Synthesis Method |
|---------|-----------|---------------------|-------------------------------|--------------|------------------|
| 461 | 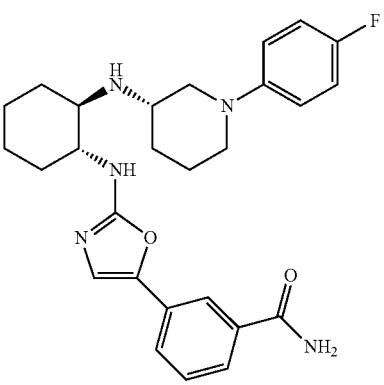 [SMILES: NC(=O)c1cccc(-c2cnc(N[C@@H]3CCCC[C@H]3N[C@H]3CCCN(c4ccc(F)cc4)C3)o2)c1] | 55 | 2.103 (B) | 478.3 | Scheme 1 |
| 462 | 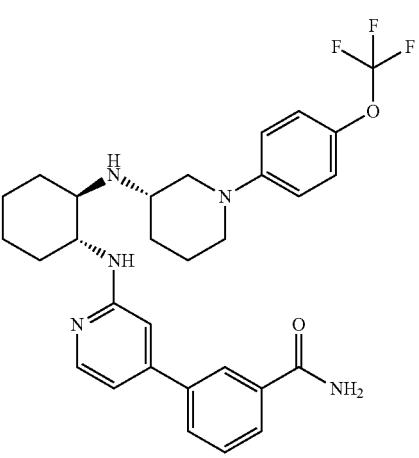 [SMILES: NC(=O)c1cccc(-c2ccnc(N[C@@H]3CCCC[C@H]3N[C@H]3CCCN(c4ccc(OC(F)(F)F)cc4)C3)c2)c1] | 8 | 2.343 (B) | 554.3 | Scheme 2 |
| 463 | 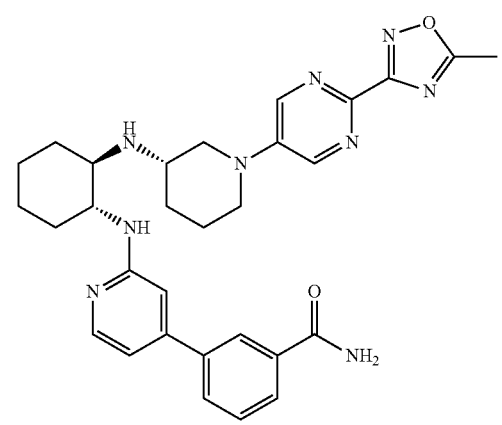 [SMILES: Cc1nc(-c2ncc(N3CCC[C@H](N[C@@H]4CCCC[C@H]4Nc4cc(-c5cccc(C(N)=O)c5)ccn4)C3)cn2)no1] | 39 | 1.24 (C) | 554.3 | Scheme 9 |

TABLE 10-continued

| Example | Structure | hY4 CAMP EC50 (nM) | HPLC retention time (Method) | Mass (M + H) | Synthesis Method |
|---------|-----------|--------------------|------------------------------|--------------|------------------|
| 464 | 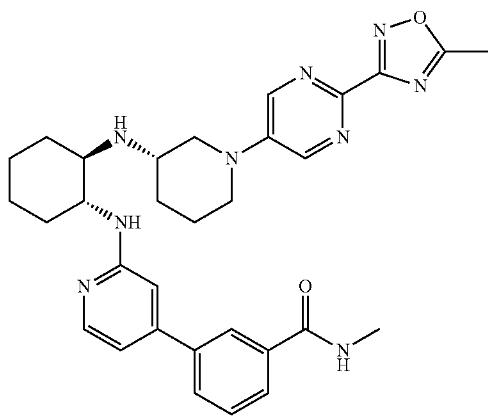 [SMILES: CNC(=O)c1cccc(-c2ccnc(N[C@@H]3CCCC[C@H]3N[C@H]3CCCN(c4cnc(-c5noc(C)n5)nc4)C3)c2)c1] | 42 | 0.94 (C) | 568.3 | Scheme 3 |
| 465 | 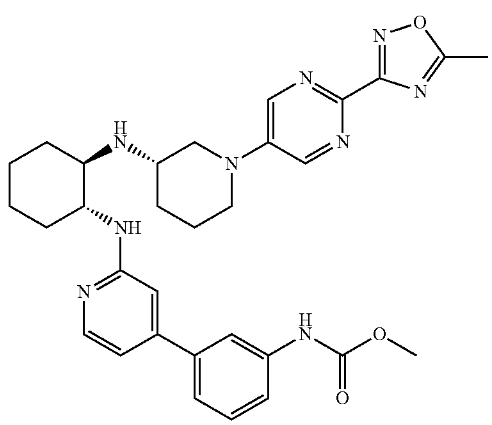 [SMILES: COC(=O)Nc1cccc(-c2ccnc(N[C@@H]3CCCC[C@H]3N[C@H]3CCCN(c4cnc(-c5noc(C)n5)nc4)C3)c2)c1] | 0.02 | 1.12 (C) | 584.3 | Scheme 3 |
| 466 | 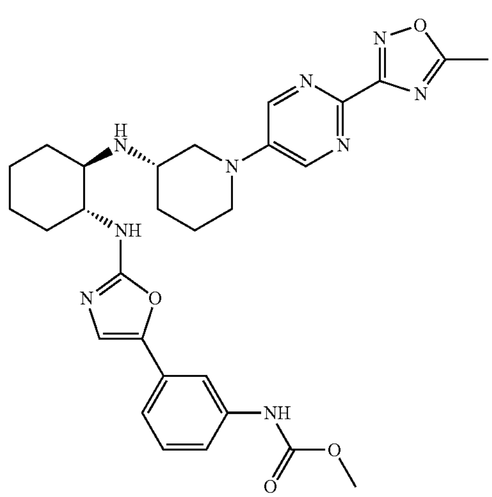 [SMILES: COC(=O)Nc1cccc(-c2cnc(N[C@@H]3CCCC[C@H]3N[C@H]3CCCN(c4cnc(-c5noc(C)n5)nc4)C3)o2)c1] | 1 | 2.61 (A) | 574.3 | Scheme 1 |

TABLE 10-continued
| Example | Structure | hY4 CAMP EC50 (nM) | HPLC retention time (Method) | Mass (M + H) | Synthesis Method |
|---|---|---|---|---|---|
| 467 | 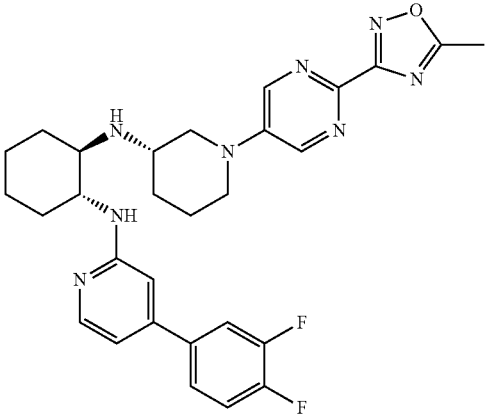 [SMILES: Cc1nc(-c2ncc(N3CCC[C@H](N[C@@H]4CCCC[C@H]4Nc4cc(-c5ccc(F)c(F)c5)ccn4)C3)cn2)no1] | 2 | 1.24 (C) | 547.3 | Scheme 3 |
| 468 | 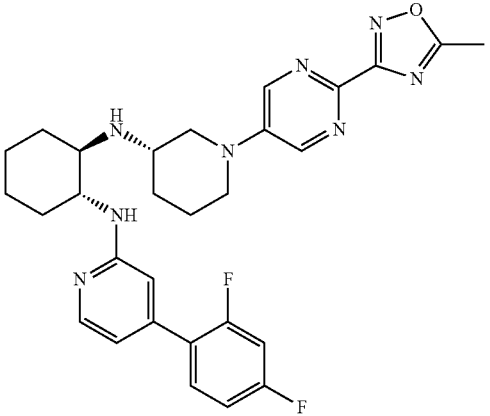 [SMILES: Cc1nc(-c2ncc(N3CCC[C@H](N[C@@H]4CCCC[C@H]4Nc4cc(-c5ccc(F)cc5F)ccn4)C3)cn2)no1] | 9 | 1.20 (C) | 547.3 | Scheme 3 |
| 469 | 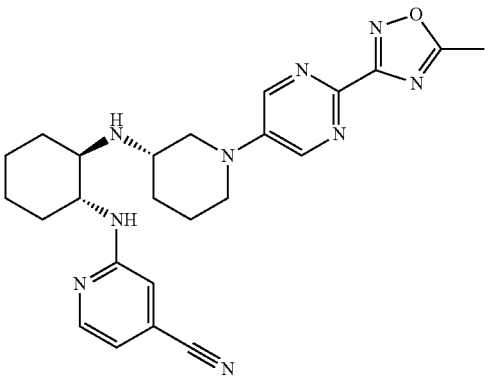 [SMILES: Cc1nc(-c2ncc(N3CCC[C@H](N[C@@H]4CCCC[C@H]4Nc4cc(C#N)ccn4)C3)cn2)no1] | 96 | 0.951 (C) | 460.4 | Scheme 1 |

TABLE 10-continued

| Example | Structure | hY4 CAMP EC50 (nM) | HPLC retention time (Method) | Mass (M + H) | Synthesis Method |
|---------|-----------|--------------------|------------------------------|--------------|------------------|
| 470 | 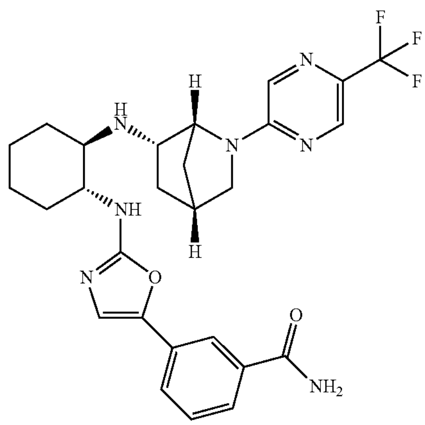 [SMILES: NC(=O)c1cccc(-c2cnc(N[C@@H]3CCCC[C@H]3N[C@H]3C[C@@H]4C[C@H]3N(c3cnc(C(F)(F)F)cn3)C4)o2)c1] | 162 | 5.802 (J) | 542.2 | Scheme 6 |
| 471 | 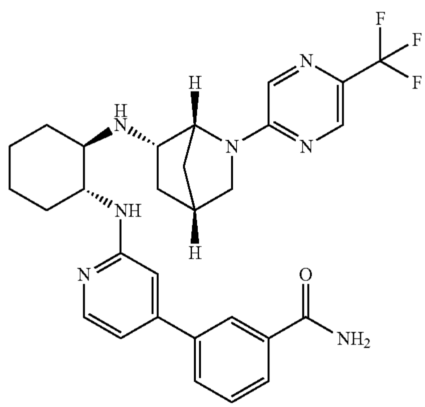 [SMILES: NC(=O)c1cccc(-c2ccnc(N[C@@H]3CCCC[C@H]3N[C@H]3C[C@@H]4C[C@H]3N(c3cnc(C(F)(F)F)cn3)C4)c2)c1] | 329 | 5.729 (J) | 552.2 | Scheme 5 |
| 472 | 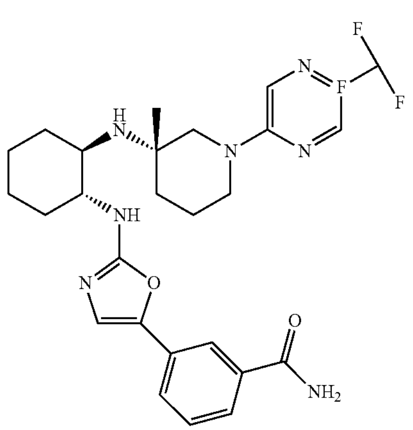 | 9 | 6.218 (J) | 544.2 | Scheme 4 |

TABLE 10-continued
| Example | Structure | hY4 CAMP EC50 (nM) | HPLC retention time (Method) | Mass (M + H) | Synthesis Method |
|---------|-----------|---------------------|------------------------------|--------------|------------------|
| 473 | 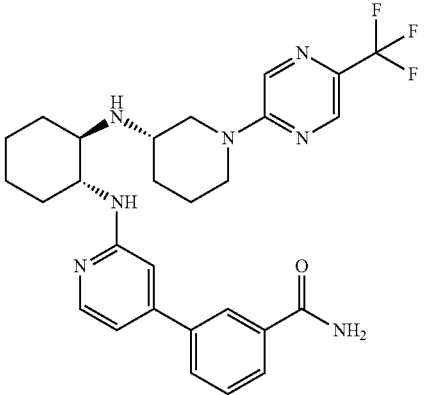 [SMILES: NC(=O)c1cccc(-c2ccnc(N[C@@H]3CCCC[C@H]3N[C@H]3CCCN(c4cnc(C(F)(F)F)cn4)C3)c2)c1] | 79 | 5.446 (J) | 540.2 | Scheme 3 |
| 474 | 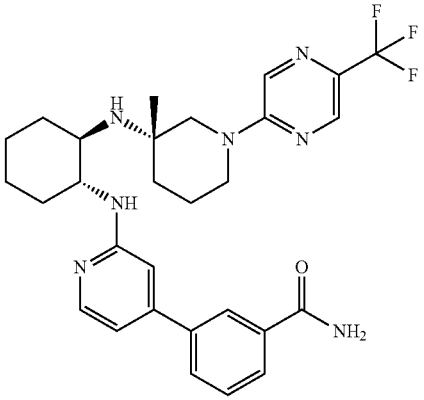 [SMILES: C[C@]1(N[C@@H]2CCCC[C@H]2Nc2cc(-c3cccc(C(N)=O)c3)ccn2)CCCN(c2cnc(C(F)(F)F)cn2)C1] | 142 | 5.857 (J) | 554.3 | Scheme 4 |
| 475 | 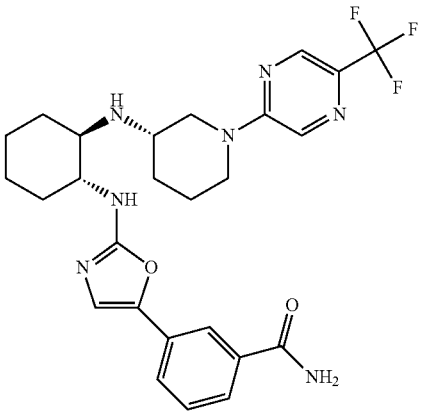 [SMILES: NC(=O)c1cccc(-c2cnc(N[C@@H]3CCCC[C@H]3N[C@H]3CCCN(c4cnc(C(F)(F)F)cn4)C3)o2)c1] | 8 | 1.60 (L) | 530.3 | Scheme 1 |

TABLE 10-continued

| Example | Structure | hY4 CAMP EC50 (nM) | HPLC retention time (Method) | Mass (M + H) | Synthesis Method |
|---------|-----------|--------------------|------------------------------|--------------|------------------|
| 476 | 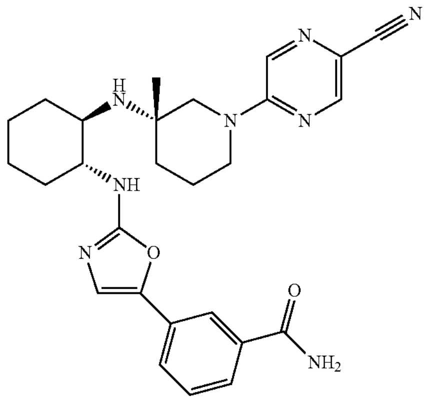 [SMILES: C[C@]1(N[C@@H]2CCCC[C@H]2Nc2ncc(-c3cccc(C(N)=O)c3)o2)CCCN(c2cnc(C#N)cn2)C1] | 49 | | 501.2 | Scheme 4 |
| 477 | 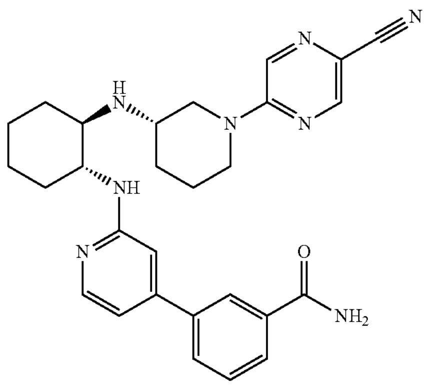 | 775 | | 497.2 | Scheme 3 |
| 478 | 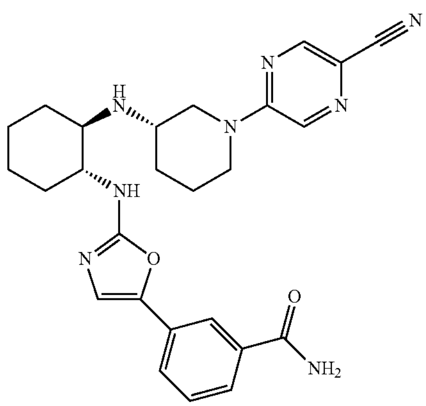 [SMILES: N#Cc1cnc(N2CCC[C@H](N[C@@H]3CCCC[C@H]3Nc3ncc(-c4cccc(C(N)=O)c4)o3)C2)cn1] | 25 | 1.22 (L) | 487.2 | Scheme 1 |
| 479 | 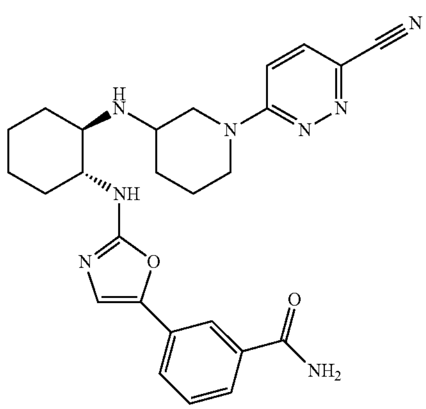 [SMILES: N#Cc1ccc(N2CCCC(N[C@@H]3CCCC[C@H]3Nc3ncc(-c4cccc(C(N)=O)c4)o3)C2)nn1] | 333 | | 487.2 | Scheme 6 |

TABLE 10-continued

| Example | Structure | hY4 CAMP EC50 (nM) | HPLC retention time (Method) | Mass (M + H) | Synthesis Method |
|---------|-----------|--------------------|------------------------------|--------------|------------------|
| 480 | 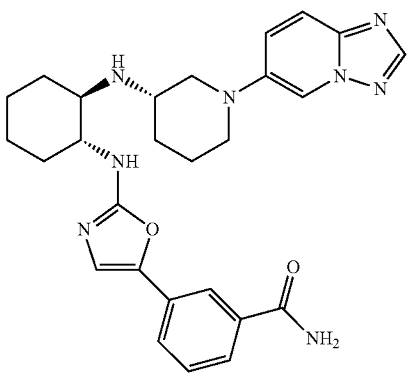 [SMILES: NC(=O)c1cccc(-c2cnc(N[C@@H]3CCCC[C@H]3N[C@H]3CCCN(c4ccc5ncnn5c4)C3)o2)c1] | 17 | 2.26 (A) | 501.3 | Scheme 1 |
| 481 | 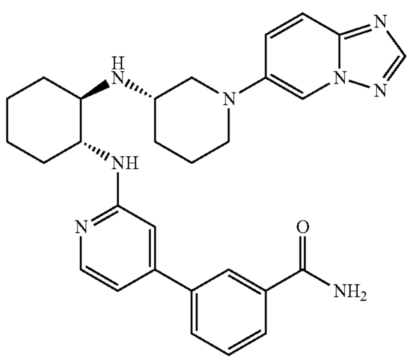 [SMILES: NC(=O)c1cccc(-c2ccnc(N[C@@H]3CCCC[C@H]3N[C@H]3CCCN(c4ccc5ncnn5c4)C3)c2)c1] | 34 | 2.28 (A) | 511.3 | Scheme 3 |
| 482 | 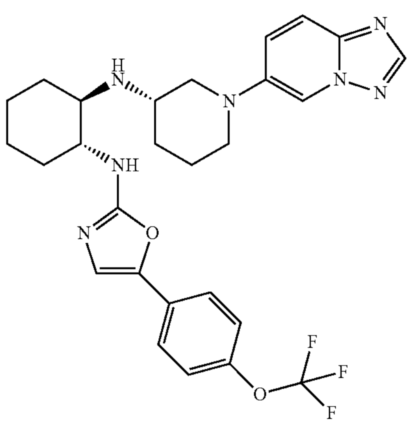 [SMILES: FC(F)(F)Oc1ccc(-c2cnc(N[C@@H]3CCCC[C@H]3N[C@H]3CCCN(c4ccc5ncnn5c4)C3)o2)cc1] | 107 | 3.09 (A) | 542.3 | Scheme 1 |
| 483 | 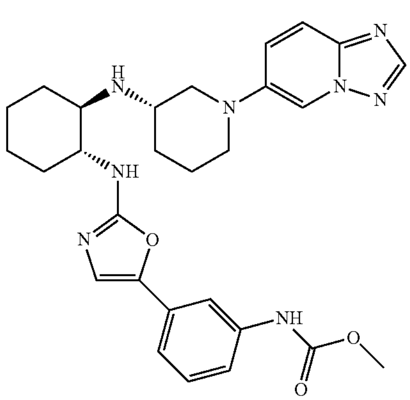 [SMILES: COC(=O)Nc1cccc(-c2cnc(N[C@@H]3CCCC[C@H]3N[C@H]3CCCN(c4ccc5ncnn5c4)C3)o2)c1] | 4 | 2.50 (A) | 531.4 | Scheme 1 |

TABLE 10-continued

| Example | Structure | hY4 CAMP EC50 (nM) | HPLC retention time (Method) | Mass (M + H) | Synthesis Method |
|---|---|---|---|---|---|
| 484 | 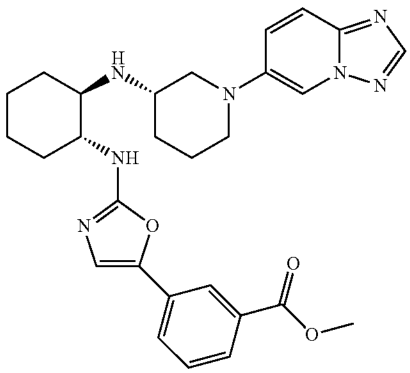 [SMILES: COC(=O)c1cccc(-c2cnc(N[C@@H]3CCCC[C@H]3N[C@H]3CCCN(c4ccc5ncnn5c4)C3)o2)c1] | 312 | 2.72 (A) | 516.3 | Scheme 1 |
| 485 | 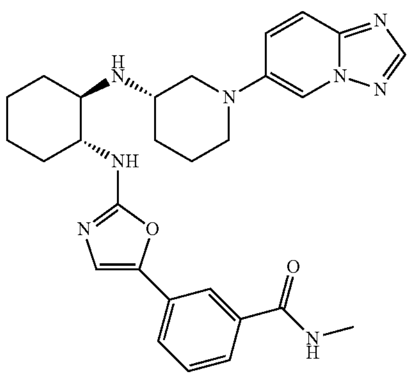 [SMILES: CNC(=O)c1cccc(-c2cnc(N[C@@H]3CCCC[C@H]3N[C@H]3CCCN(c4ccc5ncnn5c4)C3)o2)c1] | 58 | 1.34 (D) | 515 | Scheme 8 |
| 486 | 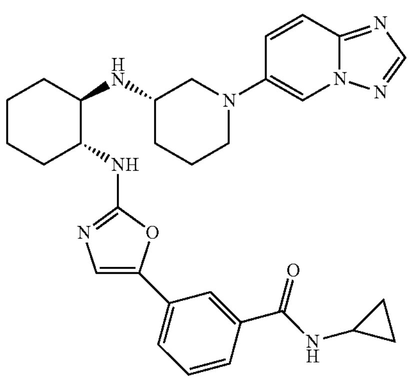 [SMILES: O=C(NC1CC1)c1cccc(-c2cnc(N[C@@H]3CCCC[C@H]3N[C@H]3CCCN(c4ccc5ncnn5c4)C3)o2)c1] | 78 | 1.47 (D) | 541 | Scheme 8 |
| 487 | 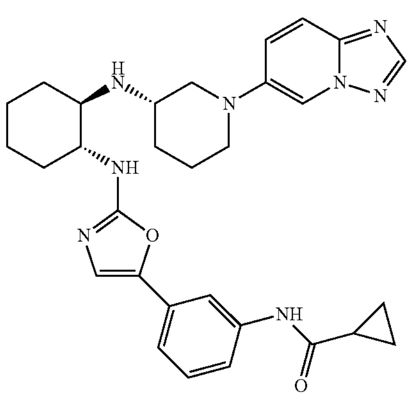 [SMILES: O=C(Nc1cccc(-c2cnc(N[C@@H]3CCCC[C@H]3N[C@H]3CCCN(c4ccc5ncnn5c4)C3)o2)c1)C1CC1] | 16 | 1.33 (D) | 541.25 | Scheme 1 |

TABLE 10-continued

| Example | Structure | hY4 CAMP EC50 (nM) | HPLC retention time (Method) | Mass (M + H) | Synthesis Method |
|---------|-----------|--------------------|-----------------------------|--------------|------------------|
| 488 | 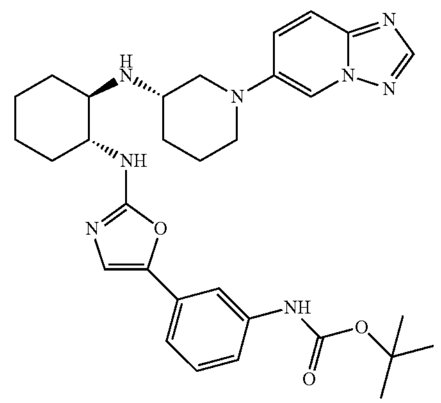 [SMILES: CC(C)(C)OC(=O)Nc1cccc(-c2cnc(N[C@@H]3CCCC[C@H]3N[C@H]3CCCN(c4ccc5ncnn5c4)C3)o2)c1] | 699 | 3.05 (A) | 573.4 | Scheme 1 |
| 489 | 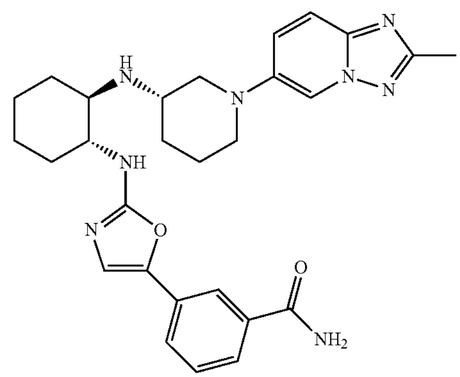 [SMILES: Cc1nc2ccc(N3CCC[C@H](N[C@@H]4CCCC[C@H]4Nc4ncc(-c5cccc(C(N)=O)c5)o4)C3)cn2n1] | 3 | 2.08 (A) | 515.3 | Scheme 1 |
| 490 | 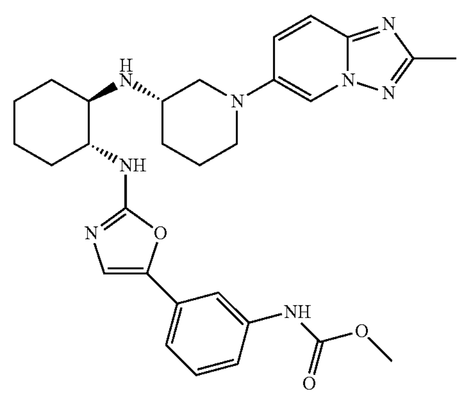 [SMILES: COC(=O)Nc1cccc(-c2cnc(N[C@@H]3CCCC[C@H]3N[C@H]3CCCN(c4ccc5nc(C)nn5c4)C3)o2)c1] | 1 | 2.50 (A) | 545.3 | Scheme 1 |
| 491 | 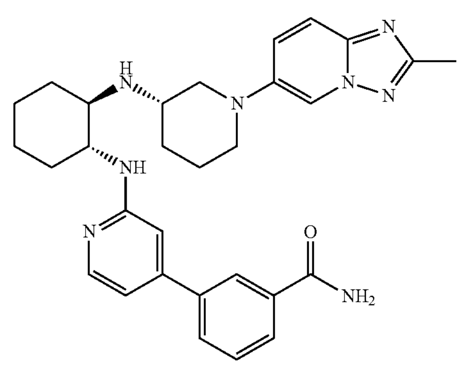 [SMILES: Cc1nc2ccc(N3CCC[C@H](N[C@@H]4CCCC[C@H]4Nc4cc(-c5cccc(C(N)=O)c5)ccn4)C3)cn2n1] | 22 | 0.95 (D) | 525 | Scheme 3 |

TABLE 10-continued

| Example | Structure | hY4 CAMP EC50 (nM) | HPLC retention time (Method) | Mass (M + H) | Synthesis Method |
|---|---|---|---|---|---|
| 492 | 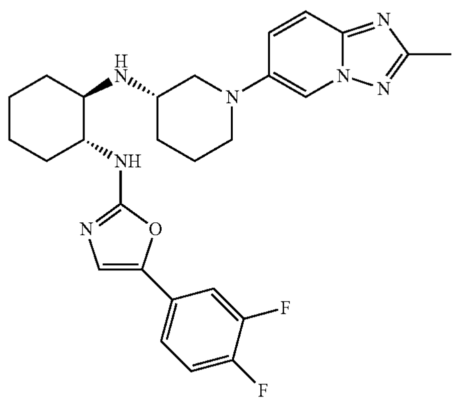 [SMILES: Cc1nc2ccc(N3CCC[C@H](N[C@@H]4CCCC[C@H]4Nc4ncc(-c5ccc(F)c(F)c5)o4)C3)cn2n1] | 38 | 1.24 (D) | 508 | Scheme 1 |
| 493 | 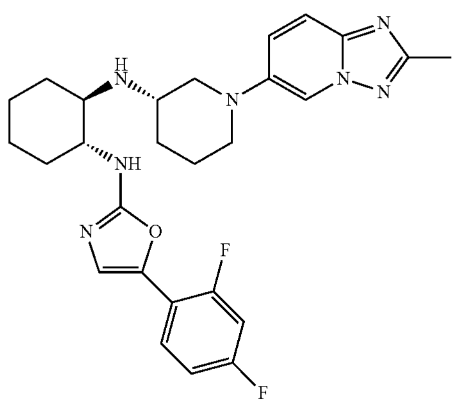 [SMILES: Cc1nc2ccc(N3CCC[C@H](N[C@@H]4CCCC[C@H]4Nc4ncc(-c5ccc(F)cc5F)o4)C3)cn2n1] | 47 | 1.24 (D) | 508 | Scheme 1 |
| 494 | 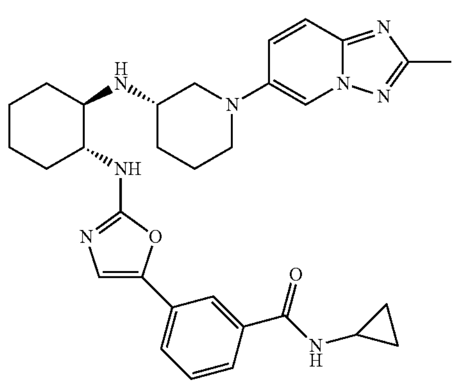 [SMILES: Cc1nc2ccc(N3CCC[C@H](N[C@@H]4CCCC[C@H]4Nc4ncc(-c5cccc(C(=O)NC6CC6)c5)o4)C3)cn2n1] | 42 | 2.43 (A) | 555.3 | Scheme 8 |
| 495 | 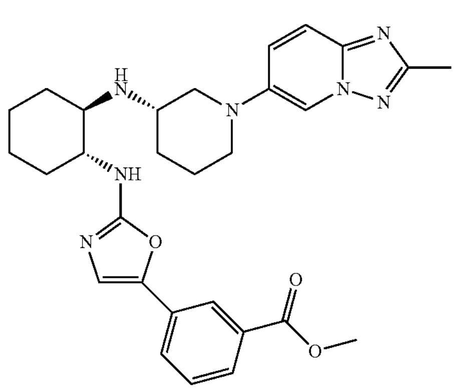 [SMILES: COC(=O)c1cccc(-c2cnc(N[C@@H]3CCCC[C@H]3N[C@H]3CCCN(c4ccc5nc(C)nn5c4)C3)o2)c1] | 49 | 2.69 (A) | 530.3 | Scheme 1 |

TABLE 10-continued
| Example | Structure | hY4 CAMP EC50 (nM) | HPLC retention time (Method) | Mass (M + H) | Synthesis Method |
|---------|-----------|--------------------|-----------------------------|--------------|------------------|
| 496 | 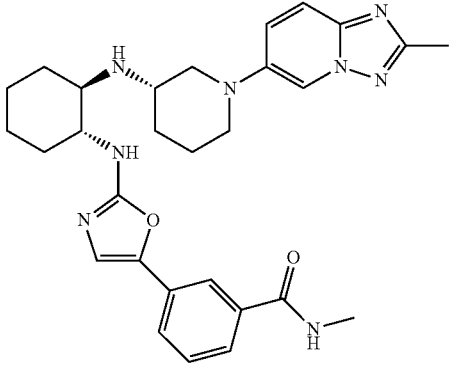 [SMILES: CNC(=O)c1cccc(-c2cnc(N[C@@H]3CCCC[C@H]3N[C@H]3CCCN(c4ccc5nc(C)nn5c4)C3)o2)c1] | 4 | 2.23 (A) | 529.3 | Scheme 8 |
| 497 | 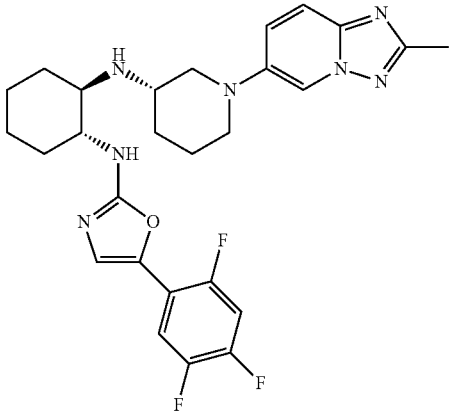 [SMILES: Cc1nc2ccc(N3CCC[C@H](N[C@@H]4CCCC[C@H]4Nc4ncc(-c5cc(F)c(F)cc5F)o4)C3)cn2n1] | 46 | 2.92 (A) | 526.2 | Scheme 1 |
| 498 | 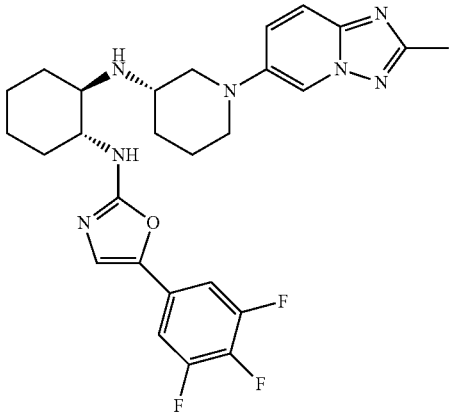 [SMILES: Cc1nc2ccc(N3CCC[C@H](N[C@@H]4CCCC[C@H]4Nc4ncc(-c5cc(F)c(F)c(F)c5)o4)C3)cn2n1] | 63 | 2.97 (A) | 526.2 | Scheme 1 |

TABLE 10-continued

| Example | Structure | hY4 CAMP EC50 (nM) | HPLC retention time (Method) | Mass (M + H) | Synthesis Method |
|---|---|---|---|---|---|
| 499 | 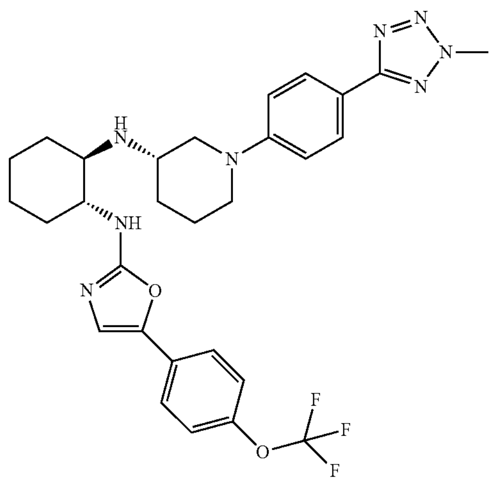 [SMILES: Cn1nnc(-c2ccc(N3CCC[C@H](N[C@@H]4CCCC[C@H]4Nc4ncc(-c5ccc(OC(F)(F)F)cc5)o4)C3)cc2)n1] | 1.40 | 3.41 (A) | 583.3 | Scheme 1 |
| 500 | 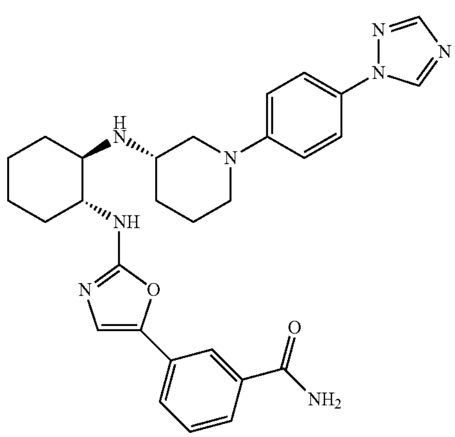 [SMILES: NC(=O)c1cccc(-c2cnc(N[C@@H]3CCCC[C@H]3N[C@H]3CCCN(c4ccc(-n5cncn5)cc4)C3)o2)c1] | 101 | 2.42 (A) | 527.2 | Scheme 1 |
| 501 | 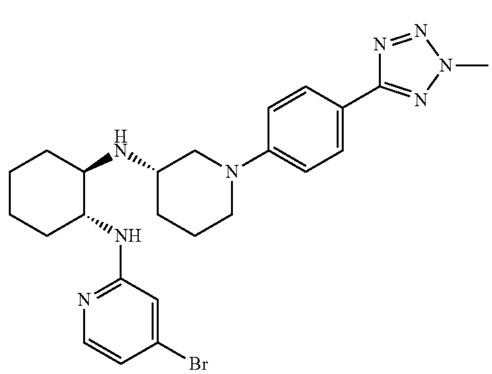 [SMILES: Cn1nnc(-c2ccc(N3CCC[C@H](N[C@@H]4CCCC[C@H]4Nc4cc(Br)ccn4)C3)cc2)n1] | 84 | 2.87 (A) | 511.2 | Scheme 1 |

TABLE 10-continued

| Example | Structure | hY4 CAMP EC50 (nM) | HPLC retention time (Method) | Mass (M + H) | Synthesis Method |
|---------|-----------|--------------------|------------------------------|--------------|------------------|
| 502 | 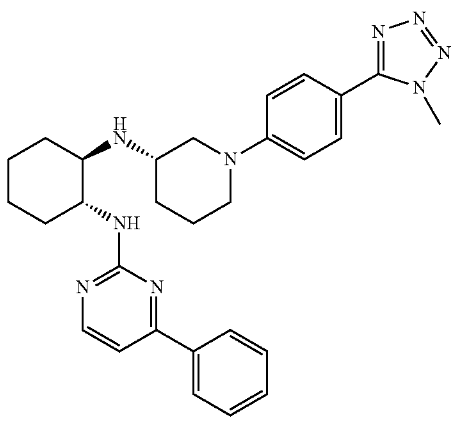 [SMILES: Cn1nnnc1-c1ccc(N2CCC[C@H](N[C@@H]3CCCC[C@H]3Nc3nccc(-c4ccccc4)n3)C2)cc1] | 98 | 2.68 (A) | 510.3 | Scheme 1 |
| 503 | 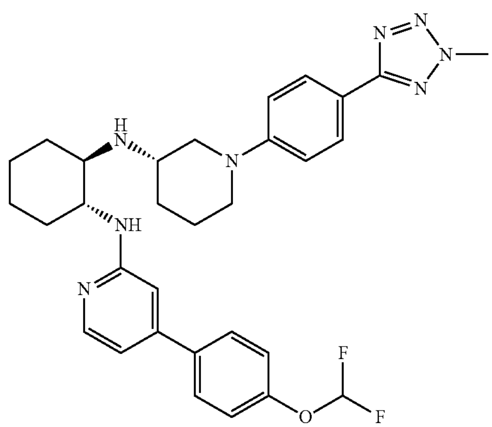 [SMILES: Cn1nnc(-c2ccc(N3CCC[C@H](N[C@@H]4CCCC[C@H]4Nc4cc(-c5ccc(OC(F)F)cc5)ccn4)C3)cc2)n1] | 150 | 3.00 (A) | 575.3 | Scheme 3 |
| 504 | 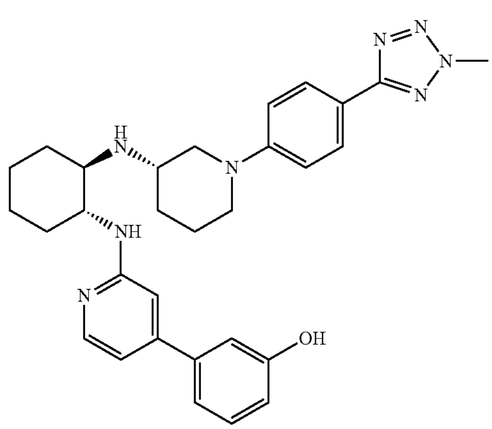 [SMILES: Cn1nnc(-c2ccc(N3CCC[C@H](N[C@@H]4CCCC[C@H]4Nc4cc(-c5cccc(O)c5)ccn4)C3)cc2)n1] | 0.3 | 2.49 (A) | 525.4 | Scheme 3 |

TABLE 10-continued

| Example | Structure | hY4 CAMP EC50 (nM) | HPLC retention time (Method) | Mass (M + H) | Synthesis Method |
|---------|-----------|--------------------|------------------------------|--------------|------------------|
| 505 | 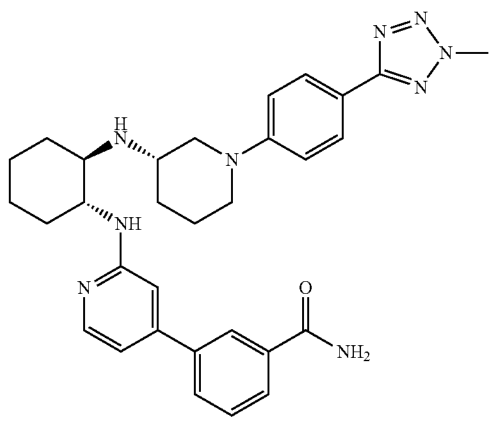 [SMILES: Cn1nnc(-c2ccc(N3CCC[C@H](N[C@@H]4CCCC[C@H]4Nc4cc(-c5cccc(C(N)=O)c5)ccn4)C3)cc2)n1] | 9 | 2.48 (A) | 552.3 | Scheme 3 |
| 506 | 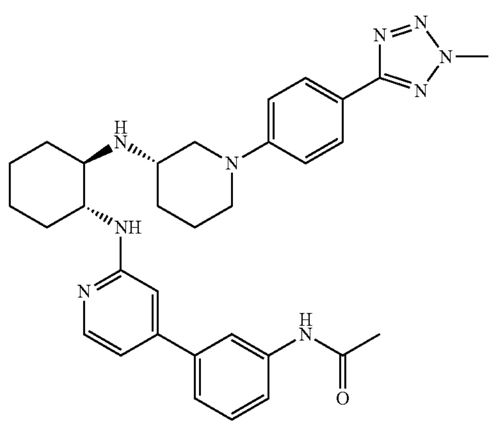 [SMILES: CC(=O)Nc1cccc(-c2ccnc(N[C@@H]3CCCC[C@H]3N[C@H]3CCCN(c4ccc(-c5nnn(C)n5)cc4)C3)c2)c1] | 0.2 | 2.73 (A) | 566.3 | Scheme 3 |
| 507 | 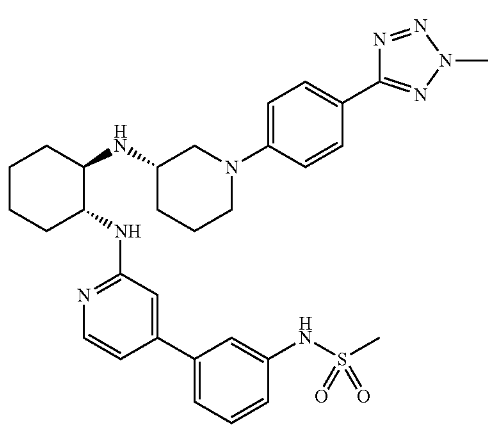 [SMILES: Cn1nnc(-c2ccc(N3CCC[C@H](N[C@@H]4CCCC[C@H]4Nc4cc(-c5cccc(NS(C)(=O)=O)c5)ccn4)C3)cc2)n1] | 6 | 2.69 (A) | 602.3 | Scheme 3 |

TABLE 10-continued

| Example | Structure | hY4 cAMP EC50 (nM) | HPLC retention time (Method) | Mass (M + H) | Synthesis Method |
|---|---|---|---|---|---|
| 508 | 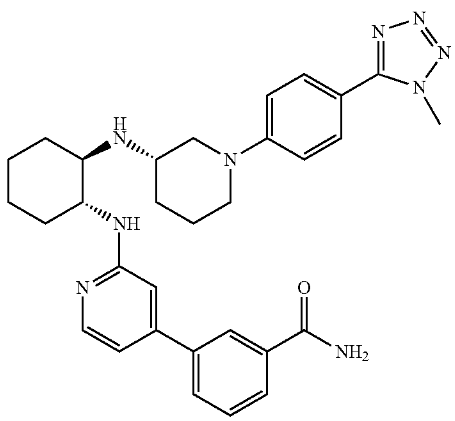 [SMILES: Cn1nnnc1-c1ccc(N2CCC[C@H](N[C@@H]3CCCC[C@H]3Nc3cc(-c4cccc(C(N)=O)c4)ccn3)C2)cc1] | 21 | 2.39 (A) | 552.3 | Scheme 3 |
| 509 | 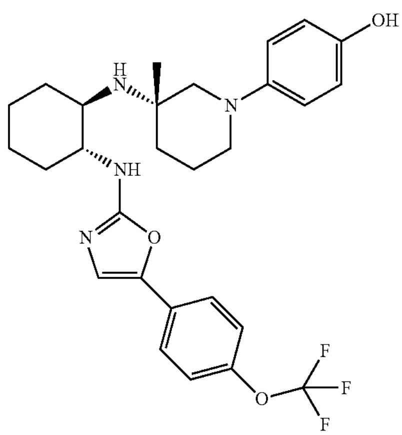 [SMILES: C[C@]1(N[C@@H]2CCCC[C@H]2Nc2ncc(-c3ccc(OC(F)(F)F)cc3)o2)CCCN(c2ccc(O)cc2)C1] | 128 | 2.92 (A) | 530.3 | Scheme 4 |
| 510 | 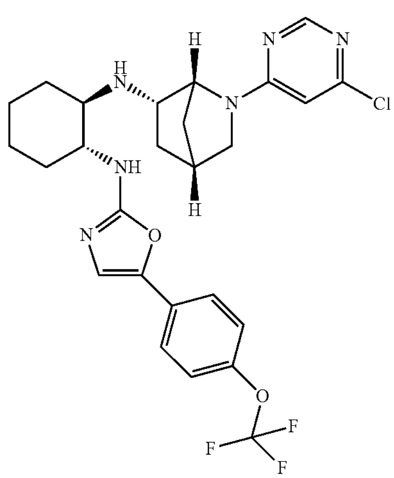 [SMILES: FC(F)(F)Oc1ccc(-c2cnc(N[C@@H]3CCCC[C@H]3N[C@H]3C[C@@H]4C[C@H]3N(c3cc(Cl)ncn3)C4)o2)cc1] | 82 | 7.773 (J) | 549.1 | Scheme 6 |

TABLE 10-continued

| Example | Structure | hY4 CAMP EC50 (nM) | HPLC retention time (Method) | Mass (M + H) | Synthesis Method |
|---|---|---|---|---|---|
| 511 | 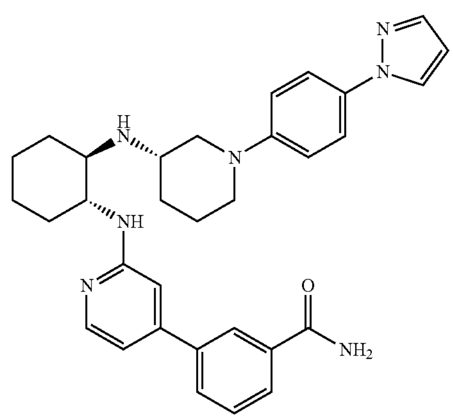 [SMILES: NC(=O)c1cccc(-c2ccnc(N[C@@H]3CCCC[C@H]3N[C@H]3CCCN(c4ccc(-n5cccn5)cc4)C3)c2)c1] | 23 | 2.51 (A) | 536.4 | Scheme 3 |
| 512 | 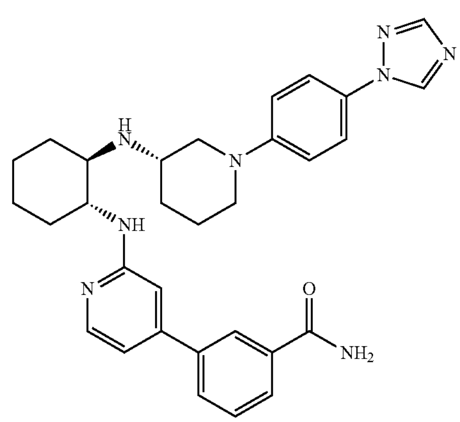 [SMILES: NC(=O)c1cccc(-c2ccnc(N[C@@H]3CCCC[C@H]3N[C@H]3CCCN(c4ccc(-n5cncn5)cc4)C3)c2)c1] | 650 | 2.27 (A) | 537.4 | Scheme 3 |
| 513 | 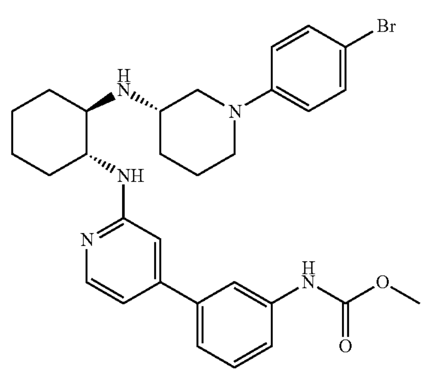 [SMILES: COC(=O)Nc1cccc(-c2ccnc(N[C@@H]3CCCC[C@H]3N[C@H]3CCCN(c4ccc(Br)cc4)C3)c2)c1] | 2 | 6.716 (J) | 578.2 | Scheme 6 |

TABLE 10-continued
| Example | Structure | hY4 CAMP EC50 (nM) | HPLC retention time (Method) | Mass (M + H) | Synthesis Method |
|---|---|---|---|---|---|
| 514 | 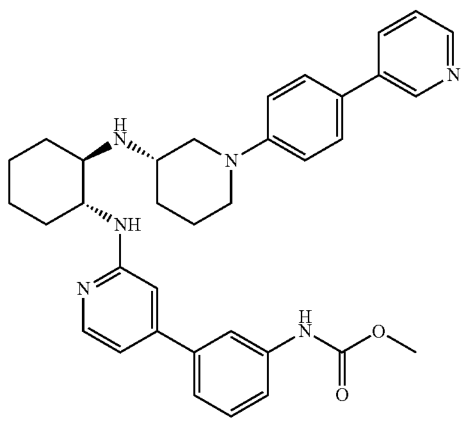 [SMILES: COC(=O)Nc1cccc(-c2ccnc(N[C@@H]3CCCC[C@H]3N[C@H]3CCCN(c4ccc(-c5cccnc5)cc4)C3)c2)c1] | 4 | | 576.9 | Scheme 7 |
| 515 | 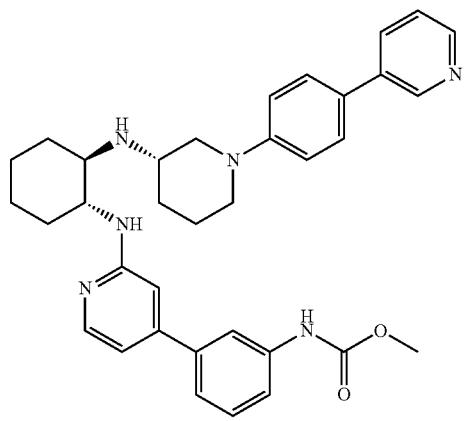 | 11 | 5.137 (J) | 577.9 | Scheme 7 |
| 516 | 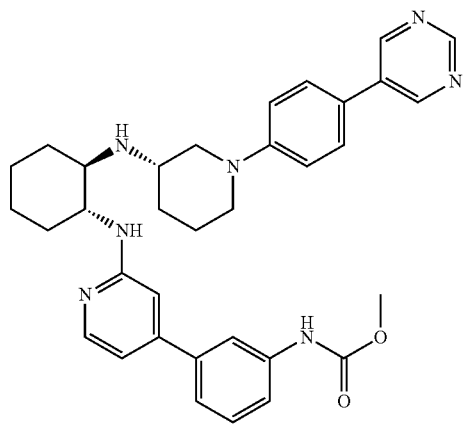 [SMILES: COC(=O)Nc1cccc(-c2ccnc(N[C@@H]3CCCC[C@H]3N[C@H]3CCCN(c4ccc(-c5cncnc5)cc4)C3)c2)c1] | 17 | 7.211 (J) | 575.9 | Scheme 7 |
| | 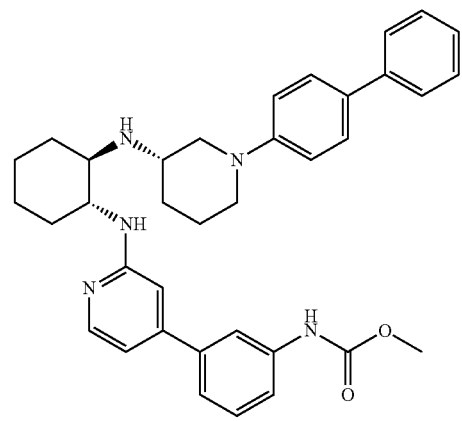 [SMILES: COC(=O)Nc1cccc(-c2ccnc(N[C@@H]3CCCC[C@H]3N[C@H]3CCCN(c4ccc(-c5ccccc5)cc4)C3)c2)c1] | | | | |

What is claimed:

1. A compound of formula Ia wherein:

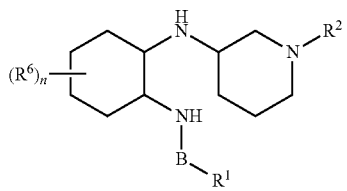

(Ia)

B is selected from the group consisting of thiazole, oxazole, oxadiazole, isoxazole, pyridine and pyrimidine, all of which may be substituted with one or more $R^1$;

$R^1$ is $(C_6)$aryl or 5- to 6-membered heteroaryl, said heteroaryl containing 1-4 heteroatoms selected from N, O, and S, wherein said aryl and heteroaryl may be optionally substituted with one or more $R^3$;

$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^3$ is independently one or more halogen, —OH, —CN, —$NO_2$, —COOH, —$CO_2(C_1-C_6)$alkyl, —$CF_3$, —$OCHF_2$, —$OCF_3$, —$(C_1-C_6)$-alkyl, —$(C_2-C_6)$alkenyl, —$(C_2-C_6)$alkynyl, $(C_3-C_8)$cycloalkyl, —$(C_1-C_6)$—alkyloxy, —$CONR^9R^{10}$, —$O(C=O)NR^9R^{10}$, —$NR^9R^{10}$, —$NHCOO(C_1-C_6)$alkyl, —$(C_1-C_6)$-alkyl-COOH, —$(C_1-C_6)$-alkyl-$CO_2(C_1-C_6)$-alkyl, —$(C_1-C_6)$-alkyl-OH, —$(C_1-C_6)$-alkylCONR$^9R^{10}$, —$SO_2(C_1-C_6)$-alkyl, —$SO_2(C_3-C_6)$-cycloalkyl, $SO_2NR^9R^{10}$, $(C_{6-10})$aryl, heteroaryl which contains 1-4 heteroatoms selected from N, O, and S; and a 5- to 10-membered heterocyclyl, which contains 1-4 heteroatoms selected from N, O, and S, wherein —$SO_2(C_1-C_6)$-alkyl, —$SO_2(C_3-C_6)$-cycloalkyl, $SO_2NR^9R^{10}$ or any alkyl, alkenyl, alkynyl, aryl, heteroaryl, and heterocyclyl groups may be optionally substituted with one or more substituents selected from halogen, —OH, cyano, nitro, —$CF_3$, —$OCF_3$, —$OCF_2H$, $(C_1-C_6)$-alkyl, $(C_2-C_6)$-alkynyl, $(C_1-C_6)$-alkyloxy, —COOH, —$CO_2(C_1-C_6)$-alkyl, —$CONR^9R^{10}$, —$NR^9R^{10}$, —$O(C=O)$—$(C_1-C_6)$-alkyl, —$O(C=O)$—$NR^9R^{10}$; —$(C_1-C_6)$-alkyl-COOH, —$(C_1-C_6)$-alkyl-OH, —$(C_1-C_6)$—alkylCONR$^9R^{10}$, —$(C_1-C_6)$-alkyl-$CO_2(C_1-C_6)$-alkyl, $(C_{6-10})$aryl, a 5- to 8-membered heteroaryl, which contains 1-4 heteroatoms selected from N, O, and S, a 5- to 10-membered heterocyclyl, which contains 1-4 heteroatoms selected from N, O, and S; and $R^4$ is fluoro, chloro, $CF_3$ —$OCF_2H$ —$OCF_3$, —CN, —$NO_2$, or a 5- to 6-membered heteroaryl containing 1-4 heteroatoms selected from N, O, and S, optionally substituted with one or more $R^5$;

$R^5$ is halogen, —OH, —$CF_3$, —$OCF_2H$, —$OCF_3$, —CN, $(C_1-C_6)$-alkyl, or $(C_1-C_6)$alkyloxy;

$R^6$ is halogen, —OH, $(C_1-C_6)$-alkyl or $(C_3-C_6)$-cycloalkyl wherein the $(C_1-C_6)$-alkyl is optionally substituted with $R^{11}$;

$R^9$ and $R^{10}$, at each occurrence, are independently hydrogen, —$(C_1-C_8)$-alkyl, —$(C_3-C_6)$alkenyl, —$(C_3-C_6)$alkynyl, —$(C_3-C_8)$-cycloalkyl, $(C_6)$aryl, 5- to 8-membered heteroaryl, —$CO(C_3-C_6)$-cycloalkyl, —$CO_2(C_3-C_6)$-cycloalkyl, —$CO(C_1-C_6)$-alkyl, —$CO_2(C_1-C_6)$-alkyl, —$CO(C_2-C_6)$-alkenyl, —$CO_2(C_3-C_6)$—alkenyl, —$CO(C_2-C_6)$-alkynyl, —$CO_2(C_3-C_6)$-alkynyl, —$CONR^9R^{10}$, —$SO_2(C_1-C_6)$-alkyl, —$SO(C_3-C_6)$—cycloalkyl, or $SO_2NR^9R^{10}$, all of which may be optionally substituted with one or more $R^{11}$; or $R^9$ and $R^{10}$, may be taken together with the nitrogen to which both are attached to form a 3-8 membered ring, which may optionally contain 1-4 heteroatoms selected from N, O, and S and be optionally substituted with one or more $R^{11}$;

$R^{11}$ is halo, —OH, cyano, —$(C_3-C_8)$-cycloalkyl, or —$(C_1-C_6)$-alkyl;

n is 0, 1, 2 or 3;

or a stereoisomer, tautomer, or pharmaceutically acceptable salt thereof.

2. The compound according to claim 1, wherein:

B is selected from the group consisting of thiazole, oxazole, oxadiazole, isoxazole, pyridine and pyrimidine, all of which may be substituted with one or more $R^1$;

$R^1$ is $(C_6)$aryl or 5- to 6-membered heteroaryl, said heteroaryl containing 1-4 heteroatoms selected from N, O, and S, wherein said aryl and heteroaryl may be optionally substituted with one or more $R^3$;

$R^2$ is $(C_6)$aryl or 5- to 6-membered heteroaryl, said heteroaryl containing 1-4 heteroatoms selected from N, and O, wherein both the aryl and heteroaryl may be optionally substituted with one or more $R^4$;

$R^4$ is fluoro, chloro, $CF_3$, —$OCF_2H$, —$OCF_3$, —CN, —$NO_2$, or a 5- to 6-membered heteroaryl containing 1-4 heteroatoms selected from N, O, and S, optionally substituted with one or more $R^5$;

$R^5$ is halogen, —OH, —$CF_3$, —$OCF_2H$, —$OCF_3$, —CN, $(C_1-C_6)$alkyl, or $(C_1-C_6)$alkyloxy; and n is 0;

or a stereoisomer, tautomer, or pharmaceutically acceptable salt thereof.

3. The compound according to claim 2, wherein:

$R^2$ is phenyl, pyridyl, pyrimidinyl, pyridazinyl, or pyrazinyl, substituted with one or more $R^4$;

$R^4$ is fluoro, chloro, $CF_3$, —$OCF_2H$, —$OCF_3$, —CN, —$NO_2$; or $R^4$ is tetrazole, oxadiazole, oxazole, pyrazole or isoxazole, optionally substituted with one or more $R^5$;

$R^5$ is halogen, —OH, —$CF_3$, —$OCF_2H$, —$OCF_3$, —CN, methyl, ethyl, methoxy, or ethoxy;

or a stereoisomer, tautomer, or pharmaceutically acceptable salt thereof.

4. The compound according to claim 3, wherein:

B is pyridine or oxazole.

5. A pharmaceutical composition comprising one or more compounds according to claim 1 and optionally a pharmaceutically acceptable carrier.

6. The pharmaceutical composition according to claim 1, further comprising a therapeutically effective amount of one or more other therapeutically active agents.

* * * * *